US008586770B2

(12) United States Patent
Frincke

(10) Patent No.: US 8,586,770 B2
(45) Date of Patent: Nov. 19, 2013

(54) UNSATURATED STEROID COMPOUNDS

(75) Inventor: James M. Frincke, Carlsbad, CA (US)

(73) Assignee: Harbor Therapeutics, Inc., San Diego, CA (US)

( * ) Notice: Subject to any disclaimer, the term of this patent is extended or adjusted under 35 U.S.C. 154(b) by 246 days.

(21) Appl. No.: 13/030,326

(22) Filed: Feb. 18, 2011

(65) Prior Publication Data

US 2011/0137057 A1 Jun. 9, 2011

Related U.S. Application Data

(63) Continuation of application No. 11/389,294, filed on Mar. 25, 2006, now Pat. No. 7,910,755, which is a continuation-in-part of application No. 11/241,670, filed on Sep. 29, 2005, now abandoned.

(60) Provisional application No. 60/614,869, filed on Sep. 29, 2004.

(51) Int. Cl.
*C07J 1/00* (2006.01)
*C07J 3/00* (2006.01)
*C07J 5/00* (2006.01)
*C07J 7/00* (2006.01)
*C07J 9/00* (2006.01)
*C07J 41/00* (2006.01)
*A61K 31/56* (2006.01)

(52) U.S. Cl.
USPC ........... 552/502; 514/169; 552/522; 552/536; 552/538; 552/540; 552/542; 552/543; 552/544; 552/546; 552/547; 552/548; 552/551; 552/552; 552/553; 552/554; 552/555; 552/557; 552/558; 552/559; 552/562; 552/564; 552/565; 552/569; 552/580; 552/581; 552/582; 552/583; 552/585; 552/586; 552/589; 552/590; 552/599; 552/603; 552/604; 552/605; 552/606; 552/607; 552/608; 552/610; 552/611; 552/612; 552/615; 552/616; 552/617; 552/618; 552/623; 552/624; 552/625; 552/626; 552/628; 552/629; 552/630; 552/633; 552/634; 552/636; 552/637; 552/638; 552/639; 552/640; 552/642; 552/643; 552/644; 552/645; 552/646; 552/647; 552/648; 552/650; 552/651

(58) Field of Classification Search
USPC .......... 514/169; 552/502, 522, 536, 538, 540, 552/542, 543, 544, 546, 547, 548, 551, 552, 552/553, 554, 555, 557, 558, 559, 562, 564, 552/565, 569, 580, 581, 582, 583, 585, 586, 552/589, 590, 599, 603, 604, 605, 606, 607, 552/608, 610, 611, 612, 615, 616, 617, 618, 552/623, 624, 625, 626, 628, 629, 630, 633, 552/634, 636, 637, 638, 639, 640, 642, 643, 552/644, 645, 646
See application file for complete search history.

(56) References Cited

U.S. PATENT DOCUMENTS

| | | | |
|---|---|---|---|
| 2,418,603 | A | 4/1947 | Schwenk |
| 3,125,495 | A | 3/1964 | Laskin et al. |
| 3,130,210 | A | 4/1964 | Wintersteiner et al. |
| 3,944,576 | A | 3/1976 | van der Broek |
| 4,152,325 | A | 5/1979 | Jouquey |
| 5,559,107 | A | 9/1996 | Gates et al. |
| 5,776,921 | A | 7/1998 | Gates et al. |
| 6,476,011 | B1 | 11/2002 | Reed et al. |
| 6,667,299 | B1 | 12/2003 | Ahlem et al. |
| 6,949,561 | B1 | 9/2005 | Reed et al. |
| 6,958,327 | B1 | 10/2005 | Hillisch et al. |
| 7,462,610 | B2 | 12/2008 | Lardy et al. |
| 7,482,334 | B2 | 1/2009 | Frincke et al. |
| 7,514,420 | B2 | 4/2009 | Lardy et al. |
| 7,691,835 | B2 | 4/2010 | Frincke |
| 7,696,189 | B1 | 4/2010 | Frincke |
| 7,842,680 | B2 | 11/2010 | Lardy et al. |
| 7,863,261 | B2 | 1/2011 | Frincke |
| 2003/0060425 | A1 | 3/2003 | Ahlem et al. |
| 2003/0083231 | A1 | 5/2003 | Ahlem et al. |
| 2004/0116359 | A1 | 6/2004 | Ahlem et al. |
| 2007/0077201 | A1 | 4/2007 | Frincke |
| 2008/0015174 | A1 | 1/2008 | Reading et al. |
| 2008/0090791 | A1 | 4/2008 | Reading et al. |
| 2011/0028711 | A1 | 2/2011 | Lardy et al. |

FOREIGN PATENT DOCUMENTS

| | | |
|---|---|---|
| DE | 2429040 A1 * | 1/1975 |
| EP | 1 422 234 | 5/2004 |
| WO | WO 01/23405 | 4/2001 |
| WO | WO 01/30802 | 5/2001 |
| WO | WO 2005/079810 | 9/2005 |

OTHER PUBLICATIONS

Yann Seimbille, François Bénard and Johan E. van Lier, "Synthesis of 16_-fluoro ICI 182,780 derivatives: powerful antiestrogens to image estrogen receptor densities in breast cancer by positron emission tomography", Journal of the Chemical Society, Perkin Transactions 1, 2002, 2275-2281.*

Carl A. Elliger, Anthony C. Waiss, Jr., Mabry Benson and Rosalind Y. Wong, "Ergostanoids from *Petunia* Parodii", Phytochemistry, 29(9), 1990, 2853-2863.*

US 2003/0060425 STN structure search result.*

Ikegawa, S., et al. "Synthesis of 3,6α,16α-trihydroxy-1,3,5(10)-estratrien-17-one 6-semisuccininate and [6,7-³H]-3,16α-dihydroxy-1,3,5(10)-estratrien-17-one", Steroids, vol. 39, No. 5, pp. 557-567 (1982).

(Continued)

*Primary Examiner* — John Pak
*Assistant Examiner* — Nathan W Schlientz
(74) *Attorney, Agent, or Firm* — Daryl D. Muenchau

(57) ABSTRACT

The invention relates to methods to manipulate stem cells in vivo and in vitro to treat, e.g., a condition where cell or tissue repair is needed.

26 Claims, No Drawings

(56) References Cited

OTHER PUBLICATIONS

Iriarte, J., et al. "Steroids XCIX. Synthesis of Ring B oxygenated estrogens", *J. Am. Chem. Soc.*, vol. 80, pp. 6105-6110 (1958).

Itoh, I., et al. "Synthesis of 6- and 7-hydroxyestratriol 17-sulfates: The potential metabolites of estradiol 17-sulfate by female rat liver microsomes", *Steroids*, vol. 64, pp. 363-370 (1999).

Napolitano, E., et al. "11β-Substituted estradiol derivatives, potential high-affinity carbon-11-labelled probes for the estrogen receptor", *J. Med. Chem.*, vol. 38, pp. 429-434 (1995).

Pearlman, W.H. "Estrogens with oxygen in Ring B I. 7-Ketoestrone and 7-hydroxyestrone", *J. Biol. Chem.*, vol. 35, pp. 35-45 (1939).

Peters, R.H., et al. "Analogues of [(triethylsilypethynyl]estradiol as potential antifetility agents", *J. Med. Chem.*, vol. 31, pp. 572-576 (1988).

Wiese, T.E., et al. "Induction of the estrogen specific mitogenic response of MCF-7 cells by selected analogues of estradiol-17β: A 3D QSAR study", *J. Med. Chem.*, vol. 40, pp. 3659-3669 (1997).

* cited by examiner

UNSATURATED STEROID COMPOUNDS

CROSS REFERENCE TO RELATED APPLICATIONS

This application is a continuation of application Ser. No. 11/389,294, filed Mar. 25, 2006 now U.S. Pat. No. 7,910,755, which is a continuation-in-part of abandoned U.S. patent application Ser. No. 11/241,670, filed Sep. 29, 2005 now abandoned, which claims priority from abandoned U.S. provisional application Ser. No. 60/614,869, filed Sep. 29, 2004, all of which are incorporated herein by reference.

FIELD OF THE INVENTION

The invention relates to methods to obtain stem cells in vivo or in vitro and uses thereof to treat conditions such as damaged or injured tissues or organs or where there is tissue damage associated with trauma, inflammation or oxidative stress.

BACKGROUND

Stem cells have been obtained from sources such as embryonic tissues, cord blood and other sources. U.S. Pat. No. 6,200,806 describes pluripotent stem cells obtained from human embryonic tissue. Such cells are capable of proliferating in vitro without significant karyotype changes while maintaining a capacity to differentiate into endoderm, mesoderm, and ectoderm tissues. These cells are negative for the SSEA-1 marker, positive for the SSEA-4 marker, express alkaline phosphatase activity and are pluripotent. These cells have euploid karyotypes and none of the chromosomes are obviously altered.

U.S. Pat. No. 5,843,780 describes a purified preparation of primate embryonic stem cells that is capable of proliferation in an in vitro culture for and maintains a karyotype in which all the chromosomes characteristic of the primate species are present and not noticeably altered through prolonged culture. These cells maintain a potential to differentiate into derivatives of endoderm, mesoderm, and ectoderm tissues throughout the culture. These cells will typically not differentiate when cultured on a fibroblast feeder layer and they can differentiate to trophoblasts and produce chorionic gonadotropin when cultured at a high density.

Pluripotent cells have been obtained from preimplantation embryos of several animals, e.g., Evans, et al., Theriogenology 33(1):125-128, 1990; Evans, et al., Theriogenology 33(1):125-128, 1990; Notarianni, et al., J. Reprod. Fertil. 41(Suppl.):51-56, 1990; Giles, et al., Mol. Reprod. Dev. 36:130-138, 1993; Graves, et al., Mol. Reprod. Dev. 36:424-433, 1993; Sukoyan, et al., Mol. Reprod. Dev. 33:418-431, 1992; Sukoyan, et al., Mol. Reprod. Dev. 36:148-158, 1993; Iannaccone, et al., Dev. Biol. 163:288-292, 1994).

Human embryonic carcinoma cells, which are pluripotent cells obtained from teratocarcinomas resemble human embryonic stem cells (Andrews, et al., Lab. Invest. 50(2):147-162, 1984; Andrews, et al., in: Robertson E., ed. *Teratocarcinomas and Embryonic Stem Cells: A Practical Approach*, Oxford: IRL press, pages 207-246, 1987). Embryonic carcinoma cells can be induced to differentiate in culture, which is characterized by the loss of specific cell surface markers (SSEA-3, SSEA-4, TRA-1-60, and TRA-1-81) and the appearance of new markers.

Stem cell populations and methods to use them have also been described elsewhere, see, e.g., U.S. Pat. Nos. 5,453,357, 6,986,887, 6,936,281, 6,967,029 and 6,872,389. Methods to obtain quantities of stem cells sufficient for treating clinical conditions are typically relatively expensive and complicated.

There is a current need for cost-effective methods for obtaining stem cells and using them to treat ameliorate various diseases associated with tissue or organ damage such as cardiovascular diseases, pulmonary conditions, neurological disorders, trauma, blood cell deficiencies and immune suppression conditions associated with aging or other causes. The invention provides methods to accomplish these. The use of these agents can be combined with one or more conventional treatments for these disorders.

DESCRIPTION OF THE INVENTION

Summary of Invention Embodiments.

In principal embodiments the invention provides methods to obtain or expand stem cells in vivo and in vitro and methods to use them.

The methods include a method to prevent, treat, ameliorate or slow the progression of one or more of a blood cell deficiency, unwanted inflammation, allergy, immune suppression condition, immunosenescence, autoimmune disorder, infection, cancer or precancer, neurological disorder, cardiovascular disorder, pulmonary disorder, trauma, hemorrhage, bone fracture, unwanted or excess bone loss, androgen deficiency, estrogen deficiency, a congenital or hereditary disorder or a symptom of any of these conditions in a subject who has the condition or who is subject to developing the condition, comprising administering to a subject, or delivering to the subject's tissues, an effective amount of a formula 1 compound

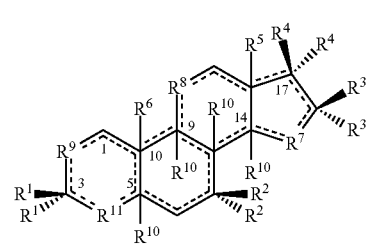

1 or a metabolic precursor, a metabolite, salt or tautomer thereof, wherein the dotted lines are optional double bonds and 0, 1, 2, 3, 4 or 5 double bonds, some of which may be conjugated, each $R^1$, $R^2$, $R^3$, $R^4$, $R^5$, $R^6$ and $R^{10}$ independently or together are —H, —OH, —$OR^{PR}$, —$SR^{PR}$, —SH, —$N(R^{PR})_2$, —$NHR^{PR}$, —$NH_2$, —O—Si—$(R^{13})_3$, —CHO, —CHS, —CN, —SCN, —$NO_2$, —$N_3$, —COOH, —CO-$OR^{PR}$, —$OSO_3H$, —$OSO_2H$, —$OPO_3H_2$, =O, =S, =N—OH, =N—$OCH_3$, =$CH_2$, =CH—$CH_3$, =CH-optionally substituted alkyl, ester, thioester, thionoester, phosphoester, phosphothioester, phosphonate, phosphonate ester, thiophosphonate, thiophosphonate ester, phosphiniester, sulfite ester, sulfate ester, sulfamate, sulfonate, sulfonamide, amide, amino acid, peptide, ether, thioether, acyl, thioacyl, carbonate, carbamate, halogen, optionally substituted alkyl, optionally substituted alkenyl, optionally substituted alkynyl, optionally substituted aryl, optionally substituted heteroaryl, optionally substituted heterocycle, optionally substituted monosaccharide, optionally substituted oligosaccharide, polymer, spiro ring, epoxide, acetal, thioacetal, ketal, thioketal, —S—S-optionally substituted alkyl, =N—O-optionally substituted alkyl, =N-optionally substituted alkyl, —NH-optionally substituted alkyl, —NH—S(O)(O)-optionally substituted alkyl, —N(optionally substituted alkyl)$_2$ where each optionally substituted alkyl is independently selected, or, one or more of two adjacent $R^1$, $R^2$, $R^3$, $R^4$, $R^5$, $R^6$ and $R^{10}$ comprise an independently selected epoxide or optionally substituted saturated or unsaturated cyclopropyl, cyclobutyl, cyclopentyl, cyclohexyl, cycloheptyl or cyclooxyl ring any of which rings optionally contain a ring heteroatom such as —O—, —S—, —NH— or =N—; $R^7$ is —O—, —S—, —S(O)(O)—, —$NR^{PR}$—, —$C(R^{10})_2$—, —$C(R^{10})_2$—$C(R^{10})_2$—, —$C(R^{10})_2$—$C(R^{10})_2$—$C(R^{10})_2$—, —$C(R^{10})_2$—O—$C(R^{10})_2$—, —$C(R^{10})_2$—S—$C(R^{10})_2$—, —$C(R^{10})_2$—$NR^{PR}$—$C(R^{10})_2$—, —O—$C(R^{10})_2$—, —S—$C(R^{10})_2$— or —$NR^{PR}$—$C(R^{10})_2$—, where each $R^{10}$ is independently selected; $R^8$ and $R^9$ independently are —$C(R^{10})_2$—, —$C(R^{10})_2$—$C(R^{10})_2$—, —O—, —O—$C(R^{10})_2$—, —S—, —S(O)(O)—, —S—$C(R^{10})_2$—, —S(O)(O)—$C(R^{10})_2$—, —$NR^{PR}$— or —$NR^{PR}$—$C(R^{10})_2$—, or one or both of $R^8$ or $R^9$ independently are absent, leaving a 5-membered ring, where each $R^{10}$ is independently selected; $R^{11}$ is —O—, —S—, —S(O)(O)—, —$NR^{PR}$—, —$CH_2$—, —$CHR^{10}$—, —$C(R^{10})_2$—, —$C(R^{10})_2$—O—$C(R^{10})_2$—, —$C(R^{10})_2$—S—$C(R^{10})_2$—, —$C(R^{10})_2$—$S(O)(O)$—$C(R^{10})_2$—, —$C(R^{10})_2$—$NR^{PR}$—$C(R^{10})_2$—, —O—$C(R^{10})_2$—, —S—$C(R^{10})_2$—, —S(O)(O)—$C(R^{10})_2$— or —$NR^{PR}$—C—$(R^{10})_2$—, where each $R^{10}$ is independently selected; $R^{13}$ independently is $C_{1-6}$ alkyl; $R^{PR}$ independently are —H or a protecting group; and optionally wherein one, two or three of the 1-, 4-, 6- and/or 12-positions are optionally substituted with (i) an independently selected $R^{10}$ moiety when a double bond is present at the corresponding 1-, 4-, 6- or 12-position, or (ii) one or two independently selected $R^{10}$ moieties when no double bond is present at the corresponding 1-, 4-, 6- and/or 12-position.

Other embodiments include (1) compositions that comprise a formula 1 compound and one or more other compounds such as an excipient(s) or a reactant or by-product of synthesis of the formula 1 compound, (2) formulations that comprise a formula 1 compound and 1, 2, 3, 4, 5, 6 or more excipients and (3) compositions that comprise partially purified or purified formula 1 compounds, optionally in a composition that comprises 1, 2, 3, 4, 5, 6 or more excipients and/or other compounds. The formulations can be designed for human or pharmaceutical use or they can be suitable for veterinary use. Therapeutic uses include the use of a formula 1 compound for the preparation of a medicament and use of a formula 1 compound for the preparation of a medicament for the prophylaxis, treatment or amelioration of a condition or symptom disclosed herein. Other embodiments are as described elsewhere in the specification or the claims.

Definitions.

As used herein and unless otherwise stated or implied by context, terms that are used herein have the meanings defined below. Unless otherwise contraindicated or implied, e.g., by including mutually exclusive elements or options, in these definitions and throughout this specification, the terms "a" and "an" mean one or more and the term "or" means and/or.

Reference to an androstene compound, e.g., 3,16α,17β-trihydroxyandrost-3,6-diene, means that the hydrogen atom or other moiety at the 5-position is in the α-configuration, which is sometimes specified in the compound name, e.g., 3,16α,17β-trihydroxy-5α-androst-3,6-diene. For androstanes with hydrogen at the 5-position in the β-configuration, the compound name will specify this configuration, e.g., 3,16α,17β-trihydroxy-5β-androst-3,6-diene, unless the configuration is otherwise apparent from a chemical structure or from context. For androstanes or androstenes, hydrogen atoms or other $R^{10}$ moieties at the 8-, 9- and 14-position, are in the β-, α- and α-configurations respectively, unless otherwise specified, e.g., by chemical structure, or implied by context.

As is apparent from the formula 1 structure, one or more variable groups may be absent when a double bond is present. Thus, when the compound contains an 8(9) double bond, $R^{10}$ at the 8- and 9-positions are both absent. Similarly, when a double bond is present at the 3-position one $R^1$ moiety will be absent and when a double bond is present at the 16-position one $R^3$ moiety and one $R^4$ moiety will be absent.

A "formulation", "pharmaceutical formulation" or the like means a composition that one can administer to a subject, e.g., human, mammal or other animal, usually without further manipulations that change the ingredients or the ingredient proportions that are present. Formulations include powders or other preparations that are prepared for use by addition of one or more liquids that act as solvents or suspension vehicles. Formulations will typically comprise a single formula 1 compound and one or more excipients. Formulations are suitable for human or veterinary applications and would typically have expected characteristics for the formulation, e.g., parenteral formulations for human use would usually be sterile and stored in a suitable closed container.

When referring to mixtures that contain a formula 1 compound, an "invention composition", "composition" or the like means a composition, that is a formulation or that can be an intermediate one can use, e.g., to make a formulation or a different formula 1 compound. Compositions also include other types of mixtures, e.g., (1) reagents for assays or cells that contain with a formula 1 compound or mixtures of compounds and (2) compounds used to make a formula 1 compound or by-products of formula 1 compound synthesis, metabolism or analysis.

Phrases such as "administration of a compound of formula 1", "treatment with a formula 1 compound", "use of a formula 1 compound" or similar terms mean that the compound(s) is administered to, contacted with or delivered to, the subject or to the subject's cells or tissues in vitro or in vivo by one or more suitable methods, e.g., in vivo delivery can be by an oral, topical, subcutaneous, subdermal, aerosol, parenteral, buccal or sublingual route.

Expressions such as "a formula 1 compound(s)", "a formula 1 compound" and the like mean compositions or formulations where one, two or more formula 1 compounds are present. Any reference to a "formula 1 compound", "one or more compounds of formula 1" or the like means that the formula 1 compound can have any structure disclosed herein that is within the definition of formula 1 compounds. The phrase formula 1 compound or formula 1 compound(s) is sometimes abbreviated as "F1C" or "F1C(s)" and formula 1 compounds may be abbreviated as "F1Cs".

Reference to subject matter "as disclosed herein" such as a "therapeutic treatment or agent as disclosed herein", a "dosing protocol as disclosed herein" or a "clinical condition or symptom as disclosed herein" or the like means a treatment, agent, protocol, condition, symptom or the like that is described herein or in any reference that is cited herein.

An "excipient", "carrier", "pharmaceutically acceptable excipient", "pharmaceutically acceptable carrier" or similar terms mean one or more component(s) or ingredient(s) that is acceptable in the sense of being compatible with the other ingredients of invention compositions or formulations and not overly deleterious to the patient, animal, tissues or cells to which the F1C, composition or formulation is to be administered.

A "subject" means a human or animal. Usually the animal is a mammal or vertebrate such as a primate, rodent, lagomorph, domestic animal or game animal. Primates include chimpanzees, Cynomolgus monkeys, spider monkeys, and macaques, e.g., Rhesus or Pan. Rodents and lagomorphs include mice, rats, woodchucks, ferrets, rabbits and hamsters. Domestic and game animals include cows, horses, pigs, sheep, deer, bison, buffalo, mink, felines, e.g., domestic cat, canines, e.g., dog, wolf and fox, avian species, e.g., chicken, turkey, emu and ostrich, and fish, e.g., trout, catfish and salmon. Subject includes any subset of the foregoing, e.g., all of the above, but excluding one or more groups or species such as humans, primates or rodents. Other subsets of subjects include subjects of a given species or group of species of varying ages, e.g., young humans, e.g., about 1 week of age to about 9 years of age, adolescent humans, e.g., about 10-19 years of age, adult humans, e.g., about 20-100 years of age, and mature adult or elderly humans, e.g., at least about 55 years of age, at least about 60 years of age, at least about 65 years of age or a range of ages such as about 55-100 years of age. Thus, as used herein, prevention or treatment of a disease, condition or symptom may include or exclude any subset of subjects that are grouped by age.

The terms "effective amount", "effective dose" or the like with reference to a F1C(s) mean an amount of the F1C(s) that is sufficient to elicit a desired or detectable response, e.g., detectable restoration of normal immune responsiveness in an immunodeficient subject to which it is administered, e.g., a human, or to detectable modulation or amelioration of cellular parameter or a clinical condition or symptom or a detectable amount for analytical or other characterization use.

Terms such as "use", "treat", "treatment", "address" or the like in the context of using the F1Cs in the treatment methods or other methods disclosed herein mean that a F1C is administered to a subject, delivered to the subject's tissues or contacted with tissues, cells or cell free systems in vivo or in vitro, e.g., as described herein or a reference cited herein. Typically such use or treatment results in, e.g., (1) detectable improvement in or amelioration of the condition or symptom being treated, (2) detectable modulation in the activity, level or numbers of a relevant biomolecule, therapeutic immune cell population or a pathological cell population, (3) slowing of the progression of a condition or delaying its onset, or reduction of the severity of a symptom(s) of the condition or (4) another detectable response as described herein. Any such amelioration may be transient, e.g., lasting for at least a few, e.g., about 1, 2 or 4 hours to about 10, 12 or 24 hours or lasting for days, e.g., about 1, 2, 3 or 4 days to about 5, 7, 10 or more days. Amelioration may be prolonged, e.g., lasting from about 10, 12, or 14 days, to about 18, 21, 28, 35, 42, 49, 60 or more days, or amelioration may be permanent. A treatment may slow the progression of a disease or symptom or it may reduce the severity thereof, e.g., onset of a disease or a symptom may be delayed in at least some subjects for about 1-24 hours, about 2-10 days, about 2-30 days or for about 1-5 years compared to subjects who are not treated with sufficient amounts of the F1C. Thus, a F1C use or treatment typically results in detectable modulation in a relevant biological parameter such as modulation of the level, activity or relative amount of a target effector or suppressor immune cell population, interleukin, cytokine, chemokine, immunoglobulin compared to a suitable control, e.g., untreated. A F1C treatment can also elicit modulation of the level or activity of a relevant transcription factor, enzyme, cell biological activity or level or activity of the etiological agent of the disease such as a pathogen, tumor cell or autoreactive immune cell subset. A treatment with a F1C may be used to delay or prevent the onset of a disease, symptom or complication or to ameliorate or slow the progression of a preexisting disease, condition, symptom or complication, or to facilitate elimination of a disease, condition, symptom or complication.

"Ameliorate", "amelioration", "improvement" or the like means a detectable improvement or a detectable change consistent with improvement occurs in a subject or in at least a minority of subjects, e.g., in at least about 2%, 5%, 10%, 15%, 20%, 25%, 30%, 40%, 50%, 60%, 70%, 75%, 80%, 85%, 90%, 95%, 98%, 100% or in a range about between any two of these values. Such improvement or change may be observed in treated subjects as compared to subjects not treated with a F1C, where the untreated subjects have, or are subject to developing, the same or similar disease, condition, symptom or the like. Amelioration of a disease, condition, symptom or assay parameter may be determined subjectively or objectively, e.g., self assessment by a subject(s), by a clinician's assessment or by conducting an appropriate assay or measurement, including, e.g., a quality of life assessment, a slowed progression of a disease(s) or condition(s), a reduced severity of a disease(s) or condition(s), or a suitable assay(s) for the level or activity(ies) of a biomolecule(s), cell(s) or by detection of cell migration within a subject. Amelioration may be transient, prolonged or permanent or it may be variable at relevant times during or after a F1C is administered to a subject or is used in an assay or other method described herein or a cited reference, e.g., within about 1 hour of the administration or use of a F1C to about 3, 6, 9 months or more after a subject(s) has received a F1C.

The "modulation" of, e.g., a symptom, level or biological activity of a molecule, replication of a pathogen, cellular response, cellular activity or the like, means that the cell, level or activity, or the like is detectably increased or decreased. Such increase or decrease may be observed in treated subjects as compared to subjects not treated with a F1C, where the untreated subjects have, or are subject to developing, the same or similar disease, condition, symptom or the like. Such increases or decreases may be at least about 2%, 5%, 10%, 15%, 20%, 25%, 30%, 40%, 50%, 60%, 70%, 75%, 80%, 85%, 90%, 95%, 98%, 100%, 150%, 200%, 250%, 300%, 400%, 500%, 1000% or more or about within any range about between any two of these values. Modulation may be determined subjectively or objectively, e.g., by the subject's self assessment, by a clinician's assessment or by conducting an appropriate assay or measurement, including, e.g., quality of life assessments or suitable assays for the level or activity of molecules, cells or cell migration within a subject. Modulation may be transient, prolonged or permanent or it may be variable at relevant times during or after a F1C is administered to a subject or is used in an assay or other method described herein or a cited reference, e.g., within about 1 hour of the administration or use of a F1C to about 3, 6, 9 months or more after a subject(s) has received a F1C.

Terms such as "antigen", "immunogen", "antigenic fragment" or the like mean a molecule that comprises one or more epitopes that are capable of stimulating a subject's immune system to make, e.g., a secretory, humoral or cellular antigen-specific response against the antigen, immunogen or fragment and/or the source from which it was derived, e.g., the source pathogen, tissue or cell. Antigenic fragments are synthetic or natural derivatives of natural or intact antigens or immunogens that retain at least a detectable capacity, e.g., at least about 10%, 20%, 30%, 40%, 50% or more of the native antigen's antigenic capacity, to stimulate a subject's immune system in a desired manner.

"Vaccine composition", "vaccine" or similar terms mean an agent suitable for stimulating a subject's immune system to ameliorate a current condition or to protect against or to reduce present or future harm or infection, e.g., reduced tumor cell proliferation or survival, reduced pathogen replication or spread in a subject or a detectably reduced unwanted symptom(s) associated with a condition. Vaccines may modulate, typically detectably enhance, humoral, cell mediated or innate immune responses.

"Immunization" means the process of inducing a detectable and continuing moderate or high level of antibody or cellular immune response that is directed against one or more antigens to which the subject has been exposed. Such responses are typically detectably maintained for at least about 3-48 months or more.

At various locations in the present disclosure, e.g., in any disclosed embodiments or in the claims, reference is made to compounds, compositions, formulations, or methods that "comprise" one or more specified components, elements or steps. Invention embodiments also specifically include those compounds, compositions, formulations or methods that are or that consist of or that consist essentially of those specified components, elements or steps. The terms "comprising", "consist of" and "consist essentially of" have their normally accepted meanings under U.S. patent law. For example, disclosed compositions or methods that "comprise" a component or step are open and they include or read on those compositions or methods plus an additional component(s) or step(s). Similarly, disclosed compositions or methods that "consist of" a component or step are closed and they would not include or read on those compositions or methods having appreciable amounts of an additional component(s) or an additional step(s).

At various locations in the present disclosure, reference is made to ranges, e.g., of unit doses of F1Cs or time periods for F1C dosing. For example, a F1C dose range may be described as "about 10 mg, 20 mg or 30 mg to about 50 mg, 100 mg or 200 mg." As used herein, this range description is intended to include all of the sub ranges, i.e., about 10 mg to about 50 mg, about 10 mg to about 100 mg, about 10 mg to about 200 mg, about 20 mg to about 50 mg and so forth. Similarly, a time range expressed as about 1, 2 or 3 days to about 7, 10 or 14 days means about 1-7 days, about 2-7 days, about 3-7 days, about 1-10 days, about 2-10 days and so on.

"Alkyl" as used here means linked normal, secondary, tertiary or cyclic carbon atoms, i.e., linear, branched, cyclic or any combination thereof. Alkyl moieties, as used herein, may be saturated, or unsaturated, i.e., the moiety may comprise one, two, three or more independently selected double bonds or triple bonds. Unsaturated alkyl moieties include moieties as described for alkenyl, alkynyl and aryl moieties described below. The number of carbon atoms in an alkyl group or moiety can vary and typically is 1 to about 50, e.g., about 1-30 or about 1-20, unless otherwise specified, e.g., $C_{1-8}$ alkyl or C1-C8 alkyl means an alkyl moiety containing 1, 2, 3, 4, 5, 6, 7 or 8 carbon atoms. Unless otherwise specified, alkyl groups will contain 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more carbon atoms, typically from 1 to 20 carbon atoms or from 1 to 8 carbon atoms. When an alkyl group is specified, species may include methyl, ethyl, 1-propyl (n-propyl), 2-propyl (i-propyl, —CH(CH$_3$)$_2$), 1-butyl (n-butyl), 2-methyl-1-propyl (i-butyl, —CH$_2$CH(CH$_3$)$_2$), 2-butyl (s-butyl, —CH(CH$_3$)CH$_2$CH$_3$), 2-methyl-2-propyl (t-butyl, —C(CH$_3$)$_3$), amyl, isoamyl, sec-amyl, 1-pentyl (n-pentyl), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), 1-hexyl, 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), 3,3-dimethyl-2-butyl (—CH(CH$_3$)C(CH$_3$)$_3$), cyclopropyl (—CH<CH$_2$CH$_2$), cyclobutyl (—CH<CH$_2$CH$_2$CH$_2$), 1-methylcyclobutyl (—CH<CH(CH$_3$)CH$_2$CH$_2$), 1,2-dimethylpropyl, 1,1-dimethylpropyl, hexyl, 4-methylpentyl, 1-methylpentyl, 2-methylpentyl, 3-methylpentyl, 1,1-dimethylbutyl, 2,2-dimethylbutyl, 3,3-dimethylbutyl, 1,2-dimethylbutyl, 1,3-dimethylbutyl, 1,2,2,-trimethylpropyl, 1,1,2-trimethylpropyl, heptyl, 5-methylhexyl, 1-methylhexyl, 2,2-dimethylpentyl, 3,3-dimethylpentyl, 4,4-dimethylpentyl, 1,2-dimethylpentyl, 1,3-dimethylpentyl, 1,4-dimethylpentyl, 1,2,3,-trimethylbutyl, 1,1,2-trimethylbutyl, 1,1,3-trimethylbutyl, normal or branched octyl, 6-methylheptyl, 1-methylheptyl, 1,1,3,3-tetramethylbutyl, normal or branched nonyl, 1-, 2-, 3-, 4-, 5-, 6- and 7-methyloctyl, 1-, 2-, 3-, 4-, 5-ethylheptyl, 1-, 2- and 3-propylhexyl, decyl, 1-, 2-, 3-, 4-, 5-, 6-, 7- and 8-methylnonyl, 1- 2-, 3-, 4-, 5- and 6-ethyloctyl, 1-, 2-, 3- and 4-propylheptyl, undecyl 1-, 2-, 3-, 4-, 5-, 6-, 7-, 8- and 9-methyldecyl, 1-, 2-, 3-, 4-, 5-, 6- and 7-ethylnonyl, 1-, 2-, 3-, 4- and 5-propyloctyl, 1-, 2- and 3-butyloctyl, 1-pentylhexyl, dodecyl, 1-, 2-, 3-, 4-, 5-, 6-, 7-, 8-, 9- and 10-methylundecyl, 1-, 2-, 3-, 4-, 5-, 6-, 7- and 8-ethyldecyl, 1-, 2-, 3-, 4-, 5- and 6-propylnonyl, 1-, 2-, 3- and 4-butyloctyl, 1-2-pentylheptyl, cyclopropyl, cyclobutyl, cyclopentyl, cyclohexyl, cycloheptyl, cyclooctyl, cyclononyl, cyclodecyl, —(CH$_2$)$_n$—(CHCH$_3$)$_m$—(CH$_2$)$_o$—CH$_3$, —(CH$_2$)$_n$—(CHC$_2$H$_5$)$_m$—(CH$_2$)$_o$—CH$_3$ and positional isomers of any of these moieties that can have one or more positional isomers, where n, m and o independently are 0, 1, 2, 3, 4, 5, 6, 7 or 8. Alkyl also includes species and groups described below for alkenyl, alkynyl groups, aryl groups, arylalkyl groups alkylaryl groups and the like. "Alkyl" thus includes vinyl, ethynyl, 1-propynyl and the like.

"Alkenyl" as used here means a moiety that comprises linked normal, secondary, tertiary or cyclic carbon atoms, i.e., linear, branched, cyclic or any combination thereof, that comprises one or more double bonds (—CH═CH—), e.g., 1, 2, 3, 4, 5, 6 or more, typically 1, 2 or 3, which can include an aryl moiety such as benzene. The number of carbon atoms in an alkenyl group or moiety can vary and typically is 2 to about 50, e.g., about 2-30 or about 2-20, unless otherwise specified, e.g., $C_{2-8}$ alkenyl or C2-8 alkenyl means an alkenyl moiety containing 2, 3, 4, 5, 6, 7 or 8 carbon atoms. Alkenyl groups will typically have 2, 3, 4, 5, 6, 7, 8, 9, 10, 11, 12, 13, 14, 15, 16, 17, 18, 18 or 20 carbon atoms. When an alkenyl group is specified, species include, e.g., any of the alkyl moieties described above that has one or more double bonds, methylene (═CH$_2$), methylmethylene (═CH—CH$_3$), ethylmethylene (═CH—CH$_2$—CH$_3$), ═CH—CH$_2$—CH$_2$—CH$_3$, vinyl (—CH═CH$_2$), allyl, 1-methylvinyl, butenyl, iso-butenyl, 3-methyl-2-butenyl, 1-pentenyl, cyclopentenyl, 1-methyl-cyclopentenyl, 1-hexenyl, 3-hexenyl, cyclohexenyl, 1-heptenyl, 3-heptenyl, 1-octenyl, cyclooctenyl, 1-nonenyl, 2-nonenyl, 3-nonenyl, 1-decenyl, 3-decenyl, 1,3-butadienyl, 1,4-pentadienyl, 1,3-cyclopentadienyl, 1,3-hexadienyl, 1,4-hexadienyl, 1,3-cyclohexadienyl, 1,4-cyclohexaidenyl, 1,3-cycloheptadienyl, 1,3,5-cycloheptatrienyl, 1,3,5,7-cyclooctatetraenyl, —(CH$_2$)$_n$—(CH═CH)—(CH$_2$)$_m$—CH$_3$, —(CH$_2$)$_n$—(CCH$_3$═CH)—(CH$_2$)$_m$—CH$_3$, —(CH$_2$)$_n$—(CH═CCH$_3$)—(CH$_2$)$_m$—CH$_3$, —(CH$_2$)$_n$—(CH═CH)$_{0-1}$—(CH$_2$)$_m$—CH$_2$CH═CH$_2$ and —(CH$_2$)$_n$—(CH═CH)$_{0-1}$—(CH$_2$)$_m$—CH$_2$—(CH═CH)$_{0-1}$—CH$_3$, where n and m independently are 0, 1, 2, 3, 4, 5, 6, 7 or 8. Unless otherwise specified, alkenyl groups will contain 2, 3, 4, 5, 6, 7, 8, 9, 10, 11, 12, 13, 14, 15, 16, 17, 18, 19, 20, 21, 22, 23, 24, 25, 26, 27, 28, 29, 30 or more carbon atoms, typically from 2 to 20 carbon atoms or from 2 to 8 carbon atoms.

"Alkynyl" as used here means a moiety that comprises linked normal, secondary, tertiary or cyclic carbon atoms, i.e., linear, branched, cyclic or any combination thereof, that comprises one or more triple bonds (—C≡C—), e.g., 1, 2, 3, 4, 5, 6 or more, typically 1 or 2 triple bonds, optionally comprising 1, 2, 3, 4, 5, 6 or more double bonds, with the remaining bonds being single bonds. The number of carbon atoms in an alkenyl group or moiety can vary and typically is 2 to about 50, e.g., about 2-30 or about 2-20, unless otherwise specified, e.g., $C_{2-8}$ alkynyl or C2-8 alkynyl means an alkynyl moiety containing 2, 3, 4, 5, 6, 7 or 8 carbon atoms. Alkynyl groups will typically have 2, 3, 4, 5, 6, 7, 8, 9, 10, 11, 12, 13, 14, 15, 16, 17, 18, 18 or 20 carbon atoms. When an alkynyl group is specified, species include, e.g., any of the alkyl moieties described above that has one or more double bonds, butynyl, iso-butynyl, 3-methyl-2-butynyl, 1-pentynyl, cyclopentynyl, 1-methyl-cyclopentynyl, 1-hexynyl, 3-hexynyl, cyclohexynyl, 1-heptynyl, 3-heptynyl, 1-octynyl, cyclooctynyl, 1-nonynyl, 2-nonynyl, 3-nonynyl, 1-decynyl, 3-decynyl, 1,3-butadiynyl, 1,4-pentadiynyl, 1,3-pentadiynyl, 1,3-hexadiynyl, 1,4-hexadynyl, 1,5-hexadynyl, 1,3-heptadynyl, 1,3,5-heptatriynyl, 1,3,5,7-octatetraynyl, —CCH, —CCCH$_3$, —CCCH$_2$CH$_3$, —CCC$_3$H$_7$, —CCCH$_2$C$_3$H$_7$, —(CH$_2$)$_n$—(C≡C)—(CH$_2$)$_m$—CH$_3$, —(CH$_2$)$_n$—(C≡C)$_{0-1}$—(CH$_2$)$_m$—CH$_2$C≡CH, —(CH$_2$)$_n$—(C≡C)$_{0-1}$—(CH$_2$)$_m$—CH$_2$—(C≡C)$_{0-1}$—CH$_3$, —(CH$_2$)$_n$—(C≡C)—CH$_2$—(C≡C)—(CH$_2$)$_m$—CH$_3$, where each n and m independently are 0, 1, 2, 3, 4, 5, 6, 7 or 8. Unless otherwise specified, alkynyl groups will contain 2, 3, 4, 5, 6, 7, 8, 9, 10, 11, 12, 13, 14, 15, 16, 17, 18, 19, 20, 21, 22, 23, 24, 25, 26, 27, 28, 29, 30 or more carbon atoms, typically from 2 to 20 carbon atoms or from 2 to 8 carbon atoms.

"Aryl" means an aromatic ring or fused ring system with no ring heteroatoms, e.g., phenyl or naphthyl.

"Alkylaryl" means a moiety where an alkyl group is bonded to an aryl group, i.e., -alkyl-aryl, where alkyl and aryl groups are as described above, e.g., —CH$_2$—C$_6$H$_5$ or —CH$_2$CH(CH$_3$)—C$_6$H$_5$.

"Arylalkyl" means a moiety where an aryl group is bonded to an alkyl group, i.e., -aryl-alkyl, where aryl and alkyl groups are as described above, e.g., —C$_6$H$_4$—CH$_3$ or —C$_6$H$_4$—CH$_2$CH(CH$_3$).

"Substituted alkyl", "substituted alkenyl", "substituted alkynyl", substituted alkylaryl", "substituted arylalkyl", "substituted heterocycle", "substituted aryl", "substituted monosaccharide" and the like mean an alkyl, alkenyl, alkynyl, alkylaryl, arylalkyl heterocycle, aryl, monosaccharide or other group or moiety as defined or disclosed herein that has a substituent(s) that replaces a hydrogen atom(s) or a substituent(s) that interrupts a carbon atom chain. Substituted heterocycles may thus have a substituent bonded to a ring carbon or a ring heteroatom such as nitrogen. Substituents for any of these moieties include 1, 2, 3, 4, 5, 6, 7, 8, 9, or 10 or more independently selected —O—, —S—, —NH—, —C(O)—, —C(O)OH, —C(O)OR$^{15A}$, —C(O)OR$^{PR}$, —C(O)SR$^{15A}$, —C(O)SR$^{PR}$, —CHO, —CHS, —CH$_2$SH, —C=N—, —OH, =O, —OR$^{15A}$, —OR$^{PR}$, —C(O)OR$^{PR}$, —O—C(O)H, —C(O)CH$_3$, —C(S)CH$_3$, —C(S)SH, —C(S)SR$^{15A}$, —C(S)SR$^{PR}$, —C(O)CH$_2$OH, —C(O)CH$_2$F, —C(O)CH$_2$Cl, —C(O)CH$_2$Br, —C(O)CH$_2$I, —C(O)CF$_2$H, —C(O)CF$_3$, —C(O)NHCH$_3$, —C(O)NHC$_2$H$_5$, —C(O)NHC(CH$_3$)$_3$, —O—CH$_2$—C(O)—C(CH$_3$)$_3$, —C(O)—C(CH$_3$)$_3$, —O—CH(CH$_3$)—O—C(CH$_3$)$_3$, —C(O)O—, —C(S)OR$^{PR}$, —C(S)O—, —OC(O)—, —C(O)H, —OCH$_2$—, —CH$_2$—O—CH$_2$—, —(CH$_2$)$_{1-2}$—O—(CH$_2$)$_2$, —OCH$_2$CH$_2$—, —OCH$_2$O—, —OCH$_2$CH$_2$O—, —CH$_2$OH, —CH$_2$F, —CHF$_2$, —CF$_3$, —CH$_2$Cl, —CH$_2$Br, —CH$_2$I, —C$_2$H$_4$Cl, —C$_2$H$_4$Br, —C$_2$H$_4$I, —CH$_2$CH$_2$F, —CH$_2$CHF$_2$, —CH$_2$CF$_3$, —NH$_2$, —NHR$^{15A}$, —N(R$^{15A}$)$_2$, —N(R$^{PR}$)$_2$, —NHR$^{PR}$, —NHC(O)—, —CH$_2$—NR$^{PR}$, —CH$_2$—NHR$^{PR}$, —CH$_2$—NHC(O)—, —C(O)NH—, —C(O)NHR$^{PR}$, —OC(O)NR$^{PR}$—, —OC(O)NHR$^{PR}$, —C(=NH)—NH$_2$, —C(=NH)OH, —C(=N—NH$_2$)OH, —C(O)NHOH, =NOH, =NOCH$_3$, =NOC$_2$H$_5$, =NOC$_3$H$_7$, =NOC$_4$H$_9$, —NHR$^{15A}$, =NR$^{15A}$, =N—, —NR$^{PR}$C(O)NR$^{PR}$—, —NR$^{PR}$C(O)NHR$^{PR}$, —NR$^{PR}$CH$_2$—, —NR$^{PR}$CH$_2$CH$_2$—, —NO$_2$, —ONO$_2$, —S—, —SH, —SR$^{15A}$, —SR$^{PR}$, =S, —S(O)R$^{15A}$, —S(O)OR$^{15A}$, —S(O)—, —S(O)(O)—, —O—S(O)(O)—NR$^{PR}$—, —O—S(O)(O)—NR$^{PR}$—CH$_2$—, —CH$_2$—O—S(O)(O)—NR$^{PR}$—, —CHR$^{15A}$—S(O)(O)—NR$^{PR}$—, —CHR$^{15A}$—S(O)(O)—NR$^{PR}$—CHR$^{15A}$—, —NH—S(O)(O)H, —CH$_2$—NH—S(O)(O)H, —CHR$^{15A}$—NH—S(O)(O)H, —O—S(O)(O)—CHR$^{15A}$—, —CHR$^{15A}$—O—S(O)(O)—, —CHR$^{15A}$—O—S(O)(O)—CHR$^{15A}$—, —S(O)(O)H, —CHR$^{15A}$—S(O)(O)H, —NH—S(O)(O)—NH—, —CHR$^{15A}$—NH—S(O)(O)—NH—, —CHR$^{15A}$—NH—S(O)(O)—NH—CHR$^{15A}$—, —NH—S(O)(O)—NHR$^{PR}$, —NH—S(O)(O)—NH$_2$, —NH—S(O)(O)—NHCH$_3$, —NH—S(O)—NH—, —CHR$^{15A}$—NH—S(O)—NH—, —CHR$^{15A}$—NH—S(O)—NH—CHR$^{15A}$—NH—S(O)—NHR$^{PR}$, —NH—S(O)—NH$_2$, —NH—S(O)—NHCH$_3$, —NH—S(O)—, —CHR$^{15A}$—NH—S(O)—, —NH—S(O)—CHR$^{15A}$, —S(O)—NHR$^{PR}$, —S(O)—NH$_2$, —S(O)—NHCH$_3$, —S(O)(O)—O—, —S(O)OR$^{PR}$, —S(O)(O)OH, —OSO$_3$H$_2$, —S(O)(O)OR$^{15A}$, —S(O)(O)OR$^{PR}$, —S(O)OH, —S(O)OR$^{15A}$, —S(O)OR$^{PR}$, —S(O)R$^{15A}$, —S(O)R$^{PR}$, —CN, —SCN, —C(O)OH, —C(O)OR$^{15A}$, —C(O)OR$^{PR}$, —C(O)SH, —C(O)SR$^{15A}$, —C(O)SR$^{PR}$, —C(S)OH, —C(S)OR$^{15A}$, —C(S)OR$^{PR}$, —O—P(O)(O)OH, —O—P(O)(O)OR$^{15A}$, —O—P(O)(O)OR$^{PR}$, —O—P(S)(O)OH, —O—P(S)(O)OR$^{15A}$, —O—P(S)(O)OR$^{PR}$, —O—P(O)(O)SH, —O—P(O)(O)SR$^{15A}$, —O—P(O)(O)SR$^{PR}$, —F, —Cl, —Br, —I, —C=NH, —C=NCH$_3$, —C=NC$_2$H$_5$, —C(=S)—, —C$_6$H$_5$, —CH$_2$C$_6$H$_5$, —O-A8, —S-A8, —C(O)-A8, —OC(O)-A8, —C(O)O-A8, —OPO$_3$(R$^{PR}$)$_2$, -amino acid-, —O-monosaccharide, —O-disaccharide, —S-monosaccharide, —S-disaccharide, a polymer, e.g., a PEG, and combinations of these moieties and salts on any of these moieties that can form a salt, where each R$^{PR}$ independently is —H, an independently selected protecting group or both R$^{PR}$ together are a protecting group, A8 is C1-C10 optionally substituted alkyl, and R$^{15A}$ independently are —H, —CH$_3$, —C$_2$H$_5$, —C$_3$H$_7$, —C$_4$H$_9$, —C(CH$_3$)$_3$, —CH$_2$OH, —C$_2$H$_4$OH, —C$_3$H$_6$OH, —C$_4$H$_8$OH—C(CH$_2$OH)(CH$_3$)$_2$, —C$_3$H$_5$, —C$_4$H$_7$, optionally substituted C1-10 alkyl, C1-10 perfluoroalkyl, optionally substituted aryl, optionally substituted C1-12 alkylaryl, optionally substituted C1-12 arylalkyl, optionally substituted allyl, optionally substituted heterocycle, optionally substituted C1-4 alkyl-optionally substituted heterocycle or optionally substituted heterocycle-optionally substituted C1-4 alkyl. Substituents are independently chosen when more than one is present. Alkenyl and alkynyl groups that comprise a substituent(s), are optionally substituted at a carbon that is one or more methylene moiety removed from the double bond, e.g., the substituent is optionally separated by one, two, three or more independently selected —CH$_2$—, —CH(C$_{1-6}$ optionally substituted alkyl)-, —CH(C$_{1-6}$ optionally substituted alkenyl)-, —CH(C$_{1-6}$ optionally substituted alkynyl)-, —CH(optionally substituted heterocycle)-, —CH(optionally substituted aryl-optionally substituted alkyl)- or —CH(optionally substituted alkyl-optionally substituted aryl)-moieties. Other substituted alkenyl and alkynyl moieties include =CHOH, =CH-halogen, =CH—COOR$^{PR}$, =CH—(CH$_2$)$_m$—NH$_2$, =CH—(CH$_2$)$_m$—NH(C1-C6 alkyl), =CH—N(C1-C6 alkyl)$_2$, =CH—CH$_2$OH, =CH—CH$_2$-halogen, =CH—CH$_2$—COOR$^{PR}$, =CH—CH$_2$—NH$_2$, =CH—CH$_2$—NH (C1-C6 alkyl), =CH—CH$_2$—N(C1-C6 alkyl)$_2$, =CH—CH$_2$—CH$_2$OH, =CH—CH$_2$—CH$_2$-halogen, =CH—CHOH—CH$_3$, =CH—CHOH—CH$_2$—CH$_3$, =CH—CH$_2$—CH$_2$—COOR$^{PR}$, =CH—CH$_2$—CH$_2$—NH$_2$, =CH—CH$_2$—CH$_2$—N(C1-C4 alkyl)$_2$, —CH=CH—(CH$_2$)$_m$—OH, —CH=CH-halogen, —CH=CH—CH$_2$OH, —CH=CH—CH$_2$-halogen, —C≡C-halogen, —C≡C—CH$_2$—NH$_2$, —C≡C—CH$_2$—NH(C1-C6 alkyl), —C≡C—CH$_2$—N(C1-C6 alkyl)$_2$, —C≡C—OH, —C≡C—CO—OR$^{PR}$, —C≡C—CH$_2$-halogen, —C≡C—CH$_2$—OH and —C≡C—CH$_2$—COOR$^{PR}$, where each alkyl moiety is the same or different, e.g., both are methyl, ethyl or propyl or one is methyl and the other is ethyl, propyl or butyl and m is 1, 2, 3 or 4. The organic moieties and substitutions described here, and for other any other moieties described herein, usually will exclude obviously unstable moieties, e.g., —O—O—, except where such unstable moieties are transient species that one can use to make a compound such as a F1C with sufficient chemical stability for the one or more of the uses described herein.

"Optionally substituted alkyl", "optionally substituted alkenyl", "optionally substituted alkynyl", substituted alkylaryl", "optionally substituted arylalkyl", "optionally substituted heterocycle", "optionally substituted aryl", "optionally substituted monosaccharide" and the like mean an alkyl, alkenyl, alkynyl, alkylaryl, arylalkyl heterocycle, aryl, monosaccharide or other group or moiety as defined or disclosed herein that has a substituent(s) that optionally replaces a hydrogen atom(s) or a substituent(s) that interrupts a carbon atom chain. Such substituents are as described above.

For any group or moiety described by a given range of carbon atoms, the designated range means that any individual number of carbon atoms is described. Thus, reference to, e.g., "C1-C4 optionally substituted alkyl", "C$_{2-6}$ alkenyl", "C3-C8 optionally substituted heterocycle", or "optionally substituted alkenyl", specifically means that a 1, 2, 3 or 4 carbon optionally substituted alkyl moiety as defined herein is present, or a 2, 3, 4, 5 or 6 carbon alkenyl, or a 3, 4, 5, 6, 7 or 8 carbon moiety comprising a heterocycle or optionally substituted alkenyl moiety as defined herein is present. All such designations are expressly intended to disclose all of the individual carbon atom groups and thus "C1-C4 optionally substituted alkyl" includes, e.g., 3 carbon alkyl, 4 carbon substituted alkyl and 4 carbon alkyl, including all positional isomers and the like are disclosed and can be expressly referred to or named.

The term "O-linked moiety" means a moiety that is bonded through an oxygen atom. Thus, when an R$^1$ group, is an O-linked moiety, that R$^1$ is bonded to the steroid at the 3-position through oxygen and it can thus be =O, —O—S(O)(O)—OR$^{PR}$, ether, ester (e.g., —O—C(O)-optionally substituted alkyl), carbonate or a carbamate (e.g., —O—C(O)—NH$_2$ or —O—C(O)—NH-optionally substituted alkyl). Similarly, the term "S-linked moiety" means a moiety that is bonded through a sulfur atom. Thus, when an R$^4$ group is an S-linked moiety, that R$^4$ is bonded to the steroid at the 17-position through sulfur and it can thus be =S, thioether (e.g., —S-optionally substituted alkyl), thioester (—S—C(O)-optionally substituted alkyl) or a disulfide (e.g., —S—S-optionally substituted alkyl). The term "N-linked moiety" means a moiety that is bonded through a nitrogen atom. Thus, when one or more of R$^2$, R$^3$ or R$^4$ group is an N-linked moiety, those R$^2$, R$^3$ or R$^4$ are bonded to the steroid at the 7-, 16- or 17-position respectively through nitrogen and one or more of these can thus be =NOH, =NOCH$_3$, =N—CH$_3$, an N-linked amino acid such as —NH—CH$_2$—COOH, a carbamate such as —NH—C(O)—O-optionally substituted alkyl, an amine such as —NH-optionally substituted alkyl, an amide such as —NH—C(O)-optionally substituted alkyl or —N$_3$. The term "C-linked moiety" means a moiety that is bonded through a carbon atom. Thus, when one or more of R$^2$, R$^3$ or R$^4$ group is a C-linked moiety, those R$^2$, R$^3$ or R$^4$ are bonded to the steroid at the 7-, 16- or 17-position respectively through carbon and one or more of these can thus be -optionally substituted alkyl such as —CH$_2$—CH$_2$—O—CH$_3$, —C(O)-optionally substituted alkyl hydroxyalkyl, mercaptoalkyl, aminoalkyl or =CH-optionally substituted alkyl.

"Heterocycle" or "heterocyclic" includes by way of example and not limitation the heterocycles described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and *J. Am. Chem. Soc.* 1960, 82:5566. Heterocycles are typically bonded to the steroid nucleus through a carbon, nitrogen or sulfur atom in the heterocycle ring.

The term C-linked heterocycle means a heterocycle that is bonded to the steroid ring nucleus through a carbon atom, e.g. steroid-(CH$_2$)$_n$-heterocycle where n is 1, 2 or 3 or steroid-C<heterocycle where C< represents a carbon atom in a heterocycle ring. Similarly, R$^{10}$ moieties that are N-linked heterocycles mean a heterocycle that is bonded to the steroid ring nucleus through a heterocycle ring nitrogen atom, e.g. steroid-N<heterocycle where N< represents a nitrogen atom in a heterocycle ring. A variable group such as R$^1$, R$^3$, R$^4$, R$^6$, R$^{10H}$ or other R$^{10}$ moieties, e.g., at R$^8$ or R$^9$, that is bonded to a formula 1 compound can be a C-linked heterocycle or a N-linked heterocycle, These heterocycles include those listed below or described elsewhere herein.

Examples of heterocycles include by way of example and not limitation pyridyl, thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathiinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, and isatinoyl.

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at the nitrogen atom or position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Typically, nitrogen bonded heterocycles include 1-aziridyl, 1-azetedyl, 1-pyrrolyl, 1-imidazolyl, 1-pyrazolyl, and 1-piperidinyl and structures such as

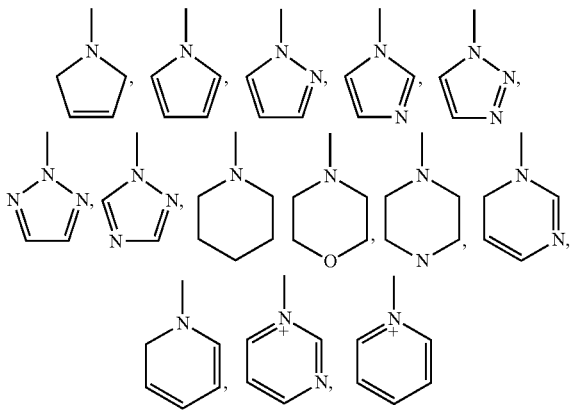

and tautomers of any of these.

"Heteroaryl" means an aromatic ring or two or more fused rings that contain one or more aromatic rings where the ring or fused rings comprise 1, 2, 3 or more heteroatoms, usually oxygen (—O—), nitrogen (—NX—) or sulfur (—S—) where X is —H, a protecting group or $C_{1-6}$ optionally substituted alkyl. Examples are as described for heterocycle.

"Alcohol" as used herein means an alcohol that comprises a $C_{1-12}$ alkyl moiety substituted at a hydrogen atom with one hydroxyl group. Alcohols include methanol, ethanol, n-propanol, i-propanol, n-butanol, i-butanol, s-butanol, t-butanol, n-pentanol, i-pentanol, n-hexanol, cyclohexanol, n-heptanol, n-octanol, n-nonanol and n-decanol. The carbon atoms in alcohols can be straight, branched or cyclic. Alcohol includes any subset of the foregoing, e.g., $C_{1-4}$ alcohols (alcohols having 1, 2, 3 or 4 carbon atoms).

"Halogen" or "halo" means fluorine, chlorine, bromine or iodine.

"Protecting group" means a moiety that prevents or reduces the atom or functional group to which it is linked from participating in unwanted reactions. For example, for —$OR^{PR}$, $R^{PR}$ may be hydrogen or a protecting group for the oxygen atom found in a hydroxyl, while for —C(O)—$OR^{PR}$, $R^{PR}$ may be hydrogen or a carboxyl protecting group, for —$SR^{PR}$, $R^{PR}$ may be hydrogen or a protecting group for sulfur in thiols for instance, and for —$NHR^{PR}$ or —$N(R^{PR})_2$—, $R^{PR}$ may be hydrogen or a nitrogen atom protecting group for primary or secondary amines. Hydroxyl, amine, ketones and other reactive groups are found in F1Cs at, e.g., $R^1$ or $R^2$. These groups may require protection against reactions taking place elsewhere in the molecule. The protecting groups for oxygen, sulfur or nitrogen atoms are usually used to prevent unwanted reactions with electrophilic compounds, such as acylating agents used, e.g., in steroid chemistry.

"Ester" means a moiety that contains a —C(O)—O— structure. Typically, esters as used here comprise an organic moiety containing about 1-50 carbon atoms (e.g., about 2-20 carbon atoms) and 0 to about 10 independently selected heteroatoms (e.g., O, S, N, P, Si), where the organic moiety is bonded to a formula 1 steroid nucleus at, e.g., $R^1$ or $R^2$ through the —C(O)—O— structure, e.g., organic moiety-C(O)—O-steroid organic moiety-O—C(O)-steroid. The organic moiety usually comprises one or more of any of the organic groups described herein, e.g., $C_{1-20}$ alkyl moieties, $C_{2-20}$ alkenyl moieties, $C_{2-20}$ alkynyl moieties, aryl moieties, $C_{2-9}$ heterocycles or substituted derivatives of any of these, e.g., comprising 1, 2, 3, 4 or more substituents, where each substituent is independently chosen. Exemplary substitutions for hydrogen or carbon atoms in these organic groups are as described above for substituted alkyl and other substituted moieties. Substitutions are independently chosen. The organic moiety includes compounds defined by the $R_4$ variable. The organic moieties exclude obviously unstable moieties, e.g., —O—O—, except where such unstable moieties are transient species that one can use to make a compound with sufficient chemical stability for one or more of the uses described herein, including for synthesis of the formula 1 or other compounds. The substitutions listed above are typically substituents that one can use to replace one or more carbon atoms, e.g., —O— or —C(O)—, or one or more hydrogen atom, e.g., halogen, —$NH_2$ or —OH. Exemplary esters include one or more independently selected acetate, enanthate, propionate, isopropionate, isobutyrate, butyrate, valerate, caproate, isocaproate, hexanoate, heptanoate, octanoate, nonanoate, decanoate, undecanoate, phenylacetate or benzoate, which are typically hydroxyl esters.

"Thioester" means a moiety that comprises a —C(O)—S— structure. Typically, thioesters as used here comprise an organic moiety containing about 1-50 carbon atoms (e.g., about 1-20 carbon atoms) and 0 to about 10 independently selected heteroatoms (e.g., O, S, N, P, Si), where the organic moiety is bonded to a formula 1 steroid nucleus at a variable group such as $R^1$, $R^2$, $R^3$, $R^4$ or $R^{10}$ through the —C(O)—S— structure, e.g., organic moiety-C(O)—S-steroid organic moiety-S—C(O)-steroid. The organic moiety is as described above for esters.

"Thionoester" means a moiety that comprises a —C(S)—O— structure. Typically, thionoesters as used here comprise an organic moiety containing about 1-50 carbon atoms (e.g., about 1-20 carbon atoms) and 0 to about 10 independently selected heteroatoms (e.g., O, S, N, P, Si), where the organic moiety is bonded to a formula 1 steroid nucleus at a variable group such as $R^1$, $R^2$, $R^3$, $R^4$ or $R^{10}$ through the —C(S)—O— structure, e.g., organic moiety-C(S)—O-steroid organic moiety-O—C(S)-steroid. The organic moiety is as described above for esters.

"Acetal", "thioacetal", "ketal", "thioketal" "spiro ring" and the like mean a cyclic organic moiety that is bonded to a steroid ring atom in the F1Cs, e.g., steroid nucleus atoms at one, two or more of the 1, 2, 3, 4, 6, 7, 11, 12, 15, 16, 17, 18 or 19 positions. Typically, acetals comprise an organic moiety containing about 1-20 carbon atoms (e.g., about 1-10 carbon atoms) and 0 to about 10 independently selected heteroatoms (e.g., O, S, N, P, Si). For acetals (or ketals), the steroid nucleus atoms are usually carbons and the acetal is bonded to a steroid carbon through two oxygen atoms. Thioacetals (or thioketals) are bonded to the steroid nucleus through one oxygen and one sulfur atom or, more often, through two sulfur atoms. One, two or more of e.g., $R^1$, $R^2$, $R^3$, $R^4$, $R^{10}$ at the 2, 11 or 15 positions, $R^{10A}$, $R^{10B}$, $R^{10C}$ and $R^{10D}$, may be an independently selected acetal, thioacetal or spiro ring in any of the F1Cs disclosed herein. The oxygen or sulfur atoms in ketals and thioketals are linked by an optionally substituted alkyl moiety. Typically the alkyl moiety is an optionally substituted C1-C6 alkylene or branched alkyl structure such as —C(CH$_3$)$_2$—, —CH(CH$_3$)—, —CH$_2$—, —CH$_2$—CH$_2$—, —C[(C2-C4 alkyl)$_2$]$_{1,2,3}$- or —[CH(C2-C4 alkyl)]$_{1,2,3}$-. Acetals include moieties having the structure —O—[C(R$^{36}$)$_2$]$_{1-6}$—O—, —O—CH$_2$—[C(R$^{36}$)$_2$]$_2$—O—, —O—CH$_2$—CH$_2$—[C(R$^{36}$)$_2$]$_2$—O—, —O—CH$_2$—[C(R$^{36}$)$_2$]$_2$—CH$_2$—O—, and —O—CH$_2$—C(R$^{36}$)$_2$—O—, where each $R^{36}$ independently is —H, —OH, =O, =S, —SH, —F, —Cl, —Br, —I or an organic moiety such as C1-C6 alkyl (e.g., methyl, ethyl, hydroxymethyl or halomethyl), C2-C6 alkenyl, C2-C6 alkenyl, aryl or an heterocycle, any of which are optionally substituted, e.g., —CF$_3$ or —CH$_2$OH. In some of these embodiments, one $R^{36}$ is —H and the other is another atom or moiety, e.g., —OH, methyl or a halogen. In other embodiments, neither $R^{36}$ is —H, e.g., both are methyl. Thioacetals include moieties that comprise a —S—[C(R$^{36}$)$_2$]$_{1-6}$—O— or —S—[C(R$^{36}$)$_2$]$_{1-6}$—S— structure where the open valences are bonded to the same carbon on the steroid nucleus. Typically, thioacetals as used here comprise an organic moiety containing about 1-50 carbon atoms (e.g., about 2-20 carbon atoms) and 0 to about 10 independently selected heteroatoms (e.g., O, S, N, P, Si), where the organic moiety is bonded to a formula 1 steroid nucleus at variable groups such as $R^1$, $R^2$, $R^3$, $R^4$ or $R^{10}$ through the —S—[C(R$^{36}$)$_2$]$_m$—O— or —S—[C(R$^{36}$)$_2$]$_m$—S— structure, e.g., 17-steroid-S—[C(R$^{36}$)$_2$]$_m$—O-17-steroid, 17-steroid-S—CH$_2$—CH$_2$—O-17-steroid, 17-steroid-O—[C(R$^{36}$)$_2$]$_m$—S-17-steroid, 17-steroid-S—[C(R$^{36}$)$_2$]$_m$—S-17-steroid, 17-steroid-S—[C(R$^{36}$)$_2$]$_m$—O-17-steroid, where m is 1, 2, 3, 4, 5 or 6. The organic moiety is as described above for esters. Other exemplary acetal and thioacetals are —O—C(CH$_3$)$_2$—O—, —O—CH$_2$—CH$_2$—CH$_2$—O—, —O—CH$_2$—CH$_2$—O—, —O—CH$_2$—O—, —O—C(CH$_3$)(heterocycle)-O—, —O—CH(heterocycle)-O—, —O—C(CH$_3$)(aryl)-O—, —O—CH(aryl)—O—, —S—C(CH$_3$)$_2$—O—, —S—C(CH$_3$)$_2$—S—, —S—CH$_2$—CH$_2$—O—, —S—CH$_2$—CH$_2$—S—, —S—CH$_2$—O—, —S—CH$_2$—S—, —O—C(CH$_3$)$_2$—CH$_2$—O—, —O—C(CH$_3$)$_2$—C(CH$_3$)$_2$—O—, —S—C(CH$_3$)$_2$—CH$_2$—O— and —O—C(CH$_3$)$_2$—CH$_2$—S—. Some of these moieties can serve as protecting groups for a ketone or hydroxyl, e.g., acetals such as —O—CH$_2$—CH$_2$—CH$_2$—O— or —O—CH$_2$—CH$_2$—O— for ketones, which form a spiro ring that can be removed by chemical synthesis methods or by metabolism in cells or biological fluids. For any spiro ring disclosed herein and unless otherwise specified, the 1$^{st}$ and 2$^{nd}$ open valences can be bonded to the carbon in the steroid nucleus in the α- and β-configurations respectively or in the α- and β-configurations respectively. For example, in a spiro —NH—CH$_2$—CH$_2$—O— structure, the 1$^{st}$ open valence, i.e., at the nitrogen atom, can be, e.g., at the 17-position in the β-configuration and the 2$^{nd}$ open valence, i.e., at the oxygen, would then be in the α-configuration.

"Phosphoester", "phosphate ester" or "phosphate" means a moiety that comprises a —O—P(OR$^{PR}$)(O)—O—, —O—P(O)(OR$^{PR}$)—OR$^{PR}$ or a salt where $R^{PR}$ independently are —H, a protecting group or an organic moiety as described for esters. Phosphoesters may comprise a hydrogen atom, a protecting group or an organic moiety containing about 1-50 carbon atoms and 0 to about 10 independently selected heteroatoms (e.g., O, S, N, P, Si) linked to a formula 1 steroid nucleus at a variable group such as $R^1$, $R^2$, $R^3$, $R^4$, $R^5$, $R^6$, $R^{10}$, $R^{15}$, $R^{17}$ or $R^{18}$ through the —O—P(O)(O)—O— structure, e.g., organic moiety-O—P(O)(OH)—O-steroid, HO—P(O)(OR$^{PR}$)—O-steroid or HO—P(O)(OH)—O-steroid. The organic moiety is as described for esters or optionally substituted alkyl groups. Exemplary phosphoesters include —O—P(O)(OH)—O—CH$_3$, —O—P(O)(OCH$_3$)—O—CH$_3$, —O—P(O)(OH)—O—CH$_2$—CH$_3$, —O—P(O)(OC$_2$H$_5$)—O—CH$_2$—CH$_3$, —O—P(O)(OH)—O—CH$_2$—CH$_2$—CH$_3$, —O—P(O)(OH)—O—CH(CH$_3$)—CH$_3$, —O—P(O)(OH)—O—CH$_2$—CH$_2$—CH$_2$—CH$_3$, —O—P(O)(O(CH$_3$)$_3$)—O—C(CH$_3$)$_3$, —O—P(O)(OH)—O—C(CH$_3$)$_3$, —O—P(O)(OH)—O—(CH$_2$)$_n$—CH$_3$, —O—P(O)(O(CH$_2$)$_n$CH$_3$)—O—(CH$_2$)$_n$—CH$_3$, —O—P(O)(O-optionally substituted alkyl)-OR$^{PR}$ and —O—P(O)(O-optionally substituted alkyl)-O-optionally substituted alkyl, where optionally substituted alkyl moieties are independently chosen and n independently are 1, 2, 3, 4, 5, 6, 7, 8, 9, 10, 11, 12, 13, 14, 15 or 16.

"Phosphothioester" or "thiophosphate" means a moiety that comprises a —O—P(SR$^{PR}$)(O)—O—, —O—P(O)(SR$^{PR}$)—OH, —O—P(O)(SR$^{PR}$)—O-, —O—P(O)(SR$^{PR}$)—O-optionally substituted alkyl structure or a salt where $R^{PR}$ is —H, a protecting group or an organic moiety as described for esters. Typically, phosphothioesters as used here comprise a hydrogen atom, a protecting group or an organic moiety containing about 1-50 carbon atoms and 0 to about 10 independently selected heteroatoms (e.g., O, S, N, P, Si) linked to a formula 1 steroid nucleus at a variable group such as $R^1$, $R^2$, $R^3$, $R^4$, $R^5$, $R^6$, $R^{10}$, $R^{15}$, $R^{17}$ or $R^{18}$ through the —O—P(O)(SR$^{PR}$)—O— structure, e.g., organic moiety-O—P(O)(SH)—O-steroid. The organic moiety is as described above for esters. Exemplary phosphothioesters are as described for phosphoesters, except that sulfur replaces the appropriate oxygen atom.

"Phosphonate", "phosphonate ester" or the like mean moieties that comprise —P(O)(OR$^{PR}$)—O—, —O—P—(O)(OH)—, —P(O)(O-optionally substituted alkyl)-O— or a salt where $R^{PR}$ independently are —H, a protecting group or an organic moiety as described for esters. Phosphonates or phosphonate esters as used here may comprise a hydrogen atom, a protecting group or an organic moiety containing about 1-50 carbon atoms and 0 to about 10 independently selected heteroatoms (e.g., O, S, N, P, Si) linked to a formula 1 steroid nucleus at a variable group such as $R^1$, $R^2$, $R^3$, $R^4$, $R^5$, $R^6$, $R^{10}$, $R^{15}$, $R^{17}$ or $R^{18}$ through the —O—P(O)(O)— structure, e.g., organic moiety-P(O)(OH)—O-steroid, steroid-P(O)(OR$^{PR}$)—O-organic moiety or steroid-O—P(O)(OR$^{PR}$)—C1-C10 optionally substituted alkyl. The organic moiety and optionally substituted alkyl is as described for esters or optionally substituted alkyl groups. Exemplary phosphonate esters include —O—P(O)(OH)—CH$_3$, —O—P(O)(OR$^{PR}$)—CH$_3$, —O—P(O)(OCH$_3$)—CH$_3$, —O—P(O)(OH)—CH$_2$—CH$_3$, —O—P(O)(OC$_2$H$_5$)—CH$_2$—CH$_3$, —O—P(O)(OH)—CH$_2$—CH$_2$—CH$_3$, —O—P(O)(OH)—CH(CH$_3$)—CH$_3$, —O—P(O)(OH)—CH$_2$—CH$_2$—CH$_3$, —O—P(O)(O(CH$_3$)$_3$)—C(CH$_3$)$_3$, —O—P(O)(OH)—C(CH$_3$)$_3$, —O—P(O)(OH)—(CH$_2$)$_n$—CH$_3$, —O—P(O)(O(CH$_2$)$_n$CH$_3$)—(CH$_2$)$_n$—CH$_3$, —O—P(O)(O-optionally substituted alkyl)-(CH$_2$)$_n$—CH$_3$, —O—P(O)(OR$^{PR}$)-heterocycle, —O—P(O)(O-optionally substituted alkyl)-optionally substituted alkyl, —P(O)(OH)—OCH$_3$, —P(O)(OCH$_3$)—OCH$_3$, —P(O)(OH)—OCH$_2$—CH$_3$, —P(O)(OC$_2$H$_5$)—

$OCH_2$—$CH_3$, —P(O)(OR$^{PR}$)—O—C1-C10 optionally substituted alkyl, —O—P(O)(OR$^{PR}$)—$C_6H_5$, —P(O)(OR$^{PR}$)—O—$C_6H_5$, —O—P(O)(O$C_2H_5$)—O—C1-C10 optionally substituted alkyl, —P(O)(O—C1-C10 optionally substituted alkyl)-O—C1-C10 optionally substituted alkyl, where optionally substituted alkyl moieties are independently chosen, alkylene (—($CH_2$)$_n$—) and phenyl groups are optionally substituted with 1, 2, 3, 4 or 5 independently selected substitutions and n independently are 1, 2, 3, 4, 5, 6, 7, 8, 9, 10, 11, 12, 13, 14, 15 or 16.

"Thiophosphonate", "thiophosphonate ester" and the like mean moieties that comprise a —P(S)(OR$^{PR}$)—O—, —O—P(S)(OR$^{PR}$)— or a related structure where R$^{PR}$ is —H, a protecting group or an organic moiety as described for esters, alkyl groups or substituted alkyl groups. Typically, thiophosphonate esters as used here comprise a protecting group or an organic moiety containing about 1-50 carbon atoms and 0 to about 10 independently selected heteroatoms (e.g., O, S, N, P, Si) linked to a formula 1 steroid nucleus at a variable group such as $R^1$, $R^2$, $R^3$, $R^4$, $R^5$, $R^6$, $R^{10}$, $R^{15}$, $R^{17}$ or $R^{18}$ through the —P(S)(OR$^{PR}$)—O— structure, e.g., organic moiety-P(S)(OR$^{PR}$)—O-steroid or steroid-P(S)(OR$^{PR}$)(O)-organic moiety. Exemplary thiophosphonates and thiophosphonate esters include —O—P(S)(OH)—$CH_3$, —O—P(S)(OR$^{PR}$)—$CH_3$, —O—P(S)(O$CH_3$)—$CH_3$, —O—P(S)(OH)—$CH_2$—$CH_3$, —O—P(S)(O$C_2H_5$)—$CH_2$—$CH_3$, —O—P(S)(OH)—$CH_2$—$CH_2$—$CH_3$, —O—P(S)(OH)—CH($CH_3$)—$CH_3$, —O—P(S)(OH)—$CH_2$—$CH_2$—$CH_2$—$CH_3$, —O—P(S)(O($CH_3$)$_3$)—C($CH_3$)$_3$, —O—P(S)(OH)—C($CH_3$)$_3$, —O—P(S)(OH)—($CH_2$)$_n$—$CH_3$, —O—P(S)(O($CH_2$)$_n$$CH_3$)—($CH_2$)$_n$—$CH_3$, —O—P(S)(O-optionally substituted alkyl)-($CH_2$)$_n$—$CH_3$, —O—P(S)(OR$^{PR}$)-heterocycle, —O—P(S)(O-optionally substituted alkyl)-optionally substituted alkyl, —P(S)(OH)—O$CH_3$, —P(S)(O$CH_3$)—O$CH_3$, —P(S)(OH)—O$CH_2$—$CH_3$, —P(S)(O$C_2H_5$)—O$CH_2$—$CH_3$, —P(S)(OR$^{PR}$)—O—C1-C10 optionally substituted alkyl, —O—P(S)(OR$^{PR}$)—$C_6H_5$, —P(S)(OR$^{PR}$)—O—$C_6H_5$, —O—P(S)(O$C_2H_5$)—O—C1-C10 optionally substituted alkyl, —P(S)(O—C1-C10 optionally substituted alkyl)-O—C1-C10 optionally substituted alkyl, where optionally substituted alkyl moieties are independently chosen, alkylene and phenyl groups are optionally substituted with 1, 2, 3, 4 or 5 independently selected substitutions and n independently are 1, 2, 3, 4, 5, 6, 7, 8, 9, 10, 11, 12, 13, 14, 15 or 16.

"Phosphiniester" means a moiety that comprises a —P(O)H— structure where R$^{PR}$ is —H, a protecting group or an organic moiety as described for esters. Typically, phosphiniesters as used here comprise a hydrogen atom, a protecting group or an organic moiety containing about 1-50 carbon atoms and 0 to about 10 independently selected heteroatoms (e.g., O, S, N, P, Si) linked to a formula 1 steroid nucleus at a variable group such as $R^1$, $R^2$, $R^3$, $R^4$, $R^5$, $R^6$, $R^{10}$, $R^{15}$, $R^{17}$ or $R^{18}$ through the —P(O)H— structure, i.e., organic moiety-P(O)H-steroid or steroid-P(O)H-organic moiety. The organic moiety is as described herein for any ester, alkyl or optionally substituted alkyl group.

"Sulfate ester" and sulfate means a moiety that comprises a —O—S(O)(O)—O— or —O—S(O)(O)—OH structure. Typically, sulfate esters as used here comprise a hydrogen atom, a protecting group or an organic moiety containing about 1-50 carbon atoms and 0 to about 10 independently selected heteroatoms (e.g., O, S, N, P, Si) linked to a formula 1 steroid nucleus at a variable group such as $R^1$, $R^2$, $R^3$, $R^4$, $R^5$, $R^6$, $R^{10}$, $R^{15}$, $R^{17}$ or $R^{18}$ through the —O—S(O)(O)—O— structure, e.g., organic moiety-O—S(O)(O)—O-steroid. The organic moiety is as described herein for any ester, alkyl or optionally substituted alkyl group.

"Sulfite ester" means a moiety that comprises a —O—S(O)—O-structure. Typically, sulfite esters as used here comprise an organic moiety containing about 1-50 carbon atoms and 0 to about 10 independently selected heteroatoms (e.g., O, S, N, P, Si) linked to a formula 1 steroid nucleus at a variable group such as $R^1$, $R^2$, $R^3$, $R^4$, $R^5$, $R^6$, $R^{10}$, $R^{15}$, $R^{17}$ or $R^{18}$ through the —O—S(O)—O-structure, e.g., organic moiety-O—S(O)—O-steroid. The organic moiety is as described herein for any ester, alkyl or optionally substituted alkyl group.

"Sulfamate ester", "sulfamate derivative", "sulfamate" and the like mean a moiety that comprises a —O—S(O)(O)—NH—, —O—S(O)(O)—$NH_2$, —O—S(O)(O)—NH-optionally substituted alkyl or —O—S(O)(O)—N-(optionally substituted alkyl)$_2$ structure or a salt of any of these, where each optionally substituted alkyl moiety is independently selected and each optionally substituted alkyl moiety optionally independently contains 1, 2, 3, 4, 5, 6, 7, 8, 9, 10, 11, 12 or more carbon atoms and 1, 2, 3, 4, 5, 6 or more independently selected substitutions. Typically, sulfamate derivatives as used here comprise an organic moiety containing about 1-50 carbon atoms and 0 to about 10 independently selected heteroatoms (e.g., O, S, N, P, Si) linked to a formula 1 steroid nucleus at a variable group such as $R^1$, $R^2$, $R^3$, $R^4$, $R^5$, $R^6$, $R^{10}$, $R^{15}$, $R^{17}$ or $R^{18}$ through a suitable structure such as —O—S(O)(O)—NH—, e.g., organic moiety-O—S(O)(O)—NH-steroid, steroid-O—S(O)(O)—NH-organic moiety, steroid-O—S(O)(O)—NH—C1-C8 alkyl, steroid-O—S(O)(O)—N(C1-C8 alkyl)$_2$, steroid-O—S(O)(O)—NHR$^{PR}$, steroid-NH—S(O)(O)—OH or steroid-O—S(O)(O)—$NH_2$, where R$^{PR}$ is —H or a protecting group and alkyl groups are independently chosen. The organic moiety, alkyl group and optionally substituted alkyl is any moiety described herein, e.g., as described herein for any ester, alkyl or optionally substituted alkyl moiety.

"Sulfamide" and the like mean a moiety that comprises a —NH—S(O)(O)—NH— or —NH—S(O)(O)—$NH_2$ structure. Typically, sulfamide moieties comprise an organic moiety containing about 1-50 carbon atoms and 0 to about 10 independently selected heteroatoms (e.g., O, S, N, P, Si) linked to a formula 1 steroid nucleus at a variable group such as $R^1$, $R^2$, $R^3$, $R^4$, $R^5$, $R^6$, $R^{10}$, $R^{15}$, $R^{17}$ or $R^{18}$ through a suitable structure such as —NH—S(O)(O)—NH—, e.g., steroid-NH—S(O)(O)—NH-organic moiety, steroid-NH—S(O)(O)—$NH_2$, steroid-NH—S(O)(O)—NHR$^{PR}$ or steroid-NH—S(O)(O)—N(R$^{PR}$)$_2$, where R$^{PR}$ independently or together are a protecting group such as C1-C8 optionally substituted alkyl. The organic moiety is as described herein for any ester, alkyl or optionally substituted alkyl group.

"Sulfinamide" and the like mean a moiety that comprises a —C—S(O)—NH-structure. Typically, sulfinamide moieties comprise an organic moiety containing about 1-50 carbon atoms and 0 to about 10 independently selected heteroatoms (e.g., O, S, N, P, Si) linked to a formula 1 steroid nucleus at a variable group such as $R^1$, $R^2$, $R^3$, $R^4$, $R^5$, $R^6$, $R^{10}$, $R^{15}$, $R^{17}$ or $R^{18}$ through a suitable structure such as steroid-S(O)—NH-organic moiety, steroid-NH—S(O)-organic moiety, steroid-S(O)—$NH_2$, steroid-S(O)—NHR$^{PR}$ moiety or steroid-S(O)—N(R$^{PR}$)$_2$, where R$^{PR}$ independently or together are a protecting group such as C1-C8 optionally substituted alkyl. The organic moiety is as described herein for any ester, alkyl or optionally substituted alkyl group.

"Sulfurous diamide" and the like mean a moiety that comprises a —NH—S(O)—NH— or —NH—S(O)—$NH_2$ structure. Typically, sulfurous diamide moieties comprise an organic moiety containing about 1-50 carbon atoms and 0 to about 10 independently selected heteroatoms (e.g., O, S, N, P, Si) linked to a formula 1 steroid nucleus at a variable group such as $R^1$, $R^2$, $R^3$, $R^4$, $R^5$, $R^6$, $R^{10}$, $R^{15}$, $R^{17}$ or $R^{18}$ through a suitable structure such as —C—NH—S(O)—NH—C— or —CH$_2$—NH—S(O)—NH—CH$_2$—, e.g., steroid-NH—S(O)—NH-organic moiety, steroid-NH—S(O)—NH$_2$, steroid-NH—S(O)—NHR$^{PR}$ or steroid-NH—S(O)—N(R$^{PR}$)$_2$, where R$^{PR}$ independently or together are a protecting group such as C1-C8 optionally substituted alkyl. The organic moiety is as described herein for any ester, alkyl or optionally substituted alkyl group.

"Sulfonate ester", "sulfonate derivative", "sulfonate" and the like mean a moiety that comprises a —O—S(O)(O)— or —S(O)(O)—OR$^{PR}$ structure where R$^{PR}$ is —H or a protecting group. Typically, sulfonate derivatives comprise an organic moiety containing about 1-50 carbon atoms and 0 to about 10 independently selected heteroatoms (e.g., O, S, N, P, Si) linked to a formula 1 steroid nucleus at a variable group such as $R^1$, $R^2$, $R^3$, $R^4$, $R^5$, $R^6$, $R^{10}$, $R^{15}$, $R^{17}$ or $R^{18}$ through a suitable structure such as —S(O)(O)—O—, e.g., organic moiety-O—S(O)(O)-steroid, HO—S(O)(O)-steroid, H—S(O)(O)—O-steroid, steroid-O—S(O)(O)—C1-C10 optionally substituted alkyl, steroid-O—S(O)(O)-heterocycle, steroid-O—S(O)(O)-aryl, steroid-S(O)(O)—O—C1-C10 optionally substituted alkyl, steroid-S(O)(O)—O-heterocycle, steroid-S(O)(O)—O-aryl, where the aryl or heterocycle moiety is optionally substituted with 1, 2, 3, 4 or 5 independently selected substitutions. The organic moiety is as described herein for any ester, alkyl or optionally substituted alkyl group.

"Amide", "amide derivative" and the like mean an organic moiety as described for ester that comprises a —C(O)—NR$^{PR}$— or —C(O)—NH— moiety, where R$^{PR}$ is —H or a protecting group. In some embodiments, the —C(O)NR$^{PR}$— group is linked to the steroid nucleus at a variable group such as $R^1$, $R^2$, $R^3$, $R^4$, $R^5$, $R^6$, $R^{10}$, $R^{15}$, $R^{17}$ or $R^{18}$, i.e., organic moiety-C(O)NR$^{PR}$-steroid, organic moiety-C(O)—NH-steroid or steroid-C(O)NR$^{PR}$-organic moiety. The organic moiety is as described above for esters.

"Ether" means an organic moiety as described for ester that comprises 1, 2, 3, 4 or more —O— moieties, usually 1 or 2. In some embodiments, the —O— group is linked to the steroid nucleus at a variable group such as $R^1$, $R^2$, $R^3$, $R^4$, $R^5$, $R^6$, $R^{10}$, $R^{15}$, $R^{17}$ or $R^{18}$, e.g., organic moiety-O-steroid. The organic moiety is as described above for esters.

"Thioether" means an organic moiety as described for ester that comprises 1, 2, 3, 4 or more —S— moieties, usually 1 or 2. In some embodiments, the —S— group is linked to the steroid nucleus at a variable group such as $R^1$, $R^2$, $R^3$, $R^4$, $R^5$, $R^6$, $R^{10}$, $R^{15}$, $R^{17}$ or $R^{18}$, e.g., organic moiety-S-steroid, organic moiety-S—CH$_2$—S-steroid organic moiety-S—S-steroid. The organic moiety is as described above for esters.

"Acyl group" or "acyl" means an organic moiety as described for ester that comprises 1, 2, 3, 4 or more —C(O)— groups. In some embodiments, the —C(O)— group is linked to the steroid nucleus at a variable group such as $R^1$, $R^2$, $R^3$, $R^4$, $R^5$, $R^6$, $R^{10}$, $R^{15}$, $R^{17}$ or $R^{18}$, e.g., organic moiety-C(O)-steroid. The organic moiety is as described above for esters. Exemplary acyl moieties include moieties such as —C(O)—N(C1-C6 alkyl)$_2$, —C(O)—NH(C1-C6 alkyl), —C(O)—NH—C(CH$_3$)$_3$, —C(O)—NH—CH(CH$_3$)$_2$, —C(O)—NH—C(CH$_3$)$_2$—CH$_3$, —C(O)—NH—CH(CH$_3$)—CH$_3$, —C(O)—NH—C(CH$_3$)—CH$_2$—CH$_3$, —C(O)NH$_2$, —C(O)NHR$^{PR}$, —C(O)—CH$_3$, —C(O)—CH$_2$—CH$_3$, —C(O)—CH$_2$—CH$_2$—CH$_3$, —C(O)—CH$_2$OH, —C(O)—CH$_2$OR$^{PR}$, —C(O)—CH$_2$—CH$_2$OH, —C(O)—CH$_2$—CH$_2$OR$^{PR}$, —C(O)—CH$_2$-halogen, —C(O)—CH$_2$—CH$_2$-halogen, —C(O)—CH$_2$—COOR$^{PR}$, —C(O)—CH$_2$—CH$_2$—CO-OR$^{PR}$, —C(O)—CH$_2$—CH$_2$—CHOH, —C(O)—CH$_2$—NH$_2$, —C(O)—CH$_2$—NHR$^{PR}$, —C(O)—CH$_2$—N(R$^{PR}$)$_2$, —C(O)—CH$_2$—NH—(C1-C6 alkyl), —C(O)—CH$_2$—N(C1-C6 alkyl)$_2$, —C(O)—NH—CH=CH$_2$, —C(O)—NH—C≡CH, —C(O)—NH—CH$_3$, —C(O)—NH—CN, —C(O)—NH—CH$_2$—CN, where each alkyl is the same or different and is optionally independently substituted and each R$^{PR}$ is —H or an independently selected protecting group for the atom or functional group to which it is attached, or two R$^{PR}$ together are a protecting group for the atom or functional group to which they are attached.

"Thioacyl" means an organic moiety as described for ester that comprises 1, 2, 3, 4 or more —C(S)— groups. In some embodiments, the —C(S)— group is linked to the steroid nucleus at a variable group such as $R^1$, $R^2$, $R^3$, $R^4$, $R^5$, $R^6$, $R^{10}$, $R^{15}$, $R^{17}$ or $R^{18}$, e.g., organic moiety-C(S)-steroid. The organic moiety is as described above for esters. Exemplary thioacyl moieties include moieties as described above for the acyl group, except that sulfur replaces the appropriate oxygen atom.

"Carbonate" means an organic moiety as described for ester that comprises 1, 2, 3, 4 or more —O—C(O)—O— structures. Typically, carbonate groups as used here comprise an organic moiety containing about 1-50 carbon atoms and 0 to about 10 independently selected heteroatoms (e.g., O, S, N, P, Si) linked to a formula 1 steroid nucleus at a variable group such as $R^1$, $R^2$, $R^3$, $R^4$, $R^5$, $R^6$, $R^{10}$, $R^{15}$, $R^{17}$ or $R^{18}$ through the —O—C(O)—O— structure, e.g., organic moiety-O—C(O)—O-steroid. The organic moiety is as described above for esters.

"Carbamate" means an organic moiety as described for ester that comprises 1, 2, 3, 4 or more —O—C(O)NR$^{PR}$— structures where R$^{PR}$ is —H, a protecting group or an organic moiety as described for ester. Typically, carbamate groups as used here comprise an organic moiety containing about 1-50 carbon atoms and 0 to about 10 independently selected heteroatoms (e.g., O, S, N, P, Si) linked to a formula 1 steroid nucleus at a variable group such as $R^1$, $R^2$, $R^3$, $R^4$, $R^5$, $R^6$, $R^{10}$, $R^{15}$, $R^{17}$ or $R^{18}$ through the —O—C(O)—NR$^{PR}$— structure, e.g., organic moiety-O—C(O)—NR$^{PR}$-steroid or steroid-O—C(O)—NR$^{PR}$-organic moiety. The organic moiety is as described above for esters.

As used herein, "monosaccharide" means a polyhydroxy aldehyde or ketone having the empirical formula $(CH_2O)_n$ where n is 3, 4, 5, 6, 7 or 8. Typically, monosaccharides as used herein will contain 3, 4, 5, 6, 7 or 8 carbon atoms and can be linked to a formula 1 steroid nucleus at a variable group such as $R^1$, $R^2$, $R^3$, $R^4$, $R^5$, $R^6$ or $R^{10}$, where the linkage with the steroid is in the α- or β-configuration. Monosaccharide includes open chain and closed chain forms, but will usually be closed chain forms. Monosaccharide includes hexofuranose and pentofuranose sugars such as 2'-deoxyribose, ribose, arabinose, xylose, their 2'-deoxy and 3'-deoxy derivatives and their 2',3'-dideoxy derivatives. Monosaccharide also includes the 2',3' dideoxydidehydro derivative of ribose. Monosaccharides include the D-, L- and DL-isomers of glucose, fructose, mannose, idose, galactose, allose, gulose, altrose, talose, fucose, erythrose, threose, lyxose, erythrulose, ribulose, xylulose, ribose, arabinose, xylose, psicose, sorbose, tagatose, glyceraldehyde, dihydroxyacetone and their monodeoxy or other derivatives such as rhamnose and glucuronic acid or a salt of glucuronic acid. Monosaccharides are optionally protected or partially protected. Exemplary monosaccharides include

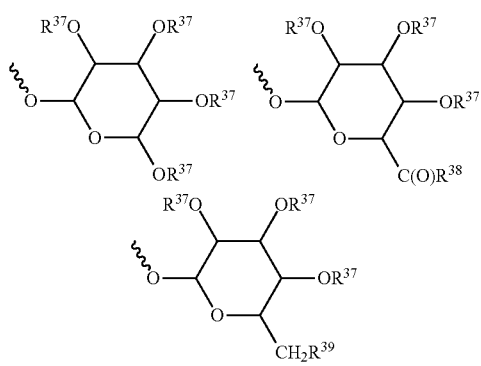

where $R^{37}$ independently is hydrogen, a protecting group, acetamido (—NH—Ac), optionally substituted alkyl such as methyl or ethyl, or an ester such as acetate or proprionate, $R^{38}$ is hydrogen, hydroxyl, —$NH_2$, —$NHR^{PR}$, optionally substituted alkyl such as methyl or ethyl, or a cation such as $NH_4^+$, $Na^+$ or $K^+$ and $R^{39}$ is hydrogen, hydroxyl, acetate, proprionate, optionally substituted alkyl such as methyl, ethyl, methoxy or ethoxy.

Optionally substituted alkyl group, optionally substituted alkenyl group, optionally substituted alkynyl group, optionally substituted aryl moiety and optionally substituted heterocycle mean an alkyl, alkenyl, alkynyl, aryl or heterocycle moiety that contains an optional substitution(s). Such moieties include $C_{1-20}$ alkyl moieties, $C_{2-20}$ alkenyl moieties, $C_{2-20}$ alkynyl moieties, aryl moieties, $C_{2-9}$ heterocycles or substituted derivatives of any of these.

Optionally substituted "monosaccharide" comprise any C3-C7 sugar, D-, L- or DL-configurations, e.g., erythrose, glycerol, ribose, deoxyribose, arabinose, glucose, mannose, galactose, fucose, mannose, glucosamine, N-acetylneuraminic acid, N-acetylglucosamine, N-acetylgalactosamine that is optionally substituted at one or more hydroxyl groups or hydrogen or carbon atoms. Suitable substitutions are as described above for substituted alkyl moieties and include independently selected hydrogen, hydroxyl, protected hydroxyl, carboxyl, azido, cyano, —O—$C_{1-6}$ alkyl, —S—$C_{1-6}$ alkyl, —O—$C_{2-6}$ alkenyl, —S—$C_{2-6}$ alkenyl, ester, e.g., acetate or proprionate, optionally protected amine, optionally protected carboxyl, halogen, thiol or protected thiol. The linkage between the monosaccharide and the steroid is α or β.

Optionally substituted "oligosaccharide" comprises two, three, four or more of any C3-C7 sugars that are covalently linked to each other. The linked sugars may have D-, L- or DL-configurations. Suitable sugars and substitutions are as described for monosaccharides. The linkage between the oligosaccharide and the steroid is α or β, as are the linkages between the monosaccharides that comprise the oligosaccharide. Adjacent monosaccharides may be linked by, e.g., 1→2, 1→3, 1→4, and/or 1→6 glycosidic bonds.

As used herein, "polymer" includes biocompatible organic polymers, e.g., polyethyleneglycols ("PEGs"), polypropyleneglycol ethers, poloxalenes, polyhydroxyalkyl polymers or poloxamers. PEG means an ethylene glycol polymer that contains about 4-50 or more linked monomers, e.g., about 50-1000 linked monomers. Average PEG molecular weights can be about 80, 100, 200, 300, 400, 500, 600, 1000, 1200, 1500, 2000, 8000, 10,000, 20,000 or 30,000 and mixtures thereof are included, e.g., PEG100 and PEG200, PEG200 and PEG300, PEG100 and PEG300, PEG100 and PEG400 or PEG200 and PEG400. PEG polymers include methyl or alkyl ethers, thiol and amine analogs and their protected derivatives, e.g., H(OCH$_2$HC$_2$)$_n$—OH, H(OCH$_2$HC$_2$)$_n$—CH$_3$, H(OCH$_2$HC$_2$)$_n$—OR$^{PR}$, H(OCH$_2$HC$_2$)$_n$—SH, H(OCH$_2$HC$_2$)$_n$—SR$^{PR}$, H(OCH$_2$HC$_2$)$_n$—NH$_2$ or H(OCH$_2$HC$_2$)$_n$—NHR$^{PR}$, where R$^{PR}$ is a protecting group and n or the average value of n is about 2, 3, 4, 5, 6, 7, 8, 9, 10, 11, 12, 13, 14, 15, 20, 25, 30, 35, 40, 45, 50, 60 or more, e.g., for PEG200, the average value of n is about 4, while for PEG 600, the average value of n is about 12.5 to 14.

Poloxamers typically have average molecular weights of one, two or more of about 1000, 2000, 4000, 5000, 6000, 8000, 10,000, 12,000, 14,000, 15,000 and/or 16,000, with structures such as HO(CH$_2$CH$_2$O)$_a$—(CH(CH$_3$)CH$_2$OH)$_b$—(CH$_2$CH$_2$O)$_c$—H, R$^{PR}$HN—(CH$_2$CH$_2$O)$_a$—(CH(CH$_3$)CH$_2$OH)$_b$—(CH$_2$CH$_2$O)$_c$—H HS(CH$_2$CH$_2$O)$_a$—(CH(CH$_3$)CH$_2$OH)$_b$—(CH$_2$CH$_2$O)$_c$—H or R$^{PR}$O—(CH$_2$CH$_2$O)$_a$—(CH(CH$_3$)CH$_2$OH)$_b$—(CH$_2$CH$_2$O)$_c$—H, where R$^{PR}$ is a protecting group and n or the average value of b is at least about 15 or 20 and a+c varies from about 20% to about 90% by weight of the molecule, e.g., a and/or c is about 5, 7, 10, 15, 20, 25, 30, 35, 40, 45, 50, 55, 60, 65, 70, 75 and/or 80. Exemplary poloxamers include pluronic L62LF where a is about 7, b is about 30 and c is about 7, pluronic F68 where a is about 75, b is about 30 and c is about 75 and pluronic L101 where a is about 7, b is about 54 and c is about 7. Exemplary poloxalenes include structures such as HO(CH$_2$CH$_2$O)$_a$—(CH(CH$_3$)CH$_2$OH)$_b$—(CH$_2$CH$_2$O)$_c$—H or R$^{PR}$O—(CH$_2$CH$_2$O)$_a$—(CH(CH$_3$)CH$_2$OH)$_b$—(CH$_2$CH$_2$O)$_c$—H, where R$^{PR}$ is a protecting group and the average value for a is about 12, b is about 34 and c is about 12 or the average molecular weight is about 3000. Polymers also include derivatives of any of these molecules where one or both terminal hydroxyl groups and/or one, two, three or more internal hydroxyl groups are derivatized, e.g., to independently selected moieties such as —C(O)—OR$^{PR}$, —C(O)—OH, —C(S)—OH, —SH, —SR$^{PR}$, —C(O)—SH, —C(O)—SR$^{PR}$, —NH$_2$, —NHR$^{PR}$, —N(R$^{PR}$)$_2$, —C(O)NH$_2$, —C(O)NHR$^{PR}$, —C(O)N(R$^{PR}$)$_2$ or a salt, where R$^{PR}$ independently or together are a protecting group or C1-C8 optionally substituted alkyl.

Position numbers that are given for the F1Cs use the numbering convention for cholesterol.

Spiro ring substituents are cyclic structures that are usually 3, 4, 5, 6, 7 or 8 membered rings, e.g., they include 3,4-, 5-, 6-, 7- or 8-sided rings. In some embodiments, spiro structures share a carbon atom that is present in the steroid ring system, e.g., at the 2, 3, 7, 11, 15, 16 or 17 positions of the F1Cs. Spiro structures include, acetals, thioacetals and lactone rings or cyclic esters. Spirolactones, spiro ring compounds and dihydroxy F1Cs containing cyclic diol groups include F1Cs having the structures

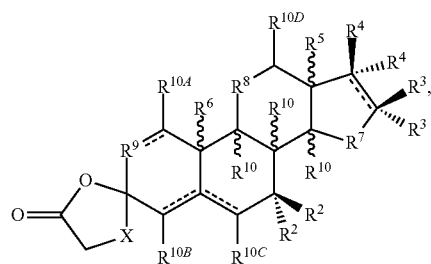

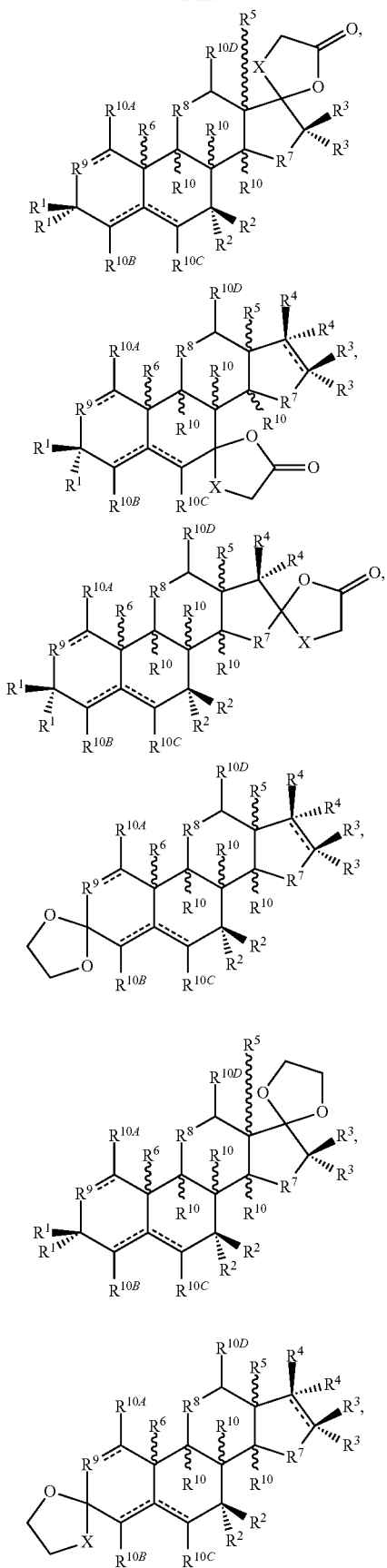
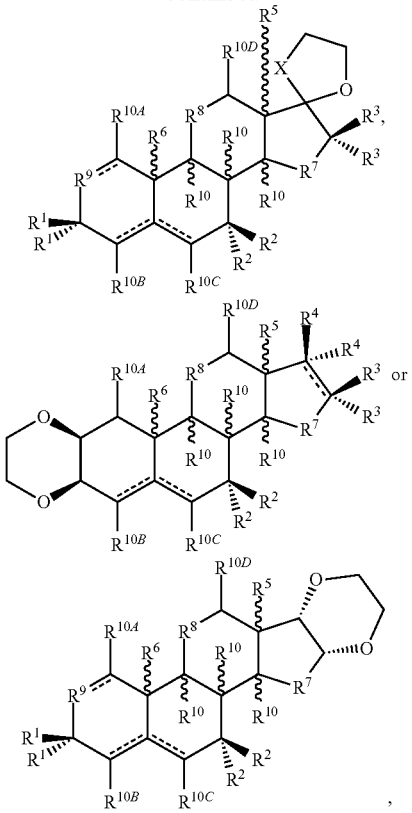

where X is —C(R$^{10}$)$_2$— or —CHR$^{10}$—, and R$^{10}$ are independently selected. In some of these embodiments, the R$^{10}$, R$^{10A}$, R$^{10B}$, R$^{10C}$ and R$^{10D}$ variable groups are independently selected R$^{10}$ moieties in the α- or β-configuration, e.g., they are independently selected from —H, —F, —Cl, —Br, —OH, —OCH$_3$, —OC$_2$H$_5$, an optionally substituted ester such as acetate or propionate, an optionally substituted alkyl such as methyl or ethyl or an amino acid.

Unless otherwise specified, any of the groups described herein, e.g., substituted or unsubstituted groups such as alkyl, alkenyl, alkynyl, =CH-optionally substituted alkyl, ester, thioester, thionoester, phosphoester, phosphothioester, phosphonate, phosphonate ester, thiophosphonate, thiophosphonate ester, phosphiniester, sulfite ester, sulfate ester, sulfamate, sulfonate, sulfonamide, amide, amino acid, peptide, ether, thioether, acyl, thioacyl, carbonate, carbamate, halogen, optionally substituted aryl, optionally substituted heteroaryl, optionally substituted heterocycle, optionally substituted monosaccharide, optionally substituted oligosaccharide, polymer, spiro ring, acetal, thioacetal, ketal, thioketal, —S—S-optionally substituted alkyl, =N—O-optionally substituted alkyl, =N-optionally substituted alkyl, —NH-optionally substituted alkyl, —NH—S(O)(O)-optionally substituted alkyl, —N(optionally substituted alkyl)$_2$ where each optionally substituted alkyl is independently selected, optionally substituted saturated or unsaturated cyclopropyl, cyclobutyl, cyclopentyl, cyclohexyl, cycloheptyl, cyclooxyl ring can contain 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or more carbon atoms. Any of these moieties including peptide, oligosaccharide, optionally substituted alkyl and polymer moieties, can contain about 50, 100, 200, 300 or more carbon atoms, e.g., about 40 or 50 carbon atoms to about 75, 100, 200 or 400 carbon atoms.

As used herein, "innate immunity" refers to one or more components typically associated with nonspecific immune defense mechanisms in a subject. These components include the alternate complement pathway, e.g., Factor B, Factor D and properdin; NK cells, phagocytes (monocytes, macrophages), neutrophils, eosinophils, dendritic cells, fibrocytes; anti-microbial chemicals, e.g., one or more of defensins; physical barriers—skin, mucosal epithelium; or certain interleukins, chemokines, cytokines, lung or alveolar macrophage respiratory burst activity or a lung surfactant protein such as surfactant protein A or surfactant protein D.

Terms such as "immune dysregulation", "immune dysregulation condition", "unwanted immune response" and the like mean that a subject has or is subject to developing an immune response that is not desirable or is suboptimal for the subject's condition. Such dysregulation or unwanted responses can arise from various clinical conditions or diseases or as a result of treatment of such conditions or diseases, e.g., inflammation, autoimmunity, organ or tissue transplant rejection (e.g., allograft, xenograft), infections, cancers, immunosuppressive chemotherapy treatments, trauma, allergy conditions or in conditions where a subject mounts a Th1, Tc1, Th2 or Tc2 immune response that is considered to be pathogenic, ineffective, insufficient or suboptimal. Immune dysregulation conditions are as described herein or in the cited references.

Terms such as "cellular response", "cellular activity", "biological response", "biological activity" and the like mean a response or activity that is detectably modulated in response to the presence of a F1C. Such responses or activities can be direct effects or indirect effects on one or more cellular activities or on the expression or level of one or more molecules that the affected cell(s) bind, sequester, synthesize or respond to. Such responses or activities include a detectable change in the synthesis or level of one or more cytokines, growth factors, transcription factors (including receptors and their cofactors), enzymes, Th1- or Th2-associated antibody subtype responses or the like. Typically, the cytokines, growth factors, transcription factors, enzymes or antibodies that are modulated are involved in the amelioration of a pathological condition or in the establishment, maintenance, severity or progression of a pathological condition.

As used herein, references to CD molecules, specific immune cell subsets, immune responses and the like, generally use nomenclature that applies to molecules, cells or the like that are found in humans. Analogs or counterparts of such molecules, cells or the like in other species may have a differing nomenclature, but are included in this invention. A description of the nomenclature and function of various CD molecules and immune cell subsets are as found in the scientific literature. References to Th0, Th1 or Th2 cells and references to Th1 or Th2 immune responses in the context of human patients refer to the human counterparts of the murine Th0, Th1 or Th2 immune cells or responses. For reviews see, e.g., A. K. Abbas et al., editors, *Cellular and Molecular Immunology*, W.B. Saunders Company, third edition, 1997, ISBN 0-7216-4024-9, pages 4-469, and I. Kimber and M. K. Selgrade, editors, *T Lymphocyte Subpopulations in Immunotoxicology*, John Wiley & Sons Ltd., 1998, ISBN 0-471-97194-4, pages 1-53.

"Immunosuppressive molecule" means molecules such as cyclosporin, cyclohexamide, mitomycin C, Adriamycin, taxol and amphotericin B. These molecules tend to have toxicities toward the immune system and are directly or indirectly immunosuppressive, e.g., they are toxic to dividing cells, they inhibit proliferation of immune cell precursors or they can downregulate an otherwise desired or improved immune response or condition.

"Nuclear hormone receptor" means a gene product, typically as a protein monomer or dimer that can bind to a ligand and affect transcription of one or more genes. Ligands include, e.g., certain natural steroids, steroid analogs, F1Cs or another ligand such as a lipid, e.g., a prostaglandin, or the like. Nuclear hormone receptors include orphan steroid receptors, which typically function as heterodimers and the classical steroid receptors, e.g., androgen receptor ("AR"), estrogen receptor α ("ERα"), estrogen receptor β ("ERβ"), that function as homodimers. Nuclear hormone receptors include species that form heterodimers, e.g., VDR-RXR or TR-RXR. Nuclear hormone receptors also include isoforms, e.g., PXR.1 and PXR.2 for the PXR receptor. The natural ligand and/or biological function for some orphan steroid receptors is at least partially unknown. Nuclear hormone receptors include the homologs of the receptors, e.g., the homolog of CARβ known as MB67. Isoforms are typically generated by different splicing pathways for a nuclear RNA from one gene, while homologs are typically a distinct copy of a nuclear hormone receptor gene, where the gene copy encodes only relatively small differences compared to the reference nuclear hormone receptor gene product. Such differences are most often found in areas other than the dimerization region and the steroid binding region of the nuclear hormone receptor's structure. Typically isoforms and homologs bind the same or similar ligands as the reference gene product or nuclear hormone receptor. Nuclear hormone receptors may be of human or animal origin, e.g., obtained from cells, tissues or cDNA expression libraries derived from cells or tissues of any primate, rodent (including murine), avian, ovine, bovine, equine, canine, feline, insect species, e.g., *Drosophila*, nematode, e.g., *Caenorhabditis elegans*, or any of the species within any group (e.g., Family or Genus) of species mentioned herein or in any reference cited herein. Modulation of nuclear hormone receptors by F1Cs can arise from (1) their direct interaction with the receptor or a cofactor thereof or (2) indirect effects such as (A) detectably increased or decreased synthesis or level of the receptor or (B) generation of a signal or stimulus that leads to detectable modulation of one or more biological activities of the receptor, e.g., detectable inhibition of receptor mediated gene transcription or detectable enhancement of receptor mediated gene transcription.

An "agonist" or an "antagonist" is a compound or composition, usually containing a F1C, that respectively, either detectably increases or decreases the activity of a receptor, an enzyme or another biological molecule, which can lead to increased or decreased transcription or mRNA levels of a regulated gene or to another measurable effect such as altered level of activity of the gene product or protein. The increase or decrease in a receptors or enzyme's activity will be an increase or a decrease of at least about 5%, 10%, 20%, 30%, 40%, 50%, 60%, 70%, 80%, 90%, 95% or a range about between any two of these values, for one or more measurable activities. Receptors, their accessory factors and associated transcription factors can modulate transcription of their target gene(s) by detectably increasing or decreasing transcription or mRNA levels. Biological activities of receptors may also include modulating biological responses such as signal transduction within a cell or ion flux, e.g., sodium, potassium or calcium, across cell organelle membranes, e.g., across mitochondria.

Terms such as "biologically active metabolite" and the like mean derivatives of the F1Cs that retain a detectable level, e.g., at least about 10%, at least about 20%, at least about 30% or at least about 50%, of at least one desired activity of the parent compound, e.g., antiinflammatory activity or stimulation of a desired immune response. Determination of a desired activity is accomplished essentially as described herein. Such metabolites can be generated in the gastrointestinal tract, in blood or in one or more subject tissues. Such metabolites are detected using standard analytical methods, e.g., GC-MS analysis of an optionally radiolabeled F1C and its metabolites, in blood, urine or other biological samples after it is administered to a subject by one or more routes as disclosed herein. Terms such as "metabolic precursor" of F1Cs and the like can include compounds that generate a detectable level of the F1C or a detectable level, e.g., at least about 10%, at least about 20%, at least about 30% or at least about 50%, of at least one desired activity of the F1C. Determination of a desired activity is accomplished essentially as described herein. Conversion of metabolic precursors can occur in the gastrointestinal tract, in blood or in one or more subject tissues.

"Amino acid" means an amino acid moiety that comprises any naturally-occurring or synthetic amino acid residue, i.e., any moiety comprising at least one carboxyl and at least one amino residue directly linked by one, two three or more carbon atoms, typically one ($\alpha$) carbon atom. The nature and identity of the intervening structure located between the carboxyl and amino groups can have a variety of structures including those described herein. Typically, amino acids linked to the steroid through the amine group ("N-linked amino acid") have sufficient conformation and length to be capable of autocatalytic hydrolysis of the amino acid-steroid bond and release of the steroid. This can occur when the free carboxyl is generated in vivo by deesterification, deamidation or peptidolytic cleavage of the precursor containing a linkage between the amino acid's amine group and the steroid. Hydrolysis of the bond between an amino acid's carboxyl or amino group and the steroid can also occur by chemical or enzymatic activity, e.g., esterase cleavage or non-enzymatic hydrolysis.

Peptide means 2, 3 or more of the two or more amino acids as defined above are bonded together, usually by an amide bond or normal peptide bond. Variable groups in the F1Cs such as $R^1$-$R^{10}$ can comprise a peptide. Typically the amino acids are linked through normal peptide bonds, e.g., —CO—NH—, between adjacent amino acid residues. Peptides comprise dipeptides (dimers), tripeptides (trimers), short peptides of 4, 5, 6, 8, 10 or 15 residues, and longer peptides or proteins having about 100 or more residues. F1Cs that comprise a peptide can be used as immunogens, prodrugs or as synthetic precursors for other steroid derivatives.

Examples of suitable dipeptidyl groups (designated by their single letter symbols) are shown in the table below. The single letter designations are: Y tyrosine, G glycine, F phenylalanine, M methionine, A alanine, S serine, I isoleucine, L leucine, T threonine, V valine, P praline, L lysine, H histidine, Q glutamine, E glutamic acid, W tryptophan, R arginine, D aspartic acid, N asparagine and C cysteine.

| Dipeptides |
|---|
| AA, AR, AN, AD, AC, AE, AQ, AG, AH, AI, AL, AK, AM, AF, AP, AS, AT, AW, AY, AV, RA, RR, RN, RD, RC, RE, RQ, RG, RH, RI, RL, RK, RM, RF, RP, RS, RT, RW, RY, RV, NA, NR, NN, ND, NC, NE, NQ, NG, NH, NI, NL, NK, NM, NF, NP, NS, NT, NW, NY, NV, DA, DR, DN, DD, DC, DE, DQ, DG, DH, DI, DL, DK, DM, DF, DP, DS, DT, DW, DY, DV, CA, CR, CN, CD, CC, CE, CQ, CG, CH, CI, CL, CK, CM, CF, CP, CS, CT, CW, CY, CV, EA, ER, EN, ED, EC, EE, EQ, EG, EH, EI, EL, EK, EM, EF, EP, ES, ET, EW, EY, EV, QA, QR, QN, QD, QC, QE, QQ, QG, QH, QI, QL, QK, QM, QF, QP, QS, QT, QW, QY, QV, GA, GR, GN, GD, GC, GE, GQ, GG, GH, GI, GL, GK, GM, GF, GP, GS, GT, GW, GY, GV, HA, HR, HN, HD, HC, HE, HQ, HG, HH, HI, HL, HK, HM, HF, HP, HS, HT, HW, HY, HV, IA, IR, IN, ID, IC, IE, IQ, IG, IH, II, IL, IK, IM, IF, IP, IS, IT, IW, IY, IV, LA, LR, LN, LD, LC, LE, LQ, LG, LH, LI, LL, LK, LM, LF, LP, LS, LT, LW, LY, LV, KA, KR, KN, KD, KC, KE, KQ, KG, KH, KI, KL, KK, KM, KF, KP, KS, KT, KW, KY, KV, MA, MR, MN, MD, MC, ME, MQ, MG, MH, MI, ML, MK, MM, MF, MP, MS, MT, MW, MY, MV, FA, FR, FN, FD, FC, FE, FQ, FG, FH, FI, FL, FK, FM, FF, FP, FS, FT, FW, FY, FV, PA, PR, PN, PD, PC, PE, PQ, PG, PH, PI, PL, PK, PM, PF, PP, PS, PT, PW, PY, PV, SA, SR, SN, SD, SC, SE, SQ, SG, SH, SI, SL, SK, SM, SF, SP, SS, ST, SW, SY, SV, TA, TR, TN, TD, TC, TE, TQ, TG, TH, TI, TL, TK, TM, TF, TP, TS, TT, TW, TY, TV, WA, WR, WN, WD, WC, WE, WQ, WG, WH, WI, WL, WK, WM, WF, WP, WS, WT, WW, WY, WV, YA, YR, YN, YD, YC, YE, YQ, YG, YH, YI, YL, YK, YM, YF, YP, YS, YT, YW, YY, YV, VA, VR, VN, VD, VC, VE, VQ, VG, VH, VI, VL, VK, VM, VF, VP, VS, VT, VW, VY, VV |

Such dipeptides include species where both amino acids are in the L configuration, the D configuration or mixtures of configurations.

Tripeptides, i.e., 3 linked amino acid residues, are also useful embodiments. Each amino acid in a tripeptide may be in an L, D or mixed configuration. Tripeptides include those where A, C, D, E, F, G, H, I, K, L, M, N, P, Q, R, S, T, V, W or Y is linked by a standard peptide bond to the amino or the carboxyl terminus of any of the dipeptides listed above. Other embodiments include tetrapeptides such as ones where any two of the dipeptides listed above, which may be the same or different dipeptides (e.g., AA and AA linked together or, e.g., AA and GI linked together), are linked to each other by a peptide bond through the amino terminus or carboxyl terminus.

In some embodiments, the formula 1 compound comprises one or more amino acids or peptides having the structure (A), (B) or (C): (A) $R^{32}$—NH—$\{[C(R^{29})(R^{30})]_b$—C(O)—N$(R^{31})\}_f$—$[C(R^{29})(R^{30})]_a$—C(O)—O-steroid; (B) $R^{33}$—O—$\{C(O)$—$[C(R^{29})(R^{30})]_d$—N$(R^{31})\}_g$—C(O)—$[C(R^{29})(R^{30})]_c$—N$(R^{31})$—O-steroid; or (C)$R^{33}$—O—$\{C(O)$—$[C(R^{29})(R^{30})]_d$—N$(R^{31})\}_e$—C(O)—$[C(R^{29})(R^{30})]_c$—N$(R^{31})$—C(O)—O-steroid, wherein (A), (B) or (C) are independently selected and they are bonded to 1, 2, 3 or more of $R^1$ through $R^4$, where each $R^{29}$-$R^{31}$ is independently selected; $R^{29}$ independently are —H or a C1-C20 organic moiety (e.g., $C_{1-6}$ alkyl, e.g. —$CH_3$ or —$C_2H_5$); $R^{30}$ independently are the side chain of an amino acid, including the side chain of naturally occurring amino acids as described above, e.g., —H, —$CH_3$, —$CH_2C_6H_5$; $R^{31}$ is —H or a protecting group;

$R^{32}$ and $R^{33}$ independently comprise —H, a protecting group, an ester or an amide where each atom or group is independently chosen; a, b, c and d independently are 1, 2, 3, 4 or 5, usually 1; e, f and g independently are an integer from 0 to about 1000, typically they independently are 0, 1, 2, 3, 4, 5, 6, 7 or 8; a, b, c and d independently are 1 or 2; e, f and g independently are 0, 1, 2, 3, 4 or 5.

If the amino acid(s) or residue(s) has 2 or more amine groups, e.g., a lysinyl or arginyl, ornithinyl residue, then $R^{29}$ is usually —H and $R^{30}$ may comprise —$[C(R^{34})_2]_{n2}N$ $(R^{PR})$— where n2 is 0, 1, 2, 3, 4, 5 or 6, $R^{PR}$ is —H or a protecting group and each $R^{34}$ independently is —H, $C_1$-$C_{20}$ optionally substituted alkyl, $C_6$-$C_{20}$ optionally substituted aryl, $C_7$-$C_{20}$ optionally substituted alkylaryl, $C_7$-$C_{20}$ optionally substituted arylalkyl, $C_7$-$C_{20}$ optionally substituted alkoxy, $C_6$-$C_{20}$ optionally substituted aryloxy or hydroxyl. Such compounds will contain a plurality of steroid moieties. For example when both the epsilon ($\epsilon$) or delta ($\delta$) and alpha ($\alpha$) amino groups of lysine ornithine are substituted with steroid moieties the amidate is believed to be capable of releasing two molecules of active drug, each expected to affect pharmacokinetics.

Salts of F1Cs.

Invention embodiments include salts and complexes of F1Cs, including pharmaceutically acceptable or salts that are relatively non-toxic. Some of the F1Cs have one or more moieties that carry at least a partial positive or negative charge in aqueous solutions, typically at a pH of about 4-10, that can participate in forming a salt, a complex, a composition with partial salt and partial complex properties or other noncovalent interactions, all of which are "salt(s)". Salts are usually biologically compatible or pharmaceutically acceptable or non-toxic, particularly for mammalian cells. Salts that are biologically toxic are optionally used with synthetic intermediates of F1Cs. When a water-soluble composition is desired, monovalent salts are usually used.

Metal salts typically are prepared by reacting the metal hydroxide with a compound of this invention. Examples of metal salts that are optionally prepared in this way are salts containing $Li^+$, $Na^+$ and $K^+$. A less soluble metal salt can be precipitated from the solution of a more soluble salt by adding a suitable metal compound. Invention salts may be formed from acid addition of certain organic acids, such as organic carboxylic acids, and inorganic acids, such as alkylsulfonic acids or hydrogen halide acids, to acidic or basic centers on F1Cs. Other metal salts may contain aluminum, barium, strontium, cadmium, bismuth, arsenic or zinc ion.

Salt(s) of F1Cs may comprise a combination of appropriate cations such as alkali and alkaline earth metal ions or ammonium and quaternary ammonium ions with the acid anion moiety of the phosphoric acid or phosphonic acid group, which may be present in polymers or monomers.

Suitable amine salts include amines having sufficient basicity to form a stable salt, usually amines of low toxicity including trialkyl amines (tripropylamine, triethylamine, trimethylamine), procaine, dibenzylamine, N-benzyl-betaphenethylamine, ephenamine, N,N'-dibenzylethylenediamine, N-ethylpiperidine, benzylamine and dicyclohexylamine.

Salts include organic sulfonic acid organic carboxylic acid salts, made for example by addition of the acids to basic centers, typically amines. Exemplary sulfonic acid salts include salts from $C_{6-16}$ aryl sulfonic acids, $C_{6-16}$ heteroaryl sulfonic acids and $C_{1-16}$ alkyl sulfonic acids such as phenyl sulfonic acid, α-naphthalene sulfonic acid, β-naphthalene sulfonic acid, (S)-camphorsulfonic acid, methyl sulfonic acid ($CH_3SO_3H$), ethyl sulfonic acid ($C_2H_5SO_3H$), and n-propyl, propyl, n-butyl, s-butyl, i-butyl, t-butyl, pentyl and hexyl sulfonic acid salts. Exemplary organic carboxylic and other acid salts include $C_{1-16}$ alkyl, $C_{6-16}$ aryl carboxylic acids and $C_{4-16}$ heteroaryl carboxylic acids such as acetic, glycolic, lactic, pyruvic, malonic, glutaric, tartaric, citric, fumaric, succinic, malic, maleic, oxalic, hydroxymaleic, benzoic, hydroxybenzoic, phenylacetic, cinnamic, salicylic, nicotinic, 2-phenoxybenzoic, methanesulfonic, pamoic, propionic, toluenesulfonic and trifluoroacetic acids.

Invention salts include those made from inorganic acids, e.g., HF, HCl, HBr, HI, $H_2SO_4$, $H_3PO_4$, $Na_2CO_3$, $K_2CO_3$, $CaCO_3$, $MgCO_3$ and $NaClO_3$. Suitable anions include arsenate, arsenite formate, sorbate, chlorate, perchlorate, periodate, dichromate, glycodeoxycholate, cholate, deoxycholate, desoxycholate, taurocholate, taurodeoxycholate, taurolithocholate, tetraborate, nitrate, nitrite, sulfite, sulfamate, hyposulfite, bisulfite, metabisulfite, thiosulfate, thiocyanate, silicate, metasilicate, CN—, gluconate, glucuronate, hippurate, picrate, hydrosulfite, hexafluorophosphate, hypochlorite, hypochlorate, borate, metaborate, tungstate and urate.

Stereoisomers.

The F1Cs include enriched or resolved optical isomers at any or all asymmetric atoms as are apparent from the depictions or are included in the compound structures. Both racemic and diasteromeric mixtures, as well as the individual optical isomers can be isolated or synthesized so as to be substantially free of their enantiomeric or diastereomeric partners, and these are all within the scope of the invention. Chiral centers may be found in F1Cs at, for example, one or more of $R^1$, $R^2$, $R^3$, $R^4$ or $R^{10}$.

Stereospecific synthesis usually does not does not produce undesired enantiomers that must be removed from the final product. In general, those skilled in the art would understand what starting materials and reaction conditions should be used to obtain the desired enantiomerically enriched or pure isomers by stereospecific synthesis. Methods to make related compounds been described, see, e.g., U.S. Pat. Nos. 2,833,793, 2,911,418, 3,148,198, 3,471,480, 3,976,691, 4,000,125, 4,083,969, 4,268,441, 4,427,649, 4,542,129, 4,666,898, 4,956,355, 5,001,119, 5,043,165, 5,077,284, 5,028,631, 5,110,810, 5,157,031, 5,162,198, 5,175,154, 5,277,907, 5,292,730, 5,296,481, 5,372,996, 5,387,583, 5,407,684, 5,424,463, 5,461,042, 5,478,566, 5,506,223, 5,518,725, 5,527,788, 5,527,789, 5,532,230, 5,559,107, 5,562,910, 5,583,126, 5,585,371, 5,587,369, 5,591,736, 5,593,981, 5,629,295, 5,610,150, 5,635,496, 5,641,766, 5,641,768, 5,656,621, 5,660,835, 5,686,438, 5,696,106, 5,700,793, 5,707,983, 5,709,878, 5,710,143, 5,714,481, 5,728,688, 5,736,537, 5,744,462, 5,753,237, 5,756,482, 5,776,921, 5,776,923, 5,780,460, 5,795,880, 5,798,347, 5,798,348, 5,804,576, 5,807,848, 5,807,849, 5,811,418, 5,824,313, 5,824,668, 5,824,671, 5,827,841, 5,837,269, 5,837,700, 5,843,932, 5,846,963, 5,859,000, 5,872,114, 5,872,147, 5,162,198, 5,206,008, 5,292,730, 5,407,684, 5,461,042, 5,461,768, 5,478,566, 5,585,371, 5,635,496, 5,641,766, 5,837,269, 5,885,977, 5,846,963, 5,919,465, 5,869,090, 5,863,910, 5,856,340, 5,804,576, 5,714,481, 6,150,336, 4,978,532, 4,898,694, 4,542,129, 3,711,606, 3,710,795, 3,189,597, 3,137,710, 2,531,441, 4,908,358, 4,902,681, 5,532,230, 5,686,438, 5,753,640, 5,811,418, 5,859,000, 5,763,433, 6,372,732, 5,925,630, 5,939,545 and 5,962,443.

Embodiments of Formula 1 Compounds.

For formula 1 compounds ("F1Cs"), 2, 3 or more of $R^1$, $R^2$, $R^3$ and $R^4$ are usually not —H, and typically one or both $R^1$ and $R^4$, $R^3$ and $R^4$, $R^2$, $R^3$ and $R^4$ or $R^2$ and $R^4$ are not —H, and/or 1 or 2 of $R^{10A}$, $R^{10B}$, $R^{10C}$ and $R^{10D}$ are optionally not —H. For any F1C disclosed herein, steroid nucleus carbon atoms that contain two variable groups (e.g., two $R^{10}$ at $R^8$ or $R^9$ or two $R^3$ or $R^4$ at the 16- or 17-position), each variable group is independently selected and each can thus be the same or different, e.g., both can be methyl, ethyl, methoxy, ethoxy, —F, —Cl, —Br, —I, or they can be different. Exemplary F1C include compounds where no double bond is present at the 3-position, one $R^1$ is an O-linked, S-linked or N-linked moiety and the other $R^1$ is —H or a C-linked moiety or both $R^1$ together are =O or another double bonded moiety, and/or no double bond is present at the 17-position, one $R^4$, in the α- or β-configuration, is an O-linked, S-linked or N-linked moiety and the other $R^4$ is —H or a C-linked moiety and/or no double bond is present at the 16-position, one $R^3$ is an O-linked, S-linked or N-linked moiety and the other $R^3$ is —H or a C-linked moiety or both $R^3$ are a halogen or together are =O or another double bonded moiety. Other embodiments are described elsewhere herein.

The formula 1 compounds may contain 0, 1, 2, 3, 4 or 5 carbon-carbon or carbon-nitrogen double bonds within the fused four-ring system, such that the compound is unsaturated. Classes of formula 1 compounds include, androstanes (or 5α-androstanes), 5β-androstanes, 1-ene, 2-ene, 3-ene, 4-ene, 5(6)-ene (or a "5-ene"), 5(10)-ene, 6-ene, 7-ene, 8(9)-ene, 8(14)-ene, 9(10)-ene, 9(11)-ene, 11-ene, 12-ene, 13(17)-ene, 14-ene, 15-ene, 16-ene, 1,3-diene, 1,4-diene, 1,5-diene, 1,5(10)-diene, 1,6-diene, 1,7-diene, 1,8(9)-diene, 1,8(14)-diene, 1,9(11)-diene, 1,11-diene, 1,12-diene, 1,13(17)-diene, 1,15-diene, 1,16-diene, 2,4-diene, 2,5-diene, 2,5(10)-diene, 2,6-diene, 2,7-diene, 2,8(9)-diene, 2,8(14)-diene, 2,9-diene, 2,9(11)-diene, 2,11-diene, 2,12-diene, 2,13(17)-diene, 2,14-diene, 2,15-diene, 2,16-diene, 3,5-diene, 3,6-diene, 3,7-diene, 3,8(9)-diene, 3,8(14)-diene, 3,9(10)-diene, 3,9(11)-diene, 3,11-diene, 3,12-diene, 3,13(17)-diene, 3,14-diene, 3,15-diene, 3,16-diene, 4,6-diene, 4,7-diene, 4,8(9)-diene, 4,8(14)-diene, 4,9(10)-diene, 4,9(11)-diene, 4,11-diene, 4,12-diene, 4,13(17)-diene, 4,14-diene, 4,15-diene, 4,16-diene, 5(6),15-diene (or a "5,15-diene"), 5,7-diene, 5,8(9)-diene, 5,8(14)-diene, 5,9(11)-diene, 5,11-diene, 5,12-diene, 5,13(17)-diene, 5,14-diene, 5,15-diene, 5,16-diene, 5(10),7-diene, 5(10),8(9)-diene, 5(10),8(14)-diene, 5,9(11)-diene, 5(10),11-diene, 5(10),12-diene, 5(10),13(17)-diene, 5(10),14-diene, 5(10),15-diene, 5(10),16-diene, 6,9(11)-diene, 6,9(14)-diene, 6,10-diene, 6,11-diene, 6,13(17)-diene, 6,14-diene, 6,15-diene, 6,16-diene, 7,9(10)-diene, 7,9(11)-diene, 7,12-diene, 7,13(17)-diene, 7,14-diene, 7,15-diene, 7,16-diene, 8(9),11-diene, 8(9),12-diene, 8(9),13(17)-diene, 8(9),14-diene, 8(9),15-diene, 8(9),16-diene, 8(14),9-diene, 8(14),11-diene, 8(14),12-diene, 8(14),13(17)-diene, 8(14),15-diene, 8(14),16-diene, 9(10),11-diene, 9(10),12-diene, 9(10),13(17)-diene, 9(10),14-diene, 9(10),15-diene, 9(10),16-diene, 9(11),13-diene, 9(11),13(17)-diene, 9(11),14-diene, 9(11),15-diene, 9(11),16-diene, 11,13(17)-diene, 11,14-diene, 11,15-diene, 11,16-diene, 12,14-diene, 12,15-diene, 12,16-diene, 13(17),14-diene, 13(17),15-diene, 14,16-diene, 1,3,5-triene, 1,3,5(10)-triene, 1,3,6-triene, 1,3,7-triene, 1,3,8-triene, 1,3,8(14)-triene, 1,3,9-triene, 1,3,9(11)-triene, 1,3,12-triene, 1,3,13(17)-triene, 1,3,14-triene, 1,3,15-triene, 1,3,16-triene, 1,4,6-triene, 1,4,7-triene, 1,4,8-triene, 1,4,8(14)-triene, 1,4,9-triene, 1,4,11-triene, 1,4,9(11)-triene, 1,4,12-triene, 1,4,13(17)-triene, 1,4,14-triene, 1,4,15-triene, 1,4,16-triene, 1,5,7-triene, 1,5,8-triene, 1,5,8(14)-triene, 1,5,9-triene, 1,5,9(11)-triene, 1,5,11-triene, 1,5,12-triene, 1,5,13(17)-triene, 1,5,14-triene, 1,5,15-triene, 1,5,16-triene, 1,5(10),6-triene, 1,5(10),7-triene, 1,5(10),8-triene, 1,5(10),8(14)-triene, 1,5(10),9(11)-triene, 1,5(10),12-triene, 1,5(10),13(17)-triene, 1,5(10),14-triene, 1,5(10),15-triene, 1,5(10),16-triene, 1,6,8-triene, 1,6,8(14)-triene, 1,6,9-triene, 1,6,9(11)-triene, 1,6,11-triene, 1,6,12-triene, 1,6,13(17)-triene, 1,6,14-triene, 1,6,15-triene, 1,6,16-triene, 1,7,9-triene, 1,7,9(11)-triene, 1,7,11-triene, 1,7,12-triene, 1,7,13(17)-triene, 1,7,14-triene, 1,7,15-triene, 1,7,16-triene, 2,4,6-triene, 2,5,6-triene, 2,5(10),6-triene, 2,4,7-triene, 2,5,7-triene, 2,5(10),7-triene, 2,4,8-triene, 2,5,8-triene, 2,5(10),8-triene, 2,4,8(14)-triene, 2,5,8(14)-triene, 2,5(10),8(14)-triene, 2,4,9-triene, 2,4,9(11)-triene, 2,5,9(11)-triene, 2,5(10),9(11)-triene, 2,4,11-triene, 2,5,11-triene, 2,5(10),11-triene, 2,4,12-triene, 2,5,12-triene, 2,5(10),12-triene, 2,4,14-triene, 2,5,14-triene, 2,5(10),14-triene, 2,4,15-triene, 2,5,15-triene, 2,5(10),15-triene, 2,4,16-triene, 2,5,16-triene, 2,5(10),16-triene, 2,6,8-triene, 2,6,8(14)-triene, 2,6,9-triene, 2,6,9(11)-triene, 2,6,12-triene, 2,6,13(17)-triene, 2,6,14-triene, 2,6,15-triene, 2,6,16-triene, 2,7,9-triene, 2,7,9(11)-triene, 2,7,12-triene, 2,7,13(17)-triene, 2,7,14-triene, 2,7,15-triene, 2,7,16-triene, 3,5,9-triene, 3,5,11-triene, 3,5,12-triene, 3,5,13-triene, 3,5,14-triene, 3,5,15-triene, 3,5,16-triene, 3,6,8-triene, 3,6,8(14)-triene, 3,6,9-triene, 3,6,9(11)-triene, 3,6,11-triene, 3,6,12-triene, 3,6,13(17)-triene, 3,6,14-triene, 3,6,15-triene, 3,6,16-triene, 3,7,9-triene, 3,7,11-triene, 3,7,12-triene, 3,7,13(17)-triene, 3,7,14-triene, 3,7,15-triene, 3,7,16-triene, 3,8,11-triene, 3,8,12-triene, 3,8,13(17)-triene, 3,8,14-triene, 3,8,15-triene, 3,8,16-triene, 3,8(14),11-triene, 3,8(14),12-triene, 3,8(14),13(17)-triene, 3,8(14),15-triene, 3,8(14),16-triene, 3,9,11-triene, 3,9,12-triene, 3,9,13(17)-triene, 3,9,14-triene, 3,9,15-triene, 3,9,16-triene, 3,9(11),12-triene, 3,9(11),13(17)-triene, 3,9(11),14-triene, 3,9(11),15-triene, 3,9(11),16-triene, 3,11,13(17)-triene, 3,11,14-triene, 3,11,15-triene, 3,11,16-triene, 3,12,14-triene, 3,12,15-triene, 3,12,16-triene, 3,13(17),14-triene, 3,13(17),15-triene, 3,14,16-triene, 4,6,8-triene, 4,6,8(14)-triene, 4,6,9-triene, 4,6,9(11)-triene, 4,6,11-triene, 4,6,12-triene, 4,6,13(17)-triene, 4,6,14-triene, 4,6,15-triene, 4,6,16-triene, 4,7,9-triene, 4,7,11-triene, 4,7,12-triene, 4,7,13(17)-triene, 4,7,14-triene, 4,7,15-triene, 4,7,16-triene, 4,8,9-triene, 4,8,9(11)-triene, 4,8,11-triene, 4,8,12-triene, 4,8,13(17)-triene, 4,8,14-triene, 4,8,15-triene, 4,8,16-triene, 4,8(14),9-triene, 4,8(14),9(11)-triene, 4,8(14),11-triene, 4,8(14),12-triene, 4,8(14),13(17)-triene, 4,8(14),15-triene, 4,8(14),16-triene, 4,9,11-triene, 4,9,12-triene, 4,9,13(17)-triene, 4,9,14-triene, 4,9,15-triene, 4,9,16-triene, 4,9(11),12-triene, 4,9(11),13(17)-triene, 4,9(11),14-triene, 4,9(11),15-triene, 4,9(11),16-triene, 4,11,13(17)-triene, 4,11,14-triene, 4,11,15-triene, 4,11,16-triene, 4,12,14-triene, 4,12,15-triene, 4,12,16-triene, 4,13(17),14-triene, 4,13(17),15-triene, 4,14,16-triene, 5,7,9-triene, 5,7,9(11)-triene, 5,7,12-triene, 5,7,13(17)-triene, 5,7,14-triene, 5,7,15-triene, 5,7,16-triene, 5,8,11-triene, 5,8,12-triene, 5,8,13(17)-triene, 5,8,14-triene, 5,8,15-triene, 5,8,16-triene, 5,8(14),9-triene, 5,8(14),9(11)-triene, 5,8(14),12-triene, 5,8(14),13(17)-triene, 5,8(14),15-triene, 5,8(14),16-triene, 5,9,11-triene, 5,9,12-triene, 5,9,13(17)-triene, 5,9,14-triene, 5,9,15-triene, 5,9,16-triene, 5,9(11),12-triene, 5,9(11),13(17)-triene, 5,9(11),14-triene, 5,9(11),15-triene, 5,9(11),16-triene, 5,11,13(17)-triene, 5,11,14-triene, 5,11,15-triene, 5,11,16-triene, 5,12,14-triene, 5,12,15-triene, 5,12,16-triene, 5,13(17),14-triene, 5,13(17),15-triene, 5,14,16-triene, 6,8,11-triene, 6,8,12-triene, 6,8,13(17)-triene, 6,8,14-triene, 6,8,15-triene, 6,8,16-triene, 6,8(14),9-triene, 6,8(14),9(11)-triene, 6,8(14),11-triene, 6,8(14),12-triene, 6,8(14),13(17)-triene, 6,8(14),15-triene, 6,8(14),16-triene, 6,9,11-triene, 6,9,12-triene, 6,9,13(17)-triene, 6,9,14-triene, 6,9,15-triene, 6,9,16-triene, 6,9(11),12-triene, 6,9(11),13(17)-triene, 6,9(11),14-triene, 6,9(11),15-triene, 6,9(11),16-triene, 6,11,13(17)-triene, 6,11,14-triene, 6,11,15-triene, 6,11,16-triene, 6,12,14-triene, 6,12,15-triene, 6,12,16-triene, 6,13(17),14-triene, 6,13(17),15-triene, 6,14,16-triene, 7,9,11-triene, 7,9,12-triene, 7,9,13

(17)-triene, 7,9,14-triene, 7,9,15-triene, 7,9,16-triene, 7,9 (11),12-triene, 7,9(11),13(17)-triene, 7,9(11),14-triene, 7,9 (11),15-triene, 7,9(11),16-triene, 7,12,14-triene, 7,12,15-triene, 7,12,16-triene, 7,13(17),14-triene, 7,13(17),15-triene, 7,14,16-triene, 8,11,13(17)-triene, 8,11,14-triene, 8,11,15-triene, 8,11,16-triene, 8,12,14-triene, 8,12,15-triene, 8,12, 16-triene, 8,13(17),14-triene, 8,13(17),15-triene, 8,14,16-triene, 8(14),9,11-triene, 8(14),9,12-triene, 8(14),9,13(17)-triene, 8(14),9,15-triene, 8(14),9,16-triene, 8(14),9(11),12-triene, 8(14),9(11),13(17)-triene, 8(14),9(11),15-triene, 8(14),9(11),16-triene, 9,11,13(17)-triene, 9,11,14-triene, 9,11,15-triene, 9,11,16-triene, 9(11),13(17),14-triene, 9(11), 13(17),15-triene, 11,13(17),14-triene, 11,13(17),15-triene, 12,14,16-triene, 1,3,5(10),6-tetraene, 1,3,5(10),7-tetraene, 1,3,5(10),8(9)-tetraene, 1,3,5(10),8(14)-tetraene, 1,3,5(10),9 (11)-tetraene, 1,3,5(10),11-tetraene, 1,3,5(10),12-tetraene, 1,3,5(10),13(17)-tetraene, 1,3,5(10),14-tetraene, 1,3,5(10), 15-tetraene, 1,3,5(10),16-tetraene, 1,3,5,7-tetraene, 1,3,5,8-tetraene, 1,3,5,8(14)-tetraene, 1,3,5,9-tetraene, 1,3,5,9(11)-tetraene, 1,3,5,12-tetraene, 1,3,5,13(17)-tetraene, 1,3,5,14-tetraene, 1,3,5,15-tetraene, 1,3,5,16-tetraene, 1,3,6,8-tetraene, 1,3,6,8(14)-tetraene, 1,3,6,9-tetraene, 1,3,6,9(11)-tetraene, 1,3,6,12-tetraene, 1,3,6,13(17)-tetraene, 1,3,6,14-tetraene, 1,3,6,15-tetraene, 1,3,6,16-tetraene, 1,3,7,9-tetraene, 1,3,7,9(11)-tetraene, 1,3,7,11-tetraene, 1,3,7,12-tetraene, 1,3,7,13(17)-tetraene, 1,3,7,14-tetraene, 1,3,7,15-tetraene, 1,3,7,16-tetraene, 1,3,8,9-tetraene, 1,3,8,9(11)-tetraene, 1,3,8,12-tetraene, 1,3,8,13(17)-tetraene, 1,3,8,14-tetraene, 1,3,8,15-tetraene, 1,3,8,16-tetraene, 1,3,8(14)-9-tetraene, 1,3,8(14)9(11)-tetraene, 1,3,8(14)12-tetraene, 1,3,8 (14)13(17)-tetraene, 1,3,8(14)15-tetraene, 1,3,8(14)16-tetraene, 1,3,9,11-tetraene, 1,3,9,12-tetraene, 1,3,9,13(17)-tetraene, 1,3,9,14-tetraene, 1,3,9,15-tetraene, 1,3,9,16-tetraene, 1,3,9(11),12-tetraene, 1,3,9(11),113(17)-tetraene, 1,3,9(11),14-tetraene, 1,3,9(11),15-tetraene, 1,3,9(11),16-tetraene, 1,3,12,14-tetraene, 1,3,12,15-tetraene, 1,3,12,16-tetraene, 1,3,13(17),14-tetraene, 1,3,13(17),15-tetraene, 1,3, 13(17),16-tetraene, 1,3,14,16-tetraene, 1,4,6,8-tetraene, 1,4, 6,8(14)-tetraene, 1,4,6,9-tetraene, 1,4,6,9(11)-tetraene, 1,4, 6,11-tetraene, 1,4,6,12-tetraene, 1,4,6,13(17)-tetraene, 1,4,6, 14-tetraene, 1,4,6,15-tetraene, 1,4,6,16-tetraene, 1,5,7,9-tetraene, 1,5,7,9(11)-tetraene, 1,5,7,11-tetraene, 1,5,7,12-tetraene, 1,5,7,13(17)-tetraene, 1,5,7,14-tetraene, 1,5,7,15-tetraene, 1,5,7,16-tetraene, 1,5,8,11-tetraene, 1,5,8,12-tetraene, 1,5,8,13(17)-tetraene, 1,5,8,14-tetraene, 1,5,8,15-tetraene, 1,5,8,16-tetraene, 1,5,8(14),9-tetraene, 1,5,8(14), (11)-tetraene, 1,5,8(14),11-tetraene, 1,5,8(14),12-tetraene, 1,5,8(14),13(17)-tetraene, 1,5,8(14),15-tetraene, 1,5,8(14), 16-tetraene, 1,5,9,11-tetraene, 1,5,9,12-tetraene, 1,5,9,13 (17)-tetraene, 1,5,9,14-tetraene, 1,5,9,15-tetraene, 1,5,9,16-tetraene, 1,5,9(11),12-tetraene, 1,5,9(11),13(17)-tetraene, 1,5,9(11),14-tetraene, 1,5,9(11),15-tetraene, 1,5,9(11),16-tetraene, 1,5,11,13(17)-tetraene, 1,5,11,14-tetraene, 1,5,11, 15-tetraene, 1,5,11,16-tetraene, 1,5,12,14-tetraene, 1,5,12, 15-tetraene, 1,5,12,16-tetraene, 1,5,13(17),14-tetraene, 1,5, 13(17),15-tetraene, 1,5,14,16-tetraene, 1,4,7,15-tetraene, 1,5,7,15-tetraene, 1,3,7,16-tetraene, 1,4,6,8-tetraene, 1,4,6, 9-tetraene, 1,4,6,9(11)-tetraene, 1,4,6,11-tetraene, 1,4,6,12-tetraene, 1,4,6,13(17)-tetraene, 1,4,6,14-tetraene, 1,4,6,15-tetraene, 1,4,6,16-tetraene, 1,4,7,9-tetraene, 1,4,7,9(11)-tetraene, 1,4,7,11-tetraene, 1,4,7,12-tetraene, 1,4,7,13(17)-tetraene, 1,4,7,14-tetraene, 1,4,7,15-tetraene, 1,4,7,16-tetraene, 1,6,8,11-tetraene, 1,6,8,12-tetraene, 1,6,8,13(17)-tetraene, 1,6,8,14-tetraene, 1,6,8,15-tetraene, 1,6,8,16-tetraene, 1,6,8(14),9-tetraene, 1,6,8(14),9(11)-tetraene, 1,6,8 (14),11-tetraene, 1,6,8(14),12-tetraene, 1,6,8(14),13(17)-tetraene, 1,6,8(14),15-tetraene, 1,6,8(14),16-tetraene, 1,6,9, 11-tetraene, 1,6,9,12-tetraene, 1,6,9,13(17)-tetraene, 1,6,9, 14-tetraene, 1,6,9,15-tetraene, 1,6,9,16-tetraene, 1,6,9(11), 12-tetraene, 1,6,9(11),13(17)-tetraene, 1,6,9(11),14-tetraene, 1,6,9(11),15-tetraene, 1,6,9(11),16-tetraene, 1,6,11, 13(17)-tetraene, 1,6,11,14-tetraene, 1,6,11,15-tetraene, 1,6, 12,14-tetrane, 1,6,12,15-tetrane, 1,6,12,16-tetrane, 1,6,13 (17),14-tetraene, 1,6,13(17),15-tetraene, 1,6,14,16-tetraene, 1,7,9,11-tetraene, 1,7,9,12-tetraene, 1,7,9,13(17)-tetraene, 1,7,9,14-tetraene, 1,7,9,15-tetraene, 1,7,9,16-tetraene, 1,8, 11,13(17)-tetraene, 1,8,11,14-tetraene, 1,8,11,15-tetraene, 1,8,11,16-tetraene, 1,8(14),9,11-tetraene, 1,8(14),9,12-tetraene, 1,8(14),9,13(17)-tetraene, 1,8(14),9,15-tetraene, 1,8 (14),9,16-tetraene, 1,9,11,13(17)-tetraene, 1,9,11,14-tetraene, 1,9,11,15-tetraene, 1,9,11,16-tetraene, 1,9(11),12,14-tetraene, 1,9(11),12,15-tetraene, 1,9(11),12,16-tetraene, 1,11,13(17),14-tetraene, 1,11,13(17),15-tetraene, 1,11,13 (17),16-tetraene, 1,12,14,16-tetraene, 1,8,11,13(17)-tetraene, 1,8,11,14-tetraene, 1,8,11,15-tetraene, 1,9,11,13(17)-tetraene, 1,9,11,14-tetraene, 1,9,11,15-tetraene, 1,9,11,16-tetraene, 1,9(11),12,14-tetraene, 1,9(11),12,15-tetraene, 1,9 (11),12,16-tetraene, 1,11,13(17),14-tetraene, 1,11,13(17), 15-tetraene, 1,11,13(17),16-tetraene, 1,12,14,16-tetraene, 2,4,6,8-tetraene, 2,4,6,8(14)-tetraene, 2,4,6,9-tetraene, 2,4,6, 9(11)-tetraene, 2,4,6,11-tetraene, 2,4,6,12-tetraene, 2,4,6,13 (17)-tetraene, 2,4,6,14-tetraene, 2,4,6,15-tetraene, 2,4,6,16-tetraene, 2,5,7,9-tetraene, 2,5,7,9(11)-tetraene, 2,5,7,11-tetraene, 2,5,7,12-tetraene, 2,5,7,13(17)-tetraene, 2,5,7,14-tetraene, 2,5,7,15-tetraene, 2,5,7,16-tetraene, 2,5,8,11-tetraene, 2,5,8,12-tetraene, 2,5,8,13(17)-tetraene, 2,5,8,14-tetraene, 2,5,8,15-tetraene, 2,5,8,16-tetraene, 2,5,8(14),9-tetraene, 2,5,8(14),9(11)-tetraene, 2,5,8(14),11-tetraene, 2,5, 8(14),12-tetraene, 2,5,8(14),13(17)-tetraene, 2,5,8(14),15-tetraene, 2,5,8(14),16-tetraene, 2,5,9,11-tetraene, 2,5,9,12-tetraene, 2,5,9,13(17)-tetraene, 2,5,9,14-tetraene, 2,5,9,15-tetraene, 2,5,9,16-tetraene, 2,5,9(11),12-tetraene, 2,5,9(11), 13(17)-tetraene, 2,5,9(11),14-tetraene, 2,5,9(11),15-tetraene, 2,5,9(11),16-tetraene, 2,5,11,13(17)-tetraene, 2,5, 11,14-tetraene, 2,5,11,15-tetraene, 2,5,11,16-tetraene, 2,5, 12,14-tetraene, 2,5,12,15-tetraene, 2,5,12,16-tetraene, 2,5,13 (17),14-tetraene, 2,5,13(17),15-tetraene, 2,5,14,16-tetraene, 2,4,7,15-tetraene, 2,5,7,15-tetraene, 2,4,6,8-tetraene, 2,4,6, 9-tetraene, 2,4,6,9(11)-tetraene, 2,4,6,11-tetraene, 2,4,6,12-tetraene, 2,4,6,13(17)-tetraene, 2,4,6,14-tetraene, 2,4,6,15-tetraene, 2,4,6,16-tetraene, 2,4,7,9-tetraene, 2,4,7,9(11)-tetraene, 2,4,7,11-tetraene, 2,4,7,12-tetraene, 2,4,7,13(17)-tetraene, 2,4,7,14-tetraene, 2,4,7,15-tetraene, 2,4,7,16-tetraene, 2,6,8,11-tetraene, 2,6,8,12-tetraene, 2,6,8,13(17)-tetraene, 2,6,8,14-tetraene, 2,6,8,15-tetraene, 2,6,8,16-tetraene, 2,6,8(14),9-tetraene, 2,6,8(14),9(11)-tetraene, 2,6,8 (14),11-tetraene, 2,6,8(14),12-tetraene, 2,6,8(14),13(17)-tetraene, 2,6,8(14),15-tetraene, 2,6,8(14),16-tetraene, 2,6,9, 11-tetraene, 2,6,9,12-tetraene, 2,6,9,13(17)-tetraene, 2,6,9, 14-tetraene, 2,6,9,15-tetraene, 2,6,9,16-tetraene, 2,6,9(11), 12-tetraene, 2,6,9(11),13(17)-tetraene, 2,6,9(11),14-tetraene, 2,6,9(11),15-tetraene, 2,6,9(11),16-tetraene, 2,6,11, 13(17)-tetraene, 2,6,11,14-tetraene, 2,6,11,15-tetraene, 2,6, 12,14-tetrane, 2,6,12,15-tetrane, 2,6,12,16-tetrane, 2,6,13 (17),14-tetraene, 2,6,13(17),15-tetraene, 2,6,14,16-tetraene, 2,7,9,11-tetraene, 2,7,9,12-tetraene, 2,7,9,13(17)-tetraene, 2,7,9,14-tetraene, 2,7,9,15-tetraene, 2,7,9,16-tetraene, 2,8, 11,13(17)-tetraene, 2,8,11,14-tetraene, 2,8,11,15-tetraene, 2,8,11,16-tetraene, 2,8(14),9,11-tetraene, 2,8(14),9,12-tetraene, 2,8(14),9,13(17)-tetraene, 2,8(14),9,15-tetraene, 2,8 (14),9,16-tetraene, 2,9,11,13(17)-tetraene, 2,9,11,14-tetraene, 2,9,11,15-tetraene, 2,9,11,16-tetraene, 2,9(11),12,14-tetraene, 2,9(11),12,15-tetraene, 2,9(11),12,16-tetraene, 2,11,13(17),14-tetraene, 2,11,13(17),15-tetraene, 2,11,13

(17),16-tetraene, 2,12,14,16-tetraene, 2,8,11,13(17)-tetraene, 2,8,11,14-tetraene, 2,8,11,15-tetraene, 2,9,11,13(17)-tetraene, 2,9,11,14-tetraene, 2,9,11,15-tetraene, 2,9,11,16-tetraene, 2,9(11),12,14-tetraene, 2,9(11),12,15-tetraene, 2,9(11),12,16-tetraene, 2,11,13(17),14-tetraene, 2,11,13(17),15-tetraene, 2,11,13(17),16-tetraene, 2,12,14,16-tetraene, 3,5,7,9-tetraene, 3,5,7,9(11)-tetraene, 3,5,7,11-tetraene, 3,5,7,12-tetraene, 3,5,7,13(17)-tetraene, 3,5,7,14-tetraene, 3,5,7,15-tetraene, 3,5,7,16-tetraene, 3,5,8,11-tetraene, 3,5,8,12-tetraene, 3,5,8,13(17)-tetraene, 3,5,8,14-tetraene, 3,5,8,15-tetraene, 3,5,8,16-tetraene, 3,5,8(14),9-tetraene, 3,5,8(14),9(11)-tetraene, 3,5,8(14),11-tetraene, 3,5,8(14),12-tetraene, 3,5,8(14),13(17)-tetraene, 3,5,8(14),15-tetraene, 3,5,8(14),16-tetraene, 3,5,9,11-tetraene, 3,5,9,12-tetraene, 3,5,9,13(17)-tetraene, 3,5,9,14-tetraene, 3,5,9,15-tetraene, 3,5,9,16-tetraene, 3,5,9(11),12-tetraene, 3,5,9(11),13(17)-tetraene, 3,5,9(11),14-tetraene, 3,5,9(11),15-tetraene, 3,5,9(11),16-tetraene, 3,5,11,13(17)-tetraene, 3,5,11,14-tetraene, 3,5,11,15-tetraene, 3,5,11,16-tetraene, 3,5,12,14-tetraene, 3,5,12,15-tetraene, 3,5,12,16-tetraene, 3,5,13(17),14-tetraene, 3,5,13(17),15-tetraene, 3,5,14,16-tetraene, 3,4,7,15-tetraene, 3,5,7,15-tetraene, 3,5,7,16-tetraene, 3,4,6,8-tetraene, 3,4,6,9-tetraene, 3,4,6,9(11)-tetraene, 3,4,6,11-tetraene, 3,4,6,12-tetraene, 3,4,6,13(17)-tetraene, 3,4,6,14-tetraene, 3,4,6,15-tetraene, 3,4,6,16-tetraene, 3,4,7,9-tetraene, 3,4,7,9(11)-tetraene, 3,4,7,11-tetraene, 3,4,7,12-tetraene, 3,4,7,13(17)-tetraene, 3,4,7,14-tetraene, 3,4,7,15-tetraene, 3,4,7,16-tetraene, 3,6,8,11-tetraene, 3,6,8,12-tetraene, 3,6,8,13(17)-tetraene, 3,6,8,14-tetraene, 3,6,8,15-tetraene, 3,6,8,16-tetraene, 3,6,8(14),9-tetraene, 3,6,8(14),9(11)-tetraene, 3,6,8(14),11-tetraene, 3,6,8(14),12-tetraene, 3,6,8(14),13(17)-tetraene, 3,6,8(14),15-tetraene, 3,6,8(14),16-tetraene, 3,6,9,11-tetraene, 3,6,9,12-tetraene, 3,6,9,13(17)-tetraene, 3,6,9,14-tetraene, 3,6,9,15-tetraene, 3,6,9,16-tetraene, 3,6,9(11),12-tetraene, 3,6,9(11),13(17)-tetraene, 3,6,9(11),14-tetraene, 3,6,9(11),15-tetraene, 3,6,9(11),16-tetraene, 3,6,11,13(17)-tetraene, 3,6,11,14-tetraene, 3,6,11,15-tetraene, 3,6,12,14-tetrane, 3,6,12,15-tetrane, 3,6,12,16-tetrane, 3,6,13(17),14-tetraene, 3,6,13(17),15-tetraene, 3,6,14,16-tetraene, 3,7,9,11-tetraene, 3,7,9,12-tetraene, 3,7,9,13(17)-tetraene, 3,7,9,14-tetraene, 3,7,9,15-tetraene, 3,7,9,16-tetraene, 3,8,11,13(17)-tetraene, 3,8,11,14-tetraene, 3,8,11,15-tetraene, 3,8,11,16-tetraene, 3,8(14),9,11-tetraene, 3,8(14),9,12-tetraene, 3,8(14),9,13(17)-tetraene, 3,8(14),9,15-tetraene, 3,8(14),9,16-tetraene, 3,9,11,13(17)-tetraene, 3,9,11,15-tetraene, 3,9,11,16-tetraene, 3,9(11),12,14-tetraene, 3,9(11),12,15-tetraene, 3,9(11),12,16-tetraene, 3,11,13(17),14-tetraene, 3,11,13(17),15-tetraene, 3,11,13(17),16-tetraene, 3,12,14,16-tetraene, 3,8,11,13(17)-tetraene, 3,8,11,14-tetraene, 3,8,11,15-tetraene, 3,9,11,13(17)-tetraene, 3,9,11,14-tetraene, 3,9,11,15-tetraene, 3,9,11,16-tetraene, 3,9(11),12,14-tetraene, 3,9(11),12,15-tetraene, 3,9(11),12,16-tetraene, 3,11,13(17),14-tetraene, 3,11,13(17),15-tetraene, 3,11,13(17),16-tetraene, 3,12,14,16-tetraene, 3,5(10),7,9(11)-tetraene, 3,5(10),7,11-tetraene, 3,5(10),7,12-tetraene, 3,5(10),7,13(17)-tetraene, 3,5(10),7,14-tetraene, 3,5(10),7,15-tetraene, 3,5(10),7,16-tetraene, 3,5(10),8,11-tetraene, 3,5(10),8,12-tetraene, 3,5(10),8,13(17)-tetraene, 3,5(10),8,14-tetraene, 3,5(10),8,15-tetraene, 3,5(10),8,16-tetraene, 3,5(10),8(14),9-tetraene, 3,5(10),8(14),9(11)-tetraene, 3,5(10),8(14),11-tetraene, 3,5(10),8(14),12-tetraene, 3,5(10),8(14),13(17)-tetraene, 3,5(10),8(14),15-tetraene, 3,5(10),8(14),16-tetraene, 3,5(10),9,11-tetraene, 3,5(10),9,12-tetraene, 3,5(10),9,13(17)-tetraene, 3,5(10),9,14-tetraene, 3,5(10),9,15-tetraene, 3,5(10),9,16-tetraene, 3,5(10),9(11),12-tetraene, 3,5(10),9(11),13(17)-tetraene, 3,5(10),9(11),14-tetraene, 3,5(10),9(11),15-tetraene, 3,5(10),9(11),16-tetraene, 3,5(10),11,13(17)-tetraene, 3,5(10),11,14-tetraene, 3,5(10),11,15-tetraene, 3,5(10),11,16-tetraene, 3,5(10),12,14-tetraene, 3,5(10),12,15-tetraene, 3,5(10),12,16-tetraene, 3,5(10),13(17),14-tetraene, 3,5(10),13(17),15-tetraene, 3,5(10),14,16-tetraene, 4,6,8,11-tetraene, 4,6,8,12-tetraene, 4,6,8,13(17)-tetraene, 4,6,8,14-tetraene, 4,6,8,15-tetraene, 4,6,8,16-tetraene, 4,6,8(14),9-tetraene, 4,6,8(14),9(11)-tetraene, 4,6,8(14),11-tetraene, 4,6,8(14),12-tetraene, 4,6,8(14),13(17)-tetraene, 4,6,8(14),15-tetraene, 4,6,8(14),16-tetraene, 4,6,9,11-tetraene, 4,6,9,12-tetraene, 4,6,9,13(17)-tetraene, 4,6,9,14-tetraene, 4,6,9,15-tetraene, 4,6,9,16-tetraene, 4,6,9(11),12-tetraene, 4,6,9(11),13(17)-tetraene, 4,6,9(11),14-tetraene, 4,6,9(11),15-tetraene, 4,6,9(11),16-tetraene, 4,6,11,13(17)-tetraene, 4,6,11,14-tetraene, 4,6,11,15-tetraene, 4,6,12,14-tetrane, 4,6,12,15-tetrane, 4,6,12,16-tetrane, 4,6,13(17),14-tetraene, 4,6,13(17),15-tetraene, 4,6,14,16-tetraene, 4,7,9,11-tetraene, 4,7,9,12-tetraene, 4,7,9,13(17)-tetraene, 4,7,9,14-tetraene, 4,7,9,15-tetraene, 4,7,9,16-tetraene, 4,8,11,13(17)-tetraene, 4,8,11,14-tetraene, 4,8,11,15-tetraene, 4,8,11,16-tetraene, 4,8(14),9,11-tetraene, 4,8(14),9,12-tetraene, 4,8(14),9,13(17)-tetraene, 4,8(14),9,15-tetraene, 4,8(14),9,16-tetraene, 4,9,11,13(17)-tetraene, 4,9,11,14-tetraene, 4,9,11,15-tetraene, 4,9,11,16-tetraene, 4,9(11),12,14-tetraene, 4,9(11),12,15-tetraene, 4,9(11),12,16-tetraene, 4,11,13(17),14-tetraene, 4,11,13(17),15-tetraene, 4,11,13(17),16-tetraene, 4,12,14,16-tetraene, 4,8,11,13(17)-tetraene, 4,8,11,14-tetraene, 4,8,11,15-tetraene, 4,9,11,13(17)-tetraene, 4,9,11,14-tetraene, 4,9,11,15-tetraene, 4,9,11,16-tetraene, 4,9(11),12,14-tetraene, 4,9(11),12,15-tetraene, 4,9(11),12,16-tetraene, 4,11,13(17),14-tetraene, 4,11,13(17),15-tetraene, 4,11,13(17),16-tetraene, 4,12,14,16-tetraene, 5,7,9,11-tetraene, 5,7,9,12-tetraene, 5,7,9,13(17)-tetraene, 5,7,9,14-tetraene, 5,7,9,15-tetraene, 5,7,9,16-tetraene, 5,8,11,13(17)-tetraene, 5,8,11,14-tetraene, 5,8,11,15-tetraene, 5,8,11,16-tetraene, 5,8(14),9,11-tetraene, 5,8(14),9,12-tetraene, 5,8(14),9,13(17)-tetraene, 5,8(14),9,15-tetraene, 5,8(14),9,16-tetraene, 5,9,11,13(17)-tetraene, 5,9,11,14-tetraene, 5,9,11,15-tetraene, 5,9,11,16-tetraene, 5,9(11),12,14-tetraene, 5,9(11),12,15-tetraene, 5,9(11),12,16-tetraene, 5,11,13(17),14-tetraene, 5,11,13(17),15-tetraene, 5,11,13(17),16-tetraene, 5,12,14,16-tetraene, 5,8,11,13(17)-tetraene, 5,8,11,14-tetraene, 5,8,11,15-tetraene, 5,9,11,13(17)-tetraene, 5,9,11,14-tetraene, 5,9,11,15-tetraene, 5,9,11,16-tetraene, 5,9(11),12,14-tetraene, 5,9(11),12,15-tetraene, 5,9(11),12,16-tetraene, 5,11,13(17),14-tetraene, 5,11,13(17),15-tetraene, 5,11,13(17),16-tetraene, 5,12,14,16-tetraene, 5(10),8,11,13(17)-tetraene, 5(10),8,11,14-tetraene, 5(10),8,11,15-tetraene, 5(10),8,11,16-tetraene, 5(10),8(14),9,11-tetraene, 5(10),8(14),9,12-tetraene, 5(10),8(14),9,13(17)-tetraene, 5(10),8(14),9,15-tetraene, 5(10),8(14),9,16-tetraene, 5(10),9,11,13(17)-tetraene, 5(10),9,11,14-tetraene, 5(10),9,11,15-tetraene, 5(10),9,11,16-tetraene, 5(10),9(11),12,14-tetraene, 5(10),9(11),12,15-tetraene, 5(10),9(11),12,16-tetraene, 5(10),11,13(17),14-tetraene, 5(10),11,13(17),15-tetraene, 5(10),11,13(17),16-tetraene, 5(10),12,14,16-tetraene, 5(10),8,11,13(17)-tetraene, 5(10),8,11,14-tetraene, 5(10),8,11,15-tetraene, 5(10),9,11,13(17)-tetraene, 5(10),9,11,14-tetraene, 5(10),9,11,15-tetraene, 5(10),9,11,16-tetraene, 5(10),9(11),12,14-tetraene, 5(10),9(11),12,15-tetraene, 5(10),9(11),12,16-tetraene, 5(10),11,13(17),14-tetraene, 5(10),11,13(17),15-tetraene, 5(10),11,13(17),16-tetraene, 5(10),12,14,16-tetraene, 6,8,11,13(17)-tetraene, 6,8,11,14-tetraene, 6,8,11,15-tetraene, 6,8,11,16-tetraene, 6,9,11,13(17)-tetraene, 6,9,11,14-tetraene, 6,9,11,15-tetraene, 6,9,11,16-tetraene, 6,9(11),12,14-tetraene, 6,9(11),12,15-tetraene, 6,9(11),12,16-tetraene, 6,11,13(17),14-tetraene, 6,11,13(17),15-tetraene, 6,12,14,16-tetraene, 7,9,11,13(17)- tetraene, 7,9,11,14-tetraene, 7,9,11,15-tetraene, 7,9,11,16-tetraene, 7,9(11),12,14-tetraene, 7,9(11),12,15-tetraene, 7,9(11),12,16-tetraene, 8,11,13(17),14-tetraene, 8,11,13(17),15-tetraene, 8(14),9,11,13(17)-tetraene, 8(14),9,11,15-tetraene, 8(14),9,11,16-tetraene, 9,11,13(17),14-tetraene, 9,11,13(17),15-tetraene, 9(11),12,14,16-tetraene, 11,13(17),14,16-tetraene, 1,3,5(10),6,8-pentaene, 1,3,5(10),6,9(11)-pentaene, 1,3,5(10),6,11-pentaene, 1,3,5(10),6,12-pentaene, 1,3,5(10),6,13(17)-pentaene, 1,3,5(10),6,14-pentaene, 1,3,5(10),6,15-pentaene, 1,3,5(10),6,16-pentaene, 1,3,5(10),7,9(11)-pentaene, 1,3,5(10),7,11-pentaene, 1,3,5(10),7,12-pentaene, 1,3,5(10),7,13(17)-pentaene, 1,3,5(10),7,14-pentaene, 1,3,5(10),7,15-pentaene, 1,3,5(10),7,16-pentaene, 1,3,5(10),8,11-pentaene, 1,3,5(10),8,12-pentaene, 1,3,5(10),8,13(17)-pentaene, 1,3,5(10),8,14-pentaene, 1,3,5(10),8,15-pentaene, 1,3,5(10),8,16-pentaene, 1,3,5(10),8(14),9(11)-pentaene, 1,3,5(10),8(14),11-pentaene, 1,3,5(10),8(14),12-pentaene, 1,3,5(10),8(14),13(17)-pentaene, 1,3,5(10),8(14),15-pentaene, 1,3,5(10),8(14),16-pentaene, 1,3,5(10),9(11),12-pentaene, 1,3,5(10),9(11),13(17)-pentaene, 1,3,5(10),9(11),14-pentaene, 1,3,5(10),9(11),15-pentaene, 1,3,5(10),9(11),16-pentaene, 1,3,5(10),11,13(17)-pentaene, 1,3,5(10),11,14-pentaene, 1,3,5(10),11,15-pentaene, 1,3,5(10),11,16-pentaene, 1,3,5(10),12,14-pentaene, 1,3,5(10),12,15-pentaene, 1,3,5(10),12,16-pentaene, 1,3,5(10),13(17),14-pentaene, 1,3,5(10),13(17),15-pentaene or a 1,3,5(10),14,16-pentaene androstene.

As is apparent from the F1C structure, when a double bond is present at a given position in any of these androstenes, one or two variable groups at the steroid ring atoms will be absent. Thus, when a double bond is present at the 16-position, one $R^3$ and one $R^4$ will be absent, when a double bond is present at the 5-position, $R^{10}$ at the 5-position will be absent, when a double bond is present at the 5(10)-position, $R^{10}$ at the 5-position and $R^6$ will be absent as shown in the structures or when a double bond is present at the 5(10)- and 6-positions, $R^{10}$ at the 5-position, $R^6$ and one $R^2$ will be absent as shown in the structures

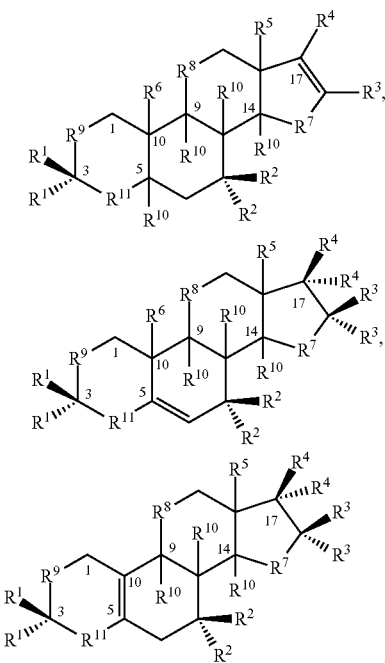

and

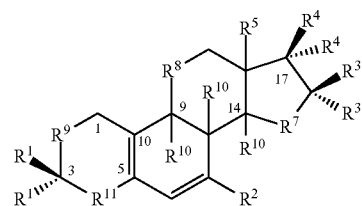

wherein 0, 1, 2, 3 or 4 additional double bonds are present in the rings.

In some embodiments, the formula 1 compound contains no double bonds and is a 5α- or 5β-androstane compound or an analog thereof. Reference to a 1-ene compound means that a double bond is present at the 1-2 position, reference to a 5-ene or a 5(6)-ene compound means that a double bond is present at the 5-6 position, reference to a 5(10)-ene compound means that a double bond is present at the 5-10 position, while reference to a 5(10),16-diene compound means that a double bond is present at the 5-10 and at the 16-17 positions. Similarly, reference to a 13(17) double bond means a double bond is between the 13- and 17-positions and reference to a 9(11) double bond means a double bond is between the 9- and 11-positions, while a 9 and a 9(10) double bond means a double bond is between the 9- and 10-positions. Other double bond positions in the steroid rings are defined in an analogous manner. When a compound such as an androstane or an androstene without a double bond at the 5-position is described, the hydrogen atom or other substituent at the 5-position will be in the α-configuration, unless specified otherwise explicitly or by context. When the hydrogen atom or other substituent at the 5-position is in the β-configuration, the compound name or description will usually specify this. Thus, for 3α-amino-16α,17β-dihydroxyandrostane, 3β-amino-16α,17β-dihydroxyandrostane or 3α-amino-16α,17β-dihydroxyandrost-1,9(11)-diene the hydrogen atom at the 5-position is in the α-configuration. Similarly, for 3α-amino-16α,17β-dihydroxy-5β-androstane, 3β-amino-16α,17β-dihydroxy-5β-androstane or 3α-amino-16α,17β-dihydroxy-5β-androst-1,9(11)-diene the hydrogen atom at the 5-position is in the β-configuration. Other classes of compounds are defined in an analogous manner.

F1Cs include compounds having the structure 5, 6, 7, 8, 9 and 10,

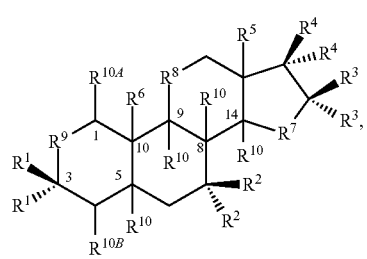

-continued

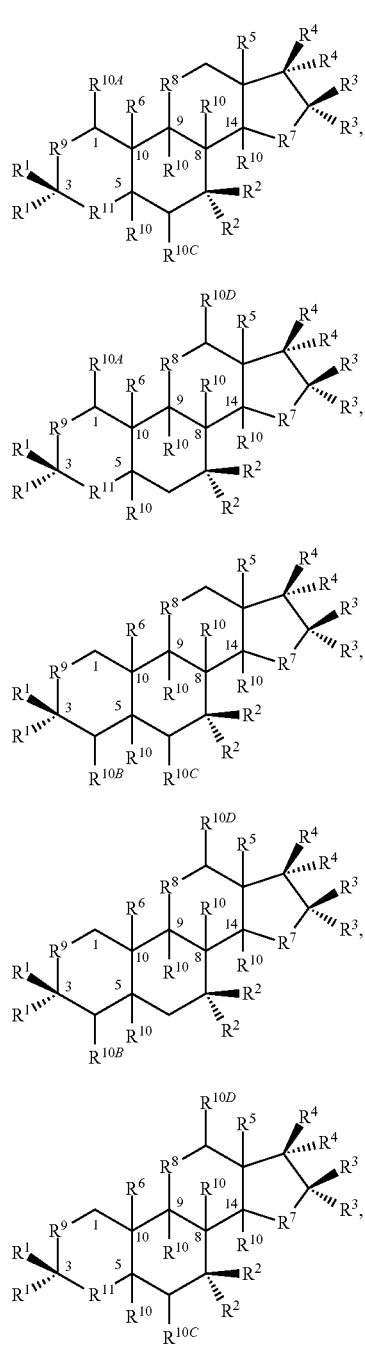

6

7

8

9

10 or a metabolic precursor, a metabolite, salt or tautomer thereof, wherein there is 0, 1, 2, 3, 4 or 5 double bonds in the steroid rings at the 1-, 2-, 3-, 4-, 5-, 5(10), 6-, 7-, 8-, 8(14)-, 9-, 9(11)-, 11-, 12-, 13(17)-, 14-, 15- or 16-positions; each $R^1$, $R^2$, $R^3$, $R^4$, $R^{10}$ at the 2, 11 and 15 positions, $R^{10A}$, $R^{10B}$, $R^{10C}$ and $R^{10D}$ independently are —H, —OH, —OR$^{PR}$, —SR$^{PR}$, —SH, —N(R$^{PR}$)$_2$, —NHR$^{PR}$, —NH$_2$, —NO$_2$, —ONO$_2$, —O—Si—(R$^{13}$)$_3$, —CHO, —CHS, —CN, —SCN, —NO$_2$, —COOH, —COOR$^{PR}$, —OSO$_3$H, —OPO$_3$H$_2$, =O, =S, =N—OH, =N—OCH$_3$, =CH$_2$, =CH—CH$_3$, an ester, a thioester, or another R$^{10}$ moiety described herein, or, one or more of two adjacent R$^1$-R$^4$, R$^{10}$, R$^{10A}$, R$^{10B}$, R$^{10C}$ and R$^{10D}$ are an independently selected epoxide or cyclopropyl ring; $R^5$, $R^6$ and $R^{10}$ at the 5 (if present), 8, 9 and 14 positions independently are $R^{10}$ moieties described herein, e.g., —H, —CH$_3$, —C$_2$H$_5$, —OH, —OR$^{PR}$, —SR$^{PR}$, —N(R$^{PR}$)$_2$, —O—Si—(R$^{13}$)$_3$, —CHO, —CHS, —CN, —SCN, —N$_3$, —COOH, —OS(O)(O)OH, an ester, a thioester, a halogen, optionally substituted alkyl, or, one, two or more of $R^5$, $R^6$ and $R^{10}$ at the 5, 8, 9 and 14 positions, together with a carbon atom that is adjacent to the carbon to which the $R^5$, $R^6$ or $R^{10}$ at the 5-, 8-, 9- or 14-position is bonded are an independently selected epoxide or cyclopropyl ring; $R^7$ is —C(R$^{10}$)$_2$—, —C(R$^{10}$)$_2$—C(R$^{10}$)$_2$—, —O—, or another $R^7$ moiety described herein; $R^8$ and $R^9$ independently as previously described; $R^{13}$ independently is C$_{1-6}$ alkyl; and R$^{PR}$ independently are —H, a protecting group or together are a protecting group, wherein 0, 1, 2, 3 or 4 of $R^{10A}$, $R^{10B}$, $R^{10C}$ and $R^{10D}$ are —H, $R^5$ and $R^6$ respectively are in the β,β, α,β, β,α or α,α configurations, and wherein, $R^{10}$ moieties at the 5 (if present), 8, 9 and 14 positions respectively are in the α,α,α,α, α,α,α,β, α,α,β,α, α,β,α,α, β,α,α,α, α,α,β,β, α,β,α,β, β,α,α,β, β,α,β, α, β,β,α,α, α,β,β,α, α,β,β,β, β,α,β,β, β,β,α,β, β,β,β,α or β,β,β,β configurations. For any of the F1Cs of structure 5, 6, 7, 8, 9 or 10 where two variable groups are bonded to the same carbon, e.g., $R^1$, $R^2$, $R^3$, $R^4$ or $R^{10}$ at the 11 position, each variable group at that position is independently selected.

In the F1Cs, each $R^1$, $R^2$, $R^3$, $R^4$, $R^{10}$ at the 2, 11 and 15 positions, is independently selected. In some embodiments one of the $R^1$, $R^2$, $R^3$, $R^4$, $R^{10}$ at the 2, 11 and 15 positions is hydrogen and the other is —H another moiety, but usually 2, 3, 4, 5 or 6 of the remaining variable groups are not —H, i.e., they are another moiety as defined for those groups. In other embodiments, both $R^1$, $R^2$, $R^3$, $R^4$, $R^{10}$ at the 2, 11 and 15 positions, are independently selected moieties other than hydrogen, i.e., they are another moiety as defined for those groups such as a C1-C20 organic moiety or C1-C20 optionally substituted alkyl group. In many embodiments $R^1$ at the 1-position in the β-configuration or $R^1$ at the 1-position in the α-configuration is not —H and $R^4$ at the 1-position in the β-configuration or $R^1$ at the 1-position in the α-configuration is not —H.

F1Cs include compounds having structure 2

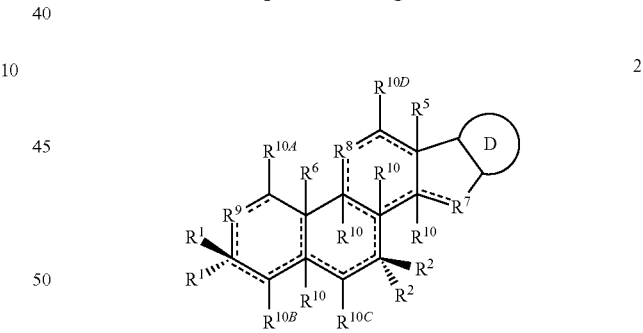

2 wherein, each $R^1$, $R^2$, $R^3$, $R^4$, $R^5$, $R^6$, $R^7$, $R^8$, $R^9$, $R^{10}$ at the 2, 5, 8, 9, 11, 14 and 15 positions, $R^{10A}$, $R^{10B}$, $R^{10C}$ and $R^{10D}$ are each independently chosen and have the meanings given above for compounds of structure 5, 6, 7, 8, 9 or 10;

$R^3$ and $R^4$ are, if present, both in the α-configuration or the β-configuration or one of $R^3$ and $R^4$ is in the α-configuration and the other is in the β-configuration;

D is a heterocycle, a 4-, 5-, 6- or 7-membered carbon ring, or two fused rings, each being 4-, 5-, 6- or 7-membered carbon ring, wherein 1, 2 or 3 ring carbon atoms of the 4-, 5-, 6- or 7-membered carbon ring(s) are optionally independently substituted with substituents described for substituted alkyl groups, e.g., —O—, —S— or —NR$^{PR}$— or where 1, 2 or 3 hydrogen atoms of the heterocycle or where 1, 2 or 3 hydrogen atoms of the 4-, 5-, 6- or 7-membered ring are substituted with —$OR^{PR}$, —$SR^{PR}$, —$N(R^{PR})_2$, —O—Si—$(R^{13})_3$, —CHO, —CHS, —CN, —$NO_2$, —$OSO_3H$, —$OPO_3H_2$, =O, =S, =N—OH, =$CH_2$ or a spiro ring an ester, a thioester, a thionoester, a phosphoester, a phosphothioester, a phosphonoester, a phosphiniester, a sulfite ester, a sulfate ester, a sulfoxide, a sulfamate, a sulfonate, a sulfamide, a sulfinamide, a sulfurous diamide, an amide, an amino acid, a peptide, an ether, a thioether, an acyl group, a thioacyl group, a carbonate, a carbamate, an acetal, a thioacetal, a halogen, optionally substituted alkyl, optionally substituted alkenyl, optionally substituted alkynyl, an optionally substituted aryl moiety, an optionally substituted heteroaryl moiety, an optionally substituted monosaccharide, an optionally substituted oligosaccharide, a nucleoside, a nucleotide or a polymer.

In some embodiments, the D structure comprises two 5- or 6-membered rings, wherein the rings are fused or are linked by 1 or 2 bonds, wherein 0, 1, 2 or 3 of $R^7$, $R^8$ and $R^9$ are not —$CHR^{10}$— or —$C(R^{10})_2$—.

Exemplary F1C of structure 2 include the following structures,

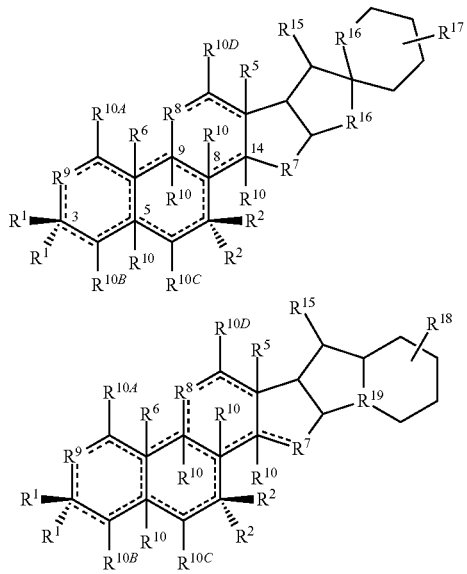

wherein, $R^{16}$ independently are —$CH_2$—, —O—, —S— or —NH—; $R^{15}$, $R^{17}$ and $R^{18}$ are independently selected $R^1$ moieties, e.g., —H, —OH, —$OR^{PR}$, =O, —$SR^{PR}$, =S, —O—Si—$(R^{13})_3$, ester, ether, acyl, halogen or optionally substituted alkyl; and $R^{19}$ is nitrogen or CH; $R^1$-$R^{10}$, $R^{10A}$, $R^{10B}$, $R^{10C}$ and $R^{10D}$ are each independently chosen and have the meanings given above for compounds of structure 5, 6, 7, 8, 9 or 10; $R^{10}$ moieties at the 5 (if present), 8, 9 and 14 positions respectively are in the α,α,α,α, α,α,α,β, α,α,β,α, α,β,α,α, β,α,α,α, α,α,β,β, α,β,α,β, β,α,α,β, β,α,β,α, β,β,α,α, α, α,β,β,α, α,β,β,β, β,α,β,β, β,β,α,β, β,β,β,α or β,β,β,β, configurations; and $R^5$ and $R^6$ are in the β,β, β,α, α,β or α,α configurations. For F1Cs of structure 2 where two variable groups are bonded to the same carbon, e.g., $R^1$ at the 3-position, $R^2$ at the 7-position or $R^{10}$ at the 11-position, the each variable group at that position is independently selected. As shown in the structure, the $R^{17}$ moiety can be bonded to the ring carbon adjacent to $R^{16}$, or it can be bonded to the adjacent 1, 2 or 3 ring carbons. Similarly, the $R^{18}$ moiety can be bonded to the ring carbon adjacent to $R^{19}$, or it can be bonded to the adjacent 1, 2 or 3 ring carbons. Structure 2 F1Cs can have 1, 2, 3 or 4 of $R^{10A}$, $R^{10B}$, $R^{10C}$ and $R^{10D}$ as —H, but usually 2 or 3 of $R^{10A}$, $R^{10B}$, $R^{10C}$ and $R^{10D}$ are —H.

Structure 2 compounds include structures wherein one, two or three of $R^7$, $R^8$ and $R^9$ are independently —O—, —S—, or —NH— or wherein one or both of $R^5$ and $R^6$ independently are —H, —$CH_3$, —$CH_2OR^{PR}$, —$CH_2OH$, —$CH_2SH$, —$CH_2SR^{PR}$, —$CH_2$O—C(O)—$C_{1-10}$ alkyl, —$CH_2$S—C(O)—$C_{1-10}$ alkyl, —$CH_2$O—C(O)—$C_{1-10}$ alkenyl, —$CH_2$S—C(O)—$C_{1-10}$ alkenyl, —$CH_2$O—C(O)—$C_{0-4}$ alkyl-heterocycle, —$CH_2$S—C(O)—$C_{0-4}$ alkyl-heterocycle, —$CH_2$O—C(O)—$C_{0-4}$ alkyl-phenyl, —$CH_2$S—C(O)—$C_{0-4}$ alkyl-phenyl, wherein any $C_{1-10}$ alkyl, heterocycle or phenyl moiety is optionally substituted with one or more substituents, wherein the one or more substituents are one, two, three or more independently selected —O—, =O, —$OR^{PR}$, —S—, =S, —$SR^{PR}$, —NH—, —$N(R^{PR})_2$ or —C(O)—NH—, wherein each $R^{PR}$ independently is —H or a protecting group.

The structure 2 compounds described above include

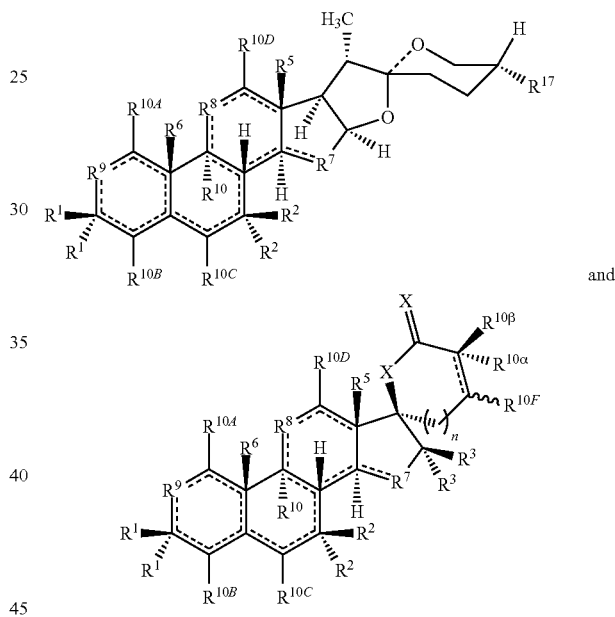

and where X independently are O or S, typically both X are O, $R^{10α}$ is an independently selected $R^{10}$ moiety in the α-configuration, or if a double bond is present, $R^{10α}$ is absent, $R^{10β}$ is an independently selected $R^{10}$ moiety in the β-configuration, $R^{10F}$ is an independently selected $R^{10}$ moiety in the α- or β-configuration, n is 0, 1 or 2, and remaining variable groups are as defined above. These compounds include ones where $R^1$ in the α- and β-configurations independently are an $R^1$ moiety such as H, OH, halogen, an optionally substituted monosaccharide, an optionally substituted disaccharide or a dicarboxylic acid ester such as —OC(O)—$(CH_2)_2$—COOH, —OC(O)—$(CH_2)_3$—COOH or —OC(O)—$(CH_2)_4$—COOH, $R^2$ in the α- and β-configurations independently are an $R^2$ moiety such as —H, —OH, =O, —SH, =S, halogen, optionally substituted alkyl, a monosaccharide or a disaccharide, $R^5$ is C1-C4 alkyl, $R^6$ is —H, halogen or C1-C4 alkyl or $R^7$ and $R^8$ independently are moieties as previously defined such as independently selected —$CH_2$—, —CH(α-$OR^{PR}$)—, —CH(β-$OR^{PR}$)—, —C(O)— or —O—, $R^9$ is a moiety as previously defined such as —$CH_2$—, —CH(α-halogen)-, —CH(α-OH)—, —CH(α-optionally substituted alkyl)-, —C(halogen)$_2$—, —C(β-optionally substituted alkyl)(α-OH)—, —CH(α-optionally substituted alkyl)-, $R^{10}$ at the 9-position is a $R^{10}$ moiety such as —H, —F, —Cl, or optionally substituted alkyl, $R^{PR}$ is —H or a protecting group such as an ester or optionally substituted alkyl and other variable groups are as previously defined. For any of these compounds, 1, 2, 3 or 4 of $R^{10A}$, $R^{10B}$, $R^{10C}$ and $R^{10D}$ may be substituted, or they all be —H, while $R^{17}$ may be a moiety defined previously such as C1-C6 optionally substituted alkyl, e.g., —CH$_3$ or —C$_2$H$_5$.

Monosaccharides and disaccharides are described above and are optionally bonded at one or more of $R^1$ or other variable groups in these structure 2 or other formula 1 compounds include

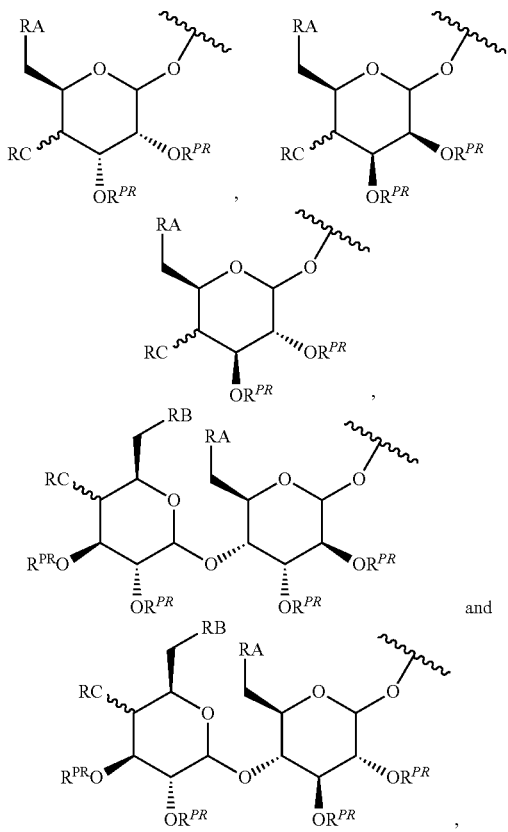

where RA and RB independently are —H, —OH, halogen, —NH$_2$, —NHR$^{PR}$, —N$_3$, C1-C6 alkoxy or —RD-RE, RC is —H, —OH, halogen, —NH$_2$, —NHR$^{PR}$, —N$_3$, C1-C6 alkoxy or a monosaccharide or disaccharide linked through a glycosidic bond, RD is —NH—C(O)—, —O—C(O)—, —O—C(O)—N(R$^{PR}$)—, —NH—C(O)—N(R$^{PR}$)—, —O—C(S)—N(R$^{PR}$)— or —O—C(O)—N—(R$^{PR}$)—, RE is aryl, arylalkyl, alkenyl, alkyl, cycloalkyl or cycloalkylalkyl, where each RE is optionally independently substituted with 1, 2 or 3 independently selected halogens, —OH, =O, —SH, =S, —NO$_2$, —CF$_3$, C1-C6 alkyl, phenoxy, C1-C6 alkoxy, methylenedioxy, C1-C6 alkylsulfanyl, C1-C6 alkylsulfinyl, C1-C6 alkylsulfonyl, dimethylamino, mono- or di-C1-C6 alkylaminocarbonyl, C1-C6 alkylcarbonyl, C1-C6 alkoxycarbonyl or pyrrolidinylcarbonyl, $R^{PR}$ independently is —H or a protecting group such as C1-C6 optionally substituted alkyl, ester such as acetate or, if bonded to nitrogen, $R^{PR}$ together with the nitrogen to which it is attached is pyrrolidinyl, piperidinyl, N-methylpiperazinyl, indolinyl or morpholinyl, where the cyclic group may be monosubstituted on a carbon atom with C1-C6 alkoxycarbonyl or C1-C6 optionally substituted alkyl. In some of these embodiments, RA, RB and RC are —OH.

F1C variable groups may include one or more independently chosen moieties such as —O—CHR$^{24}$C(O)OR$^{25}$, —S—CHR$^{24}$C(O)OR$^{25}$, —NH—CHR$^{24}$C(O)OR$^{25}$, —O—CHR$^{24}$C(S)OR$^{25}$, —S—CHR$^{24}$C(S)OR$^{25}$, —NH—CHR$^{24}$C(S)OR$^{25}$, —O—CHR$^{24}$OC(O)R$^{25}$, —S—CHR$^{24}$OC(O)R$^{25}$, —NH—CHR$^{24}$OC(O)R$^{25}$, —O—CHR$^{24}$C(O)N(R$^{25}$)$_2$, —S—CHR$^{24}$C(O)N(R$^{25}$)$_2$, —NH—CHR$^{24}$C(O)N(R$^{25}$)$_2$, —O—CHR$^{24}$OR$^{25}$, —S—CHR$^{24}$OR$^{25}$, —NH—CHR$^{24}$OR$^{25}$, —O—CHR$^{24}$C(R$^{25}$)$_2$CH$_2$OX, —S—CHR$^{24}$C(R$^{25}$)$_2$CH$_2$OX, —NH—CHR$^{24}$C(R$^{25}$)$_2$CH$_2$OX, —O—CHR$^{24}$C(R$^{25}$)$_2$OX, —S—CHR$^{24}$C(R$^{25}$)$_2$OX, —NH—CHR$^{24}$C(R$^{25}$)$_2$OX, —C(O)—NHR$^{24}$ or —CH$_2$—NHR$^{24}$ groups that one or more of $R^1$-$R^6$, $R^{10}$, $R^{15}$, $R^{17}$ and $R^{18}$ comprise. For these moieties, $R^{24}$ independently are —H, —CH$_2$—C$_6$H$_5$, —CH$_2$CH$_2$—C$_6$H$_5$, C$_{1-8}$ alkyl, C$_{2-8}$ alkenyl, aryl or heterocycle where each alkyl, alkenyl, aryl and heterocycle moiety is independently optionally substituted with 1, 2, or 3, usually 1, —O—, —S—, —NH—, halogen, aryl, —OX, —SX, —NHX, ketone (=O) or —CN moieties or the C$_{1-8}$ alkyl is optionally substituted with 3, 4, 5 or 6 halogens, and X is —H or a protecting group. Exemplary $R^{24}$ are —H, —CH$_3$, —C$_2$H$_5$, —C(CH$_3$)$_3$, —CH$_2$—C$_{1-5}$ optionally substituted alkyl, —CH$_2$CH$_2$—C$_{1-4}$ optionally substituted alkyl and —CH$_2$CH$_2$—O—C$_{1-4}$ optionally substituted alkyl. $R^{25}$ independently are —H or a C$_{1-30}$ organic moiety such as —CH$_2$—C$_6$H$_5$, —CH$_2$CH$_2$—C$_6$H$_5$, C$_{1-12}$ alkyl, C$_{2-12}$ alkenyl, C$_{2-12}$ alkynyl, aryl, a heterocycle, —CH$_2$-heterocycle or —CH$_2$-aryl, where each alkyl, alkenyl, alkynyl, aryl, heterocycle, —CH$_2$-heterocycle or —CH$_2$-aryl moiety is independently optionally substituted with 1 or 2, usually 1, —O—, —S—, —NH—, halogen, aryl, —OX, —SX, —NHX, ketone (=O), —C(O)OX or —CN moieties or the C$_{1-12}$ alkyl, C$_{2-12}$ alkenyl or aryl, are optionally independently substituted with 3, 4, 5 or 6 halogens, where X is —H or a protecting group, or the aryl, heterocycle, —CH$_2$-heterocycle or —CH$_2$-aryl moieties are optionally independently substituted with 1, 2 or 3 C$_{1-4}$ alkyl moieties or with 1, 2 or 3 C$_{1-4}$ alkoxy moieties at the aryl moiety or at the heterocycle, usually at a ring carbon. Exemplary $R^{25}$ are —H, —CH$_3$, —C$_2$H$_5$, —C$_3$H$_7$, —C$_4$H$_9$, —C$_6$H$_{13}$, —C$_6$H$_5$, —C$_6$H$_4$OH, —C$_6$H$_4$OCH$_3$, —C$_6$H$_4$F, —CH$_2$—C$_{1-5}$ optionally substituted alkyl, —CH$_2$CH$_2$—(S)$_{0-1}$—C$_{1-4}$ optionally substituted alkyl and —CH$_2$CH$_2$—O—C$_{1-4}$ optionally substituted alkyl.

For any F1C, whenever a variable moiety such as $R^7$, $R^8$ or $R^9$ or a substitution at a variable group includes moieties such as —O—CHR$^{10}$—, —NR$^{PR}$—CHR$^{10}$—, or =N— it is intended that such moieties can be present in either orientation relative to the other ring atoms that may be present, i.e., —O—CHR$^{10}$—, —NR$^{PR}$—CHR$^{10}$—, —CHR$^{10}$—O—, —CHR$^{10}$—NR$^{PR}$—, =N— and —N= are all included, unless defined or implied otherwise by the structure.

Invention embodiments include a composition comprising a F1C and 1, 2, 3, 4 or more nonaqueous liquid excipients. These compositions can contain less than about 3% w/v water, less than about 2% w/v water, less than about 1.5% w/v water, less than about 1% w/v water, less than about 0.8% w/v water, less than about 0.5% w/v water, less than about 0.3% w/v water or less than about 0.1% w/v water. Typically, the nonaqueous liquid excipients include propylene glycol and a PEG or a PEG mixture and can optionally include one or both of benzyl alcohol and benzyl benzoate.

Embodiments of F1Cs include or exclude any subset of compounds within the definition of formula 1, provided that at least one F1C remains. For example, a subset of F1Cs that are may be included, for example in the invention nonaqueous formulations and in the invention intermittent dosing protocols and immune modulation methods, are (1) F1Cs where $R^2$ is hydroxyl, or a group that can hydrolyze or metabolize to hydroxyl or thiol, in either configuration and $R^5$ and $R^6$ are methyl in the β-configuration or (2) any 1, 2, 3, 4, 5, 6 or more of the F1Cs or genera of compounds that are disclosed herein. Another group of compounds that are optionally excluded from F1Cs comprises one or all compounds that are disclosed in one or more prior art references or publications, e.g., one or more compounds that are disclosed in one or more of the references cited herein.

Other embodiments of species and genera of F1Cs include compounds of structures B, C, D, E, F and G B
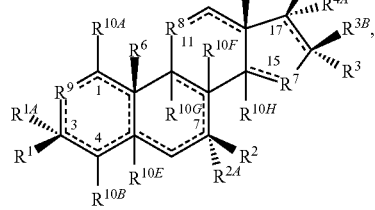

C
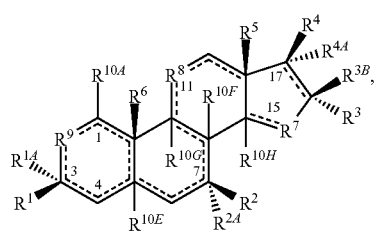

D
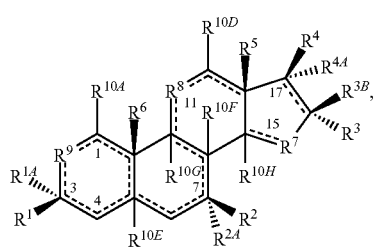

E
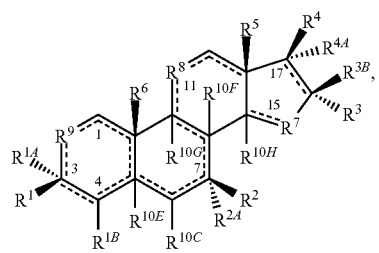

F
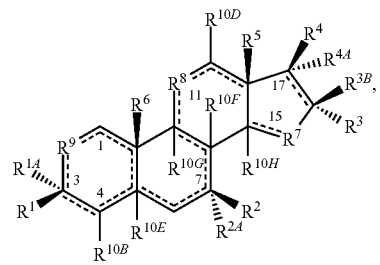

G
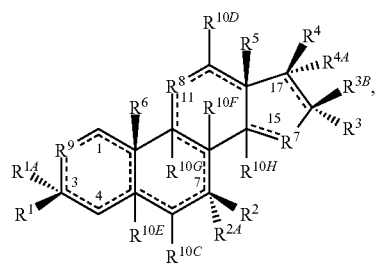

where the dotted lines represent double or single bonds, each $R^{10A}$, $R^{10B}$, $R^{10C}$, $R^{10D}$, $R^{10E}$ (when present), $R^{10F}$, $R^{10G}$ and $R^{10H}$ is an independently selected single bonded $R^{10}$ moiety in the α-configuration or the β-configuration, or each $R^{10A}$, $R^{10B}$, $R^{10C}$ and $R^{10D}$ is an independently selected double bonded $R^{10}$ moiety (e.g., =O or =CH$_2$), $R^{1A}$ is a single bonded $R^1$ moiety in the α-configuration, or $R^{1A}$ together with $R^1$ is a double bonded moiety (e.g., =O, =NOH, =CH$_2$ or =CH—CH$_3$), $R^{2A}$ is a single bonded $R^2$ moiety in the α-configuration, or $R^{2A}$ together with $R^2$ is a double bonded moiety, $R^{3B}$ is a single bonded $R^3$ moiety in the β-configuration, or $R^{3B}$ together with $R^3$ is a double bonded moiety, or $R^{3B}$ is absent if a double bond is present at the 16-17 position, $R^{4A}$ is a single bonded $R^4$ moiety in the α-configuration, or $R^{4A}$ together with $R^4$ is a double bonded moiety, or $R^{4A}$ is absent if a double bond is present at the 16-17 position, and $R^5$, $R^6$, $R^7$, $R^8$ and $R^9$ are as previously defined. When a double bond is present at the 4-5 or the 5-6 positions, $R^{10E}$ is absent. For these structures, $R^{10A}$, $R^{10B}$, $R^{10C}$ and $R^{10D}$ may be in the α,α, α,β, β,α, or β,β configurations respectively, while $R^{10E}$, $R^{10F}$, $R^{10G}$ and $R^{10H}$ may be in the α,α,α,α, α,α,α,β, α,α,β,α, α,β,α,α, β,α,α,α, α,α,β,β, α,β,α,β, β,α,α,β, β,α,β,α, β,β,α,α, α,β,β,α, α,β,β,β, β,α,β,β, β,β,α,β, β,β,β,α or β,β,β,β configurations respectively, typically the α,β,α,α or β,β,α,α configurations.

Thus, when $R^{10E}$, $R^{10F}$, $R^{10G}$ and $R^{10H}$ respectively are in the α,β,α,α configurations and $R^{10A}$ and $R^{10B}$ or $R^{10A}$ and $R^{10C}$ or $R^{10A}$ and $R^{10D}$ or $R^{10B}$ and $R^{10C}$ or $R^{10B}$ and $R^{10D}$ or $R^{10C}$ and $R^{10D}$ are both in α-configurations exemplary B, C, D, E, F and G structures with 0, 1, 2, 3, 4 or 5 double bonds in the steroid rings include

B

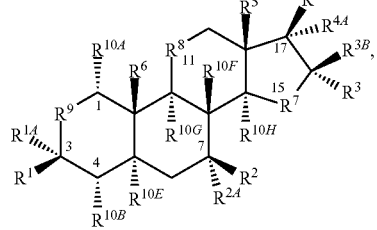

C

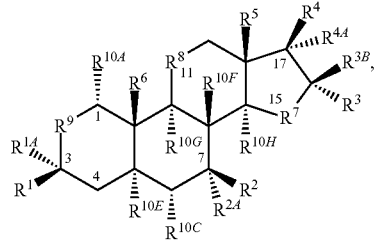

D

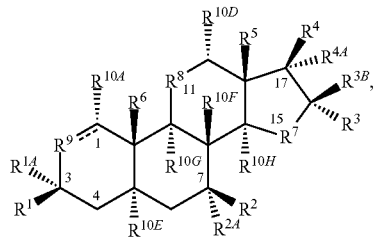

E

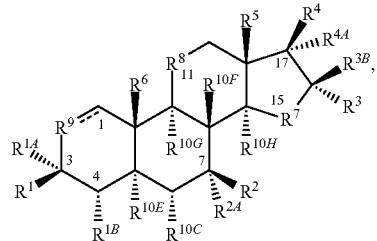

F

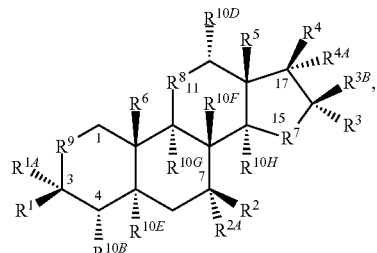

G

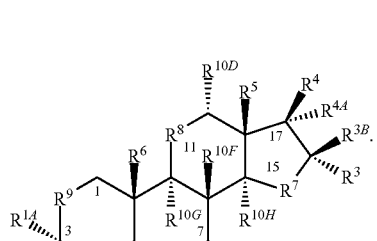
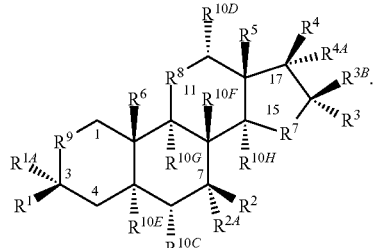

Similarly, when $R^{10E}$, $R^{10F}$, $R^{10G}$ and $R^{10H}$ respectively are in the $\alpha,\beta,\alpha,\alpha$ configurations and $R^{10A}$ and $R^{10B}$ or $R^{10A}$ and $R^{10C}$ or $R^{10A}$ and $R^{10D}$ or $R^{10B}$ and $R^{10C}$ or $R^{10B}$ and $R^{10D}$ or $R^{10C}$ and $R^{10D}$ respectively are in the $\beta,\alpha$ configurations exemplary B, C, D, E, F and G structures with 0, 1, 2, 3, 4 or 5 double bonds in the steroid rings include

B

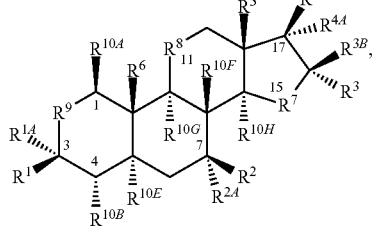
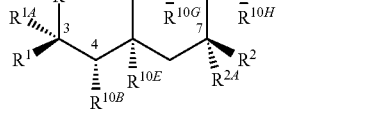

C

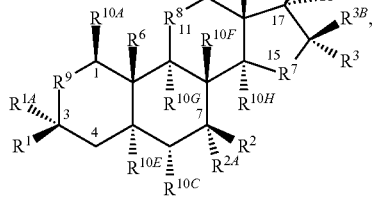

D

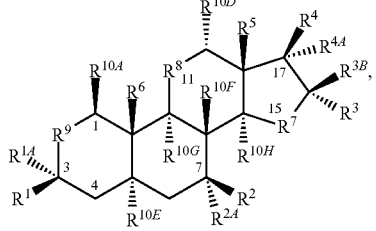

E

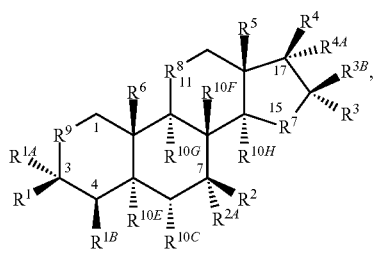

F

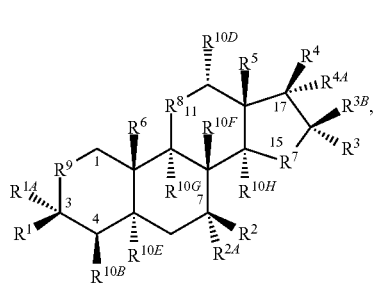

G
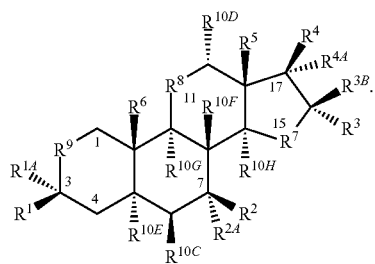
When $R^{10E}$, $R^{10F}$, $R^{10G}$ and $R^{10H}$ respectively are in the β,β,α,α configurations exemplary B, C, D, E, F and G structures with one, two or more optional double bonds at 3, 4, 5(6), 5(10), 6, 7, 8(9), 8(14), 11, 12, 13(17) and/or 14 include
B
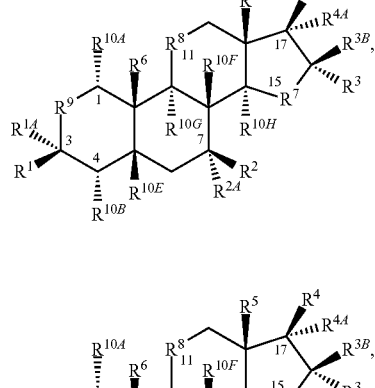
C
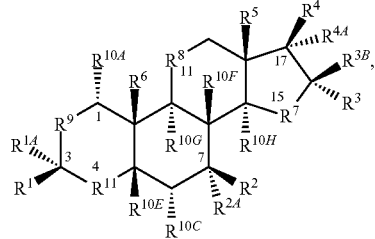
D
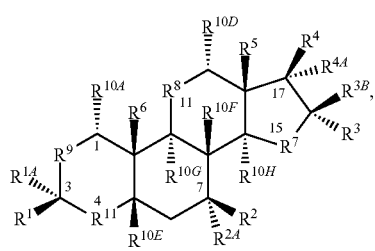
E
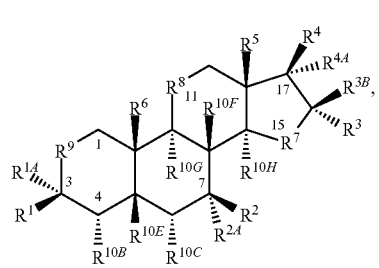
F
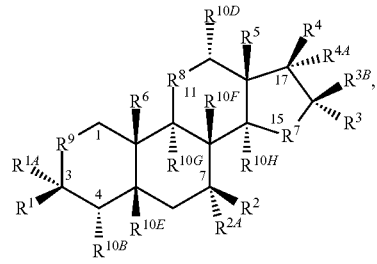
G
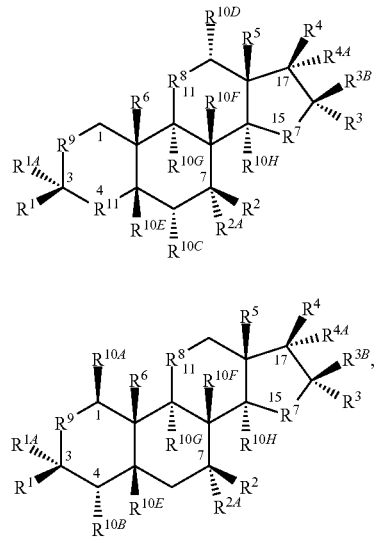
B
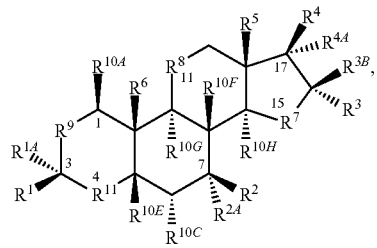
C
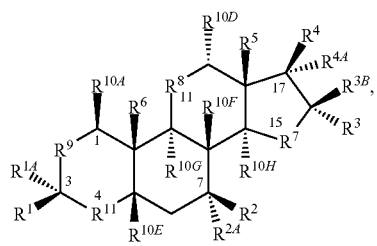
D
E 51
-continued
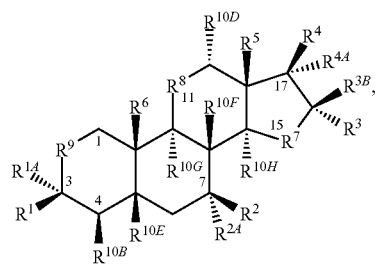
F
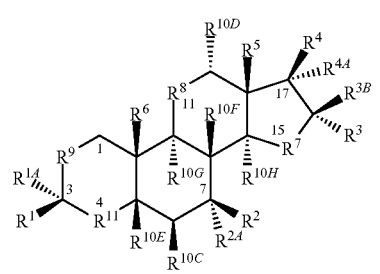
G
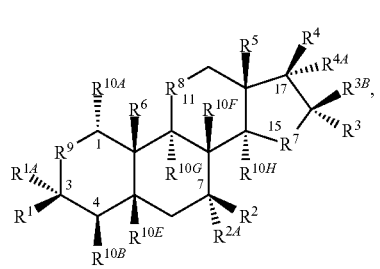
B
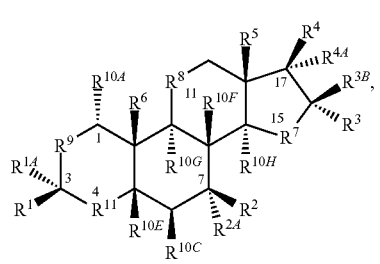
C
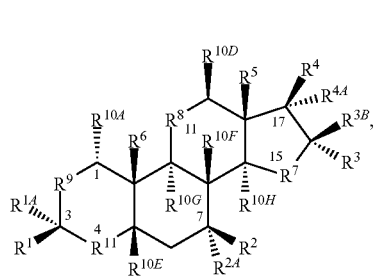
D
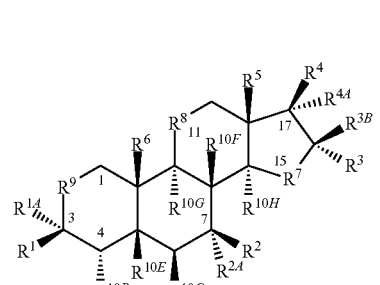
E
52
-continued
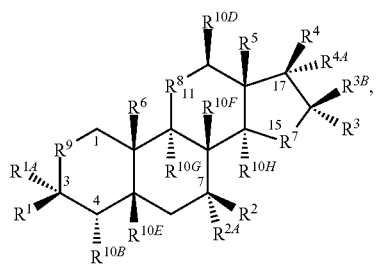
F
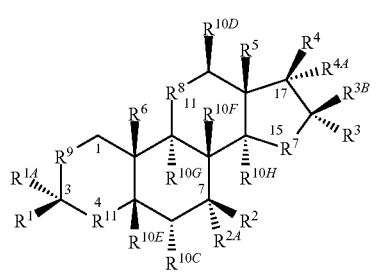
G
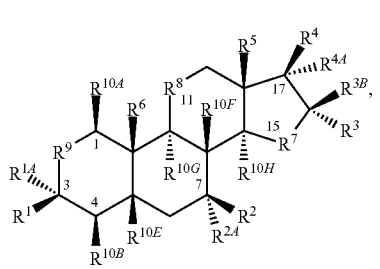
B
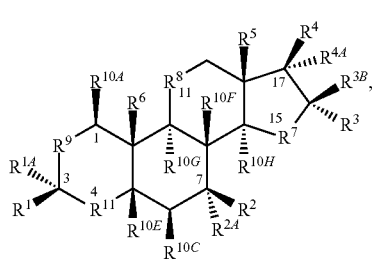
C
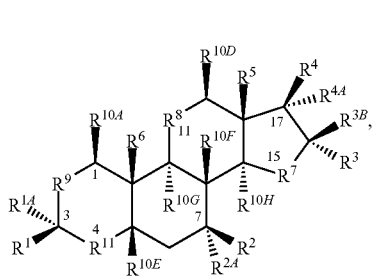
D
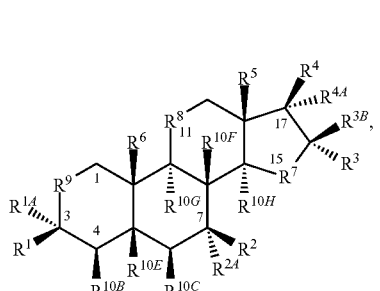
E

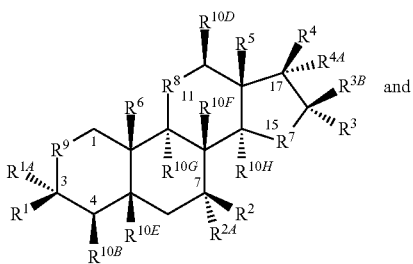
F and

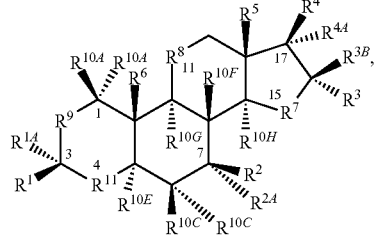

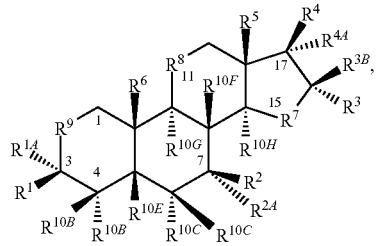

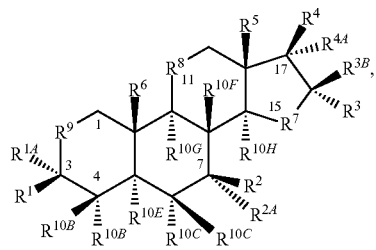

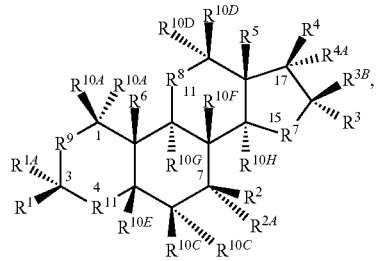

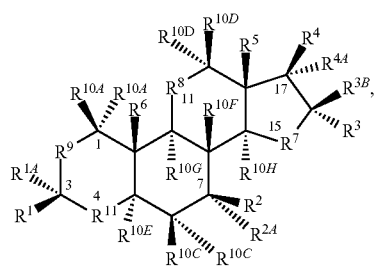

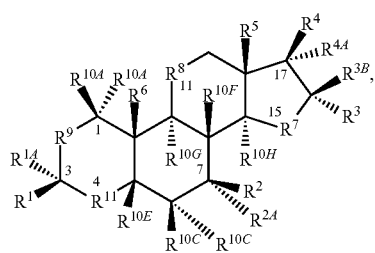
G where $R^{11}$ is a moiety as defined herein such as —O—, —S—, —CH(α-$R^{10B}$)—, —CH(β-$R^{10B}$)—, —N$R^{10B}$— or, —C($R^{10B}$)$_2$— where the $R^{10B}$ are the same or different, when no double bond is present at the 4-position, or =N—, =CH— or =C$R^{10B}$—, when a double bond is present at the 4-position, and $R^{1A}$, $R^{2A}$ and $R^{4A}$ respectively are independently selected $R^1$, $R^2$ and $R^4$ moieties in the α-configuration and $R^{3B}$ is an $R^3$ moiety in the β-configuration. In these structures, each $R^1$, $R^2$, $R^3$ and $R^4$ is the same or different. In any of these structures exemplary $R^{11}$ moieties include —C(CH$_3$)$_2$—, —C(C$_2$H$_5$)$_2$—, —CF$_2$—, —CH(α-OH)—, —CH(β-OH)—, —C(β-C1-C8 optionally substituted alkyl)(α-OH)—, —C(α-C1-C8 optionally substituted alkyl)(β-OH)—, —CH(α-NO$_2$)—, —CH(β-NO$_2$)—, —CH(α-ether)-, —CH(β-ether)-, —CH(α-thioether)-, —CH(β-thioether)-, —CH(α-C1-C8 optionally substituted alkyl)-, —CH(β-C1-C8 optionally substituted alkyl)-, —CH(C1-C8 optionally substituted alkyl)$_2$- where each C1-C8 optionally substituted alkyl is the same or different, —C(O)—, —C(S)—, —C(NOH)—, —CH(α-NH—C1-C8 optionally substituted alkyl)- and —CH(β-NH—C1-C8 optionally substituted alkyl)-.

Other F1C structures include compounds with no double bonds in the four steroid rings or with 1, 2, 3, 4 or 5 double bonds at, e.g., the 1-, 2-, 3-, 4-, 5-, 6-, 7-, 8-, 8(14)-, 9-, 11-, 12-, 13(17)-, 14-, 15-, or 16-positions have the structures

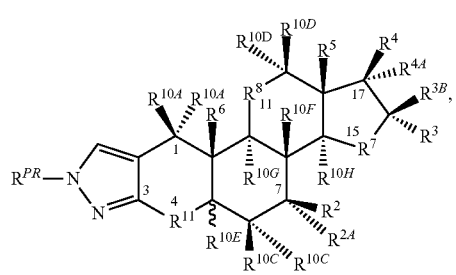

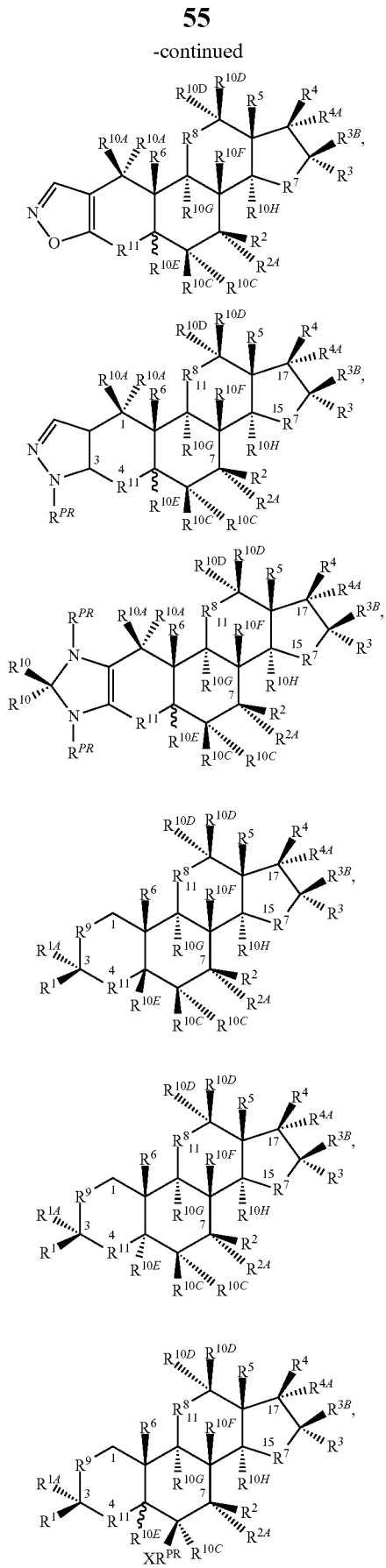
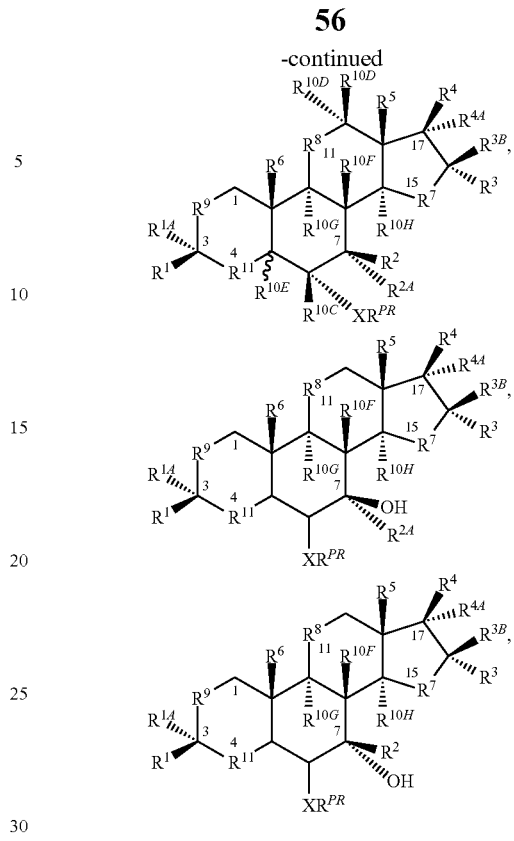

where 0, 1, 2, 3, 4 or 5 double bonds are present in the four steroid rings, X is —O—, —S— or —NH— and $R^{PR}$ independently are —H, a protecting group or optionally substituted alkyl such as —CH$_3$, —C$_2$H$_5$ or —C$_6$H$_5$ and each $R^{10A}$, $R^{10B}$, $R^{10C}$ and $R^{10D}$ are independently selected. In some embodiments, (i) $R^{10C}$ in the β-configuration is —H or a C-linked moiety and $R^{10C}$ in the α-configuration is —H, an O-linked moiety, a S-linked moiety or an N-linked moiety, (ii) $R^{10A}$ in the β-configuration is —H or a C-linked moiety and $R^{10A}$ in the α-configuration is —H, an O-linked moiety, a S-linked moiety or an N-linked moiety, (iii) $R^{10B}$ in the β-configuration is —H or a C-linked moiety and $R^{10B}$ in the α-configuration is —H, an O-linked moiety, a S-linked moiety or an N-linked moiety and/or (iv) $R^{10D}$ in the β-configuration is —H or a C-linked moiety and $R^{10D}$ in the α-configuration is —H, an O-linked moiety, a S-linked moiety or an N-linked moiety. In other embodiments, (i) $R^{10C}$ in the α-configuration is —H or a C-linked moiety and $R^{10C}$ in the β-configuration is —H, an O-linked moiety, a S-linked moiety or an N-linked moiety, (ii) $R^{10A}$ in the α-configuration is —H or a C-linked moiety and $R^{10A}$ in the β-configuration is —H, an O-linked moiety, a S-linked moiety or an N-linked moiety, (iii) $R^{10B}$ in the α-configuration is —H or a C-linked moiety and $R^{10B}$ in the β-configuration is —H, an O-linked moiety, a S-linked moiety or an N-linked moiety, (iii) $R^{10D}$ in the α-configuration is —H or a C-linked moiety and $R^{10D}$ in the β-configuration is —H, an O-linked moiety, a S-linked moiety or an N-linked moiety and/or (iv) one or two of both $R^{10B}$, $R^{10C}$ and $R^{10D}$ together are an independently selected double bonded moiety such as =O, =S, =NOH, =N-optionally substituted alkyl, =CH$_2$ or =CH-optionally substituted alkyl. For any of these compounds, $R^{11}$ is a moiety as defined herein such as —O—, —S—, —CH(α-$R^{10B}$)—, —CH(β-$R^{10B}$)—, —NR$^{10B}$— or, —C(R$^{10B}$)$_2$— where the $R^{10B}$ are the same or different, when no double bond is present at the 4-position, or =N—, =CH— or =CR$^{10B}$— when a double bond is present at the 4-position. The $R^{10B}$ moieties are as described herein such as independently selected —H, —F, —Cl, =O, =S, =NOH, O-linked moiety, S-linked moiety or N-linked moiety. The —$XR^{PR}$ moiety can be —OH, —SH, —NH$_2$, ether, thioether, ester, thioester, optionally substituted alkyl, alkylamine or dialkylamine such as —NHCH$_3$, —NHC$_2$H$_5$—N(CH$_3$)$_2$, —N(C$_2$H$_5$)$_2$. $R^1$ and $R^{1A}$ independently or together can be moieties described herein such as —H, —OH, =O, —SH, =S, ether, ester, monosaccharide, carbonate, carbamate, —NH$_2$, —NHCH$_3$, —NHC$_2$H$_5$—N(CH$_3$)$_2$ or —N(C$_2$H$_5$)$_2$ and $R^{10G}$ can be a moiety described herein such as —H, —F, —Cl or —OH. Exemplary $XR^{PR}$ moieties include —OH, —SH, ester, ether, thioester, thioether and alkylamine such as —NHCH$_3$ and —NHC$_2$H$_5$. Other variable groups, e.g., $R^{10}$, $R^{10D}$ and $R^6$ are independently selected moieties described herein.

Other F1C structures include compounds with no double bonds in the four steroid rings or with 1, 2, 3, 4 or 5 double bonds at, e.g., the 4-, 5-, 6-, 7-, 8-, 8(14)-, 9-, 9(11)-, 11-, 12-, 13(17)-, 14-, 15-, or 16-positions have the structure

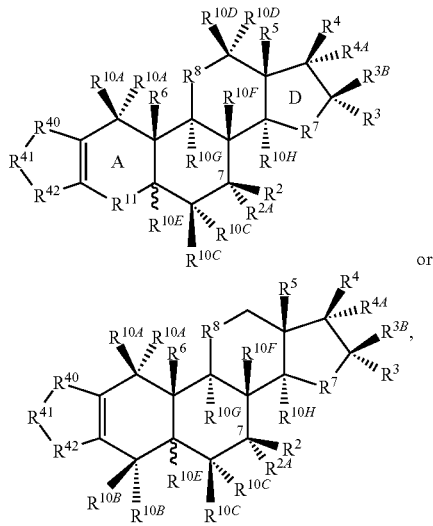

where 0, 1, 2, 3, 4 or 5 double bonds are present in the four steroid rings, $R^{40}$, $R^{41}$ and $R^{42}$ independently are —O—, —S—, —S(O)(O)—, —C($R^{10}$)$_2$—, —CH$_2$—, —CF$_2$—, —NR$^{10}$— or —NH— where $R^{10}$ are moieties as described herein such as independently selected —H, —OH, —SH, =O, =S, halogen, phenyl optionally substituted with 1, 2, or 3 independently selected halogens —OH, C1-C4 alkyl or C1-C4 alkoxy moieties, or optionally substituted alkyl such as —CH$_3$, —C$_2$H$_5$ or —C$_6$H$_5$. Each $R^{10A}$, $R^{10B}$, $R^{10C}$ and $R^{10D}$ is independently selected. One or none of $R^{40}$, $R^{41}$ and $R^{42}$ can be —O— or —S—. In some embodiments, $R^7$ is —CH$_2$—CH$_2$—, —C(O)—CH$_2$—, —C(S)—CH$_2$—, —C(NOH)—CH$_2$—, —CH$_2$—C($R^{10}$)$_2$—, —CH$_2$—CH($\alpha$-$R^{10}$)—, —CH$_2$—CH($\beta$-$R^{10}$)—, —CH($\beta$-$R^{10}$)—CH($\alpha$-$R^{10}$)—, —CH($\alpha$-$R^{10}$)—CH($\beta$-$R^{10}$)—, —CH$_2$—CH($\beta$C(O)-optionally substituted alkyl)-, —CH$_2$—CH($\beta$-NR$^{PR}$-optionally substituted alkyl)-, —CH$_2$—CH($\beta$-optionally substituted alkyl)-, —CH$_2$—CH($\beta$-C(O)—NR$^{PR}$-optionally substituted alkyl)-, —CH$_2$—CH($\beta$-NR$^{PR}$—C(O)-optionally substituted alkyl)-, —CH$_2$—CH($\beta$-NR$^{PR}$-optionally substituted alkyl)-, —CH$_2$—CH($\beta$-NR$^{PR}$—S-optionally substituted alkyl)-, —CH$_2$—CH($\beta$-NR$^{PR}$—S(O)-optionally substituted alkyl)-, —CH$_2$—CH($\beta$-NR$^{PR}$—S(O)(O)-optionally substituted alkyl)-, —CH$_2$—CH($\alpha$-C(O)-optionally substituted alkyl)-, —CH$_2$—CH($\alpha$-NR$^{PR}$-optionally substituted alkyl)-, —CH$_2$—CH($\alpha$-optionally substituted alkyl)-, —CH$_2$—CH($\alpha$-C(O)—NR$^{PR}$-optionally substituted alkyl)-, —CH$_2$—CH($\alpha$-NR$^{PR}$—C(O)-optionally substituted alkyl)-, —CH$_2$—CH($\alpha$-NR$^{PR}$-optionally substituted alkyl)-, —CH$_2$—CH($\alpha$-NR$^{PR}$—S-optionally substituted alkyl)-, —CH$_2$—CH($\alpha$-NR$^{PR}$—S(O)-optionally substituted alkyl)-, —CH$_2$—CH($\alpha$-NR$^{PR}$—S(O)(O)-optionally substituted alkyl)-, or another $R^7$ moiety described herein. For these $R^7$ moieties that are asymmetric, the moiety can be present in either orientation in the D ring, e.g., —CH$_2$—CH($\alpha$-NR$^{PR}$—S(O)-optionally substituted alkyl)- can be present as —CH($\alpha$-NR$^{PR}$—S(O)-optionally substituted alkyl)-CH$_2$—.

In some embodiments, (i) $R^{10C}$ in the $\beta$-configuration is —H or a C-linked moiety and $R^{10C}$ in the $\alpha$-configuration is —H, an O-linked moiety, a S-linked moiety or an N-linked moiety, (ii) $R^{10A}$ in the $\beta$-configuration is —H or a C-linked moiety and $R^{10A}$ in the $\alpha$-configuration is —H, an O-linked moiety, a S-linked moiety or an N-linked moiety, (iii) $R^{10B}$ in the $\beta$-configuration is —H or a C-linked moiety and $R^{10B}$ in the $\alpha$-configuration is —H, an O-linked moiety, a S-linked moiety or an N-linked moiety and/or (iv) $R^{10D}$ in the $\beta$-configuration is —H or a C-linked moiety and $R^{10D}$ in the $\alpha$-configuration is —H, an O-linked moiety, a S-linked moiety or an N-linked moiety. In other embodiments, (i) $R^{10C}$ in the $\alpha$-configuration is —H or a C-linked moiety and $R^{10C}$ in the $\beta$-configuration is —H, an O-linked moiety, a S-linked moiety or an N-linked moiety, (ii) $R^{10A}$ in the $\alpha$-configuration is —H or a C-linked moiety and $R^{10A}$ in the $\beta$-configuration is —H, an O-linked moiety, a S-linked moiety or an N-linked moiety, (iii) $R^{10B}$ in the $\alpha$-configuration is —H or a C-linked moiety and $R^{10B}$ in the $\beta$-configuration is —H, an O-linked moiety, a S-linked moiety or an N-linked moiety, (iii) $R^{10D}$ in the $\alpha$-configuration is —H or a C-linked moiety and $R^{10D}$ in the $\beta$-configuration is —H, an O-linked moiety, a S-linked moiety or an N-linked moiety and/or (iv) one or two of both $R^{10B}$, $R^{10C}$ and $R^{10D}$ together are an independently selected double bonded moiety such as =O, =S, =NOH, =N-optionally substituted alkyl, a spiro ring, e.g., ethylene ketal or protected ketone, =CH$_2$ or =CH-optionally substituted alkyl. For any of these compounds, $R^{11}$ is a moiety as defined herein such as —O—, —S—, —CH($\alpha$-$R^{10B}$)—, —CH($\beta$-$R^{10B}$)—, —NR$^{10B}$— or, —C($R^{10B}$)$_2$— where the $R^{10B}$ are the same or different, when no double bond is present at the 4-position, or =N—, =CH— or =CR$^{10B}$— when a double bond is present at the 4-position. The $R^{10B}$ moieties are as described herein such as independently selected —H, —F, —Cl, =O, =S, =NOH, O-linked moiety, S-linked moiety or N-linked moiety. The —$XR^{PR}$ moiety can be —OH, —SH, —NH$_2$, ether, thioether, ester, thioester, alkylamine or dialkylamine such as —NHCH$_3$, —NHC$_2$H$_5$—N(CH$_3$)$_2$, —N(C$_2$H$_5$)$_2$. $R^1$ and $R^{1A}$ independently or together can be moieties described herein such as —H, —OH, =O, —SH, =S, ether, ester, monosaccharide, carbonate, carbamate, —NH$_2$, —NHCH$_3$, —NHC$_2$H$_5$—N(CH$_3$)$_2$ or —N(C$_2$H$_5$)$_2$ and $R^{10G}$ can be a moiety described herein such as —H, —F, —Cl or —OH. Exemplary $XR^{PR}$ moieties include —OH, —SH, ester, ether, thioester, thioether and alkylamine such as —NHCH$_3$ and —NHC$_2$H$_5$. Other variable groups, e.g., $R^{10}$, $R^{10D}$ and $R^6$ are independently selected moieties described herein.

When $R^6$ and $R^{10C}$ are linked through a —CH$_2$—O— moiety there is no double bond at the 5-6 position and exemplary F1C structures with one, two or more optional double bonds at one, two, three or more of the 1-, 2-, 3-, 4-, 7-, 8(9)-, 8(14)-, 11-, 12-, 13(17)-, 14-, 15- and/or 16-positions include C
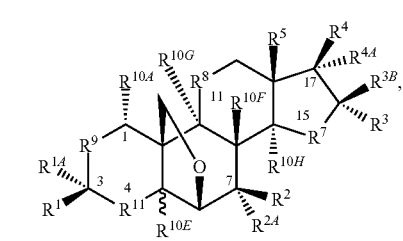
E
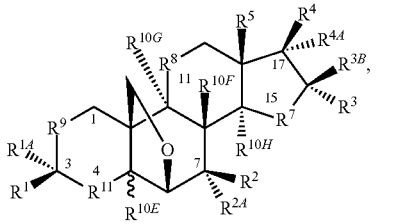
and
G
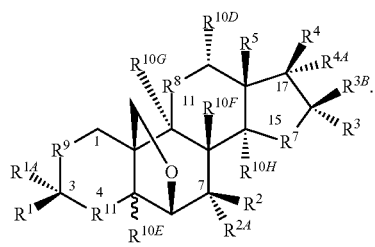
When adjacent variable groups are an epoxide or an optionally substituted cyclopropyl ring or when a spiro or other ring is present, exemplary F1C structures with one, two or more optional double bonds at one, two, three or more of the 1-, 2-, 3-, 4-, 5-, 5(10)-, 6-, 7-, 8(9)-, 8(14)-, 9-, 11-, 12-, 13(17)-, 14-, 15- and/or 16-positions, where the structure permits, include
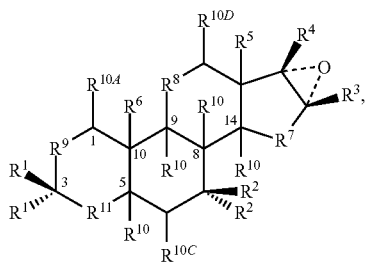
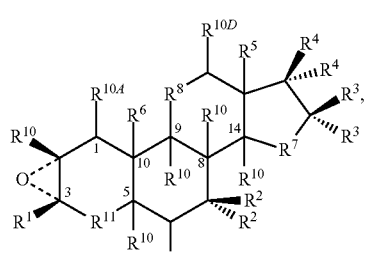
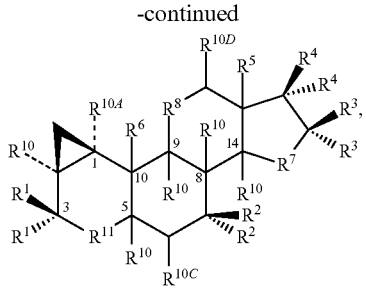
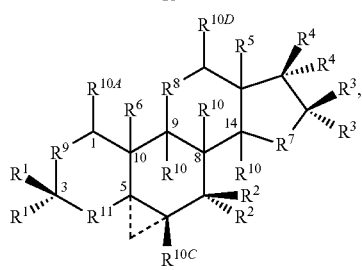
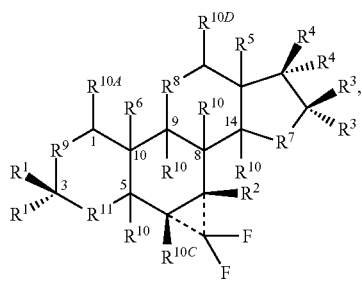
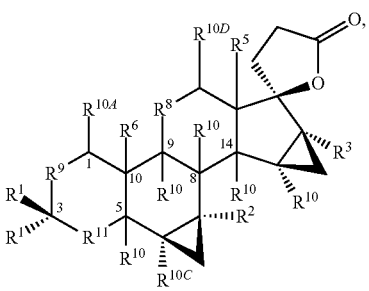
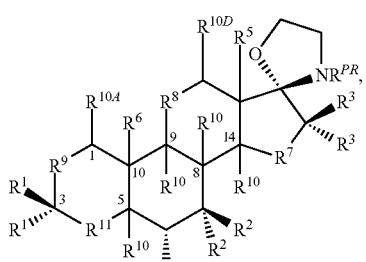
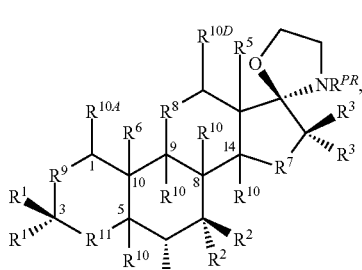

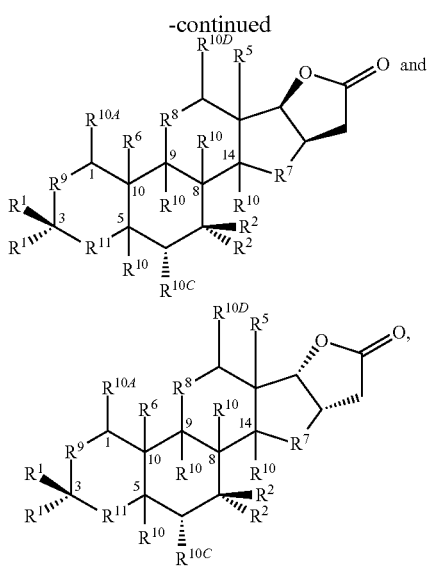

wherein variable groups, e.g., $R^1$, $R^2$, $R^3$, $R^4$, $R^5$, $R^6$, and each $R^{10}$, are independently selected and, when not specified otherwise, independently are in the α- or β-configuration and wherein $R^{PR}$ is —H or a protecting group such as C1-C8 optionally substituted alkyl, e.g., —CH$_3$, —C$_2$H$_5$, —C$_3$H$_7$ or —C$_3$H$_5$. Substituents at the cyclopropyl ring include one or two halogen atoms, e.g., dichloro, dibromo or difluoro.

F1Cs include compounds having the structure

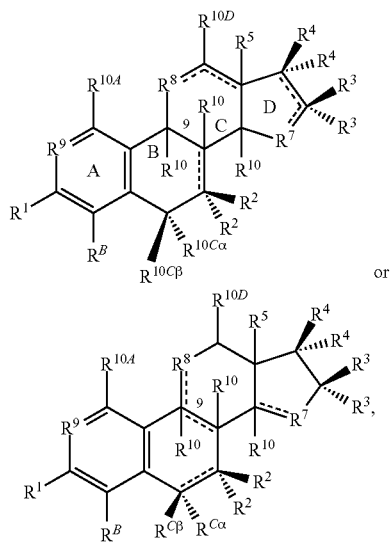

where $R^{10C\alpha}$ and $R^{10C\beta}$ are independently selected $R^{10C}$ moieties, e.g., one of $R^{10C\alpha}$ and $R^{10C\beta}$ is —H, optionally substituted alkyl, —CN, —SCN or a C-linked moiety and the other of $R^{10C\alpha}$ and $R^{10C\beta}$ is —H, —OH, —SH, —NH$_2$, —NH-optionally substituted alkyl, —N-(optionally substituted alkyl)$_2$ where each optionally substituted alkyl is the same or different, an oxygen-linked moiety, a sulfur-linked moiety or a nitrogen-linked moiety, or together they are =O, =S, =CH$_2$, =CH-optionally substituted alkyl, =NOH, =NO-optionally substituted alkyl, =N-optionally substituted alkyl. In these F1Cs, exemplary $R^1$ moieties include —OH, —SH, —NH$_2$, —O—S(O)(O)—NH$_2$, —O—S(O)(O)—NH-optionally substituted alkyl, —O—S(O)(O)—N-(optionally substituted alkyl)$_2$ where each optionally substituted alkyl is the same or different, —NH—S(O)(O)—O-optionally substituted alkyl, —NH—S(O)(O)—OH, an N-linked amino acid, an O-linked amino acid, an optionally substituted monosaccharide, an optionally substituted disaccharide or a polymer. Exemplary $R^9$ moieties include =N—, =C(OH)—, =C(SH)—, =C(NH$_2$)—, =C(CH$_3$)—, =C(C$_2$H$_5$)—, =C(C$_3$H$_7$)—, =C(C$_5$H$_9$)—, =C(optionally substituted alkyl)-, =C(NHCH$_3$)—, =C(NHC$_2$H$_5$)—, =C(N(CH$_3$)$_2$)—, =C(NHC$_3$H$_7$)—, =C(N(C$_2$H$_5$)$_2$)—, =C(OCH$_3$), =C(SCH$_3$), =C(OC$_2$H$_5$), =C(SC$_2$H$_5$)—, =C(COOH)—, =CBr—, =CI—, where the optionally substituted alkyl is a moiety such as —CH$_2$OH, —CH$_2$SH, —(CH$_2$)$_n$—COOH where n is 1, 2, 3 or 4, —(CH$_2$)$_n$—NH$_2$ where n is 1, 2, 3 or 4 or a fluoroalkyl like —CF$_3$ or —(CF$_2$)$_n$—CF$_3$, where n is 1, 2, 3 or 4. Exemplary $R^7$ moieties are —CH$_2$—, —C(R$^{10}$)$_2$—, —CH(α-R$^{10}$)—, —CH(β-R$^{10}$)—, —C(β-optionally substituted alkyl)(α-R$^{10}$)—, —C(α-optionally substituted alkyl)(β-R$^{10}$)—, —CH(α-R$^{10}$)—CH$_2$—, —CH(β-R$^{10}$)—CH$_2$—, —C(β-optionally substituted alkyl)(α-R$^{10}$)—CH$_2$—, —C(α-optionally substituted alkyl)(β-R$^{10}$)—CH$_2$—, —C(R$^{10}$)$_2$—CH$_2$—, —C(O)—, —C(O)—CH$_2$—, —C(S)—, —C(S)—CH$_2$—, =CH—, —CH=CH—, where $R^{10}$ independently are —H, halogen, —OH, —SH, =O, =S, =NOH or an oxygen-linked moiety, a sulfur-linked moiety or a nitrogen-linked moiety described herein. Exemplary $R^5$ moieties include —H, —F, —CH$_3$, —C$_2$H$_5$ or optionally substituted alkyl in the α-configuration or the β-configuration. $R^{10}$ moieties at the 9-position include —H, —F, —Cl, —CH$_3$, —C$_2$H$_5$ or optionally substituted alkyl in the α-configuration. $R^2$, $R^3$ and $R^4$ are independently selected moieties as described herein. In some embodiments, there is no double bond in the B, C or D rings, and in others there is a single double bond in 1 or 2 of the B, C or D rings, e.g., a double bond can be at the 11-12 position, 14-15 position or at the 15-16 position in addition to the aromatic A ring. Any of the optionally substituted alkyl groups for any of these variable groups is optionally selected from a C1-C6 moiety, a C1-C8 moiety, a C1-C10 moiety and a C1-C12 moiety or optionally contains 1, 2, 3, 4, 5, 6, 7, 8, 9, 10, 11 or 12 carbon atoms.

F1Cs include compounds having the structure

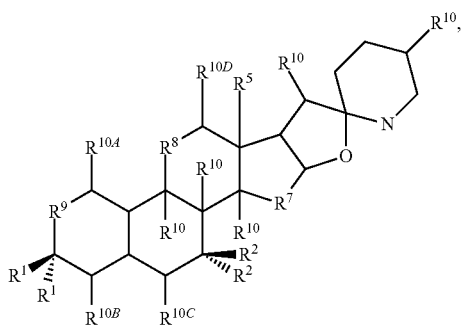

-continued

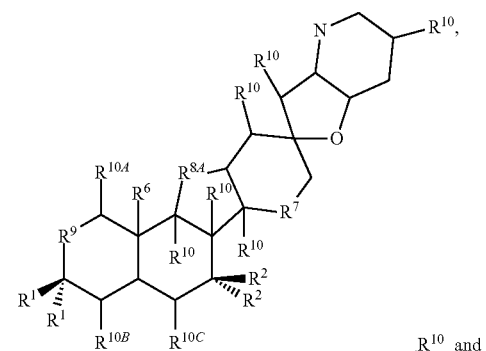

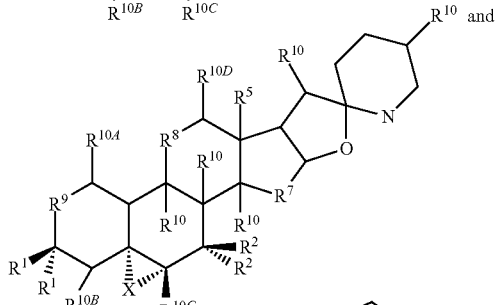

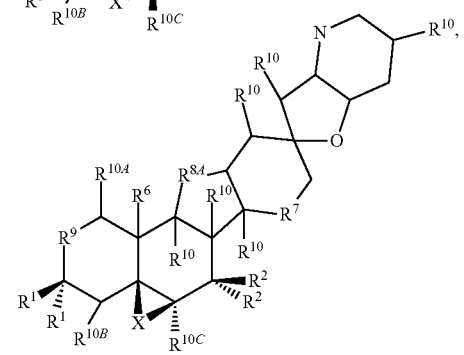

where $R^{8A}$ is —CH$_2$—, —CHR$^{10}$—, =CH—, =CR$^{10}$—, —O—, —NHR$^{10}$—, =NR$^{10}$— or —S—, X is —CH$_2$—, —O— or —CF$_2$—, $R^{10A}$, $R^{10B}$, $R^{10C}$ and $R^{10D}$ independently are in the α- or β-configuration and other variable groups are as previously defined. Exemplary $R^{10}$ moieties at $R^{8A}$ are —H, —CH$_3$, —C$_2$H$_5$, =O, =S, =NOH and C1-C8 optionally substituted alkyl and one, two, three, four or five double bonds are optionally present in the steroid rings at the 1-, 2-, 3-, 4-, 5-, 5(10)-, 6-, 7-, 8-, 8(14)-, 9-, 9(11)-, 11-, 12-, 13(17)-, 14-, 15- or 16-positions. Other variable groups, e.g., $R^{10}$, $R^{11}$, $R^2$ and $R^{10C}$, are independently selected. Related structures include ones where $R^{11}$ is present at the 4-position.

F1Cs include compounds having the structure

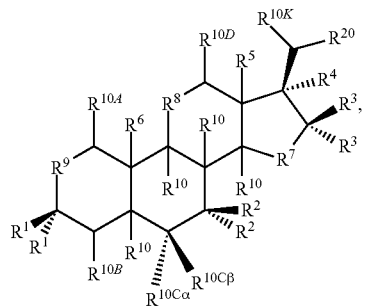

-continued

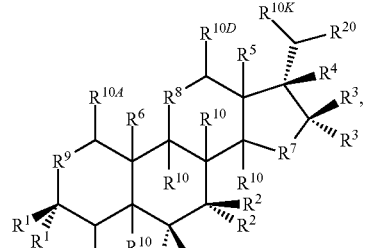

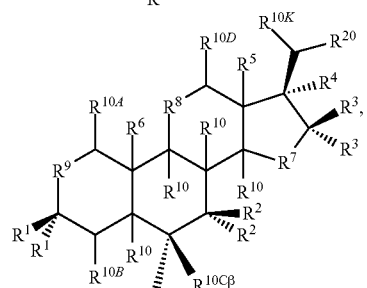

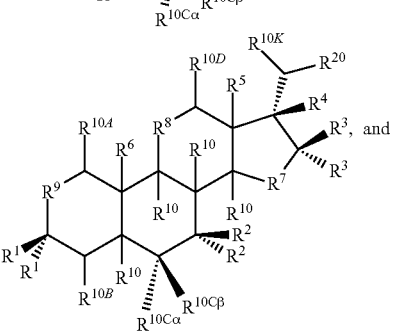

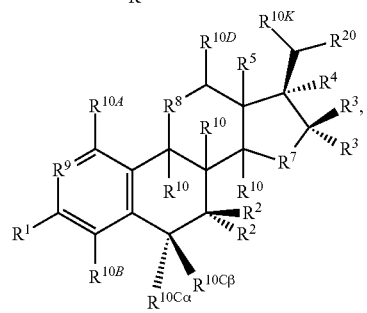

where 1, 2, 3, 4 or 5 double bonds are present in the four steroid rings, $R^{10K}$ is $R^{10}$, $R^{10C\alpha}$ and $R^{10C\beta}$ are independently selected $R^{10}$ moieties, e.g., one of $R^{10C\alpha}$ and $R^{10C\beta}$ is —H, optionally substituted alkyl, —CN, —SCN or a C-linked moiety and the other of $R^{10C\alpha}$ and $R^{10C\beta}$ is —H, —OH, —SH, —NH$_2$, —NH-optionally substituted alkyl, —N-(optionally substituted alkyl)$_2$ where each optionally substituted alkyl is the same or different, -optionally substituted alkyl, an oxygen-linked moiety, a sulfur-linked moiety or a nitrogen-linked moiety, or together they are =O, =S, =CH$_2$, =CH-optionally substituted alkyl, =NOH, =NO-optionally substituted alkyl, =N-optionally substituted alkyl, $R^{20}$ is —C1-C16 optionally substituted alkyl such as —(CH$_2$)$_m$—(CH=CH)$_n$—C(R$^{21}$)$_3$, —(CH$_2$)$_m$—(C≡C)$_n$—C(R$^{21}$)$_3$, —(CH$_2$)$_m$—C≡C—C(R$^{21}$)$_3$, —(CH$_2$)$_m$—(CH=CH)$_n$— (CH$_2$)$_p$—C(R$^{21}$)$_3$, —(CH$_2$)$_m$—(C≡C)$_n$—C(R$^{21}$)$_3$, —(CH$_2$)$_m$—C≡C—(CH$_2$)$_p$—C(R$^{21}$)$_3$, —(CH$_2$)$_m$—X—C(R$^{21}$)$_3$, —(CH$_2$)$_m$—X—(CH$_2$)$_p$—C(R$^{21}$)$_3$, —(CH$_2$)$_m$—

(CH=CH)$_n$—C(CH$_3$)(NHCH$_3$)(R$^{21}$), —(CH$_2$)$_m$—(CH=CH)$_n$—C(CH$_3$)(O—C1-C4 optionally substituted alkyl)(R$^{21}$), —(CH$_2$)$_m$—(CH=CH)$_n$—C(CH$_3$)(S—C1-C4 optionally substituted alkyl)(R$^{21}$), —(CH$_2$)$_m$—(CH=CH)$_n$—C(CH$_3$)(NH—C1-C4 optionally substituted alkyl)(R$^{21}$), —(CH$_2$)$_m$—(CH=CH)$_n$—C(CH$_3$)(NH$_2$)(R$^{21}$), —(CH$_2$)$_m$—(CH=CH)$_n$—C(O)—(CH$_2$)$_p$—CH$_3$, —(CH$_2$)$_m$—(CH=CH)$_n$—C(S)—(CH$_2$)$_p$—CH$_3$, where R$^{21}$ are independently selected R$^{10}$ moieties, m is 0, 1, 2, 3, 4 or 5, n is 0 or 1, p is 1, 2 or 3 and X is —O—, —S—, —NH—, =N— or —NR$^{10}$—. Exemplary R$^{21}$ are independently selected —H, —OH, —SH, —NH$_2$, ether, thioether, alkylamine or dialkylamine such as —NHCH$_3$, —NHC$_2$H$_5$, —N(CH$_3$)$_2$, —N(C$_2$H$_5$)$_2$, where alkyl moiety is optionally substituted and optionally contains 1, 2, 3, 4, 5 or 6 carbon atoms. In these F1Cs, exemplary R$^{10K}$ moieties include —H, —OH, —OR$^{PR}$, —SH, —SR$^{PR}$, —NH$_2$—NHR$^{PR}$, =O, =S, =NOH, =NO—C1-C6 optionally substituted alkyl, =CH$_2$, or -optionally substituted alkyl such as C1-C6 optionally substituted alkyl, —CH$_3$, —CH$_2$OH, —CH$_2$F, —CH$_2$Cl or —C$_2$H$_5$. Other R$^{20}$ moieties are —(CH$_2$)$_2$—C(O)—NCH$_3$—OCH$_3$, —(CH$_2$)$_2$—C(CF$_3$)$_2$—OR$^{PR}$ where R$^{PR}$ is —H or a protecting group, —(CH$_2$)$_3$—C(O)—NCH$_3$—OCH$_3$, —(CH$_2$)$_3$—C(CF$_3$)$_2$—OR$^{PR}$, —CH$_2$—C(O)—NCH$_3$—OCH$_3$, —CH$_2$—C(CF$_3$)$_2$—OR$^{PR}$, —(CH$_2$)$_2$—C(S)—NCH$_3$—OCH$_3$, —(CH$_2$)$_2$—C(CF$_3$)$_2$—SR$^{PR}$, —(CH$_2$)$_3$—C(S)—NCH$_3$—OCH$_3$, —(CH$_2$)$_2$—C(O)—NCH$_3$—SCH$_3$, —(CH$_2$)$_3$—C(CF$_3$)$_2$—SR$^{PR}$, —(CH$_2$)$_2$—C(O)—NCH$_3$—OCH$_2$CH$_3$, —(CH$_2$)$_2$—C(O)—NC$_2$H$_5$—OCH$_3$, —(CH$_2$)—C(O)—NC$_2$H$_5$—OCH$_2$CH$_3$, —(CH$_2$)$_3$—C(O)—NC$_2$H$_5$—OCH$_3$, —(CH$_2$)$_3$—C(O)—NC$_2$H$_5$—OCH$_2$CH$_3$, —CH$_2$—C(O)—NC$_2$H$_5$—OCH$_3$, —CH$_2$—C(O)—NC$_2$H$_5$—OCH$_2$CH$_3$, —(CH$_2$)$_2$—C(O)—OCH$_3$, —(CH$_2$)—C(O)—SCH$_3$, —(CH$_2$)—C(O)—NH—CH$_2$CH$_2$Cl, —(CH$_2$)—C(O)—NH—CH$_2$CF$_3$, —(CH$_2$)$_2$—C(O)—NH—CH(C(O)OCH$_3$)CH$_2$—C$_6$H$_5$, —(CH$_2$)—C(O)—CH$_2$—C(S)—CH$_3$, In some embodiments such as those described here, R$^{10C\alpha}$ is —OH, —SH, —NH$_2$, ether, thioether, ester, thioester, alkylamine or dialkylamine where each alkyl moiety is the same or different and optionally contains 1, 2, 3, 4, or 5 carbon atoms, optionally where a double bond is present at the 5-position or the 6-position and R$^{10C\beta}$ is absent. In some embodiments, double bonds are present at the 1-2 and 5-6 positions or at the 2-3 and 5-6 positions and in others, a double bond is present at the 5-10 position and another double bond is optionally present at the 6-, 7-, 11-, 14- or 15-position. Other variable groups are as described anywhere herein. Related structures include ones where R$^{11}$ is present at the 4-position.

For any of F1C structure disclosed herein, when a single bonded R$^4$ is present, the R$^4$ can be (i) a C3-C20 dicarboxylic acid ester, e.g., —O—C(O)—(CH$_2$)$_n$—C(O)—OR$^{PR}$ or —O—C(O)—CH(CH$_3$)—(CH$_2$)$_n$—C(O)—OR$^{PR}$ where n is 1, 2, 3, 4, 5 or 6 and R$^{PR}$ is —H, a protecting group such as C1-C8 optionally substituted alkyl, or a counter ion or salt such as Na$^+$ or K$^+$, (ii) —P(O)—(OR$^{PR}$)$_2$ or —O—P(O)—(OR$^{PR}$)$_2$ where R$^{PR}$ independently are —H, a protecting group such as C1-C8 optionally substituted alkyl, or a counter ion or salt, (iii) a substituted ester or thioester, e.g., —O—C(O)—(CH$_2$)$_n$—O—P(O)—(OR$^{PR}$)$_2$, —S—C(O)—(CH$_2$)$_n$—O—P(O)—(OR$^{PR}$)$_2$, —S—C(O)—(CH$_2$)$_n$—P(O)—(OR$^{PR}$)(SR$^{PR}$) or —O—C(O)—(CH$_2$)—P(O)—(OR$^{PR}$)(SR$^{PR}$) where n is 1, 2, 3, 4, 5 or 6 and R$^{PR}$ independently are —H, a protecting group such as C1-C8 optionally substituted alkyl, or a counter ion or salt such as Na$^+$ or K$^+$, (iv) an amino acid ester, e.g., —O—C(O)—CHR$^{44}$—NH$_2$ or an ionized form of the free amine where R$^{44}$ is C1-C6 optionally substituted alkyl or the side chain of a naturally occurring amino acid such as —H, —CH$_3$ or —CH$_2$OH, (v) an amino ester such as —O—C(O)—(CH$_2$)$_n$—NHR$^{PR}$ or —O—C(O)—(CH$_2$)$_n$—N(C1-C8 optionally substituted alkyl)$_2$ where n is 1, 2, 3, 4, 5 or 6, R$^{PR}$ is —H or a protecting group such as C1-C8 optionally substituted alkyl, or an ionized form of the amine or substituted amine and the C1-C8 optionally substituted alkyl are the same or different such as dimethyl or diethyl, (vi) a carbamate —O—C(O)—O—NHR$^{PR}$ or —O—C(O)—N(C1-C8 optionally substituted alkyl)$_2$ where R$^{PR}$ is —H or a protecting group such as C1-C8 optionally substituted alkyl, or an ionized form of the amine or substituted amine and the C1-C8 optionally substituted alkyl are the same or different such as dimethyl or diethyl, (vii) an ether such as —OCH$_3$, —OCH$_2$CH$_3$, —OCH$_2$CH$_2$CH$_3$—OCH$_2$CH$_2$CH$_2$CH$_3$, —OCH$_2$CH$_2$SH or —OCH$_2$CH$_2$OH. Any of these moieties can be in the β- or α-configuration or (viii) C1-C8 optionally substituted alkyl. In embodiments when no double bond is present at the 17-position, a second R$^4$ is present, which can be —H, a C-linked moiety such as C1-C8 optionally substituted alkyl such as —CH$_3$, —CF$_3$, —CH$_2$OH or —C≡CH, an O-linked moiety such as an ether or an S-linked moiety such as a thioether, where the second R$^4$ is in the α- or β-configuration. In related embodiments when a single bonded R$^1$ is present, the R$^1$ can be any of these moieties in the α- or β-configuration and, when a single bonded R$^4$ is present, it can be the same or different as the R$^1$.

Exemplary F1Cs include structures where (1) no double bond is present at the 3-position, one R$^1$ is an O-linked moiety, an S-linked moiety, an N-linked moiety or both are a double bonded moiety such as =O, =S or =NOH and the other R$^1$ is —H, an O-linked moiety or a C-linked moiety, (2) no double bond is present at the 7-position, one R$^2$ is an O-linked moiety, an S-linked moiety, an N-linked moiety or both are a double bonded moiety such as =O, =S or =NOH and the other R$^2$ is —H or a C-linked moiety, (3) no double bond is present at the 16-position, one R$^3$ is an O-linked moiety, an S-linked moiety, an N-linked moiety, a halogen or both are a double bonded moiety such as =O, =S, =NOH, =CH$_2$ or =CH-optionally substituted alkyl and the other R$^3$ is —H, a halogen or a C-linked moiety, (4) no double bond is present at the 17-position, one R$^4$ is an O-linked moiety, an S-linked moiety, an N-linked moiety or both are a double bonded moiety such as =O, =S or =NOH and the other R$^4$ is —H, an O-linked moiety or a C-linked moiety, (5) no double bond is present at the 2-position, one R$^{10}$ at the 2-position is an O-linked moiety, an S-linked moiety, an N-linked moiety or both are a double bonded moiety such as =O, =S or =NOH and the other R$^{10}$ at the 2-position is —H or a C-linked moiety, (6) no double bond is present at the 4-position, one R$^{10}$ at the 4-position is an O-linked moiety, an S-linked moiety, an N-linked moiety, a C-linked moiety or both are a double bonded moiety such as =O, =S or =NOH and the other R$^{10}$ at the 4-position is —H or a C-linked moiety, (7) no double bond is present at the 6-position, one R$^{10}$ at the 6-position is an O-linked moiety, an S-linked moiety, an N-linked moiety, a C-linked moiety, a halogen or both are a double bonded moiety such as =O, =S or =NOH and the other R$^{10}$ at the 6-position is —H, a halogen or a C-linked moiety, (8) no double bond is present at the 11-position, one R$^{10}$ at the 11-position is an O-linked moiety, an S-linked moiety, an N-linked moiety, a C-linked moiety, a halogen or both are a double bonded moiety such as =O, =S or =NOH and the other R$^{10}$ at the 11-position is —H, a halogen or a C-linked moiety, (9) no double bond is present at the 12-position, one R$^{10}$ at the 12-position is an O-linked moiety, an S-linked moiety, an N-linked moiety, a C-linked moiety, a halogen or both are a double bonded moiety such as =O, =S or =NOH and the other $R^{10}$ at the 12-position is —H, a halogen or a C-linked moiety and (10) no double bond is present at the 15-position, one $R^{10}$ at the 15-position is an O-linked moiety, an S-linked moiety, an N-linked moiety, a C-linked moiety, a halogen or both are a double bonded moiety such as =O, =S or =NOH and the other $R^{10}$ at the 15-position is —H, a halogen or a C-linked moiety. For any of these $R^{10}$ at the 9-position can be —H or another moiety such as —F, —Cl, —OH, —SH or C1-C8 optionally substituted alkyl in the α- or the β-configuration, or a double bond can be present at the 9-position and that $R^{10}$ will be absent and/or $R^{10}$ at the 14-position can be —H or another moiety such as —F, —Cl, —OH, —SH or C1-C8 optionally substituted alkyl in the α- or the β-configuration, or a double bond can be present at the 14-position and that $R^{10}$ will be absent. For these structures, O-linked, S-linked, N-linked or halogen $R^1$, $R^2$, $R^3$ or $R^4$ may respectively be in, e.g., the β-, β-, α- and β-configurations, the β-, β-, β- and β-configurations, the α-, β-, α- and β-configurations, the β-, β-, α- and α-configurations, the β-, α-, α- and β-configurations, the α-, β-, α- and α-configurations, the α-, α-, α- and β-configurations or the α-, β-, β- and α-configurations, while the —H, O-linked, C-linked or halogen $R^1$, $R^2$, $R^3$ or $R^4$ may respectively be in, e.g., the α-, α-, β- and α-configurations, the α-, α-, α- and α-configurations, the β-, α-, β- and α-configurations, the α-, α-, β- and β-configurations, the α-, β-, β- and α-configurations, the β-, α-, β- and β-configurations, the β-, β-, β- and α-configurations or the β-, α-, α- and β-configurations. Similarly, when two $R^{10}$ are at the 1-, 4-, 6- or 12-positions, the O-linked, S-linked, N-linked or halogen $R^{10}$ moiety can be in the R— or α-configuration, while the —H, C-linked moiety or halogen $R^{10}$ moiety can be in the α- or β-configuration. When two halogens or O-linked moieties are at a given position, they can be the same or different. Specific embodiments include structures where one, two, three or more of $R^1$, $R^2$, $R^3$, $R^4$ and $R^{10}$ is an O-linked moiety or an N-linked moiety in the α- or β-configuration and the other $R^1$, $R^2$, $R^3$, $R^4$ or $R^{10}$ moiety is —H or a C-linked moiety. For any of these structures $R^9$ can be —CH(α-$R^{10}$)—, —CH(β-$R^{10}$)—, —C($R^{10}$)$_2$—, —C(β-C-linked moiety)(α-$R^{10}$)—, —C(α-C-linked moiety)(β-$R^{10}$)—, —NH—, =N—, —CH$_2$—, —CF$_2$—, —CBr$_2$—, —C(S)—, —C(NOH)—, —C(CH$_3$)$_2$—, —CH(α-$R^{10}$)—CH(β-$R^{10}$)—, —CH(α-$R^{10}$)—CH(α-$R^{10}$)—, —CH(β-$R^{10}$)—CH(β-$R^{10}$)—, —C($R^{10}$)$_2$—CH(β-$R^{10}$)—, —C($R^{10}$)$_2$—CH(α-$R^{10}$)— or $R^9$ can be absent where $R^{10}$ are independently chosen and are an $R^{10}$ moiety described herein such as —H, —OH, —OR$^{PR}$, —SH, —SR$^{PR}$, —NH$_2$, —NHR$^{PR}$, —C1-C8 optionally substituted alkyl, —NH—C1-C8 optionally substituted alkyl or —N(C1-C8 optionally substituted alkyl)$_2$ where the optionally substituted alkyl are the same or different.

Thus, exemplary F1C, e.g., 2, 5, 6, 7, 8, 9, 10, B, C, D, E, F and G structures are characterized as having a steroid ring double bond described herein and:

(1) a double bond at the 5-6 position, no double bonds with $R^{10E}$ at the 5 position in the α-configuration, no double bonds with $R^{10E}$ in the β-configuration, a double bond at the 4-5 position, a double bond at the 1-2 position with $R^{10E}$ in the α-configuration, a double bond at the 1-2 position with $R^{10E}$ in the β-configuration, double bonds at the 1-2 and 4-5 positions, double bonds at the 1-2 and 5-6 positions, a double bond at the 16-17 position with $R^{10E}$ in the α-configuration, a double bond at the 16-17 position with $R^{10E}$ in the β-configuration, double bonds at the 4-5 and 16-17 positions, double bonds at the 5-6 and 16-17 positions, double bonds at the 1-2 and 16-17 positions with $R^{10E}$ in the α-configuration, double bonds at the 1-2 and 16-17 positions with $R^{10E}$ in the β-configuration, double bonds at the 1-2, 5-6 and 16-17 positions or double bonds at the 1-2, 4-5 and 16-17 positions, (2) $R^{10A}$, $R^{10B}$, $R^{10C}$ and $R^{10D}$ are independently selected $R^{10}$ groups in the α,α, α,β, β,α, or β,β configurations respectively, and/or (3) $R^{10E}$, $R^{10F}$, $R^{10G}$ and $R^{10H}$ are independently selected $R^{10}$ groups in the α,α,α,α, α,α,α,β, α,α,β,α, α,β,α,α, β,α,α,α, α,α,β,β, α,β,α,β, β,α,α,β, β,α,β,α, β,β,α,α, α,β,β,α, α,β,β,β, β,α,β,β, β,β,α,β, β,β,β,α or β,β,β,β configurations respectively, and/or (4) $R^{1A}$, $R^{3B}$ and $R^{4A}$ are —H, $R^{1A}$ is not —H and $R^{2A}$, $R^{3B}$ and $R^{4A}$ are —H, $R^{2A}$ is not —H and $R^{1A}$, $R^{3B}$ and $R^{4A}$ are —H, $R^{3B}$ is not —H and $R^{1A}$, $R^{2A}$ and $R^{4A}$ are —H, $R^{4A}$ is not —H and $R^{1A}$, $R^{2A}$ and $R^{3B}$ are —H, $R^{1A}$ and $R^{2A}$ are not —H and $R^{3B}$ and $R^{4A}$ are —H, $R^{1A}$ and $R^{3B}$ are not —H and $R^{2A}$ and $R^{4A}$ are —H, $R^{1A}$ and $R^{4A}$ are not —H and $R^{2A}$ and $R^{3B}$ are —H, $R^{2A}$ and $R^{3B}$ are not —H and $R^{1A}$ and $R^{4A}$ are —H, $R^{2A}$ and $R^{4A}$ are not —H and $R^{1A}$ and $R^{3B}$ are —H, $R^{3B}$ and $R^{4A}$ are not —H and $R^{1A}$ and $R^{2A}$ are —H, $R^{1A}$, $R^{2A}$ and $R^{3B}$ are not —H and $R^{4A}$ is —H, $R^{1A}$, $R^{2A}$ and $R^{4A}$ are not —H and $R^{3B}$ is —H, $R^{1A}$, $R^{3B}$ and $R^{4A}$ are not —H and $R^{2A}$ is —H, $R^{2A}$, $R^{3B}$ and $R^{4A}$ are not —H and $R^{1A}$ is —H, $R^{1A}$, $R^{2A}$, $R^{3B}$ and $R^{4A}$ are not —H, $R^{1A}$ and $R^{2A}$ are —H and $R^{3B}$ and $R^{4A}$ are absent (i.e., a 16-17 double bond is present), $R^{1A}$ is —H and $R^{2A}$ is not —H and $R^{3B}$ and $R^{4A}$ are absent, $R^{2A}$ is —H and $R^{1A}$ is not —H and $R^{3B}$ and $R^{4A}$ are absent, or, $R^{1A}$ and $R^{2A}$ are not —H and $R^{3B}$ and $R^{4A}$ are absent, where each $R^{1A}$, $R^{2A}$, $R^{3B}$ and $R^{4A}$ are independently selected, and/or (5) each $R^1$, $R^2$, $R^3$ and $R^4$ is independently selected.

For these exemplary formula B, C, D, E, F and G structures and any other F1C structures disclosed herein, including any F1C structure described in any compound group, embodiment or claim described herein, each $R^1$, $R^{1A}$, $R^2$, $R^{2A}$, $R^3$, $R^{3B}$, $R^4$, $R^{4A}$, $R^{10}$, $R^{10A}$, $R^{10B}$, $R^{10C}$, $R^{10D}$, $R^{10E}$, $R^{10F}$ and $R^{10G}$ are an independently selected atom or moiety as described herein, e.g., —H, —OH, =O, —SH, =S, —F, —Cl, —Br, —I, —CN, —SCN, —N$_3$, —NH—C1-C8 optionally substituted alkyl, —N(C1-C8 optionally substituted alkyl)$_2$ where each optionally substituted alkyl moiety is the same or different, protected ketone, e.g., ethylene ketal (—O—CH$_2$—CH$_2$—O—), —NO$_2$, —ONO$_2$, —(CH$_2$)$_n$—CH(O), —(CH$_2$)$_n$—COOH, —(CH$_2$)$_n$-COOR$^{PR}$, —(CH$_2$)$_n$—NHCH$_3$, —(CH$_2$)$_n$—NHR$^{PR}$, —(CH$_2$)$_n$—CH(S), —O—S(O)(O)—OH, —O—P(O)(O)—OH, where n is 0, 1, 2, 3, 4, 5 or 6, —O-β-D-glucopyranosiduronate or —OP(O)(OH)—NH—C(=NH)—N(CH$_3$)—CH$_2$—C(O)OH.

Other F1C substituents for variable groups such as each $R^1$, $R^2$, $R^3$, $R^4$ and $R^{10}$ include, or a group such as optionally substituted alkyl, e.g., optionally substituted alkyl, e.g., —CH$_3$, —C$_2$H$_5$, —CH$_2$CH$_2$CH$_3$, —CH$_2$(CH$_3$)$_2$, —CH$_2$CH$_2$(CH$_3$)$_2$, —CH$_2$CH$_2$CH$_2$CH$_3$, —CH$_2$CH$_2$OCH$_2$CH$_3$, —CH$_2$OH, —CH$_2$CH$_2$OH, —CHOHCH$_3$, —CH(OC(O)CH$_3$)—CH$_3$, —CH(OR$^{PR}$)—CH$_3$, —CHOH—(CH$_2$)$_n$—OH, —CH(OR$^{PR}$)—(CH$_2$)$_n$—OR$^{PR}$, —CHOH—(CH$_2$)$_n$—CH$_2$OH, —CH(OR$^{PR}$)—(CH$_2$)$_n$—CH$_2$OR$^{PR}$, —CHOH—(CH$_2$)$_n$—CH$_2$SH, —CH(OR$^{PR}$)—(CH$_2$)$_n$—CH$_2$SR$^{PR}$, —CH$_2$—(CH$_2$)$_n$—OCH$_3$, —CF$_3$, —(CH$_2$)$_t$—CF$_3$, —(CH$_2$)$_t$—NH$_2$, —(CH$_2$)$_2$—NH$_2$, —(CH$_2$)$_3$—NH$_2$, —CH$_2$—NHCH$_3$, —(CH$_2$)$_2$—NHCH$_3$, —(CH$_2$)$_3$—NHCH$_3$, —(CH$_2$)$_t$—N(CH$_3$)$_2$, —(CH$_2$)$_n$—CH$_2$OH, —(CH$_2$)$_n$—CH$_2$F, —(CH$_2$)$_n$—CH$_2$Cl, —(CH$_2$)$_n$—CH$_2$Br, —CH(CH$_3$)—(CH$_2$)$_3$—CH(CH$_3$)$_2$, —CH(CH$_3$)—(CH$_2$)$_n$—CH(CH$_3$)$_2$, —CH(CH$_3$)—(CH$_2$)$_3$—CH(CH$_3$)—CH$_2$OH, —CH(CH$_3$)—(CH$_2$)$_n$—CH(CH$_3$)—CH$_2$OH, —CH(CH$_3$)—(CH$_2$)$_3$—CH(CH$_3$)—CH$_2$F, —CH(CH$_3$)—(CH$_2$)$_n$—CH(CH$_3$)—CH$_2$F, —CH(CH$_3$)—(CH$_2$)$_3$—CH(CH$_3$)—CH$_2$Cl, —CH(CH$_3$)—(CH$_2$)$_n$—CH(CH$_3$)—

—CH$_2$Cl, —CH(CH$_3$)—(CH$_2$)$_3$—CH(CH$_3$)—CH$_2$Br, —CH(CH$_3$)—(CH$_2$)$_n$—CH(CH$_3$)—CH$_2$Br, —CH(CH$_3$)—(CH$_2$)$_3$—CH(CH$_2$F)$_2$, —CH(CH$_3$)—(CH$_2$)$_n$—CH(CH$_2$F)$_2$, —(CH$_2$)$_3$—CH(CH$_3$)$_2$, —(CH$_2$)$_n$—CH(CH$_3$)$_2$, —(CH$_2$)$_3$—CH(CH$_3$)—CH$_2$OH, —(CH$_2$)$_n$—CH(CH$_3$)—CH$_2$OH, —(CH$_2$)$_3$—CH(CH$_3$)—CH$_2$F, —(CH$_2$)$_n$—CH(CH$_3$)—CH$_2$F, —(CH$_2$)$_3$—CH(CH$_3$)—CH$_2$Cl, —(CH$_2$)$_n$—CH(CH$_3$)—CH$_2$Cl, —(CH$_2$)$_3$—CH(CH$_3$)—CH$_2$Br, —(CH$_2$)$_n$—CH(CH$_3$)—CH$_2$Br, —(CH$_2$)$_3$—CH(CH$_2$F)$_2$, —CH$_3$, —CH$_2$CH$_3$, —CH$_2$CH$_2$CH$_3$, —CH$_2$OH, —CH$_2$CH$_2$OH, —CH$_2$CH$_2$CH$_2$OH, —CH$_2$CH(OH)CH$_3$, —(CH$_2$)$_n$—CH(CH$_2$F)$_2$, —CH(CH$_3$)—(CH$_2$)$_n$—CH(CH$_2$CH$_3$)—CH(CH$_3$)$_m$(CH$_2$R$^{51}$)$_p$, —C≡CH, —C≡CCH$_3$, —C≡CCF$_3$, —C≡CCl, —CH=CH$_2$, —CF=CF$_2$, —CF=CFCH$_3$, —CH=CHCH$_3$, —C(O)—NH—C$_6$H$_5$, —C(O)—NH—CH$_3$, —C(O)—NH—C$_2$H$_5$, —C(CH$_3$)=N—OH, —C(CH$_3$)=N—NH—C(O)—OC$_2$H$_5$, —C(CH$_3$)=N—NH—C(O)—OC$_4$H$_9$, —C(CH$_3$)=N—NH—C(O)—OC$_6$H$_5$, —CH$_2$—C$_6$H$_5$, —CH$_2$—C$_6$H$_5$(CH$_2$)$_n$—F, —C$_6$H$_5$, —C$_6$H$_4$(CH$_2$)$_n$—F, —C$_6$H$_4$(CH$_2$)$_n$—OH, —(CH$_2$)$_p$—CH=[z]CH—(CH$_2$)$_m$—C$_6$H$_4$—O—NH$_2$ (where o means ortho substituted), —(CH$_2$)$_p$—CH=[E]CH—(CH$_2$)$_m$—C$_6$H$_4$-o-NH$_2$, —(CH$_2$)$_p$—CH=[z]CH—(CH$_2$)$_m$—C$_6$H$_4$-m-NH$_2$ (where m means meta substituted), —(CH$_2$)$_p$—CH=[E]CH—(CH$_2$)$_m$—C$_6$H$_4$-m-NH$_2$, —(CH$_2$)$_p$—CH=[z]CH—(CH$_2$)$_m$—C$_6$H$_4$-p-NH$_2$ (where p means para substituted), —(CH$_2$)$_p$—CH=[E]CH—(CH$_2$)$_m$—C$_6$H$_4$-p-NH$_2$, —(CH$_2$)$_p$—CH=[z]CH—(CH$_2$)$_m$—C$_6$H$_4$—O—NHCH$_3$, —(CH$_2$)$_p$—CH=[E]CH—(CH$_2$)$_m$—C$_6$H$_4$-o-NHCH$_3$, —(CH$_2$)$_p$—CH=[z]CH—(CH$_2$)$_m$—C$_6$H$_4$-m-NHCH$_3$, —(CH$_2$)$_p$—CH=[E]CH—(CH$_2$)$_m$—C$_6$H$_4$-m-NHCH$_3$, —(CH$_2$)$_p$—CH=[z]CH—(CH$_2$)$_m$—C$_6$H$_4$-p-NHCH$_3$, —(CH$_2$)$_p$—CH=[E]CH—(CH$_2$)$_m$—C$_6$H$_4$-p-NHCH$_3$, —(CH$_2$)$_p$—CH=[z]CH—(CH$_2$)$_m$—C$_6$H$_4$—O—NHC$_2$H$_5$, —(CH$_2$)$_p$—CH=[E]CH—(CH$_2$)$_m$—C$_6$H$_4$—O—NHC$_2$H$_5$, —(CH$_2$)$_p$—CH=[z]CH—(CH$_2$)$_m$—C$_6$H$_4$-m-NHC$_2$H$_5$, —(CH$_2$)$_p$—CH=[E]CH—(CH$_2$)$_m$—C$_6$H$_4$-m-NHC$_2$H$_5$, —(CH$_2$)$_p$—CH=[z]CH—(CH$_2$)$_m$—C$_6$H$_4$-p-NHC$_2$H$_5$, —(CH$_2$)$_p$—CH=[E]CH—(CH$_2$)$_m$—C$_6$H$_4$-p-NHC$_2$H$_5$, —(CH$_2$)$_p$—CH=[z]CH—(CH$_2$)$_m$—C$_6$H$_4$—O—N(C$_2$H$_5$)$_2$, —(CH$_2$)$_p$—CH=[E]CH—(CH$_2$)$_m$—C$_6$H$_4$—O—N(C$_2$H$_5$)$_2$, —(CH$_2$)$_p$—CH=[z]CH—(CH$_2$)$_m$—C$_6$H$_4$-m-N(C$_2$H$_5$)$_2$, —(CH$_2$)$_p$—CH=[E]CH—(CH$_2$)$_m$—C$_6$H$_4$-m-N(C$_2$H$_5$)$_2$, —(CH$_2$)$_p$—CH=[z]CH—(CH$_2$)$_m$—C$_6$H$_4$-p-N(C$_2$H$_5$)$_2$, —(CH$_2$)$_p$—CH=[E]CH—(CH$_2$)$_m$—C$_6$H$_4$-p-N(C$_2$H$_5$)$_2$, —(CH$_2$)$_p$—CH=[z]CH—(CH$_2$)$_m$—C$_6$H$_4$—O—N(CH$_3$)$_2$, —(CH$_2$)$_p$—CH=[E]CH—(CH$_2$)$_m$—C$_6$H$_4$—O—N(CH$_3$)$_2$, —(CH$_2$)$_p$—CH=[z]CH—(CH$_2$)$_m$—C$_6$H$_4$-m-N(CH$_3$)$_2$, —(CH$_2$)$_p$—CH=[E]CH—(CH$_2$)$_m$—C$_6$H$_4$-m-N(CH$_3$)$_2$, —(CH$_2$)$_p$—CH=[z]CH—(CH$_2$)$_m$—C$_6$H$_4$-p-N—N(CH$_3$)$_2$, —(CH$_2$)$_p$—CH=[E]CH—(CH$_2$)$_m$—C$_6$H$_4$-p-N(CH$_3$)$_2$, —(CH$_2$)$_p$—CH=[z]CH—(CH$_2$)$_m$—C$_6$H$_4$—O—NH—C1-6 optionally substituted alkyl, —(CH$_2$)$_p$—CH=[E]CH—(CH$_2$)$_m$—C$_6$H$_4$-o-NH—C1-6 optionally substituted alkyl, —(CH$_2$)$_p$—CH=[z]CH—(CH$_2$)$_m$—C$_6$H$_4$-m-NH—C1-6 optionally substituted alkyl, —(CH$_2$)$_p$—CH=[E]CH—(CH$_2$)$_m$—C$_6$H$_4$-m-NH—C1-6 optionally substituted alkyl, —(CH$_2$)$_p$—CH=[z]CH—(CH$_2$)$_m$—C$_6$H$_4$-p-NH—C1-6 optionally substituted alkyl, —(CH$_2$)$_p$—CH=[E]CH—(CH$_2$)$_m$—C$_6$H$_4$-p-NH—C1-6 optionally substituted alkyl, —(CH$_2$)$_p$—CH=[z]CH—(CH$_2$)$_m$—C$_6$H$_4$-o-N(C1-6 optionally substituted alkyl)$_2$, —(CH$_2$)$_p$—CH=[E]CH—(CH$_2$)$_m$—C$_6$H$_4$-o-N(C1-6 optionally substituted alkyl)$_2$, —(CH$_2$)$_p$—CH=[z]CH—(CH$_2$)$_m$—C$_6$H$_4$-m-N(C1-6 optionally substituted alkyl)$_2$, —(CH$_2$)$_p$—CH=[E]CH—(CH$_2$)$_m$—C$_6$H$_4$-m-N(C1-6 optionally substituted alkyl)$_2$, —(CH$_2$)$_p$—CH=[z]CH—(CH$_2$)$_m$—C$_6$H$_4$-p-N(C1-6 optionally substituted alkyl)$_2$, —(CH$_2$)$_p$—CH=[E]CH—(CH$_2$)$_m$—C$_6$H$_4$-p-N(C1-6 optionally substituted alkyl)$_2$, —C$_6$H$_4$(CH$_2$)$_n$—C(O)OH, —C$_6$H$_4$(CH$_2$)$_n$—C(O)OCH$_3$, —CH=CH—(CH$_2$)$_n$—CH$_3$, —CH(CH$_3$)—(CH$_2$)$_n$—CH$_2$—C(H)$_q$(CH$_3$)$_m$(CH$_2$R$^{51}$)$_p$, —CH(CH$_3$)—(CH$_2$)$_n$—CH=C(CH$_3$)(CH$_2$OH), —CH(CH$_2$OH)—(CH$_2$)$_n$—CH=C(CH$_3$)$_2$, =CH—(CH$_2$)$_n$—R$^{45}$, =CH—(CH$_2$)$_t$—(CH=CH)—R$^{45}$, =C(CH$_3$)—CH$_2$—C(O)—N(C1-C6 alkyl)$_2$, =C(CH$_3$)—(CH$_2$)$_2$—C(O)—N(C1-C6 alkyl)$_2$, =C(CH$_3$)—CH$_2$—C(O)—NH—C1-C6 alkyl, =C(CH$_3$)—(CH$_2$)$_2$—C(O)—NH—C1-C6 alkyl, =C(CH$_3$)—CH$_2$—N(C1-C6 alkyl)$_2$, =C(CH$_3$)—(CH$_2$)$_2$—N(C1-C6 alkyl)$_2$, =C(CH$_3$)—CH$_2$—NH—C1-C6 alkyl, =C(CH$_3$)—(CH$_2$)$_2$—NH—C1-C6 alkyl, =CH—CH$_2$—C(O)—N(C1-C6 alkyl)$_2$, =CH—(CH$_2$)$_2$—C(O)—N(C1-C6 alkyl)$_2$, =CH—CH$_2$—C(O)—NH—C1-C6 alkyl, =CH—(CH$_2$)$_2$—C(O)—NH—C1-C6 alkyl, =CH—CH$_2$—N(C1-C6 alkyl)$_2$, =CH—(CH$_2$)$_2$—N(C1-C6 alkyl)$_2$, =CH—CH$_2$—NH—C1-C6 alkyl, =CH—(CH$_2$)$_2$—NH—C1-C6 alkyl, =C(CH$_3$)—CH$_2$—C(O)—NH$_2$, =C(CH$_3$)—(CH$_2$)$_2$—C(O)—NH$_2$, =C(CH$_3$)—(CH$_2$)$_2$—NH$_2$, =C(CH$_3$)—CH$_2$—NH$_2$, =CH—CH$_2$—C(O)—NH$_2$, =CH—(CH$_2$)$_2$—C(O)—NH$_2$, =CH—CH$_2$—NH$_2$, =CH—(CH$_2$)$_2$—NH$_2$, —(CH$_2$)$_3$—X—(CH$_2$)$_3$—C$_2$F$_5$, —(CH$_2$)$_3$—X—(CH$_2$)$_3$—C$_2$F$_5$, —(CH2)5-N(CH3)-(CH2)3-S—(CH2)3-S—(CH2)3-C2F5, —(CH2)5-NH—(CH2)3-S—(CH2)3-C2F5, —(CH2)5-N(CH3)-(CH2)3-S—CH2-2-pyridyl, —(CH2)5-N(CH3)-(CH2)3-SO—CH2-2-pyridyl, —(CH2)5-N(CH3)-(CH2)3-S—CH2-p-CF3-phenyl, —(CH2)5-N(CH3)-(CH2)3-SO—CH2-p-CF3-phenyl, —(CH2)5-[2-pyrrolidine-1-yl]CH2-S-p-CF3-phenyl, —(CH2)5-[2-pyrrolidine-1-yl]-CH2-SO-p-CF3-phenyl, —(CH2)5-N(CH3)-(CH2)3C2F5, —(CH2)5-N(CH3)-(CH2)6C2F5, —(CH2)5-N(CH3)-(CH2)7-C2F5, —(CH2)5-N(CH3)-(CH2)8-C2F5, —(CH2)6-N(CH3)-(CH2)6-C2F5, —(CH2)6-N(CH3)-(CH2)7-C2F5, —(CH2)6-N(CH3)-(CH2)8-C2F5, —(CH2)5-N(CH3)-(CH2)2-C4F9, —(CH2)5-N(CH3)-(CH2)3-C6F13, —(CH2)5-N(CH3)-(CH2)3-C8F17, —(CH2)5-N(CH3)-(CH2)6-C4F9, —(CH2)5-N(CH3)-(CH2)6-C6F13, —(CH2)5-N(CH3)-(CH2)6-C8F17, —(CH2)5-N(CH3)H, —(CH2)5-N(CH3)(CH2)9-H, —(CH2)5-N(CH3)CH2 CH=CF—C2F5, —(CH2)5-N(CH3)CH2-CH=CF—C3F7, —(CH2)5-N(CH3)CH2 CH=CF—C5F11, —(CH2)5-N(CH3)CH2 CH=CF—C7F15, —(CH2)5-1-pyrrolidinyl, —(CH2)5-N(CH3)(CH2)3-O-phenyl, —(CH2)5-N(CH3)-(CH2)3-O-benzyl, —(CH2)5-N(CH3)(CH2)3-O(CH2)3C2F5, —(CH2)5-N(CH3)(CH2)3-CH(CH3)2, —(CH2)5-N(CH3)-(CH2)-3-pyridyl, —(CH2)5-N(CH3)-(CH2)-3-phenyl, —(CH2)5-N(CH3)—(CH2)-3-p-tolyl, —(CH2)5-N(CH3)(CH2)-3-p-ethoxyphenyl, —(CH2)5-N(CH3)(CH2)-3-p-tolyl, —(CH2)5-N(CH3)-(CH2)-3-p-chlorophenyl, —(CH2)5-N(CH3)-(CH2)3-O—CH2-phenyl, —(CH$_2$)$_3$—N(C$_{1-3}$ alkyl)-R$^{45}$, —(CH$_2$)$_4$—N(C$_{1-3}$ alkyl)-R$^{45}$, —(CH$_2$)$_5$—N(C$_{1-3}$ alkyl)-R$^{45}$, —(CH$_2$)$_6$—N(C$_{1-3}$ alkyl)-R$^{45}$, —(CH$_2$)$_7$—N(C$_{1-3}$ alkyl)-R$^{45}$, where R$^{45}$ is an R$^1$ substituent disclosed herein, e.g., —H, —OH, —F, —Cl, —Br, —I, —OCH$_3$, —C(O)OH, —C(O)OCH$_3$, —OR$^{PR}$, —SH, —SR$^{PR}$, —NH$_2$—NH—C1-C8 optionally substituted alkyl, —N(C1-C8 optionally substituted alkyl)$_2$ where each optionally substituted alkyl moiety is the same or different, —NHR$^{PR}$, R$^{51}$ independently are an R$^1$ substituent disclosed herein, e.g., an ester, —F, —Cl, —Br, —I, alkyl (e.g., —CH$_3$), an ether (e.g., —OCH$_3$), a thioether (e.g., —SCH$_3$), an optionally substituted heterocycle, —C(O)OH, —NH$_2$ or —CN, X is —O— or —S—, m is 0, 1, 2 or 3, n independently are 0, 1, 2, 3, 4, 5 or 6, p is 0, 1, 2 or 3, q is 0, 1, 2 or 3, t is 1, 2, 3, 4, 5 or 6 and R$^{PR}$ are —H or independently selected protecting groups, or optionally substituted alkenyl, e.g., =CH$_2$, =CH$_2$CH$_3$, =CH—CH$_2$OH, =CH—(CH$_2$)$_n$—OR$^{PR}$, —CH=CH$_2$, —CH=CHF, —CH=CHCl, —CH=CHBr, —CH=CHI, —CH=CH—(CH$_2$)$_n$—OH, —CH=CH—(CH$_2$)$_n$—F, —CH=CH—(CH$_2$)$_n$—Cl, —CH=CH—(CH$_2$)$_n$—Br, —CH=CH—(CH$_2$)$_n$-I, —CH=NCH$_3$, —CH=NR$^{PR}$, —CH=N—CH$_3$, —CH=CH—CH$_3$, —CH=CH—(CH$_2$)$_n$—COOR$^{PR}$, —CH=CH—(CH$_2$)$_n$—NHR$^{PR}$, —CH=CH—CH$_2$—OR$^{PR}$, —CH=CH—CH$_2$—CF$_3$, —CH=CH$_2$—CH$_2$-halogen, —CH=CH—(CH$_2$)$_n$OCH$_3$, —CH=CH—(CH$_2$)$_n$—C(O)—O-optionally substituted alkyl, —CH=CH—(CH$_2$)$_n$—C(O)—S-optionally substituted alkyl, =CH—CH$_2$—(CH$_2$)$_n$—SR$^{PR}$, =CH—(CH$_2$)$_n$—C(O)NHR$^{PR}$, =CH—(CH$_2$)$_n$—C(O)NHCH$_3$, =CH—(CH$_2$)$_n$—C(O)NHC$_2$H$_5$, =CH—CH$_2$CH$_3$, =CH—(CH$_2$)$_n$—CH(CH$_3$)$_2$, =CH—(CH$_2$)$_n$—CH(CH$_3$)(CH$_2$OR$^{PR}$), =CH—(CH$_2$)$_n$—CH(CH$_3$)(CH$_2$C(O)OR$^{PR}$), =CH—(CH$_2$)$_n$—OH, =CCH$_3$—(CH$_2$)$_n$—OR$^{PR}$, =CCH$_3$—(CH$_2$)$_n$—C(O)OR$^{PR}$, =CCH$_3$—(CH$_2$)$_n$—C(O)NHR$^{PR}$, =CCH$_3$—(CH$_2$)$_n$-halogen, =CH—CHOH—CH$_2$—OH or =CH—CH$_2$CH$_2$-halogen, where R$^{PR}$ is —H or a protecting group and n is 0, 1, 2, 3, 4, 5 or 6, or optionally substituted alkynyl, e.g., —C≡CH, —C≡C—(CH$_2$)$_m$—OH, —C≡C-halogen, —C≡C—CH$_3$, —C≡CCF$_3$, —C≡CCH$_2$F, —C≡CCH$_2$Cl, —C≡CCH$_2$Br, —C≡CCH$_2$I, —C≡C—CH$_2$OH, —C≡C—CH$_2$-halogen, —C≡C—CH$_2$—C(O)OR$^{PR}$, —C≡C—CH$_2$—CH$_3$, —C≡CCH$_2$CF$_3$, —C≡C—CH$_2$—CH$_2$OH, —C≡C—CH$_2$—CH$_2$-halogen, —C≡C—(CH$_2$)$_n$—C$_6$H$_5$, —C≡C—(CH$_2$)$_n$—C$_6$H$_4$OH, —C≡C—(CH$_2$)$_n$—C$_6$H$_4$COOR$^{PR}$, —C≡C—(CH$_2$)$_n$—C$_6$H$_3$(OH)$_2$, —C≡C—(CH$_2$)$_n$—C$_6$H$_4$F, —C≡C—(CH$_2$)$_n$—C$_6$H$_4$Br, —C≡C—CH$_2$—CH$_2$—C(O)OR$^{PR}$, —C≡C—(CH$_2$)$_n$—CH$_3$, —C≡C—CH(CH$_3$)—(CH$_2$)$_n$—CH$_3$, —C≡C—(CH$_2$)$_n$—CHOR$^{PR}$, —C≡C—CH(CH$_3$)—(CH$_2$)$_n$—CHOR$^{PR}$, —C≡C—(CH$_2$)$_n$—CHCOOR$^{PR}$, —C≡C—CH(CH$_3$)—(CH$_2$)$_n$—NHR$^{PR}$, —C≡C—(CH$_2$)$_n$—NHR$^{PR}$, —C≡C—(CH$_2$)$_n$—C(O)NHR$^{PR}$, —C≡C—(CH$_2$)$_n$—C(O)NH—(CH$_2$)$_n$—CH$_3$, —C≡C—C≡C—(CH$_2$)$_n$—CH$_3$, —C≡C—C≡C—(CH$_2$)$_n$-halogen, —C≡C—(CH$_2$)$_n$—OS(O)(O)—O—R$^{PR}$, —C≡C—(CH$_2$)$_n$—OS(O)(O)—O-optionally substituted alkyl, —C≡C—C≡C—(CH$_2$)$_n$—OR$^{PR}$ or —C≡C—CH(CH$_3$)—(CH$_2$)$_n$—CHOR$^{PR}$, where n is 0, 1, 2, 3, 4, 5 or 6, m is 1, 2, 3 or 4 and R$^{PR}$ is —H or a protecting group, or optionally substituted aryl, optionally substituted alkylaryl, optionally substituted alkenylaryl or optionally substituted alkynylaryl, e.g., optionally substituted phenyl, optionally substituted benzyl, —(CH$_2$)$_n$—C$_6$H$_4$OH, —(CH$_2$)$_n$—C$_6$H$_4$OR$^{PR}$, —(CH$_2$)$_n$—C$_6$H$_3$(OH)$_2$, —(CH$_2$)$_n$—C$_6$H$_4$F, —(CH$_2$)$_n$—C$_6$H$_4$Br, —(CH$_2$)$_n$—C$_6$H$_4$C(O)OR$^{PR}$, —(CH$_2$)$_n$—C$_6$H$_4$C(O)SR$^{PR}$, —(CH$_2$)$_n$—C$_6$H$_4$—C1-4 ether, —(CH$_2$)$_n$—C$_6$H$_4$—C1-4 thioether, —(CH$_2$)$_n$—C$_6$H$_4$—C2-4 ester, —(CH$_2$)$_n$—C$_6$H$_4$—C2-4 thioester, —(CH$_2$)$_n$—C$_6$H$_4$—C1-4 optionally substituted alkyl, —(CH$_2$)$_n$—C$_6$H$_4$—C(O)—OR$^{PR}$, —(CH$_2$)$_n$—C$_6$H$_4$—C(O)—OC1-6 optionally substituted alkyl, where substitutions on the phenyl ring are at the 2-, 3- or 4-position, or analogs where the aromatic ring is substituted with 1, 2, 3 or 4 independently chosen substituents such as independently chosen halogen, —OH, —OR$^{PR}$, —SH, —SR$^{PR}$, —NH$_2$, —NHR$^{PR}$, —N(R$^{PR}$)$_2$, —NO$_2$, —CN, —SCN, —N$_3$, C1-C6 ester, C1-C6 alkyl, C1-C6 ether, C1-C6 thioether, —OR$^{PR}$, —(CH$_2$)$_n$—C(O)OR$^{PR}$, —(CH$_2$)$_n$—NHR$^{PR}$, —(CH$_2$)$_n$—OR$^{PR}$ or —(CH$_2$)$_m$—O—(CH$_2$)$_m$—OR$^{PR}$ where n independently are 0, 1, 2, 3, 4, 5 or 6, m independently are 1, 2 or 3 and R$^{PR}$ independently are —H, a protecting group or together R$^{PR}$ are a protecting group, or ether, e.g., optionally substituted alkoxy, optionally substituted alkenyloxy, optionally substituted alkynyloxy, optionally substituted aryloxy, —OCH$_3$, —OC$_2$H$_5$, —OC$_3$H$_7$, —OC$_4$H$_9$, —OC$_2$H$_3$, —OC$_3$H$_5$, —OC$_4$H$_7$, —O—C(CH$_3$)$_3$, —OCH$_2$CH$_2$OH, —O(CH$_2$)$_2$—O—CH$_3$, —O(CH$_2$)$_3$—O—CH$_3$, —O—CH(CH$_3$)CH$_3$, —O—CH$_2$CH$_2$CH$_3$, —OCH$_2$CH$_2$F, —OCH$_2$CHF$_2$, —OCH$_2$CF$_3$, —OCH$_2$CH$_2$Cl, —OCH$_2$CH$_2$Br, —OCH$_2$CH$_2$I, —OCH$_2$CH$_2$CH$_2$F, —O—CH$_2$—CH(C(O)—NH—CH$_2$C(O)OH)—NH—C(O)—(CH$_2$)$_2$—CH(NH$_2$)—C(O)—OH, —O—(CH$_2$)$_2$—N$^+$(CH$_3$)$_3$), —O—(CH$_2$)$_{0-3}$—(CH=CH)$_{0-1}$—(CH$_2$)$_{0-3}$—CH$_3$, —O—(CH$_2$)$_{0-3}$—(CH=CH)—(CH$_2$)$_{0-3}$—CH$_2$F, —O—(CH$_2$)$_{1-3}$—(C≡C)—(CH$_2$)$_{0-3}$—CH$_3$, —O—(CH$_2$)$_{1-3}$—(C≡C)—(CH$_2$)$_{0-3}$—CH$_2$F, —O—C$_6$H$_5$, —O—CH$_2$—C$_6$H$_5$, —O—C1-C20 organic moiety where the organic moiety is, e.g., —CH$_3$, —C$_2$H$_5$, i-propyl, n-propyl, t-butyl, n-butyl, 1-butyl, n-hexyl, n-octyl, n-decyl, —(CH$_2$)$_{1-8}$—OH, —CHO, —(CH$_2$)$_{1-8}$—NH$_2$, —(CH$_2$)$_{1-8}$—C(O)—OH, —(CH$_2$)$_{0-3}$—(CH=CH)$_{0-1}$—(CH$_2$)$_{0-3}$—CH$_3$, —(CH$_2$)$_{0-3}$—(CH=CH)$_{0-1}$—(CH$_2$)$_{0-3}$—CH$_2$F, —(CH$_2$)$_{0-3}$—(CH=CH)$_{0-1}$—(CH$_2$)$_{0-3}$—CH$_2$Br, —(CH$_2$)$_{0-3}$—(CH=CH)$_{0-1}$—(CH$_2$)$_{0-3}$—C(O)—OR$^{PR}$, —(CH$_2$)$_{0-3}$—(CH=CH)$_{0-1}$—(CH$_2$)$_{0-3}$—NHR$^{PR}$, —C(O)—CH$_3$, —C(O)—C$_2$H$_5$, —C(O)—C$_6$H$_5$, —CF$_3$, —CH$_2$CF$_3$ or —C$_2$F$_5$, wherein R$^{PR}$ is —H or a protecting group, —O—C$_{1-10}$ optionally substituted alkyl such as i-propyl, n-propyl, t-butyl, n-butyl, n-hexyl, n-octyl, n-decyl, —(CH$_2$)$_{1-8}$—OH, —(CH$_2$)$_{1-8}$—NH$_2$, —(CH$_2$)$_{1-8}$—C(O)—OH, —(CH$_2$)$_{0-3}$—(CH=CH)$_{0-1}$—(CH$_2$)$_{0-3}$—CH$_3$, —(CH$_2$)$_{0-3}$—(CH=CH)$_{0-1}$—(CH$_2$)$_{0-3}$—CH$_2$F, —(CH$_2$)$_{0-3}$—(CH=CH)$_{0-1}$—(CH$_2$)$_{0-3}$—CH$_2$Br, —(CH$_2$)$_{0-3}$—(CH=CH)$_{0-1}$—(CH$_2$)$_{0-3}$—C(O)—OR$^{PR}$, —(CH$_2$)$_{0-3}$—(CH=CH)$_{0-1}$—(CH$_2$)$_{0-3}$—NHR$^{PR}$, —CF$_3$ and —C$_2$F$_5$, wherein R$^{PR}$ is —H or a protecting group, or ester, e.g., —OC(O)CH$_3$, —OC(O)C$_2$H$_5$, —OC(O)C$_2$H$_3$, —OC(O)CH$_2$CH$_2$CH$_3$, —OC(O)CH(CH$_3$)$_2$, —O—C(O)—(CH$_2$)$_2$—C(O)OH, —O—C(O)—(CH$_2$)$_2$—C(O)OR$^{PR}$, —O—C(O)—(CH$_2$)$_3$—C(O)OH, —O—C(O)—(CH$_2$)$_3$—C(O)OR$^{PR}$, —O—C(O)—(CH$_2$)$_4$—C(O)OH, —O—C(O)—(CH$_2$)$_5$—C(O)OH, —O—C(O)—(CH$_2$)$_5$—C(O)OR$^{PR}$, —O—C(O)—(CH$_2$)$_4$—C(O)OR$^{PR}$, —O—C(O)—(CH$_2$)$_2$—C(O)ONH$_2$, —O—C(O)—(CH$_2$)$_2$—C(O)ONHCH$_3$, —O—C(O)—(CH$_2$)$_2$—C(O)ONHC$_2$H$_5$, —O—C(O)—(CH$_2$)$_2$—C(O)ONHC$_3$H$_7$, —O—C(O)—(CH$_2$)$_2$—C(O)ONHC$_3$H$_5$, —O—C(O)—(CH$_2$)$_2$—C(O)ONHR$^{PR}$, —O—C(O)—(CH$_2$)$_2$—C(O)ON(R$^{PR}$)$_2$, —OC(O)—C(CH$_3$)$_2$—(CH$_2$)$_m$—CH$_3$, —OC(O)—(CH$_2$)$_m$—CH$_3$, —OC(O)—CH(CH$_3$)—(CH$_2$)$_m$—CH$_3$, —OC(O)—C(CF$_3$)$_2$—(CH$_2$)$_m$—CH$_3$, —OC(O)—CH(CF$_3$)—(CH$_2$)$_m$—CH$_3$, —OC(O)C$_3$H$_7$, —OC(O)C$_3$H$_5$, —OC(O)C$_4$H$_9$, —OC(O)C$_4$H$_7$, —OC(O)C(CH$_3$)$_3$, —OC(O)CH$_2$CH$_2$CH$_3$, —OC(O)C$_6$H$_5$, —OC(O)CH$_2$C$_6$H$_5$, —OC(O)—(CH$_2$)$_2$—C(O)OH, —OC(O)—(CH$_2$)$_2$—C(O)OCH$_3$, —OC(O)—(CH$_2$)$_3$—C(O)OH, —OC(O)—(CH$_2$)$_3$—C(O)OCH$_3$, —OC(O)—(CH$_2$)$_4$—C(O)OH, —OC(O)—(CH$_2$)$_4$—C(O)OCH$_3$, —OC(O)—CH(CH$_3$)—CH$_2$—C(O)OH, —OC(O)—CH(CH$_3$)—CH$_2$—C(O)OCH$_3$, —OC(O)—CH(CH$_3$)—(CH$_2$)$_2$—C(O)OH, —OC(O)—CH(CH$_3$)—(CH$_2$)$_2$—C(O)OCH$_3$, —OC(O)—C(CH$_3$)$_2$—CH$_2$—C(O)OH, —OC(O)—C(CH$_3$)$_2$—CH$_2$—C(O)OCH$_3$, —OC(O)—C(CH$_3$)$_2$—(CH$_2$)$_2$—C(O)OH, —OC(O)—C(CH$_3$)$_2$—(CH$_2$)$_2$—C(O)OCH$_3$, —OC(O)—(CH$_2$)$_2$—C(O)OH, —O—C(O)—C(O)—O—(CH$_2$)$_m$—CH$_3$, —O—C(O)—C(O)—O—(CH$_2$)$_m$—CH$_2$OH, —O—C(O)—(CH$_2$)$_n$—C(O)—O—

$-(CH_2)_m-CH_3$, $-O-C(O)-(CH_2)_n-C(O)-O-(CH_2)_m-CH_2OH$, $-O-C(O)-CH(NH_2)-CH_2OH$, $-O-C(O)-CH_2-N(CH_3)-C(=NH)-NH_2$, $-O-C(O)-CH_2-NH-C(O)-CH(CH_2SH)-NH-C(O)-(CH_2)_2-CH(NH_2)-C(O)-OH$, a C2-C20 ester such as $-O-C(O)-CH_3$, $-O-C(O)-CF_3$, $-O-C(O)-CCl_3$, $-O-C(O)-C_2H_5$, $-O-C(O)-C_4H_7$, $-O-C(O)-C_6H_5$, $-O-C(O)-(CH_2)_2-CH_3$, $-O-C(O)-(CH_2)_3-CH_3$, $-O-C(O)-(CH_2)_4-CH_3$, $-O-C(O)-(CH_2)_5-CH_3$, $-O-C(O)-(CH_2)_6-CH_3$, $-O-C(O)$-2 furanyl, $-O-C(O)$-2 thiophenyl, $-O-C(O)$-2 pyrrolyl, $-O-C(O)$-2 pyrimidinyl, $-O-C(O)$-3 pyrimidinyl, $-O-C(O)$-2 pyridyl, $-O-C(O)$-3 pyridyl, $-O-C(O)$-heterocycle, $-O-C(O)-(CH_2)_m-C(O)O-$C1-C10 optionally substituted alkyl, $-O-C(O)-(CH_2)_m-C(O)O-$C2-C10 optionally substituted alkenyl, $-O-C(O)-(CH_2)_m-O-(CH_2)_m-C(O)O-$C1-C10 optionally substituted alkyl, $-O-C(O)-(CH_2)_m-O-(CH_2)_m-C(O)OR^{PR}$, $-O-C(O)-(CH_2)_m-S-(CH_2)_m-C(O)O-$C1-C10 optionally substituted alkyl, $-O-C(O)-(CH_2)_m-S-(CH_2)_m-C(O)OR^{PR}$, $-O-C(O)-(CH_2)_m-NR^{PR}-(CH_2)_m-C(O)O-$C1-C10 optionally substituted alkyl, $-O-C(O)-(CH_2)_m-NR^{PR}-(CH_2)_m-C(O)OR^{PR}$, $-O-C(O)-C_{1-12}$ optionally substituted alkyl, $-OC(O)-(CH_2)_q-C(O)OH$, $-OC(O)-(CH_2)_q-C(O)O-C_{1-8}$ optionally substituted alkyl, $-OC(O)-CH(CH_3)-(CH_2)_q-C(O)OH$, $-OC(O)-CH(CH_3)-(CH_2)_q-C(O)O-C_{1-8}$ optionally substituted alkyl, $-OC(O)-C(CH_3)_2-(CH_2)_q-C(O)OH$, $-OC(O)-C(CH_3)_2-(CH_2)_q-C(O)O-C_{1-8}$ optionally substituted alkyl, $-OC(O)-C(C_2H_5)(CH_3)-(CH_2)_q-C(O)OH$, $-OC(O)-C(C_2H_5)(CH_3)-(CH_2)_q-C(O)O-C_{1-8}$ optionally substituted alkyl, $-OC(O)-C(C_2H_5)_2-(CH_2)_q-C(O)OH$, $-OC(O)-C(C_2H_5)_2-(CH_2)_q-C(O)O-C_{1-8}$ optionally substituted alkyl, $-OC(O)-C(C_2H_5)(C_3H_7)-(CH_2)_q-C(O)OH$, $-OC(O)-C(C_2H_5)(C_3H_7)-(CH_2)_q-C(O)O-C_{1-8}$ optionally substituted alkyl, where the optionally substituted alkyl optionally is methyl, ethyl, i-propyl, n-propyl, t-butyl, n-butyl, n-hexyl, n-octyl, n-decyl, vinyl, allyl, phenyl, monosubstituted phenyl, disubstituted phenyl, trisubstituted phenyl, $-CH_2OH$, $-CH_2OR^{PR}$, $-CH_2F$, $-CF_2H$, $-(CH_2)_n-CH_3$, $-(CH_2)_n-OH$, $-(CH_2)_n-F$, $-(CH_2)_n-Br$, $-(CH_2)_n-NH_2$, $-(CH_2)_n-C(O)-OR^{PR}$, $-(CH_2)_n-O-CH_3$, $-(CH_2)_n-S-CH_3$, $-(CH_2)_m-(CH=CH)_p-(CH_2)_q-CH_3$, $-(CH_2)_m-(CH=CH)_p-(CH_2)_q-CH_2F$, $-(CH_2)_m-(CH=CH)_p-(CH_2)_q-CH_2Br$, $-(CH_2)_m-(CH=CH)_p-(CH_2)_q-C(O)-OR^{PR}$, $-(CH_2)_m-(CH=CH)_p-(CH_2)_q-NHR^{PR}$, $-CF_3$, $-CH_2CF_3$ or $-C_2F_5$, wherein $R^{PR}$ independently are $-H$, a protecting group such as C1-C10 optionally substituted alkyl (e.g., $-CH_3$, $-C_2H_5$, $-C_3H_6OH$) or together are a protecting group, n is 1, 2, 3, 4, 5, 6, 7 or 8, m is 0, 1, 2, 3, 4, 5 or 6, p is 0 or 1 and q is 0, 1, 2, 3, 4, 5 or 6, or acyl, e.g., $-C(O)OH$, $-C(O)-CH_2OH$, $-C(O)-CH_2F$, $-C(O)-CH_2Cl$, $-C(O)-CH_2Br$, $-C(O)-CH_2I$, $-C(O)-CH_2COOH$, $-C(O)-CH_2COOR^{PR}$, $-C(O)-CH_3$, $-C(O)-CF_3$, $-C(O)-CH_2CF_3$, $-C(O)-CH(NH_2)-CH_2OH$, $-C(O)-CH_2-N(CH_3)-C(=NH)-NH_2$, $-C(O)-(CH_2)_n-CH_2OH$, $-C(O)-O-C(O)-C(CH_3)_3$, $-C(O)-O-C(O)-CH(CH_3)_2$, $-C(O)-O-C(O)-CH_3$, $-C(O)-O-C(O)-C_2H_5$, $-C(O)(CH_2)_n-CH_2F$, $-C(O)-N(CH_3)_2$, $-C(O)-N(C_2H_5)_2$, $-C(O)-N(CH_3)(C_2H_5)$, $-C(O)-NH[C(CH_3)_3]$, $-C(O)-NH(CH_3)$, $-C(O)NH_2$, $-C(O)-N(R^{PR})_2$, $-C(O)-(CH_2)_n-CH_2Cl$, $-C(O)-(CH_2)_n-CH_2Br$, $-C(O)-(CH_2)_n-CH_2-C(O)OH$, $-C(O)-(CH_2)_n-CH_2-NH_2$, $-C(O)-CH(CH_3)-(CH_2)_3-CH(CH_3)_2$, $-C(O)-CH(CH_3)-(CH_2)_n-CH(CH_3)_2$, $-C(O)-CH(CH_3)-(CH_2)_3-CH(CH_3)-CH_2OH$, $-C(O)-CH(CH_3)-(CH_2)_n-CH(CH_3)-CH_2OH$, $-C(O)-CH(CH_3)-(CH_2)_3-CH(CH_3)-CH_2F$, $-C(O)-CH(CH_3)-(CH_2)_n-CH(CH_3)-CH_2F$, $-C(O)-CH(CH_3)-(CH_2)_3-CH(CH_3)-CH_2Cl$, $-C(O)-CH(CH_3)-(CH_2)_n-CH(CH_3)-CH_2Cl$, $-C(O)CH_3$, $-C(O)CHO$, $-C(O)CH_2OH$, $-C(O)CH_2F$, $-C(O)CH_2Cl$, $-C(O)CH_2Br$, $-C(O)-CH_2OH$, $-C(O)-CH_2OR^{PR}$, $-C(O)-(CH_2)_n-CH_2OH$, $-C(O)-(CH_2)_n-CH_2OR^{PR}$, $-C(O)-S-(CH_2)_n-CH_2F$, $-C(O)-S-(CH_2)_n-CHF_2$, $-C(O)-S-(CH_2)_n-CF_3$, $-C(O)$-2 furanyl, $-C(O)$-2 thiophenyl, $-C(O)$-2 pyrrolyl, $-C(O)$-2 pyrimidinyl, $-C(O)$-3 pyrimidinyl, $-C(O)$-2 pyridyl, $-C(O)$-3 pyridyl, $-C(O)$-heterocycle, $-C(O)-$C1-C10-optionally substituted alkyl, $-C(O)-NH$-optionally substituted phenyl, $-C(O)-NH$-optionally substituted heterocycle, $-C(O)-(CH_2)_n$-optionally substituted heterocycle, $-C(O)-(CH_2)_n$-optionally substituted phenyl, or $-C(O)NR^{50}R^{51}$ where $R^{PR}$ independently are $-H$ or a protecting group such as C1-C10 optionally substituted alkyl, m is 0 or 1, n is 0, 1, 2, 3, 4, 5 or 6, and $R^{50}$ and $R^{51}$ independently are $-H$, optionally substituted phenyl, optionally substituted phenylalkyl, optionally substituted alkyl optionally substituted alkenyl, or an optionally substituted heterocycle, e.g., pyridyl, pyrrolyl, pyrimidyl, benzimidazolyl, benzoxazolyl, benzofuranyl, $-CH_3$, $-C_2H_5$, 2-, 3- or 4-fluorophenyl, 2-, 3- or 4-chlorophenyl, 2-, 3- or 4-methoxyphenyl 2-, 3- or 4-methylphenyl or 2-, 3- or 4-trifluoromethylphenyl, or thioester, e.g., $-SC(O)CH_3$, $-SC(O)C_2H_5$, $-SC(O)C_3H_7$, $-SC(O)C_4H_9$, $-SC(O)C_6H_5$, $-SC(O)CH_2C_6H_5$, $-C(O)SCH_3$, $-CS(O)C_2H_5$, $-CS(O)C_3H_7$, $-CS(O)C_4H_9$, $-CS(O)C_6H_5$, $-CS(O)CH_2C_6H_5$, $-S-C(O)-(CH_2)_2-C(O)OH$, $-S-C(O)-(CH_2)_2-C(O)OR^{PR}$, $-S-C(O)-(CH_2)_3-C(O)OH$, $-S-C(O)-(CH_2)_3-C(O)OR^{PR}$, $-S-C(O)-(CH_2)_4-C(O)OH$, $-S-C(O)-(CH_2)_5-C(O)OH$, $-S-C(O)-(CH_2)_5-C(O)OR^{PR}$, $-S-C(O)-(CH_2)_4-C(O)OR^{PR}$, $-S-C(O)-CH(NH_2)-CH_2OH$, $-S-C(O)-CH_2-N(CH_3)-C(=NH)-NH_2$, $-S-C(O)-CH_2-NH-C(O)-CH(CH_2SH)-NH-C(O)-(CH_2)_2-CH(NH_2)-C(O)-OH$), a C2-C20 such as $-S-C(O)-CH_3$, $-S-C(O)-CF_3$, $-S-C(O)-CCl_3$, $-S-C(O)-C_2H_5$, $-S-C(O)-C_6H_5$, $-S-C(O)-C_6H_4-OCH_3$, $-S-C(O)-C_6H_4-F$, $-S-C(O)-C_6H_4-Cl$, $-S-C(O)-C_6H_4-CH_3$, $-S-C(O)-C_{1-12}$ optionally substituted alkyl, $-S-C(O)-CH_2-NHR^{PR}$, $-S-C(O)-CHOH-NHR^{PR}$, $-S-C(O)-CH[(CH(OH)(CH_3)]-NHR^{PR}$, $-S-C(O)-CH(CH_3)-NHR^{PR}$, $-S-C(O)-CH[(CH_2)_2C(O)OR^{PR}]-NHR^{PR}$, $-S-C(O)-CH(CH_2C(O)OR^{PR}-NHR^{PR}$, $-S-C(O)-CH[(CH_2)_4NHR^{PR}]-NHR^{PR}$, $-S-C(O)-CH[(CH_2)_2C(O)NHR^{PR}]-NHR^{PR}$, $-S-C(O)-CH(CH_2C(O)NHR^{PR})-NHR^{PR}$, $-S-C(O)-(CH_2)_m-C(O)ON(R^{PR})_2$, $-S-C(O)-(CH_2)_m-O-(CH_2)_m-C(O)OR^{PR}$, $-S-C(O)-(CH_2)_m-S-(CH_2)_m-C(O)OR^{PR}$, $-S-C(O)-(CH_2)_m-NR^{PR}-(CH_2)_m-C(O)OR^{PR}$, $-S-C(O)-(CH_2)_m-O-(CH_2)_m-C(O)ON(R^{PR})_2$, $-S-C(O)-(CH_2)_m-O-(CH_2)_m-C(O)O-$C1-C10 optionally substituted alkyl, $-S-C(O)-(CH_2)_m-O-(CH_2)_m-C(O)OR^{PR}$, $-S-C(O)-(CH_2)_m-S-(CH_2)_m-C(O)O-$C1-C10 optionally substituted alkyl, $-S-C(O)-(CH_2)_m-S-(CH_2)_m-C(O)OR^{PR}$, $-S-C(O)-(CH_2)_m-NR^{PR}-(CH_2)_m-C(O)O-$C1-C10 optionally substituted alkyl, $-S-C(O)-(CH_2)_m-NR^{PR}-(CH_2)_m-C(O)OR^{PR}$, where the optionally substituted alkyl optionally is methyl, ethyl, i-propyl, n-propyl, t-butyl, n-butyl, n-hexyl, n-octyl, n-decyl, vinyl, allyl, phenyl, $-CH_2OH$, $-CH_2F$, $-CF_2H$, $-(CH_2)_n-CH_3$, $-(CH_2)_n-$ OH, —$(CH_2)_n$—F, —$(CH_2)_n$—Br, —$(CH_2)_n$—$NH_2$, —$(CH_2)_n$—C(O)—$OR^{PR}$, —$(CH_2)_n$—O—$CH_3$, —$(CH_2)_n$—S—$CH_3$, —$(CH_2)_m$—(CH=CH)$_p$—$(CH_2)_q$—$CH_3$, —$(CH_2)_m$(CH=CH)$_p$—$(CH_2)_q$—$CH_2F$, —$(CH_2)_m$(CH=CH)$_p$—$(CH_2)_q$—$CH_2Br$, —$(CH_2)_m$—(CH=CH)$_p$—$(CH_2)_q$—C(O)—$OR^{PR}$, —$(CH_2)_m$—(CH=CH)$_p$—$(CH_2)_q$—$NHR^{PR}$, —$CF_3$, —$CH_2CF_3$, —$C_2F_5$, or a thio analog of any ester moiety described herein, wherein $R^{PR}$ independently are —H, a protecting group such as C1-C10 optionally substituted alkyl (e.g., —$CH_3$, —$C_2H_5$, —$C_3H_6OH$) or together are a protecting group, n is 1, 2, 3, 4, 5, 6, 7 or 8, m is 0, 1, 2, 3, 4, 5 or 6, p is 0 or 1 and q is 0, 1, 2, 3, 4, 5 or 6, or thioether, e.g., —$SCH_3$, —$SC_2H_5$, —$SC_3H_7$, —$SC_4H_9$, —$SC_2H_3$, —$SC_3H_5$, —$SC_4H_7$, —$SCH_2CH_2OH$, —S—$CH_2$—CH(C(O)—NH—$CH_2$C(O)OH)—NH—C(O)—$(CH_2)_2$—CH($NH_2$)—C(O)—OH, —S—$(CH_2)_2$—$N^+$($CH_3$)$_3$), —$SCH_2CH_2F$, —$SCH_2CHF_2$, —$SCH_2CF_3$, —$SCH_2CH_2Cl$, —$SCH_2CH_2Br$, —$SCH_2CH_2I$, —$SCH_2CH_2CH_2F$, —S—$SCH_3$, —S—$SC_2H_5$, —S—$SC_3H_7$, —S—$SC_4H_9$, —S—$C_{1-20}$ organic moiety, —S—S—$C_{1-20}$ organic moiety, —S—$CH_2$—S—$C_{1-20}$ organic moiety, —S—$(CH_2)_2$—S—$C_{1-20}$ organic moiety, —S—$(CH_2)_2$—O—$C_{1-20}$ organic moiety, —S—S—$CH_3$, —S—S—$C_2H_5$, where the organic moiety is any moiety described herein such as —$CH_3$, —$C_2H_5$, i-propyl, n-propyl, t-butyl, n-butyl, n-hexyl, n-octyl, n-decyl, —$(CH_2)_{1-8}$—OH, —$(CH_2)_{1-8}$—$NH_2$, —$(CH_2)_{1-8}$—C(O)—OH, —$(CH_2)_{0-3}$—(CH=CH)$_{0-1}$—$(CH_2)_{0-3}$—$CH_3$, —$(CH_2)_{0-3}$—(CH=CH)$_{0-1}$—$(CH_2)_{0-3}$—$CH_2F$, —$(CH_2)_{0-3}$—(CH=CH)$_{0-1}$—$(CH_2)_{0-3}$—$CH_2Br$, —$(CH_2)_{0-3}$—(CH=CH)$_{0-1}$—$(CH_2)_{0-3}$—C(O)—$OR^{PR}$, —$(CH_2)_{0-3}$—(CH=CH)$_{0-1}$—$(CH_2)_{0-3}$—$NHR^{PR}$, —$(CH_2)_{0-3}$—C(O)—$CH_3$, —C(O)—$C_2H_5$, —C(O)—$C_6H_5$, —S—$C_{3-8}$ alkyl, —S—$C_{3-8}$ substituted alkyl, —$CF_3$, —$CH_2CF_3$ or —$C_2F_5$, wherein $R^{PR}$ is —H or a protecting group, —S—$C_{1-10}$ optionally substituted alkyl such as i-propyl, n-propyl, t-butyl, n-butyl, n-hexyl, n-octyl, n-decyl, —$(CH_2)_{1-8}$—OH, —$(CH_2)_{1-8}$—$NH_2$, —$(CH_2)_{1-8}$—C(O)—OH, —$(CH_2)_{0-3}$—(CH=CH)$_{0-1}$—$(CH_2)_{0-3}$—$CH_3$, —$(CH_2)_{0-3}$—(CH=CH)$_{0-1}$—$(CH_2)_{0-3}$—$CH_2F$, —$(CH_2)_{0-3}$—(CH=CH)$_{0-1}$—$(CH_2)_{0-3}$—$CH_2Br$, —$(CH_2)_{0-3}$—(CH=CH)$_{0-1}$—$(CH_2)_{0-3}$—C(O)—$OR^{PR}$, —$(CH_2)_{0-3}$—(CH=CH)$_{0-1}$—$(CH_2)_{0-3}$—$NHR^{PR}$, —$CF_3$, —$C_2F_5$, wherein $R^{PR}$ is —H or a protecting group, or thioacyl, e.g., —C(S)—$(CH_2)_n$—$CH_2OH$, —C(S)—$(CH_2)_n$—$CH_2F$, —C(S)—$(CH_2)_n$—$CH_2Cl$, —C(S)—$(CH_2)_n$—$CH_2Br$, —C(S)—CH($CH_3$)—$(CH_2)_3$—CH($CH_3$)$_2$, —C(S)—CH($CH_3$)—$(CH_2)_n$—CH($CH_3$)$_2$, —C(S)—CH($CH_3$)—$(CH_2)_3$—CH($CH_3$)—$CH_2OH$, —C(S)—CH($CH_3$)—$(CH_2)_n$—CH($CH_3$)—$CH_2OH$, —C(S)—CH($CH_3$)—$(CH_2)_3$—CH($CH_3$)—$CH_2F$, —C(S)—CH($CH_3$)—$(CH_2)_n$—CH($CH_3$)—$CH_2F$, —C(S)—CH($CH_3$)—$(CH_2)_3$—CH($CH_3$)—$CH_2Cl$, —C(S)—CH($CH_3$)—$(CH_2)_n$—CH($CH_3$)—$CH_2Cl$, —C(S)$CH_3$, —C(S)$CH_2OH$, —C(S)$CH_2F$, —C(S)$CH_2Cl$, —C(S)$CH_2Br$, —C(S)-2 furanyl, —C(S)-2 thiophenyl, —C(S)-2 pyrrolyl, —C(S)-2 pyrimidinyl, —C(S)-3 pyrimidinyl, —C(S)-2 pyridyl, —C(S)-3 pyridyl, —C(S)-heterocycle, —C(S)—C1-C20-optionally substituted alkyl or a thio analog of any acyl moiety described herein, where n is 0, 1, 2, 3, 4, 5 or 6, or optionally substituted amine, e.g., —$NH_2$, —$NH_3^+Cl^-$, —$NH_3^+Br^-$, —$NH_3^+I^-$, alkylamine, dialkylamine, —NH—$CH_3$, —N($CH_3$)$_2$, —$N^+$($CH_3$)$_3$, —$N^+$($C_2H_5$)$_3$, —NHOH, —$NHR^{PR}$, —N($R^{PR}$)$_2$, —NH—C(O)$CH_3$, —NH—C(O)$CF_3$, —N(C(O)$CF_3$)$_2$, —NH—C(O)$CCl_3$, —N(C(O)$CCl_3$)$_2$, —NH—C(O)$C_6H_5$, —N(C(O)$C_6H_5$)$_2$, —NH—$C_2H_5$, —N($C_2H_5$)$_2$, —NH—$CH_2OH$, —NH—$CH_2$—$CH_2OH$, —NH—$C_3H_7$, —N($C_3H_7$)$_2$, —NH—C(=NH)—N($CH_3$)—$CH_2$—C(O)$OR^{PR}$, —N($CH_3$)$_2$, —N($C_2H_5$)$_2$, —N($CH_3$)($C_2H_5$)—N($CH_2OH$)($CH_3$), —N=C[$(CH_2)_n$—H]—OH, —NH—NH—C(O)-optionally substituted alkyl, —NH—C(NH-optionally substituted alkyl)=N-optionally substituted alkyl, —N=C[$(CH_2)_n$—H]-O-optionally substituted alkyl, —NH-organic moiety, —NH—C(O)-organic moiety, e.g., —NH—C(O)—$CH_3$, optionally substituted phenyl, —NH-optionally substituted alkyl, —N(optionally substituted alkyl)$_2$, —N(C(O)-optionally substituted alkyl)$_2$, —NH—C(O)-optionally substituted alkyl or —NH—$(CH_2)_n$-optionally substituted alkyl, wherein any of the phenyl or alkyl moieties are the same or different and are optionally substituted with 1, 2, 3 or more independently selected with substituents described herein, e.g., —O—, —NH—, —S—, —F, —Cl, —Br, —I, —OH, —$OR^{PR}$, —SH, —$SR^{PR}$, —$CH_3$, —$C_2H_5$, —O—$CH_3$, —O—$C_2H_5$, —$NO_2$, —CN, —SCN, —$NH_2$, —C(O)$OR^{PR}$ or —$(CH_2)_n$—C(O)—$OR^{PR}$, wherein n is 0, 1, 2, 3 or 4, $R^{PR}$ independently or together are —H or a protecting group and the organic moiety is as described herein, e.g., optionally substituted alkyl or an ester, or optionally substituted amide, e.g., —C(O)—$NH_2$, —C(O)—NH—C($CH_3$)$_3$, —C(O)—$NH_2$, —C(O)—NH—$CH_3$, —C(O)—NH—$(CH_2)_m$—$CH_3$, —C(O)—NH—$(CH_2)_m$—$NH_2$, —C(O)—NH—$(CH_2)_m$—$NHR^{PR}$, —C(O)—NH—$(CH_2)_m$—NH—$(CH_2)_n$—$CH_3$, —NH—C(O)H, —NH—C(O)—$CH_2$—$CH_2$—C(O)OH, —NH—C(O)—$CH_2$—$CH_2$—C(O)$OR^{PR}$, —NH—C(O)—$(CH_2)_m$—C(O)OH, —NH—C(O)—$(CH_2)_m$—C(O)$OR^{PR}$, —NH—C(O)—$CH_3$, —NH—C(O)—$(CH_2)_m$—$CH_3$, —NH—C(O)—$(CH_2)_m$—$NH_2$, —NH—C(O)—$(CH_2)_m$—$NHR^{PR}$, —NH—C(O)—O—C($CH_3$)$_3$, —NH—C(O)—O—$CH_3$, —NH—C(O)—$(CH_2)_m$—NH—$(CH_2)_n$—$CH_3$, —C(O)—NH-organic moiety, —C(O)—NH-optionally substituted alkyl, —C(O)—$NR^{49}$—(O)$_p$-organic moiety, —C(O)—NH—(O)$_p$—$(CH_2)_n$-optionally substituted phenyl, —C(O)—NH—$(CH_2)_n$—(O)$_p$-optionally substituted alkyl, —NH—C(O)—(O)$_p$-optionally substituted alkyl, —NH—C(S)—(O)$_p$-optionally substituted alkyl, —NH—C(O)—(S)$_p$-optionally substituted alkyl, wherein 1, 2 or more of any organic, phenyl, alkyl, alkylene, e.g., —$(CH_2)$—, —$(CH_2)_m$— or —$(CH_2)_n$—, methyl, ethyl, n-butyl or t-butyl, moieties are optionally substituted with 1, 2, 3, 4, 5 or more independently selected substituents described herein, e.g., —F, —Cl, —Br, —I, —OH, —$CH_3$, —$C_2H_5$, —O—$CH_3$, —O—$C_2H_5$, —$NO_2$, —CN, —SCN, —$NH_2$, —C(O)$OR^{PR}$ or —$(CH_2)_{1-4}$—C(O)—$OR^{PR}$, where $R^{49}$ is a protecting group, an organic moiety comprising about 1-10 carbon atoms or $R^{49}$ together with the organic moiety is a protecting group and the organic group optionally is optionally substituted alkyl such as i-propyl, n-propyl, t-butyl, n-butyl, n-hexyl, n-octyl, n-decyl, —$(CH_2)_m$—OH, —$(CH_2)_m$—F, —$(CH_2)_m$—Cl, —$(CH_2)_m$—Br, —$(CH_2)_m$—$NH_2$, —$(CH_2)_m$—C(O)—OH, —$(CH_2)_m$—C(O)—H, —$(CH_2)_m$—C(O)—$CH_3$, —$(CH_2)_n$—(CH=CH)$_p$—$(CH_2)_n$—$CH_3$, —$(CH_2)_n$—(CH=CH)$_p$—$(CH_2)_n$—$CH_2F$, —$(CH_2)_n$—(CH=CH)$_p$—$(CH_2)_n$—$CH_2Br$, —$(CH_2)_n$—(CH=CH)$_p$—$(CH_2)_n$—C(O)—$OR^{PR}$, —$(CH_2)_n$—(CH=CH)$_p$—$(CH_2)_n$—$NHR^{PR}$, —$CF_3$ or —$C_2F_5$, and $R^{PR}$ is —H or a protecting group, optionally substituted alkyl moieties contain 1, 2, 3, 4, 5, 6, 7, 8, 9, 10 or more carbon atoms and wherein m independently are 1, 2, 3, 4, 5 or 6, n independently are 0, 1, 2, 3 or 4 and p is 0 or 1, or epoxide or optionally substituted cyclopropyl, when taken together with a hydrogen at an adjacent position on the steroid nucleus, usually where the epoxide or optionally substituted cyclopropyl bonds are both in the α-configuration or the β-configuration, e.g., one or more independently selected epoxide or optionally substituted cyclopropyl ring is present at the 1-2 positions, the 2-3 positions, the 4-5 positions, the 5-6 positions, the 10-11 positions, the 11-12 positions, the 15-16 positions, the 16-17 positions, or at the 2-3 and 16-17 positions of the steroid nucleus, or —O—Si(C1-C6 alkyl)$_3$ where each alkyl is independently chosen, e.g., —O—Si(CH$_3$)$_3$, —O—Si[C(CH$_3$)$_3$](CH$_3$)$_2$, —O—Si[C(CH$_3$)$_3$](C$_2$H$_5$)$_2$, or phosphate ester, phosphoester, or an ether or thioether derivative thereof, e.g., —O—P(O)(OH)—OCH$_3$, —O—P(O)(OH)—OC$_2$H$_5$, —O—P(O)(OH)—OC$_3$H$_7$, —O—P(O)(OH)—OCH$_2$CH=CH$_2$, —O—P(O)(OCH$_3$)—OCH$_3$, —O—P(O)(OC$_2$H$_5$)—OC$_2$H$_5$, —O—P(O)(OH)—O—(CH$_2$)$_2$—N$^+$(CH$_3$)$_3$, —O—P(O)(OH)—O—(CH$_2$)$_2$—NH$_2$, —O—P(O)(OH)—OH, —O—P(O)(OH)—SH, —O—P(O)(OR$^{PR}$)—OH, —O—P(O)(OR$^{PR}$)—SH, —S—P(O)(OH)—OH, —O—P(O)(OH)—S—(CH$_2$)$_2$—NH—(CH$_2$)$_3$—NH$_2$, —O—P(O)(OH)—O—CH$_3$, —O—P(O)(OCH$_3$)$_2$, —O—P(O)(OH)—O—C$_2$H$_5$, —O—P(O)(OC$_2$H$_5$)$_2$, —O—P(O)(OH)—O—C$_3$H$_7$, —O—P(O)(OC$_3$H$_7$)$_2$, —O—P(O)(OH)—O—CH$_2$—CH(O—C(O)—(CH$_2$)$_y$(CH=CH)$_q$(CH$_2$)$_y$—CH$_3$)—CH$_2$—O—C(O)—(CH$_2$)$_y$(CH=CH)$_q$(CH$_2$)$_y$—CH$_3$, —O—P—(O)(OH)—O—CH$_2$—CH(O—C(O)—(CH$_2$)$_x$CH$_3$)—CH$_2$—O—C(O)—(CH$_2$)$_x$CH$_3$), —O—P—(O)(OH)—O—CH$_2$—CH(O—C(O)—(CH$_2$)$_{14}$—CH$_3$)—CH$_2$—O—C(O)—(CH$_2$)$_{14}$CH$_3$), —O—P—(O)(OH)—O—CH$_2$—CH(O—C(O)—(CH$_2$)$_{12}$CH$_3$)—CH$_2$—O—C(O)—(CH$_2$)$_{12}$CH$_3$), —O—P(O)(OH)—O-optionally substituted alkyl, —S—P(O)(OH)—O-optionally substituted alkyl, —O—P(O)(OH)—S-optionally substituted alkyl, —O—P(O)(O-optionally substituted alkyl)-O-optionally substituted alkyl, —S—P(O)(O-optionally substituted alkyl)-O-optionally substituted alkyl, —O—P(O)(O-optionally substituted alkyl)-S-optionally substituted alkyl, where the optionally substituted alkyl moieties are as described herein and are independently selected, e.g., i-propyl, n-propyl, t-butyl, n-butyl, n-hexyl, n-octyl, n-decyl, —(CH$_2$)$_m$—OH, —(CH$_2$)$_m$—F, —(CH$_2$)$_m$—Cl, —(CH$_2$)$_m$—Br, —(CH$_2$)$_m$—NH$_2$, —(CH$_2$)$_m$—C(O)—OH, —(CH$_2$)$_m$—C(O)—H, —(CH$_2$)$_m$—C(O)—CH$_3$, —(CH$_2$)$_n$—(O)$_p$—(CH$_2$)$_n$—CH$_3$, —(CH$_2$)$_n$—(O)$_p$—(CH$_2$)$_n$—CH$_2$OH, —(CH$_2$)$_n$—(CH=CH)$_p$—(CH$_2$)$_n$—CH$_3$, —(CH$_2$)$_n$—(CH=CH)$_p$—(CH$_2$)$_n$—CH$_2$OH, —(CH$_2$)$_n$—(CH=CH)$_p$—(CH$_2$)$_n$—CH$_2$F, —(CH$_2$)$_n$—(CH=CH)$_p$—(CH$_2$)$_n$—CH$_2$Br, —(CH$_2$)$_n$—(CH=CH)$_p$—(CH$_2$)$_n$—C(O)—OR$^{PR}$, —(CH$_2$)$_n$—(CH=CH)$_p$—(CH$_2$)$_n$—NHR$^{PR}$, —(CH$_2$)$_n$—(C≡C)$_p$—(CH$_2$)$_n$—CH$_3$, —(CH$_2$)$_n$—(C≡C)$_p$—(CH$_2$)$_n$—CH$_2$OH, —(CH$_2$)$_n$(C≡C)$_p$—(CH$_2$)$_n$—CH$_2$F, —(CH$_2$)$_n$—(C≡C)$_p$—(CH$_2$)$_n$—CH$_2$Br, —(CH$_2$)$_n$—(C≡C)$_p$—(CH$_2$)$_n$—C(O)—OR$^{PR}$, —(CH$_2$)$_n$—(C≡C)$_p$—(CH$_2$)$_n$—NHR$^{PR}$, —CF$_3$ or —C$_2$F$_5$, wherein R$^{PR}$ is —H or a protecting group, m is 1, 2, 3, 4, 5 or 6, n independently are 0, 1, 2, 3, 4, 5 or 6 and p is 0 or 1, q is 0 or 1, x independently are 0, 1, 2, 3, 4, 5, 6, 7, 8, 9, 10, 11, 12, 13, 14, 15, 16 or 17, y independently are 0, 1, 2, 3, 4, 5, 6, 7, 8 or 9 and substituents bonded at double bonds are in the cis, trans or mixed cis and trans configuration, wherein In some embodiments, both n and p are 1 or p is 1 and both n are 2 or one n is 1, the other n is 2 and p is 1, or thionoester, e.g., a C2-C20 thionoester such as —O—C(S)—CH$_3$, —O—C(S)—CF$_3$, —O—C(S)—C$_2$H$_5$ or —O—C(S)—C$_{1-12}$ optionally substituted alkyl where the optionally substituted alkyl optionally is i-propyl, n-propyl, t-butyl, n-butyl, n-hexyl, n-octyl, n-decyl, vinyl, allyl, phenyl, —CH$_2$OH, —CH$_2$F, —CF$_2$H, —(CH$_2$)$_n$—CH$_3$, —(CH$_2$)$_n$—OH, —(CH$_2$)$_n$—F, —(CH$_2$)$_n$—Br, —(CH$_2$)$_n$—NH$_2$, —(CH$_2$)$_n$—C(O)—OR$^{PR}$, —(CH$_2$)$_n$—O—CH$_3$, —(CH$_2$)$_n$—S—CH$_3$, —(CH$_2$)$_m$—(CH=CH)$_p$—(CH$_2$)$_q$—CH$_3$, —(CH$_2$)$_m$(CH=CH)$_p$—(CH$_2$)$_q$—CH$_2$F, —(CH$_2$)$_m$—(CH=CH)$_p$—(CH$_2$)$_q$—CH$_2$Br, —(CH$_2$)$_m$—(CH=CH)$_p$—(CH$_2$)$_q$—C(O)—OR$^{PR}$, —(CH$_2$)$_m$—(CH=CH)$_p$—(CH$_2$)$_q$—NHR$^{PR}$, —CF$_3$, —CH$_2$CF$_3$ or —C$_2$F$_5$, wherein R$^{PR}$ is —H or a protecting group, n is 1, 2, 3, 4, 5, 6, 7 or 8, m is 0, 1, 2, 3, 4, 5 or 6, p is 0 or 1 and q is 0, 1, 2, 3, 4, 5 or 6, or amino acid or peptide, e.g., a dipeptide, —O—C(O)—CH$_2$—NHR$^{PR}$, —O—C(O)—CHOH—NHR$^{PR}$, —O—C(O)—CH[(CH(OH)(CH$_3$)]—NHR$^{PR}$, —O—C(O)—CH(CH$_3$)—NHR$^{PR}$, —O—C(O)—CH[(CH$_2$)$_2$C(O)OR$^{PR}$]—NHR$^{PR}$, —O—C(O)—CH(CH$_2$C(O)OR$^{PR}$—NHR$^{PR}$, —O—C(O)—CH[(CH$_2$)$_4$NHR$^{PR}$]—NHR$^{PR}$, —O—C(O)—CH[(CH$_2$)$_2$C(O)NHR$^{PR}$]—NHR$^{PR}$, —O—C(O)—CH(CH$_2$C(O)NHR$^{PR}$)—NHR$^{PR}$, —O—C(O)—CHR$^{42}$—NHR$^{PR}$, —NH—(CH$_2$)$_{14}$—C(O)OR$^{46}$ or —O—C(O)—(CH$_2$)$_{1-4}$—NHR$^{47}$ where R$^{42}$ is —H, —CH$_3$, —C$_2$H$_5$, —(CH$_2$)$_n$—C(O)—OR$^{PR}$, —CH$_2$—C(O)—OH, —CH$_2$—C(O)—NHR$^{PR}$, —CH$_2$F, —CH$_2$Cl, —CH$_2$Br, —CHOH—CH$_3$ or —CH$_2$OH, R$^{46}$ is —H, optionally substituted alkyl (e.g., —CH$_3$, —C$_2$H$_5$, —C$_2$H$_3$, —C$_3$H$_7$, —C$_3$H$_5$, —(CH$_2$)$_{1-8}$—OH, —(CH$_2$)$_{1-8}$—NH$_2$, —(CH$_2$)$_{1-8}$—C(O)—OH, —(CH$_2$)$_{0-3}$—(CH=CH)$_{0-1}$—(CH$_2$)$_{0-3}$—CH$_3$, —(CH$_2$)$_{0-3}$—(CH=CH)$_{0-1}$—(CH$_2$)$_{0-3}$—CH$_2$F, —(CH$_2$)$_{0-3}$—(CH=CH)$_{0-1}$—(CH$_2$)$_{0-3}$—CH$_2$Br, —(CH$_2$)$_{0-3}$—(CH=CH)$_{0-1}$—(CH$_2$)$_{0-3}$—C(O)—OH, —(CH$_2$)$_{0-3}$—(CH=CH)$_{0-1}$—(CH$_2$)$_{0-3}$—NH$_2$, —CF$_3$ or —C$_2$F$_5$) or a protecting group (e.g., t-butyl, phenyl, benzyl or substituted phenyl), R$^{47}$ is —H, optionally substituted alkyl (e.g., —CH$_3$, —C$_2$H$_5$, —C$_2$H$_3$, —C$_3$H$_7$, —C$_3$H$_5$, —(CH$_2$)$_{1-8}$—OH, —(CH$_2$)$_{1-8}$—NH$_2$, —(CH$_2$)$_{1-8}$—C(O)—OH, —(CH$_2$)$_{0-3}$—(CH=CH)$_{0-1}$—(CH$_2$)$_{0-3}$—CH$_3$, —(CH$_2$)$_{0-3}$—(CH=CH)$_{0-1}$—(CH$_2$)$_{0-3}$—CH$_2$F, —(CH$_2$)$_{0-3}$—(CH=CH)$_{0-1}$—(CH$_2$)$_{0-3}$—CH$_2$Br, —(CH$_2$)$_{0-3}$—(CH=CH)$_{0-1}$—(CH$_2$)$_{0-3}$—C(O)—OH, —(CH$_2$)$_{0-3}$—(CH=CH)$_{0-1}$—(CH$_2$)$_{0-3}$—NH$_2$, —CF$_3$ or —C$_2$F$_5$) or a protecting group (e.g., t-butyl, phenyl, benzyl or substituted phenyl) and R$^{PR}$ is —H or an independently selected protecting group such as C1-C8 optionally substituted alkyl and n is 0, 1, 2, or 3, or optionally substituted heterocycle, —O—[C(O)]$_m$—(CH$_2$)$_n$-optionally substituted heterocycle, —(CH$_2$)$_n$-optionally substituted heterocycle or optionally substituted cycloalkyl, where the heterocycle is C-linked or N-linked, e.g., 2-pyridinyl, N-pyridinyl, 3-pyridinyl, 4-pyridinyl, 2-pyridyl, 3-pyridyl, 4-pyridyl, 5-pyridyl, 6-pyridyl, 1-pyrimidinyl, 2-pyrimidinyl, 4-pyrimidinyl, 5-pyrimidinyl, 6-pyrimidinyl, 3-pyridazinyl, 4-pyridazinyl, 2-pyrazinyl, 3-pyrazinyl, 5-pyrazinyl, 6-pyrazinyl, N-pyrrolyl, 2-pyrrolyl, 3-pyrrolyl, 2-imidazolyl, 4-imidazolyl, 5-imidazolyl, N-imidazolyl, 3-pyrazolyl, 4-pyrazolyl, 3-pyridazinyl, 4-pyridazinyl, 5-pyridazinyl, 6-pyridazinyl, 3-isothiazolyl, 4-isothiazolyl, 5-isothiazolyl, 3-isoxazolyl, 4-isoxazolyl, 5-isoxazolyl, 2-thiazolyl, 4-thiazolyl, 5-thiazolyl, 2-oxazolyl, 3-oxazolyl, 4-oxazolyl, 5-oxazolyl, 1,2,4-oxadiazol-5-yl, 1,2,4-triazol-3-yl, 1,2,3-triazol-4-yl, tetrazol-5-yl, benzimidazol-2-yl, indol-3-yl, 1H-indazol-3-yl, 1H-pyrrolo[2,3-b]pyrazin-2-yl, 1H-pyrrolo[2,3-b]pyridin-6yl, 1H-imidazo[4,5-b]pyridin-2-yl, 1H-imidazo[4,5-c]pyridin-2-yl, 1H-imidazo[4,5-b]pyrazin-2-yl, benzopyranyl, furyl, thienyl, pyrrolyl, oxazolyl, isoxazolyl, thiazolyl, isothiazolyl, imidazolyl, pyrazolyl, 1,2,3-oxadiazolyl, 1,2,4,-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, 1-isoquinolyl, 4-isoquinolyl, 2-quinazolinyl, 1-methyl-2-indolyl, tetrazolyl, pyridyl, pyridazinyl, pyrimidinyl, pyrazinyl, triazinyl, benzofuranyl, isobenzofuranyl, benzo[b]thienyl, indolyl, isoindolyl, 1H-indazolyl, benzimidazolyl, benzoxazolyl, 1,2-benzoisoxazolyl, benzothiazolyl, 1,2-benzoisothiazolyl, 1H-benzotriazolyl, 2-silabenzenyl, 3-silabenzenyl, 4-silabenzenyl, 5-silabenzenyl, quinolyl, isoquinolyl, cinnolinyl, quinazolinyl, quinoxalinyl, phthalazinyl, naphthylidinyl, purinyl, pteridinyl, carbazolyl, α-carbolinyl, β-carbolinyl, γ-carbolinyl, acridinyl, phenoxazinyl, phenothiazinyl, phenazinyl, phenoxathiinyl, thianthrenyl, phenathridinyl, phenathrolinyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, 1,2,4-triazolo[4,3-b]pyridazinyl, 2-benzothiazolyl, 2-benzoxazolyl, 2-benzimidazolyl, 3-isoxazolyl, 5-isoxazolyl, 5-methyl-3-isoxazolyl, 5-phenyl-3-isoxazolyl, 4-thiazolyl, 3-methyl-2-pyrazinyl, 5-methyl-2-pyrazinyl, 6-methyl-2-pyrazinyl, 5-chloro-2-thienyl, 3-furyl, benzofuran-2-yl, benzothien-2-yl, 2H-1-benzopyran-3-yl, 2,3-dihydrobenzopyran-5-yl, 1-methylimidazol-2-yl, quinoxalin-2-yl, piperon-5-yl, 4,7-dichlorobenzoxazol-2-yl, 4,6-dimethylpyrimidin-2-yl, 4-methylpyrimidin-2-yl, 2,4-dimethylpyrimidin-6-yl, 2-methylpyrimidin-4-yl, 4-methylpyrimidin-6-yl, 6-chloropiperon-5-yl, 5-chloroimidazo[1,2-a]pyridin-2-yl, 1-H-inden-3-yl, 1-H-2-methyl-inden-2-yl, 3,4-dihydronaphth-1-yl, S-4-isopropenylcyclohexen-1-yl, 4-dihydronaphth-2-yl, 3-hydroxy-5-hydroxymethyl-2-methyl-4-pyridinyl, 5-methoxycarbonyl-2-furanyl, cycloheptyl, cyclohexyl, cyclopentyl, cyclooxyl, cyclobutyl, cyclobutenyl, 5-chloro-2-hydroxyphenyl, 5-chloro-2-methoxyphenyl, 2-methanesulfonylaminophenyl, 3-aminophenyl, 2-methoxyphenyl, 5-ethyl-2-furanyl, 3-methoxyphenyl, 2-aminophenyl, 2-furanyl, 3,5-dimethyl-4-hydroxyphenyl, 5-acetyloxymethyl-2-furanyl, 5-(4-carboxyphenyl)-2-furanyl, 5-(4-methanesulfonylphenyl)-2-furanyl, 5-(3,4-dimethoxyphenyl)-2-furanyl, 5-(4-methanesulfonylaminophenyl)-2-furanyl, 5-(4-bromophenyl)-2-oxazolyl, 5-(4-methoxyphenyl)-2-furanyl, 5-(1-cyclohexen-1-yl)-2-furanyl, 5-cyclohexyl-2-furanyl, 5-3-trifluoromethylphenyl)-2-furanyl, 5-(4-methylphenyl)-2-furanyl, 2-(4-chlorophenyl)-3-furanyl, 5-(4-chlorophenyl)-2-furanyl, 5-(4-fluorophenyl)-2-furanyl, 2-benzyloxy-5-chlorophenyl, 4-benzyloxyphenyl, 3-(4-t-butylphenyloxy)phenyl, 3-benzoyl-2,4-dichlorophenyl, 2-chloro-3-benzyloxyphenyl, 3-(4-chlorophenoxy)phenyl, 1H-indol-3-yl, 2-fluorenyl, 2-naphthyl, 2-hydroxy-1-naphthyl, 2-quinolinyl, 5-chloro-2-benzofuranyl, 1-aziridinyl, 2-aziridinyl, N-pyrrolidinyl, 1-pyrrolidinyl, 2-pyrrolidinyl, 1-aziridyl, 1-azetedyl, 1-pyrrolyl, 1-imidazolyl, 1-pyrazolyl, 1-piperidinyl, 3-oxathiolanyl, 4-oxathiolanyl, 5-oxathiolanyl, N-2H-1,5,2-dithiazinyl, 3-2H-1,5,2-dithiazinyl, 4-2H-1,5,2-dithiazinyl, 6-2H-1,5,2-dithiazinyl, 1-cyclohexenyl, 2-cyclohexenyl, 3-cyclohexenyl, 4-cyclohexenyl, 5-cyclohexenyl, 1-cyclopentenyl, 2-cyclopentenyl, 3-cyclopentenyl, 1,3-cyclopentadienyl, 1-cycloheptenyl, 1,3-cycloheptadienyl, isothiazolyl, isoxazolyl, oxiranyl, azetidinyl, oxetanyl, thietanyl, pyrrolidinyl, tetrahydrofuryl, thiolanyl, piperidyl, tetrahydropyranyl, morpholinyl, thiomorpholinyl, piperazinyl, pyrrolidino, piperidino, N-morpholino, morpholino or thiomorpholino, any of which optionally has 1, 2, 3 or 4 independently selected substitutions as described herein, e.g., —OH, —OR$^{PR}$, =O, —SH, —SR$^{PR}$, =S, —F, —Cl, —Br, —I, —C(O)OR$^{PR}$, —C(O)SR$^{PR}$, —C(O)OCH$_3$, —C(O)O— C1-8 optionally substituted alkyl, C1-8 optionally substituted alkyl, C1-8 ether, C1-8 thioether, C1-8 ester, C1-8 thioester, —CN, —SCN, —NO$_2$, —N$_3$, —NH$_2$, —NHR$^{PR}$, —NH— C1-8 optionally substituted alkyl, —N(C1-8 optionally substituted alkyl)$_2$, where each optionally substituted alkyl is independently selected, C1-8 haloalkyl, C1-8 hydroxyalkyl, C1-8 aralkyl, C1-8 alkenyl, C1-8 alkoxy, C1-8 haloalkyloxy, C1-8 alkylthio, C1-8 cycloalkyl, C1-8 cycloalkylalkyl, C1-8 cycloalkyloxy, C1-8 alkylsulfonyl, C1-8 sulfamoyl, C1-8 alkanoyl, C1-8 alkoxycarbonyl or another substituent described herein, where R$^{PR}$ independently are —H or a protecting group, m is 0 or 1 and n is 0, 1, 2 or 3, e.g., m and n are both 0, m is 1 and n is 0, m is 0 and n is 1 or m and n are both 1, and where exemplary substitutions include a halogen such as —F or —Cl at the 1-, 2-, 3-, 4- or 5-position of any of these moieties, an ester or hydroxyl at the 1-, 2-, 3-, 4- or 5-position of any of these moieties, an ether or thioether at the 1-, 2-, 3-, 4- or 5-position of any of these moieties and/or optionally substituted alkyl at the 1-, 2-, 3-, 4- or 5-position of any of these moieties, where any such substitution is compatible with the chemical structure and/or nomenclature of the cyclic moiety, e.g., cyclobutyl moieties can not be substituted at the 5-position and ring oxygen atoms can not be substituted, or carboxyl which is optionally substituted, e.g., —C(O)OH, —C(O)OR$^{PR}$, —C(O)OM, —C(O)O—CH$_3$, —C(O)—O—(CH$_2$)$_n$—CH$_3$, —C(O)—O—CH(CH$_3$)—(CH$_2$)$_n$—CH$_3$, —C(O)—O—C(CH$_3$)$_2$—(CH$_2$)$_n$—CH$_3$, —C(O)—O—(CH$_2$)$_n$—C(O)OR$^{PR}$, —C(O)—O—CH(CH$_3$)—(CH$_2$)$_n$—C(O)OR$^{PR}$, —C(O)—O—C(CH$_3$)$_2$—(CH$_2$)$_n$—C(O)OR$^{PR}$, —C(O)—O—(CH$_2$)$_n$—CH$_2$OR$^{PR}$, —C(O)—O—CH(CH$_3$)—(CH$_2$)$_n$—CH$_2$OR$^{PR}$, —C(O)—O—C(CH$_3$)$_2$—(CH$_2$)$_n$—CH$_2$OR$^{PR}$, —C(O)—O—(CH$_2$)$_n$—CH$_2$NHR$^{PR}$, —C(O)—O—CH(CH$_3$)—(CH$_2$)$_n$—CH$_2$NHR$^{PR}$, —C(O)—O—C(CH$_3$)$_2$—(CH$_2$)$_n$—CH$_2$NHR$^{PR}$, —C(O)—O—(CH$_2$)$_n$—CH$_2$SR$^{PR}$, —C(O)—O—CH(CH$_3$)—(CH$_2$)$_n$—CH$_2$SR$^{PR}$, —C(O)—O—C(CH$_3$)$_2$—(CH$_2$)$_n$—CH$_2$SR$^{PR}$, —C(O)O-organic moiety, —C(O)O—(CH$_2$)$_n$-optionally substituted phenyl or —C(O)O—(CH$_2$)$_n$-optionally substituted alkyl, wherein the phenyl or alkyl moieties are optionally substituted with 1, 2 or 3 independently selected with substituents described herein, e.g., —F, —Cl, —Br, —I, —OH, —CH$_3$, —C$_2$H$_5$, —O—CH$_3$, —O—C$_2$H$_5$, —NO$_2$, —CN, —SCN, —NH$_2$, —C(O)OR$^{PR}$ or —(CH$_2$)$_{1-4}$—C(O)—OR$^{PR}$, where n is 0, 1, 2, 3, 4, 5 or 6, R$^{PR}$ is —H or a protecting group such as methyl, ethyl, propyl or butyl, and M is a metal such as an alkali metal, e.g., Li$^+$, Na$^+$ or K$^+$ or M is another counter ion such as an ammonium ion, or carbonate, e.g., —O—C(O)—O—CH$_3$, —O—C(O)—O—(CH$_2$)$_n$—CH$_3$, —O—C(O)—O—CH(CH$_3$)—(CH$_2$)$_n$—CH$_3$, —O—C(O)—O—CH$_2$-halogen, —O—C(O)—O—(CH$_2$)$_n$—CH$_2$-halogen, —O—C(O)—O—CH(CH$_3$)—(CH$_2$)$_n$—CH$_2$-halogen, —O—C(O)—O—C(CH$_3$)$_2$—(CH$_2$)$_n$—CH$_3$, —O—C(O)—O—(CH$_2$)$_n$—C(O)OR$^{PR}$, —O—C(O)—O—CH(CH$_3$)—(CH$_2$)$_n$—C(O)OR$^{PR}$, —O—C(O)—O—C(CH$_3$)$_2$—(CH$_2$)$_n$—C(O)OR$^{PR}$, —O—C(O)—O—(CH$_2$)$_n$—CH$_2$OR$^{PR}$, —O—C(O)—O—CH(CH$_3$)—(CH$_2$)$_n$—CH$_2$OR$^{PR}$, —O—C(O)—O—C(CH$_3$)$_2$—(CH$_2$)$_n$—CH$_2$OR$^{PR}$, —O—C(O)—O—(CH$_2$)$_n$—CH$_2$NHR$^{PR}$, —O—C(O)—O—CH(CH$_3$)—(CH$_2$)$_n$—CH$_2$NHR$^{PR}$, —O—C(O)—O—C(CH$_3$)$_2$—(CH$_2$)$_n$—CH$_2$NHR$^{PR}$, —O—C(O)—O—(CH$_2$)$_n$—CH$_2$SR$^{PR}$, —O—C(O)—O—CH(CH$_3$)—(CH$_2$)$_n$—CH$_2$SR$^{PR}$, —O—C(O)—O—C(CH$_3$)$_2$—(CH$_2$)$_n$—CH$_2$SR$^{PR}$, —O—C(O)—O-organic moiety, —O—C(O)—O—(CH$_2$)$_n$-optionally substituted phenyl or —C(O)—O—(CH$_2$)$_n$-optionally substituted alkyl, wherein the phenyl or alkyl moieties are optionally substituted with 1, 2 or 3, 4 or more independently selected with substituents described herein, e.g., —F, —Cl, —Br, —I, —OH, —CH$_3$, —C$_2$H$_5$, —O—CH$_3$, —O—C$_2$H$_5$, —NO$_2$, —CN, —SCN, —NH$_2$, —C(O)OR$^{PR}$ or —(CH$_2$)$_{1-4}$—C(O)—OR$^{PR}$, and wherein n is 0, 1, 2, 3, 4, 5 or 6 and R$^{PR}$ is —H or a protecting group, or carbamate, e.g., —O—C(O)—NH$_2$, —O—C(O)—NH—CH$_3$, —O—C(O)—NH—C$_2$H$_5$, —O—C(O)—NH—C$_3$H$_7$, —O—C(O)—NH—C$_4$H$_9$, —O—C(O)—NH—C$_2$H$_3$, —O—C(O)—NH—C$_3$H$_5$, —O—C(O)—NH—C$_4$H$_7$, —O—C(O)—NHR$^{PR}$, —O—C(O)—N[(CH$_2$)$_n$CH$_3$]—CH$_3$, —O—C(O)—N[(CH$_2$)$_n$CH$_3$]—C$_2$H$_5$, —O—C(O)—N[(CH$_2$)$_n$CH$_3$]—C$_3$H$_7$, —O—C(O)—N[(CH$_2$)$_n$CH$_3$]—C$_4$H$_9$, —O—C(O)—N[(CH$_2$)$_n$CH$_3$]—C$_2$H$_3$, —O—C(O)—N[(CH$_2$)$_n$CH$_3$]—C$_3$H$_5$, —O—C(O)—N[(CH$_2$)$_n$CH$_3$]—C$_4$H$_7$, —O—C(O)—NH-organic moiety, —O—C(O)—NR$^{48}$-organic moiety, —NH—C(O)—O-organic moiety, —NR$^{48}$—C(O)—O-organic moiety, wherein the organic moiety is as described herein, e.g., it optionally comprises about 1-20 carbon atoms, and wherein R$^{48}$ is —H, a protecting group, an organic moiety or R$^{48}$ together with the organic moiety is a protecting group and the organic moiety optionally is optionally substituted alkyl such as i-propyl, n-propyl, t-butyl, n-butyl, n-hexyl, n-octyl, n-decyl, —(CH$_2$)$_m$—OH, —(CH$_2$)$_m$—F, —(CH$_2$)$_m$—Cl, —(CH$_2$)$_m$—Br, —(CH$_2$)$_m$—NH$_2$, —(CH$_2$)$_m$—C(O)—OH, —(CH$_2$)$_m$—C(O)—H, —(CH$_2$)$_m$—C(O)—CH$_3$, —(CH$_2$)$_n$—(O)$_p$—(CH$_2$)$_n$—CH$_3$, —(CH$_2$)$_n$—(O)$_p$—(CH$_2$)$_n$—CH$_2$OH, —(CH$_2$)$_n$—(CH=CH)$_p$—(CH$_2$)$_n$—CH$_3$, —(CH$_2$)$_n$—(CH=CH)$_p$—(CH$_2$)$_n$—CH$_2$OH, —(CH$_2$)$_n$—(CH=CH)$_p$—(CH$_2$)$_n$—CH$_2$F, —(CH$_2$)$_n$—(CH=CH)$_p$—(CH$_2$)$_n$—CH$_2$Br, —(CH$_2$)$_n$—(CH=CH)$_p$—(CH$_2$)$_n$—C(O)—OR$^{PR}$, —(CH$_2$)$_n$—(CH=CH)$_p$—(CH$_2$)$_n$—NHR$^{PR}$, —(CH$_2$)$_n$—(C≡C)$_p$—(CH$_2$)$_n$—CH$_3$, —(CH$_2$)$_n$—(C≡C)$_p$—(CH$_2$)$_n$—CH$_2$OH, —(CH$_2$)$_n$—(C≡C)$_p$—(CH$_2$)$_n$—CH$_2$F, —(CH$_2$)$_n$—(C≡C)$_p$—(CH$_2$)$_n$—CH$_2$Br, —(CH$_2$)$_n$—(C≡C)$_p$—(CH$_2$)$_n$—C(O)—OR$^{PR}$, —(CH$_2$)$_n$—(C≡C)$_p$—(CH$_2$)$_n$—NHR$^{PR}$, —CF$_3$ or —C$_2$F$_5$, wherein R$^{PR}$ is —H or a protecting group, m is 1, 2, 3, 4, 5 or 6, n independently are 0, 1, 2, 3, 4, 5 or 6 and p is 0 or 1, e.g., both n and p are 1 or p is 1 and both n are 2 or one n is 1, the other n is 2 and p is 1, or phosphothioester or thiophosphate or an ether or thioether derivative thereof, e.g., —O—P(S)(OH)—OH, —O—P(S)(OH)—SH, —O—P(S)(OR$^{PR}$)—OH, —O—P(S)(OR$^{PR}$)—SH, —S—P(S)(OH)—OH, —O—P(S)(OH)—O—CH$_3$, —O—P(S)(OH)—O—C$_2$H$_5$, —O—P(S)(OH)—O—C$_3$H$_7$, —O—P(S)(OH)—O-optionally substituted alkyl, —S—P(S)(OH)—O-optionally substituted alkyl, —O—P(S)(OH)—S-optionally substituted alkyl, —O—P(S)(O-optionally substituted alkyl)-O-optionally substituted alkyl, —S—P(S)(O-optionally substituted alkyl)-O-optionally substituted alkyl, —O—P(S)(O-optionally substituted alkyl)-S-optionally substituted alkyl, where the optionally substituted alkyl moieties are as described herein and are independently selected, e.g., i-propyl, n-propyl, t-butyl, n-butyl, n-hexyl, n-octyl, n-decyl, —(CH$_2$)$_m$—OH, —(CH$_2$)$_m$—F, —(CH$_2$)$_m$—Cl, —(CH$_2$)$_m$—Br, —(CH$_2$)$_m$—NH$_2$, —(CH$_2$)$_m$—C(O)—OH, —(CH$_2$)$_m$—C(O)—H, —(CH$_2$)$_m$—C(O)—CH$_3$, —(CH$_2$)$_n$—(O)$_p$—(CH$_2$)$_n$—CH$_3$, —(CH$_2$)$_n$—(O)$_p$—(CH$_2$)$_n$—CH$_2$OH, —(CH$_2$)$_n$—(CH=CH)$_p$—(CH$_2$)—CH$_3$, —(CH$_2$)$_n$—(CH=CH)$_p$—(CH$_2$)—CH$_2$OH, —(CH$_2$)$_n$—(CH=CH)$_p$—(CH$_2$)—CH$_2$F, —(CH$_2$)$_n$—(CH=CH)$_p$—(CH$_2$)—CH$_2$Br, —(CH$_2$)$_n$—(CH=CH)$_p$—(CH$_2$)$_n$—C(O)—OR$^{PR}$, —(CH$_2$)$_n$—(CH=CH)$_p$—(CH$_2$)$_n$—NHR$^{PR}$, —(CH$_2$)$_n$—(C≡C)$_p$—(CH$_2$)$_n$—CH$_3$, —(CH$_2$)$_n$—(C≡C)$_p$—(CH$_2$)$_n$—CH$_2$OH, —(CH$_2$)$_n$—(C≡C)$_p$—(CH$_2$)$_n$—CH$_2$F, —(CH$_2$)$_n$—(C≡C)$_p$—(CH$_2$)$_n$—CH$_2$Br, —(CH$_2$)$_n$—(C≡C)$_p$—(CH$_2$)$_n$—C(O)—OR$^{PR}$, —(CH$_2$)$_n$—(C≡C)$_p$—(CH$_2$)$_n$—NHR$^{PR}$, —CF$_3$ or —C$_2$F$_5$, wherein R$^{PR}$ is —H or a protecting group, m is 1, 2, 3, 4, 5 or 6, n independently are 0, 1, 2, 3, 4, 5 or 6 and p is 0 or 1, e.g., both n and p are 1 or p is 1 and both n are 2 or one n is 1, the other n is 2 and p is 1, or phosphonoester, phosphonate or an ether or thioether derivative thereof, e.g., —P(O)(OH)—OH, —P(O)(OH)—SH, —P(O)(OR$^{PR}$)—OH, —P(O)(OR$^{PR}$)—SH, —P(O)(OH)—OH, —P(O)(OH)—O—CH$_3$, —P(O)(OH)—O—C$_2$H$_5$, —P(O)(OH)—O—C$_3$H$_7$, —O—P(O)(OH)—H, —S—P(O)(OH)—H, —O—P(O)(OR$^{PR}$)—H, —S—P(O)(OR$^{PR}$)—H, —O—P(O)(OH)—CH$_3$, —O—P(O)(OH)—C$_2$H$_5$, —O—P(O)(OH)—C$_3$H$_7$, —O—P(O)(OH)-optionally substituted alkyl, —S—P(O)(OH)-optionally substituted alkyl, —P(O)(OH)—O-optionally substituted alkyl, —P(O)(OH)—S-optionally substituted alkyl, —P(O)(O-optionally substituted alkyl)-O-optionally substituted alkyl, —P(O)(O-optionally substituted alkyl)-S-optionally substituted alkyl, where the optionally substituted alkyl moieties are as described herein and are independently selected, e.g., i-propyl, n-propyl, t-butyl, n-butyl, n-hexyl, n-octyl, n-decyl, —(CH$_2$)$_m$—OH, —(CH$_2$)$_m$—F, —(CH$_2$)$_m$—Cl, —(CH$_2$)$_m$—Br, —(CH$_2$)$_m$—NH$_2$, —(CH$_2$)$_m$—C(O)—OH, —(CH$_2$)$_m$—C(O)—H, —(CH$_2$)$_m$—C(O)—CH$_3$, —(CH$_2$)$_n$—(O)$_p$—(CH$_2$)$_n$—CH$_3$, —(CH$_2$)$_n$—(O)$_p$—(CH$_2$)$_n$—CH$_2$OH, —(CH$_2$)$_n$—(CH=CH)$_p$—(CH$_2$)$_n$—CH$_3$, —(CH$_2$)$_n$—(CH=CH)$_p$—(CH$_2$)$_n$—CH$_2$OH, —(CH$_2$)$_n$—(CH=CH)$_p$—(CH$_2$)$_n$—CH$_2$F, —(CH$_2$)$_n$—(CH=CH)$_p$—(CH$_2$)$_n$—CH$_2$Br, —(CH$_2$)$_n$—(CH=CH)$_p$—(CH$_2$)$_n$—C(O)—OR$^{PR}$, —(CH$_2$)$_n$—(CH=CH)$_p$—(CH$_2$)$_n$—NHR$^{PR}$, —(CH$_2$)$_n$—(C≡C)$_p$—(CH$_2$)$_n$—CH$_3$, —(CH$_2$)$_n$—(C≡C)$_p$—(CH$_2$)$_n$—CH$_2$OH, —(CH$_2$)$_n$—(C≡C)$_p$—(CH$_2$)$_n$—CH$_2$F, —(CH$_2$)$_n$—(C≡C)$_p$—(CH$_2$)$_n$—CH$_2$Br, —(CH$_2$)$_n$—(C≡C)$_p$—(CH$_2$)$_n$—C(O)—OR$^{PR}$, —(CH$_2$)$_n$—(C≡C)$_p$—(CH$_2$)$_n$—NHR$^{PR}$, —CF$_3$ or —C$_2$F$_5$, wherein R$^{PR}$ is —H or a protecting group, m is 1, 2, 3, 4, 5 or 6, n independently are 0, 1, 2, 3, 4, 5 or 6 and p is 0 or 1, e.g., both n and p are 1 or p is 1 and both n are 2 or one n is 1, the other n is 2 and p is 1, or sulfate ester or an ether or thioether derivative thereof, e.g., —O—S(O)(O)—OH, —O—S(O)(O)—SH, —O—S(O)(O)—OR$^{PR}$, —O—S(O)(O)—O—CH$_3$, —O—S(O)(O)—O—C$_2$H$_5$, —O—S(O)(O)—O—C$_3$H$_7$, —O—S(O)(O)—S—CH$_3$, —O—S—(O)(O)—O—CH$_2$—CH(O—C(O)—(CH$_2$)$_y$(CH=CH)$_q$(CH$_2$)$_y$—CH$_3$)—CH$_2$—O—C(O)—(CH$_2$)$_y$(CH=CH)$_q$(CH$_2$)$_y$—CH$_3$), —O—S—(O)(O)—O—CH$_2$—CH(O—C(O)—(CH$_2$)$_x$CH$_3$)—CH$_2$—O—C(O)—(CH$_2$)$_x$CH$_3$), —O—S—(O)(O)—O—CH$_2$—CH(O—C(O)—(CH$_2$)$_{14}$CH$_3$)—CH$_2$—O—C(O)—(CH$_2$)$_{14}$CH$_3$), —O—S—(O)(O)—O—CH$_2$—CH(O—C(O)—(CH$_2$)$_{12}$CH$_3$)—CH$_2$—O—C(O)—(CH$_2$)$_{12}$CH$_3$), —O—S(O)(O)—O-optionally substituted alkyl, —O—S(O)(OH)—S-optionally substituted alkyl, where the optionally substituted alkyl moiety is as described herein, e.g., i-propyl, n-propyl, t-butyl, n-butyl, n-hexyl, n-octyl, n-decyl, —(CH$_2$)$_m$—OH, —(CH$_2$)$_m$—F, —(CH$_2$)$_m$—Cl, —(CH$_2$)$_m$—Br, —(CH$_2$)$_m$—NH$_2$, —(CH$_2$)$_m$—C(O)—OH, —(CH$_2$)$_m$—C(O)—H, —(CH$_2$)$_m$—C(O)—CH$_3$, —(CH$_2$)$_n$—(O)$_p$—(CH$_2$)$_n$—CH$_3$, —(CH$_2$)$_n$—(O)$_p$—(CH$_2$)$_n$—CH$_2$OH, —(CH$_2$)$_n$—(CH=CH)$_p$—(CH$_2$)—CH$_3$, —(CH$_2$)$_n$—(CH=CH)$_p$—(CH$_2$)—CH$_2$OH, —(CH$_2$)$_n$—(CH=CH)$_p$—(CH$_2$)—CH$_2$F, —(CH$_2$)$_n$—(CH=CH)$_p$—(CH$_2$)—CH$_2$Br, —(CH$_2$)$_n$—(CH=CH)$_p$—(CH$_2$)$_n$—C(O)—OR$^{PR}$, —(CH$_2$)$_n$—(CH=CH)$_p$—(CH$_2$)$_n$—NHR$^{PR}$, —(CH$_2$)$_n$—(C≡C)$_p$—(CH$_2$)$_n$—CH$_3$, —(CH$_2$)$_n$—(C≡C)$_p$—(CH$_2$)$_n$—CH$_2$OH, —(CH$_2$)$_n$—(C≡C)$_p$—(CH$_2$)$_n$—CH$_2$F, —(CH$_2$)$_n$—(C≡C)$_p$—(CH$_2$)$_n$—CH$_2$Br, —(CH$_2$)$_n$—(C≡C)$_p$—(CH$_2$)$_n$—C(O)—OR$^{PR}$, —(CH$_2$)$_n$—(C≡C)$_p$—(CH$_2$)$_n$—NHR$^{PR}$, —CF$_3$ or —C$_2$F$_5$, wherein R$^{PR}$ is —H or a protecting group, m is 1, 2, 3, 4, 5 or 6, n independently are 0, 1, 2, 3, 4, 5 or 6, p is 0 or 1, q is 0 or 1, x independently are 0, 1, 2, 3, 4, 5, 6, 7, 8, 9, 10, 11, 12, 13, 14, 15, 16 or 17, y independently are 0, 1, 2, 3, 4, 5, 6, 7, 8 or 9 and substituents bonded at double bonds are in the cis, trans or mixed cis and trans configuration, wherein In some embodiments, both n and p are 1 or p is 1 and both n are 2 or one n is 1, the other n is 2 and p is 1, or optionally substituted oxime, e.g., =NOH, =NOCH$_3$, =NOC$_2$H$_5$, =NOC$_3$H$_7$, =N—(CH$_2$)$_n$—(X)$_q$—(CH$_2$)$_n$-optionally substituted alkyl, where X is —O—, —C(O)—, —S— or —NH— and the optionally substituted alkyl moiety is as described herein, e.g., i-propyl, n-propyl, t-butyl, n-butyl, n-hexyl, n-octyl, n-decyl, —(CH$_2$)$_m$—OH, —(CH$_2$)$_m$—F, —(CH$_2$)$_m$—Cl, —(CH$_2$)$_m$—Br, —(CH$_2$)$_m$—NH$_2$, —(CH$_2$)$_m$—C(O)—OH, —(CH$_2$)$_m$—C(O)—H, —(CH$_2$)$_m$—C(O)—CH$_3$, —(CH$_2$)$_m$-heterocycle, —(CH$_2$)$_n$—(O)$_p$—(CH$_2$)$_n$—CH$_3$, —(CH$_2$)$_n$—(O)$_p$—(CH$_2$)$_n$—CH$_2$OH, —(CH$_2$)$_n$—(CH=CH)$_p$—(CH$_2$)$_n$—CH$_3$, —(CH$_2$)$_n$—(CH=CH)$_p$—(CH$_2$)$_n$—CH$_2$OH, —(CH$_2$)$_n$—(CH=CH)$_p$—(CH$_2$)$_n$—CH$_2$F, —(CH$_2$)$_n$—(CH=CH)$_p$—(CH$_2$)$_n$—CH$_2$Br, —(CH$_2$)$_n$—(CH=CH)$_p$—(CH$_2$)$_n$—C(O)—OR$^{PR}$, —(CH$_2$)$_n$—(CH=CH)$_p$—(CH$_2$)$_n$—NHR$^{PR}$, —(CH$_2$)$_n$—(C≡C)$_p$—(CH$_2$)$_n$—CH$_3$, —(CH$_2$)$_n$—(C≡C)$_p$—(CH$_2$)$_n$—CH$_2$OH, —(CH$_2$)$_n$—(C≡C)$_p$—(CH$_2$)$_n$—CH$_2$F, —(CH$_2$)$_n$—(C≡C)$_p$—(CH$_2$)$_n$—CH$_2$Br, —(CH$_2$)$_n$—(C≡C)$_p$—(CH$_2$)$_n$—C(O)—OR$^{PR}$, —(CH$_2$)$_n$—(C≡C)$_p$—(CH$_2$)$_n$—NHR$^{PR}$, —CF$_3$ or —C$_2$F$_5$, wherein R$^{PR}$ is —H or a protecting group, m is 1, 2, 3, 4, 5 or 6, n independently are 0, 1, 2, 3, 4, 5 or 6, p is 0 or 1, and q is 0 or 1, e.g., both n and p are 1 or p is 1 and both n are 2 or one n is 1, the other n is 2 and p is 1, or sulfite ester, sulfite ether, sulfite or sulfoxide, e.g., —O—S(O)—OH, —O—S(O)—OR$^{PR}$, —O—S(O)—O—CH$_3$, —O—S(O)—O—C$_2$H$_5$, —O—S(O)—O—C$_3$H$_7$, —O—S(O)—O-organic moiety, —O—S(O)—O-optionally substituted alkyl, —S(O)—O—CH$_3$, —S(O)—O—C$_2$H$_5$, —S(O)—O—C$_3$H$_7$, —S(O)-organic moiety, —S(O)-optionally substituted alkyl, where the optionally substituted alkyl moiety is as described herein, e.g., i-propyl, n-propyl, t-butyl, n-butyl, n-hexyl, n-octyl, n-decyl, —(CH$_2$)$_m$—OH, —(CH$_2$)$_m$—F, —(CH$_2$)$_m$—Cl, —(CH$_2$)$_m$—Br, —(CH$_2$)$_m$—NH$_2$, —(CH$_2$)$_m$—C(O)—OH, —(CH$_2$)$_m$—C(O)—H, —(CH$_2$)$_m$—C(O)—CH$_3$, —(CH$_2$)$_n$—(O)$_p$—(CH$_2$)$_n$—CH$_3$, —(CH$_2$)$_n$—(O)$_p$—(CH$_2$)$_n$—CH$_2$OH, —(CH$_2$)$_n$—(CH=CH)$_p$—(CH$_2$)$_n$—CH$_3$, —(CH$_2$)$_n$—(CH=CH)$_p$—(CH$_2$)$_n$—CH$_2$OH, —(CH$_2$)$_n$—(CH=CH)$_p$—(CH$_2$)$_n$—CH$_2$F, —(CH$_2$)$_n$—(CH=CH)$_p$—(CH$_2$)$_n$—CH$_2$Br, —(CH$_2$)$_n$—(CH=CH)$_p$—(CH$_2$)$_n$—C(O)—OR$^{PR}$, —(CH$_2$)$_n$—(CH=CH)$_p$—(CH$_2$)$_n$—NHR$^{PR}$, —(CH$_2$)$_n$—(C≡C)$_p$—(CH$_2$)$_n$—CH$_3$, —(CH$_2$)$_n$—(C≡C)$_p$—(CH$_2$)$_n$—CH$_2$OH, —(CH$_2$)$_n$—(C≡C)$_p$—(CH$_2$)$_n$—CH$_2$F, —(CH$_2$)$_n$—(C≡C)$_p$—(CH$_2$)$_n$—CH$_2$Br, —(CH$_2$)$_n$—(C≡C)$_p$—(CH$_2$)$_n$—C(O)—OR$^{PR}$, —(CH$_2$)$_n$—(C≡C)$_p$—(CH$_2$)$_n$—NHR$^{PR}$, —CF$_3$ or —C$_2$F$_5$, wherein R$^{PR}$ is —H or a protecting group, m is 1, 2, 3, 4, 5 or 6, n independently are 0, 1, 2, 3, 4, 5 or 6 and p is 0 or 1, e.g., both n and p are 1 or p is 1 and both n are 2 or one n is 1, the other n is 2 and p is 1, and the organic moiety is as described herein, or sulfonamide or a sulfonamide derivative, e.g., —S(O)(O)—NH$_2$, —S(O)(O)—NHR$^{PR}$, —S(O)(O)—NH-optionally substituted alkyl, —NH—S(O)(O)-optionally substituted alkyl, —S(O)(O)—NH—CH$_3$, —S(O)(O)—NH—C$_2$H$_5$, —S(O)(O)—NH—C$_3$H$_7$, —NH—S(O)(O)—CH$_3$, —NH—S(O)(O)—C$_2$H$_5$, —NH—S(O)(O)—C$_3$H$_7$, where the optionally substituted alkyl moiety is as described herein, e.g., i-propyl, n-propyl, t-butyl, n-butyl, n-hexyl, n-octyl, n-decyl, —(CH$_2$)$_m$—OH, —(CH$_2$)$_m$—F, —(CH$_2$)$_m$—Cl, —(CH$_2$)$_m$—Br, —(CH$_2$)$_m$—NH$_2$, —(CH$_2$)$_m$—C(O)—OH, —(CH$_2$)$_m$—C(O)—H, —(CH$_2$)$_m$—C(O)—CH$_3$, —(CH$_2$)$_n$—(O)$_p$—(CH$_2$)$_n$—CH$_3$, —(CH$_2$)$_n$—(O)$_p$—(CH$_2$)$_n$—CH$_2$OH, —(CH$_2$)$_n$—(CH=CH)$_p$—(CH$_2$)$_n$—CH$_3$, —(CH$_2$)$_n$—(CH=CH)$_p$—(CH$_2$)$_n$—CH$_2$OH, —(CH$_2$)$_n$—(CH=CH)$_p$—(CH$_2$)$_n$—CH$_2$F, —(CH$_2$)$_n$—(CH=CH)$_p$—(CH$_2$)$_n$—CH$_2$Br, —(CH$_2$)$_n$—(CH=CH)$_p$—(CH$_2$)$_n$—C(O)—OR$^{PR}$, —(CH$_2$)$_n$—NHR$^{PR}$, —(CH$_2$)$_n$—(C≡C)$_p$—(CH$_2$)$_n$—CH$_3$, —(CH$_2$)$_n$—(C≡C)$_p$—(CH$_2$)$_n$—CH$_2$OH, —(CH$_2$)$_n$—(C≡C)$_p$—(CH$_2$)$_n$—CH$_2$F, —(CH$_2$)$_n$—(C≡C)$_p$—(CH$_2$)$_n$—CH$_2$Br, —(CH$_2$)$_n$—(C≡C)$_p$—(CH$_2$)$_n$—C(O)—OR$^{PR}$, —(CH$_2$)$_n$—(C≡C)$_p$—(CH$_2$)$_n$—NHR$^{PR}$, —CF$_3$ or —C$_2$F$_5$, wherein R$^{PR}$ is —H or a protecting group, m is 1, 2, 3, 4, 5 or 6, n independently are 0, 1, 2, 3, 4, 5 or 6 and p is 0 or 1, e.g., both n and p are 1 or p is 1 and both n are 2 or one n is 1, the other n is 2 and p is 1, or sulfamate or a sulfamate derivative, e.g., —O—S(O)(O)—NH$_2$, —O—S(O)(O)—NHR$^{PR}$, —O—S(O)(O)—N(RD)$_2$, —O—S(O)(O)—NH-optionally substituted alkyl, —NH—S(O)(O)—O-optionally substituted alkyl, —O—S(O)(O)—NH—C(O)—CH$_3$, —O—S(O)(O)—NH—C(O)-optionally substituted alkyl, —O—S(O)(O)—NH—CH$_3$, —O—S(O)(O)—NH—C$_2$H$_5$, —O—S(O)(O)—NH—C$_3$H$_7$, —O—S(O)(O)—N(C(O)-optionally substituted alkyl)-R$^{52}$, —O—S(O)(O)—N(C(O)—N-optionally substituted alkyl)-R$^{52}$, —NH—S(O)(O)—O—CH$_3$, —NH—S(O)(O)—O—C$_2$H$_5$, —NH—S(O)(O)—O—C$_3$H$_7$, —NH—S(O)(O)—O-optionally substituted alkyl, where any optionally substituted alkyl moiety is as described herein, e.g., i-propyl, n-propyl, t-butyl, n-butyl, n-hexyl, n-octyl, n-decyl, —(CH$_2$)$_m$—OH, —(CH$_2$)$_m$—F, —(CH$_2$)$_m$—Cl, —(CH$_2$)$_m$—Br, —(CH$_2$)$_m$—NH$_2$, —(CH$_2$)$_m$—C(O)—OH, —(CH$_2$)$_m$—C(O)—H, —(CH$_2$)$_m$—C(O)—CH$_3$, —(CH$_2$)$_n$—(O)$_p$—(CH$_2$)$_n$—CH$_3$, —(CH$_2$)$_n$—(O)$_p$—(CH$_2$)$_n$—CH$_2$OH, —(CH$_2$)$_n$—(CH=CH)$_p$—(CH$_2$)$_n$—CH$_3$, —(CH$_2$)$_n$—(CH=CH)$_p$—(CH$_2$)$_n$—CH$_2$OH, —(CH$_2$)$_n$—(CH=CH)$_p$—(CH$_2$)$_n$—CH$_2$F, —(CH$_2$)$_n$—(CH=CH)$_p$—(CH$_2$)$_n$—CH$_2$Br, —(CH$_2$)$_n$—(CH=CH)$_p$—(CH$_2$)$_n$—C(O)—OR$^{PR}$, —(CH$_2$)$_n$—(CH=CH)$_p$—(CH$_2$)$_n$—NHR$^{PR}$, —(CH$_2$)$_n$—(C≡C)$_p$—(CH$_2$)$_n$—CH$_3$, —(CH$_2$)$_n$—(C≡C)$_p$—(CH$_2$)$_n$—CH$_2$OH, —(CH$_2$)$_n$—(C≡C)$_p$—(CH$_2$)$_n$—CH$_2$F, —(CH$_2$)$_n$—(C≡C)$_p$—(CH$_2$)$_n$—CH$_2$Br, —(CH$_2$)$_n$—(C≡C)$_p$—(CH$_2$)$_n$—C(O)—OR$^{PR}$, —(CH$_2$)$_n$—(C≡C)$_p$—(CH$_2$)$_n$—NHR$^{PR}$, —CF$_3$ or —C$_2$F$_5$, wherein R$^{PR}$ is —H or a protecting group, RD independently are —H, optionally substituted alkyl (e.g., —CH$_3$, —C$_2$H$_5$, —C$_3$H$_7$, —CHO, —CH$_2$OH), acyl, benzoyl or benzyl, R$^{52}$ is —H, optionally substituted alkyl, —COOH, —COOR$^{PR}$, —COO-optionally substituted alkyl or —C(O)—N(R$^{53}$)$_2$, R$^{53}$ independently are —H, optionally substituted alkyl, optionally substituted aryl, optionally substituted alkylaryl or optionally substituted arylalkyl, or both R$^{53}$ together with the nitrogen atom to which they are bonded are an N-containing ring such as morpholino or a C2-C6 polyemthyleneimino residue, m is 1, 2, 3, 4, 5 or 6, n independently are 0, 1, 2, 3, 4, 5 or 6 and p is 0 or 1, e.g., both n and p are 1 or p is 1 and both n are 2 or one n is 1, the other n is 2 and p is 1, or a sulfonate, a sulfamide, a sulfinamide or a sulfurous diamide, e.g., —O—S(O)(O)—CH$_2$-optionally substituted alkyl, —O—S(O)(O)-optionally substituted alkyl, —NH—S(O)(O)—NHR$^{PR}$, —NH—S(O)(O)—NH-optionally substituted alkyl, —NH—S(O)—NHR$^{PR}$, —NH—S(O)—NH-optionally substituted alkyl, —S(O)—NHR$^{PR}$, —S(O)—NHCH$_3$, —S(O)—N(CH$_3$)$_2$, —S(O)—NHC$_2$H$_5$, —S(O)—NH-optionally substituted alkyl, —NH—S(O)—NHR$^{PR}$, —NH—S(O)—NHCH$_3$, —NH—S(O)—NHC$_2$H$_5$ or —NH—S(O)—NH-optionally substituted alkyl, or a monosaccharide, e.g., a D-, L- or DL-mixture of glucose, fructose, mannose, idose, galactose, allose, gulose, altrose, talose, fucose, erythrose, threose, lyxose, erythrulose, ribulose, xylulose, ribose, arabinose, xylose, psicose, sorbose, tagatose, glyceraldehyde, dihydroxyacetone, a monodeoxy derivative of these monosaccharides such as rhamnose, glucuronic acid or a salt of glucuronic acid, any of which are unprotected, partially protected (e.g., less than all hydroxyl groups are protected) or fully protected with independently selected protecting groups (e.g., acetoxy or propionoxy), including moieties such β-D-glucopyranosyl, β-D-glucopyranuronosyl, β-D-2-acetamido-2-deoxy-glucopyranosyl, β-D-galactopyranosyl, β-D-fucopyranosyl, β-L-fucopyranosyl, α-D-fructofuranosyl, β-D-fructofuranosyl, β-D-xylopyranosyl, β-L-xylopyranosyl, α-D-arabanopyranosyl, α-L-arabanopyranosyl, α-L-rhamnopyranosyl, α-D-rhamnopyranosyl, β-D-cellobiosyl, β-D-lactosyl, β-D-maltosyl, β-D-gentiobiosyl, 3-O-β-D-galactopyranosyl-α-D-arabanopyranosyl or β-D-maltotriosyl, any of which are optionally protected and where the variable group to which they are bonded is in the α- or β-configuration, or an oligosaccharide, e.g., 2, 3, 4 or more linked and independently selected monosaccharides that comprise a D-, L- or DL-mixture of glucose, fructose, mannose, idose, galactose, allose, gulose, altrose, talose, fucose, erythrose, threose, lyxose, erythrulose, ribulose, xylulose, ribose, arabinose, xylose, psicose, sorbose, tagatose, glyceraldehyde, N-acetylglucosamine, dihydroxyacetone or a monodeoxy or dideoxy derivative of any of these, with adjacent monosaccharides having the glycosidic linkage at the anomeric carbon of each monosaccharide unit independently alpha or beta linked, e.g., 1→2, 1→3, 1→4, and/or 1→6 glycosidic bonds in the α- and/or β-configuration, e.g., -glucose-mannose-, -glucose-mannose-mannose-, -mannose-mannose-, -mannose-mannose-mannose-, -glucose-galactose-, -galactose-glucose-, -fructose-galactose-, -galactose-fructose-, -galactose-galactose-, -galactose-mannose-, -glucuronic acid-glucose-, -glucose-glucose-, —(O-1β)-D-glucopyranosyl-(1α-O-4)-D-glucopyranoside, —(O-1β)-tetra-O-acetyl-D-glucopyranosyl-(1α-O-4)-tri-O-acetyl-D-glucopyranoside, —(O-1β)-D-galactopyranosyl-(1β-O-4)-D-glucopyranoside, wherein one or more of the monosaccharides are optionally partially or fully protected, e.g., with —C(O)—CH$_3$ or —C(O)—C$_2$H$_5$ to protect 1, 2, 3, 4 or more hydroxyl groups, including moieties such α-D-cellobiosyl, β-D-cellobiosyl, β-D-lactosyl, β-D-maltosyl, β-D-gentiobiosyl, 3-O-β-D-galactopyranosyl-α-D-arabanopyranosyl or β-D-maltotriosyl, any of which are optionally protected and where the variable group to which they are bonded is in the α- or β-configuration, or a glycol or polyethyleneglycol or a derivative, e.g., propylene glycol, ethylene glycol, 1,4-butylene glycol, 1,3-butylene glycol, 1,2-butylene glycol, —O—C(O)—O—(CH$_2$CH$_2$O)$_n$—H, —C(O)—CH$_2$—O—C(O)—O—(CH$_2$CH$_2$O)$_n$—H or —O—(CH$_2$CH$_2$O)$_n$—H, where n is 1, 2, 3, 4, 5, 6, 7, 8, 9 or 10, or an acetal or spiro ring, e.g., —O—CH$_2$—O—, —O—(CH$_2$)$_2$—O—, —O—(CH$_2$)$_3$—O— or —[C(R$^{36}$)$_2$]$_{1-4}$—O—, —O—C(O)—CH$_2$—, —O—C(O)—CH$_2$—CH$_2$—, —O—C(O)—CH$_2$—CH$_2$—CH$_2$—, —O—C(O)—CHR$^{10}$—, —O—C(O)—CHR$^{10}$—CHR$^{10}$—, —O—C(O)—(CHR$^{10}$)$_3$—, —NH—(CH$_2$)$_2$—O—, —NH—(CH$_2$)$_2$—NH—, —NH—(CH$_2$)$_2$—S—, —CH$_2$—N=CH—NH—, —NH—(CH$_2$)$_3$—O—, —NH—(CH$_2$)$_3$—S—, —NH—(CH$_2$)$_3$—O—, where R$^{10}$ are independently selected and optionally independently are —H, —F, —Cl, —Br, —I, —CH$_3$, —C$_2$H$_5$, —CF$_3$, —C$_2$F$_5$, —CH$_2$CF$_3$, —OH, —CN, —SCN, —OCH$_3$ or —OC$_2$H$_5$, and where each R$^{36}$ independently is —H, —F, —Cl, —Br, —I or an organic moiety such as C1-C10 optionally substituted alkyl (e.g., methyl or ethyl), C2-10 alkenyl, aryl or a heterocycle, any of which are optionally substituted as described herein, e.g., —CF$_3$ or —CH$_2$OH, or thioacetal, e.g., —S—CH$_2$—O—, —S—(CH$_2$)$_2$—O—, —S—(CH$_2$)$_3$—O—, —S—CH$_2$—S—, —S—(CH$_2$)$_2$—S—, —S—(CH$_2$)$_3$—S— or —S—[C(R$^{36}$)$_2$]$_{1-4}$—S— where each R$^{36}$ independently is —H, —F, —Cl, —Br, —I or an organic moiety such as C1-C10 optionally substituted alkyl (e.g., methyl or ethyl), C2-10 alkenyl, aryl or a heterocycle, any of which are optionally substituted as described herein, e.g., —CF$_3$ or —CH$_2$OH. The salts, ionized forms and solvates of any of these moieties are also included, e.g., where a group such as —NH$_2$ or —COOH is ionized to generate a moiety such as —NH$_3^+$Cl$^-$, —NH$_3^+$Br$^-$, —COO$^-$ Na$^+$ or —COO$^-$ K$^+$.

For any of these exemplary F1C, e.g., the B, C, D, E, F and G structures, some embodiments are characterized by the presence of one or two independently selected substitutions at R$^{10A}$, R$^{10B}$, R$^{10C}$ and R$^{10D}$ and optionally:

(a) R$^{10E}$ (when present at the 5-position), R$^{10F}$, R$^{10G}$ and R$^{10H}$ are independently selected R$^{10}$ groups in the α,β,α,α or β,β,α,α configurations respectively, R$^1$ is an oxygen-bonded, nitrogen-bonded or a sulfur-bonded moiety such as —OH, =O, —SH, =NOH, —NH(C1-C8 optionally substituted alkyl), an ester, an ether, a thioester, or a thioether, R$^{1A}$ is —H, absent, a carbon-bonded moiety such as an acyl moiety, optionally substituted alkyl or optionally substituted alkylaryl, R$^2$ is a halogen or an oxygen-bonded or a sulfur-bonded moiety, R$^{2A}$ is —H, absent, a carbon-bonded moiety, R$^3$ is a halogen or an oxygen-bonded or a sulfur-bonded moiety, R$^{3B}$ is —H, absent, a carbon-bonded moiety, R$^4$ is a halogen, an oxygen-bonded or a sulfur-bonded moiety, R$^{4A}$ is —H, absent, a carbon-bonded moiety such as an acyl moiety, optionally substituted alkyl or optionally substituted alkylaryl, (b) R$^{10E}$ (if present), R$^{10F}$, R$^{10G}$ and R$^{10H}$ are independently selected R$^{10}$ groups in the α,β,α,α or β,β,α,α configurations respectively, R$^{1A}$ is —H, an oxygen-bonded, nitrogen-bonded or a sulfur-bonded moiety, R$^1$ is —H, a carbon-bonded moiety, R$^2$ is a halogen or an oxygen-bonded or a sulfur-bonded moiety, R$^{2A}$ is —H, absent, a carbon-bonded moiety, R$^3$ is a halogen or an oxygen-bonded or a sulfur-bonded moiety, R$^{3B}$ is —H, absent, a carbon-bonded moiety, R$^4$ is a halogen, an oxygen-bonded or a sulfur-bonded moiety, R$^{4A}$ is —H, absent or a carbon-bonded moiety, (c) R$^{10E}$ (if present), R$^{10F}$, R$^{10G}$ and R$^{10H}$ are independently selected R$^{10}$ groups in the α,β,α,α or β,β,α,α configurations respectively, R$^1$ is an oxygen-bonded, nitrogen-bonded or a sulfur-bonded moiety, R$^{1A}$ is —H, absent or a carbon-bonded moiety, R$^2$ is a halogen or an oxygen-bonded or a sulfur-bonded moiety, R$^{2A}$ is —H, absent or a carbon-bonded moiety, R$^3$ is a halogen or an oxygen-bonded or a sulfur-bonded moiety, R$^{3B}$ is —H, absent or a carbon-bonded moiety, R$^{4A}$ is a halogen, an oxygen-bonded or a sulfur-bonded moiety, R$^4$ is —H, a halogen or a carbon-bonded moiety, (d) R$^{10E}$ (if present), R$^{10F}$, R$^{10G}$ and R$^{10H}$ are independently selected R$^{10}$ groups in the α,β,α,α or β,β,α,α configurations respectively, R$^1$ is an oxygen-bonded, nitrogen-bonded or a sulfur-bonded moiety, R$^{1A}$ is —H, absent, a carbon-bonded moiety, R$^2$ is a halogen or an oxygen-bonded or a sulfur-bonded moiety, R$^{2A}$ is —H, absent or a carbon-bonded moiety, R$^3$ is a halogen or an oxygen-bonded or a sulfur-bonded moiety, R$^{3B}$ is —H, absent or a carbon-bonded moiety, R$^4$ is a halogen, an oxygen-bonded or a sulfur-bonded moiety, R$^{4A}$ is —H, absent or a carbon-bonded moiety, (e) R$^{10E}$ (if present), R$^{10F}$, R$^{10G}$ and R$^{10H}$ are independently selected R$^{10}$ groups in the α,β,α,α or β,β,α,α configurations respectively, R$^1$ is an oxygen-bonded, nitrogen-bonded or a sulfur-bonded moiety, R$^{1A}$ is —H, absent or a carbon-bonded moiety, R$^2$ is a halogen or an oxygen-bonded or a sulfur-bonded moiety, R$^{2A}$ is —H, absent or a carbon-bonded moiety, R$^{3B}$ is a halogen or an oxygen-bonded or a sulfur-bonded moiety, R$^3$ is —H, a carbon-bonded moiety, R$^4$ is a halogen, an oxygen-bonded or a sulfur-bonded moiety, $R^{4A}$ is —H, absent or a carbon-bonded moiety, (f) $R^{10E}$ (if present), $R^{10F}$, $R^{10G}$ and $R^{10H}$ are independently selected $R^{10}$ groups in the α,β,α,α or β,β,α,α configurations respectively, $R^{1A}$ is —H, an oxygen-bonded, nitrogen-bonded or a sulfur-bonded moiety, $R^1$ is —H, a carbon-bonded moiety, $R^2$ is a halogen or an oxygen-bonded or a sulfur-bonded moiety, $R^{2A}$ is —H, absent or a carbon-bonded moiety, $R^3$ is a halogen or an oxygen-bonded or a sulfur-bonded moiety, $R^{3B}$ is —H, absent or a carbon-bonded moiety, $R^{4A}$ is a halogen, an oxygen-bonded or a sulfur-bonded moiety, $R^4$ is —H, a carbon-bonded moiety, or (g) $R^{10E}$ (if present), $R^{10F}$, $R^{10G}$ and $R^{10H}$ are independently selected $R^{10}$ groups in the α,β,α,α or β,β,α,α configurations respectively, $R^1$ is a halogen or an oxygen-bonded, nitrogen-bonded, carbon bonded or a sulfur-bonded moiety, $R^{1A}$ is —H, a carbon-bonded or nitrogen-bonded moiety and $R^2$, $R^{2A}$, $R^3$ $R^{3B}$, $R^4$ and $R^{4A}$ are as described any of in the foregoing embodiments or elsewhere herein. In any of these embodiments, $R^5$-$R^9$ are independently selected moieties as described herein and the oxygen-bonded, nitrogen-bonded, carbon bonded or sulfur-bonded moieties at $R^1$, $R^{1A}$, $R^2$, $R^{2A}$, $R^3$, $R^{3B}$, $R^4$, and $R^{4A}$ include atoms or groups described herein. These embodiments contain formula B, C, D, E, F and G compounds wherein one or two of $R^1$, $R^{1A}$, $R^2$, $R^{2A}$, $R^3$, $R^{3B}$, $R^4$ and $R^{4A}$ are independently selected nitrogen-bonded moieties, one, two or three of $R^1$, $R^{1A}$, $R^2$, $R^{2A}$, $R^3$, $R^{3B}$, $R^4$, and $R^{4A}$ are independently selected carbon-bonded moieties and one, two, three, four or five of $R^2$, $R^{2A}$, $R^3$, $R^{3B}$, $R^4$, and $R^{4A}$ are independently selected or halogen atoms or oxygen-bonded or sulfur-bonded moieties.

These embodiments contain F1C, such as the B, C, D, E, F and G structures wherein $R^4$ and $R^{4A}$ are present, i.e., no 16-17 double bond is present, and both are the same, such as optionally substituted alkyl, halogen, ether, ester, thioether, thioester, e.g., —$OR^{PR}$, —$SR^{PR}$, —F, —Cl, —Br, —I, methyl, ethyl, methoxy, ethoxy acetate or propionate. However, in many embodiments, when they are both present, $R^4$ and $R^{4A}$ are two independently selected dissimilar moieties defined herein, e.g., independently selected —H, —OH, —$OR^{PR}$, an ester (e.g., —OC(O)—CH₃, —OC(O)—C₂H₅, —OC(O)—C3 alkyl, —OC(O)—C4 alkyl), ether (e.g., —OCH₃, —OC₂H₅, —OCH₂CH₂CH₃, or —OCH(CH₃)CH₃, —O—C4 alkyl, —O—C6 alkyl or —O—C6 alkyl), a thioether, a thioether, an acyl moiety, a carbonate, a carbamate an amide, a monosaccharide, a disaccharide, or an amino acid, optionally substituted alkyl, optionally substituted alkenyl, optionally substituted alkynyl or another moiety described herein.

For any F1C, examples of dissimilar $R^4$ and $R^{4A}$ moieties at the 17-position include (α-ester, β-optionally substituted alkynyl), (β-ester, α-optionally substituted alkynyl), (α-thioester, β-optionally substituted alkynyl), (β-thioester, α-optionally substituted alkynyl), (α-ester, β-optionally substituted alkenyl), (β-ester, α-optionally substituted alkenyl), (α-thioester, β-optionally substituted alkenyl), (β-thioester, α-optionally substituted alkenyl), (α-optionally substituted alkyl, β-ester), (β-optionally substituted alkyl, α-ester), (α-optionally substituted alkyl, β-optionally substituted amine), (β-optionally substituted alkyl, α-optionally substituted amine), (α-optionally substituted alkyl, β-halogen)-, (β-optionally substituted alkyl, α-halogen), (α-halogen, β-ether), (β-halogen, α-ether), (α-halogen, β-optionally substituted alkyl), (β-halogen, α-optionally substituted alkyl), (β-ester, α-acyl), (α-ester, β-acyl), (β-ester, α-C(O)—C1-C10 optionally substituted alkyl), (α-ester, β—C(O)—C1-C10 optionally substituted alkyl), (β-thioester, α—C(O)—C1-C10 optionally substituted alkyl), (α-thioester, β-C(O)—C1-C10 optionally substituted alkyl), (β-OH, α-ester), (α-OH, β-ester), (β-OH, α-ether), (α-OH, β-ether), (β-OH, α-acyl), (α-OH, β-acyl), (α-halogen, β-$OR^{PR}$), (β-halogen, α-$OR^{PR}$), (α-F, β-ester), (β-F, α-ester), (α-F, β-ether), (β-F, α-ether), (α-Br, β-ether), (β-Br, α-ether), (α-F, β-optionally substituted alkyl), (β-F, α-optionally substituted alkyl), (α-OH, β-optionally substituted alkynyl), (β-OH, α-optionally substituted alkynyl), (α-OH, β-C≡CCH₂-halogen), (β-OH, α-C≡CCH₂-halogen), (α-OH, β-C≡C-halogen), (β-OH, α-C≡C-halogen), (β-epoxy, α-halogen, where the epoxy is formed with an adjacent steroid nucleus atom), (α-epoxy, β-halogen), (α-cyclopropyl, β-halogen), (β-cyclopropyl, α-halogen), (α-cyclopropyl, β-optionally substituted alkyl), (β-cyclopropyl, α-optionally substituted alkyl), (α-optionally substituted alkyl, β-NH—C1-C8 optionally substituted alkyl), (β-optionally substituted alkyl, α-NH—C1-C8 optionally substituted alkyl), α-ether, β-NH—C1-C8 optionally substituted alkyl), (β-ether, α-NH—C1-C8 optionally substituted alkyl), (α-thioester, β-NH—C1-C8 optionally substituted alkyl), (β-thioester, α-NH—C1-C8 optionally substituted alkyl), (α-ester, β-NH—C1-C8 optionally substituted alkyl), (β-ester, α-NH—C1-C8 optionally substituted alkyl), (α-C(O)CH₃, β-NH—C1-C8 optionally substituted alkyl), (β-C(O)CH₃, α-NH—C1-C8 optionally substituted alkyl), (α-OH, β-NH—C1-C8 optionally substituted alkyl), (β-OH, α-NH—C1-C8 optionally substituted alkyl) and other combinations of groups that are within the scope of $R^4$ and $R^{4A}$. Such moieties, which are the same or different can also be at 1, 2, 3 or more $R^1$ and $R^{1A}$, $R^2$ and $R^{2A}$, $R^3$ and $R^{3B}$ variable groups, and/or the $R^{10}$ variable groups at $R^7$, $R^8$ and $R^9$.

Specific dissimilar $R^4$ and $R^{4A}$ moieties include, e.g., (α-F, β-CH₃), (β-F, α-CH₃), (α-F, β-C₂H₅), (βF, α-C₂H₅), (α-Br, βOCH₃), (β-Br, α-OCH₃), (α-F, β-OCH₃), (β-F, α-OCH₃), (α-F, β-OH), (β-F, α-OH), (α-Br, βOCH₃), (β-Br, α-OCH₃), (α-F, β-CH₃), (β-F, α-CH₃), (α-Br, β-CH₃), (β-Br, α-CH₃), (α-OH, β-CCCH₃), (β-OH, α-CCCH₃), (α-OH, β-CCCH₂OH), (β-OH, α-CCCH₂OH), (α-OH, β-CCH), (β-OH, α-CCH), (α-CH₃, βOC(O)CH₃), (β-CH₃, α-OC(O)CH₃), (α-C₂H₅, βOC(O)CH₃), (β-C₂H₅, α-OC(O)CH₃), (α-C₃H₇, β-C(O)CH₃), (β-C₃H₇, α-OC(O)CH₃), (α-C₄H₉, β-OC(O)CH₃), (β-C₄H₉, α-OC(O)CH₃), (α-C₂H₃, βOC(O)CH₃), (β-C₂H₃, α-OC(O)CH₃), (α-C₂H₄OH, βOC(O)CH₃), (β-C₂H₄OH, α-OC(O)CH₃), (α-C₃H₅, βOC(O)CH₃), (β-C₃H₅, α-OC(O)CH₃), (α-C₄H₇, β-OC(O)CH₃), (β-C₄H₇, α-OC(O)CH₃), (α-C₃H₃, β-OC(O)CH₃), (β-C₃H₃, α-OC(O)CH₃), (α-C₄H₅, βOC(O)CH₃), (β-C₄H₅, α-OC(O)CH₃), (α-CH₃, βOC(O)C₂H₅), (β-CH₃, α-OC(O)C₂H₅), (α-C₂H₅, β-OC(O)C₂H₅), (β-C₂H₅, α-OC(O)C₂H₅), (α-C₃H₇, β-OC(O)C₂H₅), (β-C₃H₇, α-OC(O)C₂H₅), (α-C₄H₉, β-OC(O)C₂H₅), (β-C₄H₉, α-OC(O)C₂H₅), (α-C₂H₃, β-OC(O)C₂H₅), (β-C₂H₃, α-OC(O)C₂H₅), (α-C₂H₄OH, β-OC(O)C₂H₅), (β-C₂H₄OH, α-OC(O)C₂H₅), (α-C₃H₅, β-OC(O)C₂H₅), (β-C₃H₅, α-OC(O)C₂H₅), (α-C₄H₇, β-OC(O)C₂H₅), (β-C₄H₇, α-OC(O)C₂H₅), (α-C₃H₃, β-OC(O)C₂H₅), (β-C₃H₃, α-OC(O)C₂H₅), (α-C₄H₅, β-OC(O)C₂H₅), (β-C₄H₅, α-OC(O)C₂H₅), (α-C(O)CH₃, β-OC(O)CH₃), (βC(O)CH₃, α-OC(O)CH₃), (α-C(O)C₂H₅, β-OC(O)CH₃), (βC(O)C₂H₅, α-OC(O)CH₃), (α-CH₃, β-SC(O)CH₃), (β-CH₃, α-SC(O)CH₃), (α-C₂H₅, β-SC(O)CH₃), (β-C₂H₅, α-SC(O)CH₃), (α-C₃H₇, β-SC(O)CH₃), (β-C₃H₇, α-SC(O)CH₃), (α-C₄H₉, β-SC(O)CH₃), (β-C₄H₉, α-SC(O)CH₃), (α-C₂H₃, β-SC(O)CH₃), (β-C₂H₃, α-SC(O)CH₃), (α-C₂H₄OH, β—SC(O)CH₃), (β-C₂H₄OH, α-SC(O)CH₃), (α-C₃H₅, β-SC(O)CH₃), (β-C₃H₅, α-SC(O)CH₃), (α-C₄H₇, β-SC(O)CH₃), (β-C₄H₇, α-SC(O)CH₃), (α-C₃H₃, β-SC(O)CH₃), (β-C₃H₃, α-SC(O)CH$_3$), (α-C$_4$H$_5$, β-SC(O)CH$_3$), (β-C$_4$H$_5$, α-SC(O)CH$_3$), (α-CH$_3$, β-SC(O)C$_2$H$_5$), (β-CH$_3$, α-SC(O)C$_2$H$_5$), (α-C$_2$H$_5$, β-SC(O)C$_2$H$_5$), (β-C$_2$H$_5$, α-SC(O)C$_2$H$_5$), (α-C$_3$H$_7$, β-SC(O)C$_2$H$_5$), (β-C$_3$H$_7$, α-SC(O)C$_2$H$_5$), (α-C$_4$H$_9$, β-SC(O)C$_2$H$_5$), (β-C$_4$H$_9$, α-SC(O)C$_2$H$_5$), (α-C$_2$H$_3$, β-SC(O)C$_2$H$_5$), (β-C$_2$H$_3$, α-SC(O)C$_2$H$_5$), (α-C$_2$H$_4$OH, β-SC(O)C$_2$H$_5$), (β-C$_2$H$_4$OH, α-SC(O)C$_2$H$_5$), (α-C$_3$H$_5$, β-SC(O)C$_2$H$_5$), (β-C$_3$H$_5$, α-SC(O)C$_2$H$_5$), (α-C$_4$H$_7$, β-SC(O)C$_2$H$_5$), (β-C$_4$H$_7$, α-SC(O)C$_2$H$_5$), (α-C$_3$H$_3$, β-SC(O)C$_2$H$_5$), (β-C$_3$H$_3$, α-SC(O)C$_2$H$_5$), (α-C$_4$H$_5$, β-SC(O)C$_2$H$_5$), (β-C$_4$H$_5$, α-SC(O)C$_2$H$_5$), (α-C(O)CH$_3$, β-SC(O)CH$_3$), (βC(O)CH$_3$, α-SC(O)CH$_3$), (α-C(O)C$_2$H$_5$, β-SC(O)CH$_3$), (βC(O)C$_2$H$_5$, α-SC(O)CH$_3$), (α-C(O)CH$_3$, βNH—CH$_3$), (βC(O)CH$_3$, α—NH—CH$_3$), (α-OH, βNH—CH$_3$), (β-OH, α—NH—CH$_3$), (α-C(O)CH$_3$, β-N(CH$_3$)$_2$), (βC(O)CH$_3$, α-N(CH$_3$)$_2$), (α-OH, β-N(CH$_3$)$_2$), (β-OH, α-N(CH$_3$)$_2$), (α-C(O)CH$_3$, β-N(C$_2$H$_5$)$_2$), (βC(O)CH$_3$, α-N(C$_2$H$_5$)$_2$), (α-OH, β-N(C$_2$H$_5$)$_2$), (β-OH, α-N(C$_2$H$_5$)$_2$), (β-epoxy, α-H), (α-epoxy, β-H), (β-epoxy, α-Br), (α-epoxy, β-Br), (β-epoxy, α-F), (α-epoxy, β-F), (β-cyclopropyl, α-H), (α-cyclopropyl, β-H), (β-cyclopropyl, α-F) and (α-cyclopropyl, β-F). For moieties that contain an epoxy, cyclopropyl or other cyclic moiety, the cyclic moiety can be formed with an adjacent variable group, e.g., $R^3$ or $R^{3B}$. As is apparent from the foregoing disclosure, these or other dissimilar moieties can also be present at one or more of, e.g., the 2-, 3-, 7-, 11-, 15- or 16-positions.

Additional embodiments of the F1Cs include any F1Cs or any 2, 5, 6, 7, 8, 9, 10, B, C, D, E, F or G structures, e.g., any of the F1Cs or F1C genera disclosed herein, wherein one or both of $R^5$ or $R^6$ independently are —H, —CH$_3$, —CF$_3$, —CH$_2$SH, —CHO, —CH$_2$NRPR, —CH$_2$NH$_2$, —C$_4$H$_9$, —C$_3$H$_7$, —C$_2$H$_5$, —CH$_3$, —C$_2$H$_4$OH, —C$_2$H$_4$SH, —C$_2$H$_4$NH$_2$, —CH$_2$CHO, —CH$_2$CH$_2$NR$^{PR}$, —CH$_2$CH$_2$OH, —CH$_2$CH$_2$SH, —CH$_2$CH$_2$C$_6$H$_5$, —CH$_2$C$_6$H$_5$, —C$_6$H$_5$ or optionally substituted alkyl wherein any phenyl (C$_6$H$_5$) moiety in the foregoing groups is optionally substituted at the phenyl ring with 1, 2, 3, 4 or 5 moieties independently selected from those described for esters herein and including C1-C6 alkyl (optionally substituted with 1 or 2 independently selected —OH, —SH, —O—, —S— or —NH—) C1-C6 alkoxy, —F, —Cl, —Br, —I, —CN, —NO$_2$, —OH, —SH, —COOR$^{PR}$, —NHR$^{PR}$ and —C(O)—C1-C6 alkyl. Typically $R^5$ or $R^6$ are both in the β-configuration, but they may be in, e.g., the α,β or β,α configurations respectively.

F1C embodiments also include compounds where 1, 2 or more of, e.g., $R^1$, $R^2$, $R^3$, $R^4$, $R^{10A}$, $R^{10B}$, $R^{10C}$ or another $R^{10}$ moiety are an independently selected lipid moiety such as a fatty acid, a monoacylglyceride, a diacylglyceride, a phospholipid, a glycolipid, a sphingolipid or a glycerophospholipid that is esterified, linked through an ether (—O—) or acyl moiety or otherwise bonded to the F1C. The lipid can be bonded to the steroid in the α- or the β-configuration when no double bond is present the position where the lipid is bonded or without a specified configuration when a double bond is present in the steroid at the position where the polymer is bonded. Exemplary fatty acid esters include —C(O)—(CH$_2$)$_m$—H where m is 4, 5, 6, 7, 8, 9, 10, 11, 12, 14, 13, 15, 16, 17, 18, 19 or 21 and —C(O)—(CH$_2$)$_n$—CH=CH—(CH$_2$)$_n$—H where each n independently is 1, 2, 3, 4, 5, 6, 7 or 8 and the configuration around the double bond is cis or trans. Other lipid moieties that can be bonded to the steroid include phosphatidic acid, phosphatidylethanolamine, phosphatidylcholine, phosphatidylserine and phosphatidylglycerol. The lipid moiety may be bonded to the steroid through a hydroxyl or oxygen, phosphate, sulfate or amine at a variable group.

Such lipid moieties may be bonded to any of the F1Cs or genera of F1Cs disclosed herein. F1Cs can thus comprise a lipid at, e.g., one or two of, e.g., the 1-, 2-, 3-, 4-, 5-, 6-, 7-, 11-, 12-, 14-, 15-, 16-, 17- or 19-positions in the α- or β-configurations. Lipids that contain ionizable moieties such as carboxyl or amine groups can be present as salts, ionized forms, unionized forms, tautomers or mixtures thereof.

When a variable group such as an $R^1$, $R^2$, $R^3$, $R^4$, $R^{10A}$, $R^{10B}$, $R^{10C}$ or another $R^{10}$ moiety is a polymer, the polymer can be bonded to the steroid through an ether or thioether linkage or through an acyl, thioacyl or another moiety. The polymer can be bonded to the steroid in the α- or the β-configuration when no double bond is present the position where the polymer is bonded. Polymers such as polyethyleneglycols can be prepared by reaction of a steroid chloroformate (steroid-O—C(O)—Cl) intermediate with a polymer containing a free hydroxyl, thiol or other reactive group such as CH$_3$—(O—CH$_2$—CH$_2$)$_n$—OH, $R^{PR}$—O—CH$_2$—(O—CH$_2$—CH$_2$)$_n$—OH, $R^{PR}$—S—CH$_2$—(O—CH$_2$—CH$_2$)$_n$—OH, $R^{PR}$—OC(O)—CH$_2$—(O—CH$_2$—CH$_2$)$_n$—OH, $R^{PR}$—NH—CH$_2$—(O—CH$_2$—CH$_2$)$_n$—OH or $R^{PR}$—NH—C(O)—CH$_2$—(O—CH$_2$—CH$_2$)$_n$—OH to obtain, e.g., steroid-O—C(O)—O—(CH$_2$—CH$_2$O)$_n$—CH$_3$, steroid-O—C(O)—O—(CH$_2$—CH$_2$O)$_n$—CH$_2$—C(O)OR$^{PR}$, steroid-O—C(O)—O—(CH$_2$—CH$_2$O)$_n$—CH$_3$—OR$^{PR}$, CH$_3$—(CH$_2$)$_m$—OH, CH$_3$—(CH$_2$)$_m$—C(O)—OH, CH$_3$—(CH$_2$)$_m$—SH, CH$_3$—(CH$_2$)$_m$—C(O)—SH, $R^{PR}$—O—CH$_2$—(CH$_2$)$_m$—OH, $R^{PR}$—O—CH$_2$—(CH$_2$)$_m$—C(O)—OH, $R^{PR}$—O—CH$_2$—(CH$_2$)$_m$—SH, $R^{PR}$—O—CH$_2$—(CH$_2$)$_m$—C(O)—SH, $R^{PR}$—NH—CH$_2$—(CH$_2$)$_m$—OH, $R^{PR}$—NH—CH$_2$—(CH$_2$)$_m$—C(O)—OH, $R^{PR}$—NH—CH$_2$—(CH$_2$)$_m$—SH or $R^{PR}$—NH—CH$_2$—(CH$_2$)$_m$—C(O)—SH, where $R^{PR}$ is —H or a protecting group and m and n are integers or an average number of monomer units from the polymer used to make the steroid conjugate. Typically n is about 1, 2, 3, 4, 6, 8, 10, 12, 14, 16, 18, 20, 22, 25, 30, 35, 40, 45, 50 or 60. Typically m is about 1, 2, 3, 4, 6, 8, 10, 12, 14, 16, 18, 20 or 22. When a variable group is a polymer, usually no more than 1 or 2 variable groups in F1Cs will be a polymer.

Exemplary F1Cs that comprise a polymer include steroid-O—C(O)—O—(CH$_2$—CH$_2$O)$_n$—CH$_3$, steroid-O—C(O)—O—(CH$_2$—CH$_2$O)$_n$—OH, steroid-O—C(O)—O—(CH$_2$—CH$_2$O)$_n$—OR$^{PR}$, steroid-O—C(O)—O—(CH$_2$—CH$_2$O)$_n$—NHR$^{PR}$, steroid-O—C(O)—O—(CH$_2$—CH$_2$O)$_n$—C(O)OH, steroid-O—C(O)—O—(CH$_2$—CH$_2$O)$_n$—C(O)OR$^{PR}$, steroid-S—C(O)—O—(CH$_2$—CH$_2$O)$_n$—CH$_3$, steroid-S—C(O)—O—(CH$_2$—CH$_2$O)$_n$—OH, steroid-S—C(O)—O—(CH$_2$—CH$_2$O)$_n$—OR$^{PR}$, steroid-S—C(O)—O—(CH$_2$—CH$_2$O)$_n$—NHR$^{PR}$, steroid-S—C(O)—O—(CH$_2$—CH$_2$O)$_n$—C(O)OH, steroid-S—C(O)—O—(CH$_2$—CH$_2$O)$_n$—C(O)OR$^{PR}$, steroid-NH—(CH$_2$—CH$_2$O)$_n$—CH$_3$, steroid-NH—(CH$_2$—CH$_2$O)$_n$—OH, steroid-NH—(CH$_2$—CH$_2$O)$_n$—OR$^{PR}$, steroid-NH—(CH$_2$—CH$_2$O)$_n$—NHR$^{PR}$, steroid-NH—(CH$_2$—CH$_2$O)$_n$—C(O)OH, steroid-NH—(CH$_2$—CH$_2$O)$_n$—C(O)OR$^{PR}$, steroid-NH—(CH$_2$—CH$_2$O)$_n$—CH$_3$, steroid-NH—(CH$_2$—CH$_2$O)$_n$—OH, steroid-NH—(CH$_2$—CH$_2$O)$_n$—OR$^{PR}$, steroid-NH—(CH$_2$—CH$_2$O)$_n$—NHR$^{PR}$, steroid-NH—(CH$_2$—CH$_2$O)$_n$—C(O)OH, steroid-NH—(CH$_2$—CH$_2$O)$_n$—C(O)OR$^{PR}$, steroid-NH—C(O)—(CH$_2$—CH$_2$O)$_n$—CH$_3$, steroid-NH—C(O)—(CH$_2$—CH$_2$O)$_n$—OH, steroid-NH—C(O)—(CH$_2$—CH$_2$O)$_n$—OR$^{PR}$, steroid-NH—C(O)—(CH$_2$—CH$_2$O)$_n$—NHR$^{PR}$, steroid-NH—C(O)—(CH$_2$—CH$_2$O)$_n$—C(O)OH, steroid-NH—C(O)—(CH$_2$—CH$_2$O)$_n$—C(O)OR$^{PR}$, steroid-NH—C(O)—(CH$_2$—CH$_2$O)$_n$—CH$_3$, steroid-NH—C(O)—(CH$_2$—CH$_2$O)$_n$—OH, steroid-NH—C(O)—(CH$_2$—CH$_2$O)$_n$—OR$^{PR}$, steroid-NH—C(O)—(CH$_2$—CH$_2$O)$_n$—NHR$^{PR}$, steroid—NH—C(O)—(CH$_2$—CH$_2$O)$_n$—C(O)OH, steroid-NH—C(O)—(CH$_2$—CH$_2$O)$_n$—C(O)OR$^{PR}$, steroid-NH—C(O)—O—(CH$_2$—CH$_2$O)$_n$—CH$_3$, steroid-NH—C(O)—O—(CH$_2$—CH$_2$O)$_n$—OH, steroid-NH—C(O)—O—(CH$_2$—CH$_2$O)$_n$—OR$^{PR}$, steroid-NH—C(O)—O—(CH$_2$—CH$_2$O)$_n$—NHR$^{PR}$, steroid-NH—C(O)—O—(CH$_2$—CH$_2$O)$_n$—C(O)OH, steroid-NH—C(O)—O—(CH$_2$—CH$_2$O)$_n$—C(O)OR$^{PR}$, steroid-NH—C(O)—O—(CH$_2$—CH$_2$O)$_n$—CH$_3$, steroid-NH—C(O)—O—(CH$_2$—CH$_2$O)$_n$—OH, steroid-NH—C(O)—O—(CH$_2$—CH$_2$O)$_n$—OR$^{PR}$, steroid-NH—C(O)—O—(CH$_2$—CH$_2$O)$_n$—NHR$^{PR}$, steroid-NH—C(O)—O—(CH$_2$—CH$_2$O)$_n$—C(O)OH, steroid-NH—C(O)—O—(CH$_2$—CH$_2$O)$_n$—C(O)OR$^{PR}$, steroid-O—(CH$_2$—CH$_2$O)$_n$—CH$_3$, steroid-O—(CH$_2$—CH$_2$O)$_n$—OH, steroid-O—(CH$_2$—CH$_2$O)$_n$—OR$^{PR}$, steroid-O—(CH$_2$—CH$_2$O)$_n$—NHR$^{PR}$, steroid-O—(CH$_2$—CH$_2$O)$_n$—C(O)OH, steroid-O—(CH$_2$—CH$_2$O)$_n$—C(O)OR$^{PR}$, steroid-S—(CH$_2$—CH$_2$O)$_n$—CH$_3$, steroid-S—(CH$_2$—CH$_2$O)$_n$—OH, steroid-S—(CH$_2$—CH$_2$O)$_n$—OR$^{PR}$, steroid-S—(CH$_2$—CH$_2$O)$_n$—NHR$^{PR}$, steroid-S—(CH$_2$—CH$_2$O)$_n$—C(O)OH and steroid-S—(CH$_2$—CH$_2$O)$_n$—C(O)OR$^{PR}$, where R$^{PR}$ are —H, a protecting group or optionally substituted alkyl and the polymer moiety is linked to the steroid in the α- or β-configuration when no double bond is present or in no specified configuration if a double bond is present in the steroid at the position where the polymer is bonded. F1Cs can thus comprise a polymer at, e.g., one or two of, e.g., the 1-, 2-, 3-, 4-, 5-, 6-, 7-, 11-, 12-, 14-, 15-, 16-, 17- or 19-positions. Polymers that contain ionizable moieties such as carboxyl or amine groups can be present as salts, ionized forms, unionized forms, tautomers or mixtures thereof.

F1C embodiments include structures where 1, 2, 3 or 4 variable groups such as R$^1$, R$^2$, R$^3$, R$^4$, R$^{10A}$, R$^{10B}$, R$^{10C}$ or another R$^{10}$ moiety are an independently selected oxygen linked moiety and 0, 1, 2 or 3 variable groups such as R$^2$, R$^3$, R$^4$, R$^5$, R$^6$, R$^{10A}$, R$^{10B}$, R$^{10C}$ or another R$^{10}$ moiety are an independently selected carbon linked moiety. Oxygen linked moieties are moieties where oxygen is bonded to the steroid ring, e.g., —OH, =O, —OR$^{PR}$, carbonate, ester, ether, —O-monosaccharide, —O-polymer, —O—C(O)—NH$_2$ or —O—C(O)—NH-optionally substituted alkyl. Carbon linked moieties are moieties where carbon is bonded to the steroid ring, e.g., optionally substituted alkyl, —C(O)-optionally substituted alkyl, —C(O)—O-optionally substituted alkyl, optionally substituted alkenyl or optionally substituted alkynyl such as —CH$_3$, —CF$_3$, —CH$_2$OH, —C$_2$H$_5$ or —C$_2$H$_4$OH. These F1Cs include compounds where (1) one R$^1$ is an oxygen linked moiety (an 'O-linked' moiety), an S-linked moiety or an N-linked moiety and the other R$^1$ is —H or a carbon linked moiety (a 'C-linked' moiety), (2) one R$^4$ is an oxygen linked moiety and the other R$^4$ is —H or a C-linked moiety, (3) one R$^3$ is an oxygen linked moiety and the other R$^3$ is —H or a C-linked moiety and/or (4) one R$^2$ is an oxygen linked moiety and the other R$^2$ is —H or a C-linked moiety, where the oxygen linked moiety or moieties independently are in the α- or β-configuration.

For any of these F1C embodiments or other F1Cs described elsewhere herein, one, two or three of R$^{10A}$, R$^{10B}$, R$^{10C}$, R$^{10D}$, R$^{10E}$, R$^{10F}$, R$^{10G}$ and R$^{10H}$ are optionally substituted with an independently selected halogen, oxygen linked moiety, nitrogen linked moiety, carbon linked moiety or sulfur linked moiety. These substitutions can be linked to the steroid in the α- or β-configuration when no double bond is present or in no specified configuration if a double bond is present in the steroid at the position where the variable group is bonded.

Exemplary substituents for R$^{10E}$, R$^{10F}$, R$^{10G}$ and R$^{10H}$ include independently selected α-F, i.e., fluorine in the α-configuration, β-F, α-Cl, β-Cl, α-OH, β-OH, α-SH, β-SH, α-NH$_2$, β-NH$_2$, α-ether, β-ether, α-optionally substituted alkyl, β-optionally substituted alkyl and any other substituent or moiety described herein. Exemplary substituents for R$^{10A}$, R$^{10B}$, R$^{10C}$ and R$^{10D}$ include independently selected α-F, β-F, α-Cl, β-Cl, α-OH, β-OH, α-SH, β-SH, α-NH$_2$, β-NH$_2$, α-optionally substituted alkyl, β-optionally substituted alkyl, α-ether, β-ether, α-ester, β-ester, α-thioester, β-thioester, α-O-monosaccharide, β-O-monosaccharide and, when no double bond is present at the 1-, 4-, 6- or 12-positions of the steroid, a double bonded moiety such as =O, =S, =NH, =NCH$_3$, =NOH, =N-optionally substituted alkyl, =CH$_2$, =CH-optionally substituted alkyl and any other single bonded or double bonded substituent or moiety described herein.

Compound Groups.

Specific F1Cs or genera of F1Cs that can be used in the assay methods, clinical treatments, e.g., blood cell deficiency treatments, cancer or infection treatment methods, radiation protection treatment methods, autoimmune disease treatment methods or trauma treatment methods, and other methods described herein include the following compound groups.

Group 1. Exemplary embodiments include the formula 1 compounds named according to the compound structure designations given in Tables A and B below. Each compound named in Table B is depicted as a compound having the structure

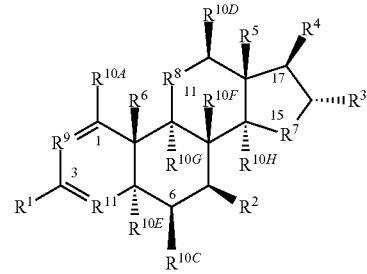

where R$^5$ and R$^6$ are both —CH$_3$, there is a double bond at the 1-2- and 3-4 positions, R$^7$, R$^8$ and R$^9$ are all —CH$_2$— or =CH—, R$^{11}$ is =CR$^{10B}$—, R$^{10A}$, R$^{10B}$, R$^{10C}$, R$^{10D}$, R$^{10E}$, R$^{10F}$, R$^{10G}$ and R$^{10H}$ are all —H and R$^1$, R$^2$, R$^3$ and R$^4$ are the substituents designated in Table A. The compounds named according to Tables A and B are referred to as "group 1" compounds.

Compounds named in Table B are named by numbers assigned to R$^1$, R$^2$, R$^3$ and R$^4$ according to the following compound naming convention, R$^1$.R$^2$.R$^3$.R$^4$, using the numbered chemical substituents in Table A. Each Table A number specifies a different structure for each of R$^1$, R$^2$, R$^3$ and R$^4$. When R$^1$, R$^2$, R$^3$ or R$^4$ is a divalent moiety, e.g., =O, the hydrogen at the corresponding position is absent. Thus, the group 1 compound named 1.2.4.9 is a group 1 compound with a 6-hydroxyl bonded to carbons at the 3- and 7-positions (the variable groups R$^1$ and R$^2$ respectively), an α-fluorine bonded to carbon 16 (the variable group R$^3$) and acetate at carbon 17 (the variable group R$^4$), i.e., 1.2.4.9 is 3,7β,17β-trihydroxy-16α-fluoroandrost-1,3-diene, which has the structure

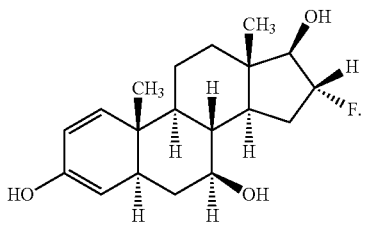

Similarly, group 1 compound 1.2.4.1 is 3,7β-dihydroxy-16α-fluoro-17β-aminoandrost-1,3-diene, group 1 compound 1.1.5.9 is 3,17β-dihydroxyandrost-1,3-diene, 1.1.7.1, which is 3-hydroxy-16α-acetoxy-17β-aminoandrost-1,3-diene and compound 1.1.4.10, which is 3-hydroxy-16α-fluoro-17β-acetoxyandrost-1,3-diene. Other exemplary group 1 compounds include 3,17β-dihydroxy-7β-acetoxyandrost-1,3-diene, 3,17β-dihydroxy-7β-methylandrost-1,3-diene, 3,17β-dihydroxy-7β-methoxyandrost-1,3-diene, 3,7β,17β-trihydroxyandrost-1,3-diene, 3-amino-17β-hydroxyandrost-1,3-diene, 3-amino-7β,17β-dihydroxyandrost-1,3-diene, 3-hydroxy-17β-aminoandrost-1,3-diene, 3,7β-dihydroxy-17β-aminoandrost-1,3-diene, 3,17β-dihydroxy-7β-aminoandrost-1,3-diene, 3-hydroxy-7β,17β-diacetylaminoandrost-1,3-diene, 3-hydroxy-7β,17β-dimethylaminoandrost-1,3-diene and 16α-hydroxy, 16α-methyl, 16α-amino, 16α-aminomethyl, 16α-acetate and 16α-halo analogs of any of these compounds.

TABLE A

| | $R^1$ | | $R^2$ |
|---|---|---|---|
| 1 | —OH | 1 | —H |
| 2 | —OCH$_3$ | 2 | —OH |
| 3 | —SH | 3 | —OCH$_3$ |
| 4 | —O—C(O)—CH$_3$ | 4 | —N(CH$_3$)$_2$ |
| 5 | —NHCH$_3$ | 5 | —CH$_3$ |
| 6 | —NH$_2$ | 6 | —NH$_2$ |
| 7 | —NH—C(O)—CH$_3$ | 7 | —NH—C(O)—CH$_3$ |
| 8 | —N(CH$_3$)$_2$ | 8 | —NH—CH$_3$ |
| 9 | —O-D-β-glucoside | 9 | —O—C(O)—CH$_3$ |
| 10 | —O—S(O)(OH)—OH | 10 | —SH |

| | $R^3$ | | $R^4$ |
|---|---|---|---|
| 1 | —Br | 1 | —NH$_2$ |
| 2 | —Cl | 2 | —NH—C(O)—CH$_3$ |
| 3 | —I | 3 | —NH—C(O)—OCH$_3$ |
| 4 | —F | 4 | —NH—CH$_3$ |
| 5 | —H | 5 | —N(CH$_3$)$_2$ |
| 6 | —OH | 6 | —OCH$_3$ |
| 7 | —O—C(O)—CH$_3$ | 7 | —O—S(O)(OH)—OH |
| 8 | —CH$_3$ | 8 | —O—C(O)—CH$_2$CH$_3$ |
| 9 | —NH$_2$ | 9 | —OH |
| 10 | —NHCH$_3$ | 10 | —O—C(O)—CH$_3$ |

TABLE B 1.1.1.1, 1.1.1.2, 1.1.1.3, 1.1.1.4, 1.1.1.5, 1.1.1.6, 1.1.1.7, 1.1.1.8, 1.1.1.9, 1.1.1.10, 1.1.2.1, 1.1.2.2, 1.1.2.3, 1.1.2.4, 1.1.2.5, 1.1.2.6, 1.1.2.7, 1.1.2.8, 1.1.2.9, 1.1.2.10, 1.1.3.1, 1.1.3.2, 1.1.3.3, 1.1.3.4, 1.1.3.5, 1.1.3.6, 1.1.3.7, 1.1.3.8, 1.1.3.9, 1.1.3.10, 1.1.4.1, 1.1.4.2, 1.1.4.3, 1.1.4.4, 1.1.4.5, 1.1.4.6, 1.1.4.7, 1.1.4.8, 1.1.4.9, 1.1.4.10, 1.1.5.1, 1.1.5.2, 1.1.5.3, 1.1.5.4, 1.1.5.5, 1.1.5.6, 1.1.5.7, 1.1.5.8, 1.1.5.9, 1.1.5.10, 1.1.6.1, 1.1.6.2, 1.1.6.3, 1.1.6.4, 1.1.6.5, 1.1.6.6, 1.1.6.7, 1.1.6.8, 1.1.6.9, 1.1.6.10, 1.1.7.1, 1.1.7.2, 1.1.7.3, 1.1.7.4, 1.1.7.5, 1.1.7.6, 1.1.7.7, 1.1.7.8, 1.1.7.9, 1.1.7.10, 1.1.8.1, 1.1.8.2, 1.1.8.3, 1.1.8.4, 1.1.8.5, 1.1.8.6, 1.1.8.7, 1.1.8.8, 1.1.8.9, 1.1.8.10, 1.1.9.1, 1.1.9.2, 1.1.9.3, 1.1.9.4, 1.1.9.5, 1.1.9.6, 1.1.9.7, 1.1.9.8, 1.1.9.9, 1.1.9.10, 1.1.10.1, 1.1.10.2, 1.1.10.3, 1.1.10.4, 1.1.10.5, 1.1.10.6, 1.1.10.7, 1.1.10.8, 1.1.10.9, 1.1.10.10, 1.2.1.1, 1.2.1.2, 1.2.1.3, 1.2.1.4, 1.2.1.5, 1.2.1.6, 1.2.1.7, 1.2.1.8, 1.2.1.9, 1.2.1.10, 1.2.2.1, 1.2.2.2, 1.2.2.3, 1.2.2.4, 1.2.2.5, 1.2.2.6, 1.2.2.7, 1.2.2.8, 1.2.2.9, 1.2.2.10, 1.2.3.1, 1.2.3.2, 1.2.3.3, 1.2.3.4, 1.2.3.5, 1.2.3.6, 1.2.3.7, 1.2.3.8, 1.2.3.9, 1.2.3.10, 1.2.4.1, 1.2.4.2, 1.2.4.3, 1.2.4.4, 1.2.4.5, 1.2.4.6, 1.2.4.7, 1.2.4.8, 1.2.4.9, 1.2.4.10, 1.2.5.1, 1.2.5.2, 1.2.5.3, 1.2.5.4, 1.2.5.5, 1.2.5.6, 1.2.5.7, 1.2.5.8, 1.2.5.9, 1.2.5.10, 1.2.6.1, 1.2.6.2, 1.2.6.3, 1.2.6.4, 1.2.6.5, 1.2.6.6, 1.2.6.7, 1.2.6.8, 1.2.6.9, 1.2.6.10, 1.2.7.1, 1.2.7.2, 1.2.7.3, 1.2.7.4, 1.2.7.5, 1.2.7.6, 1.2.7.7, 1.2.7.8, 1.2.7.9, 1.2.7.10, 1.2.8.1, 1.2.8.2, 1.2.8.3, 1.2.8.4, 1.2.8.5, 1.2.8.6, 1.2.8.7, 1.2.8.8, 1.2.8.9, 1.2.8.10, 1.2.9.1, 1.2.9.2, 1.2.9.3, 1.2.9.4, 1.2.9.5, 1.2.9.6, 1.2.9.7, 1.2.9.8, 1.2.9.9, 1.2.9.10, 1.2.10.1, 1.2.10.2, 1.2.10.3, 1.2.10.4, 1.2.10.5, 1.2.10.6, 1.2.10.7, 1.2.10.8, 1.2.10.9, 1.2.10.10, 1.3.1.1, 1.3.1.2, 1.3.1.3, 1.3.1.4, 1.3.1.5, 1.3.1.6, 1.3.1.7, 1.3.1.8, 1.3.1.9, 1.3.1.10, 1.3.2.1, 1.3.2.2, 1.3.2.3, 1.3.2.4, 1.3.2.5, 1.3.2.6, 1.3.2.7, 1.3.2.8, 1.3.2.9, 1.3.2.10, 1.3.3.1, 1.3.3.2, 1.3.3.3, 1.3.3.4, 1.3.3.5, 1.3.3.6, 1.3.3.7, 1.3.3.8, 1.3.3.9, 1.3.3.10, 1.3.4.1, 1.3.4.2, 1.3.4.3, 1.3.4.4, 1.3.4.5, 1.3.4.6, 1.3.4.7, 1.3.4.8, 1.3.4.9, 1.3.4.10, 1.3.5.1, 1.3.5.2, 1.3.5.3, 1.3.5.4, 1.3.5.5, 1.3.5.6, 1.3.5.7, 1.3.5.8, 1.3.5.9, 1.3.5.10, 1.3.6.1, 1.3.6.2, 1.3.6.3, 1.3.6.4, 1.3.6.5, 1.3.6.6, 1.3.6.7, 1.3.6.8, 1.3.6.9, 1.3.6.10, 1.3.7.1, 1.3.7.2, 1.3.7.3, 1.3.7.4, 1.3.7.5, 1.3.7.6, 1.3.7.7, 1.3.7.8, 1.3.7.9, 1.3.7.10, 1.3.8.1, 1.3.8.2, 1.3.8.3, 1.3.8.4, 1.3.8.5, 1.3.8.6, 1.3.8.7, 1.3.8.8, 1.3.8.9, 1.3.8.10, 1.3.9.1, 1.3.9.2, 1.3.9.3, 1.3.9.4, 1.3.9.5, 1.3.9.6, 1.3.9.7, 1.3.9.8, 1.3.9.9, 1.3.9.10, 1.3.10.1, 1.3.10.2, 1.3.10.3, 1.3.10.4, 1.3.10.5, 1.3.10.6, 1.3.10.7, 1.3.10.8, 1.3.10.9, 1.3.10.10, 1.4.1.1, 1.4.1.2, 1.4.1.3, 1.4.1.4, 1.4.1.5, 1.4.1.6, 1.4.1.7, 1.4.1.8, 1.4.1.9, 1.4.1.10, 1.4.2.1, 1.4.2.2, 1.4.2.3, 1.4.2.4, 1.4.2.5, 1.4.2.6, 1.4.2.7, 1.4.2.8, 1.4.2.9, 1.4.2.10, 1.4.3.1, 1.4.3.2, 1.4.3.3, 1.4.3.4, 1.4.3.5, 1.4.3.6, 1.4.3.7, 1.4.3.8, 1.4.3.9, 1.4.3.10, 1.4.4.1, 1.4.4.2, 1.4.4.3, 1.4.4.4, 1.4.4.5, 1.4.4.6, 1.4.4.7, 1.4.4.8, 1.4.4.9, 1.4.4.10, 1.4.5.1, 1.4.5.2, 1.4.5.3, 1.4.5.4, 1.4.5.5, 1.4.5.6, 1.4.5.7, 1.4.5.8, 1.4.5.9, 1.4.5.10, 1.4.6.1, 1.4.6.2, 1.4.6.3, 1.4.6.4, 1.4.6.5, 1.4.6.6, 1.4.6.7, 1.4.6.8, 1.4.6.9, 1.4.6.10, 1.4.7.1, 1.4.7.2, 1.4.7.3, 1.4.7.4, 1.4.7.5, 1.4.7.6, 1.4.7.7, 1.4.7.8, 1.4.7.9, 1.4.7.10, 1.4.8.1, 1.4.8.2, 1.4.8.3, 1.4.8.4, 1.4.8.5, 1.4.8.6, 1.4.8.7, 1.4.8.8, 1.4.8.9, 1.4.8.10, 1.4.9.1, 1.4.9.2, 1.4.9.3, 1.4.9.4, 1.4.9.5, 1.4.9.6, 1.4.9.7, 1.4.9.8, 1.4.9.9, 1.4.9.10, 1.4.10.1, 1.4.10.2, 1.4.10.3, 1.4.10.4, 1.4.10.5, 1.4.10.6, 1.4.10.7, 1.4.10.8, 1.4.10.9, 1.4.10.10, 1.5.1.1, 1.5.1.2, 1.5.1.3, 1.5.1.4, 1.5.1.5, 1.5.1.6, 1.5.1.7, 1.5.1.8, 1.5.1.9, 1.5.1.10, 1.5.2.1, 1.5.2.2, 1.5.2.3, 1.5.2.4, 1.5.2.5, 1.5.2.6, 1.5.2.7, 1.5.2.8, 1.5.2.9, 1.5.2.10, 1.5.3.1, 1.5.3.2, 1.5.3.3, 1.5.3.4, 1.5.3.5, 1.5.3.6, 1.5.3.7, 1.5.3.8, 1.5.3.9, 1.5.3.10, 1.5.4.1, 1.5.4.2, 1.5.4.3, 1.5.4.4, 1.5.4.5, 1.5.4.6, 1.5.4.7, 1.5.4.8, 1.5.4.9, 1.5.4.10, 1.5.5.1, 1.5.5.2, 1.5.5.3, 1.5.5.4, 1.5.5.5, 1.5.5.6, 1.5.5.7, 1.5.5.8, 1.5.5.9, 1.5.5.10, 1.5.6.1, 1.5.6.2, 1.5.6.3, 1.5.6.4, 1.5.6.5, 1.5.6.6, 1.5.6.7, 1.5.6.8, 1.5.6.9, 1.5.6.10, 1.5.7.1, 1.5.7.2, 1.5.7.3, 1.5.7.4, 1.5.7.5, 1.5.7.6, 1.5.7.7, 1.5.7.8, 1.5.7.9, 1.5.7.10, 1.5.8.1, 1.5.8.2, 1.5.8.3, 1.5.8.4, 1.5.8.5, 1.5.8.6, 1.5.8.7, 1.5.8.8, 1.5.8.9, 1.5.8.10, 1.5.9.1, 1.5.9.2, 1.5.9.3, 1.5.9.4,

TABLE B-continued 1.5.9.5, 1.5.9.6, 1.5.9.7, 1.5.9.8, 1.5.9.9, 1.5.9.10, 1.5.10.1, 1.5.10.2, 1.5.10.3, 1.5.10.4, 1.5.10.5, 1.5.10.6, 1.5.10.7, 1.5.10.8, 1.5.10.9, 1.5.10.10, 1.6.1.1, 1.6.1.2, 1.6.1.3, 1.6.1.4, 1.6.1.5, 1.6.1.6, 1.6.1.7, 1.6.1.8, 1.6.1.9, 1.6.1.10, 1.6.2.1, 1.6.2.2, 1.6.2.3, 1.6.2.4, 1.6.2.5, 1.6.2.6, 1.6.2.7, 1.6.2.8, 1.6.2.9, 1.6.2.10, 1.6.3.1, 1.6.3.2, 1.6.3.3, 1.6.3.4, 1.6.3.5, 1.6.3.6, 1.6.3.7, 1.6.3.8, 1.6.3.9, 1.6.3.10, 1.6.4.1, 1.6.4.2, 1.6.4.3, 1.6.4.4, 1.6.4.5, 1.6.4.6, 1.6.4.7, 1.6.4.8, 1.6.4.9, 1.6.4.10, 1.6.5.1, 1.6.5.2, 1.6.5.3, 1.6.5.4, 1.6.5.5, 1.6.5.6, 1.6.5.7, 1.6.5.8, 1.6.5.9, 1.6.5.10, 1.6.6.1, 1.6.6.2, 1.6.6.3, 1.6.6.4, 1.6.6.5, 1.6.6.6, 1.6.6.7, 1.6.6.8, 1.6.6.9, 1.6.6.10, 1.6.7.1, 1.6.7.2, 1.6.7.3, 1.6.7.4, 1.6.7.5, 1.6.7.6, 1.6.7.7, 1.6.7.8, 1.6.7.9, 1.6.7.10, 1.6.8.1, 1.6.8.2, 1.6.8.3, 1.6.8.4, 1.6.8.5, 1.6.8.6, 1.6.8.7, 1.6.8.8, 1.6.8.9, 1.6.8.10, 1.6.9.1, 1.6.9.2, 1.6.9.3, 1.6.9.4, 1.6.9.5, 1.6.9.6, 1.6.9.7, 1.6.9.8, 1.6.9.9, 1.6.9.10, 1.6.10.1, 1.6.10.2, 1.6.10.3, 1.6.10.4, 1.6.10.5, 1.6.10.6, 1.6.10.7, 1.6.10.8, 1.6.10.9, 1.6.10.10, 1.7.1.1, 1.7.1.2, 1.7.1.3, 1.7.1.4, 1.7.1.5, 1.7.1.6, 1.7.1.7, 1.7.1.8, 1.7.1.9, 1.7.1.10, 1.7.2.1, 1.7.2.2, 1.7.2.3, 1.7.2.4, 1.7.2.5, 1.7.2.6, 1.7.2.7, 1.7.2.8, 1.7.2.9, 1.7.2.10, 1.7.3.1, 1.7.3.2, 1.7.3.3, 1.7.3.4, 1.7.3.5, 1.7.3.6, 1.7.3.7, 1.7.3.8, 1.7.3.9, 1.7.3.10, 1.7.4.1, 1.7.4.2, 1.7.4.3, 1.7.4.4, 1.7.4.5, 1.7.4.6, 1.7.4.7, 1.7.4.8, 1.7.4.9, 1.7.4.10, 1.7.5.1, 1.7.5.2, 1.7.5.3, 1.7.5.4, 1.7.5.5, 1.7.5.6, 1.7.5.7, 1.7.5.8, 1.7.5.9, 1.7.5.10, 1.7.6.1, 1.7.6.2, 1.7.6.3, 1.7.6.4, 1.7.6.5, 1.7.6.6, 1.7.6.7, 1.7.6.8, 1.7.6.9, 1.7.6.10, 1.7.7.1, 1.7.7.2, 1.7.7.3, 1.7.7.4, 1.7.7.5, 1.7.7.6, 1.7.7.7, 1.7.7.8, 1.7.7.9, 1.7.7.10, 1.7.8.1, 1.7.8.2, 1.7.8.3, 1.7.8.4, 1.7.8.5, 1.7.8.6, 1.7.8.7, 1.7.8.8, 1.7.8.9, 1.7.8.10, 1.7.9.1, 1.7.9.2, 1.7.9.3, 1.7.9.4, 1.7.9.5, 1.7.9.6, 1.7.9.7, 1.7.9.8, 1.7.9.9, 1.7.9.10, 1.7.10.1, 1.7.10.2, 1.7.10.3, 1.7.10.4, 1.7.10.5, 1.7.10.6, 1.7.10.7, 1.7.10.8, 1.7.10.9, 1.7.10.10, 1.8.1.1, 1.8.1.2, 1.8.1.3, 1.8.1.4, 1.8.1.5, 1.8.1.6, 1.8.1.7, 1.8.1.8, 1.8.1.9, 1.8.1.10, 1.8.2.1, 1.8.2.2, 1.8.2.3, 1.8.2.4, 1.8.2.5, 1.8.2.6, 1.8.2.7, 1.8.2.8, 1.8.2.9, 1.8.2.10, 1.8.3.1, 1.8.3.2, 1.8.3.3, 1.8.3.4, 1.8.3.5, 1.8.3.6, 1.8.3.7, 1.8.3.8, 1.8.3.9, 1.8.3.10, 1.8.4.1, 1.8.4.2, 1.8.4.3, 1.8.4.4, 1.8.4.5, 1.8.4.6, 1.8.4.7, 1.8.4.8, 1.8.4.9, 1.8.4.10, 1.8.5.1, 1.8.5.2, 1.8.5.3, 1.8.5.4, 1.8.5.5, 1.8.5.6, 1.8.5.7, 1.8.5.8, 1.8.5.9, 1.8.5.10, 1.8.6.1, 1.8.6.2, 1.8.6.3, 1.8.6.4, 1.8.6.5, 1.8.6.6, 1.8.6.7, 1.8.6.8, 1.8.6.9, 1.8.6.10, 1.8.7.1, 1.8.7.2, 1.8.7.3, 1.8.7.4, 1.8.7.5, 1.8.7.6, 1.8.7.7, 1.8.7.8, 1.8.7.9, 1.8.7.10, 1.8.8.1, 1.8.8.2, 1.8.8.3, 1.8.8.4, 1.8.8.5, 1.8.8.6, 1.8.8.7, 1.8.8.8, 1.8.8.9, 1.8.8.10, 1.8.9.1, 1.8.9.2, 1.8.9.3, 1.8.9.4, 1.8.9.5, 1.8.9.6, 1.8.9.7, 1.8.9.8, 1.8.9.9, 1.8.9.10, 1.8.10.1, 1.8.10.2, 1.8.10.3, 1.8.10.4, 1.8.10.5, 1.8.10.6, 1.8.10.7, 1.8.10.8, 1.8.10.9, 1.8.10.10, 1.9.1.1, 1.9.1.2, 1.9.1.3, 1.9.1.4, 1.9.1.5, 1.9.1.6, 1.9.1.7, 1.9.1.8, 1.9.1.9, 1.9.1.10, 1.9.2.1, 1.9.2.2, 1.9.2.3, 1.9.2.4, 1.9.2.5, 1.9.2.6, 1.9.2.7, 1.9.2.8, 1.9.2.9, 1.9.2.10, 1.9.3.1, 1.9.3.2, 1.9.3.3, 1.9.3.4, 1.9.3.5, 1.9.3.6, 1.9.3.7, 1.9.3.8, 1.9.3.9, 1.9.3.10, 1.9.4.1, 1.9.4.2, 1.9.4.3, 1.9.4.4, 1.9.4.5, 1.9.4.6, 1.9.4.7, 1.9.4.8, 1.9.4.9, 1.9.4.10, 1.9.5.1, 1.9.5.2, 1.9.5.3, 1.9.5.4, 1.9.5.5, 1.9.5.6, 1.9.5.7, 1.9.5.8, 1.9.5.9, 1.9.5.10, 1.9.6.1, 1.9.6.2, 1.9.6.3, 1.9.6.4, 1.9.6.5, 1.9.6.6, 1.9.6.7, 1.9.6.8, 1.9.6.9, 1.9.6.10, 1.9.7.1, 1.9.7.2, 1.9.7.3, 1.9.7.4, 1.9.7.5, 1.9.7.6, 1.9.7.7, 1.9.7.8, 1.9.7.9, 1.9.7.10, 1.9.8.1, 1.9.8.2, 1.9.8.3, 1.9.8.4, 1.9.8.5, 1.9.8.6, 1.9.8.7, 1.9.8.8, 1.9.8.9, 1.9.8.10, 1.9.9.1, 1.9.9.2, 1.9.9.3, 1.9.9.4, 1.9.9.5, 1.9.9.6, 1.9.9.7, 1.9.9.8, 1.9.9.9, 1.9.9.10, 1.9.10.1, 1.9.10.2, 1.9.10.3, 1.9.10.4, 1.9.10.5, 1.9.10.6, 1.9.10.7, 1.9.10.8, 1.9.10.9, 1.9.10.10, 1.10.1.1, 1.10.1.2, 1.10.1.3, 1.10.1.4, 1.10.1.5, 1.10.1.6, 1.10.1.7, 1.10.1.8, 1.10.1.9, 1.10.1.10, 1.10.2.1, 1.10.2.2, 1.10.2.3, 1.10.2.4, 1.10.2.5, 1.10.2.6, 1.10.2.7, 1.10.2.8, 1.10.2.9, 1.10.2.10, 1.10.3.1, 1.10.3.2, 1.10.3.3, 1.10.3.4, 1.10.3.5, 1.10.3.6, 1.10.3.7, 1.10.3.8, 1.10.3.9, 1.10.3.10, 1.10.4.1, 1.10.4.2, 1.10.4.3, 1.10.4.4, 1.10.4.5, 1.10.4.6, 1.10.4.7, 1.10.4.8, 1.10.4.9, 1.10.4.10, 1.10.5.1, 1.10.5.2, 1.10.5.3, 1.10.5.4, 1.10.5.5, 1.10.5.6, 1.10.5.7, 1.10.5.8, 1.10.5.9, 1.10.5.10, 1.10.6.1, 1.10.6.2, 1.10.6.3, 1.10.6.4, 1.10.6.5, 1.10.6.6, 1.10.6.7, 1.10.6.8, 1.10.6.9, 1.10.6.10, 1.10.7.1, 1.10.7.2, 1.10.7.3, 1.10.7.4, 1.10.7.5, 1.10.7.6, 1.10.7.7, 1.10.7.8, 1.10.7.9, 1.10.7.10, 1.10.8.1, 1.10.8.2, 1.10.8.3, 1.10.8.4, 1.10.8.5, 1.10.8.6, 1.10.8.7, 1.10.8.8, 1.10.8.9, 1.10.8.10, 1.10.9.1, 1.10.9.2, 1.10.9.3, 1.10.9.4, 1.10.9.5, 1.10.9.6, 1.10.9.7, 1.10.9.8, 1.10.9.9, 1.10.9.10, 1.10.10.1, 1.10.10.2, 1.10.10.3, 1.10.10.4, 1.10.10.5, 1.10.10.6, 1.10.10.7, 1.10.10.8, 1.10.10.9, 1.10.10.10, 2.1.1.1, 2.1.1.2, 2.1.1.3, 2.1.1.4, 2.1.1.5, 2.1.1.6, 2.1.1.7, 2.1.1.8, 2.1.1.9, 2.1.1.10, 2.1.2.1, 2.1.2.2, 2.1.2.3, 2.1.2.4, 2.1.2.5, 2.1.2.6, 2.1.2.7, 2.1.2.8, 2.1.2.9, 2.1.2.10, 2.1.3.1, 2.1.3.2, 2.1.3.3, 2.1.3.4, 2.1.3.5, 2.1.3.6, 2.1.3.7, 2.1.3.8, 2.1.3.9, 2.1.3.10, 2.1.4.1, 2.1.4.2, 2.1.4.3, 2.1.4.4, 2.1.4.5, 2.1.4.6, 2.1.4.7, 2.1.4.8, 2.1.4.9, 2.1.4.10, 2.1.5.1, 2.1.5.2, 2.1.5.3, 2.1.5.4, 2.1.5.5, 2.1.5.6, 2.1.5.7, 2.1.5.8, 2.1.5.9, 2.1.5.10, 2.1.6.1, 2.1.6.2, 2.1.6.3, 2.1.6.4, 2.1.6.5, 2.1.6.6, 2.1.6.7, 2.1.6.8, 2.1.6.9, 2.1.6.10, 2.1.7.1, 2.1.7.2, 2.1.7.3, 2.1.7.4, 2.1.7.5, 2.1.7.6, 2.1.7.7, 2.1.7.8, 2.1.7.9, 2.1.7.10, 2.1.8.1, 2.1.8.2, 2.1.8.3, 2.1.8.4, 2.1.8.5, 2.1.8.6, 2.1.8.7, 2.1.8.8, 2.1.8.9, 2.1.8.10, 2.1.9.1, 2.1.9.2, 2.1.9.3, 2.1.9.4, 2.1.9.5, 2.1.9.6, 2.1.9.7, 2.1.9.8, 2.1.9.9, 2.1.9.10, 2.1.10.1, 2.1.10.2, 2.1.10.3, 2.1.10.4, 2.1.10.5, 2.1.10.6, 2.1.10.7, 2.1.10.8, 2.1.10.9, 2.1.10.10, 2.2.1.1, 2.2.1.2, 2.2.1.3, 2.2.1.4, 2.2.1.5, 2.2.1.6, 2.2.1.7, 2.2.1.8, 2.2.1.9, 2.2.1.10, 2.2.2.1, 2.2.2.2, 2.2.2.3, 2.2.2.4, 2.2.2.5, 2.2.2.6, 2.2.2.7, 2.2.2.8, 2.2.2.9, 2.2.2.10, 2.2.3.1, 2.2.3.2, 2.2.3.3, 2.2.3.4, 2.2.3.5, 2.2.3.6, 2.2.3.7, 2.2.3.8, 2.2.3.9, 2.2.3.10, 2.2.4.1, 2.2.4.2, 2.2.4.3, 2.2.4.4, 2.2.4.5, 2.2.4.6, 2.2.4.7, 2.2.4.8, 2.2.4.9, 2.2.4.10, 2.2.5.1, 2.2.5.2, 2.2.5.3, 2.2.5.4, 2.2.5.5, 2.2.5.6, 2.2.5.7, 2.2.5.8, 2.2.5.9, 2.2.5.10, 2.2.6.1, 2.2.6.2, 2.2.6.3, 2.2.6.4, 2.2.6.5, 2.2.6.6, 2.2.6.7, 2.2.6.8, 2.2.6.9, 2.2.6.10, 2.2.7.1, 2.2.7.2, 2.2.7.3, 2.2.7.4, 2.2.7.5, 2.2.7.6, 2.2.7.7, 2.2.7.8, 2.2.7.9, 2.2.7.10, 2.2.8.1, 2.2.8.2, 2.2.8.3, 2.2.8.4, 2.2.8.5, 2.2.8.6, 2.2.8.7, 2.2.8.8, 2.2.8.9, 2.2.8.10, 2.2.9.1, 2.2.9.2, 2.2.9.3, 2.2.9.4, 2.2.9.5, 2.2.9.6, 2.2.9.7, 2.2.9.8, 2.2.9.9, 2.2.9.10, 2.2.10.1, 2.2.10.2, 2.2.10.3, 2.2.10.4, 2.2.10.5, 2.2.10.6, 2.2.10.7, 2.2.10.8, 2.2.10.9, 2.2.10.10, 2.3.1.1, 2.3.1.2, 2.3.1.3, 2.3.1.4, 2.3.1.5, 2.3.1.6, 2.3.1.7, 2.3.1.8, 2.3.1.9, 2.3.1.10, 2.3.2.1, 2.3.2.2, 2.3.2.3, 2.3.2.4, 2.3.2.5, 2.3.2.6, 2.3.2.7, 2.3.2.8, 2.3.2.9, 2.3.2.10, 2.3.3.1, 2.3.3.2, 2.3.3.3, 2.3.3.4, 2.3.3.5, 2.3.3.6, 2.3.3.7, 2.3.3.8, 2.3.3.9, 2.3.3.10, 2.3.4.1, 2.3.4.2, 2.3.4.3, 2.3.4.4, 2.3.4.5, 2.3.4.6, 2.3.4.7, 2.3.4.8, 2.3.4.9, 2.3.4.10, 2.3.5.1, 2.3.5.2, 2.3.5.3, 2.3.5.4, 2.3.5.5, 2.3.5.6, 2.3.5.7, 2.3.5.8, 2.3.5.9, 2.3.5.10, 2.3.6.1, 2.3.6.2, 2.3.6.3, 2.3.6.4, 2.3.6.5, 2.3.6.6, 2.3.6.7, 2.3.6.8, 2.3.6.9, 2.3.6.10, 2.3.7.1, 2.3.7.2, 2.3.7.3, 2.3.7.4, 2.3.7.5, 2.3.7.6, 2.3.7.7, 2.3.7.8, 2.3.7.9, 2.3.7.10, 2.3.8.1, 2.3.8.2, 2.3.8.3, 2.3.8.4, 2.3.8.5, 2.3.8.6, 2.3.8.7, 2.3.8.8, 2.3.8.9, 2.3.8.10, 2.3.9.1, 2.3.9.2, 2.3.9.3, 2.3.9.4, 2.3.9.5, 2.3.9.6, 2.3.9.7, 2.3.9.8, 2.3.9.9, 2.3.9.10, 2.3.10.1, 2.3.10.2, 2.3.10.3, 2.3.10.4, 2.3.10.5, 2.3.10.6, 2.3.10.7, 2.3.10.8, 2.3.10.9, 2.3.10.10, 2.4.1.1, 2.4.1.2, 2.4.1.3, 2.4.1.4, 2.4.1.5, 2.4.1.6, 2.4.1.7, 2.4.1.8, 2.4.1.9, 2.4.1.10, 2.4.2.1, 2.4.2.2, 2.4.2.3, 2.4.2.4, 2.4.2.5, 2.4.2.6, 2.4.2.7, 2.4.2.8, 2.4.2.9, TABLE B-continued 2.4.2.10, 2.4.3.1, 2.4.3.2, 2.4.3.3, 2.4.3.4, 2.4.3.5, 2.4.3.6, 2.4.3.7, 2.4.3.8, 2.4.3.9, 2.4.3.10,
2.4.4.1, 2.4.4.2, 2.4.4.3, 2.4.4.4, 2.4.4.5, 2.4.4.6, 2.4.4.7, 2.4.4.8, 2.4.4.9, 2.4.4.10, 2.4.5.1,
2.4.5.2, 2.4.5.3, 2.4.5.4, 2.4.5.5, 2.4.5.6, 2.4.5.7, 2.4.5.8, 2.4.5.9, 2.4.5.10, 2.4.6.1, 2.4.6.2,
2.4.6.3, 2.4.6.4, 2.4.6.5, 2.4.6.6, 2.4.6.7, 2.4.6.8, 2.4.6.9, 2.4.6.10, 2.4.7.1, 2.4.7.2, 2.4.7.3,
2.4.7.4, 2.4.7.5, 2.4.7.6, 2.4.7.7, 2.4.7.8, 2.4.7.9, 2.4.7.10, 2.4.8.1, 2.4.8.2, 2.4.8.3, 2.4.8.4,
2.4.8.5, 2.4.8.6, 2.4.8.7, 2.4.8.8, 2.4.8.9, 2.4.8.10, 2.4.9.1, 2.4.9.2, 2.4.9.3, 2.4.9.4, 2.4.9.5,
2.4.9.6, 2.4.9.7, 2.4.9.8, 2.4.9.9, 2.4.9.10, 2.4.10.1, 2.4.10.2, 2.4.10.3, 2.4.10.4, 2.4.10.5,
2.4.10.6, 2.4.10.7, 2.4.10.8, 2.4.10.9, 2.4.10.10, 2.5.1.1, 2.5.1.2, 2.5.1.3, 2.5.1.4, 2.5.1.5,
2.5.1.6, 2.5.1.7, 2.5.1.8, 2.5.1.9, 2.5.1.10, 2.5.2.1, 2.5.2.2, 2.5.2.3, 2.5.2.4, 2.5.2.5, 2.5.2.6,
2.5.2.7, 2.5.2.8, 2.5.2.9, 2.5.2.10, 2.5.3.1, 2.5.3.2, 2.5.3.3, 2.5.3.4, 2.5.3.5, 2.5.3.6, 2.5.3.7,
2.5.3.8, 2.5.3.9, 2.5.3.10, 2.5.4.1, 2.5.4.2, 2.5.4.3, 2.5.4.4, 2.5.4.5, 2.5.4.6, 2.5.4.7, 2.5.4.8,
2.5.4.9, 2.5.4.10, 2.5.5.1, 2.5.5.2, 2.5.5.3, 2.5.5.4, 2.5.5.5, 2.5.5.6, 2.5.5.7, 2.5.5.8, 2.5.5.9,
2.5.5.10, 2.5.6.1, 2.5.6.2, 2.5.6.3, 2.5.6.4, 2.5.6.5, 2.5.6.6, 2.5.6.7, 2.5.6.8, 2.5.6.9, 2.5.6.10,
2.5.7.1, 2.5.7.2, 2.5.7.3, 2.5.7.4, 2.5.7.5, 2.5.7.6, 2.5.7.7, 2.5.7.8, 2.5.7.9, 2.5.7.10, 2.5.8.1,
2.5.8.2, 2.5.8.3, 2.5.8.4, 2.5.8.5, 2.5.8.6, 2.5.8.7, 2.5.8.8, 2.5.8.9, 2.5.8.10, 2.5.9.1, 2.5.9.2,
2.5.9.3, 2.5.9.4, 2.5.9.5, 2.5.9.6, 2.5.9.7, 2.5.9.8, 2.5.9.9, 2.5.9.10, 2.5.10.1, 2.5.10.2,
2.5.10.3, 2.5.10.4, 2.5.10.5, 2.5.10.6, 2.5.10.7, 2.5.10.8, 2.5.10.9, 2.5.10.10, 2.6.1.1,
2.6.1.2, 2.6.1.3, 2.6.1.4, 2.6.1.5, 2.6.1.6, 2.6.1.7, 2.6.1.8, 2.6.1.9, 2.6.1.10, 2.6.2.1, 2.6.2.2,
2.6.2.3, 2.6.2.4, 2.6.2.5, 2.6.2.6, 2.6.2.7, 2.6.2.8, 2.6.2.9, 2.6.2.10, 2.6.3.1, 2.6.3.2, 2.6.3.3,
2.6.3.4, 2.6.3.5, 2.6.3.6, 2.6.3.7, 2.6.3.8, 2.6.3.9, 2.6.3.10, 2.6.4.1, 2.6.4.2, 2.6.4.3, 2.6.4.4,
2.6.4.5, 2.6.4.6, 2.6.4.7, 2.6.4.8, 2.6.4.9, 2.6.4.10, 2.6.5.1, 2.6.5.2, 2.6.5.3, 2.6.5.4, 2.6.5.5,
2.6.5.6, 2.6.5.7, 2.6.5.8, 2.6.5.9, 2.6.5.10, 2.6.6.1, 2.6.6.2, 2.6.6.3, 2.6.6.4, 2.6.6.5, 2.6.6.6,
2.6.6.7, 2.6.6.8, 2.6.6.9, 2.6.6.10, 2.6.7.1, 2.6.7.2, 2.6.7.3, 2.6.7.4, 2.6.7.5, 2.6.7.6, 2.6.7.7,
2.6.7.8, 2.6.7.9, 2.6.7.10, 2.6.8.1, 2.6.8.2, 2.6.8.3, 2.6.8.4, 2.6.8.5, 2.6.8.6, 2.6.8.7, 2.6.8.8,
2.6.8.9, 2.6.8.10, 2.6.9.1, 2.6.9.2, 2.6.9.3, 2.6.9.4, 2.6.9.5, 2.6.9.6, 2.6.9.7, 2.6.9.8, 2.6.9.9,
2.6.9.10, 2.6.10.1, 2.6.10.2, 2.6.10.3, 2.6.10.4, 2.6.10.5, 2.6.10.6, 2.6.10.7, 2.6.10.8,
2.6.10.9, 2.6.10.10, 2.7.1.1, 2.7.1.2, 2.7.1.3, 2.7.1.4, 2.7.1.5, 2.7.1.6, 2.7.1.7, 2.7.1.8,
2.7.1.9, 2.7.1.10, 2.7.2.1, 2.7.2.2, 2.7.2.3, 2.7.2.4, 2.7.2.5, 2.7.2.6, 2.7.2.7, 2.7.2.8, 2.7.2.9,
2.7.2.10, 2.7.3.1, 2.7.3.2, 2.7.3.3, 2.7.3.4, 2.7.3.5, 2.7.3.6, 2.7.3.7, 2.7.3.8, 2.7.3.9, 2.7.3.10,
2.7.4.1, 2.7.4.2, 2.7.4.3, 2.7.4.4, 2.7.4.5, 2.7.4.6, 2.7.4.7, 2.7.4.8, 2.7.4.9, 2.7.4.10, 2.7.5.1,
2.7.5.2, 2.7.5.3, 2.7.5.4, 2.7.5.5, 2.7.5.6, 2.7.5.7, 2.7.5.8, 2.7.5.9, 2.7.5.10, 2.7.6.1, 2.7.6.2,
2.7.6.3, 2.7.6.4, 2.7.6.5, 2.7.6.6, 2.7.6.7, 2.7.6.8, 2.7.6.9, 2.7.6.10, 2.7.7.1, 2.7.7.2, 2.7.7.3,
2.7.7.4, 2.7.7.5, 2.7.7.6, 2.7.7.7, 2.7.7.8, 2.7.7.9, 2.7.7.10, 2.7.8.1, 2.7.8.2, 2.7.8.3, 2.7.8.4,
2.7.8.5, 2.7.8.6, 2.7.8.7, 2.7.8.8, 2.7.8.9, 2.7.8.10, 2.7.9.1, 2.7.9.2, 2.7.9.3, 2.7.9.4, 2.7.9.5,
2.7.9.6, 2.7.9.7, 2.7.9.8, 2.7.9.9, 2.7.9.10, 2.7.10.1, 2.7.10.2, 2.7.10.3, 2.7.10.4, 2.7.10.5,
2.7.10.6, 2.7.10.7, 2.7.10.8, 2.7.10.9, 2.7.10.10, 2.8.1.1, 2.8.1.2, 2.8.1.3, 2.8.1.4, 2.8.1.5,
2.8.1.6, 2.8.1.7, 2.8.1.8, 2.8.1.9, 2.8.1.10, 2.8.2.1, 2.8.2.2, 2.8.2.3, 2.8.2.4, 2.8.2.5, 2.8.2.6,
2.8.2.7, 2.8.2.8, 2.8.2.9, 2.8.2.10, 2.8.3.1, 2.8.3.2, 2.8.3.3, 2.8.3.4, 2.8.3.5, 2.8.3.6, 2.8.3.7,
2.8.3.8, 2.8.3.9, 2.8.3.10, 2.8.4.1, 2.8.4.2, 2.8.4.3, 2.8.4.4, 2.8.4.5, 2.8.4.6, 2.8.4.7, 2.8.4.8,
2.8.4.9, 2.8.4.10, 2.8.5.1, 2.8.5.2, 2.8.5.3, 2.8.5.4, 2.8.5.5, 2.8.5.6, 2.8.5.7, 2.8.5.8, 2.8.5.9,
2.8.5.10, 2.8.6.1, 2.8.6.2, 2.8.6.3, 2.8.6.4, 2.8.6.5, 2.8.6.6, 2.8.6.7, 2.8.6.8, 2.8.6.9, 2.8.6.10,
2.8.7.1, 2.8.7.2, 2.8.7.3, 2.8.7.4, 2.8.7.5, 2.8.7.6, 2.8.7.7, 2.8.7.8, 2.8.7.9, 2.8.7.10, 2.8.8.1,
2.8.8.2, 2.8.8.3, 2.8.8.4, 2.8.8.5, 2.8.8.6, 2.8.8.7, 2.8.8.8, 2.8.8.9, 2.8.8.10, 2.8.9.1, 2.8.9.2,
2.8.9.3, 2.8.9.4, 2.8.9.5, 2.8.9.6, 2.8.9.7, 2.8.9.8, 2.8.9.9, 2.8.9.10, 2.8.10.1, 2.8.10.2,
2.8.10.3, 2.8.10.4, 2.8.10.5, 2.8.10.6, 2.8.10.7, 2.8.10.8, 2.8.10.9, 2.8.10.10, 2.9.1.1,
2.9.1.2, 2.9.1.3, 2.9.1.4, 2.9.1.5, 2.9.1.6, 2.9.1.7, 2.9.1.8, 2.9.1.9, 2.9.1.10, 2.9.2.1, 2.9.2.2,
2.9.2.3, 2.9.2.4, 2.9.2.5, 2.9.2.6, 2.9.2.7, 2.9.2.8, 2.9.2.9, 2.9.2.10, 2.9.3.1, 2.9.3.2, 2.9.3.3,
2.9.3.4, 2.9.3.5, 2.9.3.6, 2.9.3.7, 2.9.3.8, 2.9.3.9, 2.9.3.10, 2.9.4.1, 2.9.4.2, 2.9.4.3, 2.9.4.4,
2.9.4.5, 2.9.4.6, 2.9.4.7, 2.9.4.8, 2.9.4.9, 2.9.4.10, 2.9.5.1, 2.9.5.2, 2.9.5.3, 2.9.5.4, 2.9.5.5,
2.9.5.6, 2.9.5.7, 2.9.5.8, 2.9.5.9, 2.9.5.10, 2.9.6.1, 2.9.6.2, 2.9.6.3, 2.9.6.4, 2.9.6.5, 2.9.6.6,
2.9.6.7, 2.9.6.8, 2.9.6.9, 2.9.6.10, 2.9.7.1, 2.9.7.2, 2.9.7.3, 2.9.7.4, 2.9.7.5, 2.9.7.6, 2.9.7.7,
2.9.7.8, 2.9.7.9, 2.9.7.10, 2.9.8.1, 2.9.8.2, 2.9.8.3, 2.9.8.4, 2.9.8.5, 2.9.8.6, 2.9.8.7, 2.9.8.8,
2.9.8.9, 2.9.8.10, 2.9.9.1, 2.9.9.2, 2.9.9.3, 2.9.9.4, 2.9.9.5, 2.9.9.6, 2.9.9.7, 2.9.9.8, 2.9.9.9,
2.9.9.10, 2.9.10.1, 2.9.10.2, 2.9.10.3, 2.9.10.4, 2.9.10.5, 2.9.10.6, 2.9.10.7, 2.9.10.8,
2.9.10.9, 2.9.10.10, 2.10.1.1, 2.10.1.2, 2.10.1.3, 2.10.1.4, 2.10.1.5, 2.10.1.6, 2.10.1.7,
2.10.1.8, 2.10.1.9, 2.10.1.10, 2.10.2.1, 2.10.2.2, 2.10.2.3, 2.10.2.4, 2.10.2.5, 2.10.2.6,
2.10.2.7, 2.10.2.8, 2.10.2.9, 2.10.2.10, 2.10.3.1, 2.10.3.2, 2.10.3.3, 2.10.3.4, 2.10.3.5,
2.10.3.6, 2.10.3.7, 2.10.3.8, 2.10.3.9, 2.10.3.10, 2.10.4.1, 2.10.4.2, 2.10.4.3, 2.10.4.4,
2.10.4.5, 2.10.4.6, 2.10.4.7, 2.10.4.8, 2.10.4.9, 2.10.4.10, 2.10.5.1, 2.10.5.2, 2.10.5.3,
2.10.5.4, 2.10.5.5, 2.10.5.6, 2.10.5.7, 2.10.5.8, 2.10.5.9, 2.10.5.10, 2.10.6.1, 2.10.6.2,
2.10.6.3, 2.10.6.4, 2.10.6.5, 2.10.6.6, 2.10.6.7, 2.10.6.8, 2.10.6.9, 2.10.6.10, 2.10.7.1,
2.10.7.2, 2.10.7.3, 2.10.7.4, 2.10.7.5, 2.10.7.6, 2.10.7.7, 2.10.7.8, 2.10.7.9, 2.10.7.10,
2.10.8.1, 2.10.8.2, 2.10.8.3, 2.10.8.4, 2.10.8.5, 2.10.8.6, 2.10.8.7, 2.10.8.8, 2.10.8.9,
2.10.8.10, 2.10.9.1, 2.10.9.2, 2.10.9.3, 2.10.9.4, 2.10.9.5, 2.10.9.6, 2.10.9.7, 2.10.9.8,
2.10.9.9, 2.10.9.10, 2.10.10.1, 2.10.10.2, 2.10.10.3, 2.10.10.4, 2.10.10.5, 2.10.10.6,
2.10.10.7, 2.10.10.8, 2.10.10.9, 2.10.10.10, 3.1.1.1, 3.1.1.2, 3.1.1.3, 3.1.1.4, 3.1.1.5,
3.1.1.6, 3.1.1.7, 3.1.1.8, 3.1.1.9, 3.1.1.10, 3.1.2.1, 3.1.2.2, 3.1.2.3, 3.1.2.4, 3.1.2.5, 3.1.2.6,
3.1.2.7, 3.1.2.8, 3.1.2.9, 3.1.2.10, 3.1.3.1, 3.1.3.2, 3.1.3.3, 3.1.3.4, 3.1.3.5, 3.1.3.6, 3.1.3.7,
3.1.3.8, 3.1.3.9, 3.1.3.10, 3.1.4.1, 3.1.4.2, 3.1.4.3, 3.1.4.4, 3.1.4.5, 3.1.4.6, 3.1.4.7, 3.1.4.8,
3.1.4.9, 3.1.4.10, 3.1.5.1, 3.1.5.2, 3.1.5.3, 3.1.5.4, 3.1.5.5, 3.1.5.6, 3.1.5.7, 3.1.5.8, 3.1.5.9,
3.1.5.10, 3.1.6.1, 3.1.6.2, 3.1.6.3, 3.1.6.4, 3.1.6.5, 3.1.6.6, 3.1.6.7, 3.1.6.8, 3.1.6.9, 3.1.6.10,
3.1.7.1, 3.1.7.2, 3.1.7.3, 3.1.7.4, 3.1.7.5, 3.1.7.6, 3.1.7.7, 3.1.7.8, 3.1.7.9, 3.1.7.10, 3.1.8.1,
3.1.8.2, 3.1.8.3, 3.1.8.4, 3.1.8.5, 3.1.8.6, 3.1.8.7, 3.1.8.8, 3.1.8.9, 3.1.8.10, 3.1.9.1, 3.1.9.2,
3.1.9.3, 3.1.9.4, 3.1.9.5, 3.1.9.6, 3.1.9.7, 3.1.9.8, 3.1.9.9, 3.1.9.10, 3.1.10.1, 3.1.10.2,
3.1.10.3, 3.1.10.4, 3.1.10.5, 3.1.10.6, 3.1.10.7, 3.1.10.8, 3.1.10.9, 3.1.10.10, 3.2.1.1,
3.2.1.2, 3.2.1.3, 3.2.1.4, 3.2.1.5, 3.2.1.6, 3.2.1.7, 3.2.1.8, 3.2.1.9, 3.2.1.10, 3.2.2.1, 3.2.2.2,
3.2.2.3, 3.2.2.4, 3.2.2.5, 3.2.2.6, 3.2.2.7, 3.2.2.8, 3.2.2.9, 3.2.2.10, 3.2.3.1, 3.2.3.2, 3.2.3.3,
3.2.3.4, 3.2.3.5, 3.2.3.6, 3.2.3.7, 3.2.3.8, 3.2.3.9, 3.2.3.10, 3.2.4.1, 3.2.4.2, 3.2.4.3, 3.2.4.4,
3.2.4.5, 3.2.4.6, 3.2.4.7, 3.2.4.8, 3.2.4.9, 3.2.4.10, 3.2.5.1, 3.2.5.2, 3.2.5.3, 3.2.5.4, 3.2.5.5,
3.2.5.6, 3.2.5.7, 3.2.5.8, 3.2.5.9, 3.2.5.10, 3.2.6.1, 3.2.6.2, 3.2.6.3, 3.2.6.4, 3.2.6.5, 3.2.6.6, TABLE B-continued 3.2.6.7, 3.2.6.8, 3.2.6.9, 3.2.6.10, 3.2.7.1, 3.2.7.2, 3.2.7.3, 3.2.7.4, 3.2.7.5, 3.2.7.6, 3.2.7.7,
3.2.7.8, 3.2.7.9, 3.2.7.10, 3.2.8.1, 3.2.8.2, 3.2.8.3, 3.2.8.4, 3.2.8.5, 3.2.8.6, 3.2.8.7, 3.2.8.8,
3.2.8.9, 3.2.8.10, 3.2.9.1, 3.2.9.2, 3.2.9.3, 3.2.9.4, 3.2.9.5, 3.2.9.6, 3.2.9.7, 3.2.9.8, 3.2.9.9,
3.2.9.10, 3.2.10.1, 3.2.10.2, 3.2.10.3, 3.2.10.4, 3.2.10.5, 3.2.10.6, 3.2.10.7, 3.2.10.8,
3.2.10.9, 3.2.10.10, 3.3.1.1, 3.3.1.2, 3.3.1.3, 3.3.1.4, 3.3.1.5, 3.3.1.6, 3.3.1.7, 3.3.1.8,
3.3.1.9, 3.3.1.10, 3.3.2.1, 3.3.2.2, 3.3.2.3, 3.3.2.4, 3.3.2.5, 3.3.2.6, 3.3.2.7, 3.3.2.8, 3.3.2.9,
3.3.2.10, 3.3.3.1, 3.3.3.2, 3.3.3.3, 3.3.3.4, 3.3.3.5, 3.3.3.6, 3.3.3.7, 3.3.3.8, 3.3.3.9, 3.3.3.10,
3.3.4.1, 3.3.4.2, 3.3.4.3, 3.3.4.4, 3.3.4.5, 3.3.4.6, 3.3.4.7, 3.3.4.8, 3.3.4.9, 3.3.4.10, 3.3.5.1,
3.3.5.2, 3.3.5.3, 3.3.5.4, 3.3.5.5, 3.3.5.6, 3.3.5.7, 3.3.5.8, 3.3.5.9, 3.3.5.10, 3.3.6.1, 3.3.6.2,
3.3.6.3, 3.3.6.4, 3.3.6.5, 3.3.6.6, 3.3.6.7, 3.3.6.8, 3.3.6.9, 3.3.6.10, 3.3.7.1, 3.3.7.2, 3.3.7.3,
3.3.7.4, 3.3.7.5, 3.3.7.6, 3.3.7.7, 3.3.7.8, 3.3.7.9, 3.3.7.10, 3.3.8.1, 3.3.8.2, 3.3.8.3, 3.3.8.4,
3.3.8.5, 3.3.8.6, 3.3.8.7, 3.3.8.8, 3.3.8.9, 3.3.8.10, 3.3.9.1, 3.3.9.2, 3.3.9.3, 3.3.9.4, 3.3.9.5,
3.3.9.6, 3.3.9.7, 3.3.9.8, 3.3.9.9, 3.3.9.10, 3.3.10.1, 3.3.10.2, 3.3.10.3, 3.3.10.4, 3.3.10.5,
3.3.10.6, 3.3.10.7, 3.3.10.8, 3.3.10.9, 3.3.10.10, 3.4.1.1, 3.4.1.2, 3.4.1.3, 3.4.1.4, 3.4.1.5,
3.4.1.6, 3.4.1.7, 3.4.1.8, 3.4.1.9, 3.4.1.10, 3.4.2.1, 3.4.2.2, 3.4.2.3, 3.4.2.4, 3.4.2.5, 3.4.2.6,
3.4.2.7, 3.4.2.8, 3.4.2.9, 3.4.2.10, 3.4.3.1, 3.4.3.2, 3.4.3.3, 3.4.3.4, 3.4.3.5, 3.4.3.6, 3.4.3.7,
3.4.3.8, 3.4.3.9, 3.4.3.10, 3.4.4.1, 3.4.4.2, 3.4.4.3, 3.4.4.4, 3.4.4.5, 3.4.4.6, 3.4.4.7, 3.4.4.8,
3.4.4.9, 3.4.4.10, 3.4.5.1, 3.4.5.2, 3.4.5.3, 3.4.5.4, 3.4.5.5, 3.4.5.6, 3.4.5.7, 3.4.5.8, 3.4.5.9,
3.4.5.10, 3.4.6.1, 3.4.6.2, 3.4.6.3, 3.4.6.4, 3.4.6.5, 3.4.6.6, 3.4.6.7, 3.4.6.8, 3.4.6.9, 3.4.6.10,
3.4.7.1, 3.4.7.2, 3.4.7.3, 3.4.7.4, 3.4.7.5, 3.4.7.6, 3.4.7.7, 3.4.7.8, 3.4.7.9, 3.4.7.10, 3.4.8.1,
3.4.8.2, 3.4.8.3, 3.4.8.4, 3.4.8.5, 3.4.8.6, 3.4.8.7, 3.4.8.8, 3.4.8.9, 3.4.8.10, 3.4.9.1, 3.4.9.2,
3.4.9.3, 3.4.9.4, 3.4.9.5, 3.4.9.6, 3.4.9.7, 3.4.9.8, 3.4.9.9, 3.4.9.10, 3.4.10.1, 3.4.10.2,
3.4.10.3, 3.4.10.4, 3.4.10.5, 3.4.10.6, 3.4.10.7, 3.4.10.8, 3.4.10.9, 3.4.10.10, 3.5.1.1,
3.5.1.2, 3.5.1.3, 3.5.1.4, 3.5.1.5, 3.5.1.6, 3.5.1.7, 3.5.1.8, 3.5.1.9, 3.5.1.10, 3.5.2.1, 3.5.2.2,
3.5.2.3, 3.5.2.4, 3.5.2.5, 3.5.2.6, 3.5.2.7, 3.5.2.8, 3.5.2.9, 3.5.2.10, 3.5.3.1, 3.5.3.2, 3.5.3.3,
3.5.3.4, 3.5.3.5, 3.5.3.6, 3.5.3.7, 3.5.3.8, 3.5.3.9, 3.5.3.10, 3.5.4.1, 3.5.4.2, 3.5.4.3, 3.5.4.4,
3.5.4.5, 3.5.4.6, 3.5.4.7, 3.5.4.8, 3.5.4.9, 3.5.4.10, 3.5.5.1, 3.5.5.2, 3.5.5.3, 3.5.5.4, 3.5.5.5,
3.5.5.6, 3.5.5.7, 3.5.5.8, 3.5.5.9, 3.5.5.10, 3.5.6.1, 3.5.6.2, 3.5.6.3, 3.5.6.4, 3.5.6.5, 3.5.6.6,
3.5.6.7, 3.5.6.8, 3.5.6.9, 3.5.6.10, 3.5.7.1, 3.5.7.2, 3.5.7.3, 3.5.7.4, 3.5.7.5, 3.5.7.6, 3.5.7.7,
3.5.7.8, 3.5.7.9, 3.5.7.10, 3.5.8.1, 3.5.8.2, 3.5.8.3, 3.5.8.4, 3.5.8.5, 3.5.8.6, 3.5.8.7, 3.5.8.8,
3.5.8.9, 3.5.8.10, 3.5.9.1, 3.5.9.2, 3.5.9.3, 3.5.9.4, 3.5.9.5, 3.5.9.6, 3.5.9.7, 3.5.9.8, 3.5.9.9,
3.5.9.10, 3.5.10.1, 3.5.10.2, 3.5.10.3, 3.5.10.4, 3.5.10.5, 3.5.10.6, 3.5.10.7, 3.5.10.8,
3.5.10.9, 3.5.10.10, 3.6.1.1, 3.6.1.2, 3.6.1.3, 3.6.1.4, 3.6.1.5, 3.6.1.6, 3.6.1.7, 3.6.1.8,
3.6.1.9, 3.6.1.10, 3.6.2.1, 3.6.2.2, 3.6.2.3, 3.6.2.4, 3.6.2.5, 3.6.2.6, 3.6.2.7, 3.6.2.8, 3.6.2.9,
3.6.2.10, 3.6.3.1, 3.6.3.2, 3.6.3.3, 3.6.3.4, 3.6.3.5, 3.6.3.6, 3.6.3.7, 3.6.3.8, 3.6.3.9, 3.6.3.10,
3.6.4.1, 3.6.4.2, 3.6.4.3, 3.6.4.4, 3.6.4.5, 3.6.4.6, 3.6.4.7, 3.6.4.8, 3.6.4.9, 3.6.4.10, 3.6.5.1,
3.6.5.2, 3.6.5.3, 3.6.5.4, 3.6.5.5, 3.6.5.6, 3.6.5.7, 3.6.5.8, 3.6.5.9, 3.6.5.10, 3.6.6.1, 3.6.6.2,
3.6.6.3, 3.6.6.4, 3.6.6.5, 3.6.6.6, 3.6.6.7, 3.6.6.8, 3.6.6.9, 3.6.6.10, 3.6.7.1, 3.6.7.2, 3.6.7.3,
3.6.7.4, 3.6.7.5, 3.6.7.6, 3.6.7.7, 3.6.7.8, 3.6.7.9, 3.6.7.10, 3.6.8.1, 3.6.8.2, 3.6.8.3, 3.6.8.4,
3.6.8.5, 3.6.8.6, 3.6.8.7, 3.6.8.8, 3.6.8.9, 3.6.8.10, 3.6.9.1, 3.6.9.2, 3.6.9.3, 3.6.9.4, 3.6.9.5,
3.6.9.6, 3.6.9.7, 3.6.9.8, 3.6.9.9, 3.6.9.10, 3.6.10.1, 3.6.10.2, 3.6.10.3, 3.6.10.4, 3.6.10.5,
3.6.10.6, 3.6.10.7, 3.6.10.8, 3.6.10.9, 3.6.10.10, 3.7.1.1, 3.7.1.2, 3.7.1.3, 3.7.1.4, 3.7.1.5,
3.7.1.6, 3.7.1.7, 3.7.1.8, 3.7.1.9, 3.7.1.10, 3.7.2.1, 3.7.2.2, 3.7.2.3, 3.7.2.4, 3.7.2.5, 3.7.2.6,
3.7.2.7, 3.7.2.8, 3.7.2.9, 3.7.2.10, 3.7.3.1, 3.7.3.2, 3.7.3.3, 3.7.3.4, 3.7.3.5, 3.7.3.6, 3.7.3.7,
3.7.3.8, 3.7.3.9, 3.7.3.10, 3.7.4.1, 3.7.4.2, 3.7.4.3, 3.7.4.4, 3.7.4.5, 3.7.4.6, 3.7.4.7, 3.7.4.8,
3.7.4.9, 3.7.4.10, 3.7.5.1, 3.7.5.2, 3.7.5.3, 3.7.5.4, 3.7.5.5, 3.7.5.6, 3.7.5.7, 3.7.5.8, 3.7.5.9,
3.7.5.10, 3.7.6.1, 3.7.6.2, 3.7.6.3, 3.7.6.4, 3.7.6.5, 3.7.6.6, 3.7.6.7, 3.7.6.8, 3.7.6.9, 3.7.6.10,
3.7.7.1, 3.7.7.2, 3.7.7.3, 3.7.7.4, 3.7.7.5, 3.7.7.6, 3.7.7.7, 3.7.7.8, 3.7.7.9, 3.7.7.10, 3.7.8.1,
3.7.8.2, 3.7.8.3, 3.7.8.4, 3.7.8.5, 3.7.8.6, 3.7.8.7, 3.7.8.8, 3.7.8.9, 3.7.8.10, 3.7.9.1, 3.7.9.2,
3.7.9.3, 3.7.9.4, 3.7.9.5, 3.7.9.6, 3.7.9.7, 3.7.9.8, 3.7.9.9, 3.7.9.10, 3.7.10.1, 3.7.10.2,
3.7.10.3, 3.7.10.4, 3.7.10.5, 3.7.10.6, 3.7.10.7, 3.7.10.8, 3.7.10.9, 3.7.10.10, 3.8.1.1,
3.8.1.2, 3.8.1.3, 3.8.1.4, 3.8.1.5, 3.8.1.6, 3.8.1.7, 3.8.1.8, 3.8.1.9, 3.8.1.10, 3.8.2.1, 3.8.2.2,
3.8.2.3, 3.8.2.4, 3.8.2.5, 3.8.2.6, 3.8.2.7, 3.8.2.8, 3.8.2.9, 3.8.2.10, 3.8.3.1, 3.8.3.2, 3.8.3.3,
3.8.3.4, 3.8.3.5, 3.8.3.6, 3.8.3.7, 3.8.3.8, 3.8.3.9, 3.8.3.10, 3.8.4.1, 3.8.4.2, 3.8.4.3, 3.8.4.4,
3.8.4.5, 3.8.4.6, 3.8.4.7, 3.8.4.8, 3.8.4.9, 3.8.4.10, 3.8.5.1, 3.8.5.2, 3.8.5.3, 3.8.5.4, 3.8.5.5,
3.8.5.6, 3.8.5.7, 3.8.5.8, 3.8.5.9, 3.8.5.10, 3.8.6.1, 3.8.6.2, 3.8.6.3, 3.8.6.4, 3.8.6.5, 3.8.6.6,
3.8.6.7, 3.8.6.8, 3.8.6.9, 3.8.6.10, 3.8.7.1, 3.8.7.2, 3.8.7.3, 3.8.7.4, 3.8.7.5, 3.8.7.6, 3.8.7.7,
3.8.7.8, 3.8.7.9, 3.8.7.10, 3.8.8.1, 3.8.8.2, 3.8.8.3, 3.8.8.4, 3.8.8.5, 3.8.8.6, 3.8.8.7, 3.8.8.8,
3.8.8.9, 3.8.8.10, 3.8.9.1, 3.8.9.2, 3.8.9.3, 3.8.9.4, 3.8.9.5, 3.8.9.6, 3.8.9.7, 3.8.9.8, 3.8.9.9,
3.8.9.10, 3.8.10.1, 3.8.10.2, 3.8.10.3, 3.8.10.4, 3.8.10.5, 3.8.10.6, 3.8.10.7, 3.8.10.8,
3.8.10.9, 3.8.10.10, 3.9.1.1, 3.9.1.2, 3.9.1.3, 3.9.1.4, 3.9.1.5, 3.9.1.6, 3.9.1.7, 3.9.1.8,
3.9.1.9, 3.9.1.10, 3.9.2.1, 3.9.2.2, 3.9.2.3, 3.9.2.4, 3.9.2.5, 3.9.2.6, 3.9.2.7, 3.9.2.8, 3.9.2.9,
3.9.2.10, 3.9.3.1, 3.9.3.2, 3.9.3.3, 3.9.3.4, 3.9.3.5, 3.9.3.6, 3.9.3.7, 3.9.3.8, 3.9.3.9, 3.9.3.10,
3.9.4.1, 3.9.4.2, 3.9.4.3, 3.9.4.4, 3.9.4.5, 3.9.4.6, 3.9.4.7, 3.9.4.8, 3.9.4.9, 3.9.4.10, 3.9.5.1,
3.9.5.2, 3.9.5.3, 3.9.5.4, 3.9.5.5, 3.9.5.6, 3.9.5.7, 3.9.5.8, 3.9.5.9, 3.9.5.10, 3.9.6.1, 3.9.6.2,
3.9.6.3, 3.9.6.4, 3.9.6.5, 3.9.6.6, 3.9.6.7, 3.9.6.8, 3.9.6.9, 3.9.6.10, 3.9.7.1, 3.9.7.2, 3.9.7.3,
3.9.7.4, 3.9.7.5, 3.9.7.6, 3.9.7.7, 3.9.7.8, 3.9.7.9, 3.9.7.10, 3.9.8.1, 3.9.8.2, 3.9.8.3, 3.9.8.4,
3.9.8.5, 3.9.8.6, 3.9.8.7, 3.9.8.8, 3.9.8.9, 3.9.8.10, 3.9.9.1, 3.9.9.2, 3.9.9.3, 3.9.9.4, 3.9.9.5,
3.9.9.6, 3.9.9.7, 3.9.9.8, 3.9.9.9, 3.9.9.10, 3.9.10.1, 3.9.10.2, 3.9.10.3, 3.9.10.4, 3.9.10.5,
3.9.10.6, 3.9.10.7, 3.9.10.8, 3.9.10.9, 3.9.10.10, 3.10.1.1, 3.10.1.2, 3.10.1.3, 3.10.1.4,
3.10.1.5, 3.10.1.6, 3.10.1.7, 3.10.1.8, 3.10.1.9, 3.10.1.10, 3.10.2.1, 3.10.2.2, 3.10.2.3,
3.10.2.4, 3.10.2.5, 3.10.2.6, 3.10.2.7, 3.10.2.8, 3.10.2.9, 3.10.2.10, 3.10.3.1, 3.10.3.2,
3.10.3.3, 3.10.3.4, 3.10.3.5, 3.10.3.6, 3.10.3.7, 3.10.3.8, 3.10.3.9, 3.10.3.10, 3.10.4.1,
3.10.4.2, 3.10.4.3, 3.10.4.4, 3.10.4.5, 3.10.4.6, 3.10.4.7, 3.10.4.8, 3.10.4.9, 3.10.4.10,
3.10.5.1, 3.10.5.2, 3.10.5.3, 3.10.5.4, 3.10.5.5, 3.10.5.6, 3.10.5.7, 3.10.5.8, 3.10.5.9,
3.10.5.10, 3.10.6.1, 3.10.6.2, 3.10.6.3, 3.10.6.4, 3.10.6.5, 3.10.6.6, 3.10.6.7, 3.10.6.8,
3.10.6.9, 3.10.6.10, 3.10.7.1, 3.10.7.2, 3.10.7.3, 3.10.7.4, 3.10.7.5, 3.10.7.6, 3.10.7.7,
3.10.7.8, 3.10.7.9, 3.10.7.10, 3.10.8.1, 3.10.8.2, 3.10.8.3, 3.10.8.4, 3.10.8.5, 3.10.8.6,
3.10.8.7, 3.10.8.8, 3.10.8.9, 3.10.8.10, 3.10.9.1, 3.10.9.2, 3.10.9.3, 3.10.9.4, 3.10.9.5,
3.10.9.6, 3.10.9.7, 3.10.9.8, 3.10.9.9, 3.10.9.10, 3.10.10.1, 3.10.10.2, 3.10.10.3, 3.10.10.4,

TABLE B-continued 3.10.10.5, 3.10.10.6, 3.10.10.7, 3.10.10.8, 3.10.10.9, 3.10.10.10, 4.1.1.1, 4.1.1.2, 4.1.1.3,
4.1.1.4, 4.1.1.5, 4.1.1.6, 4.1.1.7, 4.1.1.8, 4.1.1.9, 4.1.1.10, 4.1.2.1, 4.1.2.2, 4.1.2.3, 4.1.2.4,
4.1.2.5, 4.1.2.6, 4.1.2.7, 4.1.2.8, 4.1.2.9, 4.1.2.10, 4.1.3.1, 4.1.3.2, 4.1.3.3, 4.1.3.4, 4.1.3.5,
4.1.3.6, 4.1.3.7, 4.1.3.8, 4.1.3.9, 4.1.3.10, 4.1.4.1, 4.1.4.2, 4.1.4.3, 4.1.4.4, 4.1.4.5, 4.1.4.6,
4.1.4.7, 4.1.4.8, 4.1.4.9, 4.1.4.10, 4.1.5.1, 4.1.5.2, 4.1.5.3, 4.1.5.4, 4.1.5.5, 4.1.5.6, 4.1.5.7,
4.1.5.8, 4.1.5.9, 4.1.5.10, 4.1.6.1, 4.1.6.2, 4.1.6.3, 4.1.6.4, 4.1.6.5, 4.1.6.6, 4.1.6.7, 4.1.6.8,
4.1.6.9, 4.1.6.10, 4.1.7.1, 4.1.7.2, 4.1.7.3, 4.1.7.4, 4.1.7.5, 4.1.7.6, 4.1.7.7, 4.1.7.8, 4.1.7.9,
4.1.7.10, 4.1.8.1, 4.1.8.2, 4.1.8.3, 4.1.8.4, 4.1.8.5, 4.1.8.6, 4.1.8.7, 4.1.8.8, 4.1.8.9, 4.1.8.10,
4.1.9.1, 4.1.9.2, 4.1.9.3, 4.1.9.4, 4.1.9.5, 4.1.9.6, 4.1.9.7, 4.1.9.8, 4.1.9.9, 4.1.9.10, 4.1.10.1,
4.1.10.2, 4.1.10.3, 4.1.10.4, 4.1.10.5, 4.1.10.6, 4.1.10.7, 4.1.10.8, 4.1.10.9, 4.1.10.10,
4.2.1.1, 4.2.1.2, 4.2.1.3, 4.2.1.4, 4.2.1.5, 4.2.1.6, 4.2.1.7, 4.2.1.8, 4.2.1.9, 4.2.1.10, 4.2.2.1,
4.2.2.2, 4.2.2.3, 4.2.2.4, 4.2.2.5, 4.2.2.6, 4.2.2.7, 4.2.2.8, 4.2.2.9, 4.2.2.10, 4.2.3.1, 4.2.3.2,
4.2.3.3, 4.2.3.4, 4.2.3.5, 4.2.3.6, 4.2.3.7, 4.2.3.8, 4.2.3.9, 4.2.3.10, 4.2.4.1, 4.2.4.2, 4.2.4.3,
4.2.4.4, 4.2.4.5, 4.2.4.6, 4.2.4.7, 4.2.4.8, 4.2.4.9, 4.2.4.10, 4.2.5.1, 4.2.5.2, 4.2.5.3, 4.2.5.4,
4.2.5.5, 4.2.5.6, 4.2.5.7, 4.2.5.8, 4.2.5.9, 4.2.5.10, 4.2.6.1, 4.2.6.2, 4.2.6.3, 4.2.6.4, 4.2.6.5,
4.2.6.6, 4.2.6.7, 4.2.6.8, 4.2.6.9, 4.2.6.10, 4.2.7.1, 4.2.7.2, 4.2.7.3, 4.2.7.4, 4.2.7.5, 4.2.7.6,
4.2.7.7, 4.2.7.8, 4.2.7.9, 4.2.7.10, 4.2.8.1, 4.2.8.2, 4.2.8.3, 4.2.8.4, 4.2.8.5, 4.2.8.6, 4.2.8.7,
4.2.8.8, 4.2.8.9, 4.2.8.10, 4.2.9.1, 4.2.9.2, 4.2.9.3, 4.2.9.4, 4.2.9.5, 4.2.9.6, 4.2.9.7, 4.2.9.8,
4.2.9.9, 4.2.9.10, 4.2.10.1, 4.2.10.2, 4.2.10.3, 4.2.10.4, 4.2.10.5, 4.2.10.6, 4.2.10.7,
4.2.10.8, 4.2.10.9, 4.2.10.10, 4.3.1.1, 4.3.1.2, 4.3.1.3, 4.3.1.4, 4.3.1.5, 4.3.1.6, 4.3.1.7,
4.3.1.8, 4.3.1.9, 4.3.1.10, 4.3.2.1, 4.3.2.2, 4.3.2.3, 4.3.2.4, 4.3.2.5, 4.3.2.6, 4.3.2.7, 4.3.2.8,
4.3.2.9, 4.3.2.10, 4.3.3.1, 4.3.3.2, 4.3.3.3, 4.3.3.4, 4.3.3.5, 4.3.3.6, 4.3.3.7, 4.3.3.8, 4.3.3.9,
4.3.3.10, 4.3.4.1, 4.3.4.2, 4.3.4.3, 4.3.4.4, 4.3.4.5, 4.3.4.6, 4.3.4.7, 4.3.4.8, 4.3.4.9, 4.3.4.10,
4.3.5.1, 4.3.5.2, 4.3.5.3, 4.3.5.4, 4.3.5.5, 4.3.5.6, 4.3.5.7, 4.3.5.8, 4.3.5.9, 4.3.5.10, 4.3.6.1,
4.3.6.2, 4.3.6.3, 4.3.6.4, 4.3.6.5, 4.3.6.6, 4.3.6.7, 4.3.6.8, 4.3.6.9, 4.3.6.10, 4.3.7.1, 4.3.7.2,
4.3.7.3, 4.3.7.4, 4.3.7.5, 4.3.7.6, 4.3.7.7, 4.3.7.8, 4.3.7.9, 4.3.7.10, 4.3.8.1, 4.3.8.2, 4.3.8.3,
4.3.8.4, 4.3.8.5, 4.3.8.6, 4.3.8.7, 4.3.8.8, 4.3.8.9, 4.3.8.10, 4.3.9.1, 4.3.9.2, 4.3.9.3, 4.3.9.4,
4.3.9.5, 4.3.9.6, 4.3.9.7, 4.3.9.8, 4.3.9.9, 4.3.9.10, 4.3.10.1, 4.3.10.2, 4.3.10.3, 4.3.10.4,
4.3.10.5, 4.3.10.6, 4.3.10.7, 4.3.10.8, 4.3.10.9, 4.3.10.10, 4.4.1.1, 4.4.1.2, 4.4.1.3, 4.4.1.4,
4.4.1.5, 4.4.1.6, 4.4.1.7, 4.4.1.8, 4.4.1.9, 4.4.1.10, 4.4.2.1, 4.4.2.2, 4.4.2.3, 4.4.2.4, 4.4.2.5,
4.4.2.6, 4.4.2.7, 4.4.2.8, 4.4.2.9, 4.4.2.10, 4.4.3.1, 4.4.3.2, 4.4.3.3, 4.4.3.4, 4.4.3.5, 4.4.3.6,
4.4.3.7, 4.4.3.8, 4.4.3.9, 4.4.3.10, 4.4.4.1, 4.4.4.2, 4.4.4.3, 4.4.4.4, 4.4.4.5, 4.4.4.6, 4.4.4.7,
4.4.4.8, 4.4.4.9, 4.4.4.10, 4.4.5.1, 4.4.5.2, 4.4.5.3, 4.4.5.4, 4.4.5.5, 4.4.5.6, 4.4.5.7, 4.4.5.8,
4.4.5.9, 4.4.5.10, 4.4.6.1, 4.4.6.2, 4.4.6.3, 4.4.6.4, 4.4.6.5, 4.4.6.6, 4.4.6.7, 4.4.6.8, 4.4.6.9,
4.4.6.10, 4.4.7.1, 4.4.7.2, 4.4.7.3, 4.4.7.4, 4.4.7.5, 4.4.7.6, 4.4.7.7, 4.4.7.8, 4.4.7.9, 4.4.7.10,
4.4.8.1, 4.4.8.2, 4.4.8.3, 4.4.8.4, 4.4.8.5, 4.4.8.6, 4.4.8.7, 4.4.8.8, 4.4.8.9, 4.4.8.10, 4.4.9.1,
4.4.9.2, 4.4.9.3, 4.4.9.4, 4.4.9.5, 4.4.9.6, 4.4.9.7, 4.4.9.8, 4.4.9.9, 4.4.9.10, 4.4.10.1,
4.4.10.2, 4.4.10.3, 4.4.10.4, 4.4.10.5, 4.4.10.6, 4.4.10.7, 4.4.10.8, 4.4.10.9, 4.4.10.10,
4.5.1.1, 4.5.1.2, 4.5.1.3, 4.5.1.4, 4.5.1.5, 4.5.1.6, 4.5.1.7, 4.5.1.8, 4.5.1.9, 4.5.1.10, 4.5.2.1,
4.5.2.2, 4.5.2.3, 4.5.2.4, 4.5.2.5, 4.5.2.6, 4.5.2.7, 4.5.2.8, 4.5.2.9, 4.5.2.10, 4.5.3.1, 4.5.3.2,
4.5.3.3, 4.5.3.4, 4.5.3.5, 4.5.3.6, 4.5.3.7, 4.5.3.8, 4.5.3.9, 4.5.3.10, 4.5.4.1, 4.5.4.2, 4.5.4.3,
4.5.4.4, 4.5.4.5, 4.5.4.6, 4.5.4.7, 4.5.4.8, 4.5.4.9, 4.5.4.10, 4.5.5.1, 4.5.5.2, 4.5.5.3, 4.5.5.4,
4.5.5.5, 4.5.5.6, 4.5.5.7, 4.5.5.8, 4.5.5.9, 4.5.5.10, 4.5.6.1, 4.5.6.2, 4.5.6.3, 4.5.6.4, 4.5.6.5,
4.5.6.6, 4.5.6.7, 4.5.6.8, 4.5.6.9, 4.5.6.10, 4.5.7.1, 4.5.7.2, 4.5.7.3, 4.5.7.4, 4.5.7.5, 4.5.7.6,
4.5.7.7, 4.5.7.8, 4.5.7.9, 4.5.7.10, 4.5.8.1, 4.5.8.2, 4.5.8.3, 4.5.8.4, 4.5.8.5, 4.5.8.6, 4.5.8.7,
4.5.8.8, 4.5.8.9, 4.5.8.10, 4.5.9.1, 4.5.9.2, 4.5.9.3, 4.5.9.4, 4.5.9.5, 4.5.9.6, 4.5.9.7, 4.5.9.8,
4.5.9.9, 4.5.9.10, 4.5.10.1, 4.5.10.2, 4.5.10.3, 4.5.10.4, 4.5.10.5, 4.5.10.6, 4.5.10.7,
4.5.10.8, 4.5.10.9, 4.5.10.10, 4.6.1.1, 4.6.1.2, 4.6.1.3, 4.6.1.4, 4.6.1.5, 4.6.1.6, 4.6.1.7,
4.6.1.8, 4.6.1.9, 4.6.1.10, 4.6.2.1, 4.6.2.2, 4.6.2.3, 4.6.2.4, 4.6.2.5, 4.6.2.6, 4.6.2.7, 4.6.2.8,
4.6.2.9, 4.6.2.10, 4.6.3.1, 4.6.3.2, 4.6.3.3, 4.6.3.4, 4.6.3.5, 4.6.3.6, 4.6.3.7, 4.6.3.8, 4.6.3.9,
4.6.3.10, 4.6.4.1, 4.6.4.2, 4.6.4.3, 4.6.4.4, 4.6.4.5, 4.6.4.6, 4.6.4.7, 4.6.4.8, 4.6.4.9, 4.6.4.10,
4.6.5.1, 4.6.5.2, 4.6.5.3, 4.6.5.4, 4.6.5.5, 4.6.5.6, 4.6.5.7, 4.6.5.8, 4.6.5.9, 4.6.5.10, 4.6.6.1,
4.6.6.2, 4.6.6.3, 4.6.6.4, 4.6.6.5, 4.6.6.6, 4.6.6.7, 4.6.6.8, 4.6.6.9, 4.6.6.10, 4.6.7.1, 4.6.7.2,
4.6.7.3, 4.6.7.4, 4.6.7.5, 4.6.7.6, 4.6.7.7, 4.6.7.8, 4.6.7.9, 4.6.7.10, 4.6.8.1, 4.6.8.2, 4.6.8.3,
4.6.8.4, 4.6.8.5, 4.6.8.6, 4.6.8.7, 4.6.8.8, 4.6.8.9, 4.6.8.10, 4.6.9.1, 4.6.9.2, 4.6.9.3, 4.6.9.4,
4.6.9.5, 4.6.9.6, 4.6.9.7, 4.6.9.8, 4.6.9.9, 4.6.9.10, 4.6.10.1, 4.6.10.2, 4.6.10.3, 4.6.10.4,
4.6.10.5, 4.6.10.6, 4.6.10.7, 4.6.10.8, 4.6.10.9, 4.6.10.10, 4.7.1.1, 4.7.1.2, 4.7.1.3, 4.7.1.4,
4.7.1.5, 4.7.1.6, 4.7.1.7, 4.7.1.8, 4.7.1.9, 4.7.1.10, 4.7.2.1, 4.7.2.2, 4.7.2.3, 4.7.2.4, 4.7.2.5,
4.7.2.6, 4.7.2.7, 4.7.2.8, 4.7.2.9, 4.7.2.10, 4.7.3.1, 4.7.3.2, 4.7.3.3, 4.7.3.4, 4.7.3.5, 4.7.3.6,
4.7.3.7, 4.7.3.8, 4.7.3.9, 4.7.3.10, 4.7.4.1, 4.7.4.2, 4.7.4.3, 4.7.4.4, 4.7.4.5, 4.7.4.6, 4.7.4.7,
4.7.4.8, 4.7.4.9, 4.7.4.10, 4.7.5.1, 4.7.5.2, 4.7.5.3, 4.7.5.4, 4.7.5.5, 4.7.5.6, 4.7.5.7, 4.7.5.8,
4.7.5.9, 4.7.5.10, 4.7.6.1, 4.7.6.2, 4.7.6.3, 4.7.6.4, 4.7.6.5, 4.7.6.6, 4.7.6.7, 4.7.6.8, 4.7.6.9,
4.7.6.10, 4.7.7.1, 4.7.7.2, 4.7.7.3, 4.7.7.4, 4.7.7.5, 4.7.7.6, 4.7.7.7, 4.7.7.8, 4.7.7.9, 4.7.7.10,
4.7.8.1, 4.7.8.2, 4.7.8.3, 4.7.8.4, 4.7.8.5, 4.7.8.6, 4.7.8.7, 4.7.8.8, 4.7.8.9, 4.7.8.10, 4.7.9.1,
4.7.9.2, 4.7.9.3, 4.7.9.4, 4.7.9.5, 4.7.9.6, 4.7.9.7, 4.7.9.8, 4.7.9.9, 4.7.9.10, 4.7.10.1,
4.7.10.2, 4.7.10.3, 4.7.10.4, 4.7.10.5, 4.7.10.6, 4.7.10.7, 4.7.10.8, 4.7.10.9, 4.7.10.10,
4.8.1.1, 4.8.1.2, 4.8.1.3, 4.8.1.4, 4.8.1.5, 4.8.1.6, 4.8.1.7, 4.8.1.8, 4.8.1.9, 4.8.1.10, 4.8.2.1,
4.8.2.2, 4.8.2.3, 4.8.2.4, 4.8.2.5, 4.8.2.6, 4.8.2.7, 4.8.2.8, 4.8.2.9, 4.8.2.10, 4.8.3.1, 4.8.3.2,
4.8.3.3, 4.8.3.4, 4.8.3.5, 4.8.3.6, 4.8.3.7, 4.8.3.8, 4.8.3.9, 4.8.3.10, 4.8.4.1, 4.8.4.2, 4.8.4.3,
4.8.4.4, 4.8.4.5, 4.8.4.6, 4.8.4.7, 4.8.4.8, 4.8.4.9, 4.8.4.10, 4.8.5.1, 4.8.5.2, 4.8.5.3, 4.8.5.4,
4.8.5.5, 4.8.5.6, 4.8.5.7, 4.8.5.8, 4.8.5.9, 4.8.5.10, 4.8.6.1, 4.8.6.2, 4.8.6.3, 4.8.6.4, 4.8.6.5,
4.8.6.6, 4.8.6.7, 4.8.6.8, 4.8.6.9, 4.8.6.10, 4.8.7.1, 4.8.7.2, 4.8.7.3, 4.8.7.4, 4.8.7.5, 4.8.7.6,
4.8.7.7, 4.8.7.8, 4.8.7.9, 4.8.7.10, 4.8.8.1, 4.8.8.2, 4.8.8.3, 4.8.8.4, 4.8.8.5, 4.8.8.6, 4.8.8.7,
4.8.8.8, 4.8.8.9, 4.8.8.10, 4.8.9.1, 4.8.9.2, 4.8.9.3, 4.8.9.4, 4.8.9.5, 4.8.9.6, 4.8.9.7, 4.8.9.8,
4.8.9.9, 4.8.9.10, 4.8.10.1, 4.8.10.2, 4.8.10.3, 4.8.10.4, 4.8.10.5, 4.8.10.6, 4.8.10.7,
4.8.10.8, 4.8.10.9, 4.8.10.10, 4.9.1.1, 4.9.1.2, 4.9.1.3, 4.9.1.4, 4.9.1.5, 4.9.1.6, 4.9.1.7,
4.9.1.8, 4.9.1.9, 4.9.1.10, 4.9.2.1, 4.9.2.2, 4.9.2.3, 4.9.2.4, 4.9.2.5, 4.9.2.6, 4.9.2.7, 4.9.2.8,
4.9.2.9, 4.9.2.10, 4.9.3.1, 4.9.3.2, 4.9.3.3, 4.9.3.4, 4.9.3.5, 4.9.3.6, 4.9.3.7, 4.9.3.8, 4.9.3.9,
4.9.3.10, 4.9.4.1, 4.9.4.2, 4.9.4.3, 4.9.4.4, 4.9.4.5, 4.9.4.6, 4.9.4.7, 4.9.4.8, 4.9.4.9, 4.9.4.10,
4.9.5.1, 4.9.5.2, 4.9.5.3, 4.9.5.4, 4.9.5.5, 4.9.5.6, 4.9.5.7, 4.9.5.8, 4.9.5.9, 4.9.5.10, 4.9.6.1, TABLE B-continued 4.9.6.2, 4.9.6.3, 4.9.6.4, 4.9.6.5, 4.9.6.6, 4.9.6.7, 4.9.6.8, 4.9.6.9, 4.9.6.10, 4.9.7.1, 4.9.7.2, 4.9.7.3, 4.9.7.4, 4.9.7.5, 4.9.7.6, 4.9.7.7, 4.9.7.8, 4.9.7.9, 4.9.7.10, 4.9.8.1, 4.9.8.2, 4.9.8.3, 4.9.8.4, 4.9.8.5, 4.9.8.6, 4.9.8.7, 4.9.8.8, 4.9.8.9, 4.9.8.10, 4.9.9.1, 4.9.9.2, 4.9.9.3, 4.9.9.4, 4.9.9.5, 4.9.9.6, 4.9.9.7, 4.9.9.8, 4.9.9.9, 4.9.9.10, 4.9.10.1, 4.9.10.2, 4.9.10.3, 4.9.10.4, 4.9.10.5, 4.9.10.6, 4.9.10.7, 4.9.10.8, 4.9.10.9, 4.9.10.10, 4.10.1.1, 4.10.1.2, 4.10.1.3, 4.10.1.4, 4.10.1.5, 4.10.1.6, 4.10.1.7, 4.10.1.8, 4.10.1.9, 4.10.1.10, 4.10.2.1, 4.10.2.2, 4.10.2.3, 4.10.2.4, 4.10.2.5, 4.10.2.6, 4.10.2.7, 4.10.2.8, 4.10.2.9, 4.10.2.10, 4.10.3.1, 4.10.3.2, 4.10.3.3, 4.10.3.4, 4.10.3.5, 4.10.3.6, 4.10.3.7, 4.10.3.8, 4.10.3.9, 4.10.3.10, 4.10.4.1, 4.10.4.2, 4.10.4.3, 4.10.4.4, 4.10.4.5, 4.10.4.6, 4.10.4.7, 4.10.4.8, 4.10.4.9, 4.10.4.10, 4.10.5.1, 4.10.5.2, 4.10.5.3, 4.10.5.4, 4.10.5.5, 4.10.5.6, 4.10.5.7, 4.10.5.8, 4.10.5.9, 4.10.5.10, 4.10.6.1, 4.10.6.2, 4.10.6.3, 4.10.6.4, 4.10.6.5, 4.10.6.6, 4.10.6.7, 4.10.6.8, 4.10.6.9, 4.10.6.10, 4.10.7.1, 4.10.7.2, 4.10.7.3, 4.10.7.4, 4.10.7.5, 4.10.7.6, 4.10.7.7, 4.10.7.8, 4.10.7.9, 4.10.7.10, 4.10.8.1, 4.10.8.2, 4.10.8.3, 4.10.8.4, 4.10.8.5, 4.10.8.6, 4.10.8.7, 4.10.8.8, 4.10.8.9, 4.10.8.10, 4.10.9.1, 4.10.9.2, 4.10.9.3, 4.10.9.4, 4.10.9.5, 4.10.9.6, 4.10.9.7, 4.10.9.8, 4.10.9.9, 4.10.9.10, 4.10.10.1, 4.10.10.2, 4.10.10.3, 4.10.10.4, 4.10.10.5, 4.10.10.6, 4.10.10.7, 4.10.10.8, 4.10.10.9, 4.10.10.10, 5.1.1.1, 5.1.1.2, 5.1.1.3, 5.1.1.4, 5.1.1.5, 5.1.1.6, 5.1.1.7, 5.1.1.8, 5.1.1.9, 5.1.1.10, 5.1.2.1, 5.1.2.2, 5.1.2.3, 5.1.2.4, 5.1.2.5, 5.1.2.6, 5.1.2.7, 5.1.2.8, 5.1.2.9, 5.1.2.10, 5.1.3.1, 5.1.3.2, 5.1.3.3, 5.1.3.4, 5.1.3.5, 5.1.3.6, 5.1.3.7, 5.1.3.8, 5.1.3.9, 5.1.3.10, 5.1.4.1, 5.1.4.2, 5.1.4.3, 5.1.4.4, 5.1.4.5, 5.1.4.6, 5.1.4.7, 5.1.4.8, 5.1.4.9, 5.1.4.10, 5.1.5.1, 5.1.5.2, 5.1.5.3, 5.1.5.4, 5.1.5.5, 5.1.5.6, 5.1.5.7, 5.1.5.8, 5.1.5.9, 5.1.5.10, 5.1.6.1, 5.1.6.2, 5.1.6.3, 5.1.6.4, 5.1.6.5, 5.1.6.6, 5.1.6.7, 5.1.6.8, 5.1.6.9, 5.1.6.10, 5.1.7.1, 5.1.7.2, 5.1.7.3, 5.1.7.4, 5.1.7.5, 5.1.7.6, 5.1.7.7, 5.1.7.8, 5.1.7.9, 5.1.7.10, 5.1.8.1, 5.1.8.2, 5.1.8.3, 5.1.8.4, 5.1.8.5, 5.1.8.6, 5.1.8.7, 5.1.8.8, 5.1.8.9, 5.1.8.10, 5.1.9.1, 5.1.9.2, 5.1.9.3, 5.1.9.4, 5.1.9.5, 5.1.9.6, 5.1.9.7, 5.1.9.8, 5.1.9.9, 5.1.9.10, 5.1.10.1, 5.1.10.2, 5.1.10.3, 5.1.10.4, 5.1.10.5, 5.1.10.6, 5.1.10.7, 5.1.10.8, 5.1.10.9, 5.1.10.10, 5.2.1.1, 5.2.1.2, 5.2.1.3, 5.2.1.4, 5.2.1.5, 5.2.1.6, 5.2.1.7, 5.2.1.8, 5.2.1.9, 5.2.1.10, 5.2.2.1, 5.2.2.2, 5.2.2.3, 5.2.2.4, 5.2.2.5, 5.2.2.6, 5.2.2.7, 5.2.2.8, 5.2.2.9, 5.2.2.10, 5.2.3.1, 5.2.3.2, 5.2.3.3, 5.2.3.4, 5.2.3.5, 5.2.3.6, 5.2.3.7, 5.2.3.8, 5.2.3.9, 5.2.3.10, 5.2.4.1, 5.2.4.2, 5.2.4.3, 5.2.4.4, 5.2.4.5, 5.2.4.6, 5.2.4.7, 5.2.4.8, 5.2.4.9, 5.2.4.10, 5.2.5.1, 5.2.5.2, 5.2.5.3, 5.2.5.4, 5.2.5.5, 5.2.5.6, 5.2.5.7, 5.2.5.8, 5.2.5.9, 5.2.5.10, 5.2.6.1, 5.2.6.2, 5.2.6.3, 5.2.6.4, 5.2.6.5, 5.2.6.6, 5.2.6.7, 5.2.6.8, 5.2.6.9, 5.2.6.10, 5.2.7.1, 5.2.7.2, 5.2.7.3, 5.2.7.4, 5.2.7.5, 5.2.7.6, 5.2.7.7, 5.2.7.8, 5.2.7.9, 5.2.7.10, 5.2.8.1, 5.2.8.2, 5.2.8.3, 5.2.8.4, 5.2.8.5, 5.2.8.6, 5.2.8.7, 5.2.8.8, 5.2.8.9, 5.2.8.10, 5.2.9.1, 5.2.9.2, 5.2.9.3, 5.2.9.4, 5.2.9.5, 5.2.9.6, 5.2.9.7, 5.2.9.8, 5.2.9.9, 5.2.9.10, 5.2.10.1, 5.2.10.2, 5.2.10.3, 5.2.10.4, 5.2.10.5, 5.2.10.6, 5.2.10.7, 5.2.10.8, 5.2.10.9, 5.2.10.10, 5.3.1.1, 5.3.1.2, 5.3.1.3, 5.3.1.4, 5.3.1.5, 5.3.1.6, 5.3.1.7, 5.3.1.8, 5.3.1.9, 5.3.1.10, 5.3.2.1, 5.3.2.2, 5.3.2.3, 5.3.2.4, 5.3.2.5, 5.3.2.6, 5.3.2.7, 5.3.2.8, 5.3.2.9, 5.3.2.10, 5.3.3.1, 5.3.3.2, 5.3.3.3, 5.3.3.4, 5.3.3.5, 5.3.3.6, 5.3.3.7, 5.3.3.8, 5.3.3.9, 5.3.3.10, 5.3.4.1, 5.3.4.2, 5.3.4.3, 5.3.4.4, 5.3.4.5, 5.3.4.6, 5.3.4.7, 5.3.4.8, 5.3.4.9, 5.3.4.10, 5.3.5.1, 5.3.5.2, 5.3.5.3, 5.3.5.4, 5.3.5.5, 5.3.5.6, 5.3.5.7, 5.3.5.8, 5.3.5.9, 5.3.5.10, 5.3.6.1, 5.3.6.2, 5.3.6.3, 5.3.6.4, 5.3.6.5, 5.3.6.6, 5.3.6.7, 5.3.6.8, 5.3.6.9, 5.3.6.10, 5.3.7.1, 5.3.7.2, 5.3.7.3, 5.3.7.4, 5.3.7.5, 5.3.7.6, 5.3.7.7, 5.3.7.8, 5.3.7.9, 5.3.7.10, 5.3.8.1, 5.3.8.2, 5.3.8.3, 5.3.8.4, 5.3.8.5, 5.3.8.6, 5.3.8.7, 5.3.8.8, 5.3.8.9, 5.3.8.10, 5.3.9.1, 5.3.9.2, 5.3.9.3, 5.3.9.4, 5.3.9.5, 5.3.9.6, 5.3.9.7, 5.3.9.8, 5.3.9.9, 5.3.9.10, 5.3.10.1, 5.3.10.2, 5.3.10.3, 5.3.10.4, 5.3.10.5, 5.3.10.6, 5.3.10.7, 5.3.10.8, 5.3.10.9, 5.3.10.10, 5.4.1.1, 5.4.1.2, 5.4.1.3, 5.4.1.4, 5.4.1.5, 5.4.1.6, 5.4.1.7, 5.4.1.8, 5.4.1.9, 5.4.1.10, 5.4.2.1, 5.4.2.2, 5.4.2.3, 5.4.2.4, 5.4.2.5, 5.4.2.6, 5.4.2.7, 5.4.2.8, 5.4.2.9, 5.4.2.10, 5.4.3.1, 5.4.3.2, 5.4.3.3, 5.4.3.4, 5.4.3.5, 5.4.3.6, 5.4.3.7, 5.4.3.8, 5.4.3.9, 5.4.3.10, 5.4.4.1, 5.4.4.2, 5.4.4.3, 5.4.4.4, 5.4.4.5, 5.4.4.6, 5.4.4.7, 5.4.4.8, 5.4.4.9, 5.4.4.10, 5.4.5.1, 5.4.5.2, 5.4.5.3, 5.4.5.4, 5.4.5.5, 5.4.5.6, 5.4.5.7, 5.4.5.8, 5.4.5.9, 5.4.5.10, 5.4.6.1, 5.4.6.2, 5.4.6.3, 5.4.6.4, 5.4.6.5, 5.4.6.6, 5.4.6.7, 5.4.6.8, 5.4.6.9, 5.4.6.10, 5.4.7.1, 5.4.7.2, 5.4.7.3, 5.4.7.4, 5.4.7.5, 5.4.7.6, 5.4.7.7, 5.4.7.8, 5.4.7.9, 5.4.7.10, 5.4.8.1, 5.4.8.2, 5.4.8.3, 5.4.8.4, 5.4.8.5, 5.4.8.6, 5.4.8.7, 5.4.8.8, 5.4.8.9, 5.4.8.10, 5.4.9.1, 5.4.9.2, 5.4.9.3, 5.4.9.4, 5.4.9.5, 5.4.9.6, 5.4.9.7, 5.4.9.8, 5.4.9.9, 5.4.9.10, 5.4.10.1, 5.4.10.2, 5.4.10.3, 5.4.10.4, 5.4.10.5, 5.4.10.6, 5.4.10.7, 5.4.10.8, 5.4.10.9, 5.4.10.10, 5.5.1.1, 5.5.1.2, 5.5.1.3, 5.5.1.4, 5.5.1.5, 5.5.1.6, 5.5.1.7, 5.5.1.8, 5.5.1.9, 5.5.1.10, 5.5.2.1, 5.5.2.2, 5.5.2.3, 5.5.2.4, 5.5.2.5, 5.5.2.6, 5.5.2.7, 5.5.2.8, 5.5.2.9, 5.5.2.10, 5.5.3.1, 5.5.3.2, 5.5.3.3, 5.5.3.4, 5.5.3.5, 5.5.3.6, 5.5.3.7, 5.5.3.8, 5.5.3.9, 5.5.3.10, 5.5.4.1, 5.5.4.2, 5.5.4.3, 5.5.4.4, 5.5.4.5, 5.5.4.6, 5.5.4.7, 5.5.4.8, 5.5.4.9, 5.5.4.10, 5.5.5.1, 5.5.5.2, 5.5.5.3, 5.5.5.4, 5.5.5.5, 5.5.5.6, 5.5.5.7, 5.5.5.8, 5.5.5.9, 5.5.5.10, 5.5.6.1, 5.5.6.2, 5.5.6.3, 5.5.6.4, 5.5.6.5, 5.5.6.6, 5.5.6.7, 5.5.6.8, 5.5.6.9, 5.5.6.10, 5.5.7.1, 5.5.7.2, 5.5.7.3, 5.5.7.4, 5.5.7.5, 5.5.7.6, 5.5.7.7, 5.5.7.8, 5.5.7.9, 5.5.7.10, 5.5.8.1, 5.5.8.2, 5.5.8.3, 5.5.8.4, 5.5.8.5, 5.5.8.6, 5.5.8.7, 5.5.8.8, 5.5.8.9, 5.5.8.10, 5.5.9.1, 5.5.9.2, 5.5.9.3, 5.5.9.4, 5.5.9.5, 5.5.9.6, 5.5.9.7, 5.5.9.8, 5.5.9.9, 5.5.9.10, 5.5.10.1, 5.5.10.2, 5.5.10.3, 5.5.10.4, 5.5.10.5, 5.5.10.6, 5.5.10.7, 5.5.10.8, 5.5.10.9, 5.5.10.10, 5.6.1.1, 5.6.1.2, 5.6.1.3, 5.6.1.4, 5.6.1.5, 5.6.1.6, 5.6.1.7, 5.6.1.8, 5.6.1.9, 5.6.1.10, 5.6.2.1, 5.6.2.2, 5.6.2.3, 5.6.2.4, 5.6.2.5, 5.6.2.6, 5.6.2.7, 5.6.2.8, 5.6.2.9, 5.6.2.10, 5.6.3.1, 5.6.3.2, 5.6.3.3, 5.6.3.4, 5.6.3.5, 5.6.3.6, 5.6.3.7, 5.6.3.8, 5.6.3.9, 5.6.3.10, 5.6.4.1, 5.6.4.2, 5.6.4.3, 5.6.4.4, 5.6.4.5, 5.6.4.6, 5.6.4.7, 5.6.4.8, 5.6.4.9, 5.6.4.10, 5.6.5.1, 5.6.5.2, 5.6.5.3, 5.6.5.4, 5.6.5.5, 5.6.5.6, 5.6.5.7, 5.6.5.8, 5.6.5.9, 5.6.5.10, 5.6.6.1, 5.6.6.2, 5.6.6.3, 5.6.6.4, 5.6.6.5, 5.6.6.6, 5.6.6.7, 5.6.6.8, 5.6.6.9, 5.6.6.10, 5.6.7.1, 5.6.7.2, 5.6.7.3, 5.6.7.4, 5.6.7.5, 5.6.7.6, 5.6.7.7, 5.6.7.8, 5.6.7.9, 5.6.7.10, 5.6.8.1, 5.6.8.2, 5.6.8.3, 5.6.8.4, 5.6.8.5, 5.6.8.6, 5.6.8.7, 5.6.8.8, 5.6.8.9, 5.6.8.10, 5.6.9.1, 5.6.9.2, 5.6.9.3, 5.6.9.4, 5.6.9.5, 5.6.9.6, 5.6.9.7, 5.6.9.8, 5.6.9.9, 5.6.9.10, 5.6.10.1, 5.6.10.2, 5.6.10.3, 5.6.10.4, 5.6.10.5, 5.6.10.6, 5.6.10.7, 5.6.10.8, 5.6.10.9, 5.6.10.10, 5.7.1.1, 5.7.1.2, 5.7.1.3, 5.7.1.4, 5.7.1.5, 5.7.1.6, 5.7.1.7, 5.7.1.8, 5.7.1.9, 5.7.1.10, 5.7.2.1, 5.7.2.2, 5.7.2.3, 5.7.2.4, 5.7.2.5, 5.7.2.6, 5.7.2.7, 5.7.2.8, 5.7.2.9, 5.7.2.10, 5.7.3.1, 5.7.3.2, 5.7.3.3, 5.7.3.4, 5.7.3.5, 5.7.3.6, 5.7.3.7, 5.7.3.8, 5.7.3.9, 5.7.3.10, 5.7.4.1, 5.7.4.2, 5.7.4.3, 5.7.4.4, 5.7.4.5, 5.7.4.6, 5.7.4.7, 5.7.4.8, 5.7.4.9, 5.7.4.10, 5.7.5.1, 5.7.5.2, 5.7.5.3, 5.7.5.4, 5.7.5.5, 5.7.5.6, 5.7.5.7, 5.7.5.8, 5.7.5.9, 5.7.5.10, 5.7.6.1, 5.7.6.2, 5.7.6.3, 5.7.6.4, 5.7.6.5, 5.7.6.6, 5.7.6.7, 5.7.6.8, 5.7.6.9, 5.7.6.10, 5.7.7.1, 5.7.7.2, 5.7.7.3, 5.7.7.4, 5.7.7.5, 5.7.7.6, 5.7.7.7, 5.7.7.8, 5.7.7.9, 5.7.7.10, 5.7.8.1, 5.7.8.2, 5.7.8.3, 5.7.8.4, 5.7.8.5, 5.7.8.6, 5.7.8.7, 5.7.8.8, 5.7.8.9, 5.7.8.10, 5.7.9.1, 5.7.9.2, 5.7.9.3, 5.7.9.4, 5.7.9.5, 5.7.9.6, 5.7.9.7, 5.7.9.8, 5.7.9.9, 5.7.9.10, 5.7.10.1, TABLE B-continued 5.7.10.2, 5.7.10.3, 5.7.10.4, 5.7.10.5, 5.7.10.6, 5.7.10.7, 5.7.10.8, 5.7.10.9, 5.7.10.10,
5.8.1.1, 5.8.1.2, 5.8.1.3, 5.8.1.4, 5.8.1.5, 5.8.1.6, 5.8.1.7, 5.8.1.8, 5.8.1.9, 5.8.1.10, 5.8.2.1,
5.8.2.2, 5.8.2.3, 5.8.2.4, 5.8.2.5, 5.8.2.6, 5.8.2.7, 5.8.2.8, 5.8.2.9, 5.8.2.10, 5.8.3.1, 5.8.3.2,
5.8.3.3, 5.8.3.4, 5.8.3.5, 5.8.3.6, 5.8.3.7, 5.8.3.8, 5.8.3.9, 5.8.3.10, 5.8.4.1, 5.8.4.2, 5.8.4.3,
5.8.4.4, 5.8.4.5, 5.8.4.6, 5.8.4.7, 5.8.4.8, 5.8.4.9, 5.8.4.10, 5.8.5.1, 5.8.5.2, 5.8.5.3, 5.8.5.4,
5.8.5.5, 5.8.5.6, 5.8.5.7, 5.8.5.8, 5.8.5.9, 5.8.5.10, 5.8.6.1, 5.8.6.2, 5.8.6.3, 5.8.6.4, 5.8.6.5,
5.8.6.6, 5.8.6.7, 5.8.6.8, 5.8.6.9, 5.8.6.10, 5.8.7.1, 5.8.7.2, 5.8.7.3, 5.8.7.4, 5.8.7.5, 5.8.7.6,
5.8.7.7, 5.8.7.8, 5.8.7.9, 5.8.7.10, 5.8.8.1, 5.8.8.2, 5.8.8.3, 5.8.8.4, 5.8.8.5, 5.8.8.6, 5.8.8.7,
5.8.8.8, 5.8.8.9, 5.8.8.10, 5.8.9.1, 5.8.9.2, 5.8.9.3, 5.8.9.4, 5.8.9.5, 5.8.9.6, 5.8.9.7, 5.8.9.8,
5.8.9.9, 5.8.9.10, 5.8.10.1, 5.8.10.2, 5.8.10.3, 5.8.10.4, 5.8.10.5, 5.8.10.6, 5.8.10.7,
5.8.10.8, 5.8.10.9, 5.8.10.10, 5.9.1.1, 5.9.1.2, 5.9.1.3, 5.9.1.4, 5.9.1.5, 5.9.1.6, 5.9.1.7,
5.9.1.8, 5.9.1.9, 5.9.1.10, 5.9.2.1, 5.9.2.2, 5.9.2.3, 5.9.2.4, 5.9.2.5, 5.9.2.6, 5.9.2.7, 5.9.2.8,
5.9.2.9, 5.9.2.10, 5.9.3.1, 5.9.3.2, 5.9.3.3, 5.9.3.4, 5.9.3.5, 5.9.3.6, 5.9.3.7, 5.9.3.8, 5.9.3.9,
5.9.3.10, 5.9.4.1, 5.9.4.2, 5.9.4.3, 5.9.4.4, 5.9.4.5, 5.9.4.6, 5.9.4.7, 5.9.4.8, 5.9.4.9, 5.9.4.10,
5.9.5.1, 5.9.5.2, 5.9.5.3, 5.9.5.4, 5.9.5.5, 5.9.5.6, 5.9.5.7, 5.9.5.8, 5.9.5.9, 5.9.5.10, 5.9.6.1,
5.9.6.2, 5.9.6.3, 5.9.6.4, 5.9.6.5, 5.9.6.6, 5.9.6.7, 5.9.6.8, 5.9.6.9, 5.9.6.10, 5.9.7.1, 5.9.7.2,
5.9.7.3, 5.9.7.4, 5.9.7.5, 5.9.7.6, 5.9.7.7, 5.9.7.8, 5.9.7.9, 5.9.7.10, 5.9.8.1, 5.9.8.2, 5.9.8.3,
5.9.8.4, 5.9.8.5, 5.9.8.6, 5.9.8.7, 5.9.8.8, 5.9.8.9, 5.9.8.10, 5.9.9.1, 5.9.9.2, 5.9.9.3, 5.9.9.4,
5.9.9.5, 5.9.9.6, 5.9.9.7, 5.9.9.8, 5.9.9.9, 5.9.9.10, 5.9.10.1, 5.9.10.2, 5.9.10.3, 5.9.10.4,
5.9.10.5, 5.9.10.6, 5.9.10.7, 5.9.10.8, 5.9.10.9, 5.9.10.10, 5.10.1.1, 5.10.1.2, 5.10.1.3,
5.10.1.4, 5.10.1.5, 5.10.1.6, 5.10.1.7, 5.10.1.8, 5.10.1.9, 5.10.1.10, 5.10.2.1, 5.10.2.2,
5.10.2.3, 5.10.2.4, 5.10.2.5, 5.10.2.6, 5.10.2.7, 5.10.2.8, 5.10.2.9, 5.10.2.10, 5.10.3.1,
5.10.3.2, 5.10.3.3, 5.10.3.4, 5.10.3.5, 5.10.3.6, 5.10.3.7, 5.10.3.8, 5.10.3.9, 5.10.3.10,
5.10.4.1, 5.10.4.2, 5.10.4.3, 5.10.4.4, 5.10.4.5, 5.10.4.6, 5.10.4.7, 5.10.4.8, 5.10.4.9,
5.10.4.10, 5.10.5.1, 5.10.5.2, 5.10.5.3, 5.10.5.4, 5.10.5.5, 5.10.5.6, 5.10.5.7, 5.10.5.8,
5.10.5.9, 5.10.5.10, 5.10.6.1, 5.10.6.2, 5.10.6.3, 5.10.6.4, 5.10.6.5, 5.10.6.6, 5.10.6.7,
5.10.6.8, 5.10.6.9, 5.10.6.10, 5.10.7.1, 5.10.7.2, 5.10.7.3, 5.10.7.4, 5.10.7.5, 5.10.7.6,
5.10.7.7, 5.10.7.8, 5.10.7.9, 5.10.7.10, 5.10.8.1, 5.10.8.2, 5.10.8.3, 5.10.8.4, 5.10.8.5,
5.10.8.6, 5.10.8.7, 5.10.8.8, 5.10.8.9, 5.10.8.10, 5.10.9.1, 5.10.9.2, 5.10.9.3, 5.10.9.4,
5.10.9.5, 5.10.9.6, 5.10.9.7, 5.10.9.8, 5.10.9.9, 5.10.9.10, 5.10.10.1, 5.10.10.2, 5.10.10.3,
5.10.10.4, 5.10.10.5, 5.10.10.6, 5.10.10.7, 5.10.10.8, 5.10.10.9, 5.10.10.10, 6.1.1.1, 6.1.1.2,
6.1.1.3, 6.1.1.4, 6.1.1.5, 6.1.1.6, 6.1.1.7, 6.1.1.8, 6.1.1.9, 6.1.1.10, 6.1.2.1, 6.1.2.2, 6.1.2.3,
6.1.2.4, 6.1.2.5, 6.1.2.6, 6.1.2.7, 6.1.2.8, 6.1.2.9, 6.1.2.10, 6.1.3.1, 6.1.3.2, 6.1.3.3, 6.1.3.4,
6.1.3.5, 6.1.3.6, 6.1.3.7, 6.1.3.8, 6.1.3.9, 6.1.3.10, 6.1.4.1, 6.1.4.2, 6.1.4.3, 6.1.4.4, 6.1.4.5,
6.1.4.6, 6.1.4.7, 6.1.4.8, 6.1.4.9, 6.1.4.10, 6.1.5.1, 6.1.5.2, 6.1.5.3, 6.1.5.4, 6.1.5.5, 6.1.5.6,
6.1.5.7, 6.1.5.8, 6.1.5.9, 6.1.5.10, 6.1.6.1, 6.1.6.2, 6.1.6.3, 6.1.6.4, 6.1.6.5, 6.1.6.6, 6.1.6.7,
6.1.6.8, 6.1.6.9, 6.1.6.10, 6.1.7.1, 6.1.7.2, 6.1.7.3, 6.1.7.4, 6.1.7.5, 6.1.7.6, 6.1.7.7, 6.1.7.8,
6.1.7.9, 6.1.7.10, 6.1.8.1, 6.1.8.2, 6.1.8.3, 6.1.8.4, 6.1.8.5, 6.1.8.6, 6.1.8.7, 6.1.8.8, 6.1.8.9,
6.1.8.10, 6.1.9.1, 6.1.9.2, 6.1.9.3, 6.1.9.4, 6.1.9.5, 6.1.9.6, 6.1.9.7, 6.1.9.8, 6.1.9.9, 6.1.9.10,
6.1.10.1, 6.1.10.2, 6.1.10.3, 6.1.10.4, 6.1.10.5, 6.1.10.6, 6.1.10.7, 6.1.10.8, 6.1.10.9,
6.1.10.10, 6.2.1.1, 6.2.1.2, 6.2.1.3, 6.2.1.4, 6.2.1.5, 6.2.1.6, 6.2.1.7, 6.2.1.8, 6.2.1.9,
6.2.1.10, 6.2.2.1, 6.2.2.2, 6.2.2.3, 6.2.2.4, 6.2.2.5, 6.2.2.6, 6.2.2.7, 6.2.2.8, 6.2.2.9, 6.2.2.10,
6.2.3.1, 6.2.3.2, 6.2.3.3, 6.2.3.4, 6.2.3.5, 6.2.3.6, 6.2.3.7, 6.2.3.8, 6.2.3.9, 6.2.3.10, 6.2.4.1,
6.2.4.2, 6.2.4.3, 6.2.4.4, 6.2.4.5, 6.2.4.6, 6.2.4.7, 6.2.4.8, 6.2.4.9, 6.2.4.10, 6.2.5.1, 6.2.5.2,
6.2.5.3, 6.2.5.4, 6.2.5.5, 6.2.5.6, 6.2.5.7, 6.2.5.8, 6.2.5.9, 6.2.5.10, 6.2.6.1, 6.2.6.2, 6.2.6.3,
6.2.6.4, 6.2.6.5, 6.2.6.6, 6.2.6.7, 6.2.6.8, 6.2.6.9, 6.2.6.10, 6.2.7.1, 6.2.7.2, 6.2.7.3, 6.2.7.4,
6.2.7.5, 6.2.7.6, 6.2.7.7, 6.2.7.8, 6.2.7.9, 6.2.7.10, 6.2.8.1, 6.2.8.2, 6.2.8.3, 6.2.8.4, 6.2.8.5,
6.2.8.6, 6.2.8.7, 6.2.8.8, 6.2.8.9, 6.2.8.10, 6.2.9.1, 6.2.9.2, 6.2.9.3, 6.2.9.4, 6.2.9.5, 6.2.9.6,
6.2.9.7, 6.2.9.8, 6.2.9.9, 6.2.9.10, 6.2.10.1, 6.2.10.2, 6.2.10.3, 6.2.10.4, 6.2.10.5, 6.2.10.6,
6.2.10.7, 6.2.10.8, 6.2.10.9, 6.2.10.10, 6.3.1.1, 6.3.1.2, 6.3.1.3, 6.3.1.4, 6.3.1.5, 6.3.1.6,
6.3.1.7, 6.3.1.8, 6.3.1.9, 6.3.1.10, 6.3.2.1, 6.3.2.2, 6.3.2.3, 6.3.2.4, 6.3.2.5, 6.3.2.6, 6.3.2.7,
6.3.2.8, 6.3.2.9, 6.3.2.10, 6.3.3.1, 6.3.3.2, 6.3.3.3, 6.3.3.4, 6.3.3.5, 6.3.3.6, 6.3.3.7, 6.3.3.8,
6.3.3.9, 6.3.3.10, 6.3.4.1, 6.3.4.2, 6.3.4.3, 6.3.4.4, 6.3.4.5, 6.3.4.6, 6.3.4.7, 6.3.4.8, 6.3.4.9,
6.3.4.10, 6.3.5.1, 6.3.5.2, 6.3.5.3, 6.3.5.4, 6.3.5.5, 6.3.5.6, 6.3.5.7, 6.3.5.8, 6.3.5.9, 6.3.5.10,
6.3.6.1, 6.3.6.2, 6.3.6.3, 6.3.6.4, 6.3.6.5, 6.3.6.6, 6.3.6.7, 6.3.6.8, 6.3.6.9, 6.3.6.10, 6.3.7.1,
6.3.7.2, 6.3.7.3, 6.3.7.4, 6.3.7.5, 6.3.7.6, 6.3.7.7, 6.3.7.8, 6.3.7.9, 6.3.7.10, 6.3.8.1, 6.3.8.2,
6.3.8.3, 6.3.8.4, 6.3.8.5, 6.3.8.6, 6.3.8.7, 6.3.8.8, 6.3.8.9, 6.3.8.10, 6.3.9.1, 6.3.9.2, 6.3.9.3,
6.3.9.4, 6.3.9.5, 6.3.9.6, 6.3.9.7, 6.3.9.8, 6.3.9.9, 6.3.9.10, 6.3.10.1, 6.3.10.2, 6.3.10.3,
6.3.10.4, 6.3.10.5, 6.3.10.6, 6.3.10.7, 6.3.10.8, 6.3.10.9, 6.3.10.10, 6.4.1.1, 6.4.1.2, 6.4.1.3,
6.4.1.4, 6.4.1.5, 6.4.1.6, 6.4.1.7, 6.4.1.8, 6.4.1.9, 6.4.1.10, 6.4.2.1, 6.4.2.2, 6.4.2.3, 6.4.2.4,
6.4.2.5, 6.4.2.6, 6.4.2.7, 6.4.2.8, 6.4.2.9, 6.4.2.10, 6.4.3.1, 6.4.3.2, 6.4.3.3, 6.4.3.4, 6.4.3.5,
6.4.3.6, 6.4.3.7, 6.4.3.8, 6.4.3.9, 6.4.3.10, 6.4.4.1, 6.4.4.2, 6.4.4.3, 6.4.4.4, 6.4.4.5, 6.4.4.6,
6.4.4.7, 6.4.4.8, 6.4.4.9, 6.4.4.10, 6.4.5.1, 6.4.5.2, 6.4.5.3, 6.4.5.4, 6.4.5.5, 6.4.5.6, 6.4.5.7,
6.4.5.8, 6.4.5.9, 6.4.5.10, 6.4.6.1, 6.4.6.2, 6.4.6.3, 6.4.6.4, 6.4.6.5, 6.4.6.6, 6.4.6.7, 6.4.6.8,
6.4.6.9, 6.4.6.10, 6.4.7.1, 6.4.7.2, 6.4.7.3, 6.4.7.4, 6.4.7.5, 6.4.7.6, 6.4.7.7, 6.4.7.8, 6.4.7.9,
6.4.7.10, 6.4.8.1, 6.4.8.2, 6.4.8.3, 6.4.8.4, 6.4.8.5, 6.4.8.6, 6.4.8.7, 6.4.8.8, 6.4.8.9, 6.4.8.10,
6.4.9.1, 6.4.9.2, 6.4.9.3, 6.4.9.4, 6.4.9.5, 6.4.9.6, 6.4.9.7, 6.4.9.8, 6.4.9.9, 6.4.9.10, 6.4.10.1,
6.4.10.2, 6.4.10.3, 6.4.10.4, 6.4.10.5, 6.4.10.6, 6.4.10.7, 6.4.10.8, 6.4.10.9, 6.4.10.10,
6.5.1.1, 6.5.1.2, 6.5.1.3, 6.5.1.4, 6.5.1.5, 6.5.1.6, 6.5.1.7, 6.5.1.8, 6.5.1.9, 6.5.1.10, 6.5.2.1,
6.5.2.2, 6.5.2.3, 6.5.2.4, 6.5.2.5, 6.5.2.6, 6.5.2.7, 6.5.2.8, 6.5.2.9, 6.5.2.10, 6.5.3.1, 6.5.3.2,
6.5.3.3, 6.5.3.4, 6.5.3.5, 6.5.3.6, 6.5.3.7, 6.5.3.8, 6.5.3.9, 6.5.3.10, 6.5.4.1, 6.5.4.2, 6.5.4.3,
6.5.4.4, 6.5.4.5, 6.5.4.6, 6.5.4.7, 6.5.4.8, 6.5.4.9, 6.5.4.10, 6.5.5.1, 6.5.5.2, 6.5.5.3, 6.5.5.4,
6.5.5.5, 6.5.5.6, 6.5.5.7, 6.5.5.8, 6.5.5.9, 6.5.5.10, 6.5.6.1, 6.5.6.2, 6.5.6.3, 6.5.6.4, 6.5.6.5,
6.5.6.6, 6.5.6.7, 6.5.6.8, 6.5.6.9, 6.5.6.10, 6.5.7.1, 6.5.7.2, 6.5.7.3, 6.5.7.4, 6.5.7.5, 6.5.7.6,
6.5.7.7, 6.5.7.8, 6.5.7.9, 6.5.7.10, 6.5.8.1, 6.5.8.2, 6.5.8.3, 6.5.8.4, 6.5.8.5, 6.5.8.6, 6.5.8.7,
6.5.8.8, 6.5.8.9, 6.5.8.10, 6.5.9.1, 6.5.9.2, 6.5.9.3, 6.5.9.4, 6.5.9.5, 6.5.9.6, 6.5.9.7, 6.5.9.8,
6.5.9.9, 6.5.9.10, 6.5.10.1, 6.5.10.2, 6.5.10.3, 6.5.10.4, 6.5.10.5, 6.5.10.6, 6.5.10.7,
6.5.10.8, 6.5.10.9, 6.5.10.10, 6.6.1.1, 6.6.1.2, 6.6.1.3, 6.6.1.4, 6.6.1.5, 6.6.1.6, 6.6.1.7,
6.6.1.8, 6.6.1.9, 6.6.1.10, 6.6.2.1, 6.6.2.2, 6.6.2.3, 6.6.2.4, 6.6.2.5, 6.6.2.6, 6.6.2.7, 6.6.2.8,
6.6.2.9, 6.6.2.10, 6.6.3.1, 6.6.3.2, 6.6.3.3, 6.6.3.4, 6.6.3.5, 6.6.3.6, 6.6.3.7, 6.6.3.8, 6.6.3.9,

TABLE B-continued 6.6.3.10, 6.6.4.1, 6.6.4.2, 6.6.4.3, 6.6.4.4, 6.6.4.5, 6.6.4.6, 6.6.4.7, 6.6.4.8, 6.6.4.9, 6.6.4.10, 6.6.5.1, 6.6.5.2, 6.6.5.3, 6.6.5.4, 6.6.5.5, 6.6.5.6, 6.6.5.7, 6.6.5.8, 6.6.5.9, 6.6.5.10, 6.6.6.1, 6.6.6.2, 6.6.6.3, 6.6.6.4, 6.6.6.5, 6.6.6.6, 6.6.6.7, 6.6.6.8, 6.6.6.9, 6.6.6.10, 6.6.7.1, 6.6.7.2, 6.6.7.3, 6.6.7.4, 6.6.7.5, 6.6.7.6, 6.6.7.7, 6.6.7.8, 6.6.7.9, 6.6.7.10, 6.6.8.1, 6.6.8.2, 6.6.8.3, 6.6.8.4, 6.6.8.5, 6.6.8.6, 6.6.8.7, 6.6.8.8, 6.6.8.9, 6.6.8.10, 6.6.9.1, 6.6.9.2, 6.6.9.3, 6.6.9.4, 6.6.9.5, 6.6.9.6, 6.6.9.7, 6.6.9.8, 6.6.9.9, 6.6.9.10, 6.6.10.1, 6.6.10.2, 6.6.10.3, 6.6.10.4, 6.6.10.5, 6.6.10.6, 6.6.10.7, 6.6.10.8, 6.6.10.9, 6.6.10.10, 6.7.1.1, 6.7.1.2, 6.7.1.3, 6.7.1.4, 6.7.1.5, 6.7.1.6, 6.7.1.7, 6.7.1.8, 6.7.1.9, 6.7.1.10, 6.7.2.1, 6.7.2.2, 6.7.2.3, 6.7.2.4, 6.7.2.5, 6.7.2.6, 6.7.2.7, 6.7.2.8, 6.7.2.9, 6.7.2.10, 6.7.3.1, 6.7.3.2, 6.7.3.3, 6.7.3.4, 6.7.3.5, 6.7.3.6, 6.7.3.7, 6.7.3.8, 6.7.3.9, 6.7.3.10, 6.7.4.1, 6.7.4.2, 6.7.4.3, 6.7.4.4, 6.7.4.5, 6.7.4.6, 6.7.4.7, 6.7.4.8, 6.7.4.9, 6.7.4.10, 6.7.5.1, 6.7.5.2, 6.7.5.3, 6.7.5.4, 6.7.5.5, 6.7.5.6, 6.7.5.7, 6.7.5.8, 6.7.5.9, 6.7.5.10, 6.7.6.1, 6.7.6.2, 6.7.6.3, 6.7.6.4, 6.7.6.5, 6.7.6.6, 6.7.6.7, 6.7.6.8, 6.7.6.9, 6.7.6.10, 6.7.7.1, 6.7.7.2, 6.7.7.3, 6.7.7.4, 6.7.7.5, 6.7.7.6, 6.7.7.7, 6.7.7.8, 6.7.7.9, 6.7.7.10, 6.7.8.1, 6.7.8.2, 6.7.8.3, 6.7.8.4, 6.7.8.5, 6.7.8.6, 6.7.8.7, 6.7.8.8, 6.7.8.9, 6.7.8.10, 6.7.9.1, 6.7.9.2, 6.7.9.3, 6.7.9.4, 6.7.9.5, 6.7.9.6, 6.7.9.7, 6.7.9.8, 6.7.9.9, 6.7.9.10, 6.7.10.1, 6.7.10.2, 6.7.10.3, 6.7.10.4, 6.7.10.5, 6.7.10.6, 6.7.10.7, 6.7.10.8, 6.7.10.9, 6.7.10.10, 6.8.1.1, 6.8.1.2, 6.8.1.3, 6.8.1.4, 6.8.1.5, 6.8.1.6, 6.8.1.7, 6.8.1.8, 6.8.1.9, 6.8.1.10, 6.8.2.1, 6.8.2.2, 6.8.2.3, 6.8.2.4, 6.8.2.5, 6.8.2.6, 6.8.2.7, 6.8.2.8, 6.8.2.9, 6.8.2.10, 6.8.3.1, 6.8.3.2, 6.8.3.3, 6.8.3.4, 6.8.3.5, 6.8.3.6, 6.8.3.7, 6.8.3.8, 6.8.3.9, 6.8.3.10, 6.8.4.1, 6.8.4.2, 6.8.4.3, 6.8.4.4, 6.8.4.5, 6.8.4.6, 6.8.4.7, 6.8.4.8, 6.8.4.9, 6.8.4.10, 6.8.5.1, 6.8.5.2, 6.8.5.3, 6.8.5.4, 6.8.5.5, 6.8.5.6, 6.8.5.7, 6.8.5.8, 6.8.5.9, 6.8.5.10, 6.8.6.1, 6.8.6.2, 6.8.6.3, 6.8.6.4, 6.8.6.5, 6.8.6.6, 6.8.6.7, 6.8.6.8, 6.8.6.9, 6.8.6.10, 6.8.7.1, 6.8.7.2, 6.8.7.3, 6.8.7.4, 6.8.7.5, 6.8.7.6, 6.8.7.7, 6.8.7.8, 6.8.7.9, 6.8.7.10, 6.8.8.1, 6.8.8.2, 6.8.8.3, 6.8.8.4, 6.8.8.5, 6.8.8.6, 6.8.8.7, 6.8.8.8, 6.8.8.9, 6.8.8.10, 6.8.9.1, 6.8.9.2, 6.8.9.3, 6.8.9.4, 6.8.9.5, 6.8.9.6, 6.8.9.7, 6.8.9.8, 6.8.9.9, 6.8.9.10, 6.8.10.1, 6.8.10.2, 6.8.10.3, 6.8.10.4, 6.8.10.5, 6.8.10.6, 6.8.10.7, 6.8.10.8, 6.8.10.9, 6.8.10.10, 6.9.1.1, 6.9.1.2, 6.9.1.3, 6.9.1.4, 6.9.1.5, 6.9.1.6, 6.9.1.7, 6.9.1.8, 6.9.1.9, 6.9.1.10, 6.9.2.1, 6.9.2.2, 6.9.2.3, 6.9.2.4, 6.9.2.5, 6.9.2.6, 6.9.2.7, 6.9.2.8, 6.9.2.9, 6.9.2.10, 6.9.3.1, 6.9.3.2, 6.9.3.3, 6.9.3.4, 6.9.3.5, 6.9.3.6, 6.9.3.7, 6.9.3.8, 6.9.3.9, 6.9.3.10, 6.9.4.1, 6.9.4.2, 6.9.4.3, 6.9.4.4, 6.9.4.5, 6.9.4.6, 6.9.4.7, 6.9.4.8, 6.9.4.9, 6.9.4.10, 6.9.5.1, 6.9.5.2, 6.9.5.3, 6.9.5.4, 6.9.5.5, 6.9.5.6, 6.9.5.7, 6.9.5.8, 6.9.5.9, 6.9.5.10, 6.9.6.1, 6.9.6.2, 6.9.6.3, 6.9.6.4, 6.9.6.5, 6.9.6.6, 6.9.6.7, 6.9.6.8, 6.9.6.9, 6.9.6.10, 6.9.7.1, 6.9.7.2, 6.9.7.3, 6.9.7.4, 6.9.7.5, 6.9.7.6, 6.9.7.7, 6.9.7.8, 6.9.7.9, 6.9.7.10, 6.9.8.1, 6.9.8.2, 6.9.8.3, 6.9.8.4, 6.9.8.5, 6.9.8.6, 6.9.8.7, 6.9.8.8, 6.9.8.9, 6.9.8.10, 6.9.9.1, 6.9.9.2, 6.9.9.3, 6.9.9.4, 6.9.9.5, 6.9.9.6, 6.9.9.7, 6.9.9.8, 6.9.9.9, 6.9.9.10, 6.9.10.1, 6.9.10.2, 6.9.10.3, 6.9.10.4, 6.9.10.5, 6.9.10.6, 6.9.10.7, 6.9.10.8, 6.9.10.9, 6.9.10.10, 6.10.1.1, 6.10.1.2, 6.10.1.3, 6.10.1.4, 6.10.1.5, 6.10.1.6, 6.10.1.7, 6.10.1.8, 6.10.1.9, 6.10.1.10, 6.10.2.1, 6.10.2.2, 6.10.2.3, 6.10.2.4, 6.10.2.5, 6.10.2.6, 6.10.2.7, 6.10.2.8, 6.10.2.9, 6.10.2.10, 6.10.3.1, 6.10.3.2, 6.10.3.3, 6.10.3.4, 6.10.3.5, 6.10.3.6, 6.10.3.7, 6.10.3.8, 6.10.3.9, 6.10.3.10, 6.10.4.1, 6.10.4.2, 6.10.4.3, 6.10.4.4, 6.10.4.5, 6.10.4.6, 6.10.4.7, 6.10.4.8, 6.10.4.9, 6.10.4.10, 6.10.5.1, 6.10.5.2, 6.10.5.3, 6.10.5.4, 6.10.5.5, 6.10.5.6, 6.10.5.7, 6.10.5.8, 6.10.5.9, 6.10.5.10, 6.10.6.1, 6.10.6.2, 6.10.6.3, 6.10.6.4, 6.10.6.5, 6.10.6.6, 6.10.6.7, 6.10.6.8, 6.10.6.9, 6.10.6.10, 6.10.7.1, 6.10.7.2, 6.10.7.3, 6.10.7.4, 6.10.7.5, 6.10.7.6, 6.10.7.7, 6.10.7.8, 6.10.7.9, 6.10.7.10, 6.10.8.1, 6.10.8.2, 6.10.8.3, 6.10.8.4, 6.10.8.5, 6.10.8.6, 6.10.8.7, 6.10.8.8, 6.10.8.9, 6.10.8.10, 6.10.9.1, 6.10.9.2, 6.10.9.3, 6.10.9.4, 6.10.9.5, 6.10.9.6, 6.10.9.7, 6.10.9.8, 6.10.9.9, 6.10.9.10, 6.10.10.1, 6.10.10.2, 6.10.10.3, 6.10.10.4, 6.10.10.5, 6.10.10.6, 6.10.10.7, 6.10.10.8, 6.10.10.9, 6.10.10.10, 7.1.1.1, 7.1.1.2, 7.1.1.3, 7.1.1.4, 7.1.1.5, 7.1.1.6, 7.1.1.7, 7.1.1.8, 7.1.1.9, 7.1.1.10, 7.1.2.1, 7.1.2.2, 7.1.2.3, 7.1.2.4, 7.1.2.5, 7.1.2.6, 7.1.2.7, 7.1.2.8, 7.1.2.9, 7.1.2.10, 7.1.3.1, 7.1.3.2, 7.1.3.3, 7.1.3.4, 7.1.3.5, 7.1.3.6, 7.1.3.7, 7.1.3.8, 7.1.3.9, 7.1.3.10, 7.1.4.1, 7.1.4.2, 7.1.4.3, 7.1.4.4, 7.1.4.5, 7.1.4.6, 7.1.4.7, 7.1.4.8, 7.1.4.9, 7.1.4.10, 7.1.5.1, 7.1.5.2, 7.1.5.3, 7.1.5.4, 7.1.5.5, 7.1.5.6, 7.1.5.7, 7.1.5.8, 7.1.5.9, 7.1.5.10, 7.1.6.1, 7.1.6.2, 7.1.6.3, 7.1.6.4, 7.1.6.5, 7.1.6.6, 7.1.6.7, 7.1.6.8, 7.1.6.9, 7.1.6.10, 7.1.7.1, 7.1.7.2, 7.1.7.3, 7.1.7.4, 7.1.7.5, 7.1.7.6, 7.1.7.7, 7.1.7.8, 7.1.7.9, 7.1.7.10, 7.1.8.1, 7.1.8.2, 7.1.8.3, 7.1.8.4, 7.1.8.5, 7.1.8.6, 7.1.8.7, 7.1.8.8, 7.1.8.9, 7.1.8.10, 7.1.9.1, 7.1.9.2, 7.1.9.3, 7.1.9.4, 7.1.9.5, 7.1.9.6, 7.1.9.7, 7.1.9.8, 7.1.9.9, 7.1.9.10, 7.1.10.1, 7.1.10.2, 7.1.10.3, 7.1.10.4, 7.1.10.5, 7.1.10.6, 7.1.10.7, 7.1.10.8, 7.1.10.9, 7.1.10.10, 7.2.1.1, 7.2.1.2, 7.2.1.3, 7.2.1.4, 7.2.1.5, 7.2.1.6, 7.2.1.7, 7.2.1.8, 7.2.1.9, 7.2.1.10, 7.2.2.1, 7.2.2.2, 7.2.2.3, 7.2.2.4, 7.2.2.5, 7.2.2.6, 7.2.2.7, 7.2.2.8, 7.2.2.9, 7.2.2.10, 7.2.3.1, 7.2.3.2, 7.2.3.3, 7.2.3.4, 7.2.3.5, 7.2.3.6, 7.2.3.7, 7.2.3.8, 7.2.3.9, 7.2.3.10, 7.2.4.1, 7.2.4.2, 7.2.4.3, 7.2.4.4, 7.2.4.5, 7.2.4.6, 7.2.4.7, 7.2.4.8, 7.2.4.9, 7.2.4.10, 7.2.5.1, 7.2.5.2, 7.2.5.3, 7.2.5.4, 7.2.5.5, 7.2.5.6, 7.2.5.7, 7.2.5.8, 7.2.5.9, 7.2.5.10, 7.2.6.1, 7.2.6.2, 7.2.6.3, 7.2.6.4, 7.2.6.5, 7.2.6.6, 7.2.6.7, 7.2.6.8, 7.2.6.9, 7.2.6.10, 7.2.7.1, 7.2.7.2, 7.2.7.3, 7.2.7.4, 7.2.7.5, 7.2.7.6, 7.2.7.7, 7.2.7.8, 7.2.7.9, 7.2.7.10, 7.2.8.1, 7.2.8.2, 7.2.8.3, 7.2.8.4, 7.2.8.5, 7.2.8.6, 7.2.8.7, 7.2.8.8, 7.2.8.9, 7.2.8.10, 7.2.9.1, 7.2.9.2, 7.2.9.3, 7.2.9.4, 7.2.9.5, 7.2.9.6, 7.2.9.7, 7.2.9.8, 7.2.9.9, 7.2.9.10, 7.2.10.1, 7.2.10.2, 7.2.10.3, 7.2.10.4, 7.2.10.5, 7.2.10.6, 7.2.10.7, 7.2.10.8, 7.2.10.9, 7.2.10.10, 7.3.1.1, 7.3.1.2, 7.3.1.3, 7.3.1.4, 7.3.1.5, 7.3.1.6, 7.3.1.7, 7.3.1.8, 7.3.1.9, 7.3.1.10, 7.3.2.1, 7.3.2.2, 7.3.2.3, 7.3.2.4, 7.3.2.5, 7.3.2.6, 7.3.2.7, 7.3.2.8, 7.3.2.9, 7.3.2.10, 7.3.3.1, 7.3.3.2, 7.3.3.3, 7.3.3.4, 7.3.3.5, 7.3.3.6, 7.3.3.7, 7.3.3.8, 7.3.3.9, 7.3.3.10, 7.3.4.1, 7.3.4.2, 7.3.4.3, 7.3.4.4, 7.3.4.5, 7.3.4.6, 7.3.4.7, 7.3.4.8, 7.3.4.9, 7.3.4.10, 7.3.5.1, 7.3.5.2, 7.3.5.3, 7.3.5.4, 7.3.5.5, 7.3.5.6, 7.3.5.7, 7.3.5.8, 7.3.5.9, 7.3.5.10, 7.3.6.1, 7.3.6.2, 7.3.6.3, 7.3.6.4, 7.3.6.5, 7.3.6.6, 7.3.6.7, 7.3.6.8, 7.3.6.9, 7.3.6.10, 7.3.7.1, 7.3.7.2, 7.3.7.3, 7.3.7.4, 7.3.7.5, 7.3.7.6, 7.3.7.7, 7.3.7.8, 7.3.7.9, 7.3.7.10, 7.3.8.1, 7.3.8.2, 7.3.8.3, 7.3.8.4, 7.3.8.5, 7.3.8.6, 7.3.8.7, 7.3.8.8, 7.3.8.9, 7.3.8.10, 7.3.9.1, 7.3.9.2, 7.3.9.3, 7.3.9.4, 7.3.9.5, 7.3.9.6, 7.3.9.7, 7.3.9.8, 7.3.9.9, 7.3.9.10, 7.3.10.1, 7.3.10.2, 7.3.10.3, 7.3.10.4, 7.3.10.5, 7.3.10.6, 7.3.10.7, 7.3.10.8, 7.3.10.9, 7.3.10.10, 7.4.1.1, 7.4.1.2, 7.4.1.3, 7.4.1.4, 7.4.1.5, 7.4.1.6, 7.4.1.7, 7.4.1.8, 7.4.1.9, 7.4.1.10, 7.4.2.1, 7.4.2.2, 7.4.2.3, 7.4.2.4, 7.4.2.5, 7.4.2.6, 7.4.2.7, 7.4.2.8, 7.4.2.9, 7.4.2.10, 7.4.3.1, 7.4.3.2, 7.4.3.3, 7.4.3.4, 7.4.3.5, 7.4.3.6, 7.4.3.7, 7.4.3.8, 7.4.3.9, 7.4.3.10, 7.4.4.1, 7.4.4.2, 7.4.4.3, 7.4.4.4, 7.4.4.5, 7.4.4.6, 7.4.4.7, 7.4.4.8, 7.4.4.9, 7.4.4.10, 7.4.5.1, 7.4.5.2, 7.4.5.3, 7.4.5.4, 7.4.5.5, 7.4.5.6, 7.4.5.7, 7.4.5.8, 7.4.5.9, 7.4.5.10, 7.4.6.1, 7.4.6.2, 7.4.6.3, 7.4.6.4, 7.4.6.5, 7.4.6.6, 7.4.6.7, 7.4.6.8, 7.4.6.9, 7.4.6.10, 7.4.7.1, 7.4.7.2, 7.4.7.3, 7.4.7.4, 7.4.7.5, 7.4.7.6, 7.4.7.7, 7.4.7.8, 7.4.7.9,

TABLE B-continued 7.4.7.10, 7.4.8.1, 7.4.8.2, 7.4.8.3, 7.4.8.4, 7.4.8.5, 7.4.8.6, 7.4.8.7, 7.4.8.8, 7.4.8.9, 7.4.8.10, 7.4.9.1, 7.4.9.2, 7.4.9.3, 7.4.9.4, 7.4.9.5, 7.4.9.6, 7.4.9.7, 7.4.9.8, 7.4.9.9, 7.4.9.10, 7.4.10.1, 7.4.10.2, 7.4.10.3, 7.4.10.4, 7.4.10.5, 7.4.10.6, 7.4.10.7, 7.4.10.8, 7.4.10.9, 7.4.10.10, 7.5.1.1, 7.5.1.2, 7.5.1.3, 7.5.1.4, 7.5.1.5, 7.5.1.6, 7.5.1.7, 7.5.1.8, 7.5.1.9, 7.5.1.10, 7.5.2.1, 7.5.2.2, 7.5.2.3, 7.5.2.4, 7.5.2.5, 7.5.2.6, 7.5.2.7, 7.5.2.8, 7.5.2.9, 7.5.2.10, 7.5.3.1, 7.5.3.2, 7.5.3.3, 7.5.3.4, 7.5.3.5, 7.5.3.6, 7.5.3.7, 7.5.3.8, 7.5.3.9, 7.5.3.10, 7.5.4.1, 7.5.4.2, 7.5.4.3, 7.5.4.4, 7.5.4.5, 7.5.4.6, 7.5.4.7, 7.5.4.8, 7.5.4.9, 7.5.4.10, 7.5.5.1, 7.5.5.2, 7.5.5.3, 7.5.5.4, 7.5.5.5, 7.5.5.6, 7.5.5.7, 7.5.5.8, 7.5.5.9, 7.5.5.10, 7.5.6.1, 7.5.6.2, 7.5.6.3, 7.5.6.4, 7.5.6.5, 7.5.6.6, 7.5.6.7, 7.5.6.8, 7.5.6.9, 7.5.6.10, 7.5.7.1, 7.5.7.2, 7.5.7.3, 7.5.7.4, 7.5.7.5, 7.5.7.6, 7.5.7.7, 7.5.7.8, 7.5.7.9, 7.5.7.10, 7.5.8.1, 7.5.8.2, 7.5.8.3, 7.5.8.4, 7.5.8.5, 7.5.8.6, 7.5.8.7, 7.5.8.8, 7.5.8.9, 7.5.8.10, 7.5.9.1, 7.5.9.2, 7.5.9.3, 7.5.9.4, 7.5.9.5, 7.5.9.6, 7.5.9.7, 7.5.9.8, 7.5.9.9, 7.5.9.10, 7.5.10.1, 7.5.10.2, 7.5.10.3, 7.5.10.4, 7.5.10.5, 7.5.10.6, 7.5.10.7, 7.5.10.8, 7.5.10.9, 7.5.10.10, 7.6.1.1, 7.6.1.2, 7.6.1.3, 7.6.1.4, 7.6.1.5, 7.6.1.6, 7.6.1.7, 7.6.1.8, 7.6.1.9, 7.6.1.10, 7.6.2.1, 7.6.2.2, 7.6.2.3, 7.6.2.4, 7.6.2.5, 7.6.2.6, 7.6.2.7, 7.6.2.8, 7.6.2.9, 7.6.2.10, 7.6.3.1, 7.6.3.2, 7.6.3.3, 7.6.3.4, 7.6.3.5, 7.6.3.6, 7.6.3.7, 7.6.3.8, 7.6.3.9, 7.6.3.10, 7.6.4.1, 7.6.4.2, 7.6.4.3, 7.6.4.4, 7.6.4.5, 7.6.4.6, 7.6.4.7, 7.6.4.8, 7.6.4.9, 7.6.4.10, 7.6.5.1, 7.6.5.2, 7.6.5.3, 7.6.5.4, 7.6.5.5, 7.6.5.6, 7.6.5.7, 7.6.5.8, 7.6.5.9, 7.6.5.10, 7.6.6.1, 7.6.6.2, 7.6.6.3, 7.6.6.4, 7.6.6.5, 7.6.6.6, 7.6.6.7, 7.6.6.8, 7.6.6.9, 7.6.6.10, 7.6.7.1, 7.6.7.2, 7.6.7.3, 7.6.7.4, 7.6.7.5, 7.6.7.6, 7.6.7.7, 7.6.7.8, 7.6.7.9, 7.6.7.10, 7.6.8.1, 7.6.8.2, 7.6.8.3, 7.6.8.4, 7.6.8.5, 7.6.8.6, 7.6.8.7, 7.6.8.8, 7.6.8.9, 7.6.8.10, 7.6.9.1, 7.6.9.2, 7.6.9.3, 7.6.9.4, 7.6.9.5, 7.6.9.6, 7.6.9.7, 7.6.9.8, 7.6.9.9, 7.6.9.10, 7.6.10.1, 7.6.10.2, 7.6.10.3, 7.6.10.4, 7.6.10.5, 7.6.10.6, 7.6.10.7, 7.6.10.8, 7.6.10.9, 7.6.10.10, 7.7.1.1, 7.7.1.2, 7.7.1.3, 7.7.1.4, 7.7.1.5, 7.7.1.6, 7.7.1.7, 7.7.1.8, 7.7.1.9, 7.7.1.10, 7.7.2.1, 7.7.2.2, 7.7.2.3, 7.7.2.4, 7.7.2.5, 7.7.2.6, 7.7.2.7, 7.7.2.8, 7.7.2.9, 7.7.2.10, 7.7.3.1, 7.7.3.2, 7.7.3.3, 7.7.3.4, 7.7.3.5, 7.7.3.6, 7.7.3.7, 7.7.3.8, 7.7.3.9, 7.7.3.10, 7.7.4.1, 7.7.4.2, 7.7.4.3, 7.7.4.4, 7.7.4.5, 7.7.4.6, 7.7.4.7, 7.7.4.8, 7.7.4.9, 7.7.4.10, 7.7.5.1, 7.7.5.2, 7.7.5.3, 7.7.5.4, 7.7.5.5, 7.7.5.6, 7.7.5.7, 7.7.5.8, 7.7.5.9, 7.7.5.10, 7.7.6.1, 7.7.6.2, 7.7.6.3, 7.7.6.4, 7.7.6.5, 7.7.6.6, 7.7.6.7, 7.7.6.8, 7.7.6.9, 7.7.6.10, 7.7.7.1, 7.7.7.2, 7.7.7.3, 7.7.7.4, 7.7.7.5, 7.7.7.6, 7.7.7.7, 7.7.7.8, 7.7.7.9, 7.7.7.10, 7.7.8.1, 7.7.8.2, 7.7.8.3, 7.7.8.4, 7.7.8.5, 7.7.8.6, 7.7.8.7, 7.7.8.8, 7.7.8.9, 7.7.8.10, 7.7.9.1, 7.7.9.2, 7.7.9.3, 7.7.9.4, 7.7.9.5, 7.7.9.6, 7.7.9.7, 7.7.9.8, 7.7.9.9, 7.7.9.10, 7.7.10.1, 7.7.10.2, 7.7.10.3, 7.7.10.4, 7.7.10.5, 7.7.10.6, 7.7.10.7, 7.7.10.8, 7.7.10.9, 7.7.10.10, 7.8.1.1, 7.8.1.2, 7.8.1.3, 7.8.1.4, 7.8.1.5, 7.8.1.6, 7.8.1.7, 7.8.1.8, 7.8.1.9, 7.8.1.10, 7.8.2.1, 7.8.2.2, 7.8.2.3, 7.8.2.4, 7.8.2.5, 7.8.2.6, 7.8.2.7, 7.8.2.8, 7.8.2.9, 7.8.2.10, 7.8.3.1, 7.8.3.2, 7.8.3.3, 7.8.3.4, 7.8.3.5, 7.8.3.6, 7.8.3.7, 7.8.3.8, 7.8.3.9, 7.8.3.10, 7.8.4.1, 7.8.4.2, 7.8.4.3, 7.8.4.4, 7.8.4.5, 7.8.4.6, 7.8.4.7, 7.8.4.8, 7.8.4.9, 7.8.4.10, 7.8.5.1, 7.8.5.2, 7.8.5.3, 7.8.5.4, 7.8.5.5, 7.8.5.6, 7.8.5.7, 7.8.5.8, 7.8.5.9, 7.8.5.10, 7.8.6.1, 7.8.6.2, 7.8.6.3, 7.8.6.4, 7.8.6.5, 7.8.6.6, 7.8.6.7, 7.8.6.8, 7.8.6.9, 7.8.6.10, 7.8.7.1, 7.8.7.2, 7.8.7.3, 7.8.7.4, 7.8.7.5, 7.8.7.6, 7.8.7.7, 7.8.7.8, 7.8.7.9, 7.8.7.10, 7.8.8.1, 7.8.8.2, 7.8.8.3, 7.8.8.4, 7.8.8.5, 7.8.8.6, 7.8.8.7, 7.8.8.8, 7.8.8.9, 7.8.8.10, 7.8.9.1, 7.8.9.2, 7.8.9.3, 7.8.9.4, 7.8.9.5, 7.8.9.6, 7.8.9.7, 7.8.9.8, 7.8.9.9, 7.8.9.10, 7.8.10.1, 7.8.10.2, 7.8.10.3, 7.8.10.4, 7.8.10.5, 7.8.10.6, 7.8.10.7, 7.8.10.8, 7.8.10.9, 7.8.10.10, 7.9.1.1, 7.9.1.2, 7.9.1.3, 7.9.1.4, 7.9.1.5, 7.9.1.6, 7.9.1.7, 7.9.1.8, 7.9.1.9, 7.9.1.10, 7.9.2.1, 7.9.2.2, 7.9.2.3, 7.9.2.4, 7.9.2.5, 7.9.2.6, 7.9.2.7, 7.9.2.8, 7.9.2.9, 7.9.2.10, 7.9.3.1, 7.9.3.2, 7.9.3.3, 7.9.3.4, 7.9.3.5, 7.9.3.6, 7.9.3.7, 7.9.3.8, 7.9.3.9, 7.9.3.10, 7.9.4.1, 7.9.4.2, 7.9.4.3, 7.9.4.4, 7.9.4.5, 7.9.4.6, 7.9.4.7, 7.9.4.8, 7.9.4.9, 7.9.4.10, 7.9.5.1, 7.9.5.2, 7.9.5.3, 7.9.5.4, 7.9.5.5, 7.9.5.6, 7.9.5.7, 7.9.5.8, 7.9.5.9, 7.9.5.10, 7.9.6.1, 7.9.6.2, 7.9.6.3, 7.9.6.4, 7.9.6.5, 7.9.6.6, 7.9.6.7, 7.9.6.8, 7.9.6.9, 7.9.6.10, 7.9.7.1, 7.9.7.2, 7.9.7.3, 7.9.7.4, 7.9.7.5, 7.9.7.6, 7.9.7.7, 7.9.7.8, 7.9.7.9, 7.9.7.10, 7.9.8.1, 7.9.8.2, 7.9.8.3, 7.9.8.4, 7.9.8.5, 7.9.8.6, 7.9.8.7, 7.9.8.8, 7.9.8.9, 7.9.8.10, 7.9.9.1, 7.9.9.2, 7.9.9.3, 7.9.9.4, 7.9.9.5, 7.9.9.6, 7.9.9.7, 7.9.9.8, 7.9.9.9, 7.9.9.10, 7.9.10.1, 7.9.10.2, 7.9.10.3, 7.9.10.4, 7.9.10.5, 7.9.10.6, 7.9.10.7, 7.9.10.8, 7.9.10.9, 7.9.10.10, 7.10.1.1, 7.10.1.2, 7.10.1.3, 7.10.1.4, 7.10.1.5, 7.10.1.6, 7.10.1.7, 7.10.1.8, 7.10.1.9, 7.10.1.10, 7.10.2.1, 7.10.2.2, 7.10.2.3, 7.10.2.4, 7.10.2.5, 7.10.2.6, 7.10.2.7, 7.10.2.8, 7.10.2.9, 7.10.2.10, 7.10.3.1, 7.10.3.2, 7.10.3.3, 7.10.3.4, 7.10.3.5, 7.10.3.6, 7.10.3.7, 7.10.3.8, 7.10.3.9, 7.10.3.10, 7.10.4.1, 7.10.4.2, 7.10.4.3, 7.10.4.4, 7.10.4.5, 7.10.4.6, 7.10.4.7, 7.10.4.8, 7.10.4.9, 7.10.4.10, 7.10.5.1, 7.10.5.2, 7.10.5.3, 7.10.5.4, 7.10.5.5, 7.10.5.6, 7.10.5.7, 7.10.5.8, 7.10.5.9, 7.10.5.10, 7.10.6.1, 7.10.6.2, 7.10.6.3, 7.10.6.4, 7.10.6.5, 7.10.6.6, 7.10.6.7, 7.10.6.8, 7.10.6.9, 7.10.6.10, 7.10.7.1, 7.10.7.2, 7.10.7.3, 7.10.7.4, 7.10.7.5, 7.10.7.6, 7.10.7.7, 7.10.7.8, 7.10.7.9, 7.10.7.10, 7.10.8.1, 7.10.8.2, 7.10.8.3, 7.10.8.4, 7.10.8.5, 7.10.8.6, 7.10.8.7, 7.10.8.8, 7.10.8.9, 7.10.8.10, 7.10.9.1, 7.10.9.2, 7.10.9.3, 7.10.9.4, 7.10.9.5, 7.10.9.6, 7.10.9.7, 7.10.9.8, 7.10.9.9, 7.10.9.10, 7.10.10.1, 7.10.10.2, 7.10.10.3, 7.10.10.4, 7.10.10.5, 7.10.10.6, 7.10.10.7, 7.10.10.8, 7.10.10.9, 7.10.10.10, 8.1.1.1, 8.1.1.2, 8.1.1.3, 8.1.1.4, 8.1.1.5, 8.1.1.6, 8.1.1.7, 8.1.1.8, 8.1.1.9, 8.1.1.10, 8.1.2.1, 8.1.2.2, 8.1.2.3, 8.1.2.4, 8.1.2.5, 8.1.2.6, 8.1.2.7, 8.1.2.8, 8.1.2.9, 8.1.2.10, 8.1.3.1, 8.1.3.2, 8.1.3.3, 8.1.3.4, 8.1.3.5, 8.1.3.6, 8.1.3.7, 8.1.3.8, 8.1.3.9, 8.1.3.10, 8.1.4.1, 8.1.4.2, 8.1.4.3, 8.1.4.4, 8.1.4.5, 8.1.4.6, 8.1.4.7, 8.1.4.8, 8.1.4.9, 8.1.4.10, 8.1.5.1, 8.1.5.2, 8.1.5.3, 8.1.5.4, 8.1.5.5, 8.1.5.6, 8.1.5.7, 8.1.5.8, 8.1.5.9, 8.1.5.10, 8.1.6.1, 8.1.6.2, 8.1.6.3, 8.1.6.4, 8.1.6.5, 8.1.6.6, 8.1.6.7, 8.1.6.8, 8.1.6.9, 8.1.6.10, 8.1.7.1, 8.1.7.2, 8.1.7.3, 8.1.7.4, 8.1.7.5, 8.1.7.6, 8.1.7.7, 8.1.7.8, 8.1.7.9, 8.1.7.10, 8.1.8.1, 8.1.8.2, 8.1.8.3, 8.1.8.4, 8.1.8.5, 8.1.8.6, 8.1.8.7, 8.1.8.8, 8.1.8.9, 8.1.8.10, 8.1.9.1, 8.1.9.2, 8.1.9.3, 8.1.9.4, 8.1.9.5, 8.1.9.6, 8.1.9.7, 8.1.9.8, 8.1.9.9, 8.1.9.10, 8.1.10.1, 8.1.10.2, 8.1.10.3, 8.1.10.4, 8.1.10.5, 8.1.10.6, 8.1.10.7, 8.1.10.8, 8.1.10.9, 8.1.10.10, 8.2.1.1, 8.2.1.2, 8.2.1.3, 8.2.1.4, 8.2.1.5, 8.2.1.6, 8.2.1.7, 8.2.1.8, 8.2.1.9, 8.2.1.10, 8.2.2.1, 8.2.2.2, 8.2.2.3, 8.2.2.4, 8.2.2.5, 8.2.2.6, 8.2.2.7, 8.2.2.8, 8.2.2.9, 8.2.2.10, 8.2.3.1, 8.2.3.2, 8.2.3.3, 8.2.3.4, 8.2.3.5, 8.2.3.6, 8.2.3.7, 8.2.3.8, 8.2.3.9, 8.2.3.10, 8.2.4.1, 8.2.4.2, 8.2.4.3, 8.2.4.4, 8.2.4.5, 8.2.4.6, 8.2.4.7, 8.2.4.8, 8.2.4.9, 8.2.4.10, 8.2.5.1, 8.2.5.2, 8.2.5.3, 8.2.5.4, 8.2.5.5, 8.2.5.6, 8.2.5.7, 8.2.5.8, 8.2.5.9, 8.2.5.10, 8.2.6.1, 8.2.6.2, 8.2.6.3, 8.2.6.4, 8.2.6.5, 8.2.6.6, 8.2.6.7, 8.2.6.8, 8.2.6.9, 8.2.6.10, 8.2.7.1, 8.2.7.2, 8.2.7.3, 8.2.7.4, 8.2.7.5, 8.2.7.6, 8.2.7.7, 8.2.7.8, 8.2.7.9, 8.2.7.10, 8.2.8.1, 8.2.8.2, 8.2.8.3, 8.2.8.4, 8.2.8.5, 8.2.8.6, 8.2.8.7, 8.2.8.8, 8.2.8.9, 8.2.8.10, 8.2.9.1, 8.2.9.2, 8.2.9.3, 8.2.9.4, 8.2.9.5, 8.2.9.6, 8.2.9.7, 8.2.9.8, 8.2.9.9, 8.2.9.10, 8.2.10.1, 8.2.10.2, 8.2.10.3, 8.2.10.4, 8.2.10.5, 8.2.10.6, 8.2.10.7, 8.2.10.8, 8.2.10.9, 8.2.10.10, 8.3.1.1, 8.3.1.2, 8.3.1.3, 8.3.1.4, 8.3.1.5, 8.3.1.6, TABLE B-continued 8.3.1.7, 8.3.1.8, 8.3.1.9, 8.3.1.10, 8.3.2.1, 8.3.2.2, 8.3.2.3, 8.3.2.4, 8.3.2.5, 8.3.2.6, 8.3.2.7, 8.3.2.8, 8.3.2.9, 8.3.2.10, 8.3.3.1, 8.3.3.2, 8.3.3.3, 8.3.3.4, 8.3.3.5, 8.3.3.6, 8.3.3.7, 8.3.3.8, 8.3.3.9, 8.3.3.10, 8.3.4.1, 8.3.4.2, 8.3.4.3, 8.3.4.4, 8.3.4.5, 8.3.4.6, 8.3.4.7, 8.3.4.8, 8.3.4.9, 8.3.4.10, 8.3.5.1, 8.3.5.2, 8.3.5.3, 8.3.5.4, 8.3.5.5, 8.3.5.6, 8.3.5.7, 8.3.5.8, 8.3.5.9, 8.3.5.10, 8.3.6.1, 8.3.6.2, 8.3.6.3, 8.3.6.4, 8.3.6.5, 8.3.6.6, 8.3.6.7, 8.3.6.8, 8.3.6.9, 8.3.6.10, 8.3.7.1, 8.3.7.2, 8.3.7.3, 8.3.7.4, 8.3.7.5, 8.3.7.6, 8.3.7.7, 8.3.7.8, 8.3.7.9, 8.3.7.10, 8.3.8.1, 8.3.8.2, 8.3.8.3, 8.3.8.4, 8.3.8.5, 8.3.8.6, 8.3.8.7, 8.3.8.8, 8.3.8.9, 8.3.8.10, 8.3.9.1, 8.3.9.2, 8.3.9.3, 8.3.9.4, 8.3.9.5, 8.3.9.6, 8.3.9.7, 8.3.9.8, 8.3.9.9, 8.3.9.10, 8.3.10.1, 8.3.10.2, 8.3.10.3, 8.3.10.4, 8.3.10.5, 8.3.10.6, 8.3.10.7, 8.3.10.8, 8.3.10.9, 8.3.10.10, 8.4.1.1, 8.4.1.2, 8.4.1.3, 8.4.1.4, 8.4.1.5, 8.4.1.6, 8.4.1.7, 8.4.1.8, 8.4.1.9, 8.4.1.10, 8.4.2.1, 8.4.2.2, 8.4.2.3, 8.4.2.4, 8.4.2.5, 8.4.2.6, 8.4.2.7, 8.4.2.8, 8.4.2.9, 8.4.2.10, 8.4.3.1, 8.4.3.2, 8.4.3.3, 8.4.3.4, 8.4.3.5, 8.4.3.6, 8.4.3.7, 8.4.3.8, 8.4.3.9, 8.4.3.10, 8.4.4.1, 8.4.4.2, 8.4.4.3, 8.4.4.4, 8.4.4.5, 8.4.4.6, 8.4.4.7, 8.4.4.8, 8.4.4.9, 8.4.4.10, 8.4.5.1, 8.4.5.2, 8.4.5.3, 8.4.5.4, 8.4.5.5, 8.4.5.6, 8.4.5.7, 8.4.5.8, 8.4.5.9, 8.4.5.10, 8.4.6.1, 8.4.6.2, 8.4.6.3, 8.4.6.4, 8.4.6.5, 8.4.6.6, 8.4.6.7, 8.4.6.8, 8.4.6.9, 8.4.6.10, 8.4.7.1, 8.4.7.2, 8.4.7.3, 8.4.7.4, 8.4.7.5, 8.4.7.6, 8.4.7.7, 8.4.7.8, 8.4.7.9, 8.4.7.10, 8.4.8.1, 8.4.8.2, 8.4.8.3, 8.4.8.4, 8.4.8.5, 8.4.8.6, 8.4.8.7, 8.4.8.8, 8.4.8.9, 8.4.8.10, 8.4.9.1, 8.4.9.2, 8.4.9.3, 8.4.9.4, 8.4.9.5, 8.4.9.6, 8.4.9.7, 8.4.9.8, 8.4.9.9, 8.4.9.10, 8.4.10.1, 8.4.10.2, 8.4.10.3, 8.4.10.4, 8.4.10.5, 8.4.10.6, 8.4.10.7, 8.4.10.8, 8.4.10.9, 8.4.10.10, 8.5.1.1, 8.5.1.2, 8.5.1.3, 8.5.1.4, 8.5.1.5, 8.5.1.6, 8.5.1.7, 8.5.1.8, 8.5.1.9, 8.5.1.10, 8.5.2.1, 8.5.2.2, 8.5.2.3, 8.5.2.4, 8.5.2.5, 8.5.2.6, 8.5.2.7, 8.5.2.8, 8.5.2.9, 8.5.2.10, 8.5.3.1, 8.5.3.2, 8.5.3.3, 8.5.3.4, 8.5.3.5, 8.5.3.6, 8.5.3.7, 8.5.3.8, 8.5.3.9, 8.5.3.10, 8.5.4.1, 8.5.4.2, 8.5.4.3, 8.5.4.4, 8.5.4.5, 8.5.4.6, 8.5.4.7, 8.5.4.8, 8.5.4.9, 8.5.4.10, 8.5.5.1, 8.5.5.2, 8.5.5.3, 8.5.5.4, 8.5.5.5, 8.5.5.6, 8.5.5.7, 8.5.5.8, 8.5.5.9, 8.5.5.10, 8.5.6.1, 8.5.6.2, 8.5.6.3, 8.5.6.4, 8.5.6.5, 8.5.6.6, 8.5.6.7, 8.5.6.8, 8.5.6.9, 8.5.6.10, 8.5.7.1, 8.5.7.2, 8.5.7.3, 8.5.7.4, 8.5.7.5, 8.5.7.6, 8.5.7.7, 8.5.7.8, 8.5.7.9, 8.5.7.10, 8.5.8.1, 8.5.8.2, 8.5.8.3, 8.5.8.4, 8.5.8.5, 8.5.8.6, 8.5.8.7, 8.5.8.8, 8.5.8.9, 8.5.8.10, 8.5.9.1, 8.5.9.2, 8.5.9.3, 8.5.9.4, 8.5.9.5, 8.5.9.6, 8.5.9.7, 8.5.9.8, 8.5.9.9, 8.5.9.10, 8.5.10.1, 8.5.10.2, 8.5.10.3, 8.5.10.4, 8.5.10.5, 8.5.10.6, 8.5.10.7, 8.5.10.8, 8.5.10.9, 8.5.10.10, 8.6.1.1, 8.6.1.2, 8.6.1.3, 8.6.1.4, 8.6.1.5, 8.6.1.6, 8.6.1.7, 8.6.1.8, 8.6.1.9, 8.6.1.10, 8.6.2.1, 8.6.2.2, 8.6.2.3, 8.6.2.4, 8.6.2.5, 8.6.2.6, 8.6.2.7, 8.6.2.8, 8.6.2.9, 8.6.2.10, 8.6.3.1, 8.6.3.2, 8.6.3.3, 8.6.3.4, 8.6.3.5, 8.6.3.6, 8.6.3.7, 8.6.3.8, 8.6.3.9, 8.6.3.10, 8.6.4.1, 8.6.4.2, 8.6.4.3, 8.6.4.4, 8.6.4.5, 8.6.4.6, 8.6.4.7, 8.6.4.8, 8.6.4.9, 8.6.4.10, 8.6.5.1, 8.6.5.2, 8.6.5.3, 8.6.5.4, 8.6.5.5, 8.6.5.6, 8.6.5.7, 8.6.5.8, 8.6.5.9, 8.6.5.10, 8.6.6.1, 8.6.6.2, 8.6.6.3, 8.6.6.4, 8.6.6.5, 8.6.6.6, 8.6.6.7, 8.6.6.8, 8.6.6.9, 8.6.6.10, 8.6.7.1, 8.6.7.2, 8.6.7.3, 8.6.7.4, 8.6.7.5, 8.6.7.6, 8.6.7.7, 8.6.7.8, 8.6.7.9, 8.6.7.10, 8.6.8.1, 8.6.8.2, 8.6.8.3, 8.6.8.4, 8.6.8.5, 8.6.8.6, 8.6.8.7, 8.6.8.8, 8.6.8.9, 8.6.8.10, 8.6.9.1, 8.6.9.2, 8.6.9.3, 8.6.9.4, 8.6.9.5, 8.6.9.6, 8.6.9.7, 8.6.9.8, 8.6.9.9, 8.6.9.10, 8.6.10.1, 8.6.10.2, 8.6.10.3, 8.6.10.4, 8.6.10.5, 8.6.10.6, 8.6.10.7, 8.6.10.8, 8.6.10.9, 8.6.10.10, 8.7.1.1, 8.7.1.2, 8.7.1.3, 8.7.1.4, 8.7.1.5, 8.7.1.6, 8.7.1.7, 8.7.1.8, 8.7.1.9, 8.7.1.10, 8.7.2.1, 8.7.2.2, 8.7.2.3, 8.7.2.4, 8.7.2.5, 8.7.2.6, 8.7.2.7, 8.7.2.8, 8.7.2.9, 8.7.2.10, 8.7.3.1, 8.7.3.2, 8.7.3.3, 8.7.3.4, 8.7.3.5, 8.7.3.6, 8.7.3.7, 8.7.3.8, 8.7.3.9, 8.7.3.10, 8.7.4.1, 8.7.4.2, 8.7.4.3, 8.7.4.4, 8.7.4.5, 8.7.4.6, 8.7.4.7, 8.7.4.8, 8.7.4.9, 8.7.4.10, 8.7.5.1, 8.7.5.2, 8.7.5.3, 8.7.5.4, 8.7.5.5, 8.7.5.6, 8.7.5.7, 8.7.5.8, 8.7.5.9, 8.7.5.10, 8.7.6.1, 8.7.6.2, 8.7.6.3, 8.7.6.4, 8.7.6.5, 8.7.6.6, 8.7.6.7, 8.7.6.8, 8.7.6.9, 8.7.6.10, 8.7.7.1, 8.7.7.2, 8.7.7.3, 8.7.7.4, 8.7.7.5, 8.7.7.6, 8.7.7.7, 8.7.7.8, 8.7.7.9, 8.7.7.10, 8.7.8.1, 8.7.8.2, 8.7.8.3, 8.7.8.4, 8.7.8.5, 8.7.8.6, 8.7.8.7, 8.7.8.8, 8.7.8.9, 8.7.8.10, 8.7.9.1, 8.7.9.2, 8.7.9.3, 8.7.9.4, 8.7.9.5, 8.7.9.6, 8.7.9.7, 8.7.9.8, 8.7.9.9, 8.7.9.10, 8.7.10.1, 8.7.10.2, 8.7.10.3, 8.7.10.4, 8.7.10.5, 8.7.10.6, 8.7.10.7, 8.7.10.8, 8.7.10.9, 8.7.10.10, 8.8.1.1, 8.8.1.2, 8.8.1.3, 8.8.1.4, 8.8.1.5, 8.8.1.6, 8.8.1.7, 8.8.1.8, 8.8.1.9, 8.8.1.10, 8.8.2.1, 8.8.2.2, 8.8.2.3, 8.8.2.4, 8.8.2.5, 8.8.2.6, 8.8.2.7, 8.8.2.8, 8.8.2.9, 8.8.2.10, 8.8.3.1, 8.8.3.2, 8.8.3.3, 8.8.3.4, 8.8.3.5, 8.8.3.6, 8.8.3.7, 8.8.3.8, 8.8.3.9, 8.8.3.10, 8.8.4.1, 8.8.4.2, 8.8.4.3, 8.8.4.4, 8.8.4.5, 8.8.4.6, 8.8.4.7, 8.8.4.8, 8.8.4.9, 8.8.4.10, 8.8.5.1, 8.8.5.2, 8.8.5.3, 8.8.5.4, 8.8.5.5, 8.8.5.6, 8.8.5.7, 8.8.5.8, 8.8.5.9, 8.8.5.10, 8.8.6.1, 8.8.6.2, 8.8.6.3, 8.8.6.4, 8.8.6.5, 8.8.6.6, 8.8.6.7, 8.8.6.8, 8.8.6.9, 8.8.6.10, 8.8.7.1, 8.8.7.2, 8.8.7.3, 8.8.7.4, 8.8.7.5, 8.8.7.6, 8.8.7.7, 8.8.7.8, 8.8.7.9, 8.8.7.10, 8.8.8.1, 8.8.8.2, 8.8.8.3, 8.8.8.4, 8.8.8.5, 8.8.8.6, 8.8.8.7, 8.8.8.8, 8.8.8.9, 8.8.8.10, 8.8.9.1, 8.8.9.2, 8.8.9.3, 8.8.9.4, 8.8.9.5, 8.8.9.6, 8.8.9.7, 8.8.9.8, 8.8.9.9, 8.8.9.10, 8.8.10.1, 8.8.10.2, 8.8.10.3, 8.8.10.4, 8.8.10.5, 8.8.10.6, 8.8.10.7, 8.8.10.8, 8.8.10.9, 8.8.10.10, 8.9.1.1, 8.9.1.2, 8.9.1.3, 8.9.1.4, 8.9.1.5, 8.9.1.6, 8.9.1.7, 8.9.1.8, 8.9.1.9, 8.9.1.10, 8.9.2.1, 8.9.2.2, 8.9.2.3, 8.9.2.4, 8.9.2.5, 8.9.2.6, 8.9.2.7, 8.9.2.8, 8.9.2.9, 8.9.2.10, 8.9.3.1, 8.9.3.2, 8.9.3.3, 8.9.3.4, 8.9.3.5, 8.9.3.6, 8.9.3.7, 8.9.3.8, 8.9.3.9, 8.9.3.10, 8.9.4.1, 8.9.4.2, 8.9.4.3, 8.9.4.4, 8.9.4.5, 8.9.4.6, 8.9.4.7, 8.9.4.8, 8.9.4.9, 8.9.4.10, 8.9.5.1, 8.9.5.2, 8.9.5.3, 8.9.5.4, 8.9.5.5, 8.9.5.6, 8.9.5.7, 8.9.5.8, 8.9.5.9, 8.9.5.10, 8.9.6.1, 8.9.6.2, 8.9.6.3, 8.9.6.4, 8.9.6.5, 8.9.6.6, 8.9.6.7, 8.9.6.8, 8.9.6.9, 8.9.6.10, 8.9.7.1, 8.9.7.2, 8.9.7.3, 8.9.7.4, 8.9.7.5, 8.9.7.6, 8.9.7.7, 8.9.7.8, 8.9.7.9, 8.9.7.10, 8.9.8.1, 8.9.8.2, 8.9.8.3, 8.9.8.4, 8.9.8.5, 8.9.8.6, 8.9.8.7, 8.9.8.8, 8.9.8.9, 8.9.8.10, 8.9.9.1, 8.9.9.2, 8.9.9.3, 8.9.9.4, 8.9.9.5, 8.9.9.6, 8.9.9.7, 8.9.9.8, 8.9.9.9, 8.9.9.10, 8.9.10.1, 8.9.10.2, 8.9.10.3, 8.9.10.4, 8.9.10.5, 8.9.10.6, 8.9.10.7, 8.9.10.8, 8.9.10.9, 8.9.10.10, 8.10.1.1, 8.10.1.2, 8.10.1.3, 8.10.1.4, 8.10.1.5, 8.10.1.6, 8.10.1.7, 8.10.1.8, 8.10.1.9, 8.10.1.10, 8.10.2.1, 8.10.2.2, 8.10.2.3, 8.10.2.4, 8.10.2.5, 8.10.2.6, 8.10.2.7, 8.10.2.8, 8.10.2.9, 8.10.2.10, 8.10.3.1, 8.10.3.2, 8.10.3.3, 8.10.3.4, 8.10.3.5, 8.10.3.6, 8.10.3.7, 8.10.3.8, 8.10.3.9, 8.10.3.10, 8.10.4.1, 8.10.4.2, 8.10.4.3, 8.10.4.4, 8.10.4.5, 8.10.4.6, 8.10.4.7, 8.10.4.8, 8.10.4.9, 8.10.4.10, 8.10.5.1, 8.10.5.2, 8.10.5.3, 8.10.5.4, 8.10.5.5, 8.10.5.6, 8.10.5.7, 8.10.5.8, 8.10.5.9, 8.10.5.10, 8.10.6.1, 8.10.6.2, 8.10.6.3, 8.10.6.4, 8.10.6.5, 8.10.6.6, 8.10.6.7, 8.10.6.8, 8.10.6.9, 8.10.6.10, 8.10.7.1, 8.10.7.2, 8.10.7.3, 8.10.7.4, 8.10.7.5, 8.10.7.6, 8.10.7.7, 8.10.7.8, 8.10.7.9, 8.10.7.10, 8.10.8.1, 8.10.8.2, 8.10.8.3, 8.10.8.4, 8.10.8.5, 8.10.8.6, 8.10.8.7, 8.10.8.8, 8.10.8.9, 8.10.8.10, 8.10.9.1, 8.10.9.2, 8.10.9.3, 8.10.9.4, 8.10.9.5, 8.10.9.6, 8.10.9.7, 8.10.9.8, 8.10.9.9, 8.10.9.10, 8.10.10.1, 8.10.10.2, 8.10.10.3, 8.10.10.4, 8.10.10.5, 8.10.10.6, 8.10.10.7, 8.10.10.8, 8.10.10.9, 8.10.10.10, 9.1.1.1, 9.1.1.2, 9.1.1.3, 9.1.1.4, 9.1.1.5, 9.1.1.6, 9.1.1.7, 9.1.1.8, 9.1.1.9, 9.1.1.10, 9.1.2.1, 9.1.2.2, 9.1.2.3, 9.1.2.4, 9.1.2.5, 9.1.2.6, 9.1.2.7, 9.1.2.8, 9.1.2.9, 9.1.2.10, 9.1.3.1, 9.1.3.2, 9.1.3.3, 9.1.3.4, 9.1.3.5, 9.1.3.6, 9.1.3.7, 9.1.3.8, 9.1.3.9, 9.1.3.10, 9.1.4.1, 9.1.4.2, 9.1.4.3, 9.1.4.4, 9.1.4.5, 9.1.4.6, 9.1.4.7, 9.1.4.8, 9.1.4.9, 9.1.4.10, 9.1.5.1, 9.1.5.2, 9.1.5.3, 9.1.5.4, 9.1.5.5, 9.1.5.6,

TABLE B-continued 9.1.5.7, 9.1.5.8, 9.1.5.9, 9.1.5.10, 9.1.6.1, 9.1.6.2, 9.1.6.3, 9.1.6.4, 9.1.6.5, 9.1.6.6, 9.1.6.7, 9.1.6.8, 9.1.6.9, 9.1.6.10, 9.1.7.1, 9.1.7.2, 9.1.7.3, 9.1.7.4, 9.1.7.5, 9.1.7.6, 9.1.7.7, 9.1.7.8, 9.1.7.9, 9.1.7.10, 9.1.8.1, 9.1.8.2, 9.1.8.3, 9.1.8.4, 9.1.8.5, 9.1.8.6, 9.1.8.7, 9.1.8.8, 9.1.8.9, 9.1.8.10, 9.1.9.1, 9.1.9.2, 9.1.9.3, 9.1.9.4, 9.1.9.5, 9.1.9.6, 9.1.9.7, 9.1.9.8, 9.1.9.9, 9.1.9.10, 9.1.10.1, 9.1.10.2, 9.1.10.3, 9.1.10.4, 9.1.10.5, 9.1.10.6, 9.1.10.7, 9.1.10.8, 9.1.10.9, 9.1.10.10, 9.2.1.1, 9.2.1.2, 9.2.1.3, 9.2.1.4, 9.2.1.5, 9.2.1.6, 9.2.1.7, 9.2.1.8, 9.2.1.9, 9.2.1.10, 9.2.2.1, 9.2.2.2, 9.2.2.3, 9.2.2.4, 9.2.2.5, 9.2.2.6, 9.2.2.7, 9.2.2.8, 9.2.2.9, 9.2.2.10, 9.2.3.1, 9.2.3.2, 9.2.3.3, 9.2.3.4, 9.2.3.5, 9.2.3.6, 9.2.3.7, 9.2.3.8, 9.2.3.9, 9.2.3.10, 9.2.4.1, 9.2.4.2, 9.2.4.3, 9.2.4.4, 9.2.4.5, 9.2.4.6, 9.2.4.7, 9.2.4.8, 9.2.4.9, 9.2.4.10, 9.2.5.1, 9.2.5.2, 9.2.5.3, 9.2.5.4, 9.2.5.5, 9.2.5.6, 9.2.5.7, 9.2.5.8, 9.2.5.9, 9.2.5.10, 9.2.6.1, 9.2.6.2, 9.2.6.3, 9.2.6.4, 9.2.6.5, 9.2.6.6, 9.2.6.7, 9.2.6.8, 9.2.6.9, 9.2.6.10, 9.2.7.1, 9.2.7.2, 9.2.7.3, 9.2.7.4, 9.2.7.5, 9.2.7.6, 9.2.7.7, 9.2.7.8, 9.2.7.9, 9.2.7.10, 9.2.8.1, 9.2.8.2, 9.2.8.3, 9.2.8.4, 9.2.8.5, 9.2.8.6, 9.2.8.7, 9.2.8.8, 9.2.8.9, 9.2.8.10, 9.2.9.1, 9.2.9.2, 9.2.9.3, 9.2.9.4, 9.2.9.5, 9.2.9.6, 9.2.9.7, 9.2.9.8, 9.2.9.9, 9.2.9.10, 9.2.10.1, 9.2.10.2, 9.2.10.3, 9.2.10.4, 9.2.10.5, 9.2.10.6, 9.2.10.7, 9.2.10.8, 9.2.10.9, 9.2.10.10, 9.3.1.1, 9.3.1.2, 9.3.1.3, 9.3.1.4, 9.3.1.5, 9.3.1.6, 9.3.1.7, 9.3.1.8, 9.3.1.9, 9.3.1.10, 9.3.2.1, 9.3.2.2, 9.3.2.3, 9.3.2.4, 9.3.2.5, 9.3.2.6, 9.3.2.7, 9.3.2.8, 9.3.2.9, 9.3.2.10, 9.3.3.1, 9.3.3.2, 9.3.3.3, 9.3.3.4, 9.3.3.5, 9.3.3.6, 9.3.3.7, 9.3.3.8, 9.3.3.9, 9.3.3.10, 9.3.4.1, 9.3.4.2, 9.3.4.3, 9.3.4.4, 9.3.4.5, 9.3.4.6, 9.3.4.7, 9.3.4.8, 9.3.4.9, 9.3.4.10, 9.3.5.1, 9.3.5.2, 9.3.5.3, 9.3.5.4, 9.3.5.5, 9.3.5.6, 9.3.5.7, 9.3.5.8, 9.3.5.9, 9.3.5.10, 9.3.6.1, 9.3.6.2, 9.3.6.3, 9.3.6.4, 9.3.6.5, 9.3.6.6, 9.3.6.7, 9.3.6.8, 9.3.6.9, 9.3.6.10, 9.3.7.1, 9.3.7.2, 9.3.7.3, 9.3.7.4, 9.3.7.5, 9.3.7.6, 9.3.7.7, 9.3.7.8, 9.3.7.9, 9.3.7.10, 9.3.8.1, 9.3.8.2, 9.3.8.3, 9.3.8.4, 9.3.8.5, 9.3.8.6, 9.3.8.7, 9.3.8.8, 9.3.8.9, 9.3.8.10, 9.3.9.1, 9.3.9.2, 9.3.9.3, 9.3.9.4, 9.3.9.5, 9.3.9.6, 9.3.9.7, 9.3.9.8, 9.3.9.9, 9.3.9.10, 9.3.10.1, 9.3.10.2, 9.3.10.3, 9.3.10.4, 9.3.10.5, 9.3.10.6, 9.3.10.7, 9.3.10.8, 9.3.10.9, 9.3.10.10, 9.4.1.1, 9.4.1.2, 9.4.1.3, 9.4.1.4, 9.4.1.5, 9.4.1.6, 9.4.1.7, 9.4.1.8, 9.4.1.9, 9.4.1.10, 9.4.2.1, 9.4.2.2, 9.4.2.3, 9.4.2.4, 9.4.2.5, 9.4.2.6, 9.4.2.7, 9.4.2.8, 9.4.2.9, 9.4.2.10, 9.4.3.1, 9.4.3.2, 9.4.3.3, 9.4.3.4, 9.4.3.5, 9.4.3.6, 9.4.3.7, 9.4.3.8, 9.4.3.9, 9.4.3.10, 9.4.4.1, 9.4.4.2, 9.4.4.3, 9.4.4.4, 9.4.4.5, 9.4.4.6, 9.4.4.7, 9.4.4.8, 9.4.4.9, 9.4.4.10, 9.4.5.1, 9.4.5.2, 9.4.5.3, 9.4.5.4, 9.4.5.5, 9.4.5.6, 9.4.5.7, 9.4.5.8, 9.4.5.9, 9.4.5.10, 9.4.6.1, 9.4.6.2, 9.4.6.3, 9.4.6.4, 9.4.6.5, 9.4.6.6, 9.4.6.7, 9.4.6.8, 9.4.6.9, 9.4.6.10, 9.4.7.1, 9.4.7.2, 9.4.7.3, 9.4.7.4, 9.4.7.5, 9.4.7.6, 9.4.7.7, 9.4.7.8, 9.4.7.9, 9.4.7.10, 9.4.8.1, 9.4.8.2, 9.4.8.3, 9.4.8.4, 9.4.8.5, 9.4.8.6, 9.4.8.7, 9.4.8.8, 9.4.8.9, 9.4.8.10, 9.4.9.1, 9.4.9.2, 9.4.9.3, 9.4.9.4, 9.4.9.5, 9.4.9.6, 9.4.9.7, 9.4.9.8, 9.4.9.9, 9.4.9.10, 9.4.10.1, 9.4.10.2, 9.4.10.3, 9.4.10.4, 9.4.10.5, 9.4.10.6, 9.4.10.7, 9.4.10.8, 9.4.10.9, 9.4.10.10, 9.5.1.1, 9.5.1.2, 9.5.1.3, 9.5.1.4, 9.5.1.5, 9.5.1.6, 9.5.1.7, 9.5.1.8, 9.5.1.9, 9.5.1.10, 9.5.2.1, 9.5.2.2, 9.5.2.3, 9.5.2.4, 9.5.2.5, 9.5.2.6, 9.5.2.7, 9.5.2.8, 9.5.2.9, 9.5.2.10, 9.5.3.1, 9.5.3.2, 9.5.3.3, 9.5.3.4, 9.5.3.5, 9.5.3.6, 9.5.3.7, 9.5.3.8, 9.5.3.9, 9.5.3.10, 9.5.4.1, 9.5.4.2, 9.5.4.3, 9.5.4.4, 9.5.4.5, 9.5.4.6, 9.5.4.7, 9.5.4.8, 9.5.4.9, 9.5.4.10, 9.5.5.1, 9.5.5.2, 9.5.5.3, 9.5.5.4, 9.5.5.5, 9.5.5.6, 9.5.5.7, 9.5.5.8, 9.5.5.9, 9.5.5.10, 9.5.6.1, 9.5.6.2, 9.5.6.3, 9.5.6.4, 9.5.6.5, 9.5.6.6, 9.5.6.7, 9.5.6.8, 9.5.6.9, 9.5.6.10, 9.5.7.1, 9.5.7.2, 9.5.7.3, 9.5.7.4, 9.5.7.5, 9.5.7.6, 9.5.7.7, 9.5.7.8, 9.5.7.9, 9.5.7.10, 9.5.8.1, 9.5.8.2, 9.5.8.3, 9.5.8.4, 9.5.8.5, 9.5.8.6, 9.5.8.7, 9.5.8.8, 9.5.8.9, 9.5.8.10, 9.5.9.1, 9.5.9.2, 9.5.9.3, 9.5.9.4, 9.5.9.5, 9.5.9.6, 9.5.9.7, 9.5.9.8, 9.5.9.9, 9.5.9.10, 9.5.10.1, 9.5.10.2, 9.5.10.3, 9.5.10.4, 9.5.10.5, 9.5.10.6, 9.5.10.7, 9.5.10.8, 9.5.10.9, 9.5.10.10, 9.6.1.1, 9.6.1.2, 9.6.1.3, 9.6.1.4, 9.6.1.5, 9.6.1.6, 9.6.1.7, 9.6.1.8, 9.6.1.9, 9.6.1.10, 9.6.2.1, 9.6.2.2, 9.6.2.3, 9.6.2.4, 9.6.2.5, 9.6.2.6, 9.6.2.7, 9.6.2.8, 9.6.2.9, 9.6.2.10, 9.6.3.1, 9.6.3.2, 9.6.3.3, 9.6.3.4, 9.6.3.5, 9.6.3.6, 9.6.3.7, 9.6.3.8, 9.6.3.9, 9.6.3.10, 9.6.4.1, 9.6.4.2, 9.6.4.3, 9.6.4.4, 9.6.4.5, 9.6.4.6, 9.6.4.7, 9.6.4.8, 9.6.4.9, 9.6.4.10, 9.6.5.1, 9.6.5.2, 9.6.5.3, 9.6.5.4, 9.6.5.5, 9.6.5.6, 9.6.5.7, 9.6.5.8, 9.6.5.9, 9.6.5.10, 9.6.6.1, 9.6.6.2, 9.6.6.3, 9.6.6.4, 9.6.6.5, 9.6.6.6, 9.6.6.7, 9.6.6.8, 9.6.6.9, 9.6.6.10, 9.6.7.1, 9.6.7.2, 9.6.7.3, 9.6.7.4, 9.6.7.5, 9.6.7.6, 9.6.7.7, 9.6.7.8, 9.6.7.9, 9.6.7.10, 9.6.8.1, 9.6.8.2, 9.6.8.3, 9.6.8.4, 9.6.8.5, 9.6.8.6, 9.6.8.7, 9.6.8.8, 9.6.8.9, 9.6.8.10, 9.6.9.1, 9.6.9.2, 9.6.9.3, 9.6.9.4, 9.6.9.5, 9.6.9.6, 9.6.9.7, 9.6.9.8, 9.6.9.9, 9.6.9.10, 9.6.10.1, 9.6.10.2, 9.6.10.3, 9.6.10.4, 9.6.10.5, 9.6.10.6, 9.6.10.7, 9.6.10.8, 9.6.10.9, 9.6.10.10, 9.7.1.1, 9.7.1.2, 9.7.1.3, 9.7.1.4, 9.7.1.5, 9.7.1.6, 9.7.1.7, 9.7.1.8, 9.7.1.9, 9.7.1.10, 9.7.2.1, 9.7.2.2, 9.7.2.3, 9.7.2.4, 9.7.2.5, 9.7.2.6, 9.7.2.7, 9.7.2.8, 9.7.2.9, 9.7.2.10, 9.7.3.1, 9.7.3.2, 9.7.3.3, 9.7.3.4, 9.7.3.5, 9.7.3.6, 9.7.3.7, 9.7.3.8, 9.7.3.9, 9.7.3.10, 9.7.4.1, 9.7.4.2, 9.7.4.3, 9.7.4.4, 9.7.4.5, 9.7.4.6, 9.7.4.7, 9.7.4.8, 9.7.4.9, 9.7.4.10, 9.7.5.1, 9.7.5.2, 9.7.5.3, 9.7.5.4, 9.7.5.5, 9.7.5.6, 9.7.5.7, 9.7.5.8, 9.7.5.9, 9.7.5.10, 9.7.6.1, 9.7.6.2, 9.7.6.3, 9.7.6.4, 9.7.6.5, 9.7.6.6, 9.7.6.7, 9.7.6.8, 9.7.6.9, 9.7.6.10, 9.7.7.1, 9.7.7.2, 9.7.7.3, 9.7.7.4, 9.7.7.5, 9.7.7.6, 9.7.7.7, 9.7.7.8, 9.7.7.9, 9.7.7.10, 9.7.8.1, 9.7.8.2, 9.7.8.3, 9.7.8.4, 9.7.8.5, 9.7.8.6, 9.7.8.7, 9.7.8.8, 9.7.8.9, 9.7.8.10, 9.7.9.1, 9.7.9.2, 9.7.9.3, 9.7.9.4, 9.7.9.5, 9.7.9.6, 9.7.9.7, 9.7.9.8, 9.7.9.9, 9.7.9.10, 9.7.10.1, 9.7.10.2, 9.7.10.3, 9.7.10.4, 9.7.10.5, 9.7.10.6, 9.7.10.7, 9.7.10.8, 9.7.10.9, 9.7.10.10, 9.8.1.1, 9.8.1.2, 9.8.1.3, 9.8.1.4, 9.8.1.5, 9.8.1.6, 9.8.1.7, 9.8.1.8, 9.8.1.9, 9.8.1.10, 9.8.2.1, 9.8.2.2, 9.8.2.3, 9.8.2.4, 9.8.2.5, 9.8.2.6, 9.8.2.7, 9.8.2.8, 9.8.2.9, 9.8.2.10, 9.8.3.1, 9.8.3.2, 9.8.3.3, 9.8.3.4, 9.8.3.5, 9.8.3.6, 9.8.3.7, 9.8.3.8, 9.8.3.9, 9.8.3.10, 9.8.4.1, 9.8.4.2, 9.8.4.3, 9.8.4.4, 9.8.4.5, 9.8.4.6, 9.8.4.7, 9.8.4.8, 9.8.4.9, 9.8.4.10, 9.8.5.1, 9.8.5.2, 9.8.5.3, 9.8.5.4, 9.8.5.5, 9.8.5.6, 9.8.5.7, 9.8.5.8, 9.8.5.9, 9.8.5.10, 9.8.6.1, 9.8.6.2, 9.8.6.3, 9.8.6.4, 9.8.6.5, 9.8.6.6, 9.8.6.7, 9.8.6.8, 9.8.6.9, 9.8.6.10, 9.8.7.1, 9.8.7.2, 9.8.7.3, 9.8.7.4, 9.8.7.5, 9.8.7.6, 9.8.7.7, 9.8.7.8, 9.8.7.9, 9.8.7.10, 9.8.8.1, 9.8.8.2, 9.8.8.3, 9.8.8.4, 9.8.8.5, 9.8.8.6, 9.8.8.7, 9.8.8.8, 9.8.8.9, 9.8.8.10, 9.8.9.1, 9.8.9.2, 9.8.9.3, 9.8.9.4, 9.8.9.5, 9.8.9.6, 9.8.9.7, 9.8.9.8, 9.8.9.9, 9.8.9.10, 9.8.10.1, 9.8.10.2, 9.8.10.3, 9.8.10.4, 9.8.10.5, 9.8.10.6, 9.8.10.7, 9.8.10.8, 9.8.10.9, 9.8.10.10, 9.9.1.1, 9.9.1.2, 9.9.1.3, 9.9.1.4, 9.9.1.5, 9.9.1.6, 9.9.1.7, 9.9.1.8, 9.9.1.9, 9.9.1.10, 9.9.2.1, 9.9.2.2, 9.9.2.3, 9.9.2.4, 9.9.2.5, 9.9.2.6, 9.9.2.7, 9.9.2.8, 9.9.2.9, 9.9.2.10, 9.9.3.1, 9.9.3.2, 9.9.3.3, 9.9.3.4, 9.9.3.5, 9.9.3.6, 9.9.3.7, 9.9.3.8, 9.9.3.9, 9.9.3.10, 9.9.4.1, 9.9.4.2, 9.9.4.3, 9.9.4.4, 9.9.4.5, 9.9.4.6, 9.9.4.7, 9.9.4.8, 9.9.4.9, 9.9.4.10, 9.9.5.1, 9.9.5.2, 9.9.5.3, 9.9.5.4, 9.9.5.5, 9.9.5.6, 9.9.5.7, 9.9.5.8, 9.9.5.9, 9.9.5.10, 9.9.6.1, 9.9.6.2, 9.9.6.3, 9.9.6.4, 9.9.6.5, 9.9.6.6, 9.9.6.7, 9.9.6.8, 9.9.6.9, 9.9.6.10, 9.9.7.1, 9.9.7.2, 9.9.7.3, 9.9.7.4, 9.9.7.5, 9.9.7.6, 9.9.7.7, 9.9.7.8, 9.9.7.9, 9.9.7.10, 9.9.8.1, 9.9.8.2, 9.9.8.3, 9.9.8.4, 9.9.8.5, 9.9.8.6, 9.9.8.7, 9.9.8.8, 9.9.8.9, 9.9.8.10, 9.9.9.1, 9.9.9.2, 9.9.9.3, 9.9.9.4, 9.9.9.5, 9.9.9.6, 9.9.9.7, 9.9.9.8, 9.9.9.9, 9.9.9.10, 9.9.10.1, 9.9.10.2, 9.9.10.3, 9.9.10.4, 9.9.10.5, 9.9.10.6, 9.9.10.7, 9.9.10.8, 9.9.10.9, 9.9.10.10, 9.10.1.1, 9.10.1.2, 9.10.1.3, TABLE B-continued 9.10.1.4, 9.10.1.5, 9.10.1.6, 9.10.1.7, 9.10.1.8, 9.10.1.9, 9.10.1.10, 9.10.2.1, 9.10.2.2, 9.10.2.3, 9.10.2.4, 9.10.2.5, 9.10.2.6, 9.10.2.7, 9.10.2.8, 9.10.2.9, 9.10.2.10, 9.10.3.1, 9.10.3.2, 9.10.3.3, 9.10.3.4, 9.10.3.5, 9.10.3.6, 9.10.3.7, 9.10.3.8, 9.10.3.9, 9.10.3.10, 9.10.4.1, 9.10.4.2, 9.10.4.3, 9.10.4.4, 9.10.4.5, 9.10.4.6, 9.10.4.7, 9.10.4.8, 9.10.4.9, 9.10.4.10, 9.10.5.1, 9.10.5.2, 9.10.5.3, 9.10.5.4, 9.10.5.5, 9.10.5.6, 9.10.5.7, 9.10.5.8, 9.10.5.9, 9.10.5.10, 9.10.6.1, 9.10.6.2, 9.10.6.3, 9.10.6.4, 9.10.6.5, 9.10.6.6, 9.10.6.7, 9.10.6.8, 9.10.6.9, 9.10.6.10, 9.10.7.1, 9.10.7.2, 9.10.7.3, 9.10.7.4, 9.10.7.5, 9.10.7.6, 9.10.7.7, 9.10.7.8, 9.10.7.9, 9.10.7.10, 9.10.8.1, 9.10.8.2, 9.10.8.3, 9.10.8.4, 9.10.8.5, 9.10.8.6, 9.10.8.7, 9.10.8.8, 9.10.8.9, 9.10.8.10, 9.10.9.1, 9.10.9.2, 9.10.9.3, 9.10.9.4, 9.10.9.5, 9.10.9.6, 9.10.9.7, 9.10.9.8, 9.10.9.9, 9.10.9.10, 9.10.10.1, 9.10.10.2, 9.10.10.3, 9.10.10.4, 9.10.10.5, 9.10.10.6, 9.10.10.7, 9.10.10.8, 9.10.10.9, 9.10.10.10, 10.1.1.1, 10.1.1.2, 10.1.1.3, 10.1.1.4, 10.1.1.5, 10.1.1.6, 10.1.1.7, 10.1.1.8, 10.1.1.9, 10.1.1.10, 10.1.2.1, 10.1.2.2, 10.1.2.3, 10.1.2.4, 10.1.2.5, 10.1.2.6, 10.1.2.7, 10.1.2.8, 10.1.2.9, 10.1.2.10, 10.1.3.1, 10.1.3.2, 10.1.3.3, 10.1.3.4, 10.1.3.5, 10.1.3.6, 10.1.3.7, 10.1.3.8, 10.1.3.9, 10.1.3.10, 10.1.4.1, 10.1.4.2, 10.1.4.3, 10.1.4.4, 10.1.4.5, 10.1.4.6, 10.1.4.7, 10.1.4.8, 10.1.4.9, 10.1.4.10, 10.1.5.1, 10.1.5.2, 10.1.5.3, 10.1.5.4, 10.1.5.5, 10.1.5.6, 10.1.5.7, 10.1.5.8, 10.1.5.9, 10.1.5.10, 10.1.6.1, 10.1.6.2, 10.1.6.3, 10.1.6.4, 10.1.6.5, 10.1.6.6, 10.1.6.7, 10.1.6.8, 10.1.6.9, 10.1.6.10, 10.1.7.1, 10.1.7.2, 10.1.7.3, 10.1.7.4, 10.1.7.5, 10.1.7.6, 10.1.7.7, 10.1.7.8, 10.1.7.9, 10.1.7.10, 10.1.8.1, 10.1.8.2, 10.1.8.3, 10.1.8.4, 10.1.8.5, 10.1.8.6, 10.1.8.7, 10.1.8.8, 10.1.8.9, 10.1.8.10, 10.1.9.1, 10.1.9.2, 10.1.9.3, 10.1.9.4, 10.1.9.5, 10.1.9.6, 10.1.9.7, 10.1.9.8, 10.1.9.9, 10.1.9.10, 10.1.10.1, 10.1.10.2, 10.1.10.3, 10.1.10.4, 10.1.10.5, 10.1.10.6, 10.1.10.7, 10.1.10.8, 10.1.10.9, 10.1.10.10, 10.2.1.1, 10.2.1.2, 10.2.1.3, 10.2.1.4, 10.2.1.5, 10.2.1.6, 10.2.1.7, 10.2.1.8, 10.2.1.9, 10.2.1.10, 10.2.2.1, 10.2.2.2, 10.2.2.3, 10.2.2.4, 10.2.2.5, 10.2.2.6, 10.2.2.7, 10.2.2.8, 10.2.2.9, 10.2.2.10, 10.2.3.1, 10.2.3.2, 10.2.3.3, 10.2.3.4, 10.2.3.5, 10.2.3.6, 10.2.3.7, 10.2.3.8, 10.2.3.9, 10.2.3.10, 10.2.4.1, 10.2.4.2, 10.2.4.3, 10.2.4.4, 10.2.4.5, 10.2.4.6, 10.2.4.7, 10.2.4.8, 10.2.4.9, 10.2.4.10, 10.2.5.1, 10.2.5.2, 10.2.5.3, 10.2.5.4, 10.2.5.5, 10.2.5.6, 10.2.5.7, 10.2.5.8, 10.2.5.9, 10.2.5.10, 10.2.6.1, 10.2.6.2, 10.2.6.3, 10.2.6.4, 10.2.6.5, 10.2.6.6, 10.2.6.7, 10.2.6.8, 10.2.6.9, 10.2.6.10, 10.2.7.1, 10.2.7.2, 10.2.7.3, 10.2.7.4, 10.2.7.5, 10.2.7.6, 10.2.7.7, 10.2.7.8, 10.2.7.9, 10.2.7.10, 10.2.8.1, 10.2.8.2, 10.2.8.3, 10.2.8.4, 10.2.8.5, 10.2.8.6, 10.2.8.7, 10.2.8.8, 10.2.8.9, 10.2.8.10, 10.2.9.1, 10.2.9.2, 10.2.9.3, 10.2.9.4, 10.2.9.5, 10.2.9.6, 10.2.9.7, 10.2.9.8, 10.2.9.9, 10.2.9.10, 10.2.10.1, 10.2.10.2, 10.2.10.3, 10.2.10.4, 10.2.10.5, 10.2.10.6, 10.2.10.7, 10.2.10.8, 10.2.10.9, 10.2.10.10, 10.3.1.1, 10.3.1.2, 10.3.1.3, 10.3.1.4, 10.3.1.5, 10.3.1.6, 10.3.1.7, 10.3.1.8, 10.3.1.9, 10.3.1.10, 10.3.2.1, 10.3.2.2, 10.3.2.3, 10.3.2.4, 10.3.2.5, 10.3.2.6, 10.3.2.7, 10.3.2.8, 10.3.2.9, 10.3.2.10, 10.3.3.1, 10.3.3.2, 10.3.3.3, 10.3.3.4, 10.3.3.5, 10.3.3.6, 10.3.3.7, 10.3.3.8, 10.3.3.9, 10.3.3.10, 10.3.4.1, 10.3.4.2, 10.3.4.3, 10.3.4.4, 10.3.4.5, 10.3.4.6, 10.3.4.7, 10.3.4.8, 10.3.4.9, 10.3.4.10, 10.3.5.1, 10.3.5.2, 10.3.5.3, 10.3.5.4, 10.3.5.5, 10.3.5.6, 10.3.5.7, 10.3.5.8, 10.3.5.9, 10.3.5.10, 10.3.6.1, 10.3.6.2, 10.3.6.3, 10.3.6.4, 10.3.6.5, 10.3.6.6, 10.3.6.7, 10.3.6.8, 10.3.6.9, 10.3.6.10, 10.3.7.1, 10.3.7.2, 10.3.7.3, 10.3.7.4, 10.3.7.5, 10.3.7.6, 10.3.7.7, 10.3.7.8, 10.3.7.9, 10.3.7.10, 10.3.8.1, 10.3.8.2, 10.3.8.3, 10.3.8.4, 10.3.8.5, 10.3.8.6, 10.3.8.7, 10.3.8.8, 10.3.8.9, 10.3.8.10, 10.3.9.1, 10.3.9.2, 10.3.9.3, 10.3.9.4, 10.3.9.5, 10.3.9.6, 10.3.9.7, 10.3.9.8, 10.3.9.9, 10.3.9.10, 10.3.10.1, 10.3.10.2, 10.3.10.3, 10.3.10.4, 10.3.10.5, 10.3.10.6, 10.3.10.7, 10.3.10.8, 10.3.10.9, 10.3.10.10, 10.4.1.1, 10.4.1.2, 10.4.1.3, 10.4.1.4, 10.4.1.5, 10.4.1.6, 10.4.1.7, 10.4.1.8, 10.4.1.9, 10.4.1.10, 10.4.2.1, 10.4.2.2, 10.4.2.3, 10.4.2.4, 10.4.2.5, 10.4.2.6, 10.4.2.7, 10.4.2.8, 10.4.2.9, 10.4.2.10, 10.4.3.1, 10.4.3.2, 10.4.3.3, 10.4.3.4, 10.4.3.5, 10.4.3.6, 10.4.3.7, 10.4.3.8, 10.4.3.9, 10.4.3.10, 10.4.4.1, 10.4.4.2, 10.4.4.3, 10.4.4.4, 10.4.4.5, 10.4.4.6, 10.4.4.7, 10.4.4.8, 10.4.4.9, 10.4.4.10, 10.4.5.1, 10.4.5.2, 10.4.5.3, 10.4.5.4, 10.4.5.5, 10.4.5.6, 10.4.5.7, 10.4.5.8, 10.4.5.9, 10.4.5.10, 10.4.6.1, 10.4.6.2, 10.4.6.3, 10.4.6.4, 10.4.6.5, 10.4.6.6, 10.4.6.7, 10.4.6.8, 10.4.6.9, 10.4.6.10, 10.4.7.1, 10.4.7.2, 10.4.7.3, 10.4.7.4, 10.4.7.5, 10.4.7.6, 10.4.7.7, 10.4.7.8, 10.4.7.9, 10.4.7.10, 10.4.8.1, 10.4.8.2, 10.4.8.3, 10.4.8.4, 10.4.8.5, 10.4.8.6, 10.4.8.7, 10.4.8.8, 10.4.8.9, 10.4.8.10, 10.4.9.1, 10.4.9.2, 10.4.9.3, 10.4.9.4, 10.4.9.5, 10.4.9.6, 10.4.9.7, 10.4.9.8, 10.4.9.9, 10.4.9.10, 10.4.10.1, 10.4.10.2, 10.4.10.3, 10.4.10.4, 10.4.10.5, 10.4.10.6, 10.4.10.7, 10.4.10.8, 10.4.10.9, 10.4.10.10, 10.5.1.1, 10.5.1.2, 10.5.1.3, 10.5.1.4, 10.5.1.5, 10.5.1.6, 10.5.1.7, 10.5.1.8, 10.5.1.9, 10.5.1.10, 10.5.2.1, 10.5.2.2, 10.5.2.3, 10.5.2.4, 10.5.2.5, 10.5.2.6, 10.5.2.7, 10.5.2.8, 10.5.2.9, 10.5.2.10, 10.5.3.1, 10.5.3.2, 10.5.3.3, 10.5.3.4, 10.5.3.5, 10.5.3.6, 10.5.3.7, 10.5.3.8, 10.5.3.9, 10.5.3.10, 10.5.4.1, 10.5.4.2, 10.5.4.3, 10.5.4.4, 10.5.4.5, 10.5.4.6, 10.5.4.7, 10.5.4.8, 10.5.4.9, 10.5.4.10, 10.5.5.1, 10.5.5.2, 10.5.5.3, 10.5.5.4, 10.5.5.5, 10.5.5.6, 10.5.5.7, 10.5.5.8, 10.5.5.9, 10.5.5.10, 10.5.6.1, 10.5.6.2, 10.5.6.3, 10.5.6.4, 10.5.6.5, 10.5.6.6, 10.5.6.7, 10.5.6.8, 10.5.6.9, 10.5.6.10, 10.5.7.1, 10.5.7.2, 10.5.7.3, 10.5.7.4, 10.5.7.5, 10.5.7.6, 10.5.7.7, 10.5.7.8, 10.5.7.9, 10.5.7.10, 10.5.8.1, 10.5.8.2, 10.5.8.3, 10.5.8.4, 10.5.8.5, 10.5.8.6, 10.5.8.7, 10.5.8.8, 10.5.8.9, 10.5.8.10, 10.5.9.1, 10.5.9.2, 10.5.9.3, 10.5.9.4, 10.5.9.5, 10.5.9.6, 10.5.9.7, 10.5.9.8, 10.5.9.9, 10.5.9.10, 10.5.10.1, 10.5.10.2, 10.5.10.3, 10.5.10.4, 10.5.10.5, 10.5.10.6, 10.5.10.7, 10.5.10.8, 10.5.10.9, 10.5.10.10, 10.6.1.1, 10.6.1.2, 10.6.1.3, 10.6.1.4, 10.6.1.5, 10.6.1.6, 10.6.1.7, 10.6.1.8, 10.6.1.9, 10.6.1.10, 10.6.2.1, 10.6.2.2, 10.6.2.3, 10.6.2.4, 10.6.2.5, 10.6.2.6, 10.6.2.7, 10.6.2.8, 10.6.2.9, 10.6.2.10, 10.6.3.1, 10.6.3.2, 10.6.3.3, 10.6.3.4, 10.6.3.5, 10.6.3.6, 10.6.3.7, 10.6.3.8, 10.6.3.9, 10.6.3.10, 10.6.4.1, 10.6.4.2, 10.6.4.3, 10.6.4.4, 10.6.4.5, 10.6.4.6, 10.6.4.7, 10.6.4.8, 10.6.4.9, 10.6.4.10, 10.6.5.1, 10.6.5.2, 10.6.5.3, 10.6.5.4, 10.6.5.5, 10.6.5.6, 10.6.5.7, 10.6.5.8, 10.6.5.9, 10.6.5.10, 10.6.6.1, 10.6.6.2, 10.6.6.3, 10.6.6.4, 10.6.6.5, 10.6.6.6, 10.6.6.7, 10.6.6.8, 10.6.6.9, 10.6.6.10, 10.6.7.1, 10.6.7.2, 10.6.7.3, 10.6.7.4, 10.6.7.5, 10.6.7.6, 10.6.7.7, 10.6.7.8, 10.6.7.9, 10.6.7.10, 10.6.8.1, 10.6.8.2, 10.6.8.3, 10.6.8.4, 10.6.8.5, 10.6.8.6, 10.6.8.7, 10.6.8.8, 10.6.8.9, 10.6.8.10, 10.6.9.1, 10.6.9.2, 10.6.9.3, 10.6.9.4, 10.6.9.5, 10.6.9.6, 10.6.9.7, 10.6.9.8, 10.6.9.9, 10.6.9.10, 10.6.10.1, 10.6.10.2, 10.6.10.3, 10.6.10.4, 10.6.10.5, 10.6.10.6, 10.6.10.7, 10.6.10.8, 10.6.10.9, 10.6.10.10, 10.7.1.1, 10.7.1.2, 10.7.1.3, 10.7.1.4, 10.7.1.5, 10.7.1.6, 10.7.1.7, 10.7.1.8, 10.7.1.9, 10.7.1.10, 10.7.2.1, 10.7.2.2, 10.7.2.3, 10.7.2.4, 10.7.2.5, 10.7.2.6, TABLE B-continued 10.7.2.7, 10.7.2.8, 10.7.2.9, 10.7.2.10, 10.7.3.1, 10.7.3.2, 10.7.3.3, 10.7.3.4, 10.7.3.5,
10.7.3.6, 10.7.3.7, 10.7.3.8, 10.7.3.9, 10.7.3.10, 10.7.4.1, 10.7.4.2, 10.7.4.3, 10.7.4.4,
10.7.4.5, 10.7.4.6, 10.7.4.7, 10.7.4.8, 10.7.4.9, 10.7.4.10, 10.7.5.1, 10.7.5.2, 10.7.5.3,
10.7.5.4, 10.7.5.5, 10.7.5.6, 10.7.5.7, 10.7.5.8, 10.7.5.9, 10.7.5.10, 10.7.6.1, 10.7.6.2,
10.7.6.3, 10.7.6.4, 10.7.6.5, 10.7.6.6, 10.7.6.7, 10.7.6.8, 10.7.6.9, 10.7.6.10, 10.7.7.1,
10.7.7.2, 10.7.7.3, 10.7.7.4, 10.7.7.5, 10.7.7.6, 10.7.7.7, 10.7.7.8, 10.7.7.9, 10.7.7.10,
10.7.8.1, 10.7.8.2, 10.7.8.3, 10.7.8.4, 10.7.8.5, 10.7.8.6, 10.7.8.7, 10.7.8.8, 10.7.8.9,
10.7.8.10, 10.7.9.1, 10.7.9.2, 10.7.9.3, 10.7.9.4, 10.7.9.5, 10.7.9.6, 10.7.9.7, 10.7.9.8,
10.7.9.9, 10.7.9.10, 10.7.10.1, 10.7.10.2, 10.7.10.3, 10.7.10.4, 10.7.10.5, 10.7.10.6,
10.7.10.7, 10.7.10.8, 10.7.10.9, 10.7.10.10, 10.8.1.1, 10.8.1.2, 10.8.1.3, 10.8.1.4, 10.8.1.5,
10.8.1.6, 10.8.1.7, 10.8.1.8, 10.8.1.9, 10.8.1.10, 10.8.2.1, 10.8.2.2, 10.8.2.3, 10.8.2.4,
10.8.2.5, 10.8.2.6, 10.8.2.7, 10.8.2.8, 10.8.2.9, 10.8.2.10, 10.8.3.1, 10.8.3.2, 10.8.3.3,
10.8.3.4, 10.8.3.5, 10.8.3.6, 10.8.3.7, 10.8.3.8, 10.8.3.9, 10.8.3.10, 10.8.4.1, 10.8.4.2,
10.8.4.3, 10.8.4.4, 10.8.4.5, 10.8.4.6, 10.8.4.7, 10.8.4.8, 10.8.4.9, 10.8.4.10, 10.8.5.1,
10.8.5.2, 10.8.5.3, 10.8.5.4, 10.8.5.5, 10.8.5.6, 10.8.5.7, 10.8.5.8, 10.8.5.9, 10.8.5.10,
10.8.6.1, 10.8.6.2, 10.8.6.3, 10.8.6.4, 10.8.6.5, 10.8.6.6, 10.8.6.7, 10.8.6.8, 10.8.6.9,
10.8.6.10, 10.8.7.1, 10.8.7.2, 10.8.7.3, 10.8.7.4, 10.8.7.5, 10.8.7.6, 10.8.7.7, 10.8.7.8,
10.8.7.9, 10.8.7.10, 10.8.8.1, 10.8.8.2, 10.8.8.3, 10.8.8.4, 10.8.8.5, 10.8.8.6, 10.8.8.7,
10.8.8.8, 10.8.8.9, 10.8.8.10, 10.8.9.1, 10.8.9.2, 10.8.9.3, 10.8.9.4, 10.8.9.5, 10.8.9.6,
10.8.9.7, 10.8.9.8, 10.8.9.9, 10.8.9.10, 10.8.10.1, 10.8.10.2, 10.8.10.3, 10.8.10.4, 10.8.10.5,
10.8.10.6, 10.8.10.7, 10.8.10.8, 10.8.10.9, 10.8.10.10, 10.9.1.1, 10.9.1.2, 10.9.1.3, 10.9.1.4,
10.9.1.5, 10.9.1.6, 10.9.1.7, 10.9.1.8, 10.9.1.9, 10.9.1.10, 10.9.2.1, 10.9.2.2, 10.9.2.3,
10.9.2.4, 10.9.2.5, 10.9.2.6, 10.9.2.7, 10.9.2.8, 10.9.2.9, 10.9.2.10, 10.9.3.1, 10.9.3.2,
10.9.3.3, 10.9.3.4, 10.9.3.5, 10.9.3.6, 10.9.3.7, 10.9.3.8, 10.9.3.9, 10.9.3.10, 10.9.4.1,
10.9.4.2, 10.9.4.3, 10.9.4.4, 10.9.4.5, 10.9.4.6, 10.9.4.7, 10.9.4.8, 10.9.4.9, 10.9.4.10,
10.9.5.1, 10.9.5.2, 10.9.5.3, 10.9.5.4, 10.9.5.5, 10.9.5.6, 10.9.5.7, 10.9.5.8, 10.9.5.9,
10.9.5.10, 10.9.6.1, 10.9.6.2, 10.9.6.3, 10.9.6.4, 10.9.6.5, 10.9.6.6, 10.9.6.7, 10.9.6.8,
10.9.6.9, 10.9.6.10, 10.9.7.1, 10.9.7.2, 10.9.7.3, 10.9.7.4, 10.9.7.5, 10.9.7.6, 10.9.7.7,
10.9.7.8, 10.9.7.9, 10.9.7.10, 10.9.8.1, 10.9.8.2, 10.9.8.3, 10.9.8.4, 10.9.8.5, 10.9.8.6,
10.9.8.7, 10.9.8.8, 10.9.8.9, 10.9.8.10, 10.9.9.1, 10.9.9.2, 10.9.9.3, 10.9.9.4, 10.9.9.5,
10.9.9.6, 10.9.9.7, 10.9.9.8, 10.9.9.9, 10.9.9.10, 10.9.10.1, 10.9.10.2, 10.9.10.3, 10.9.10.4,
10.9.10.5, 10.9.10.6, 10.9.10.7, 10.9.10.8, 10.9.10.9, 10.9.10.10, 10.10.1.1, 10.10.1.2,
10.10.1.3, 10.10.1.4, 10.10.1.5, 10.10.1.6, 10.10.1.7, 10.10.1.8, 10.10.1.9, 10.10.1.10,
10.10.2.1, 10.10.2.2, 10.10.2.3, 10.10.2.4, 10.10.2.5, 10.10.2.6, 10.10.2.7, 10.10.2.8,
10.10.2.9, 10.10.2.10, 10.10.3.1, 10.10.3.2, 10.10.3.3, 10.10.3.4, 10.10.3.5, 10.10.3.6,
10.10.3.7, 10.10.3.8, 10.10.3.9, 10.10.3.10, 10.10.4.1, 10.10.4.2, 10.10.4.3, 10.10.4.4,
10.10.4.5, 10.10.4.6, 10.10.4.7, 10.10.4.8, 10.10.4.9, 10.10.4.10, 10.10.5.1, 10.10.5.2,
10.10.5.3, 10.10.5.4, 10.10.5.5, 10.10.5.6, 10.10.5.7, 10.10.5.8, 10.10.5.9, 10.10.5.10,
10.10.6.1, 10.10.6.2, 10.10.6.3, 10.10.6.4, 10.10.6.5, 10.10.6.6, 10.10.6.7, 10.10.6.8,
10.10.6.9, 10.10.6.10, 10.10.7.1, 10.10.7.2, 10.10.7.3, 10.10.7.4, 10.10.7.5, 10.10.7.6,
10.10.7.7, 10.10.7.8, 10.10.7.9, 10.10.7.10, 10.10.8.1, 10.10.8.2, 10.10.8.3, 10.10.8.4,
10.10.8.5, 10.10.8.6, 10.10.8.7, 10.10.8.8, 10.10.8.9, 10.10.8.10, 10.10.9.1, 10.10.9.2,
10.10.9.3, 10.10.9.4, 10.10.9.5, 10.10.9.6, 10.10.9.7, 10.10.9.8, 10.10.9.9, 10.10.9.10,
10.10.10.1, 10.10.10.2, 10.10.10.3, 10.10.10.4, 10.10.10.5, 10.10.10.6, 10.10.10.7,
10.10.10.8, 10.10.10.9, 10.10.10.10

Additional exemplary compound groups include the following compound groups disclosed below. Unless otherwise specified, the configurations of all hydrogen atoms and R groups for the following compound groups are as defined for the group 1 compounds above. As is apparent from the description, each of the compound groups disclose a number of unique compounds or generic structures. The compounds or generic structures specifically described in any of the compound groups are thus exemplary only and the remaining compounds or structures in each group are described by Tables A and B.

As used in the description of compounds in the compound groups, the definitive structure of compounds in the various compound groups is specified only by the structure defining portion of the compound group and in Tables A and B, which together definitively name or specify individual compound or genus structures. The structure-defining portion of the compound groups is generally contained in the first sentence of the compound groups below and in the following paragraph. This applies regardless of any name or structure, including chemical names in the exemplary compounds that are named in some of the compound groups. Thus, any name or structure for any compound or compound genus that refers to a compound or genus in a compound group and is given anywhere in the disclosure is intended only to refer to the compound or genus that is definitively specified by the compound groups together with Tables A and B.

For the following compound groups, reference to an androstene or a 5α-androstene with no double bond at the 4-5 or 5-6 position means that the hydrogen atom or other moiety at the 5-position is in the α-configuration. For androstenes with no double bond at the 4-5 or 5-6 position and a hydrogen atom or other moiety at the 5-position in the β-configuration will usually be referred to as a 5β-androstene. For compound groups where a double bond is present at the 1-2 or 2-3 position and/or when $R^9$ is substituted, $R^9$ will be =CH—, =$CR^{10}$—, —$CHR^{10}$—, —$C(R^{10})_2$— or another moiety defined for $R^9$ herein, instead of —$CH_2$—. For compound groups where a double bond is present at the 9-11 position and/or when $R^8$ is substituted, $R^8$ will be =CH—, =$CR^{10}$—, —$CHR^{10}$—, —$C(R^{10})_2$— or another moiety defined for $R^8$ herein, instead of —$CH_2$—. 9-11 and/or 15-16 positions. For compound groups where a double bond is present at the 15-16 position and/or when $R^7$ is substituted, $R^7$ will be =CH—, =$CR^{10}$—, —$CHR^{10}$—, —$C(R^{10})_2$— or another moiety defined for $R^7$ herein, instead of —$CH_2$—.

Group 2. This group comprises compounds named in Table B having $R^1$, $R^2$, $R^3$ and $R^4$ substituents defined in Table A wherein the $R^1$, $R^2$, $R^3$ and $R^4$ substituents are bonded to the steroid nucleus described for group 1 compounds, except that $R^{10E}$ is hydrogen in the β-configuration. Exemplary group 2 compounds include 1.2.4.1, which is 3,7β-dihydroxy-16α-fluoro-17β-amino-5β-androst-1,3-diene, 1.1.5.9, which is 3,17β-dihydroxy-5β-androst-1,3-diene, 1.1.7.1, which is 3-hydroxy-16α-acetoxy-17β-amino-5β-androst-1,3-diene and compound 1.1.4.10, which is 3-hydroxy-16α-fluoro-17β-acetoxy-5β-androst-1,3-diene. Other exemplary group 2 compounds include 3,17β-dihydroxy-7β-acetoxy-5β-androst-1,3-diene, 3,17β-dihydroxy-7β-methyl-5β-androst-1,3-diene, 3,17β-dihydroxy-7β-methoxy-5β-androst-1,3-diene, 3,7β,17β-trihydroxy-5β-androst-1,3-diene, 3-amino-17β-hydroxy-5β-androst-1,3-diene, 3-amino-7β,17β-dihydroxy-5β-androst-1,3-diene, 3-hydroxy-17β-amino-5β-androst-1,3-diene, 3,7β-dihydroxy-17β-amino-5β-androst-1,3-diene, 3,17β-dihydroxy-7β-amino-5β-androst-1,3-diene, 3-hydroxy-7β,17β-diacetylamino-5β-androst-1,3-diene, 3-hydroxy-7β,17β-dimethylamino-5β-androst-1,3-diene and 16α-hydroxy, 16α-methyl, 16α-amino, 16α-aminomethyl, 16α-acetate and 16α-halo analogs of any of these compounds.

Group 3. This group comprises compounds named in Table B having $R^1$, $R^2$, $R^3$ and $R^4$ substituents defined in Table A wherein the $R^1$, $R^2$, $R^3$ and $R^4$ substituents are bonded to the steroid nucleus described for group 1 compounds, except that $R^{10E}$ is absent and double bonds are present at the 1-2, 3-4 and 5-6 positions. Exemplary group 3 compounds include 1.2.4.1, which is 3,7β-dihydroxy-16α-fluoro-17β-aminoandrost-1,3,5-triene, 1.1.5.9, which is 3,17β-dihydroxyandrost-1,3,5-triene, 1.1.7.1, which is 3-hydroxy-16α-acetoxy-17β-aminoandrost-1,3,5-triene and compound 1.1.4.10, which is 3-hydroxy-16α-fluoro-17β-acetoxyandrost-1,3,5-triene.

Other exemplary group 3 compounds include 3,17β-dihydroxy-7β-acetoxyandrost-1,3,5-triene, 3,17β-dihydroxy-7β-methylandrost-1,3,5-triene, 3,17β-dihydroxy-7β-methoxyandrost-1,3,5-triene, 3,7β,17β-trihydroxyandrost-1,3,5-triene, 3-amino-17β-hydroxyandrost-1,3,5-triene, 3-amino-7β,17β-dihydroxyandrost-1,3,5-triene, 3-hydroxy-17β-aminoandrost-1,3,5-triene, 3,7β-dihydroxy-17β-aminoandrost-1,3,5-triene, 3,17β-dihydroxy-7β-aminoandrost-1,3,5-triene, 3-hydroxy-7β,17β-diacetylaminoandrost-1,3,5-triene, 3-hydroxy-7β,17β-dimethylaminoandrost-1,3,5-triene and 16α-hydroxy, 16α-methyl, 16α-amino, 16α-aminomethyl, 16α-acetate and 16α-halo analogs of any of these compounds.

Group 4. This group comprises compounds named in Table B having $R^1$, $R^2$, $R^3$ and $R^4$ substituents defined in Table A wherein the $R^1$, $R^2$, $R^3$ and $R^4$ substituents are bonded to the steroid nucleus described for group 1 compounds, except that double bonds are present at the 1-2, 3-4 and 16-17 positions. Exemplary group 4 compounds include 1.2.4.1, which is 3,7β-dihydroxy-16-fluoro-17-aminoandrost-1,3,16-triene, 1.1.5.9, which is 3,17-dihydroxyandrost-1,3,16-triene, 1.1.7.1, which is 3-hydroxy-16-acetoxy-17-aminoandrost-1,3,16-triene and compound 1.1.4.10, which is 3-hydroxy-16-fluoro-17-acetoxyandrost-1,3,16-triene. Other exemplary group 4 compounds include 3,17-dihydroxy-7β-acetoxyandrost-1,3,16-triene, 3,17-dihydroxy-7β-methylandrost-1,3,16-triene, 3,17-dihydroxy-7β-methoxyandrost-1,3,16-triene, 3,7β,17-trihydroxyandrost-1,3,16-triene, 3-amino-17-hydroxyandrost-1,3,16-triene, 3-amino-7β,17-dihydroxyandrost-1,3,16-triene, 3-hydroxy-17-aminoandrost-1,3,16-triene, 3,7β-dihydroxy-17-aminoandrost-1,3,16-triene, 3,17-dihydroxy-7β-aminoandrost-1,3,16-triene, 3-hydroxy-7β,17-diacetylaminoandrost-1,3,16-triene, 3-hydroxy-7β,17-dimethylaminoandrost-1,3,16-triene and 16-hydroxy, 16-methyl, 16-amino, 16-aminomethyl, 16-acetate and 16-halo analogs of any of these compounds.

Group 5. This group comprises compounds named in Table B having $R^1$, $R^2$, $R^3$ and $R^4$ substituents defined in Table A wherein the $R^1$, $R^2$, $R^3$ and $R^4$ substituents are bonded to the steroid nucleus described for group 1 compounds, except that $R^{10E}$ is present in the β-configuration and double bonds are present at the 1-2, 3-4 and 16-17 positions. Exemplary group 5 compounds include 1.2.4.1, which is 3,7β-dihydroxy-16-fluoro-17-amino-5β-androst-1,3,16-triene, 1.1.5.9, which is 3,17-dihydroxy-5β-androst-1,3,16-triene, 1.1.7.1, which is 3-hydroxy-16-acetoxy-17-amino-5β-androst-1,3,16-triene and compound 1.1.4.10, which is 3-hydroxy-16-fluoro-17-acetoxy-5β-androst-1,3,16-triene. Other exemplary group 5 compounds include 3,17-dihydroxy-7β-acetoxy-5β-androst-1,3,16-triene, 3,17-dihydroxy-7β-methyl-5β-androst-1,3,16-triene, 3,17-dihydroxymethoxy-5β-androst-1,3,16-triene, 3,7β,17-trihydroxy-5β-androst-1,3,16-triene, 3-amino-17-hydroxy-5β-androst-1,3,16-triene, 3-amino-7β,17-dihydroxy-5β-androst-1,3,16-triene, 3-hydroxy-17-amino-5β-androst-1,3,16-triene, 3,7β-dihydroxy-17-amino-5β-androst-1,3,16-triene, 3,17-dihydroxy-7β-amino-5β-androst-1,3,16-triene, 3-hydroxy-7β,17-diacetylamino-5β-androst-1,3,16-triene, 3-hydroxy-7β,17-dimethylamino-5β-androst-1,3,16-triene and 16-hydroxy, 16-methyl, 16-amino, 16-aminomethyl, 16-acetate and 16-halo analogs of any of these compounds.

Group 6. This group comprises compounds named in Table B having $R^1$, $R^2$, $R^3$ and $R^4$ substituents defined in Table A wherein the $R^1$, $R^2$, $R^3$ and $R^4$ substituents are bonded to the steroid nucleus described for group 1 compounds, except that $R^1$ is in the β-configuration, $R^{10E}$ is absent and double bonds are present at the 1-2 and 5-6 positions. Exemplary group 6 compounds include 1.2.4.1, which is 3β,7β-dihydroxy-16α-fluoro-17β-aminoandrost-1,5-diene, 1.1.5.9, which is 3β,17β-dihydroxyandrost-1,5-diene, 1.1.7.1, which is 3β-hydroxy-16α-acetoxy-17β-aminoandrost-1,5-diene and compound 1.1.4.10, which is 3β-hydroxy-16α-fluoro-17β-acetoxyandrost-1,5-diene. Other exemplary group 6 compounds include 3β,17β-dihydroxy-7β-acetoxyandrost-1,5-diene, 3β,17β-dihydroxy-7β-methylandrost-1,5-diene, 3β,17β-dihydroxy-7β-methoxyandrost-1,5-diene, 3β,7β,17β-trihydroxyandrost-1,5-diene, 3β-amino-17β-hydroxyandrost-1,5-diene, 3β-amino-7β,17β-dihydroxyandrost-1,5-diene, 3β-hydroxy-17β-aminoandrost-1,5-diene, 3β,7β-dihydroxy-17β-aminoandrost-1,5-diene, 3β,17β-dihydroxy-7β-aminoandrost-1,5-diene, 3β-hydroxy-7β,17β-diacetylaminoandrost-1,5-diene, 3β-hydroxy-7β,17β-dimethylaminoandrost-1,5-diene and 16α-hydroxy, 16α-methyl, 16α-amino, 16α-aminomethyl, 16α-acetate and 16α-halo analogs of any of these compounds.

Group 7. This group comprises compounds named in Table B having $R^1$, $R^2$, $R^3$ and $R^4$ substituents defined in Table A wherein the $R^1$, $R^2$, $R^3$ and $R^4$ substituents are bonded to the steroid nucleus described for group 1 compounds, except that $R^1$ is in the β-configuration and double bonds are present at the 1-2 and 6-7 positions. Exemplary group 7 compounds include 1.2.4.1, which is 3β,7β-dihydroxy-16α-fluoro-17β-aminoandrost-1,6-diene, 1.1.5.9, which is 3β,17β-dihydroxyandrost-1,6-diene, 1.1.7.1, which is 3β-hydroxy-16α-acetoxy-17β-aminoandrost-1,6-diene and compound 1.1.4.10, which is 3β-hydroxy-16α-fluoro-17β-acetoxyandrost-1,6-diene. Other exemplary group 7 compounds include 3β,17β-dihydroxy-7-acetoxyandrost-1,6-diene, 3β,17β-dihydroxy-7-methylandrost-1,6-diene, 3β,17β-dihydroxy-7-methoxyandrost-1,6-diene, 3β,7,17β-trihydroxyandrost-1,6-diene, 3β-amino-17β-hydroxyandrost-1,6-diene, 3β-amino-7,17β-dihydroxyandrost-1,6-diene, 3β-hydroxy-17β-aminoandrost-1,6-diene, 3β,7-dihydroxy-17β-aminoandrost-1,6-diene, 3β,17β-dihydroxy-7β-aminoandrost-1,6-diene, 3β-hydroxy-7,17β-diacetylaminoandrost-1,6- diene, 3β-hydroxy-7,17β-dimethylaminoandrost-1,6-diene and 16α-hydroxy, 16α-methyl, 16α-amino, 16α-aminomethyl, 16α-acetate and 16α-halo analogs of any of these compounds.

Group 8. This group comprises compounds named in Table B having $R^1$, $R^2$, $R^3$ and $R^4$ substituents defined in Table A wherein the $R^1$, $R^2$, $R^3$ and $R^4$ substituents are bonded to the steroid nucleus described for group 1 compounds, except that $R^1$ is in the β-configuration, $R^{10E}$ is in the β-configuration and double bonds are present at the 1-2 and 6-7 positions. Exemplary group 8 compounds include 1.2.4.1, which is 3β,7β-dihydroxy-16α-fluoro-17β-amino-5β-androst-1,6-diene, 1.1.5.9, which is 3β,17β-dihydroxy-5β-androst-1,6-diene, 1.1.7.1, which is 3β-hydroxy-16α-acetoxy-17β-amino-5β-androst-1,6-diene and compound 1.1.4.10, which is 3β-hydroxy-16α-fluoro-17β-acetoxy-5β-androst-1,6-diene. Other exemplary group 8 compounds include 3β,17β-dihydroxy-7-acetoxy-5β-androst-1,6-diene, 3β,17β-dihydroxy-7-methyl-5β-androst-1,6-diene, 3β,17β-dihydroxy-7-methoxy-5β-androst-1,6-diene, 3β,7,17β-trihydroxy-5β-androst-1,6-diene, 3β-amino-17β-hydroxy-5β-androst-1,6-diene, 3β-amino-7,17β-dihydroxy-5β-androst-1,6-diene, 3β-hydroxy-17β-amino-5β-androst-1,6-diene, 3β,7-dihydroxy-17β-amino-5β-androst-1,6-diene, 3β,17β-dihydroxy-7β-amino-5β-androst-1,6-diene, 3β-hydroxy-7,17β-diacetylamino-5β-androst-1,6-diene, 3β-hydroxy-7,17β-dimethylamino-5β-androst-1,6-diene and 16α-hydroxy, 16α-methyl, 16α-amino, 16α-aminomethyl, 16α-acetate and 16α-halo analogs of any of these compounds.

Group 9. This group comprises compounds named in Table B having $R^1$, $R^2$, $R^3$ and $R^4$ substituents defined in Table A wherein the $R^1$, $R^2$, $R^3$ and $R^4$ substituents are bonded to the steroid nucleus described for group 1 compounds, except that $R^1$ is in the β-configuration, $R^{10F}$ is absent and double bonds are present at the 1-2 and 7-8 positions. Exemplary group 9 compounds include 1.2.4.1, which is 3β,7β-dihydroxy-16α-fluoro-17β-aminoandrost-1,7-diene, 1.1.5.9, which is 3β,17β-dihydroxyandrost-1,7-diene, 1.1.7.1, which is 3β-hydroxy-16α-acetoxy-17β-aminoandrost-1,7-diene and compound 1.1.4.10, which is 3β-hydroxy-16α-fluoro-17β-acetoxyandrost-1,7-diene. Other exemplary group 9 compounds include 3β,17β-dihydroxy-7-acetoxyandrost-1,7-diene, 3β,17β-dihydroxy-7-methylandrost-1,7-diene, 3β,17β-dihydroxy-7-methoxyandrost-1,7-diene, 3β,7,17β-trihydroxyandrost-1,7-diene, 3β-amino-17β-hydroxyandrost-1,7-diene, 3β-amino-7,17β-dihydroxyandrost-1,7-diene, 3β-hydroxy-17β-aminoandrost-1,7-diene, 3β,7-dihydroxy-17β-aminoandrost-1,7-diene, 3β,17-dihydroxy-7β-aminoandrost-1,7-diene, 3β-hydroxy-7,17β-diacetylaminoandrost-1,7-diene, 3β-hydroxy-7,17β-dimethylaminoandrost-1,7-diene and 16α-hydroxy, 16α-methyl, 16α-amino, 16α-aminomethyl, 16α-acetate and 16α-halo analogs of any of these compounds.

Group 10. This group comprises compounds named in Table B having $R^1$, $R^2$, $R^3$ and $R^4$ substituents defined in Table A wherein the $R^1$, $R^2$, $R^3$ and $R^4$ substituents are bonded to the steroid nucleus described for group 1 compounds, except that $R^1$ is in the β-configuration, $R^{10E}$ is in the β-configuration, $R^{10F}$ is absent and double bonds are present at the 1-2 and 7-8 positions. Exemplary group 10 compounds include 1.2.4.1, which is 3β,7-dihydroxy-16α-fluoro-17β-amino-5β-androst-1,7-diene, 1.1.5.9, which is 3β,17β-dihydroxy-5β-androst-1,7-diene, 1.1.7.1, which is 3β-hydroxy-16α-acetoxy-17β-amino-5β-androst-1,7-diene and compound 1.1.4.10, which is 3β-hydroxy-16α-fluoro-17β-acetoxy-5β-androst-1,7-diene. Other exemplary group 10 compounds include 3β,17β-dihydroxy-7-acetoxy-5β-androst-1,7-diene, 3β,17β-dihydroxy-7-methyl-5β-androst-1,7-diene, 3β,17β-dihydroxy-7-methoxy-5β-androst-1,7-diene, 3β,7β,17β-trihydroxy-5β-androst-1,7-diene, 3β-amino-17β-hydroxy-5β-androst-1,7-diene, 3β-amino-7,17β-dihydroxy-5β-androst-1,7-diene, 3β-hydroxy-17β-amino-5β-androst-1,7-diene, 3β,7-dihydroxy-17β-amino-5β-androst-1,7-diene, 3β,17β-dihydroxy-7β-amino-5β-androst-1,7-diene, 3β-hydroxy-7,17β-diacetylamino-5β-androst-1,7-diene, 3β-hydroxy-7,17β-dimethylamino-5β-androst-1,7-diene and 16α-hydroxy, 16α-methyl, 16α-amino, 16α-aminomethyl, 16α-acetate and 16α-halo analogs of any of these compounds.

Group 11. This group comprises compounds named in Table B having $R^1$, $R^2$, $R^3$ and $R^4$ substituents defined in Table A wherein the $R^1$, $R^2$, $R^3$ and $R^4$ substituents are bonded to the steroid nucleus described for group 1 compounds, except that $R^1$ is in the β-configuration, $R^{10F}$ and $R^{10G}$ are absent and double bonds are present at the 1-2 and 8-9 positions. Exemplary group 11 compounds include 1.2.4.1, which is 3β,7β-dihydroxy-16α-fluoro-17β-aminoandrost-1,8(9)-diene, 1.1.5.9, which is 3β,17β-dihydroxyandrost-1,8(9)-diene, 1.1.7.1, which is 3β-hydroxy-16α-acetoxy-17β-aminoandrost-1,8(9)-diene and compound 1.1.4.10, which is 3β-hydroxy-16α-fluoro-17β-acetoxyandrost-1,8(9)-diene. Other exemplary group 11 compounds include 3β,17β-dihydroxy-7β-acetoxyandrost-1,8(9)-diene, 3β,17β-dihydroxy-7β-methylandrost-1,8(9)-diene, 3β,17β-dihydroxy-7β-methoxyandrost-1,8(9)-diene, 3β,7β,17β-trihydroxyandrost-1,8(9)-diene, 3β-amino-17β-hydroxyandrost-1,8(9)-diene, 3β-amino-7,17β-dihydroxyandrost-1,8(9)-diene, 3β-hydroxy-17β-aminoandrost-1,8(9)-diene, 3β,7β-dihydroxy-17β-aminoandrost-1,8(9)-diene, 3β,17β-dihydroxy-7β-aminoandrost-1,8(9)-diene, 3β-hydroxy-7β,17β-diacetylaminoandrost-1,8(9)-diene, 3β-hydroxy-7β,17β-dimethylaminoandrost-1,8(9)-diene and 16α-hydroxy, 16α-methyl, 16α-amino, 16α-aminomethyl, 16α-acetate and 16α-halo analogs of any of these compounds.

Group 12. This group comprises compounds named in Table B having $R^1$, $R^2$, $R^3$ and $R^4$ substituents defined in Table A wherein the $R^1$, $R^2$, $R^3$ and $R^4$ substituents are bonded to the steroid nucleus described for group 1 compounds, except that $R^1$ is in the β-configuration, $R^{10E}$ is in the β-configuration, $R^{10F}$ and $R^{10G}$ are absent and double bonds are present at the 1-2 and 8-9 positions. Exemplary group 12 compounds include 1.2.4.1, which is 3β,7β-dihydroxy-16α-fluoro-17β-amino-5β-androst-1,8(9)-diene, 1.1.5.9, which is 3β,17β-dihydroxy-5β-androst-1,8(9)-diene, 1.1.7.1, which is 3β-hydroxy-16α-acetoxy-17β-amino-5β-androst-1,8(9)-diene and compound 1.1.4.10, which is 3β-hydroxy-16α-fluoro-17β-acetoxy-5β-androst-1,8(9)-diene. Other exemplary group 12 compounds include 3β,17β-dihydroxy-7β-acetoxy-5β-androst-1,8(9)-diene, 3β,17β-dihydroxy-7β-methyl-5β-androst-1,8(9)-diene, 3β,17β-dihydroxy-7β-methoxy-5β-androst-1,8(9)-diene, 3β,7,17β-trihydroxy-5β-androst-1,8(9)-diene, 3β-amino-17β-hydroxy-5β-androst-1,8(9)-diene, 3β-amino-7,17β-dihydroxy-5β-androst-1,8(9)-diene, 3β-hydroxy-17β-amino-5β-androst-1,8(9)-diene, 3β,7β-dihydroxy-17β-amino-5β-androst-1,8(9)-diene, 3β,17β-dihydroxy-7β-amino-5β-androst-1,8(9)-diene, 3β-hydroxy-7β,17β-diacetylamino-5β-androst-1,8(9)-diene, 3β-hydroxy-7β,17β-dimethylamino-5β-androst-1,8(9)-diene and 16α-hydroxy, 16α-methyl, 16α-amino, 16α-aminomethyl, 16α-acetate and 16α-halo analogs of any of these compounds.

Group 13. This group comprises compounds named in Table B having $R^1$, $R^2$, $R^3$ and $R^4$ substituents defined in Table A wherein the $R^1$, $R^2$, $R^3$ and $R^4$ substituents are bonded to the steroid nucleus described for group 1 compounds, except that $R^1$ is in the β-configuration, $R^{10F}$ and $R^{10H}$ are absent and double bonds are present at the 1-2 and 8-14 positions. Exemplary group 13 compounds include 1.2.4.1, which is 3β,7β-dihydroxy-16α-fluoro-17β-aminoandrost-1,8(14)-diene, 1.1.5.9, which is 3β,17β-dihydroxyandrost-1,8(14)-diene, 1.1.7.1, which is 3β-hydroxy-16α-acetoxy-17β-aminoandrost-1,8(14)-diene and compound 1.1.4.10, which is 3β-hydroxy-16α-fluoro-17β-acetoxyandrost-1,8(14)-diene. Other exemplary group 13 compounds include 3β,17β-dihydroxy-7β-acetoxyandrost-1,8(14)-diene, 3β,17β-dihydroxy-7β-methylandrost-1,8(14)-diene, 3β,17β-dihydroxy-7β-methoxyandrost-1,8(14)-diene, 3β,7β,17β-trihydroxyandrost-1,8(14)-diene, 3β-amino-17β-hydroxyandrost-1,8(14)-diene, 3β-amino-7β,17β-dihydroxyandrost-1,8(14)-diene, 3β-hydroxy-17β-aminoandrost-1,8(14)-diene, 3β,7β-dihydroxy-17β-aminoandrost-1,8(14)-diene, 3β,17β-dihydroxy-7β-aminoandrost-1,8(14)-diene, 3β-hydroxy-7β,17β-diacetylaminoandrost-1,8(14)-diene, 3β-hydroxy-7β,17β-dimethylaminoandrost-1,8(14)-diene and 16α-hydroxy, 16α-methyl, 16α-amino, 16α-aminomethyl, 16α-acetate and 16α-halo analogs of any of these compounds.

Group 14. This group comprises compounds named in Table B having $R^1$, $R^2$, $R^3$ and $R^4$ substituents defined in Table A wherein the $R^1$, $R^2$, $R^3$ and $R^4$ substituents are bonded to the steroid nucleus described for group 1 compounds, except that $R^1$ is in the β-configuration, $R^{10E}$ is in the β-configuration, $R^{10F}$ and $R^{10H}$ are absent and double bonds are present at the 1-2 and 8-9 positions. Exemplary group 14 compounds include 1.2.4.1, which is 3β,7β-dihydroxy-16α-fluoro-17β-amino-5β-androst-1,8(14)-diene, 1.1.5.9, which is 3β,17β-dihydroxy-5β-androst-1,8(14)-diene, 1.1.7.1, which is 3β-hydroxy-16α-acetoxy-17β-amino-5β-androst-1,8(14)-diene and compound 1.1.4.10, which is 3β-hydroxy-16α-fluoro-17β-acetoxy-5β-androst-1,8(14)-diene. Other exemplary group 14 compounds include 3β,17β-dihydroxy-7β-acetoxy-5β-androst-1,8(14)-diene, 3β,17β-dihydroxy-7β-methyl-5β-androst-1,8(14)-diene, 3β,17β-dihydroxy-7β-methoxy-5β-androst-1,8(14)-diene, 3β,7β,17β-trihydroxy-5β-androst-1,8(14)-diene, 3β-amino-17β-hydroxy-5β-androst-1,8(14)-diene, 3β-amino-7β,17β-dihydroxy-5β-androst-1,8(14)-diene, 3β-hydroxy-17β-amino-5β-androst-1,8(14)-diene, 3β,7β-dihydroxy-17β-amino-5β-androst-1,8(14)-diene, 3β,17β-dihydroxy-7β-amino-5β-androst-1,8(14)-diene, 3β,17β-dihydroxy-7β-aminoandrost-1,8(14)-diene, 3β-hydroxy-7β,17β-diacetylamino-5β-androst-1,8(14)-diene, 3β-hydroxy-7β,17β-dimethylamino-5β-androst-1,8(14)-diene and 16α-hydroxy, 16α-methyl, 16α-amino, 16α-aminomethyl, 16α-acetate and 16α-halo analogs of any of these compounds.

Group 15. This group comprises compounds named in Table B having $R^1$, $R^2$, $R^3$ and $R^4$ substituents defined in Table A wherein the $R^1$, $R^2$, $R^3$ and $R^4$ substituents are bonded to the steroid nucleus described for group 1 compounds, except that $R^1$ is in the β-configuration and double bonds are present at the 1-2 and 15-16 positions. Exemplary group 15 compound 1.2.4.1 is 3β,7β-dihydroxy-16-fluoro-17β-aminoandrost-1,15-diene, compound 1.1.5.9 is 3β,17β-dihydroxyandrost-1,15-diene, 1.1.7.1, which is 3β-hydroxy-16-acetoxy-17β-aminoandrost-1,15-diene and compound 1.1.4.10, which is 3β-hydroxy-16-fluoro-17β-acetoxyandrost-1,15-diene. Other exemplary group 15 compounds include 3β,17β-dihydroxy-7β-acetoxyandrost-1,15-diene, 3β,17β-dihydroxy-7β-methylandrost-1,15-diene, 3β,17β-dihydroxy-7β-methoxyandrost-1,15-diene, 3β,7β,17β-trihydroxyandrost-1,15-diene, 3β-amino-17β-hydroxyandrost-1,15-diene, 3β-amino-7β,17β-dihydroxyandrost-1,15-diene, 3β-hydroxy-17β-aminoandrost-1,15-diene, 3β,7β-dihydroxy-17β-aminoandrost-1,15-diene, 3β,17β-dihydroxy-7β-aminoandrost-1,15-diene, 3β-hydroxy-7β,17β-diacetylaminoandrost-1,15-diene, 3β-hydroxy-7β,17β-dimethylaminoandrost-1,15-diene and 16-hydroxy, 16-methyl, 16-amino, 16-aminomethyl, 16-acetate and 16-halo analogs of any of these compounds.

Group 16. This group comprises compounds named in Table B having $R^1$, $R^2$, $R^3$ and $R^4$ substituents defined in Table A wherein the $R^1$, $R^2$, $R^3$ and $R^4$ substituents are bonded to the steroid nucleus described for group 1 compounds, except that $R^1$ is in the β-configuration, $R^{10E}$ is in the β-configuration and double bonds are present at the 1-2 and 15-16 positions. Exemplary group 16 compound 1.2.4.1 is 3β,7β-dihydroxy-16-fluoro-17β-amino-5β-androst-1,15-diene, compound 1.1.5.9 is 3β,17β-dihydroxy-5β-androst-1,15-diene, 1.1.7.1, which is 3β-hydroxy-16-acetoxy-17β-amino-5β-androst-1,15-diene and compound 1.1.4.10, which is 3β-hydroxy-16-fluoro-17β-acetoxy-5β-androst-1,15-diene. Other exemplary group 16 compounds include 3β,17β-dihydroxy-7β-acetoxy-5β-androst-1,15-diene, 3β,17β-dihydroxy-7β-methyl-5β-androst-1,15-diene, 3β,17β-dihydroxy-7β-methoxy-5β-androst-1,15-diene, 3β,7β,17β-trihydroxy-5β-androst-1,15-diene, 3β-amino-17β-hydroxy-5β-androst-1,15-diene, 3β-amino-7β,17β-dihydroxy-5β-androst-1,15-diene, 3β-hydroxy-17β-amino-5β-androst-1,15-diene, 3β,7β-dihydroxy-17β-amino-5β-androst-1,15-diene, 3β,17β-dihydroxy-7β-amino-5β-androst-1,15-diene, 3β-hydroxy-7β,17β-diacetylamino-5β-androst-1,15-diene, 3β-hydroxy-7β,17β-dimethylamino-5β-androst-1,15-diene and 16-hydroxy, 16-methyl, 16-amino, 16-aminomethyl, 16-acetate and 16-halo analogs of any of these compounds.

Group 17. This group comprises compounds named in Table B having $R^1$, $R^2$, $R^3$ and $R^4$ substituents defined in Table A wherein the $R^1$, $R^2$, $R^3$ and $R^4$ substituents are bonded to the steroid nucleus described for group 1 compounds, except that $R^1$ is in the β-configuration and double bonds are present at the 1-2 and 16-17 positions. Exemplary group 17 compound 1.2.4.1 is 3β,7β-dihydroxy-16-fluoro-17-aminoandrost-1,16-diene, 1.1.5.9 is 3β,17-dihydroxyandrost-1,16-diene, 1.1.7.1 is 3β-hydroxy-16-acetoxy-17-aminoandrost-1,16-diene and compound 1.1.4.10 is 3β-hydroxy-16-fluoro-17-acetoxyandrost-1,16-diene. Other exemplary group 17 compounds include 3β,17-dihydroxy-7β-acetoxyandrost-1,16-diene, 3β,17-dihydroxy-7β-methylandrost-1,16-diene, 3β,17-dihydroxy-7β-methoxyandrost-1,16-diene, 3β,7β,17-trihydroxyandrost-1,16-diene, 3β-amino-17-hydroxyandrost-1,16-diene, 3β-amino-7β,17-dihydroxyandrost-1,16-diene, 3β-hydroxy-17-aminoandrost-1,16-diene, 3β,7β-dihydroxy-17-aminoandrost-1,16-diene, 3β,17-dihydroxy-7β-aminoandrost-1,16-diene, 3β-hydroxy-7β,17-diacetylaminoandrost-1,16-diene, 3β-hydroxy-7β,17-dimethylaminoandrost-1,16-diene and 16-hydroxy, 16-methyl, 16-amino, 16-aminomethyl, 16-acetate and 16-halo analogs of any of these compounds.

Group 18. This group comprises compounds named in Table B having $R^1$, $R^2$, $R^3$ and $R^4$ substituents defined in Table A wherein the $R^1$, $R^2$, $R^3$ and $R^4$ substituents are bonded to the steroid nucleus described for group 1 compounds, except that $R^1$ is in the β-configuration, $R^{10E}$ is in the β-configuration and double bonds are present at the 1-2 and 16-17 positions. Exemplary group 18 compound 1.2.4.1 is 3β,7β-dihydroxy-16-fluoro-17-amino-5β-androst-1,16-diene, 1.1.5.9 is 3β,17-dihydroxy-5β-androst-1,16-diene, 1.1.7.1 is 3β-hydroxy-16-acetoxy-17-amino-5β-androst-1,16-diene and compound 1.1.4.10 is 3β-hydroxy-16-fluoro-17-acetoxy-5β-androst-1,16-diene. Other exemplary group 18 compounds include 3β,17-dihydroxy-7β-acetoxy-5β-androst-1,16-diene, 3β,17- dihydroxy-7β-methyl-5β-androst-1,16-diene, 3β,17-dihydroxy-7β-methoxy-5β-androst-1,16-diene, 3β,7β,17-trihydroxy-5β-androst-1,16-diene, 3β-amino-17-hydroxy-5β-androst-1,16-diene, 3β-amino-7β,17-dihydroxy-5β-androst-1,16-diene, 3β-hydroxy-17-amino-5β-androst-1,16-diene, 3β,7β-dihydroxy-17-amino-5β-androst-1,16-diene, 3β,17-dihydroxy-7β-amino-5β-androst-1,16-diene, 3β-hydroxy-7β,17-diacetylamino-5β-androst-1,16-diene, 3β-hydroxy-7β,17-dimethylamino-5β-androst-1,16-diene and 16-hydroxy, 16-methyl, 16-amino, 16-aminomethyl, 16-acetate and 16-halo analogs of any of these compounds.

Group 19. This group comprises compounds named in Table B having $R^1$, $R^2$, $R^3$ and $R^4$ substituents defined in Table A wherein the $R^1$, $R^2$, $R^3$ and $R^4$ substituents are bonded to the steroid nucleus described for group 1 compounds, except that $R^1$ is in the β-configuration, $R^{10F}$ and $R^{10G}$ are absent and double bonds are present at the 1-2, 8-9 and 15-16 positions. Exemplary group 19 compounds include 1.2.4.1, which is 3β,7β-dihydroxy-16-fluoro-17β-aminoandrost-1,8(9),15-triene, 1.1.5.9, which is 3β,17β-dihydroxyandrost-1,8(9),15-triene, 1.1.7.1, which is 3β-hydroxy-16-acetoxy-17β-aminoandrost-1,8(9),15-triene and compound 1.1.4.10, which is 3β-hydroxy-16-fluoro-17β-acetoxyandrost-1,8(9),15-triene. Other exemplary group 19 compounds include 3β,17β-dihydroxy-7β-acetoxyandrost-1,8(9),15-triene, 3β,17β-dihydroxy-7β-methylandrost-1,8(9),15-triene, 3β,17β-dihydroxy-7β-methoxyandrost-1,8(9),15-triene, 3β,7β,17β-trihydroxyandrost-1,8(9),15-triene, 3β-amino-17β-hydroxyandrost-1,8(9),15-triene, 3β-amino-7β,17β-dihydroxyandrost-1,8(9),15-triene, 3β-hydroxy-17β-aminoandrost-1,8(9),15-triene, 3β,7β-dihydroxy-17β-aminoandrost-1,8(9),15-triene, 3β,17β-dihydroxy-7β-aminoandrost-1,8(9),15-triene, 3β-hydroxy-7β,17β-diacetylaminoandrost-1,8(9),15-triene, 3β-hydroxy-7β,17β-dimethylaminoandrost-1,8(9),15-triene and 16-hydroxy, 16-methyl, 16-amino, 16-aminomethyl, 16-acetate and 16-halo analogs of any of these compounds.

Group 20. This group comprises compounds named in Table B having $R^1$, $R^2$, $R^3$ and $R^4$ substituents defined in Table A wherein the $R^1$, $R^2$, $R^3$ and $R^4$ substituents are bonded to the steroid nucleus described for group 1 compounds, except that $R^1$ is in the β-configuration, $R^{10E}$ is in the β-configuration, $R^{10F}$ and $R^{10G}$ are absent and double bonds are present at the 1-2, 8-9 and 15-16 positions. Exemplary group 20 compounds include 1.2.4.1, which is 3β,7β-dihydroxy-16-fluoro-17β-amino-5β-androst-1,8(9),15-triene, 1.1.5.9, which is 3β,17β-dihydroxy-5β-androst-1,8(9),15-triene, 1.1.7.1, which is 3β-hydroxy-16-acetoxy-17β-amino-5β-androst-1,8(9),15-triene and compound 1.1.4.10, which is 3β-hydroxy-16-fluoro-17β-acetoxy-5β-androst-1,8(9),15-triene. Other exemplary group 20 compounds include 3β,17β-dihydroxy-7β-acetoxy-5β-androst-1,8(9),15-triene, 3β,17β-dihydroxy-7β-methyl-5β-androst-1,8(9),15-triene, 3β,17β-dihydroxy-7β-methoxy-5β-androst-1,8(9),15-triene, 3β,7β,17β-trihydroxy-5β-androst-1,8(9),15-triene, 3β-amino-17β-hydroxy-5β-androst-1,8(9),15-triene, 3β-amino-7β,17β-dihydroxy-5β-androst-1,8(9),15-triene, 3β-hydroxy-17β-amino-5β-androst-1,8(9),15-triene, 3β,7β-dihydroxy-17β-amino-5β-androst-1,8(9),15-triene, 3β,17β-dihydroxy-7β-amino-5β-androst-1,8(9),15-triene, 3β-hydroxy-7β,17β-diacetylamino-5β-androst-1,8(9),15-triene, 3β-hydroxy-7β,17β-dimethylamino-5β-androst-1,8(9),15-triene and 16-hydroxy, 16-methyl, 16-amino, 16-aminomethyl, 16-acetate and 16-halo analogs of any of these compounds.

Group 21. This group comprises compounds named in Table B having $R^1$, $R^2$, $R^3$ and $R^4$ substituents defined in Table A wherein the $R^1$, $R^2$, $R^3$ and $R^4$ substituents are bonded to the steroid nucleus described for group 1 compounds, except that $R^1$ is in the β-configuration, $R^{10F}$ and $R^{10H}$ are absent and double bonds are present at the 1-2, 8-14 and 15-16 positions. Exemplary group 21 compounds include 1.2.4.1, which is 3β,7β-dihydroxy-16-fluoro-17β-aminoandrost-1,8(14),15-triene, 1.1.5.9, which is 3β,17β-dihydroxyandrost-1,8(14),15-triene, 1.1.7.1, which is 3β-hydroxy-16-acetoxy-17β-aminoandrost-1,8(14),15-triene and compound 1.1.4.10, which is 3β-hydroxy-16-fluoro-17β-acetoxyandrost-1,8(14),15-triene. Other exemplary group 21 compounds include 3β,17β-dihydroxy-7β-acetoxyandrost-1,8(14),15-triene, 3β,17β-dihydroxy-7β-methylandrost-1,8(14),15-triene, 3β,17β-dihydroxy-7β-methoxyandrost-1,8(14),15-triene, 3β,7β,17β-trihydroxyandrost-1,8(14), 15-triene, 3β-amino-17β-hydroxyandrost-1,8(14), 15-triene, 3β-amino-7β,17β-dihydroxyandrost-1,8(14),15-triene, 3β-hydroxy-17β-aminoandrost-1,8(14),15-triene, 3β,7β-dihydroxy-17β-aminoandrost-1,8(14),15-triene, 3β,17β-dihydroxy-7β-aminoandrost-1,8(14),15-triene, 3β,17β-dihydroxy-7β-aminoandrost-1,8(9),15-triene, 3β-hydroxy-7β,17β-diacetylaminoandrost-1,8(14),15-triene, 3β-hydroxy-7β,17β-dimethylaminoandrost-1,8(14),15-triene and 16-hydroxy, 16-methyl, 16-amino, 16-aminomethyl, 16-acetate and 16-halo analogs of any of these compounds.

Group 22. This group comprises compounds named in Table B having $R^1$, $R^2$, $R^3$ and $R^4$ substituents defined in Table A wherein the $R^1$, $R^2$, $R^3$ and $R^4$ substituents are bonded to the steroid nucleus described for group 1 compounds, except that $R^1$ is in the β-configuration, $R^{10E}$ is in the β-configuration, $R^{10F}$ and $R^{10H}$ are absent and double bonds are present at the 1-2, 8-14 and 15-16 positions. Exemplary group 22 compounds include 1.2.4.1, which is 3β,7β-dihydroxy-16-fluoro-17β-amino-5β-androst-1,8(14),15-triene, 1.1.5.9, which is 3β,17β-dihydroxy-5β-androst-1,8(14),15-triene, 1.1.7.1, which is 3β-hydroxy-16-acetoxy-17β-amino-5β-androst-1,8(14),15-triene and compound 1.1.4.10, which is 3β-hydroxy-16-fluoro-17β-acetoxy-5β-androst-1,8(14),15-triene. Other exemplary group 22 compounds include 3β,17β-dihydroxy-7β-acetoxy-5β-androst-1,8(14),15-triene, 3β,17β-dihydroxy-7β-methyl-5β-androst-1,8(14),15-triene, 3β,17β-dihydroxy-7β-methoxy-5β-androst-1,8(14),15-triene, 3β,7β,17β-trihydroxy-5β-androst-1,8(14),15-triene, 3β-amino-17β-hydroxy-5β-androst-1,8(14),15-triene, 3β-amino-7β,17β-dihydroxy-5β-androst-1,8(14),15-triene, 3β-hydroxy-17β-amino-5β-androst-1,8(14),15-triene, 3β,7β-dihydroxy-17β-amino-5β-androst-1,8(14),15-triene, 3β,17β-dihydroxy-7β-amino-5β-androst-1,8(14),15-triene, 3β-hydroxy-7β,17β-diacetylamino-5β-androst-1,8(14),15-triene, 3β-hydroxy-7β,17β-dimethylamino-5β-androst-1,8(14),15-triene and 16-hydroxy, 16-methyl, 16-amino, 16-aminomethyl, 16-acetate and 16-halo analogs of any of these compounds.

Group 23. This group comprises compounds named in Table B having $R^1$, $R^2$, $R^3$ and $R^4$ substituents defined in Table A wherein the $R^1$, $R^2$, $R^3$ and $R^4$ substituents are bonded to the steroid nucleus described for group 1 compounds, except that $R^1$ is in the β-configuration, $R^{10E}$, $R^{10F}$ and $R^{10H}$ are absent and double bonds are present at the 4-5, and 8-14 positions. Exemplary group 23 compounds include 1.2.4.1, which is 3β,7β-dihydroxy-16α-fluoro-17β-aminoandrost-4,8(14)-diene, 1.1.5.9, which is 3β,17β-dihydroxyandrost-4,8(14)-diene, 1.1.7.1, which is 3β-hydroxy-16α-acetoxy-17β-aminoandrost-4,8(14)-diene and compound 1.1.4.10, which is 3β-hydroxy-16α-fluoro-17β-acetoxyandrost-4,8(14)-diene. Other exemplary group 23 compounds include 3β,7β,17β-trihydroxyandrost-4,8(14)-diene, 3β,17β-dihydroxy-7β-methylandrost-4,8(14)-diene, 3β,17β-dihydroxy-7β-methoxyandrost-4,8(14)-diene, 3β,7β,17β-trihydroxyandrost-4,8(14)-diene, 3β-amino-17β-hydroxyandrost-4,8(14)-diene, 3β-amino-7β,17β-dihydroxyandrost-4,8(14)-diene, 3β-hydroxy-17β-aminoandrost-4,8(14)-diene, 3β,7β-dihydroxy-17β-aminoandrost-4,8(14)-diene, 3β,17β-dihydroxy-7β-aminoandrost-4,8(14)-diene, 3β-hydroxy-7β,17β-diacetylaminoandrost-1,8(14)-diene, 3β-hydroxy-7β,17β-dimethylaminoandrost-1,8(14)-diene and 16α-hydroxy, 16α-methyl, 16α-amino, 16α-aminomethyl, 16α-acetate and 16α-halo analogs of any of these compounds.

Group 24. This group comprises compounds named in Table B having $R^1$, $R^2$, $R^3$ and $R^4$ substituents defined in Table A wherein the $R^1$, $R^2$, $R^3$ and $R^4$ substituents are bonded to the steroid nucleus described for group 1 compounds, except that $R^1$ is in the β-configuration, $R^{10E}$, $R^{10F}$ and $R^{10G}$ are absent and double bonds are present at the 4-5, and 8-9 positions. Exemplary group 24 compounds include 1.2.4.1, which is 3β,7β-dihydroxy-16α-fluoro-17β-aminoandrost-4,8(9)-diene, 1.1.5.9, which is 3β,17β-dihydroxyandrost-4,8(9)-diene, 1.1.7.1, which is 3β-hydroxy-16α-acetoxy-17β-aminoandrost-4,8(9)-diene and compound 1.1.4.10, which is 3β-hydroxy-16α-fluoro-17β-acetoxyandrost-4,8(9)-diene. Other exemplary group 24 compounds include 3β,17β-dihydroxyandrost-4,8(9)-diene, 3β,7β,17β-trihydroxyandrost-4,8(9)-diene, 3β,17β-dihydroxy-7β-methylandrost-4,8(9)-diene, 3β,17β-dihydroxy-7β-methoxyandrost-4,8(9)-diene, 3β,7β,17β-trihydroxyandrost-4,8(9)-diene, 3β-amino-17β-hydroxyandrost-4,8(9)-diene, 3β-amino-7β,17β-dihydroxyandrost-4,8(9)-diene, 3β-hydroxy-17β-aminoandrost-4,8(9)-diene, 3β,7β-dihydroxy-17β-aminoandrost-4,8(9)-diene, 3β,17β-dihydroxy-7β-aminoandrost-4,8(9)-diene, 3β-hydroxy-7β,17β-diacetylaminoandrost-4,8(9)-diene, 3β-hydroxy-7β,17β-dimethylaminoandrost-4,8(9)-diene and 16α-hydroxy, 16α-methyl, 16α-amino, 16α-aminomethyl, 16α-acetate and 16α-halo analogs of any of these compounds.

Group 25. This group comprises compounds named in Table B having $R^1$, $R^2$, $R^3$ and $R^4$ substituents defined in Table A wherein the $R^1$, $R^2$, $R^3$ and $R^4$ substituents are bonded to the steroid nucleus described for group 1 compounds, except that double bonds are present at the 3-4, and 16-17 positions. Exemplary group 25 compounds include 1.2.4.1, which is 3,7β-dihydroxy-16-fluoro-17-aminoandrost-3,16-diene, 1.1.5.9, which is 3,17-dihydroxyandrost-3,16-diene, 1.1.7.1, which is 3-hydroxy-16-acetoxy-17-aminoandrost-3,16-diene and compound 1.1.4.10, which is 3-hydroxy-16-fluoro-17-acetoxyandrost-3,16-diene. Other exemplary group 25 compounds include 3,17-dihydroxyandrost-3,16-diene, 3,7β,17-trihydroxyandrost-3,16-diene, 3,17-dihydroxy-7β-methylandrost-3,16-diene, 3,17-dihydroxy-7β-methoxyandrost-3,16-diene, 3,7β,17-trihydroxyandrost-3,16-diene, 3-amino-17-hydroxyandrost-3,16-diene, 3-amino-7β,17-dihydroxyandrost-3,16-diene, 7β-amino-3,17-dihydroxyandrost-3,16-diene, 3-hydroxy-17-aminoandrost-3,16-diene, 3,7β-dihydroxy-17-aminoandrost-3,16-diene, 3-hydroxy-7β,17-diacetylaminoandrost-3,16-diene, 3-hydroxy-7β,17-dimethylaminoandrost-3,16-diene and 16-hydroxy, 16-methyl, 16-amino, 16-aminomethyl, 16-acetate and 16-halo analogs of any of these compounds.

Group 26. This group comprises compounds named in Table B having $R^1$, $R^2$, $R^3$ and $R^4$ substituents defined in Table A wherein the $R^1$, $R^2$, $R^3$ and $R^4$ substituents are bonded to the steroid nucleus described for group 1 compounds, except that $R^{10E}$ is present in the β-configuration and double bonds are present at the 3-4, and 16-17 positions. Exemplary group 26 compounds include 1.2.4.1, which is 3,7β-dihydroxy-16-fluoro-17-amino-5β-androst-3,16-diene, 1.1.5.9, which is 3,17-dihydroxy-5β-androst-3,16-diene, 1.1.7.1, which is 3-hydroxy-16-acetoxy-17-amino-5β-androst-3,16-diene and compound 1.1.4.10, which is 3-hydroxy-16-fluoro-17-acetoxy-5β-androst-3,16-diene. Other exemplary group 26 compounds include 3,17-dihydroxy-5β-androst-3,16-diene, 3,7β,17-trihydroxy-5β-androst-3,16-diene, 3,17-dihydroxy-7β-methyl-5β-androst-3,16-diene, 3,17-dihydroxy-7β-methoxy-5β-androst-3,16-diene, 3,7β,17-trihydroxy-5β-androst-3,16-diene, 3-amino-17-hydroxy-5β-androst-3,16-diene, 3-amino-7β,17-dihydroxy-5β-androst-3,16-diene, 3-hydroxy-17-amino-5β-androst-3,16-diene, 3,7β-dihydroxy-17-amino-5β-androst-3,16-diene, 3,17-dihydroxy-7β-amino-5β-androst-3,16-diene, 3-hydroxy-7β,17-diacetylamino-5β-androst-3,16-diene, 3-hydroxy-7β,17-dimethylamino-5β-androst-3,16-diene and 16-hydroxy, 16-methyl, 16-amino, 16-aminomethyl, 16-acetate and 16-halo analogs of any of these compounds.

Group 27. This group comprises compounds named in Table B having $R^1$, $R^2$, $R^3$ and $R^4$ substituents defined in Table A wherein the $R^1$, $R^2$, $R^3$ and $R^4$ substituents are bonded to the steroid nucleus described for group 1 compounds, except that double bonds are present at the 3-4, and 15-16 positions. Exemplary group 27 compounds include 1.2.4.1, which is 3,7β-dihydroxy-16-fluoro-17β-aminoandrost-3,15-diene, 1.1.5.9, which is 3,17-dihydroxyandrost-3,15-diene, 1.1.7.1, which is 3-hydroxy-16-acetoxy-17β-aminoandrost-3,15-diene and compound 1.1.4.10, which is 3-hydroxy-16-fluoro-17β-acetoxyandrost-3,15-diene. Other exemplary group 27 compounds include 3,17β-dihydroxyandrost-3,15-diene, 3,7β,17β-trihydroxyandrost-3,15-diene, 3,17β-dihydroxy-7β-methylandrost-3,15-diene, 3,17β-dihydroxy-7β-methoxyandrost-3,15-diene, 3,7β,17β-trihydroxyandrost-3,15-diene, 3-amino-17β-hydroxyandrost-3,15-diene, 3-amino-7β,17β-dihydroxyandrost-3,15-diene, 3-hydroxy-17β-aminoandrost-3,15-diene, 3,7β-dihydroxy-17β-aminoandrost-3,15-diene, 3,17β-dihydroxy-7β-aminoandrost-3,15-diene, 3-hydroxy-7β,17β-diacetylaminoandrost-3,15-diene, 3-hydroxy-7β,17β-dimethylaminoandrost-3,15-diene and 16-hydroxy, 16-methyl, 16-amino, 16-aminomethyl, 16-acetate and 16-halo analogs of any of these compounds.

Group 28. This group comprises compounds named in Table B having $R^1$, $R^2$, $R^3$ and $R^4$ substituents defined in Table A wherein the $R^1$, $R^2$, $R^3$ and $R^4$ substituents are bonded to the steroid nucleus described for group 1 compounds, except that $R^{10E}$ is present in the β-configuration and double bonds are present at the 3-4, and 15-16 positions. Exemplary group 28 compounds include 1.2.4.1, which is 3,7β-dihydroxy-16-fluoro-17β-amino-5β-androst-3,16-diene, 1.1.5.9, which is 3,17β-dihydroxy-5β-androst-3,16-diene, 1.1.7.1, which is 3-hydroxy-16-acetoxy-17β-amino-5β-androst-3,16-diene and compound 1.1.4.10, which is 3-hydroxy-16-fluoro-17β-acetoxy-5β-androst-3,16-diene. Other exemplary group 28 compounds include 3,7β,17β-trihydroxy-5β-androst-3,16-diene, 3,17β-dihydroxy-7β-methyl-5β-androst-3,16-diene, 3,17β-dihydroxy-7β-methoxy-5β-androst-3,16-diene, 3,7β,17β-trihydroxy-5β-androst-3,16-diene, 3-amino-17β-hydroxy-5β-androst-3,16-diene, 3-amino-7β,17β-dihydroxy-5β-androst-3,16-diene, 3-hydroxy-17β-amino-5β-androst-3,16-diene, 3,7β-dihydroxy-17β-amino-5β-androst-3,16-diene, 3,17β-dihydroxy-7β-amino-5β-androst-3,16-diene, 3-hydroxy-7β,17β-diacetylamino-5β-androst-3,15-diene, 3-hydroxy-7β,17β-dimethylamino-5β-androst-3,15-diene and 16-hydroxy, 16-methyl, 16-amino, 16-aminomethyl, 16-acetate and 16-halo analogs of any of these compounds.

Group 29. This group comprises compounds named in Table B having $R^1$, $R^2$, $R^3$ and $R^4$ substituents defined in Table A wherein the $R^1$, $R^2$, $R^3$ and $R^4$ substituents are bonded to the steroid nucleus described for group 1 compounds, except that $R^{10E}$ and $R^6$ are absent and double bonds are present at the 1-2, 3-4 and 5-10 positions, i.e., the A ring is aromatic. Exemplary group 29 compounds include 1.2.4.1, which is 3,7β-dihydroxy-16α-fluoro-17β-aminoandrost-1,3,5-triene, 1.1.5.9, which is 3,17β-dihydroxyandrost-1,3,5(10)-triene, 1.1.7.1, which is 3-hydroxy-16α-acetoxy-17β-aminoandrost-1,3,5(10)-triene and compound 1.1.4.10, which is 3-hydroxy-16α-fluoro-17β-acetoxyandrost-1,3,5(10)-triene. Other exemplary group 29 compounds include 3,17β-dihydroxy-7β-acetoxyandrost-1,3,5(10)-triene, 3,17β-dihydroxy-7β-methylandrost-1,3,5(10)-triene, 3,17β-dihydroxy-7β-methoxyandrost-1,3,5(10)-triene, 3,7β,17β-trihydroxyandrost-1,3,5(10)-triene, 3-amino-17β-hydroxyandrost-1,3,5(10)-triene, 3-amino-7β,17β-dihydroxyandrost-1,3,5(10)-triene, 3-hydroxy-17β-aminoandrost-1,3,5(10)-triene, 3,7β-dihydroxy-17β-aminoandrost-1,3,5(10)-triene, 3,17β-dihydroxy-7β-aminoandrost-1,3,5(10)-triene, 3-hydroxy-7β,17β-diacetylaminoandrost-1,3,5(10)-triene, 3-hydroxy-7β,17β-dimethylaminoandrost-1,3,5(10)-triene and 16α-hydroxy, 16α-methyl, 16α-amino, 16α-aminomethyl, 16α-acetate and 16α-halo analogs of any of these compounds.

Group 30. This group comprises compounds named in Table B having $R^1$, $R^2$, $R^3$ and $R^4$ substituents defined in Table A wherein the $R^1$, $R^2$, $R^3$ and $R^4$ substituents are bonded to the steroid nucleus described for group 1 compounds, except that $R^1$ is in the β-configuration, $R^{10E}$ is absent and double bonds are present at the 1-2, 4-5 and 6-7 positions. Exemplary group 30 compounds include 1.2.4.1, which is 3β,7-dihydroxy-16α-fluoro-17β-aminoandrost-1,4,6-triene, 1.1.5.9, which is 3β,17β-dihydroxyandrost-1,4,6-triene, 1.1.7.1, which is 3β-hydroxy-16α-acetoxy-17β-aminoandrost-1,4,6-triene and compound 1.1.4.10, which is 3β-hydroxy-16α-fluoro-17β-acetoxyandrost-1,4,6-triene. Other exemplary group 30 compounds include 3β,17β-dihydroxy-7-acetoxyandrost-1,4,6-triene, 3β,17β-dihydroxy-7-methylandrost-1,4,6-triene, 3β,17β-dihydroxy-7-methoxyandrost-1,4,6-triene, 3β,7,17β-trihydroxyandrost-1,4,6-triene, 3β-amino-17β-hydroxyandrost-1,4,6-triene, 3β-amino-7,17β-dihydroxyandrost-1,4,6-triene, 3β-hydroxy-17β-aminoandrost-1,4,6-triene, 3β,7-dihydroxy-17β-aminoandrost-1,4,6-triene, 3β,17β-dihydroxy-7β-aminoandrost-1,4,6-triene, 3β-hydroxy-7β,17β-diacetylaminoandrost-1,4,6-triene, 3β-hydroxy-7β,17β-dimethylaminoandrost-1,4,6-triene and 16α-hydroxy, 16α-methyl, 16α-amino, 16α-aminomethyl, 16α-acetate and 16α-halo analogs of any of these compounds.

Group 31. This group comprises compounds named in Table B having $R^1$, $R^2$, $R^3$ and $R^4$ substituents defined in Table A wherein the $R^1$, $R^2$, $R^3$ and $R^4$ substituents are bonded to the steroid nucleus described for group 1 compounds, except that $R^1$ is in the β-configuration, $R^{10E}$ is absent and double bonds are present at the 1-2, 5-6 and 7-8 positions. Exemplary group 31 compounds include 1.2.4.1, which is 3β,7-dihydroxy-16α-fluoro-17β-aminoandrost-1,5,7-triene, 1.1.5.9, which is 3β,17β-dihydroxyandrost-1,5,7-triene, 1.1.7.1, which is 3β-hydroxy-16α-acetoxy-17β-aminoandrost-1,5,7-triene and compound 1.1.4.10, which is 3β-hydroxy-16α-fluoro-17β-acetoxyandrost-1,5,7-triene. Other exemplary group 31 compounds include 3β,17β-dihydroxy-7-acetoxyandrost-1,5,7-triene, 3β,17β-dihydroxy-7-methylandrost-1,5,7-triene, 3β,17β-dihydroxy-7-methoxyandrost-1,5,7-triene, 3β,7,17β-trihydroxyandrost-1,5,7-triene, 3β-amino-17β-hydroxyandrost-1,5,7-triene, 3β-amino-7,17β-dihydroxyandrost-1,5,7-triene, 3β-hydroxy-17β-aminoandrost-1,5,7-triene, 3β,7-dihydroxy-17β-aminoandrost-1,5,7-triene, 3β,17β-dihydroxy-7β-aminoandrost-1,5,7-triene, 3β-hydroxy-7,17β-diacetylaminoandrost-1,5,7-triene, 3β-hydroxy-7,17β-dimethylaminoandrost-1,5,7-triene and 16α-hydroxy, 16α-methyl, 16α-amino, 16α-aminomethyl, 16α-acetate and 16α-halo analogs of any of these compounds.

Group 32. This group comprises compounds named in Table B having $R^1$, $R^2$, $R^3$ and $R^4$ substituents defined in Table A wherein the $R^1$, $R^2$, $R^3$ and $R^4$ substituents are bonded to the steroid nucleus described for group 1 compounds, except that $R^1$ is in the β-configuration, $R^{10E}$ and $R^{10F}$ are absent and double bonds are present at the 1-2, 5-6 and 15-16 positions. Exemplary group 32 compounds include 1.2.4.1, which is 3β,7β-dihydroxy-16-fluoro-17β-aminoandrost-1,5,15-triene, 1.1.5.9, which is 3β,17β-dihydroxyandrost-1,5,15-triene, 1.1.7.1, which is 3β-hydroxy-16-acetoxy-17β-aminoandrost-1,5,15-triene and compound 1.1.4.10, which is 3β-hydroxy-16-fluoro-17β-acetoxyandrost-1,5,15-triene. Other exemplary group 32 compounds include 3β,16-dihydroxy-17β-aminoandrost-1,5,15-triene, 3β,17β-dihydroxy-7β-acetoxyandrost-1,5,15-triene, 3β,17β-dihydroxy-7β-methylandrost-1,5,15-triene, 3β,17β-dihydroxy-7β-methoxyandrost-1,5,15-triene, 3β,7β,17β-trihydroxyandrost-1,5,15-triene, 3β-amino-17β-hydroxyandrost-1,5,15-triene, 3β-amino-7β,17β-dihydroxyandrost-1,5,15-triene, 3β-hydroxy-17β-aminoandrost-1,5,15-triene, 3β,7β-dihydroxy-17β-aminoandrost-1,5,15-triene, 3β,17β-dihydroxy-7β-aminoandrost-1,5,15-triene, 3β-hydroxy-7β,17β-diacetylaminoandrost-1,5,15-triene, 3β-hydroxy-7β,17β-dimethylaminoandrost-1,5,15-triene and 16-hydroxy, 16-methyl, 16-amino, 16-aminomethyl, 16-acetate and 16-halo analogs of any of these compounds.

Group 33. This group comprises compounds named in Table B having $R^1$, $R^2$, $R^3$ and $R^4$ substituents defined in Table A wherein the $R^1$, $R^2$, $R^3$ and $R^4$ substituents are bonded to the steroid nucleus described for group 1 compounds, except that $R^1$ is in the β-configuration, $R^{10E}$ is absent and double bonds are present at the 1-2, 5-6 and 16-17 positions. Exemplary group 33 compounds include 1.2.4.1, which is 3β,7β-dihydroxy-16-fluoro-17-aminoandrost-1,5,16-triene, 1.1.5.9, which is 3β,17-dihydroxyandrost-1,5,16-triene, 1.1.7.1, which is 3β-hydroxy-16-acetoxy-17-aminoandrost-1,5,16-triene and compound 1.1.4.10, which is 3β-hydroxy-16-fluoro-17-acetoxyandrost-1,5,16-triene. Other exemplary group 33 compounds include 3β,16-dihydroxy-17-aminoandrost-1,5,16-triene, 3β,17-dihydroxy-7β-acetoxyandrost-1,5,16-triene, 3β,17-dihydroxy-7β-methylandrost-1,5,16-triene, 3β,17-dihydroxy-7β-methoxyandrost-1,5,16-triene, 3β,7β,17-trihydroxyandrost-1,5,16-triene, 3β-amino-17-hydroxyandrost-1,5,16-triene, 3β-amino-7β,17-dihydroxyandrost-1,5,16-triene, 3β-hydroxy-17-aminoandrost-1,5,16-triene, 3β,7β-dihydroxy-17-aminoandrost-1,5,16-triene, 3β,17β-dihydroxy-7β-aminoandrost-1,5,16-triene, 3β-hydroxy-7β,17-diacetylaminoandrost-1,5,16-triene, 3β-hydroxy-7β,17-dimethylaminoandrost-1,5,16-triene and 16-hydroxy, 16-methyl, 16-amino, 16-aminomethyl, 16-acetate and 16-halo analogs of any of these compounds.

Group 34. This group comprises compounds named in Table B having $R^1$, $R^2$, $R^3$ and $R^4$ substituents defined in Table A wherein the $R^1$, $R^2$, $R^3$ and $R^4$ substituents are bonded to the steroid nucleus described for group 1 compounds, except that $R^{10E}$ and $R^6$ are absent and double bonds are present at the 1-2, 3-4, 5-10 and 6-7 positions. Thus, for this group, the A ring is aromatic and a double bond is present at the 6-7 position. Exemplary group 34 compounds include 1.2.4.1, which is 3,7-dihydroxy-16α-fluoro-17β-aminoandrost-1,3,5(10),6-tetraene, 1.1.5.9, which is 3,17β-dihydroxyandrost-1, 3,5(10),6-tetraene, 1.1.7.1, which is 3-hydroxy-16α-acetoxy-17β-aminoandrost-1,3,5(10),6-tetraene and compound 1.1.4.10, which is 3-hydroxy-16α-fluoro-17β-acetoxyandrost-1,3,5(10),6-tetraene. Other exemplary group 34 compounds include 3,17β-dihydroxy-7-acetoxyandrost-1,3,5(10),6-tetraene, 3,17β-dihydroxy-7-methylandrost-1,3,5(10),6-tetraene, 3,17β-dihydroxy-7-methoxyandrost-1,3,5(10),6-tetraene, 3,7,17β-trihydroxyandrost-1,3,5(10),6-tetraene, 3-amino-17β-hydroxyandrost-1,3,5(10),6-tetraene, 3-amino-7,17β-dihydroxyandrost-1,3,5(10),6-tetraene, 3-hydroxy-17β-aminoandrost-1,3,5(10),6-tetraene, 3,7β-dihydroxy-17β-aminoandrost-1,3,5(10),6-tetraene, 3,17β-dihydroxy-7β-aminoandrost-1,3,5(10),6-tetraene, 3-hydroxy-7,17β-diacetylaminoandrost-1,3,5(10),6-tetraene, 3-hydroxy-7,17β-dimethylaminoandrost-1,3,5(10),6-tetraene and 16α-hydroxy, 16α-methyl, 16α-amino, 16α-aminomethyl, 16α-acetate and 16α-halo analogs of any of these compounds.

Group 35. This group comprises compounds named in Table B having $R^1$, $R^2$, $R^3$ and $R^4$ substituents defined in Table A wherein the $R^1$, $R^2$, $R^3$ and $R^4$ substituents are bonded to the steroid nucleus described for group 1 compounds, except that $R^{10E}$, $R^{10F}$ and $R^6$ are absent and double bonds are present at the 1-2, 3-4, 5-10 and 7-8 positions. Thus, for this group, the A ring is aromatic and a double bond is present at the 7-8 position. Exemplary group 35 compounds include 1.2.4.1, which is 3,7-dihydroxy-16α-fluoro-17β-aminoandrost-1,3,5(10),7-tetraene, 1.1.5.9, which is 3,17β-dihydroxyandrost-1,3,5(10),7-tetraene, 1.1.7.1, which is 3-hydroxy-16α-acetoxy-17β-aminoandrost-1,3,5(10),7-tetraene and compound 1.1.4.10, which is 3-hydroxy-16α-fluoro-17β-acetoxyandrost-1,3,5(10),7-tetraene. Other exemplary group 35 compounds include 3,17β-dihydroxy-7-acetoxyandrost-1,3,5(10),7-tetraene, 3,17β-dihydroxy-7-methylandrost-1,3,5(10),7-tetraene, 3,17β-dihydroxy-7-methoxyandrost-1,3,5(10),7-tetraene, 3,7,17β-trihydroxyandrost-1,3,5(10),7-tetraene, 3-amino-17β-hydroxyandrost-1,3,5(10),7-tetraene, 3-amino-7,17β-dihydroxyandrost-1,3,5(10),7-tetraene, 3-hydroxy-17β-aminoandrost-1,3,5(10),7-tetraene, 3,7β-dihydroxy-17β-aminoandrost-1,3,5(10),7-tetraene, 3,17β-dihydroxy-7β-aminoandrost-1,3,5(10),7-tetraene, 3-hydroxy-7,17β-diacetylaminoandrost-1,3,5(10),7-tetraene, 3-hydroxy-7,17β-dimethylaminoandrost-1,3,5(10),7-tetraene and 16α-hydroxy, 16α-methyl, 16α-amino, 16α-aminomethyl, 16α-acetate and 16α-halo analogs of any of these compounds.

Group 36. This group comprises compounds named in Table B having $R^1$, $R^2$, $R^3$ and $R^4$ substituents defined in Table A wherein the $R^1$, $R^2$, $R^3$ and $R^4$ substituents are bonded to the steroid nucleus described for group 1 compounds, except that $R^{10E}$, $R^{10F}$, $R^{10G}$ and $R^6$ are absent and double bonds are present at the 1-2, 3-4, 5-10 and 8-9 positions. Thus, for this group, the A ring is aromatic and a double bond is present at the 8-9 position. Exemplary group 36 compounds include 1.2.4.1, which is 3,7β-dihydroxy-16α-fluoro-17β-aminoandrost-1,3,5(10),8(9)-tetraene, 1.1.5.9, which is 3,17β-dihydroxyandrost-1,3,5(10),8(9)-tetraene, 1.1.7.1, which is 3-hydroxy-16α-acetoxy-17β-aminoandrost-1,3,5(10),8(9)-tetraene and compound 1.1.4.10, which is 3-hydroxy-16α-fluoro-17β-acetoxyandrost-1,3,5(10),8(9)-tetraene. Other exemplary group 36 compounds include 3,17β-dihydroxy-7β-acetoxyandrost-1,3,5(10),8(9)-tetraene, 3,17β-dihydroxy-7β-methylandrost-1,3,5(10),8(9)-tetraene, 3,17β-dihydroxy-7β-methoxyandrost-1,3,5(10),8(9)-tetraene, 3,7β,17β-trihydroxyandrost-1,3,5(10),8(9)-tetraene, 3-amino-17β-hydroxyandrost-1,3,5(10),8(9)-tetraene, 3-amino-7β,17β-dihydroxyandrost-1,3,5(10),8(9)-tetraene, 3-hydroxy-17β-aminoandrost-1,3,5(10),8(9)-tetraene, 3,7β-dihydroxy-17β-aminoandrost-1,3,5(10),8(9)-tetraene, 3,17β-dihydroxy-7β-aminoandrost-1,3,5(10),8(9)-tetraene, 3-hydroxy-7β,17β-diacetylaminoandrost-1,3,5(10),8(9)-tetraene, 3-hydroxy-7β,17β-dimethylaminoandrost-1,3,5(10),8(9)-tetraene and 16α-hydroxy, 16α-methyl, 16α-amino, 16α-aminomethyl, 16α-acetate and 16α-halo analogs of any of these compounds.

Group 37. This group comprises compounds named in Table B having $R^1$, $R^2$, $R^3$ and $R^4$ substituents defined in Table A wherein the $R^1$, $R^2$, $R^3$ and $R^4$ substituents are bonded to the steroid nucleus described for group 1 compounds, except that $R^{10E}$, $R^{10F}$, $R^{10H}$ and $R^6$ are absent and double bonds are present at the 1-2, 3-4, 5-10 and 8-14 positions. Thus, for this group, the A ring is aromatic and a double bond is present at the 8-14 position. Exemplary group 37 compounds include 1.2.4.1, which is 3,7β-dihydroxy-16α-fluoro-17β-aminoandrost-1,3,5(10),8(14)-tetraene, 1.1.5.9, which is 3,17β-dihydroxyandrost-1,3,5(10),8(14)-tetraene, 1.1.7.1, which is 3-hydroxy-16α-acetoxy-17β-aminoandrost-1,3,5(10),8(14)-tetraene and compound 1.1.4.10, which is 3-hydroxy-16α-fluoro-17β-acetoxyandrost-1,3,5(10),8(14)-tetraene. Other exemplary group 37 compounds include 3,17β-dihydroxy-7β-acetoxyandrost-1,3,5(10),8(14)-tetraene, 3,17β-dihydroxy-7β-methylandrost-1,3,5(10),8(14)-tetraene, 3,17β-dihydroxy-7β-methoxyandrost-1,3,5(10),8(14)-tetraene, 3,7β,17β-trihydroxyandrost-1,3,5(10),8(14)-tetraene, 3-amino-17β-hydroxyandrost-1,3,5(10),8(14)-tetraene, 3-amino-7β,17β-dihydroxyandrost-1,3,5(10),8(14)-tetraene, 3-hydroxy-17β-aminoandrost-1,3,5(10),8(14)-tetraene, 3,7β-dihydroxy-17β-aminoandrost-1,3,5(10),8(14)-tetraene, 3,17β-dihydroxy-7β-aminoandrost-1,3,5(10),8(14)-tetraene, 3-hydroxy-7β,17β-diacetylaminoandrost-1,3,5(10),8(14)-tetraene, 3-hydroxy-7β,17β-dimethylaminoandrost-1,3,5(10),8(14)-tetraene and 16α-hydroxy, 16α-methyl, 16α-amino, 16α-aminomethyl, 16α-acetate and 16α-halo analogs of any of these compounds.

Group 38. This group comprises compounds named in Table B having $R^1$, $R^2$, $R^3$ and $R^4$ substituents defined in Table A wherein the $R^1$, $R^2$, $R^3$ and $R^4$ substituents are bonded to the steroid nucleus described for group 1 compounds, except that $R^{10E}$ and $R^6$ are absent and double bonds are present at the 1-2, 3-4, 5-10 and 15-16 positions. Thus, for this group, the A ring is aromatic and a double bond is present at the 15-16 position. Exemplary group 38 compounds include 1.2.4.1, which is 3,7β-dihydroxy-16-fluoro-17β-aminoandrost-1,3,5(10),15-tetraene, 1.1.5.9, which is 3,17β-dihydroxyandrost-1,3,5(10),15-tetraene, 1.1.7.1, which is 3-hydroxy-16-acetoxy-17β-aminoandrost-1,3,5(10),15-tetraene and compound 1.1.4.10, which is 3-hydroxy-16-fluoro-17β-acetoxyandrost-1,3,5(10),15-tetraene. Other exemplary group 38 compounds include 3,17β-dihydroxy-7β-acetoxyandrost-1,3,5(10),15-tetraene, 3,17β-dihydroxy-7β-methylandrost-1,3,5(10),15-tetraene, 3,17β-dihydroxy-7β-methoxyandrost-1,3,5(10),15-tetraene, 3,7β,17β-trihydroxyandrost-1,3,5(10),15-tetraene, 3-amino-17β-hydroxyandrost-1,3,5(10),15-tetraene, 3-amino-7β,17β-dihydroxyandrost-1,3,5(10),15-tetraene, 3-hydroxy-17β-aminoandrost-1,3,5(10),15-tetraene, 3,7β-dihydroxy-17β-aminoandrost-1,3,5(10),15-tetraene, 3,17β-dihydroxy-7β-aminoandrost-1,3,5(10),15-tetraene, 3-hydroxy-7β,17β-diacetylaminoandrost-1,3,5(10),15-tetraene, 3-hydroxy-7β,17β-dimethylaminoandrost-1,3,5(10),15-tetraene and 16-hydroxy, 16-methyl, 16-amino, 16-aminomethyl, 16-acetate and 16-halo analogs of any of these compounds.

Group 39. This group comprises compounds named in Table B having $R^1$, $R^2$, $R^3$ and $R^4$ substituents defined in Table A wherein the $R^1$, $R^2$, $R^3$ and $R^4$ substituents are bonded to the steroid nucleus described for group 1 compounds, except that $R^{10E}$ and $R^6$ are absent and double bonds are present at the 1-2, 3-4, 5-10 and 16-17 positions. Thus, for this group, the A ring is aromatic and a double bond is present at the 15-16 position. Exemplary group 39 compounds include 1.2.4.1, which is 3,7β-dihydroxy-16-fluoro-17-aminoandrost-1,3,5 (10),16-tetraene, 1.1.5.9, which is 3,17-dihydroxyandrost-1, 3,5(10),16-tetraene, 1.1.7.1, which is 3-hydroxy-16-acetoxy-17-aminoandrost-1,3,5(10),16-tetraene and compound 1.1.4.10, which is 3-hydroxy-16-fluoro-17-acetoxyandrost-1,3,5(10),16-tetraene. Other exemplary group 39 compounds include 3,17-dihydroxy-7β-acetoxyandrost-1,3,5(10),16-tetraene, 3,17-dihydroxy-7β-methylandrost-1,3,5(10),16-tetraene, 3,17-dihydroxy-7β-methoxyandrost-1,3,5(10),16-tetraene, 3,7β,17-trihydroxyandrost-1,3,5(10),16-tetraene, 3-amino-17-hydroxyandrost-1,3,5(10),16-tetraene, 3-amino-7β,17-dihydroxyandrost-1,3,5(10),16-tetraene, 3-hydroxy-17-aminoandrost-1,3,5(10),16-tetraene, 3,7β-dihydroxy-17-aminoandrost-1,3,5(10),16-tetraene, 3-hydroxy-7β,17-diacetylaminoandrost-1,3,5(10),16-tetraene, 3-hydroxy-7β,17-dimethylaminoandrost-1,3,5(10),16-tetraene and 16-hydroxy, 16-methyl, 16-amino, 16-aminomethyl, 16-acetate and 16-halo analogs of any of these compounds.

Group 40. This group comprises compounds named in Table B having $R^1$, $R^2$, $R^3$ and $R^4$ substituents defined in Table A wherein the $R^1$, $R^2$, $R^3$ and $R^4$ substituents are bonded to the steroid nucleus described for group 1 compounds, except that $R^{10E}$ and $R^6$ are absent and double bonds are present at the 1-2, 5-6, 7-8 and 15-16 positions. Thus, for this group, the A ring is aromatic and a double bond is present at the 15-16 position. Exemplary group 40 compounds include 1.2.4.1, which is 3β,7-dihydroxy-16-fluoro-17β-aminoandrost-1,5,7, 15-tetraene, 1.1.5.9, which is 3β,17β-dihydroxyandrost-1,5, 7,15-tetraene, 1.1.7.1, which is 3β-hydroxy-16-acetoxy-17β-aminoandrost-1,5,7,15-tetraene and compound 1.1.4.10, which is 3β-hydroxy-16-fluoro-17β-acetoxyandrost-1,5,7, 15-tetraene. Other exemplary group 40 compounds include 3β,17β-dihydroxy-7-acetoxyandrost-1,5,7,15-tetraene, 3β,17β-dihydroxy-7-methylandrost-1,5,7,15-tetraene, 3β,17β-dihydroxy-7-methoxyandrost-1,5,7,15-tetraene, 3β,7,17β-trihydroxyandrost-1,5,7,15-tetraene, 3β-amino-17β-hydroxyandrost-1,5,7,15-tetraene, 3β-amino-7,17β-dihydroxyandrost-1,5,7,15-tetraene, 3β-hydroxy-17β-aminoandrost-1,5,7,15-tetraene, 3β,7-dihydroxy-17β-aminoandrost-1,5,7,15-tetraene, 3β-hydroxy-7,17β-diacetylaminoandrost-1,5,7,15-tetraene, 3β-hydroxy-7,17β-dimethylaminoandrost-1,5,7,15-tetraene and 16-hydroxy, 16-methyl, 16-amino, 16-aminomethyl, 16-acetate and 16-halo analogs of any of these compounds.

Group 41. This group comprises compounds named in Table B having $R^1$, $R^2$, $R^3$ and $R^4$ substituents defined in Table A wherein the $R^1$, $R^2$, $R^3$ and $R^4$ substituents are bonded to the steroid nucleus described for group 1 compounds, except that $R^1$ is in the β-configuration, $R^{10G}$ is absent and double bonds are present at the 1-2 and 9-11 positions. Exemplary group 41 compounds include 1.2.4.1, which is 3β,7β-dihydroxy-16α-fluoro-17β-aminoandrost-1,9(11)-diene, 1.1.5.9, which is 3β,17β-dihydroxyandrost-1,9(11)-diene, 1.1.7.1, which is 3β-hydroxy-16α-acetoxy-17β-aminoandrost-1,9(11)-diene and compound 1.1.4.10, which is 3β-hydroxy-16α-fluoro-17β-acetoxyandrost-1,9(11)-diene. Other exemplary group 41 compounds include 3β,17β-dihydroxy-7β-acetoxyandrost-1,9(11)-diene, 3β,17β-dihydroxy-7β-methylandrost-1, 9(11)-diene, 3β,17β-dihydroxy-7β-methoxyandrost-1,9 (11)-diene, 3β,7β,17β-trihydroxyandrost-1,9(11)-diene, 3β-amino-17β-hydroxyandrost-1,9(11)-diene, 3β-amino-7β,17β-dihydroxyandrost-1,9(11)-diene, 3β-hydroxy-17β-aminoandrost-1,9(11)-diene, 3β,7β-dihydroxy-17β-aminoandrost-1,9(11)-diene, 3β,17β-dihydroxy-7β-aminoandrost-1,9(11)-diene, 3β-hydroxy-7β,17β-diacetylaminoandrost-1,9(11)-diene, 3β-hydroxy-7β,17β-dimethylaminoandrost-1,9(11)-diene and 16α-hydroxy, 16α-methyl, 16α-amino, 16α-aminomethyl, 16α-acetate and 16α-halo analogs of any of these compounds.

Group 42. This group comprises compounds named in Table B having $R^1$, $R^2$, $R^3$ and $R^4$ substituents defined in Table A wherein the $R^1$, $R^2$, $R^3$ and $R^4$ substituents are bonded to the steroid nucleus described for group 1 compounds, except that $R^1$ and $R^{10E}$ are in the β-configuration, $R^{10G}$ is absent and double bonds are present at the 1-2 and 9-11 positions. Exemplary group 42 compounds include 1.2.4.1, which is 3β,7β-dihydroxy-16α-fluoro-17β-amino-5β-androst-1,9(11)-diene, 1.1.5.9, which is 3β,17β-dihydroxy-5β-androst-1,9(11)-diene, 1.1.7.1, which is 3β-hydroxy-16α-acetoxy-17β-amino-5β-androst-1,9(11)-diene and compound 1.1.4.10, which is 3β-hydroxy-16α-fluoro-17β-acetoxy-5β-androst-1, 9(11)-diene. Other exemplary group 42 compounds include 3β,17β-dihydroxy-7β-acetoxy-5β-androst-1,9(11)-diene, 3β,17β-dihydroxy-7β-methyl-5β-androst-1,9(11)-diene, 3β,17β-dihydroxy-7β-methoxy-5β-androst-1,9(11)-diene, 3β,7β,17β-trihydroxy-5β-androst-1,9(11)-diene, 3β-amino-17β-hydroxy-5β-androst-1,9(11)-diene, 3β-amino-7β,17β-dihydroxy-5β-androst-1,9(11)-diene, 3β-hydroxy-17β-amino-5β-androst-1,9(11)-diene, 3β,7β-dihydroxy-17β-amino-5β-androst-1,9(11)-diene, 3β,17β-dihydroxy-7β-amino-5β-androst-1,9(11)-diene, 3β-hydroxy-7β,17β-diacetylamino-5β-androst-1,9(11)-diene, 3β-hydroxy-7β, 17β-dimethylamino-5β-androst-1,9(11)-diene and 16α-hydroxy, 16α-methyl, 16α-amino, 16α-aminomethyl, 16α-acetate and 16α-halo analogs of any of these compounds.

Group 43. This group comprises compounds named in Table B having $R^1$, $R^2$, $R^3$ and $R^4$ substituents defined in Table A wherein the $R^1$, $R^2$, $R^3$ and $R^4$ substituents are bonded to the steroid nucleus described for group 1 compounds, except that $R^1$ is in the β-configuration, $R^{10E}$ and $R^{10G}$ are absent and double bonds are present at the 1-2, 4-5 and 9-11 positions. Exemplary group 43 compounds include 1.2.4.1, which is 3β,7β-dihydroxy-16α-fluoro-17β-aminoandrost-1,4,9(11)-triene, 1.1.5.9, which is 3β,17β-dihydroxyandrost-1,4,9(11)-triene, 1.1.7.1, which is 3β-hydroxy-16α-acetoxy-17β-aminoandrost-1,4,9(11)-triene and compound 1.1.4.10, which is 3β-hydroxy-16α-fluoro-17β-acetoxyandrost-1,4,9(11)-triene. Other exemplary group 43 compounds include 3β,17β-dihydroxy-7β-acetoxyandrost-1,4,9(11)-triene, 3β,17β-dihydroxy-7β-methylandrost-1,4,9(11)-triene, 3β,17β-dihydroxy-7β-methoxyandrost-1,4,9(11)-triene, 3β,7β,17β-trihydroxyandrost-1,4,9(11)-triene, 3β-amino-17β-hydroxyandrost-1,4,9(11)-triene, 3β-amino-7β,17β-dihydroxyandrost-1,4,9(11)-triene, 3β-hydroxy-17β-aminoandrost-1,4,9(11)-triene, 3β,7β-dihydroxy-17β-aminoandrost-1,4,9(11)-triene, 3β,17β-dihydroxy-7β-aminoandrost-1,4,9 (11)-triene, 3β-hydroxy-7β,17β-diacetylaminoandrost-1,4,9 (11)-triene, 3β-hydroxy-7β,17β-dimethylaminoandrost-1,4, 9(11)-triene and 16α-hydroxy, 16α-methyl, 16α-amino, 16α-aminomethyl, 16α-acetate and 16α-halo analogs of any of these compounds.

Group 44. This group comprises compounds named in Table B having $R^1$, $R^2$, $R^3$ and $R^4$ substituents defined in Table A wherein the $R^1$, $R^2$, $R^3$ and $R^4$ substituents are bonded to the steroid nucleus described for group 1 compounds, except that $R^1$ is in the β-configuration, $R^{10E}$ and $R^{10F}$ are absent and double bonds are present at the 5-6 and 7-8 positions. Exemplary group 44 compounds include 1.2.4.1, which is 3β,7-dihydroxy-16α-fluoro-17β-aminoandrost-5,7-diene, 1.1.5.9, which is 3β,17β-dihydroxyandrost-5,7-diene, 1.1.7.1, which is 3β-hydroxy-16α-acetoxy-17β-aminoandrost-5,7-diene and compound 1.1.4.10, which is 3β-hydroxy-16α-fluoro-17β-acetoxyandrost-5,7-diene. Other exemplary group 44 compounds include 3β,17β-dihydroxy-7β-acetoxyandrost-5,7-diene, 3β,17β-dihydroxy-7-methylandrost-5,7-diene, 3β,17β-dihydroxy-7-methoxyandrost-5,7-diene, 3β,7,17β-trihydroxyandrost-5,7-diene, 3β-amino-17β-hydroxyandrost-5,7-diene, 3β-amino-7,17β-dihydroxyandrost-5,7-diene, 3β-hydroxy-17β-aminoandrost-5,7-diene, 3β,7-dihydroxy-17β-aminoandrost-5,7-diene, 3β,17β-dihydroxy-7-aminoandrost-5,7-diene, 3β-hydroxy-7,17β-diacetylaminoandrost-5,7-diene, 3β-hydroxy-7,17β-dimethylaminoandrost-5,7-diene and 16α-hydroxy, 16α-methyl, 16α-amino, 16α-aminomethyl, 16α-acetate and 16α-halo analogs of any of these compounds.

Group 45. This group comprises compounds named in Table B having $R^1$, $R^2$, $R^3$ and $R^4$ substituents defined in Table A wherein the $R^1$, $R^2$, $R^3$ and $R^4$ substituents are bonded to the steroid nucleus described for group 1 compounds, except that $R^1$ is in the β-configuration, $R^{10E}$, $R^{10G}$ and $R^6$ are absent and double bonds are present at the 4-5 and 9-10 positions. Exemplary group 45 compounds include 1.2.4.1, which is 3β,7β-dihydroxy-16α-fluoro-17β-aminoandrost-4,9(10)-diene, 1.1.5.9, which is 3β,17β-dihydroxyandrost-4,9(10)-diene, 1.1.7.1, which is 3β-hydroxy-16α-acetoxy-17β-aminoandrost-4,9(10)-diene and compound 1.1.4.10, which is 3β-hydroxy-16α-fluoro-17β-acetoxyandrost-4,9(10)-diene. Other exemplary group 45 compounds include 3β,17β-dihydroxy-7β-acetoxyandrost-4,9(10)-diene, 3β,17β-dihydroxy-7β-methylandrost-4,9(10)-diene, 3β,17β-dihydroxy-7β-methoxyandrost-4,9(10)-diene, 3β,7β,17β-trihydroxyandrost-4,9(10)-diene, 3β-amino-17β-hydroxyandrost-4,9(10)-diene, 3β-amino-7β,17β-dihydroxyandrost-4,9(10)-diene, 3β-hydroxy-17β-aminoandrost-4,9(10)-diene, 3β,7β-dihydroxy-17β-aminoandrost-4,9(10)-diene, 3β,17β-dihydroxy-7β-aminoandrost-4,9(10)-diene, 3β-hydroxy-7β,17β-diacetylaminoandrost-4,9(10)-diene, 3β-hydroxy-7β,17β-dimethylaminoandrost-4,9(10)-diene and 16α-hydroxy, 16α-methyl, 16α-amino, 16α-aminomethyl, 16α-acetate and 16α-halo analogs of any of these compounds.

Group 46. This group comprises compounds named in Table B having $R^1$, $R^2$, $R^3$ and $R^4$ substituents defined in Table A wherein the $R^1$, $R^2$, $R^3$ and $R^4$ substituents are bonded to the steroid nucleus described for group 1 compounds, except that $R^{10E}$ and $R^6$ are absent and double bonds are present at the 2-3 and 5-10 positions. Exemplary group 46 compounds include 1.2.4.1, which is 3,7β-dihydroxy-16α-fluoro-17β-aminoandrost-2,5(10)-diene, 1.1.5.9, which is 3,17β-dihydroxyandrost-2,5(10)-diene, 1.1.7.1, which is 3-hydroxy-16α-acetoxy-17β-aminoandrost-2,5(10)-diene and compound 1.1.4.10, which is 3-hydroxy-16α-fluoro-17β-acetoxyandrost-2,5(10)-diene. Other exemplary group 46 compounds include 3,17β-dihydroxy-7β-acetoxyandrost-2,5(10)-diene, 3,17β-dihydroxy-7β-methylandrost-2,5(10)-diene, 3,17β-dihydroxy-7β-methoxyandrost-2,5(10)-diene, 3,7β,17β-trihydroxyandrost-2,5(10)-diene, 3-amino-17β-hydroxyandrost-2,5(10)-diene, 3-amino-7β,17β-dihydroxyandrost-2,5(10)-diene, 3-hydroxy-17β-aminoandrost-2,5(10)-diene, 3,7β-dihydroxy-17β-aminoandrost-2,5(10)-diene, 3,17β-dihydroxy-7β-aminoandrost-2,5(10)-diene, 3-hydroxy-7β,17β-diacetylaminoandrost-2,5(10)-diene, 3-hydroxy-7β,17β-dimethylaminoandrost-2,5(10)-diene and 16α-hydroxy, 16α-methyl, 16α-amino, 16α-aminomethyl, 16α-acetate and 16α-halo analogs of any of these compounds.

Group 47. This group comprises compounds named in Table B having $R^1$, $R^2$, $R^3$ and $R^4$ substituents defined in Table A wherein the $R^1$, $R^2$, $R^3$ and $R^4$ substituents are bonded to the steroid nucleus described for group 1 compounds, except that $R^1$ is in the β-configuration, $R^{10E}$ and $R^6$ are absent and a double bond is present at the 5-10 position. Exemplary group 47 compounds include 1.2.4.1, which is 3,7β-dihydroxy-16α-fluoro-17β-aminoandrost-5(10)-ene, 1.1.5.9, which is 3,17β-dihydroxyandrost-5(10)-ene, 1.1.7.1, which is 3-hydroxy-16α-acetoxy-17β-aminoandrost-5(10)-ene and compound 1.1.4.10, which is 3-hydroxy-16α-fluoro-17β-acetoxyandrost-5(10)-ene. Other exemplary group 47 compounds include 3,17β-dihydroxy-7β-acetoxyandrost-5(10)-ene, 3,17β-dihydroxy-7β-methylandrost-5(10)-ene, 3,17β-dihydroxy-7β-methoxyandrost-5(10)-ene, 3,7β,17β-trihydroxyandrost-5(10)-ene, 3-amino-17β-hydroxyandrost-5(10)-ene, 3-amino-7β,17β-dihydroxyandrost-5(10)-ene, 3-hydroxy-17β-aminoandrost-5(10)-ene, 3,7β-dihydroxy-17β-aminoandrost-5(10)-ene, 3,17β-dihydroxy-7β-aminoandrost-5(10)-ene, 3-hydroxy-7β,17β-diacetylaminoandrost-5(10)-ene, 3-hydroxy-7β,17β-dimethylaminoandrost-5(10)-ene and 16α-hydroxy, 16α-methyl, 16α-amino, 16α-aminomethyl, 16α-acetate and 16α-halo analogs of any of these compounds.

Group 48. This group comprises compounds named in Table B having $R^1$, $R^2$, $R^3$ and $R^4$ substituents defined in Table A wherein the $R^1$, $R^2$, $R^3$ and $R^4$ substituents are bonded to the steroid nucleus described for group 1 compounds, except that $R^1$ is in the β-configuration, $R^{10E}$ and $R^6$ are absent and double bonds are present at the 5-10 and 15-16 positions. Exemplary group 48 compounds include 1.2.4.1, which is 3,7β-dihydroxy-16-fluoro-17β-aminoandrost-5(10),15-diene, 1.1.5.9, which is 3,17β-dihydroxyandrost-5(10),15-diene, 1.1.7.1, which is 3-hydroxy-16-acetoxy-17β-aminoandrost-5(10),15-diene and compound 1.1.4.10, which is 3-hydroxy-16-fluoro-17β-acetoxyandrost-5(10),15-diene. Other exemplary group 48 compounds include 3,17β-dihydroxy-7β-acetoxyandrost-5(10),15-diene, 3,17β-dihydroxy-7β-methylandrost-5(10),15-diene, 3,17β-dihydroxy-7β-methoxyandrost-5(10),15-diene, 3,7β,17β-trihydroxyandrost-5(10),15-diene, 3-amino-17β-hydroxyandrost-5(10),15-diene, 3-amino-7β,17β-dihydroxyandrost-5(10),15-diene, 3-hydroxy-17β-aminoandrost-5(10),15-diene, 3,7β-dihydroxy-17β-aminoandrost-5(10),15-diene, 3,17β-dihydroxy-7β-aminoandrost-5(10),15-diene, 3-hydroxy-7β,17β-diacetylaminoandrost-5(10),15-diene, 3-hydroxy-7β,17β-dimethylaminoandrost-5(10),15-diene and 16-hydroxy, 16-methyl, 16-amino, 16-aminomethyl, 16-acetate and 16-halo analogs of any of these compounds.

Group 49. This group comprises compounds named in Table B having $R^1$, $R^2$, $R^3$ and $R^4$ substituents defined in Table A wherein the $R^1$, $R^2$, $R^3$ and $R^4$ substituents are bonded to the steroid nucleus described for group 1 compounds, except that $R^1$ is in the β-configuration, $R^{10E}$ and $R^6$ are absent and double bonds are present at the 5-10 and 16-17 positions. Exemplary group 49 compounds include 1.2.4.1, which is 3β,7β-dihydroxy-16-fluoro-17-aminoandrost-5(10),16-diene, 1.1.5.9, which is 3β,17-dihydroxyandrost-5(10),16-diene, 1.1.7.1, which is 3β-hydroxy-16-acetoxy-17-aminoandrost-5(10),16-diene and compound 1.1.4.10, which is 3β-hydroxy-16-fluoro-17-acetoxyandrost-5(10),16-diene. Other exemplary group 49 compounds include 3β,17-dihydroxy-7β-acetoxyandrost-5(10),16-diene, 3β,17-dihydroxy-7β-methylandrost-5(10),16-diene, 3β,17-dihydroxy-7β-methoxyandrost-5(10),16-diene, 3β,7β,17-trihydroxyandrost-5(10),16-diene, 3β-amino-17- hydroxyandrost-5(10),16-diene, 3β-amino-7β,17-dihydroxyandrost-5(10),16-diene, 3β-hydroxy-17-aminoandrost-5(10),16-diene, 3β,7β-dihydroxy-17-aminoandrost-5(10),16-diene, 3β,17-dihydroxy-7β-aminoandrost-5(10),16-diene, 3β-hydroxy-7β,17-diacetylaminoandrost-5(10),16-diene, 3β-hydroxy-7β,17-dimethylaminoandrost-5(10),16-diene and 16-hydroxy, 16-methyl, 16-amino, 16-aminomethyl, 16-acetate and 16-halo analogs of any of these compounds.

Group 50. This group comprises compounds in compound groups 1-49 described above where no double bond is present at the 16-17 position, i.e., groups 1-3, 6-16, 19-24, 27-32, 34-38 and 40-48, and $R^4$ is in the α-configuration instead of in the β-configuration. These compound groups are specified by adding group number 50- to the included group numbers. Thus, for example, compounds in group 50-1 are compounds in group 1 where $R^4$ is in the α-configuration. Similarly, compounds in group 50-2 are compounds in group 2 where $R^4$ is in the α-configuration and compounds in group 50-3 are compounds in group 3 where $R^4$ is in the α-configuration. Other group 50 compound groups where $R^4$ is in the α-configuration are defined in a similar manner and therefore are 50-6, 50-7, 50-8, 50-9, 50-10, 50-11, 50-12, 50-13, 50-14, 50-15, 50-16, 50-19, 50-20, 50-21, 50-22, 50-23, 50-24, 50-27, 50-28, 50-29, 50-30, 50-31, 50-32, 50-34, 50-35, 50-36, 50-37, 50-38, 50-40, 50-41, 50-42, 50-43, 50-44, 50-45, 50-46, 50-47 and 50-48. For each of these compound groups, compounds 1.1.1.1 through 10.10.10.10 in Table B specifies a compound as defined by the Table A substituents and the $R^4$ α-configuration as specified in this group.

Exemplary group 50-1 compounds include 1.2.4.1, which is 3,7β-dihydroxy-16α-fluoro-17α-aminoandrost-1,3-diene, 1.1.5.9, which is 3,17α-dihydroxyandrost-1,3-diene, 1.1.6.1, which is 3,16α-dihydroxy-17α-aminoandrost-1,3-diene and 1.1.4.9, which is 3,17α-dihydroxy-16α-fluoroandrost-1,3-diene. Exemplary group 50-2 compounds include 1.2.4.1, which is 3,7β-dihydroxy-16α-fluoro-17α-amino-5β-androst-1,3-diene, 1.1.5.9, which is 3,17α-dihydroxy-5β-androst-1,3-diene, 1.1.6.1, which is 3,16α-dihydroxy-17α-amino-5β-androst-1,3-diene and 1.1.4.9, which is 3,17α-dihydroxy-16α-fluoro-5β-androst-1,3-diene. Exemplary group 50-3 compounds include 1.2.4.1, which is 3,7β-dihydroxy-16α-fluoro-17α-aminoandrost-1,3,5-triene, 1.1.5.9, which is 3,17α-dihydroxyandrost-1,3,5-triene, 1.1.6.1, which is 3,16α-dihydroxy-17α-aminoandrost-1,3,5-triene and 1.1.4.9, which is 3,17α-dihydroxy-16α-fluoroandrost-1,3,5-triene. Exemplary group 50-48 compounds include 1.2.4.1, which is 3β,7β-dihydroxy-16α-fluoro-17α-aminoandrost-5(10),15-diene, 1.1.5.9, which is 3β,17α-dihydroxyandrost-5(10),15-diene, 1.1.6.1, which is 3β,16α-dihydroxy-17α-aminoandrost-5(10),15-diene and 1.1.4.9, which is 3β,17α-dihydroxy-16α-fluoroandrost-5(10),15-diene. Compounds in the other group 50 compound groups are specified or defined in an analogous manner.

Group 51. This group comprises compounds in compound groups 1-50 described above, wherein no double bond is present at the 2-3 or 3-4 positions and $R^1$ is in the α-configuration instead of in the β-configuration, i.e., groups 6 through 24, 30 through 33, 40 through 45, 47 through 49, 50-6 through 50-16, 50-19 through 50-24, 50-30 through 50-32, 50-40 through 50-45, 50-47 and 50-48. These compound groups are specified in a manner that is similar to that described for group 50, i.e., by adding group number 51- to the included group numbers. Thus, compounds in group 51-6 are compounds in group 6 where $R^1$ is in the α-configuration, compounds in group 51-7 are compounds in group 7 where $R^1$ is in the α-configuration, compounds in group 51-47 are compounds in group 47 where $R^1$ is in the α-configuration are compounds in group where $R^1$ is in the α-configuration, group 51-50-6 are compounds in group 50-6 where $R^1$ is in the α-configuration, group 51-50-7 are compounds in group 50-7 where $R^1$ is in the α-configuration, group 51-50-47 are compounds in group 50-47 where $R^1$ is in the α-configuration and group 51-50-48 are compounds in group 50-48 where $R^1$ is in the α-configuration. Other group 51 compound groups where $R^1$ is in the α-configuration are defined in a similar manner and therefore are 51-8, 51-9, 51-10, 51-11, 51-12, 51-13, 51-14, 51-15, 51-16, 51-17, 51-18, 51-19, 51-20, 51-21, 51-22, 51-23, 51-24, 51-30, 51-31, 51-32, 51-33, 51-40, 51-41, 51-42, 51-43, 51-44, 51-45, 51-47, 51-48, 51-49, 51-50-6, 51-50-7, 51-50-8, 51-50-9, 51-50-10, 51-50-11, 51-50-12, 51-50-13, 51-50-14, 51-50-15, 51-50-16, 51-50-19, 51-50-20, 51-50-21, 51-50-22, 51-50-23, 51-50-24, 51-50-30, 51-50-31, 51-50-32, 51-50-40, 51-50-41, 51-50-42, 51-50-43, 51-50-44, 51-50-45, 51-50-47 and 51-50-48. For each of these compound groups, compounds 1.1.1.1 through 10.10.10.10 in Table B specifies a compound as defined by the Table A substituents and the $R^1$ α-configuration as specified in this group.

Exemplary group 51-6 compounds include 1.2.4.1, which is 3α,7β-dihydroxy-16α-fluoro-17-aminoandrost-1,5-diene, 1.1.5.9, which is 3α,17β-dihydroxyandrost-1,5-diene, 1.1.6.1, which is 3α,16α-dihydroxy-17β-aminoandrost-1,5-diene and 1.1.4.9, which is 3α,17β-dihydroxy-16α-fluoroandrost-1,5-diene. Exemplary group 51-7 compounds include 1.2.4.1, which is 3α,7-dihydroxy-16α-fluoro-17β-aminoandrost-1,6-diene, 1.1.5.9, which is 3α,17β-dihydroxyandrost-1,6-diene, 1.1.6.1, which is 3α,16α-dihydroxy-17β-aminoandrost-1,6-diene and 1.1.4.9, which is 3α,17β-dihydroxy-16α-fluoroandrost-1,6-diene. Exemplary group 51-50-47 compounds include 1.2.4.1, which is 3α,7β-dihydroxy-16α-fluoro-17α-aminoandrost-5(10)-ene, 1.1.5.9, which is 3α,17α-dihydroxyandrost-5(10)-ene, 1.1.6.1, which is 3α,16α-dihydroxy-17α-aminoandrost-5(10)-ene and 1.1.4.9, which is 3α,17α-dihydroxy-16α-fluoroandrost-5(10)-ene. Exemplary group 51-50-48 compounds include 1.2.4.1, which is 3α,7β-dihydroxy-16α-fluoro-17α-aminoandrost-5(10),15-diene, 1.1.5.9, which is 3α,17α-dihydroxyandrost-5(10),15-diene, 1.1.6.1, which is 3α,16α-dihydroxy-17α-aminoandrost-5(10),15-diene and 1.1.4.9, which is 3α,17α-dihydroxy-16α-fluoroandrost-5(10),15-diene. Compounds in the other group 51 compound groups are defined in an analogous manner.

Group 52. This group comprises compounds in compound groups 1-51 described above, wherein no double bond is present at the 15-16 or 16-17 positions and $R^3$ is in the β-configuration instead of in the α-configuration, i.e., groups 1 through 3, 6 through 14, 23, 24, 29 through 37, 41 through 47, 50-1, 50-2, 50-3, 50-6 through 50-14, 50-23, 50-24, 50-29, 50-30, 50-31, 50-34 through 50-37, 50-41 through 50-47, 51-6 through 51-14, 51-23, 51-24, 51-30, 51-31, 51-41 through 51-45 and 51-47. Compound groups in group 52 where $R^3$ is in the β-configuration are 52-1, 52-2, 52-3, 52-6, 52-7, 52-8, 52-9, 52-10, 52-11, 52-12, 52-13, 52-14, 52-23, 52-24, 52-29, 52-30, 52-31, 52-32, 52-33, 52-34, 52-35, 52-36, 52-37, 52-41, 52-42, 52-43, 52-44, 52-45, 52-46, 52-47, 52-50-1, 52-50-2, 52-50-3, 52-50-6, 52-50-7, 52-50-8, 52-50-9, 52-50-10, 52-50-11, 52-50-12, 52-50-13, 52-50-14, 52-50-23, 52-50-24, 52-50-29, 52-50-30, 52-50-31, 52-50-34, 52-50-35, 52-50-36, 52-50-37, 52-50-41, 52-50-42, 52-50-43, 52-50-44, 52-50-45, 52-50-46, 52-50-47, 52-51-6, 52-51-7, 52-51-8, 52-51-9, 52-51-10, 52-51-11, 52-51-12, 52-51-13, 52-51-14, 52-51-23, 52-51-24, 52-51-30, 52-51-31, 52-51-41, 52-51-42, 52-51-43, 52-51-44, 52-51-45, 52-51-47, 52-51-50-6, 52-51-50-7, 52-51-50-8, 52-51-50-9, 52-51-50-10, 52-51-50-11, 52-51-50-12, 52-51-50-13, 52-51-50-14, 52-51-50-23, 52-51-50-24, 52-51-50-30, 52-51-50-31, 52-51-50-41, 52-51-50-42, 52-51-50-43, 52-51-50-44, 52-51-50-45 and 52-51-50-47. For each of these compound groups, compounds 1.1.1.1 through 10.10.10.10 in Table B specifies a compound as defined by the Table A substituents and the $R^3$ β-configuration as specified in this group.

These compound groups are specified in a manner that is similar to that described for groups 50 and 51, i.e., by adding group number 52- to the included group numbers. Thus, for example, compounds in group 52-1 are compounds in group 1 where $R^3$ is in the β-configuration, compounds in group 52-6 are compounds in group 6 where $R^3$ is in the β-configuration, compounds in group 52-7 are compounds in group 7 where $R^3$ is in the β-configuration compounds in group 52-50-1 are compounds in group 50-1 where $R^3$ is in the β-configuration, compounds in group 52-51-50-6 are compounds in group 51-50-6 where $R^3$ is in the β-configuration and group 52-51-50-47 are compounds in group 51-50-47 where $R^3$ is in the β-configuration.

Exemplary group 52-6 compounds include 1.2.4.1, which is 3β,7β-dihydroxy-16β-fluoro-17β-aminoandrost-1,5-diene, 1.1.6.9, which is 3β,16β,17β-trihydroxyandrost-1,5-diene, 1.1.6.1, which is 3β,16β-dihydroxy-17β-aminoandrost-1,5-diene and 1.1.4.9, which is 3β,17β-dihydroxy-16β-fluoroandrost-1,5-diene. Exemplary group 52-50-7 compounds include 1.2.4.1, which is 3β,7-dihydroxy-16β-fluoro-17α-aminoandrost-1,6-diene, 1.1.6.9, which is 3β,16β,17α-dihydroxyandrost-1,6-diene, 1.1.6.1, which is 3β,16β-dihydroxy-17α-aminoandrost-1,6-diene and 1.1.4.9, which is 3β,17α-dihydroxy-16β-fluoroandrost-1,6-diene. Exemplary group 52-50-8 compounds include 1.2.4.1, which is 3β,7-dihydroxy-16β-fluoro-17α-amino-5β-androst-1,6-diene, 1.1.6.9, which is 3β,16β,17α-dihydroxy-5β-androst-1,6-diene, 1.1.6.1, which is 3β,16β-dihydroxy-17α-amino-5β-androst-1,6-diene and 1.1.4.9, which is 3β,17α-dihydroxy-16β-fluoro-5β-androst-1,6-diene. Exemplary group 52-51-7 compounds include 1.2.4.1, which is 3α,7-dihydroxy-16β-fluoro-17β-aminoandrost-1,6-diene, 1.1.6.9, which is 3α,16β,17β-dihydroxyandrost-1,6-diene, 1.1.6.1, which is 3β,16β-dihydroxy-17β-aminoandrost-1,6-diene and 1.1.4.9, which is 3α,17β-dihydroxy-16β-fluoroandrost-1,6-diene. Exemplary group 52-51-50-7 compounds include 1.2.4.1, which is 3α,7-dihydroxy-16β-fluoro-17α-aminoandrost-1,6-diene, 1.1.6.9, which is 3α,16β,17α-dihydroxyandrost-1,6-diene, 1.1.6.1, which is 3α,16β-dihydroxy-17α-aminoandrost-1,6-diene and 1.1.4.9, which is 3α,17α-dihydroxy-16β-fluoroandrost-1,6-diene. Exemplary group 52-51-47 compounds include 1.2.4.1, which is 3α,7β-dihydroxy-16β-fluoro-17β-aminoandrost-5(10)-ene, 1.1.6.9, which is 3α,16β,17β-dihydroxyandrost-5(10)-ene, 1.1.6.1, which is 3α,16β-dihydroxy-17β-aminoandrost-5(10)-ene and 1.1.4.9, which is 3α,17β-dihydroxy-16β-fluoroandrost-5(10)-ene. Exemplary group 52-51-50-47 compounds include 1.2.4.1, which is 3α,7β-dihydroxy-16β-fluoro-17α-aminoandrost-5(10)-ene, 1.1.6.9, which is 3α,16β,17α-dihydroxyandrost-5(10)-ene, 1.1.6.1, which is 3α,16β-dihydroxy-17α-aminoandrost-5(10)-ene and 1.1.4.9, which is 3α,17α-dihydroxy-16β-fluoroandrost-5(10)-ene. Compounds in the other group 52 compound groups are defined in an analogous manner.

Group 53. This group comprises compounds in the compound groups 1-52 described above, wherein $R^9$ is a moiety other than —CH$_2$— or =CH—. As is apparent from the moieties that $R^9$ can be, compounds and genera of compounds are defined in this group. Exemplary $R^9$ include —O—, —NH—, —NCH$_3$—, =N—, —S—, —S(O)—, —S(O)(O)—, —S$^+$(optionally substituted alkyl)-, —CHR$^{10}$—, —C(R$^{10}$)$_2$— or =CR$^{10}$— where R$^{10}$ are independently selected and a single R$^{10}$ can be in the α-configuration or the β-configuration. When one or both R$^{10}$ are not —H, exemplary R$^9$ include —CH(α-OH)—, —CH(β-OH)—, —C(β-CH$_3$)(α-OH)—, —C(α-CH$_3$)(β-OH)—, —CH(α-C1-6 ester)-, —CH(β-C1-6 ester)-, —CH(α-O—C1-6-CH(β-O—C1-6-CH(α-S—C1-6 alkyl)-, —CH(β-S—C1-6 alkyl)-, —CH(α-NH—C1-6-CH(8-NH—C1-6-CH(α-O—C2-6 alkenyl)-, —CH(β-O—C2-6 alkenyl)-, —CH(α-O—C2-6 alkynyl)-, —CH(β-O—C2-6 alkynyl)-, —CH(α-O—C1-6 alkoxy)-, —CH(β-O—C1-6 alkoxy)-, —CH(α-O—CH$_2$—C2-6 alkenyl)-, —CH(β-O—CH$_2$—C2-6 alkenyl)-, —CH(α-O—CH$_2$—C2-6 alkynyl)-, —CH(β-O—CH$_2$—C2-6 alkynyl)-, —CH(α-C-linked heterocycle)-, —CH(β-C-linked heterocycle)-, —CH(α-N-linked heterocycle)-, —CH(β-N-linked heterocycle)-, —CH(α-halogen), —CH(β-halogen)-, —C(F)$_2$—, —C(Cl)$_2$—, —C(Br)$_2$—, —C(I)$_2$—, —C(CH$_3$)$_2$—, —C(C$_2$H$_5$)$_2$—, —CH(α-SH)—, —CH(β-SH)—, —CH(α-NH$_2$)—, —CH(β-NH$_2$)—, —CH(α-NHCH$_3$)—, —CH(β-NHCH$_3$)—, —CH(α-N[CH$_3$]$_2$)—, —CH(β-N[CH$_3$]$_2$)—, —CH(α-N[C$_2$H$_5$]$_2$)—, —CH(β-N[C$_2$H$_5$]$_2$)—, —CH(α-NO$_2$)—, —CH(β-NO$_2$)—, —CH(α-N$_3$)—, —CH(α-CN)—, —CH(β-CN)—, —CH(α-SCN)—, —CH(β-SCN)—, —C(β-CH$_3$)(α-CN)—, —C(α-CH$_3$)(β-CN)—, —CH(α-NC(O)(CH$_2$)$_m$—CH$_3$)—, —CH(β-NC(O)—(CH$_2$)$_m$—CH$_3$)—, —CH(α-NC(O)O—(CH$_2$)$_m$—CH$_3$)—, —CH(β-NC(O)O—(CH$_2$)$_m$—CH$_3$)—, —C(C1-4 alkyl)$_2$-, —C(C1-4 alkenyl)$_2$-, where m is 0, 1, 2, 3, 4, 5 or 6, and any alkyl, alkenyl, alkynyl, alkoxy, alkenyloxy, alkynyloxy or heterocycle moiety is optionally substituted and each is independently chosen. When no double bond is present at the 1-2 or 2-3 positions, $R^9$ can be —O—, —NH— or —S—, or it can be linked to a double bonded R$^{10}$ moiety such as =O, =S, =NOH, =NCH$_3$, =NH, =CH$_2$, =CH$_2$CH$_3$, =CH$_2$CH$_2$OH, =CH$_2$C(O)OH or another moiety as defined herein for R$^{10}$. In these cases, $R^9$ is a moiety such as —C(O)—, —C(NOH)— or —C(=CH$_2$)—. When a double bond is present at the 1-2 or 2-3 positions, $R^9$ can be =N—. In other embodiments, $R^9$ is absent, leaving a 5-membered ring.

Groups of compounds in this group are defined essentially as described above for groups 50, 51 and 52. Compound groups in group 53 where $R^9$ is substituted or is absent thus include 53-1, 53-2, 53-3, 53-4, 53-5, 53-6, 53-7, 53-8, 53-9, 53-10, 53-11, 53-12, 53-13, 53-14, 53-15, 53-16, 53-17, 53-18, 53-19, 53-20, 53-21, 53-22, 53-23, 53-24, 53-25, 53-26, 53-27, 53-28, 53-29, 53-30, 53-31, 53-32, 53-33, 53-34, 53-35, 53-36, 53-37, 53-38, 53-39, 53-40, 53-41, 53-42, 53-43, 53-44, 53-45, 53-46, 53-47, 53-48, 53-49, 53-51-6, 53-51-7, 53-51-8, 53-51-9, 53-51-10, 53-51-11, 53-51-12, 53-51-13, 53-51-14, 53-51-15, 53-51-16, 53-51-17, 53-51-18, 53-51-19, 53-51-20, 53-51-21, 53-51-22, 53-51-23, 53-51-24, 53-51-30, 53-51-31, 53-51-32, 53-51-33, 53-51-40, 53-51-41, 53-51-42, 53-51-43, 53-51-44, 53-51-45, 53-51-47, 53-51-48, 53-51-49, 53-51-50-6, 53-51-50-7, 53-51-50-8, 53-51-50-9, 53-51-50-10, 53-51-50-11, 53-51-50-12, 53-51-50-13, 53-51-50-14, 53-51-50-15, 53-51-50-16, 53-51-50-19, 53-51-50-20, 53-51-50-21, 53-51-50-22, 53-51-50-23, 53-51-50-24, 53-51-50-30, 53-51-50-31, 53-51-50-32, 53-51-50-40, 53-51-50-41, 53-51-50-42, 53-51-50-43, 53-51-50-44, 53-51-50-45, 53-51-50-47, 53-51-50-48, 53-52-1, 53-52-2, 53-52-3, 53-52-6, 53-52-7, 53-52-8, 53-52-9, 53-52-10, 53-52-11, 53-52-12, 53-52-13, 53-52-14, 53-52-23, 53-52-24, 53-52-

29, 53-52-30, 53-52-31, 53-52-32, 53-52-33, 53-52-34, 53-52-35, 53-52-36, 53-52-37, 53-52-41, 53-52-42, 53-52-43, 53-52-44, 53-52-45, 53-52-46, 53-52-47, 53-52-50-1, 53-52-50-2, 53-52-50-3, 53-52-50-6, 53-52-50-7, 53-52-50-8, 53-52-50-9, 53-52-50-10, 53-52-50-11, 53-52-50-12, 53-52-50-13, 53-52-50-14, 53-52-50-23, 53-52-50-24, 53-52-50-29, 53-52-50-30, 53-52-50-31, 53-52-50-34, 53-52-50-35, 53-52-50-36, 53-52-50-37, 53-52-50-41, 53-52-50-42, 53-52-50-43, 53-52-50-44, 53-52-50-45, 53-52-50-46, 53-52-50-47, 53-52-51-6, 53-52-51-7, 53-52-51-8, 53-52-51-9, 53-52-51-10, 53-52-51-11, 53-52-51-12, 53-52-51-13, 53-52-51-14, 53-52-51-23, 53-52-51-24, 53-52-51-30, 53-52-51-31, 53-52-51-41, 53-52-51-42, 53-52-51-43, 53-52-51-44, 53-52-51-45, 53-52-51-47, 53-52-51-50-6, 53-52-51-50-7, 53-52-51-50-8, 53-52-51-50-9, 53-52-51-50-10, 53-52-51-50-11, 53-52-51-50-12, 53-52-51-50-13, 53-52-51-50-14, 53-52-51-50-23, 53-52-51-50-24, 53-52-51-50-30, 53-52-51-50-31, 53-52-51-50-41, 53-52-51-50-42, 53-52-51-50-43, 53-52-51-50-44, 53-52-51-50-45 and 53-52-51-50-47. For each of these compound groups, designations 1.1.1.1 through 10.10.10.10 in Table B specifies a compound or genus of compounds as defined by the Table A substituents and any $R^9$ moiety as described here or elsewhere herein.

Exemplary compounds in group 53-44 when $R^9$ is —O— include compound 1.2.4.1, which is 2-oxa-3β,7β-dihydroxy-16α-fluoro-17β-aminoandrost-5,7-diene, 1.1.5.9, which is 2-oxa-3β,17β-dihydroxyandrost-5,7-diene, 1.1.6.9, which is 2-oxa-3β,16α,17β-trihydroxyandrost-5,7-diene, 1.1.6.1, which is 2-oxa-3β,16α-dihydroxy-17β-aminoandrost-5,7-diene and 1.1.4.9, which is 2-oxa-3β,17β-dihydroxy-16α-fluoroandrost-5,7-diene. Exemplary compounds in group 53-44 when $R^9$ is —NH— include compound 1.2.4.1, which is 2-aza-3β,7β-dihydroxy-16α-fluoro-17β-aminoandrost-5,7-diene, 1.1.5.9, which is 2-aza-3β,17β-dihydroxyandrost-5,7-diene, 1.1.6.9, which is 2-aza-3β,16α,17β-trihydroxyandrost-5,7-diene, 1.1.6.1, which is 2-aza-3β,16α-dihydroxy-17β-aminoandrost-5,7-diene and 1.1.4.9, which is 2-aza-3β,17β-dihydroxy-16α-fluoroandrost-5,7-diene. Exemplary compounds in group 53-44 when $R^9$ is —S— include compound 1.2.4.1, which is 2-thia-3β,7β-dihydroxy-16α-fluoro-17β-aminoandrost-5,7-diene, 1.1.5.9, which is 2-thia-3β,17β-dihydroxyandrost-5,7-diene, 1.1.6.9, which is 2-thia-3β,16α,17β-trihydroxyandrost-5,7-diene, 1.1.6.1, which is 2-thia-3β,16α-dihydroxy-17β-aminoandrost-5,7-diene and 1.1.4.9, which is 2-thia-3β,17β-dihydroxy-16α-fluoroandrost-5,7-diene. Exemplary compounds in group 53-44 when $R^9$ is —CH(α-NH[CH$_3$])— include compound 1.2.4.1, which is 2α-methylamino-3β,7β-dihydroxy-16α-fluoro-17β-aminoandrost-5,7-diene, 1.1.5.9, which is 2α-methylamino-3β,17β-dihydroxyandrost-5,7-diene, 1.1.6.9, which is 2α-methylamino-3β,16α,17β-trihydroxyandrost-5,7-diene, 1.1.6.1, which is 2α-methylamino-3β,16α-dihydroxy-17β-aminoandrost-5,7-diene and 1.1.4.9, which is 2α-methylamino-3β,17β-dihydroxy-16α-fluoroandrost-5,7-diene. Exemplary compounds in group 53-44 when $R^9$ is —CH(α-OH)— include compound 1.2.4.1, which is 2α,3β,7β-trihydroxy-16α-fluoro-17β-aminoandrost-5,7-diene, 1.1.5.9, which is 2α,3β,17β-trihydroxyandrost-5,7-diene, 1.1.6.9, which is 2α,3β,16α,17β-tetrahydroxyandrost-5,7-diene, 1.1.6.1, which is 2α,3β,16α-trihydroxy-17β-aminoandrost-5,7-diene and 1.1.4.9, which is 2α,3β,17β-trihydroxy-16α-fluoroandrost-5,7-diene. Exemplary compounds in group 53-44 when $R^9$ is —CH(α-OCH$_3$)— include compound 1.2.4.1, which is 2α-methoxy-3β,7β-dihydroxy-16α-fluoro-17β-aminoandrost-5,7-diene, 1.1.5.9, which is 2α-methoxy-3β,17β-dihydroxyandrost-5,7-diene, 1.1.6.9, which is 2α-methoxy-3β,16α,17β-trihydroxyandrost-5,7-diene, 1.1.6.1, which is 2α-methoxy-3β,16α-dihydroxy-17β-aminoandrost-5,7-diene and 1.1.4.9, which is 2α-methoxy-3β,17β-dihydroxy-16α-fluoroandrost-5,7-diene. Exemplary compounds in group 53-44 when $R^9$ is —CH(β-OC(O)CH$_3$)— include compound 1.2.4.1, which is 2β-acetoxy-3β,7β-dihydroxy-16α-fluoro-17β-aminoandrost-5,7-diene, 1.1.5.9, which is 2β-acetoxy-3β,17β-dihydroxyandrost-5,7-diene, 1.1.6.9, which is 2β-acetoxy-3β,16α,17β-trihydroxyandrost-5,7-diene, 1.1.6.1, which is 2β-acetoxy-3β,16α-dihydroxy-17β-aminoandrost-5,7-diene and 1.1.4.9, which is 2β-acetoxy-3β,17β-dihydroxy-16α-fluoroandrost-5,7-diene. Exemplary compounds in group 53-50-44 when $R^9$ is —O— include compound 1.2.4.1, which is 2-oxa-3β,7β-dihydroxy-16α-fluoro-17α-aminoandrost-5,7-diene, 1.1.5.9, which is 2-oxa-3β,17α-dihydroxyandrost-5,7-diene, 1.1.6.9, which is 2-oxa-3β,16α,17α-trihydroxyandrost-5,7-diene, 1.1.6.1, which is 2-oxa-3β,16α-dihydroxy-17α-aminoandrost-5,7-diene and 1.1.4.9, which is 2-oxa-3β,17α-dihydroxy-16α-fluoroandrost-5,7-diene. Exemplary compounds in group 53-51-44 when $R^9$ is —O— include compound 1.2.4.1, which is 2-oxa-3α,7β-dihydroxy-16α-fluoro-17β-aminoandrost-5,7-diene, 1.1.5.9, which is 2-oxa-3α,17β-dihydroxyandrost-5,7-diene, 1.1.6.9, which is 2-oxa-3α,16α,17β-trihydroxyandrost-5,7-diene, 1.1.6.1, which is 2-oxa-3α,16α-dihydroxy-17β-aminoandrost-5,7-diene and 1.1.4.9, which is 2-oxa-3α,17β-dihydroxy-16α-fluoroandrost-5,7-diene. Exemplary compounds in group 53-51-50-44 when $R^9$ is —O— include compound 1.2.4.1, which is 2-oxa-3α,7β-dihydroxy-16α-fluoro-17α-aminoandrost-5,7-diene, 1.1.5.9, which is 2-oxa-3α,17α-dihydroxyandrost-5,7-diene, 1.1.6.9, which is 2-oxa-3α,16α,17α-trihydroxyandrost-5,7-diene, 1.1.6.1, which is 2-oxa-3α,16α-dihydroxy-17α-aminoandrost-5,7-diene and 1.1.4.9, which is 2-oxa-3α,17α-dihydroxy-16α-fluoroandrost-5,7-diene. Compounds or genera of compounds in the other group 53 compound groups where $R^9$ is a moiety described here or elsewhere herein are defined as described in Tables A and B in the same manner.

Group 54. This group comprises compounds and compound genera in compound groups 1-53 described above, wherein $R^8$ is a moiety other than —CH$_2$— or =CH—. Exemplary $R^8$ include —O—, —NH—, —NCH$_3$—, =N—, —S—, —S(O)—, —S(O)(O)—, —CHR$^{10}$—, —C(R$^{10}$)$_2$— or =CR$^{10}$— where $R^{10}$ are independently selected and each $R^{10}$ can be in the α-configuration or the β-configuration. When one or both $R^{10}$ are not —H, exemplary $R^8$ include —O—, —NH—, —NCH$_3$—, =N—, —S—, —S(O)—, —S(O)(O)—, —S$^+$(optionally substituted alkyl)-, —CHR$^{10}$—, —C(R$^{10}$)$_2$— or =CR$^{10}$— where $R^{10}$ are independently selected and a single $R^{10}$ can be in the α-configuration or the β-configuration. When one or both $R^{10}$ are not —H, exemplary $R^9$ include —CH(α-OH)—, —CH(β-OH)—, —CH(α-C1-6 ester)-, —CH(β-C1-6 ester)-, —CH(α-O—C1-6 alkyl)-, —CH(β-O—C1-6 alkyl)-, —CH(α-S—C1-6 alkyl)-, —CH(β-S—C1-6 alkyl)-, —CH(α-NH—C1-6 alkyl)-, —CH(β-NH—C1-6 alkyl)-, —CH(α-O—C2-6 alkenyl)-, —CH(β-O—C2-6 alkenyl)-, —CH(α-O—C2-6 alkynyl)-, —CH(β-O—C2-6 alkynyl)-, —CH(α-O—C1-6 alkoxy)-, —CH(β-O—C1-6 alkoxy)-, —CH(α-O—CH$_2$—C2-6 alkenyl)-, —CH(β-O—CH$_2$—C2-6 alkenyl)-, —CH(α-O—CH$_2$—C2-6 alkynyl)-, —CH(β-O—CH$_2$—C2-6 alkynyl)-, —CH(α-C-linked heterocycle)-, —CH(βC-linked heterocycle)-, —CH(α-N-linked heterocycle)-, —CH(β-N-linked heterocycle)-, —CH(α-halogen)-, —CH(β-halogen)-, —C(F)$_2$—, —C(Cl)$_2$—, —C(Br)$_2$—, —C(I)$_2$—, —C(CH$_3$)$_2$—, —C(C$_2$H$_5$)$_2$—, —CH(α-SH)—, —CH(β-SH)—, —CH(α-NH$_2$)—, —CH(β-NH$_2$)—, —CH(α-

NHCH₃)—, —CH(β-NHCH₃)—, —CH(α-N[CH₃]₂)—, —CH(β-N[CH₃]₂)—, —CH(α-N[C₂H₅]₂)—, —CH(β-N[C₂H₅]₂)—, —CH(α-NO₂)—, —CH(β-NO₂)—, —CH(α-N₃)—, —CH(β-N₃)—, —CH(α-CN)—, —CH(β-CN)—, —CH(α-SCN)—, —CH(α-NC(O)—(CH₂)$_m$—CH₃)—, —CH(β-NC(O)—(CH₂)$_m$—CH₃)—, —CH(α-NC(O)O—(CH₂)$_m$—CH₃)—, —CH(β-NC(O)O—(CH₂)$_m$—CH₃)—, —C(C1-4 alkyl)₂-, —C(C1-4 alkenyl)₂-, where m is 0, 1, 2, 3, 4, 5 or 6, and any alkyl, alkenyl, alkynyl, alkoxy, alkenyloxy, alkynyloxy or heterocycle moiety is optionally substituted and each is independently chosen. When no double bond is present at the 9-11 position, $R^8$ can be a =N—, —O— or —S-heteroatom, or $R^8$ can be linked to a double bonded $R^{10}$ moiety such as =O, =S, =NOH, =NCH₃, =NH, =CH₂, =CH₂CH₃, =CH₂CH₂-halogen, =CH₂CH₂OH, =CH₂C(O)OH or another moiety as defined herein for $R^{10}$. In these cases, $R^8$ is a moiety such as —C(O)—, —C(NOH)— or —C(=CH₂)—. When a double bond is present at the 9-11 position, $R^8$ can be =N—. In other embodiments, $R^8$ is absent, leaving a 5-membered ring.

Groups of compounds in this group are defined essentially as described above, e.g., for groups 52 and 53. Compound groups in group 54 where $R^8$ is substituted or is absent thus include 54-1, 54-2, 54-3, 54-4, 54-5, 54-6, 54-7, 54-8, 54-9, 54-10, 54-11, 54-12, 54-13, 54-14, 54-15, 54-16, 54-17, 54-18, 54-19, 54-20, 54-21, 54-22, 54-23, 54-24, 54-25, 54-26, 54-27, 54-28, 54-29, 54-30, 54-31, 54-32, 54-33, 54-34, 54-35, 54-36, 54-37, 54-38, 54-39, 54-40, 54-41, 54-42, 54-43, 54-44, 54-45, 54-46, 54-47, 54-48, 54-49, 54-50-1, 54-50-2, 54-50-3, 54-50-6, 54-50-7, 54-50-8, 54-50-9, 54-50-10, 54-50-11, 54-50-12, 54-50-13, 54-50-14, 54-50-15, 54-50-16, 54-50-19, 54-50-20, 54-50-21, 54-50-22, 54-50-23, 54-50-24, 54-50-27, 54-50-28, 54-50-29, 54-50-30, 54-50-31, 54-50-32, 54-50-34, 54-50-35, 54-50-36, 54-50-37, 54-50-38, 54-50-40, 54-50-41, 54-50-42, 54-50-43, 54-50-44, 54-50-45, 54-50-46, 54-50-47, 54-50-48, 54-51-6, 54-51-7, 54-51-8, 54-51-9, 54-51-10, 54-51-11, 54-51-12, 54-51-13, 54-51-14, 54-51-15, 54-51-16, 54-51-17, 54-51-18, 54-51-19, 54-51-20, 54-51-21, 54-51-22, 54-51-23, 54-51-24, 54-51-30, 54-51-31, 54-51-32, 54-51-33, 54-51-40, 54-51-41, 54-51-42, 54-51-43, 54-51-44, 54-51-45, 54-51-47, 54-51-48, 54-51-49, 54-51-50-6, 54-51-50-7, 54-51-50-8, 54-51-50-9, 54-51-50-10, 54-51-50-11, 54-51-50-12, 54-51-50-13, 54-51-50-14, 54-51-50-15, 54-51-50-16, 54-51-50-19, 54-51-50-20, 54-51-50-21, 54-51-50-22, 54-51-50-23, 54-51-50-24, 54-51-50-30, 54-51-50-31, 54-51-50-32, 54-51-50-40, 54-51-50-41, 54-51-50-42, 54-51-50-43, 54-51-50-44, 54-51-50-45, 54-51-50-47, 54-51-50-48, 54-52-1, 54-52-2, 54-52-3, 54-52-6, 54-52-7, 54-52-8, 54-52-9, 54-52-10, 54-52-11, 54-52-12, 54-52-13, 54-52-14, 54-52-23, 54-52-24, 54-52-29, 54-52-30, 54-52-31, 54-52-32, 54-52-33, 54-52-34, 54-52-35, 54-52-36, 54-52-37, 54-52-41, 54-52-42, 54-52-43, 54-52-44, 54-52-45, 54-52-46, 54-52-47, 54-52-50-1, 54-52-50-2, 54-52-50-3, 54-52-50-6, 54-52-50-7, 54-52-50-8, 54-52-50-9, 54-52-50-10, 54-52-50-11, 54-52-50-12, 54-52-50-13, 54-52-50-14, 54-52-50-23, 54-52-50-24, 54-52-50-29, 54-52-50-30, 54-52-50-31, 54-52-50-34, 54-52-50-35, 54-52-50-36, 54-52-50-37, 54-52-50-41, 54-52-50-42, 54-52-50-43, 54-52-50-44, 54-52-50-45, 54-52-50-46, 54-52-50-47, 54-52-51-6, 54-52-51-7, 54-52-51-8, 54-52-51-9, 54-52-51-10, 54-52-51-11, 54-52-51-12, 54-52-51-13, 54-52-51-14, 54-52-51-23, 54-52-51-24, 54-52-51-30, 54-52-51-31, 54-52-51-41, 54-52-51-42, 54-52-51-43, 54-52-51-44, 54-52-51-45, 54-52-51-47, 54-52-51-50-6, 54-52-51-50-7, 54-52-51-50-8, 54-52-51-50-9, 54-52-51-50-10, 54-52-51-50-11, 54-52-51-50-12, 54-52-51-50-13, 54-52-51-50-14, 54-52-51-50-23, 54-52-51-50-24, 54-52-51-50-30, 54-52-51-50-31, 54-52-51-50-41, 54-52-51-50-42, 54-52-51-50-43, 54-52-51-50-44, 54-52-51-50-45, 54-52-51-50-47, 54-53-1, 54-53-2, 54-53-3, 54-53-4, 54-53-5, 54-53-6, 54-53-7, 54-53-8, 54-53-9, 54-53-10, 54-53-11, 54-53-12, 54-53-13, 54-53-14, 54-53-15, 54-53-16, 54-53-17, 54-53-18, 54-53-19, 54-53-20, 54-53-21, 54-53-22, 54-53-23, 54-53-24, 54-53-25, 54-53-26, 54-53-27, 54-53-28, 54-53-29, 54-53-30, 54-53-31, 54-53-32, 54-53-33, 54-53-34, 54-53-35, 54-53-36, 54-53-37, 54-53-38, 54-53-39, 54-53-40, 54-53-41, 54-53-42, 54-53-43, 54-53-44, 54-53-45, 54-53-46, 54-53-47, 54-53-48, 54-53-49, 54-53-50-1, 54-53-50-2, 54-53-50-3, 54-53-50-6, 54-53-50-7, 54-53-50-8, 54-53-50-9, 54-53-50-10, 54-53-50-11, 54-53-50-12, 54-53-50-13, 54-53-50-14, 54-53-50-15, 54-53-50-16, 54-53-50-19, 54-53-50-20, 54-53-50-21, 54-53-50-22, 54-53-50-23, 54-53-50-24, 54-53-50-27, 54-53-50-28, 54-53-50-29, 54-53-50-30, 54-53-50-31, 54-53-50-32, 54-53-50-34, 54-53-50-35, 54-53-50-36, 54-53-50-37, 54-53-50-38, 54-53-50-40, 54-53-50-41, 54-53-50-42, 54-53-50-43, 54-53-50-44, 54-53-50-45, 54-53-50-46, 54-53-50-47, 54-53-50-48, 54-53-51-6, 54-53-51-7, 54-53-51-8, 54-53-51-9, 54-53-51-10, 54-53-51-11, 54-53-51-12, 54-53-51-13, 54-53-51-14, 54-53-51-15, 54-53-51-16, 54-53-51-17, 54-53-51-18, 54-53-51-19, 54-53-51-20, 54-53-51-21, 54-53-51-22, 54-53-51-23, 54-53-51-24, 54-53-51-30, 54-53-51-31, 54-53-51-32, 54-53-51-33, 54-53-51-40, 54-53-51-41, 54-53-51-42, 54-53-51-43, 54-53-51-44, 54-53-51-45, 54-53-51-47, 54-53-51-48, 54-53-51-49, 54-53-51-50-6, 54-53-51-50-7, 54-53-51-50-8, 54-53-51-50-9, 54-53-51-50-10, 54-53-51-50-11, 54-53-51-50-12, 54-53-51-50-13, 54-53-51-50-14, 54-53-51-50-15, 54-53-51-50-16, 54-53-51-50-19, 54-53-51-50-20, 54-53-51-50-21, 54-53-51-50-22, 54-53-51-50-23, 54-53-51-50-24, 54-53-51-50-30, 54-53-51-50-31, 54-53-51-50-32, 54-53-51-50-40, 54-53-51-50-41, 54-53-51-50-42, 54-53-51-50-43, 54-53-51-50-44, 54-53-51-50-45, 54-53-51-50-47, 54-53-51-50-48, 54-53-52-1, 54-53-52-2, 54-53-52-3, 54-53-52-6, 54-53-52-7, 54-53-52-8, 54-53-52-9, 54-53-52-10, 54-53-52-11, 54-53-52-12, 54-53-52-13, 54-53-52-14, 54-53-52-23, 54-53-52-24, 54-53-52-29, 54-53-52-30, 54-53-52-31, 54-53-52-32, 54-53-52-33, 54-53-52-34, 54-53-52-35, 54-53-52-36, 54-53-52-37, 54-53-52-41, 54-53-52-42, 54-53-52-43, 54-53-52-44, 54-53-52-45, 54-53-52-46, 54-53-52-47, 54-53-52-50-1, 54-53-52-50-2, 54-53-52-50-3, 54-53-52-50-6, 54-53-52-50-7, 54-53-52-50-8, 54-53-52-50-9, 54-53-52-50-10, 54-53-52-50-11, 54-53-52-50-12, 54-53-52-50-13, 54-53-52-50-14, 54-53-52-50-23, 54-53-52-50-24, 54-53-52-50-29, 54-53-52-50-30, 54-53-52-50-31, 54-53-52-50-34, 54-53-52-50-35, 54-53-52-50-36, 54-53-52-50-37, 54-53-52-50-41, 54-53-52-50-42, 54-53-52-50-43, 54-53-52-50-44, 54-53-52-50-45, 54-53-52-50-46, 54-53-52-50-47, 54-53-52-51-6, 54-53-52-51-7, 54-53-52-51-8, 54-53-52-51-9, 54-53-52-51-10, 54-53-52-51-11, 54-53-52-51-12, 54-53-52-51-13, 54-53-52-51-14, 54-53-52-51-23, 54-53-52-51-24, 54-53-52-51-30, 54-53-52-51-31, 54-53-52-51-41, 54-53-52-51-42, 54-53-52-51-43, 54-53-52-51-44, 54-53-52-51-45, 54-53-52-51-47, 54-53-52-51-50-6, 54-53-52-51-50-7, 54-53-52-51-50-8, 54-53-52-51-50-9, 54-53-52-51-50-10, 54-53-52-51-50-11, 54-53-52-51-50-12, 54-53-52-51-50-13, 54-53-52-51-50-14, 54-53-52-51-50-23, 54-53-52-51-50-24, 54-53-52-51-50-30, 54-53-52-51-50-31, 54-53-52-51-50-41, 54-53-52-51-50-42, 54-53-52-51-50-43, 54-53-52-51-50-44, 54-53-52-51-50-45 and 54-53-52-51-50-47. For each of these compound groups, designations 1.1.1.1 through 10.10.10.10 in Table B specifies a compound or genus of compounds as defined by the Table A substituents and any $R^8$ moiety as described here or elsewhere herein.

Exemplary compounds in group 54-1 when $R^8$ is —O— include compound 1.2.4.1, which is 11-oxa-3,7β-dihydroxy-16α-fluoro-17β-aminoandrost-1,3-diene, 1.1.5.9, which is 11-oxa-3,17β-dihydroxyandrost-1,3-diene, 1.1.6.9, which is 11-oxa-3,16α,17β-trihydroxyandrost-1,3-diene, 1.1.6.1, which is 11-oxa-3,16α-dihydroxy-17β-aminoandrost-1,3-diene and 1.1.4.9, which is 11-oxa-3,17β-dihydroxy-16α-fluoroandrost-1,3-diene. Exemplary compounds in group 54-7 when $R^8$ is —O— include compound 1.2.4.1, which is 11-oxa-3β,7-dihydroxy-16α-fluoro-17β-aminoandrost-1,6-diene, 1.1.5.9, which is 11-oxa-3β,17β-dihydroxyandrost-1,6-diene, 1.1.6.9, which is 11-oxa-3β,16α,17β-trihydroxyandrost-1,6-diene, 1.1.6.1, which is 11-oxa-3β,16α-dihydroxy-17β-aminoandrost-1,6-diene and 1.1.4.9, which is 11-oxa-3β,17β-dihydroxy-16α-fluoroandrost-1,6-diene. Exemplary compounds in group 54-1 when $R^8$ is —NH— include compound 1.2.4.1, which is 11-aza-3,7β-dihydroxy-16α-fluoro-17β-aminoandrost-1,3-diene, 1.1.5.9, which is 11-aza-3,17β-dihydroxyandrost-1,3-diene, 1.1.6.9, which is 11-aza-3,16α,17β-trihydroxyandrost-1,3-diene, 1.1.6.1, which is 11-aza-3,16α-dihydroxy-17β-aminoandrost-1,3-diene and 1.1.4.9, which is 11-aza-3,17β-dihydroxy-16α-fluoroandrost-1,3-diene. Exemplary compounds in group 54-1 when $R^8$ is —S— include compound 1.2.4.1, which is 11-thia-3,7β-dihydroxy-16α-fluoro-17β-aminoandrost-1,3-diene, 1.1.5.9, which is 11-thia-3,17β-dihydroxyandrost-1,3-diene, 1.1.6.9, which is 11-thia-3,16α,17β-trihydroxyandrost-1,3-diene, 1.1.6.1, which is 11-thia-3,16α-dihydroxy-17β-aminoandrost-1,3-diene and 1.1.4.9, which is 11-thia-3,17β-dihydroxy-16α-fluoroandrost-1,3-diene. Exemplary compounds in group 54-53-1 when $R^8$ and $R^9$ are —O— include compound 1.2.4.1, which is 2,11-dioxa-3,7β-dihydroxy-16α-fluoro-17β-aminoandrost-1,3-diene, 1.1.5.9, which is 2,11-dioxa-3,17β-dihydroxyandrost-1,3-diene, 1.1.6.9, which is 2,11-dioxa-3,16α,17β-trihydroxyandrost-1,3-diene, 1.1.6.1, which is 2,11-dioxa-3,16α-dihydroxy-17β-aminoandrost-1,3-diene and 1.1.4.9, which is 2,11-dioxa-3,17β-dihydroxy-16α-fluoroandrost-1,3-diene. Exemplary compounds in group 54-44 when $R^8$ is —CH(α-NH[CH$_3$])— include compound 1.2.4.1, which is 11α-methylamino-3β,7β-dihydroxy-16α-fluoro-17β-aminoandrost-5,7-diene, 1.1.5.9, which is 11α-methylamino-3β,17β-dihydroxyandrost-5,7-diene, 1.1.6.9, which is 11α-methylamino-3β,16α,17β-trihydroxyandrost-5,7-diene, 1.1.6.1, which is 11α-methylamino-3β,16α-dihydroxy-17β-aminoandrost-5,7-diene and 1.1.4.9, which is 11α-methylamino-3β,17β-dihydroxy-16α-fluoroandrost-5,7-diene. Exemplary compounds in group 54-2 when $R^8$ is —CH(β-OH)— include compound 1.2.4.1, which is 11β,3,7β-trihydroxy-16α-fluoro-17β-amino-5β-androst-1,3-diene, 1.1.5.9, which is 11β,3,17β-trihydroxy-5β-androst-1,3-diene, 1.1.6.9, which is 11β,3,16α,17β-tetrahydroxy-5β-androst-1,3-diene, 1.1.6.1, which is 11β,3,16α-trihydroxy-17β-amino-5β-androst-1,3-diene and 1.1.4.9, which is 11β,3,17β-trihydroxy-16α-fluoro-5β-androst-1,3-diene. Exemplary compounds in group 54-3 when $R^8$ is —CH(β-F)— include compound 1.2.4.1, which is 11β-fluoro-3,7β-dihydroxy-16α-fluoro-17β-aminoandrost-1,3,5-triene, 1.1.5.9, which is 11β-fluoro-3,17β-trihydroxyandrost-1,3,5-triene, 1.1.6.9, which is 11β-fluoro-3,16α,17β-tetrahydroxyandrost-1,3,5-triene, 1.1.6.1, which is 11β-fluoro-3,16α-trihydroxy-17β-aminoandrost-1,3,5-triene and 1.1.4.9, which is 11β-fluoro-3,17β-trihydroxy-16α-fluoroandrost-1,3,5-triene. Exemplary compounds in group 54-3 when $R^8$ is —CH(β-C1-3 alkyl)- include compound 1.2.4.1, which is 11β-C1-3 alkyl-3,7β-dihydroxy-16α-fluoro-17β-aminoandrost-1,3,5-triene, 1.1.5.9, which is 11β-C1-3 alkyl-3,17β-trihydroxyandrost-1,3,5-triene, 1.1.6.9, which is 11β-C1-3 alkyl-3,16α,17β-tetrahydroxyandrost-1,3,5-triene, 1.1.6.1, which is 11β-C1-3 alkyl-3,16α-trihydroxy-17β-aminoandrost-1,3,5-triene and 1.1.4.9, which is 11β-C1-3 alkyl-3,17β-trihydroxy-16α-fluoroandrost-1,3,5-triene. Compounds or genera of compounds in the other group 54 compound groups where $R^8$ is a moiety described here or elsewhere herein are defined as described in Tables A and B in the same manner.

Group 55. This group comprises compounds and compound genera in compound groups 1-54 described above, wherein $R^{10G}$ is (1) a moiety other than hydrogen in the α-configuration or (2) hydrogen or another moiety as defined for this variable group in the β-configuration, instead of being in the α-configuration as shown in group 1. Exemplary $R^{10G}$ moieties include —F, —Cl, —Br, —OH, —H, ester, carbonate, C1-4 optionally substituted alkyl, C2-4 optionally substituted alkenyl or C2-4 optionally substituted alkynyl such as —CH$_3$, —C$_2$H$_5$, —CH$_2$OH, —CH$_2$F, —CHO, —CH=CH$_2$, —CH=CHOH, —C≡CH, —C≡C—CH$_3$ or another moiety described herein for $R^{10G}$, where any of these moieties is in the α-configuration or the β-configuration.

Groups of compounds in this group are defined essentially as described above, e.g., for groups 53 and 54. Compound groups in group 53 where $R^{10G}$ is substituted or is in the β-configuration thus include 55-1, 55-2, 55-3, 55-4, 55-5, 55-6, 55-7, 55-8, 55-9, 55-10, 55-11, 55-12, 55-13, 55-14, 55-15, 55-16, 55-17, 55-18, 55-19, 55-20, 55-21, 55-22, 55-23, 55-24, 55-25, 55-26, 55-27, 55-28, 55-29, 55-30, 55-31, 55-32, 55-33, 55-34, 55-35, 55-36, 55-37, 55-38, 55-39, 55-40, 55-41, 55-42, 55-43, 55-44, 55-45, 55-46, 55-47, 55-48, 55-49, 55-50-1, 55-50-2, 55-50-3, 55-50-6, 55-50-7, 55-50-8, 55-50-9, 55-50-10, 55-50-11, 55-50-12, 55-50-13, 55-50-14, 55-50-15, 55-50-16, 55-50-19, 55-50-20, 55-50-21, 55-50-22, 55-50-23, 55-50-24, 55-50-27, 55-50-28, 55-50-29, 55-50-30, 55-50-31, 55-50-32, 55-50-34, 55-50-35, 55-50-36, 55-50-37, 55-50-38, 55-50-40, 55-50-41, 55-50-42, 55-50-43, 55-50-44, 55-50-45, 55-50-46, 55-50-47, 55-50-48, 55-51-6, 55-51-7, 55-51-8, 55-51-9, 55-51-10, 55-51-11, 55-51-12, 55-51-13, 55-51-14, 55-51-15, 55-51-16, 55-51-17, 55-51-18, 55-51-19, 55-51-20, 55-51-21, 55-51-22, 55-51-23, 55-51-24, 55-51-30, 55-51-31, 55-51-32, 55-51-33, 55-51-40, 55-51-41, 55-51-42, 55-51-43, 55-51-44, 55-51-45, 55-51-47, 55-51-48, 55-51-49, 55-51-50-6, 55-51-50-7, 55-51-50-8, 55-51-50-9, 55-51-50-10, 55-51-50-11, 55-51-50-12, 55-51-50-13, 55-51-50-14, 55-51-50-15, 55-51-50-16, 55-51-50-19, 55-51-50-20, 55-51-50-21, 55-51-50-22, 55-51-50-23, 55-51-50-24, 55-51-50-30, 55-51-50-31, 55-51-50-32, 55-51-50-40, 55-51-50-41, 55-51-50-42, 55-51-50-43, 55-51-50-44, 55-51-50-45, 55-51-50-47, 55-51-50-48, 55-52-1, 55-52-2, 55-52-3, 55-52-6, 55-52-7, 55-52-8, 55-52-9, 55-52-10, 55-52-11, 55-52-12, 55-52-13, 55-52-14, 55-52-23, 55-52-24, 55-52-29, 55-52-30, 55-52-31, 55-52-32, 55-52-33, 55-52-34, 55-52-35, 55-52-36, 55-52-37, 55-52-41, 55-52-42, 55-52-43, 55-52-44, 55-52-45, 55-52-46, 55-52-47, 55-52-50-1, 55-52-50-2, 55-52-50-3, 55-52-50-6, 55-52-50-7, 55-52-50-8, 55-52-50-9, 55-52-50-10, 55-52-50-11, 55-52-50-12, 55-52-50-13, 55-52-50-14, 55-52-50-23, 55-52-50-24, 55-52-50-29, 55-52-50-30, 55-52-50-31, 55-52-50-34, 55-52-50-35, 55-52-50-36, 55-52-50-37, 55-52-50-41, 55-52-50-42, 55-52-50-43, 55-52-50-44, 55-52-50-45, 55-52-50-46, 55-52-50-47, 55-52-51-6, 55-52-51-7, 55-52-51-8, 55-52-51-9, 55-52-51-10, 55-52-51-11, 55-52-51-12, 55-52-51-13, 55-52-51-14, 55-52-51-23, 55-52-51-24, 55-52-51-30, 55-52-51-31, 55-52-51-41, 55-52-51-42, 55-52-51-43, 55-52-51-44, 55-52-51-45, 55-52-51-47, 55-52-51-50-6, 55-52-51-50-7, 55-52-51-50-8, 55-52-51-50-9, 55-52-51-50-10, 55-52-51-50-11, 55-52-51-50-12, 55-52-51-50-13, 55-52-51-50-14, 55-52-51-50-23, 55-52-51-50-24, 55-52-51-50-30, 55-52-51-50-31, 55-52-51-50-41, 55-52-51-50-42, 55-52-51-50-43, 55-52-51-50-44, 55-52-51-50-45, 55-52-51-50-47, 55-53-1, 55-53-2, 55-53-3, 55-53-4, 55-53-5, 55-53-6, 55-53-7, 55-53-8, 55-53-9, 55-53-10, 55-53-11, 55-53-12, 55-53-13, 55-53-14, 55-53-15, 55-53-16, 55-53-17, 55-53-18, 55-53-19, 55-53-20, 55-53-21, 55-53-22, 55-53-23, 55-53-24, 55-53-25, 55-53-26, 55-53-27, 55-53-28, 55-53-29, 55-53-30, 55-53-31, 55-53-32, 55-53-33, 55-53-34, 55-53-35, 55-53-36, 55-53-37, 55-53-38, 55-53-39, 55-53-40, 55-53-41, 55-53-42, 55-53-43, 55-53-44, 55-53-45, 55-53-46, 55-53-47, 55-53-48, 55-53-49, 55-53-50-1, 55-53-50-2, 55-53-50-3, 55-53-50-6, 55-53-50-7, 55-53-50-8, 55-53-50-9, 55-53-50-10, 55-53-50-11, 55-53-50-12, 55-53-50-13, 55-53-50-14, 55-53-50-15, 55-53-50-16, 55-53-50-19, 55-53-50-20, 55-53-50-21, 55-53-50-22, 55-53-50-23, 55-53-50-24, 55-53-50-27, 55-53-50-28, 55-53-50-29, 55-53-50-30, 55-53-50-31, 55-53-50-32, 55-53-50-34, 55-53-50-35, 55-53-50-36, 55-53-50-37, 55-53-50-38, 55-53-50-40, 55-53-50-41, 55-53-50-42, 55-53-50-43, 55-53-50-44, 55-53-50-45, 55-53-50-46, 55-53-50-47, 55-53-50-48, 55-53-51-6, 55-53-51-7, 55-53-51-8, 55-53-51-9, 55-53-51-10, 55-53-51-11, 55-53-51-12, 55-53-51-13, 55-53-51-14, 55-53-51-15, 55-53-51-16, 55-53-51-17, 55-53-51-18, 55-53-51-19, 55-53-51-20, 55-53-51-21, 55-53-51-22, 55-53-51-23, 55-53-51-24, 55-53-51-30, 55-53-51-31, 55-53-51-32, 55-53-51-33, 55-53-51-40, 55-53-51-41, 55-53-51-42, 55-53-51-43, 55-53-51-44, 55-53-51-45, 55-53-51-47, 55-53-51-48, 55-53-51-49, 55-53-51-50-6, 55-53-51-50-7, 55-53-51-50-8, 55-53-51-50-9, 55-53-51-50-10, 55-53-51-50-11, 55-53-51-50-12, 55-53-51-50-13, 55-53-51-50-14, 55-53-51-50-15, 55-53-51-50-16, 55-53-51-50-19, 55-53-51-50-20, 55-53-51-50-21, 55-53-51-50-22, 55-53-51-50-23, 55-53-51-50-24, 55-53-51-50-30, 55-53-51-50-31, 55-53-51-50-32, 55-53-51-50-40, 55-53-51-50-41, 55-53-51-50-42, 55-53-51-50-43, 55-53-51-50-44, 55-53-51-50-45, 55-53-51-50-47, 55-53-51-50-48, 55-53-52-1, 55-53-52-2, 55-53-52-3, 55-53-52-6, 55-53-52-7, 55-53-52-8, 55-53-52-9, 55-53-52-10, 55-53-52-11, 55-53-52-12, 55-53-52-13, 55-53-52-14, 55-53-52-23, 55-53-52-24, 55-53-52-29, 55-53-52-30, 55-53-52-31, 55-53-52-32, 55-53-52-33, 55-53-52-34, 55-53-52-35, 55-53-52-36, 55-53-52-37, 55-53-52-41, 55-53-52-42, 55-53-52-43, 55-53-52-44, 55-53-52-45, 55-53-52-46, 55-53-52-47, 55-53-52-50-1, 55-53-52-50-2, 55-53-52-50-3, 55-53-52-50-6, 55-53-52-50-7, 55-53-52-50-8, 55-53-52-50-9, 55-53-52-50-10, 55-53-52-50-11, 55-53-52-50-12, 55-53-52-50-13, 55-53-52-50-14, 55-53-52-50-23, 55-53-52-50-24, 55-53-52-50-29, 55-53-52-50-30, 55-53-52-50-31, 55-53-52-50-34, 55-53-52-50-35, 55-53-52-50-36, 55-53-52-50-37, 55-53-52-50-41, 55-53-52-50-42, 55-53-52-50-43, 55-53-52-50-44, 55-53-52-50-45, 55-53-52-50-46, 55-53-52-50-47, 55-53-52-51-6, 55-53-52-51-7, 55-53-52-51-8, 55-53-52-51-9, 55-53-52-51-10, 55-53-52-51-11, 55-53-52-51-12, 55-53-52-51-13, 55-53-52-51-14, 55-53-52-51-23, 55-53-52-51-24, 55-53-52-51-30, 55-53-52-51-31, 55-53-52-51-41, 55-53-52-51-42, 55-53-52-51-43, 55-53-52-51-44, 55-53-52-51-45, 55-53-52-51-47, 55-53-52-51-50-6, 55-53-52-51-50-7, 55-53-52-51-50-8, 55-53-52-51-50-9, 55-53-52-51-50-10, 55-53-52-51-50-11, 55-53-52-51-50-12, 55-53-52-51-50-13, 55-53-52-51-50-14, 55-53-52-51-50-23, 55-53-52-51-50-24, 55-53-52-51-50-30, 55-53-52-51-50-31, 55-53-52-51-50-41, 55-53-52-51-50-42, 55-53-52-51-50-43, 55-53-52-51-50-44, 55-53-52-51-50-45, 55-53-52-51-50-47, 55-54-1, 55-54-2, 55-54-3, 55-54-4, 55-54-5, 55-54-6, 55-54-7, 55-54-8, 55-54-9, 55-54-10, 55-54-11, 55-54-12, 55-54-13, 55-54-14, 55-54-15, 55-54-16, 55-54-17, 55-54-18, 55-54-19, 55-54-20, 55-54-21, 55-54-22, 55-54-23, 55-54-24, 55-54-25, 55-54-26, 55-54-27, 55-54-28, 55-54-29, 55-54-30, 55-54-31, 55-54-32, 55-54-33, 55-54-34, 55-54-35, 55-54-36, 55-54-37, 55-54-38, 55-54-39, 55-54-40, 55-54-41, 55-54-42, 55-54-43, 55-54-44, 55-54-45, 55-54-46, 55-54-47, 55-54-48, 55-54-49, 55-54-50-1, 55-54-50-2, 55-54-50-3, 55-54-50-6, 55-54-50-7, 55-54-50-8, 55-54-50-9, 55-54-50-10, 55-54-50-11, 55-54-50-12, 55-54-50-13, 55-54-50-14, 55-54-50-15, 55-54-50-16, 55-54-50-19, 55-54-50-20, 55-54-50-21, 55-54-50-22, 55-54-50-23, 55-54-50-24, 55-54-50-27, 55-54-50-28, 55-54-50-29, 55-54-50-30, 55-54-50-31, 55-54-50-32, 55-54-50-34, 55-54-50-35, 55-54-50-36, 55-54-50-37, 55-54-50-38, 55-54-50-40, 55-54-50-41, 55-54-50-42, 55-54-50-43, 55-54-50-44, 55-54-50-45, 55-54-50-46, 55-54-50-47, 55-54-50-48, 55-54-51-6, 55-54-51-7, 55-54-51-8, 55-54-51-9, 55-54-51-10, 55-54-51-11, 55-54-51-12, 55-54-51-13, 55-54-51-14, 55-54-51-15, 55-54-51-16, 55-54-51-17, 55-54-51-18, 55-54-51-19, 55-54-51-20, 55-54-51-21, 55-54-51-22, 55-54-51-23, 55-54-51-24, 55-54-51-30, 55-54-51-31, 55-54-51-32, 55-54-51-33, 55-54-51-40, 55-54-51-41, 55-54-51-42, 55-54-51-43, 55-54-51-44, 55-54-51-45, 55-54-51-47, 55-54-51-48, 55-54-51-49, 55-54-51-50-6, 55-54-51-50-7, 55-54-51-50-8, 55-54-51-50-9, 55-54-51-50-10, 55-54-51-50-11, 55-54-51-50-12, 55-54-51-50-13, 55-54-51-50-14, 55-54-51-50-15, 55-54-51-50-16, 55-54-51-50-19, 55-54-51-50-20, 55-54-51-50-21, 55-54-51-50-22, 55-54-51-50-23, 55-54-51-50-24, 55-54-51-50-30, 55-54-51-50-31, 55-54-51-50-32, 55-54-51-50-40, 55-54-51-50-41, 55-54-51-50-42, 55-54-51-50-43, 55-54-51-50-44, 55-54-51-50-45, 55-54-51-50-47, 55-54-51-50-48, 55-54-52-1, 55-54-52-2, 55-54-52-3, 55-54-52-6, 55-54-52-7, 55-54-52-8, 55-54-52-9, 55-54-52-10, 55-54-52-11, 55-54-52-12, 55-54-52-13, 55-54-52-14, 55-54-52-23, 55-54-52-24, 55-54-52-29, 55-54-52-30, 55-54-52-31, 55-54-52-32, 55-54-52-33, 55-54-52-34, 55-54-52-35, 55-54-52-36, 55-54-52-37, 55-54-52-41, 55-54-52-42, 55-54-52-43, 55-54-52-44, 55-54-52-45, 55-54-52-46, 55-54-52-47, 55-54-52-50-1, 55-54-52-50-2, 55-54-52-50-3, 55-54-52-50-6, 55-54-52-50-7, 55-54-52-50-8, 55-54-52-50-9, 55-54-52-50-10, 55-54-52-50-11, 55-54-52-50-12, 55-54-52-50-13, 55-54-52-50-14, 55-54-52-50-23, 55-54-52-50-24, 55-54-52-50-29, 55-54-52-50-30, 55-54-52-50-31, 55-54-52-50-34, 55-54-52-50-35, 55-54-52-50-36, 55-54-52-50-37, 55-54-52-50-41, 55-54-52-50-42, 55-54-52-50-43, 55-54-52-50-44, 55-54-52-50-45, 55-54-52-50-46, 55-54-52-50-47, 55-54-52-51-6, 55-54-52-51-7, 55-54-52-51-8, 55-54-52-51-9, 55-54-52-51-10, 55-54-52-51-11, 55-54-52-51-12, 55-54-52-51-13, 55-54-52-51-14, 55-54-52-51-23, 55-54-52-51-24, 55-54-52-51-30, 55-54-52-51-31, 55-54-52-51-41, 55-54-52-51-42, 55-54-52-51-43, 55-54-52-51-44, 55-54-52-51-45, 55-54-52-51-47, 55-54-52-51-50-6, 55-54-52-51-50-7, 55-54-52-51-50-8, 55-54-52-51-50-9, 55-54-52-51-50-10, 55-54-52-51-50-11, 55-54-52-51-50-12, 55-54-52-51-50-13, 55-54-52-51-50-14, 55-54-52-51-50-23, 55-54-52-51-50-24, 55-54-52-51-50-30, 55-54-52-51-50-31, 55-54-52-51-50-41, 55-54-52-51-50-42, 55-54-52-51-50-43, 55-54-52-51-50-44, 55-54-52-51-50-45, 55-54-52-51-50-47, 55-54-53-1, 55-54-53-2, 55-54-53-3, 55-54-53-4, 55-54-53-5, 55-54-53-6, 55-54-53-7, 55-54-53-8, 55-54-53-9, 55-54-53-10, 55-54-53-11, 55-54-53-12, 55-54-53-13, 55-54-53-14, 55-54-53-15, 55-54-53-16, 55-54-53-17, 55-54-53-18, 55-54-53-19, 55-54-53-20, 55-54-53-21, 55-54-53-22, 55-54-53-23, 55-54-53-24, 55-54-53-25, 55-54-53-26, 55-54-53-27, 55-54-53-28, 55-54-53-29, 55-54-53-30, 55-54-53-31, 55-54-53-32, 55-54-53-33, 55-54-53-34, 55-54-53-35, 55-54-53-36, 55-54-53-37, 55-54-53-38, 55-54-53-39, 55-54-53-40, 55-54-53-41, 55-54-53-42, 55-54-53-43, 55-54-53-44, 55-54-53-45, 55-54-53-46, 55-54-53-47, 55-54-53-48, 55-54-53-49, 55-54-53-50-1, 55-54-53-50-2, 55-54-53-50-3, 55-54-53-50-6, 55-54-53-50-7, 55-54-53-50-8, 55-54-53-50-9, 55-54-53-50-10, 55-54-53-50-11, 55-54-53-50-12, 55-54-53-50-13, 55-54-53-50-14, 55-54-53-50-15, 55-54-53-50-16, 55-54-53-50-19, 55-54-53-50-20, 55-54-53-50-21, 55-54-53-50-22, 55-54-53-50-23, 55-54-53-50-24, 55-54-53-50-27, 55-54-53-50-28, 55-54-53-50-29, 55-54-53-50-30, 55-54-53-50-31, 55-54-53-50-32, 55-54-53-50-34, 55-54-53-50-35, 55-54-53-50-36, 55-54-53-50-37, 55-54-53-50-38, 55-54-53-50-40, 55-54-53-50-41, 55-54-53-50-42, 55-54-53-50-43, 55-54-53-50-44, 55-54-53-50-45, 55-54-53-50-46, 55-54-53-50-47, 55-54-53-50-48, 55-54-53-51-6, 55-54-53-51-7, 55-54-53-51-8, 55-54-53-51-9, 55-54-53-51-10, 55-54-53-51-11, 55-54-53-51-12, 55-54-53-51-13, 55-54-53-51-14, 55-54-53-51-15, 55-54-53-51-16, 55-54-53-51-17, 55-54-53-51-18, 55-54-53-51-19, 55-54-53-51-20, 55-54-53-51-21, 55-54-53-51-22, 55-54-53-51-23, 55-54-53-51-24, 55-54-53-51-30, 55-54-53-51-31, 55-54-53-51-32, 55-54-53-51-33, 55-54-53-51-40, 55-54-53-51-41, 55-54-53-51-42, 55-54-53-51-43, 55-54-53-51-44, 55-54-53-51-45, 55-54-53-51-47, 55-54-53-51-48, 55-54-53-51-49, 55-54-53-51-50-6, 55-54-53-51-50-7, 55-54-53-51-50-8, 55-54-53-51-50-9, 55-54-53-51-50-10, 55-54-53-51-50-11, 55-54-53-51-50-12, 55-54-53-51-50-13, 55-54-53-51-50-14, 55-54-53-51-50-15, 55-54-53-51-50-16, 55-54-53-51-50-19, 55-54-53-51-50-20, 55-54-53-51-50-21, 55-54-53-51-50-22, 55-54-53-51-50-23, 55-54-53-51-50-24, 55-54-53-51-50-30, 55-54-53-51-50-31, 55-54-53-51-50-32, 55-54-53-51-50-40, 55-54-53-51-50-41, 55-54-53-51-50-42, 55-54-53-51-50-43, 55-54-53-51-50-44, 55-54-53-51-50-45, 55-54-53-51-50-47, 55-54-53-51-50-48, 55-54-53-52-1, 55-54-53-52-2, 55-54-53-52-3, 55-54-53-52-6, 55-54-53-52-7, 55-54-53-52-8, 55-54-53-52-9, 55-54-53-52-10, 55-54-53-52-11, 55-54-53-52-12, 55-54-53-52-13, 55-54-53-52-14, 55-54-53-52-23, 55-54-53-52-24, 55-54-53-52-29, 55-54-53-52-30, 55-54-53-52-31, 55-54-53-52-32, 55-54-53-52-33, 55-54-53-52-34, 55-54-53-52-35, 55-54-53-52-36, 55-54-53-52-37, 55-54-53-52-41, 55-54-53-52-42, 55-54-53-52-43, 55-54-53-52-44, 55-54-53-52-45, 55-54-53-52-46, 55-54-53-52-47, 55-54-53-52-50-1, 55-54-53-52-50-2, 55-54-53-52-50-3, 55-54-53-52-50-6, 55-54-53-52-50-7, 55-54-53-52-50-8, 55-54-53-52-50-9, 55-54-53-52-50-10, 55-54-53-52-50-11, 55-54-53-52-50-12, 55-54-53-52-50-13, 55-54-53-52-50-14, 55-54-53-52-50-23, 55-54-53-52-50-24, 55-54-53-52-50-29, 55-54-53-52-50-30, 55-54-53-52-50-31, 55-54-53-52-50-34, 55-54-53-52-50-35, 55-54-53-52-50-36, 55-54-53-52-50-37, 55-54-53-52-50-41, 55-54-53-52-50-42, 55-54-53-52-50-43, 55-54-53-52-50-44, 55-54-53-52-50-45, 55-54-53-52-50-46, 55-54-53-52-50-47, 55-54-53-52-51-6, 55-54-53-52-51-7, 55-54-53-52-51-8, 55-54-53-52-51-9, 55-54-53-52-51-10, 55-54-53-52-51-11, 55-54-53-52-51-12, 55-54-53-52-51-13, 55-54-53-52-51-14, 55-54-53-52-51-23, 55-54-53-52-51-24, 55-54-53-52-51-30, 55-54-53-52-51-31, 55-54-53-52-51-41, 55-54-53-52-51-42, 55-54-53-52-51-43, 55-54-53-52-51-44, 55-54-53-52-51-45, 55-54-53-52-51-47, 55-54-53-52-51-50-6, 55-54-53-52-51-50-7, 55-54-53-52-51-50-8, 55-54-53-52-51-50-9, 55-54-53-52-51-50-10, 55-54-53-52-51-50-11, 55-54-53-52-51-50-12, 55-54-53-52-51-50-13, 55-54-53-52-51-50-14, 55-54-53-52-51-50-23, 55-54-53-52-51-50-24, 55-54-53-52-51-50-30, 55-54-53-52-51-50-31, 55-54-53-52-51-50-41, 55-54-53-52-51-50-42, 55-54-53-52-51-50-43, 55-54-53-52-51-50-44, 55-54-53-52-51-50-45 and 55-54-53-52-51-50-47. For each of these compound groups, designations 1.1.1.1 through 10.10.10.10 in Table B specifies a compound or genus of compounds as defined by the Table A substituents and any $R^{10G}$ moiety as described here or elsewhere herein.

Exemplary group 55-1 compounds where $R^{10G}$ is fluorine in the α-configuration include 1.2.4.1, which is 3,7β-dihydroxy-16α,9α-difluoro-17β-aminoandrost-1,3-diene, 1.1.6.9, which is 3,16α,17β-trihydroxy-9α-fluoroandrost-1,3-diene, 1.1.6.1, which is 3,16α-dihydroxy-9α-fluoro-17β-aminoandrost-1,3-diene and 1.1.4.9, which is 3,17β-dihydroxy-16α,9α-difluoroandrost-1,3-diene. Exemplary group 55-2 compounds where $R^{10G}$ is fluorine in the α-configuration include 1.2.4.1, which is 3,7β-dihydroxy-16α,9α-difluoro-17β-amino-5β-androst-1,3-diene, 1.1.6.9, which is 3,16α,17β-trihydroxy-9α-fluoro-5β-androst-1,3-diene, 1.1.6.1, which is 3,16α-dihydroxy-9α-fluoro-17β-amino-5β-androst-1,3-diene and 1.1.4.9, which is 3,17β-dihydroxy-16α,9α-difluoro-5β-androst-1,3-diene. Exemplary group 55-3 compounds where $R^{10G}$ is fluorine in the β-configuration include 1.2.4.1, which is 3,7β-dihydroxy-16α,9β-difluoro-17β-aminoandrost-1,3,5-triene, 1.1.6.9, which is 3,16α,17β-trihydroxy-9β-fluoroandrost-1,3,5-triene, 1.1.6.1, which is 3,16α-dihydroxy-9β-fluoro-17β-aminoandrost-1,3,5-triene and 1.1.4.9, which is 3,17β-dihydroxy-16α,9α-difluoroandrost-1,3,5-triene. Exemplary group 55-51-7 compounds where $R^{10G}$ is fluorine in the α-configuration include 1.2.4.1, which is 3α,7-dihydroxy-16α,9α-difluoro-17β-aminoandrost-1,6-diene, 1.1.6.9, which is 3α,16α,17β-trihydroxy-9α-fluoroandrost-1,6-diene, 1.1.6.1, which is 3α,16α-dihydroxy-9α-fluoro-17β-aminoandrost-1,6-diene and 1.1.4.9, which is 3α,17β-dihydroxy-16α,9α-difluoroandrost-1,6-diene. Exemplary group 55-51-7 compounds where $R^{10G}$ is chlorine in the α-configuration include 1.2.4.1, which is 3α,7-dihydroxy-9α-chloro-16α-fluoro-17β-aminoandrost-1,6-diene, 1.1.6.9, which is 3α,16α,17β-trihydroxy-9α-chloroandrost-1,6-diene, 1.1.6.1, which is 3α,16α-dihydroxy-9α-chloro-17β-aminoandrost-1,6-diene and 1.1.4.9, which is 3α,17β-dihydroxy-9α-chloro-16α-fluoroandrost-1,6-diene. Exemplary group 55-51-7 compounds where $R^{10G}$ is fluorine in the β-configuration include 1.2.4.1, which is 3α,7-dihydroxy-16α,9β-difluoro-17β-aminoandrost-1,6-diene, 1.1.6.9, which is 3α,16α,17β-trihydroxy-9β-fluoroandrost-1,6-diene, 1.1.6.1, which is 3α,16α-dihydroxy-9β-fluoro-17β-aminoandrost-1,6-diene and 1.1.4.9, which is 3α,17β-dihydroxy-16α,9β-difluoroandrost-1,6-diene. Exemplary group 55-51-7 compounds where $R^{10G}$ is hydroxyl in the α-configuration include 1.2.4.1, which is 3α,7,9α-trihydroxy-16α-fluoro-17β-aminoandrost-1,6-diene, 1.1.6.9, which is 3α,9α,16α,17β-tetrahydroxyandrost-1,6-diene, 1.1.6.1, which is 3α,16α-dihydroxy-9α-fluoro-17β-aminoandrost-1,6-diene and 1.1.4.9, which is 3α,9α,17β-trihydroxy-16α-fluoroandrost-1,6-diene. Compounds or genera of compounds in the other group 55 compound groups where $R^{10G}$ is a moiety described here or elsewhere herein are defined as described in Tables A and B in the same manner. Exemplary $R^{10G}$ moieties include C1-6 optionally substituted alkyl, —Cl, —Br, —I, —OH, —SH, —NH$_2$, —NHR$^{PR}$, ether, thioether, ester, thioester, C2-6 optionally substituted alkenyl and C2-6 optionally substituted alkynyl, which is in the α- or β-configuration.

Group 56. This group comprises compounds in the compound groups 1-55 described above, wherein (1) one, two, three or four of $R^{10A}$, $R^{10B}$, $R^{10C}$ and $R^{10D}$ is an independently selected moiety other than hydrogen and (2) each of $R^{10A}$, $R^{10B}$, $R^{10C}$ and $R^{10D}$ independently is in the α-configuration or the β-configuration when a double bond is not present at the steroid carbon atom to which it is bonded, i.e., there is no double bond at the 1-, 4- or 6-position. In this group, one or more of $R^{10A}$, $R^{10B}$, $R^{10C}$ and $R^{10D}$ is an independently selected moiety as defined herein, e.g., —H, halogen, hydroxyl, ketone, thiol, amino or optionally substituted alkyl. Other exemplary moieties include independently selected C1-4 optionally substituted alkyl, C1-4 optionally substituted alkenyl, C1-4 optionally substituted alkynyl, C1-4 optionally substituted alkoxy, optionally substituted monosaccharide, optionally substituted disaccharide, carbonate, carbamate, amide, amino acid and thioether. Exemplary moieties include independently selected —H, —$^2$H, —$^3$H, —F, —Cl, —Br, —I, —OH, =O, —SH, =S, —NH$_2$, =NOH, =NCH$_3$, =NC$_2$H$_5$, =NH, —CH$_3$, —C$_2$H$_5$, —CH$_2$OR$^X$, —OCH$_3$, —OC$_2$H$_5$, —OCH$_2$OR$^X$, —SCH$_3$, —SC$_2$H$_5$, —SCH$_2$OR$^X$, —OR$^X$, —SR$^X$, —NHR$^X$, —N(R$^X$)$_2$, —CH$_2$F, —CH=CH$_2$, —CH=CHOR$^X$, —C=CF, —C=CCl, —C=CBr, ==CI, —C=COR$^X$, —C=C—CH$_3$, —C=CCH$_2$F, —C=CCH$_2$Cl, —C=CCH$_2$Br, —C=CCH$_2$I, —C=CCH$_2$OR$^X$, —C(O)CH$_3$, —C(O)CH$_2$R$^X$, —C(O)OCH$_3$, —C(O)CHOR$^X$, —C(O)OCH$_3$, =CH$_2$, =CHCH$_3$, =CHCH$_2$OR$^X$, =CHCH$_2$SR$^X$, =CHCH$_2$NHR$^X$, =CH$_2$CH$_2$OR$^X$, =CH$_2$C(O)OR$^X$, —OCH$_2$OR$^X$, —OCH$_2$C(O)OR$^X$, —OCH$_2$CH$_2$C(O)OR$^X$, —OCH$_2$CH$_2$CH$_2$C(O)OR$^X$, —OCH$_2$NHR$^X$, —OCH$_2$CH$_2$NHR$^X$, —OCH$_2$CH$_2$CH$_2$NHR$^X$, —OC(O)CH$_2$NHR$^X$, —OC(O)CH$_2$CH$_2$NHR$^X$, —OC(O)CH$_2$CH$_2$CH$_2$NHR$^X$, —OCF$_3$, —OC$_2$H$_4$OR$^X$, —OC(O)CH$_3$, —OC(O)C$_2$H$_5$, —OC(O)C$_2$H$_4$OR$^X$, —OC(S)CH$_3$, —OC(S)C$_2$H$_5$, —SCH$_2$C(O)OR$^X$, —SCF$_3$, —SC$_2$H$_4$OR$^X$, —SC(O)CH$_3$, —SC(O)C$_2$H$_5$, —SC(O)C$_2$H$_4$OR$^X$, —NHCH$_3$, —N(CH$_3$)$_2$, —NHCH$_2$OR$^X$, —NHCH$_2$C(O)OR$^X$, —NHCF$_3$, —NHC$_2$H$_5$, —N(C$_2$H$_5$)$_2$, —N(C$_3$H$_7$)$_2$, —NHC$_2$H$_4$OR$^X$, —NHC(O)CH$_3$, —NHC(O)CF$_3$, —NHC(O)C$_2$H$_5$, —NHC(O)C$_2$H$_4$OR$^X$, —NHC(O)C$_2$H$_4$C(O)OR$^X$, —NHC(O)OCH$_3$, —NHC(O)OCF$_3$, —NHC(O)OC$_2$H$_5$, —NHC(O)OC$_2$H$_4$OR$^X$, —NHC(O)OC$_2$H$_4$C(O)OR$^X$, —NHCH$_2$C(O)OR$^X$, —NHCH(CH$_3$)C(O)OR$^X$, —O—S(O)(O)OR$^X$, —O—P(O)(O)OR$^X$, —S—P(O)(O)OR$^X$ and —O—P(S)(O)OR$^X$ moieties, where R$^X$ independently are —H, a protecting group, optionally substituted alkyl or a counter ion for ionizable moieties, e.g., —CH$_3$, —C$_2$H$_5$, —C$_3$H$_7$, Na$^+$, K$^+$, chloride, bromide, iodide, methyl sulfonate, ethyl sulfonate, fumarate, lactate, succinate, amino, methylamine, diethylamine or another ion or another suitable salt or ion described herein.

As is apparent from the foregoing description, when no double bond is present at the carbon atoms at the 1-, 4-, 6- or 12-positions, $R^{10A}$, $R^{10B}$, $R^{10C}$ and $R^{10D}$ respectively can be in the α,α,α,α, α,α,α,β, α,α,β,α, α,β,α,α, β,α,α,α, α,α,β,β, α,β,α,β, β,α,α,β, α,β,β,α, β,α,β,α, β,β,α,α, α,β,β,β, β,α,β,β, β,β,α,β, β,β,β,α or β,β,β,β configurations. As used here, reference to, e.g., $R^{10A}$, $R^{10B}$, $R^{10C}$ and $R^{10D}$ respectively being in the α,β,α,β configurations means that $R^{10A}$ is in the α-configuration, $R^{10B}$ is in the β-configuration, $R^{10C}$ is in the α-configuration and $R^{10D}$ is in the β-configuration. Similarly, when $R^{10A}$, $R^{10B}$, $R^{10C}$ and $R^{10D}$ respectively are in the α,α, β,α configurations, $R^{10A}$ is in the α-configuration, $R^{10B}$ is in the α-configuration, $R^{10C}$ is in the β-configuration and $R^{10D}$ is in the α-configuration.

Thus, when a double bond is present at one or more of the 1-, 4- or 6-positions, the corresponding $R^{10A}$, $R^{10B}$ or $R^{10C}$ moiety will not be in a specified configuration. Group 56 contains compounds and genera of compounds in groups 1 through 55 above having structures where (1) a double bond is present at the 1-position $R^{10B}$, $R^{10C}$ and $R^{10D}$ respectively are in the α,α,α, α,α,β, α,β,α, β,α,α, α,β,β, β,α,β, β,β,α or β,β,β configurations and $R^{10A}$ is present at the 1-position with no specified configuration, (2) a double bond is present at the 4-position, $R^{10A}$, $R^{10C}$ and $R^{10D}$ respectively are in the α,α,α, α,α,β, α,β,α, β,α,α, α,β,β, β,α,β, β,β,α or β,β,β configurations and $R^{10B}$ is present at the 4-position with no specified configuration, (3) a double bond is present at the 6-position, $R^{10A}$, $R^{10B}$ and $R^{10D}$ respectively are in the α,α,α, α,α,β, α,β,α, β,α,α, α,β,β, β,α,β, β,β,α or β,β,β configurations, and $R^{10C}$ is present at the 6-position with no specified configuration, (4) a double bond is present at the 1-position and at the 4-position, $R^{10C}$ and $R^{10D}$ respectively are in the α,α, α,β, β,α or β,β configurations and $R^{10A}$ and $R^{10B}$ are present at the 1- and 4-positions with no specified configuration, (5) a double bond is present at the 1-position and at the 6-position, $R^{10B}$ and $R^{10D}$ respectively are in the α,α, α,β, β,α, or β,β configurations and $R^{10A}$ and $R^{10C}$ are present at the 1- and 6-positions with no specified configuration, (6) a double bond is present at the 4-position and at the 6-position, $R^{10A}$ and $R^{10D}$ respectively are in the α,α, α,β, β,α, or β,β configurations and $R^{10B}$ and $R^{10C}$ are present at the 4- and 6-positions with no specified configuration, (7) a double bond is present at the 1-, 4- and 6-position, $R^{10D}$ is in the α-configuration or the β-configuration, while $R^{10A}$, $R^{10B}$ and $R^{10C}$ are present at the 1-, 4- and 6-positions with no specified configuration and (8) one, two or more additional double bonds are optionally also present at the 8-, 9-, 11-, 14-, 15- or 16-positions for any compound or genus of compounds described in (1), (2), (3), (4), (5), (6) or (7).

Groups of compounds in this group are defined essentially as described above, e.g., for groups 53, 54 and 55. Exemplary compound groups with structures (1), (2), (3), (4), (5), (6), (7) or (8) described above include 56-1, 56-2, 56-3, 56-4, 56-5, 56-6, 56-7, 56-8, 56-9, 56-10, 56-11, 56-12, 56-13, 56-14, 56-15, 56-16, 56-17, 56-18, 56-19, 56-20, 56-21, 56-22, 56-23, 56-24, 56-25, 56-26, 56-27, 56-28, 56-29, 56-30, 56-31, 56-32, 56-33, 56-34, 56-35, 56-36, 56-37, 56-38, 56-39, 56-40, 56-41, 56-42, 56-43, 56-44, 56-45, 56-46, 56-47, 56-48, 56-49, 56-50-1, 56-50-2, 56-50-3, 56-50-6, 56-50-7, 56-50-8, 56-50-9, 56-50-10, 56-50-11, 56-50-12, 56-50-13, 56-50-14, 56-50-15, 56-50-16, 56-50-19, 56-50-20, 56-50-21, 56-50-22, 56-50-23, 56-50-24, 56-50-27, 56-50-28, 56-50-29, 56-50-30, 56-50-31, 56-50-32, 56-50-34, 56-50-35, 56-50-36, 56-50-37, 56-50-38, 56-50-40, 56-50-41, 56-50-42, 56-50-43, 56-50-44, 56-50-45, 56-50-46, 56-50-47, 56-50-48, 56-51-6, 56-51-7, 56-51-8, 56-51-9, 56-51-10, 56-51-11, 56-51-12, 56-51-13, 56-51-14, 56-51-15, 56-51-16, 56-51-17, 56-51-18, 56-51-19, 56-51-20, 56-51-21, 56-51-22, 56-51-23, 56-51-24, 56-51-30, 56-51-31, 56-51-32, 56-51-33, 56-51-40, 56-51-41, 56-51-42, 56-51-43, 56-51-44, 56-51-45, 56-51-47, 56-51-48, 56-51-49, 56-51-50-6, 56-51-50-7, 56-51-50-8, 56-51-50-9, 56-51-50-10, 56-51-50-11, 56-51-50-12, 56-51-50-13, 56-51-50-14, 56-51-50-15, 56-51-50-16, 56-51-50-19, 56-51-50-20, 56-51-50-21, 56-51-50-22, 56-51-50-23, 56-51-50-24, 56-51-50-30, 56-51-50-31, 56-51-50-32, 56-51-50-40, 56-51-50-41, 56-51-50-42, 56-51-50-43, 56-51-50-44, 56-51-50-45, 56-51-50-47, 56-51-50-48, 56-52-1, 56-52-2, 56-52-3, 56-52-6, 56-52-7, 56-52-8, 56-52-9, 56-52-10, 56-52-11, 56-52-12, 56-52-13, 56-52-14, 56-52-23, 56-52-24, 56-52-29, 56-52-30, 56-52-31, 56-52-32, 56-52-33, 56-52-34, 56-52-35, 56-52-36, 56-52-37, 56-52-41, 56-52-42, 56-52-43, 56-52-44, 56-52-45, 56-52-46, 56-52-47, 56-52-50-1, 56-52-50-2, 56-52-50-3, 56-52-50-6, 56-52-50-7, 56-52-50-8, 56-52-50-9, 56-52-50-10, 56-52-50-11, 56-52-50-12, 56-52-50-13, 56-52-50-14, 56-52-50-23, 56-52-50-24, 56-52-50-29, 56-52-50-30, 56-52-50-31, 56-52-50-34, 56-52-50-35, 56-52-50-36, 56-52-50-37, 56-52-50-41, 56-52-50-42, 56-52-50-43, 56-52-50-44, 56-52-50-45, 56-52-50-46, 56-52-50-47, 56-52-51-6, 56-52-51-7, 56-52-51-8, 56-52-51-9, 56-52-51-10, 56-52-51-11, 56-52-51-12, 56-52-51-13, 56-52-51-14, 56-52-51-23, 56-52-51-24, 56-52-51-30, 56-52-51-31, 56-52-51-41, 56-52-51-42, 56-52-51-43, 56-52-51-44, 56-52-51-45, 56-52-51-47, 56-52-51-50-6, 56-52-51-50-7, 56-52-51-50-8, 56-52-51-50-9, 56-52-51-50-10, 56-52-51-50-11, 56-52-51-50-12, 56-52-51-50-13, 56-52-51-50-14, 56-52-51-50-23, 56-52-51-50-24, 56-52-51-50-30, 56-52-51-50-31, 56-52-51-50-41, 56-52-51-50-42, 56-52-51-50-43, 56-52-51-50-44, 56-52-51-50-45, 56-52-51-50-47, 56-53-1, 56-53-2, 56-53-3, 56-53-4, 56-53-5, 56-53-6, 56-53-7, 56-53-8, 56-53-9, 56-53-10, 56-53-11, 56-53-12, 56-53-13, 56-53-14, 56-53-15, 56-53-16, 56-53-17, 56-53-18, 56-53-19, 56-53-20, 56-53-21, 56-53-22, 56-53-23, 56-53-24, 56-53-25, 56-53-26, 56-53-27, 56-53-28, 56-53-29, 56-53-30, 56-53-31, 56-53-32, 56-53-33, 56-53-34, 56-53-35, 56-53-36, 56-53-37, 56-53-38, 56-53-39, 56-53-40, 56-53-41, 56-53-42, 56-53-43, 56-53-44, 56-53-45, 56-53-46, 56-53-47, 56-53-48, 56-53-49, 56-53-50-1, 56-53-50-2, 56-53-50-3, 56-53-50-6, 56-53-50-7, 56-53-50-8, 56-53-50-9, 56-53-50-10, 56-53-50-11, 56-53-50-12, 56-53-50-13, 56-53-50-14, 56-53-50-15, 56-53-50-16, 56-53-50-19, 56-53-50-20, 56-53-50-21, 56-53-50-22, 56-53-50-23, 56-53-50-24, 56-53-50-27, 56-53-50-28, 56-53-50-29, 56-53-50-30, 56-53-50-31, 56-53-50-32, 56-53-50-34, 56-53-50-35, 56-53-50-36, 56-53-50-37, 56-53-50-38, 56-53-50-40, 56-53-50-41, 56-53-50-42, 56-53-50-43, 56-53-50-44, 56-53-50-45, 56-53-50-46, 56-53-50-47, 56-53-50-48, 56-53-51-50-6, 56-53-51-50-7, 56-53-51-50-8, 56-53-51-50-9, 56-53-51-50-10, 56-53-51-50-11, 56-53-51-50-12, 56-53-51-50-13, 56-53-51-50-14, 56-53-51-50-15, 56-53-51-50-16, 56-53-51-50-19, 56-53-51-50-20, 56-53-51-50-21, 56-53-51-50-22, 56-53-51-50-23, 56-53-51-50-24, 56-53-51-50-30, 56-53-51-50-31, 56-53-51-50-32, 56-53-51-50-40, 56-53-51-50-41, 56-53-51-50-42, 56-53-51-50-43, 56-53-51-50-44, 56-53-51-50-45, 56-53-51-50-47, 56-53-51-50-48, 53-51-6, 53-51-7, 53-51-8, 53-51-9, 53-51-10, 53-51-11, 53-51-12, 53-51-13, 53-51-14, 53-51-15, 53-51-16, 53-51-17, 53-51-18, 53-51-19, 53-51-20, 53-51-21, 53-51-22, 53-51-23, 53-51-24, 53-51-30, 53-51-31, 53-51-32, 53-51-33, 53-51-40, 53-51-41, 53-51-42, 53-51-43, 53-51-44, 53-51-45, 53-51-47, 53-51-48, 53-51-49, 56-53-52-1, 56-53-52-2, 56-53-52-3, 56-53-52-6, 56-53-52-7, 56-53-52-8, 56-53-52-9, 56-53-52-10, 56-53-52-11, 56-53-52-12, 56-53-52-13, 56-53-52-14, 56-53-52-23, 56-53-52-24, 56-53-52-29, 56-53-52-30, 56-53-52-31, 56-53-52-32, 56-53-52-33, 56-53-52-34, 56-53-52-35, 56-53-52-36, 56-53-52-37, 56-53-52-41, 56-53-52-42, 56-53-52-43, 56-53-52-44, 56-53-52-45, 56-53-52-46, 56-53-52-47, 56-53-52-50-1, 56-53-52-50-2, 56-53-52-50-3, 56-53-52-50-6, 56-53-52-50-7, 56-53-52-50-8, 56-53-52-50-9, 56-53-52-50-10, 56-53-52-50-11, 56-53-52-50-12, 56-53-52-50-13, 56-53-52-50-14, 56-53-52-50-23, 56-53-52-50-24, 56-53-52-50-29, 56-53-52-50-30, 56-53-52-50-31, 56-53-52-50-34, 56-53-52-50-35, 56-53-52-50-36, 56-53-52-50-37, 56-53-52-50-41, 56-53-52-50-42, 56-53-52-50-43, 56-53-52-50-44, 56-53-52-50-45, 56-53-52-50-46, 56-53-52-50-47, 56-53-52-51-6, 56-53-52-51-7, 56-53-52-51-8, 56-53-52-51-9, 56-53-52-51-10, 56-53-52-51-11, 56-53-52-51-12, 56-53-52-51-13, 56-53-52-51-14, 56-53-52-51-23, 56-53-52-51-24, 56-53-52-51-30, 56-53-52-51-31, 56-53-52-51-41, 56-53-52-51-42, 56-53-52-51-43, 56-53-52-51-44, 56-53-52-51-45, 56-53-52-51-47, 56-53-52-51-50-6, 56-53-52-51-50-7, 56-53-52-51-50-8, 56-53-52-51-50-9, 56-53-52-51-50-10, 56-53-52-51-50-11, 56-53-52-51-50-12, 56-53-52-51-50-13, 56-53-52-51-50-14, 56-53-52-51-50-23, 56-53-52-51-50-24, 56-53-52-51-50-30, 56-53-52-51-50-31, 56-53-52-51-50-41, 56-53-52-51-50-42, 56-53-52-51-50-43, 56-53-52-51-50-44, 56-53-52-51-50-45, 56-53-52-51-50-47, 56-54-1, 56-54-2, 56-54-3, 56-54-4, 56-54-5, 56-54-6, 56-54-7, 56-54-8, 56-54-9, 56-54-10, 56-54-11, 56-54-12, 56-54-13, 56-54-14, 56-54-15, 56-54-16, 56-54-17, 56-54-18, 56-54-19, 56-54-20, 56-54-21, 56-54-22, 56-54-23, 56-54-24, 56-54-25, 56-54-26, 56-54-27, 56-54-28, 56-54-29, 56-54-30, 56-54-31, 56-54-32, 56-54-33, 56-54-34, 56-54-35, 56-54-36, 56-54-37, 56-54-38, 56-54-39, 56-54-40, 56-54-41, 56-54-42, 56-54-43, 56-54-44, 56-54-45, 56-54-46, 56-54-47, 56-54-48, 56-54-49, 56-54-50-1, 56-54-50-2, 56-54-50-3, 56-54-50-6, 56-54-50-7, 56-54-50-8, 56-54-50-9, 56-54-50-10, 56-54-50-11, 56-54-50-12, 56-54-50-13, 56-54-50-14, 56-54-50-15, 56-54-50-16, 56-54-50-19, 56-54-50-20, 56-54-50-21, 56-54-50-22, 56-54-50-23, 56-54-50-24, 56-54-50-27, 56-54-50-28, 56-54-50-29, 56-54-50-30, 56-54-50-31, 56-54-50-32, 56-54-50-34, 56-54-50-35, 56-54-50-36, 56-54-50-37, 56-54-50-38, 56-54-50-40, 56-54-50-41, 56-54-50-42, 56-54-50-43, 56-54-50-44, 56-54-50-45, 56-54-50-46, 56-54-50-47, 56-54-50-48, 56-54-51-6, 56-54-51-7, 56-54-51-8, 56-54-51-9, 56-54-51-10, 56-54-51-11, 56-54-51-12, 56-54-51-13, 56-54-51-14, 56-54-51-15, 56-54-51-16, 56-54-51-17, 56-54-51-18, 56-54-51-19, 56-54-51-20, 56-54-51-21, 56-54-51-22, 56-54-51-23, 56-54-51-24, 56-54-51-30, 56-54-51-31, 56-54-51-32, 56-54-51-33, 56-54-51-40, 56-54-51-41, 56-54-51-42, 56-54-51-43, 56-54-51-44, 56-54-51-45, 56-54-51-47, 56-54-51-48, 56-54-51-49, 56-54-51-50-6, 56-54-51-50-7, 56-54-51-50-8, 56-54-51-50-9, 56-54-51-50-10, 56-54-51-50-11, 56-54-51-50-12, 56-54-51-50-13, 56-54-51-50-14, 56-54-51-50-15, 56-54-51-50-16, 56-54-51-50-19, 56-54-51-50-20, 56-54-51-50-21, 56-54-51-50-22, 56-54-51-50-23, 56-54-51-50-24, 56-54-51-50-30, 56-54-51-50-31, 56-54-51-50-32, 56-54-51-50-40, 56-54-51-50-41, 56-54-51-50-42, 56-54-51-50-43, 56-54-51-50-44, 56-54-51-50-45, 56-54-51-50-47, 56-54-51-50-48, 56-54-52-1, 56-54-52-2, 56-54-52-3, 56-54-52-6, 56-54-52-7, 56-54-52-8, 56-54-52-9, 56-54-52-10, 56-54-52-11, 56-54-52-12, 56-54-52-13, 56-54-52-14, 56-54-52-23, 56-54-52-24, 56-54-52-29, 56-54-52-30, 56-54-52-31, 56-54-52-32, 56-54-52-33, 56-54-52-34, 56-54-52-35, 56-54-52-36, 56-54-52-37, 56-54-52-41, 56-54-52-42, 56-54-52-43, 56-54-52-44, 56-54-52-45, 56-54-52-46, 56-54-52-47, 56-54-52-50-1, 56-54-52-50-2, 56-54-52-50-3, 56-54-52-50-6, 56-54-52-50-7, 56-54-52-50-8, 56-54-52-50-9, 56-54-52-50-10, 56-54-52-50-11, 56-54-52-50-12, 56-54-52-50-13, 56-54-52-50-14, 56-54-52-50-23, 56-54-52-50-24, 56-54-52-50-29, 56-54-52-50-30, 56-54-52-50-31, 56-54-52-50-34, 56-54-52-50-35, 56-54-52-50-36, 56-54-52-50-37, 56-54-52-50-41, 56-54-52-50-42, 56-54-52-50-43, 56-54-52-50-44, 56-54-52-50-45, 56-54-52-50-46, 56-54-52-50-47, 56-54-52-51-6, 56-54-52-51-7, 56-54-52-51-8, 56-54-52-51-9, 56-54-52-51-10, 56-54-52-51-11, 56-54-52-51-12, 56-54-52-51-13, 56-54-52-51-14, 56-54-52-51-23, 56-54-52-51-24, 56-54-52-51-30, 56-54-52-51-31, 56-54-52-51-41, 56-54-52-51-42, 56-54-52-51-43, 56-54-52-51-44, 56-54-52-51-45, 56-54-52-51-47, 56-54-

52-51-50-6, 56-54-52-51-50-7, 56-54-52-51-50-8, 56-54-52-51-50-9, 56-54-52-51-50-10, 56-54-52-51-50-11, 56-54-52-51-50-12, 56-54-52-51-50-13, 56-54-52-51-50-14, 56-54-52-51-50-23, 56-54-52-51-50-24, 56-54-52-51-50-30, 56-54-52-51-50-31, 56-54-52-51-50-41, 56-54-52-51-50-42, 56-54-52-51-50-43, 56-54-52-51-50-44, 56-54-52-51-50-45, 56-54-52-51-50-47, 56-54-53-1, 56-54-53-2, 56-54-53-3, 56-54-53-4, 56-54-53-5, 56-54-53-6, 56-54-53-7, 56-54-53-8, 56-54-53-9, 56-54-53-10, 56-54-53-11, 56-54-53-12, 56-54-53-13, 56-54-53-14, 56-54-53-15, 56-54-53-16, 56-54-53-17, 56-54-53-18, 56-54-53-19, 56-54-53-20, 56-54-53-21, 56-54-53-22, 56-54-53-23, 56-54-53-24, 56-54-53-25, 56-54-53-26, 56-54-53-27, 56-54-53-28, 56-54-53-29, 56-54-53-30, 56-54-53-31, 56-54-53-32, 56-54-53-33, 56-54-53-34, 56-54-53-35, 56-54-53-36, 56-54-53-37, 56-54-53-38, 56-54-53-39, 56-54-53-40, 56-54-53-41, 56-54-53-42, 56-54-53-43, 56-54-53-44, 56-54-53-45, 56-54-53-46, 56-54-53-47, 56-54-53-48, 56-54-53-49, 56-54-53-50-1, 56-54-53-50-2, 56-54-53-50-3, 56-54-53-50-6, 56-54-53-50-7, 56-54-53-50-8, 56-54-53-50-9, 56-54-53-50-10, 56-54-53-50-11, 56-54-53-50-12, 56-54-53-50-13, 56-54-53-50-14, 56-54-53-50-15, 56-54-53-50-16, 56-54-53-50-19, 56-54-53-50-20, 56-54-53-50-21, 56-54-53-50-22, 56-54-53-50-23, 56-54-53-50-24, 56-54-53-50-27, 56-54-53-50-28, 56-54-53-50-29, 56-54-53-50-30, 56-54-53-50-31, 56-54-53-50-32, 56-54-53-50-34, 56-54-53-50-35, 56-54-53-50-36, 56-54-53-50-37, 56-54-53-50-38, 56-54-53-50-40, 56-54-53-50-41, 56-54-53-50-42, 56-54-53-50-43, 56-54-53-50-44, 56-54-53-50-45, 56-54-53-50-46, 56-54-53-50-47, 56-54-53-50-48, 56-54-53-51-6, 56-54-53-51-7, 56-54-53-51-8, 56-54-53-51-9, 56-54-53-51-10, 56-54-53-51-11, 56-54-53-51-12, 56-54-53-51-13, 56-54-53-51-14, 56-54-53-51-15, 56-54-53-51-16, 56-54-53-51-17, 56-54-53-51-18, 56-54-53-51-19, 56-54-53-51-20, 56-54-53-51-21, 56-54-53-51-22, 56-54-53-51-23, 56-54-53-51-24, 56-54-53-51-30, 56-54-53-51-31, 56-54-53-51-32, 56-54-53-51-33, 56-54-53-51-40, 56-54-53-51-41, 56-54-53-51-42, 56-54-53-51-43, 56-54-53-51-44, 56-54-53-51-45, 56-54-53-51-47, 56-54-53-51-48, 56-54-53-51-49, 56-54-53-51-50-6, 56-54-53-51-50-7, 56-54-53-51-50-8, 56-54-53-51-50-9, 56-54-53-51-50-10, 56-54-53-51-50-11, 56-54-53-51-50-12, 56-54-53-51-50-13, 56-54-53-51-50-14, 56-54-53-51-50-15, 56-54-53-51-50-16, 56-54-53-51-50-19, 56-54-53-51-50-20, 56-54-53-51-50-21, 56-54-53-51-50-22, 56-54-53-51-50-23, 56-54-53-51-50-24, 56-54-53-51-50-30, 56-54-53-51-50-31, 56-54-53-51-50-32, 56-54-53-51-50-40, 56-54-53-51-50-41, 56-54-53-51-50-42, 56-54-53-51-50-43, 56-54-53-51-50-44, 56-54-53-51-50-45, 56-54-53-51-50-47, 56-54-53-51-50-48, 56-54-53-52-1, 56-54-53-52-2, 56-54-53-52-3, 56-54-53-52-6, 56-54-53-52-7, 56-54-53-52-8, 56-54-53-52-9, 56-54-53-52-10, 56-54-53-52-11, 56-54-53-52-12, 56-54-53-52-13, 56-54-53-52-14, 56-54-53-52-23, 56-54-53-52-24, 56-54-53-52-29, 56-54-53-52-30, 56-54-53-52-31, 56-54-53-52-32, 56-54-53-52-33, 56-54-53-52-34, 56-54-53-52-35, 56-54-53-52-36, 56-54-53-52-37, 56-54-53-52-41, 56-54-53-52-42, 56-54-53-52-43, 56-54-53-52-44, 56-54-53-52-45, 56-54-53-52-46, 56-54-53-52-47, 56-54-53-52-50-1, 56-54-53-52-50-2, 56-54-53-52-50-3, 56-54-53-52-50-6, 56-54-53-52-50-7, 56-54-53-52-50-8, 56-54-53-52-50-9, 56-54-53-52-50-10, 56-54-53-52-50-11, 56-54-53-52-50-12, 56-54-53-52-50-13, 56-54-53-52-50-14, 56-54-53-52-50-23, 56-54-53-52-50-24, 56-54-53-52-50-29, 56-54-53-52-50-30, 56-54-53-52-50-31, 56-54-53-52-50-34, 56-54-53-52-50-35, 56-54-53-52-50-36, 56-54-53-52-50-37, 56-54-53-52-50-41, 56-54-53-52-50-42, 56-54-53-52-50-43, 56-54-53-52-50-44, 56-54-53-52-50-45, 56-54-53-52-50-46, 56-54-53-52-50-47, 56-54-53-52-51-6, 56-54-53-52-51-7, 56-54-53-52-51-8, 56-54-53-52-51-9, 56-54-53-52-51-10, 56-54-53-52-51-11, 56-54-53-52-51-12, 56-54-53-52-51-13, 56-54-53-52-51-14, 56-54-53-52-51-23, 56-54-53-52-51-24, 56-54-53-52-51-30, 56-54-53-52-51-31, 56-54-53-52-51-41, 56-54-53-52-51-42, 56-54-53-52-51-43, 56-54-53-52-51-44, 56-54-53-52-51-45, 56-54-53-52-51-47, 56-54-53-52-51-50-6, 56-54-53-52-51-50-7, 56-54-53-52-51-50-8, 56-54-53-52-51-50-9, 56-54-53-52-51-50-10, 56-54-53-52-51-50-11, 56-54-53-52-51-50-12, 56-54-53-52-51-50-13, 56-54-53-52-51-50-14, 56-54-53-52-51-50-23, 56-54-53-52-51-50-24, 56-54-53-52-51-50-30, 56-54-53-52-51-50-31, 56-54-53-52-51-50-41, 56-54-53-52-51-50-42, 56-54-53-52-51-50-43, 56-54-53-52-51-50-44, 56-54-53-52-51-50-45, 56-54-53-52-51-50-47, 56-55-1, 56-55-2, 56-55-3, 56-55-4, 56-55-5, 56-55-6, 56-55-7, 56-55-8, 56-55-9, 56-55-10, 56-55-11, 56-55-12, 56-55-13, 56-55-14, 56-55-15, 56-55-16, 56-55-17, 56-55-18, 56-55-19, 56-55-20, 56-55-21, 56-55-22, 56-55-23, 56-55-24, 56-55-25, 56-55-26, 56-55-27, 56-55-28, 56-55-29, 56-55-30, 56-55-31, 56-55-32, 56-55-33, 56-55-34, 56-55-35, 56-55-36, 56-55-37, 56-55-38, 56-55-39, 56-55-40, 56-55-41, 56-55-42, 56-55-43, 56-55-44, 56-55-45, 56-55-46, 56-55-47, 56-55-48, 56-55-49, 56-55-50-1, 56-55-50-2, 56-55-50-3, 56-55-50-6, 56-55-50-7, 56-55-50-8, 56-55-50-9, 56-55-50-10, 56-55-50-11, 56-55-50-12, 56-55-50-13, 56-55-50-14, 56-55-50-15, 56-55-50-16, 56-55-50-19, 56-55-50-20, 56-55-50-21, 56-55-50-22, 56-55-50-23, 56-55-50-24, 56-55-50-27, 56-55-50-28, 56-55-50-29, 56-55-50-30, 56-55-50-31, 56-55-50-32, 56-55-50-34, 56-55-50-35, 56-55-50-36, 56-55-50-37, 56-55-50-38, 56-55-50-40, 56-55-50-41, 56-55-50-42, 56-55-50-43, 56-55-50-44, 56-55-50-45, 56-55-50-46, 56-55-50-47, 56-55-50-48, 56-55-51-6, 56-55-51-7, 56-55-51-8, 56-55-51-9, 56-55-51-10, 56-55-51-11, 56-55-51-12, 56-55-51-13, 56-55-51-14, 56-55-51-15, 56-55-51-16, 56-55-51-17, 56-55-51-18, 56-55-51-19, 56-55-51-20, 56-55-51-21, 56-55-51-22, 56-55-51-23, 56-55-51-24, 56-55-51-30, 56-55-51-31, 56-55-51-32, 56-55-51-33, 56-55-51-40, 56-55-51-41, 56-55-51-42, 56-55-51-43, 56-55-51-44, 56-55-51-45, 56-55-51-47, 56-55-51-48, 56-55-51-49, 56-55-51-50-6, 56-55-51-50-7, 56-55-51-50-8, 56-55-51-50-9, 56-55-51-50-10, 56-55-51-50-11, 56-55-51-50-12, 56-55-51-50-13, 56-55-51-50-14, 56-55-51-50-15, 56-55-51-50-16, 56-55-51-50-19, 56-55-51-50-20, 56-55-51-50-21, 56-55-51-50-22, 56-55-51-50-23, 56-55-51-50-24, 56-55-51-50-30, 56-55-51-50-31, 56-55-51-50-32, 56-55-51-50-40, 56-55-51-50-41, 56-55-51-50-42, 56-55-51-50-43, 56-55-51-50-44, 56-55-51-50-45, 56-55-51-50-47, 56-55-51-50-48, 56-55-52-1, 56-55-52-2, 56-55-52-3, 56-55-52-6, 56-55-52-7, 56-55-52-8, 56-55-52-9, 56-55-52-10, 56-55-52-11, 56-55-52-12, 56-55-52-13, 56-55-52-14, 56-55-52-23, 56-55-52-24, 56-55-52-29, 56-55-52-30, 56-55-52-31, 56-55-52-32, 56-55-52-33, 56-55-52-34, 56-55-52-35, 56-55-52-36, 56-55-52-37, 56-55-52-41, 56-55-52-42, 56-55-52-43, 56-55-52-44, 56-55-52-45, 56-55-52-46, 56-55-52-47, 56-55-52-50-1, 56-55-52-50-2, 56-55-52-50-3, 56-55-52-50-6, 56-55-52-50-7, 56-55-52-50-8, 56-55-52-50-9, 56-55-52-50-10, 56-55-52-50-11, 56-55-52-50-12, 56-55-52-50-13, 56-55-52-50-14, 56-55-52-50-23, 56-55-52-50-24, 56-55-52-50-29, 56-55-52-50-30, 56-55-52-50-31, 56-55-52-50-34, 56-55-52-50-35, 56-55-52-50-36, 56-55-52-50-37, 56-55-52-50-41, 56-55-52-50-42, 56-55-52-50-43, 56-55-52-50-44, 56-55-52-50-45, 56-55-52-50-46, 56-55-52-50-47, 56-55-52-51-6, 56-55-52-51-7, 56-55-52-51-8, 56-55-52-51-9, 56-55-52-51-10, 56-55-52-51-11, 56-55-52-51-12, 56-55-52-51-13, 56-55-52-51-14, 56-55-52-51-23, 56-55-52-51-24, 56-55-52-51-30, 56-55-52-51-31, 56-55-52-51-41, 56-55-52-51-42, 56-55-52-51-43, 56-55-52-51-44, 56-55-52-51-45, 56-55-52-51-47, 56-55-52-51-50-6, 56-55-52-51-50-7, 56-55-52-51-50-8, 56-55-52-51-50-9, 56-55-52-51-50-10, 56-55-52-51-50-11, 56-55-52-51-50-12, 56-55-52-51-50-13, 56-55-52-51-50-14, 56-55-52-51-50-23, 56-55-52-51-50-24, 56-55-52-51-50-30, 56-55-52-51-50-31, 56-55-52-51-50-41, 56-55-52-51-50-42, 56-55-52-51-50-43, 56-55-52-51-50-44, 56-55-52-51-50-45, 56-55-52-51-50-47, 56-55-53-1, 56-55-53-2, 56-55-53-3, 56-55-53-4, 56-55-53-5, 56-55-53-6, 56-55-53-7, 56-55-53-8, 56-55-53-9, 56-55-53-10, 56-55-53-11, 56-55-53-12, 56-55-53-13, 56-55-53-14, 56-55-53-15, 56-55-53-16, 56-55-53-17, 56-55-53-18, 56-55-53-19, 56-55-53-20, 56-55-53-21, 56-55-53-22, 56-55-53-23, 56-55-53-24, 56-55-53-25, 56-55-53-26, 56-55-53-27, 56-55-53-28, 56-55-53-29, 56-55-53-30, 56-55-53-31, 56-55-53-32, 56-55-53-33, 56-55-53-34, 56-55-53-35, 56-55-53-36, 56-55-53-37, 56-55-53-38, 56-55-53-39, 56-55-53-40, 56-55-53-41, 56-55-53-42, 56-55-53-43, 56-55-53-44, 56-55-53-45, 56-55-53-46, 56-55-53-47, 56-55-53-48, 56-55-53-49, 56-55-53-50-1, 56-55-53-50-2, 56-55-53-50-3, 56-55-53-50-6, 56-55-53-50-7, 56-55-53-50-8, 56-55-53-50-9, 56-55-53-50-10, 56-55-53-50-11, 56-55-53-50-12, 56-55-53-50-13, 56-55-53-50-14, 56-55-53-50-15, 56-55-53-50-16, 56-55-53-50-19, 56-55-53-50-20, 56-55-53-50-21, 56-55-53-50-22, 56-55-53-50-23, 56-55-53-50-24, 56-55-53-50-27, 56-55-53-50-28, 56-55-53-50-29, 56-55-53-50-30, 56-55-53-50-31, 56-55-53-50-32, 56-55-53-50-34, 56-55-53-50-35, 56-55-53-50-36, 56-55-53-50-37, 56-55-53-50-38, 56-55-53-50-40, 56-55-53-50-41, 56-55-53-50-42, 56-55-53-50-43, 56-55-53-50-44, 56-55-53-50-45, 56-55-53-50-46, 56-55-53-50-47, 56-55-53-50-48, 56-55-53-51-6, 56-55-53-51-7, 56-55-53-51-8, 56-55-53-51-9, 56-55-53-51-10, 56-55-53-51-11, 56-55-53-51-12, 56-55-53-51-13, 56-55-53-51-14, 56-55-53-51-15, 56-55-53-51-16, 56-55-53-51-17, 56-55-53-51-18, 56-55-53-51-19, 56-55-53-51-20, 56-55-53-51-21, 56-55-53-51-22, 56-55-53-51-23, 56-55-53-51-24, 56-55-53-51-30, 56-55-53-51-31, 56-55-53-51-32, 56-55-53-51-33, 56-55-53-51-40, 56-55-53-51-41, 56-55-53-51-42, 56-55-53-51-43, 56-55-53-51-44, 56-55-53-51-45, 56-55-53-51-47, 56-55-53-51-48, 56-55-53-51-49, 56-55-53-51-50-6, 56-55-53-51-50-7, 56-55-53-51-50-8, 56-55-53-51-50-9, 56-55-53-51-50-10, 56-55-53-51-50-11, 56-55-53-51-50-12, 56-55-53-51-50-13, 56-55-53-51-50-14, 56-55-53-51-50-15, 56-55-53-51-50-16, 56-55-53-51-50-19, 56-55-53-51-50-20, 56-55-53-51-50-21, 56-55-53-51-50-22, 56-55-53-51-50-23, 56-55-53-51-50-24, 56-55-53-51-50-30, 56-55-53-51-50-31, 56-55-53-51-50-32, 56-55-53-51-50-40, 56-55-53-51-50-41, 56-55-53-51-50-42, 56-55-53-51-50-43, 56-55-53-51-50-44, 56-55-53-51-50-45, 56-55-53-51-50-47, 56-55-53-51-50-48, 56-55-53-52-1, 56-55-53-52-2, 56-55-53-52-3, 56-55-53-52-6, 56-55-53-52-7, 56-55-53-52-8, 56-55-53-52-9, 56-55-53-52-10, 56-55-53-52-11, 56-55-53-52-12, 56-55-53-52-13, 56-55-53-52-14, 56-55-53-52-23, 56-55-53-52-24, 56-55-53-52-29, 56-55-53-52-30, 56-55-53-52-31, 56-55-53-52-32, 56-55-53-52-33, 56-55-53-52-34, 56-55-53-52-35, 56-55-53-52-36, 56-55-53-52-37, 56-55-53-52-41, 56-55-53-52-42, 56-55-53-52-43, 56-55-53-52-44, 56-55-53-52-45, 56-55-53-52-46, 56-55-53-52-47, 56-55-53-52-50-1, 56-55-53-52-50-2, 56-55-53-52-50-3, 56-55-53-52-50-6, 56-55-53-52-50-7, 56-55-53-52-50-8, 56-55-53-52-50-9, 56-55-53-52-50-10, 56-55-53-52-50-11, 56-55-53-52-50-12, 56-55-53-52-50-13, 56-55-53-52-50-14, 56-55-53-52-50-23, 56-55-53-52-50-24, 56-55-53-52-50-29, 56-55-53-52-50-30, 56-55-53-52-50-31, 56-55-53-52-50-34, 56-55-53-52-50-35, 56-55-53-52-50-36, 56-55-53-52-50-37, 56-55-53-52-50-41, 56-55-53-52-50-42, 56-55-53-52-50-43, 56-55-53-52-50-44, 56-55-53-52-50-45, 56-55-53-52-50-46, 56-55-53-52-50-47, 56-55-53-52-51-6, 56-55-53-52-51-7, 56-55-53-52-51-8, 56-55-53-52-51-9, 56-55-53-52-51-10, 56-55-53-52-51-11, 56-55-53-52-51-12, 56-55-53-52-51-13, 56-55-53-52-51-14, 56-55-53-52-51-23, 56-55-53-52-51-24, 56-55-53-52-51-30, 56-55-53-52-51-31, 56-55-53-52-51-41, 56-55-53-52-51-42, 56-55-53-52-51-43, 56-55-53-52-51-44, 56-55-53-52-51-45, 56-55-53-52-51-47, 56-55-53-52-51-50-6, 56-55-53-52-51-50-7, 56-55-53-52-51-50-8, 56-55-53-52-51-50-9, 56-55-53-52-51-50-10, 56-55-53-52-51-50-11, 56-55-53-52-51-50-12, 56-55-53-52-51-50-13, 56-55-53-52-51-50-14, 56-55-53-52-51-50-23, 56-55-53-52-51-50-24, 56-55-53-52-51-50-30, 56-55-53-52-51-50-31, 56-55-53-52-51-50-41, 56-55-53-52-51-50-42, 56-55-53-52-51-50-43, 56-55-53-52-51-50-44, 56-55-53-52-51-50-45, 56-55-53-52-51-50-47, 56-55-54-1, 56-55-54-2, 56-55-54-3, 56-55-54-4, 56-55-54-5, 56-55-54-6, 56-55-54-7, 56-55-54-8, 56-55-54-9, 56-55-54-10, 56-55-54-11, 56-55-54-12, 56-55-54-13, 56-55-54-14, 56-55-54-15, 56-55-54-16, 56-55-54-17, 56-55-54-18, 56-55-54-19, 56-55-54-20, 56-55-54-21, 56-55-54-22, 56-55-54-23, 56-55-54-24, 56-55-54-25, 56-55-54-26, 56-55-54-27, 56-55-54-28, 56-55-54-29, 56-55-54-30, 56-55-54-31, 56-55-54-32, 56-55-54-33, 56-55-54-34, 56-55-54-35, 56-55-54-36, 56-55-54-37, 56-55-54-38, 56-55-54-39, 56-55-54-40, 56-55-54-41, 56-55-54-42, 56-55-54-43, 56-55-54-44, 56-55-54-45, 56-55-54-46, 56-55-54-47, 56-55-54-48, 56-55-54-49, 56-55-54-50-1, 56-55-54-50-2, 56-55-54-50-3, 56-55-54-50-6, 56-55-54-50-7, 56-55-54-50-8, 56-55-54-50-9, 56-55-54-50-10, 56-55-54-50-11, 56-55-54-50-12, 56-55-54-50-13, 56-55-54-50-14, 56-55-54-50-15, 56-55-54-50-16, 56-55-54-50-19, 56-55-54-50-20, 56-55-54-50-21, 56-55-54-50-22, 56-55-54-50-23, 56-55-54-50-24, 56-55-54-50-27, 56-55-54-50-28, 56-55-54-50-29, 56-55-54-50-30, 56-55-54-50-31, 56-55-54-50-32, 56-55-54-50-34, 56-55-54-50-35, 56-55-54-50-36, 56-55-54-50-37, 56-55-54-50-38, 56-55-54-50-40, 56-55-54-50-41, 56-55-54-50-42, 56-55-54-50-43, 56-55-54-50-44, 56-55-54-50-45, 56-55-54-50-46, 56-55-54-50-47, 56-55-54-50-48, 56-55-54-51-6, 56-55-54-51-7, 56-55-54-51-8, 56-55-54-51-9, 56-55-54-51-10, 56-55-54-51-11, 56-55-54-51-12, 56-55-54-51-13, 56-55-54-51-14, 56-55-54-51-15, 56-55-54-51-16, 56-55-54-51-17, 56-55-54-51-18, 56-55-54-51-19, 56-55-54-51-20, 56-55-54-51-21, 56-55-54-51-22, 56-55-54-51-23, 56-55-54-51-24, 56-55-54-51-30, 56-55-54-51-31, 56-55-54-51-32, 56-55-54-51-33, 56-55-54-51-40, 56-55-54-51-41, 56-55-54-51-42, 56-55-54-51-43, 56-55-54-51-44, 56-55-54-51-45, 56-55-54-51-47, 56-55-54-51-48, 56-55-54-51-49, 56-55-54-51-50-6, 56-55-54-51-50-7, 56-55-54-51-50-8, 56-55-54-51-50-9, 56-55-54-51-50-10, 56-55-54-51-50-11, 56-55-54-51-50-12, 56-55-54-51-50-13, 56-55-54-51-50-14, 56-55-54-51-50-15, 56-55-54-51-50-16, 56-55-54-51-50-19, 56-55-54-51-50-20, 56-55-54-51-50-21, 56-55-54-51-50-22, 56-55-54-51-50-23, 56-55-54-51-50-24, 56-55-54-51-50-30, 56-55-54-51-50-31, 56-55-54-51-50-32, 56-55-54-51-50-40, 56-55-54-51-50-41, 56-55-54-51-50-42, 56-55-54-51-50-43, 56-55-54-51-50-44, 56-55-54-51-50-45, 56-55-54-51-50-47, 56-55-54-51-50-48, 56-55-54-52-1, 56-55-54-52-2, 56-55-54-52-3, 56-55-54-52-6, 56-55-54-52-7, 56-55-54-52-8, 56-55-54-52-9, 56-55-54-52-10, 56-55-54-52-11, 56-55-54-52-12, 56-55-54-52-13, 56-55-54-52-14, 56-55-54-52-23, 56-55-54-52-24, 56-55-54-52-29, 56-55-54-52-

30, 56-55-54-52-31, 56-55-54-52-32, 56-55-54-52-33, 56-55-54-52-34, 56-55-54-52-35, 56-55-54-52-36, 56-55-54-52-37, 56-55-54-52-41, 56-55-54-52-42, 56-55-54-52-43, 56-55-54-52-44, 56-55-54-52-45, 56-55-54-52-46, 56-55-54-52-47, 56-55-54-52-50-1, 56-55-54-52-50-2, 56-55-54-52-50-3, 56-55-54-52-50-6, 56-55-54-52-50-7, 56-55-54-52-50-8, 56-55-54-52-50-9, 56-55-54-52-50-10, 56-55-54-52-50-11, 56-55-54-52-50-12, 56-55-54-52-50-13, 56-55-54-52-50-14, 56-55-54-52-50-23, 56-55-54-52-50-24, 56-55-54-52-50-29, 56-55-54-52-50-30, 56-55-54-52-50-31, 56-55-54-52-50-34, 56-55-54-52-50-35, 56-55-54-52-50-36, 56-55-54-52-50-37, 56-55-54-52-50-41, 56-55-54-52-50-42, 56-55-54-52-50-43, 56-55-54-52-50-44, 56-55-54-52-50-45, 56-55-54-52-50-46, 56-55-54-52-50-47, 56-55-54-52-51-6, 56-55-54-52-51-7, 56-55-54-52-51-8, 56-55-54-52-51-9, 56-55-54-52-51-10, 56-55-54-52-51-11, 56-55-54-52-51-12, 56-55-54-52-51-13, 56-55-54-52-51-14, 56-55-54-52-51-23, 56-55-54-52-51-24, 56-55-54-52-51-30, 56-55-54-52-51-31, 56-55-54-52-51-41, 56-55-54-52-51-42, 56-55-54-52-51-43, 56-55-54-52-51-44, 56-55-54-52-51-45, 56-55-54-52-51-47, 56-55-54-52-51-50-6, 56-55-54-52-51-50-7, 56-55-54-52-51-50-8, 56-55-54-52-51-50-9, 56-55-54-52-51-50-10, 56-55-54-52-51-50-11, 56-55-54-52-51-50-12, 56-55-54-52-51-50-13, 56-55-54-52-51-50-14, 56-55-54-52-51-50-23, 56-55-54-52-51-50-24, 56-55-54-52-51-50-30, 56-55-54-52-51-50-31, 56-55-54-52-51-50-41, 56-55-54-52-51-50-42, 56-55-54-52-51-50-43, 56-55-54-52-51-50-44, 56-55-54-52-51-50-45, 56-55-54-52-51-50-47, 56-55-54-53-1, 56-55-54-53-2, 56-55-54-53-3, 56-55-54-53-4, 56-55-54-53-5, 56-55-54-53-6, 56-55-54-53-7, 56-55-54-53-8, 56-55-54-53-9, 56-55-54-53-10, 56-55-54-53-11, 56-55-54-53-12, 56-55-54-53-13, 56-55-54-53-14, 56-55-54-53-15, 56-55-54-53-16, 56-55-54-53-17, 56-55-54-53-18, 56-55-54-53-19, 56-55-54-53-20, 56-55-54-53-21, 56-55-54-53-22, 56-55-54-53-23, 56-55-54-53-24, 56-55-54-53-25, 56-55-54-53-26, 56-55-54-53-27, 56-55-54-53-28, 56-55-54-53-29, 56-55-54-53-30, 56-55-54-53-31, 56-55-54-53-32, 56-55-54-53-33, 56-55-54-53-34, 56-55-54-53-35, 56-55-54-53-36, 56-55-54-53-37, 56-55-54-53-38, 56-55-54-53-39, 56-55-54-53-40, 56-55-54-53-41, 56-55-54-53-42, 56-55-54-53-43, 56-55-54-53-44, 56-55-54-53-45, 56-55-54-53-46, 56-55-54-53-47, 56-55-54-53-48, 56-55-54-53-49, 56-55-54-53-50-1, 56-55-54-53-50-2, 56-55-54-53-50-3, 56-55-54-53-50-6, 56-55-54-53-50-7, 56-55-54-53-50-8, 56-55-54-53-50-9, 56-55-54-53-50-10, 56-55-54-53-50-11, 56-55-54-53-50-12, 56-55-54-53-50-13, 56-55-54-53-50-14, 56-55-54-53-50-15, 56-55-54-53-50-16, 56-55-54-53-50-19, 56-55-54-53-50-20, 56-55-54-53-50-21, 56-55-54-53-50-22, 56-55-54-53-50-23, 56-55-54-53-50-24, 56-55-54-53-50-27, 56-55-54-53-50-28, 56-55-54-53-50-29, 56-55-54-53-50-30, 56-55-54-53-50-31, 56-55-54-53-50-32, 56-55-54-53-50-34, 56-55-54-53-50-35, 56-55-54-53-50-36, 56-55-54-53-50-37, 56-55-54-53-50-38, 56-55-54-53-50-40, 56-55-54-53-50-41, 56-55-54-53-50-42, 56-55-54-53-50-43, 56-55-54-53-50-44, 56-55-54-53-50-45, 56-55-54-53-50-46, 56-55-54-53-50-47, 56-55-54-53-50-48, 56-55-54-53-51-6, 56-55-54-53-51-7, 56-55-54-53-51-8, 56-55-54-53-51-9, 56-55-54-53-51-10, 56-55-54-53-51-11, 56-55-54-53-51-12, 56-55-54-53-51-13, 56-55-54-53-51-14, 56-55-54-53-51-15, 56-55-54-53-51-16, 56-55-54-53-51-17, 56-55-54-53-51-18, 56-55-54-53-51-19, 56-55-54-53-51-20, 56-55-54-53-51-21, 56-55-54-53-51-22, 56-55-54-53-51-23, 56-55-54-53-51-24, 56-55-54-53-51-30, 56-55-54-53-51-31, 56-55-54-53-51-32, 56-55-54-53-51-33, 56-55-54-53-51-40, 56-55-54-53-51-41, 56-55-54-53-51-42, 56-55-54-53-51-43, 56-55-54-53-51-44, 56-55-54-53-51-45, 56-55-54-53-51-47, 56-55-54-53-51-48, 56-55-54-53-51-49, 56-55-54-53-51-50-6, 56-55-54-53-51-50-7, 56-55-54-53-51-50-8, 56-55-54-53-51-50-9, 56-55-54-53-51-50-10, 56-55-54-53-51-50-11, 56-55-54-53-51-50-12, 56-55-54-53-51-50-13, 56-55-54-53-51-50-14, 56-55-54-53-51-50-15, 56-55-54-53-51-50-16, 56-55-54-53-51-50-19, 56-55-54-53-51-50-20, 56-55-54-53-51-50-21, 56-55-54-53-51-50-22, 56-55-54-53-51-50-23, 56-55-54-53-51-50-24, 56-55-54-53-51-50-30, 56-55-54-53-51-50-31, 56-55-54-53-51-50-32, 56-55-54-53-51-50-40, 56-55-54-53-51-50-41, 56-55-54-53-51-50-42, 56-55-54-53-51-50-43, 56-55-54-53-51-50-44, 56-55-54-53-51-50-45, 56-55-54-53-51-50-47, 56-55-54-53-51-50-48, 56-55-54-53-52-1, 56-55-54-53-52-2, 56-55-54-53-52-3, 56-55-54-53-52-6, 56-55-54-53-52-7, 56-55-54-53-52-8, 56-55-54-53-52-9, 56-55-54-53-52-10, 56-55-54-53-52-11, 56-55-54-53-52-12, 56-55-54-53-52-13, 56-55-54-53-52-14, 56-55-54-53-52-23, 56-55-54-53-52-24, 56-55-54-53-52-29, 56-55-54-53-52-30, 56-55-54-53-52-31, 56-55-54-53-52-32, 56-55-54-53-52-33, 56-55-54-53-52-34, 56-55-54-53-52-35, 56-55-54-53-52-36, 56-55-54-53-52-37, 56-55-54-53-52-41, 56-55-54-53-52-42, 56-55-54-53-52-43, 56-55-54-53-52-44, 56-55-54-53-52-45, 56-55-54-53-52-46, 56-55-54-53-52-47, 56-55-54-53-52-50-1, 56-55-54-53-52-50-2, 56-55-54-53-52-50-3, 56-55-54-53-52-50-6, 56-55-54-53-52-50-7, 56-55-54-53-52-50-8, 56-55-54-53-52-50-9, 56-55-54-53-52-50-10, 56-55-54-53-52-50-11, 56-55-54-53-52-50-12, 56-55-54-53-52-50-13, 56-55-54-53-52-50-14, 56-55-54-53-52-50-23, 56-55-54-53-52-50-24, 56-55-54-53-52-50-29, 56-55-54-53-52-50-30, 56-55-54-53-52-50-31, 56-55-54-53-52-50-34, 56-55-54-53-52-50-35, 56-55-54-53-52-50-36, 56-55-54-53-52-50-37, 56-55-54-53-52-50-41, 56-55-54-53-52-50-42, 56-55-54-53-52-50-43, 56-55-54-53-52-50-44, 56-55-54-53-52-50-45, 56-55-54-53-52-50-46, 56-55-54-53-52-50-47, 56-55-54-53-52-51-6, 56-55-54-53-52-51-7, 56-55-54-53-52-51-8, 56-55-54-53-52-51-9, 56-55-54-53-52-51-10, 56-55-54-53-52-51-11, 56-55-54-53-52-51-12, 56-55-54-53-52-51-13, 56-55-54-53-52-51-14, 56-55-54-53-52-51-23, 56-55-54-53-52-51-24, 56-55-54-53-52-51-30, 56-55-54-53-52-51-31, 56-55-54-53-52-51-41, 56-55-54-53-52-51-42, 56-55-54-53-52-51-43, 56-55-54-53-52-51-44, 56-55-54-53-52-51-45, 56-55-54-53-52-51-47, 56-55-54-53-52-51-50-6, 56-55-54-53-52-51-50-7, 56-55-54-53-52-51-50-8, 56-55-54-53-52-51-50-9, 56-55-54-53-52-51-50-10, 56-55-54-53-52-51-50-11, 56-55-54-53-52-51-50-12, 56-55-54-53-52-51-50-13, 56-55-54-53-52-51-50-14, 56-55-54-53-52-51-50-23, 56-55-54-53-52-51-50-24, 56-55-54-53-52-51-50-30, 56-55-54-53-52-51-50-31, 56-55-54-53-52-51-50-41, 56-55-54-53-52-51-50-42, 56-55-54-53-52-51-50-43, 56-55-54-53-52-51-50-44, 56-55-54-53-52-51-50-45, and 56-55-54-53-52-51-50-47. For each of these compound groups, designations 1.1.1.1 through 10.10.10.10 in Table B specifies a compound or genus of compounds as defined by the Table A substituents and any independently selected $R^{10A}$, $R^{10B}$, $R^{10C}$ and $R^{10D}$ moiety as described here or elsewhere herein.

For compound groups where there is no double bond at the 2-position, exemplary substituents in the α-configuration or the β-configuration for $R^{10A}$ are substituents described herein, e.g., —H, —$^2$H, —$^3$H, —OH, —OR$^{PR}$, —SH, —SR$^{PR}$, —NH$_2$, —NHR$^{PR}$, —NH—C1-6 alkyl, —NHCH$_3$, —N(CH$_3$)$_2$, —N$_3$, —NO$_2$, —CN, —SCN, —F, —Cl, —Br, —I, C1-6 optionally substituted alkyl, C1-6 optionally substituted alkylamine, C1-6 ether, C1-6 ester, C1-6 thioether, C1-6 thioester, optionally substituted monosaccharide, sulfate, sulfate ester, phosphate, phosphate ester, carbamate or carbonate such as —OC(O)—CH$_3$, —OC(O)—C$_2$H$_5$, —SC(O)—CH$_3$, —SC(O)—C$_2$H$_5$, —OCH$_3$, —OC$_2$H$_5$, —SCH$_3$, —SC$_2$H$_5$, —NHC(O)—O—CH$_3$, —NHC(O)—O—C$_2$H$_5$, —OC(O)—NH$_2$, —OC(O)—NHCH$_3$, —OC(O)—NHC$_2$H$_5$, —OC(O)—OCH$_3$, —OC(O)—OC$_2$H$_5$. R$^{10A}$ can also be a double bonded moiety, e.g., =O, =S, =NOH or =CH$_2$, when there is no double bond at the 2-position.

For compound groups where there is no double bond at the 4-position, exemplary substituents in the α-configuration or the β-configuration for R$^{10B}$ are substituents described herein, e.g., —H, —$^2$H, —$^3$H, —OH, —OR$^{PR}$, =O, —SH, —SR$^{PR}$, =S, —NH$_2$, —NHR$^{PR}$, —NH—C1-6 alkyl, —NHCH$_3$, —N(CH$_3$)$_2$, —F, —Cl, —Br, —I, C1-6 optionally substituted alkyl, C1-6 optionally substituted alkylamine, C1-6 ether, C1-6 ester, C1-6 thioether, C1-6 thioester, optionally substituted monosaccharide, sulfate, sulfate ester, phosphate, phosphate ester, carbamate or carbonate such as —OC(O)—CH$_3$, —OC(O)—C$_2$H$_5$, —SC(O)—CH$_3$, —SC(O)—C$_2$H$_5$, —OCH$_3$, —OC$_2$H$_5$, —SCH$_3$, —SC$_2$H$_5$, —CH$_3$, —C$_2$H$_5$, —NHC(O)—O—CH$_3$, —NHC(O)—O—C$_2$H$_5$, —OC(O)—NH$_2$, —OC(O)—NHCH$_3$, —OC(O)—NHC$_2$H$_5$, —OC(O)—OCH$_3$, —OC(O)—OC$_2$H$_5$. R$^{10B}$ can also be a double bonded moiety, e.g., =O, =S, =NOH or =CH$_2$, when there is no double bond at the 4-position.

For compound groups where there is no double bond at the 6-position, exemplary substituents in the α-configuration or the β-configuration for R$^{10C}$ are substituents described herein, e.g., —H, —$^2$H, —$^3$H, —OH, —OR$^{PR}$, =O, —SH, —SR$^{PR}$, =S, —NH$_2$, —NHR$^{PR}$, —NH—C1-6 alkyl, —NHCH$_3$, —N(CH$_3$)$_2$, —F, —Cl, —Br, —I, C1-6 optionally substituted alkyl, C1-6 optionally substituted alkylamine, C1-6 ether, C1-6 ester, C1-6 thioether, C1-6 thioester, optionally substituted monosaccharide, sulfate, sulfate ester, phosphate, phosphate ester, carbamate or carbonate such as -β-D-glucopyranoside, —OC(O)—CH$_3$, —OC(O)—C$_2$H$_5$, —SC(O)—CH$_3$, —SC(O)—C$_2$H$_5$, —OCH$_3$, —OC$_2$H$_5$, —SCH$_3$, —SC$_2$H$_5$, —CH$_3$, —C$_2$H$_5$, —NHC(O)—O—CH$_3$, —NHC(O)—O—C$_2$H$_5$, —OC(O)—NH$_2$, —OC(O)—NHCH$_3$, —OC(O)—NHC$_2$H$_5$, —OC(O)—OCH$_3$, —OC(O)—OC$_2$H$_5$. R$^{10C}$ can also be a double bonded moiety, e.g., =O, =S, =NOH or =CH$_2$, when there is no double bond at the 6-position.

For any of the foregoing independently selected R$^{10A}$, R$^{10B}$ and/or R$^{10C}$ substituents, R$^{10D}$ can be any one of these single bonded substituents in the α- or β-configuration or another single bonded R$^{10D}$ substituent described elsewhere herein in the α- or β-configuration, e.g., α-OH, β-OH, α-F, β-F, α-C1-6 optionally substituted alkyl or β-C1-6 optionally substituted alkyl. R$^{10D}$ can also be a double bonded moiety, e.g., =O, =S, =NOH, =CH$_2$ or =CHCH$_2$OH, as described herein.

Group 57. This group comprises compounds in the compound groups 1 through 56-55-54-53-52-51-50-47 described above, wherein 1, 2, 3 or 4 of R$^1$, R$^2$, R$^3$ and R$^4$ are a moiety defined herein other than one of the moieties listed in Table A, with exemplary moieties as described in the following paragraphs (1) through (15). Moieties or groups listed in paragraphs (1) through (15) such as optionally substituted alkyl, optionally substituted alkylamine, O-linked carbamate, N-linked carbamate and N-linked amino acid ester include the exemplary groups described (a) in the following paragraphs and (b) elsewhere herein. Optionally substituted alkyl groups for any of the moieties described in paragraphs (1) through (12) will typically be a C1-20, a C1-12 or a C1-6 optionally substituted alkyl group that is (i) optionally substituted with 1, 2, 3, 4, 5, 6 or more independently selected substitutions as described herein and (ii) saturated or unsaturated with 1, 2 or 3 or more independently selected —CH$_2$=CH$_2$—, —CHR$^{10A}$=CHR$^{10B}$—, —CH$_2$≡CH$_2$—, —CHR$^{10A}$≡CHR$^{10B}$—, where R$^{10K}$ and R$^{10L}$ independently are an R$^{10}$ moiety as defined for F1Cs, e.g., they can be independently selected —H, C1-C6 optionally substituted alkyl, C1-6 ether, C1-6 thioether, —NH—C1-6 optionally substituted alkyl, halogen or another R$^{10}$ moiety described elsewhere herein. Similarly, other organic moieties, e.g., carbamates, esters, thioesters or carbonates, will typically be a C1-20, a C1-12 or a C1-6 organic moiety that is optionally substituted with 1, 2, 3, 4, 5, 6 or more independently selected substitutions as described herein, e.g., for substituted alkyl groups.

(1) Compounds in any of the foregoing groups 1 through 56-55-54-53-52-51-50-47 where R$^1$ moieties 1 through 10 in Table A are replaced with the following moieties: 1 is —Z-optionally substituted alkyl, 2 is an ester (e.g., —O—C(O)—(CH$_2$)$_n$—CH$_3$, —O—C(O)—(CH$_2$)$_n$—NH$_2$, —O—C(O)—(CH$_2$)$_n$—N(R$^{PR}$)$_2$, —O—C(O)—(CH$_2$)$_n$—CH$_2$ZR$^{PR}$, —O—C(O)—CH(ZR$^{PR}$)—(CH$_2$)$_n$—CH$_3$ or another ester described herein, where n is 0, 1, 2, 3, 4, 5, 6, 7 or 8, Z independently are —NH—, oxygen or sulfur and R$^{PR}$ independently or together are —H, a protecting group or a counter ion, e.g., methoxymethyl, —CH$_3$ or —C$_2$H$_5$), 3 is a thioester (e.g., —S—C(O)—(CH$_2$)$_n$—CH$_3$, —S—C(O)—(CH$_2$)$_n$—NH$_2$, —S—C(O)—(CH$_2$)$_n$—NHR$^{PR}$, —S—C(O)—(CH$_2$)$_n$—CH$_2$ZR$^{PR}$, —S—C(O)—CH(ZR$^{PR}$)—(CH$_2$)$_n$—CH$_3$ or another thioester described herein, where n is 0, 1, 2, 3, 4, 5, 6, 7 or 8, Z independently are —NH—, oxygen (—O—) or sulfur (—S—) and R$^{PR}$ is —H or a protecting group, e.g., —CH$_3$ or —C$_2$H$_5$), 4 is a carbonate (e.g., —O—C(O)—O-optionally substituted alkyl), 5 is optionally substituted alkylamine (e.g., —NH-optionally substituted alkyl), 6 is optionally substituted dialkylamine (e.g., —N(optionally substituted alkyl)$_2$, where each optionally substituted alkyl is independently chosen), 7 is an N linked carbamate (e.g., —NH—C(O)—O-optionally substituted alkyl or —NH—C(O)—OH), 8 is an O linked carbamate (e.g., —O—C(O)—NH$_2$ or —O—C(O)—NH-optionally substituted alkyl), 9 is —O-optionally substituted monosaccharide and 10 is —H. Exemplary optionally substituted alkyl groups for any of these moieties include —CH$_2$CH$_2$—O—CH$_3$, —CH$_2$CH$_2$—S—CH$_3$, —CH(ZR$^{PR}$)—(CH$_2$)$_n$—CH$_2$ZR$^{PR}$, —CH(ZR$^{PR}$)—(CH$_2$)$_n$—CH$_2$NHR$^{PR}$, —CH$_2$—(CH$_2$)$_n$—C(O)OR$^{PR}$, —CH$_2$—(CH$_2$)$_n$—C(O)SR$^{PR}$, —CH$_2$—(CH$_2$)$_n$—C(O)NHR$^{PR}$, or any alkyl, alkenyl or alkynyl moiety described herein, e.g., any of which optionally having 1, 2, 3, 4, 5, 6, 7, 8, 9, 10, 11, 12 or more carbon atoms, with any of these being optionally substituted with 1, 2, 3, 4, 5, 6 or more independently selected substitutions, where n and Z are as described above.

(2) Compounds in any of the foregoing groups 1 through 56-55-54-53-52-51-50-47 where R$^1$ moieties 1 through 10 in Table A are replaced with the following moieties: 1 is —O-optionally substituted disaccharide, 2 is an N-linked amino acid, an N-linked amino acid ester or a salt (e.g., —NH—(CH$_2$)$_n$—C(O)OH, —NH—(CH$_2$)$_n$—C(O)OR$^{PR}$, —NH—(CH$_2$)$_n$—C(O)OCH$_3$, —NH—CH(CH$_3$)—C(O)OR$^{PR}$, —NH—CH(CH$_2$OH)—C(O)OR$^{PR}$ or —NH—CH$_2$—CH$_2$—C(O)OR$^{PR}$, where R$^{PR}$ is —H, a counter ion or a protecting group and chiral carbon atoms are in the D-, L- or DL-configuration), 3 is an O-linked amino acid, an O-linked amino acid ester, or a salt of any of these (e.g., —O—C(O)—(CH$_2$)$_n$—NHR$^{PR}$, —O—CH$_2$—NH$_2$, —O—CH$_2$—CH$_2$—NH$_2$, —O—C(O)—CH$_2$—CH$_2$—NHR$^{PR}$, —O—C(O)—(CH$_2$)$_n$—NH—C1-C6 optionally substituted alkyl, —O—C(O)—O—(CH$_2$)$_n$—NH—C1-C6 optionally substituted alkyl, —O—C(O)—CH(CH$_3$)—(CH$_2$)$_n$—NH$_2$, —O—C (O)—CH(CH$_3$)—(CH$_2$)$_n$—NHR$^{PR}$ or —O—C(O)—CH(CH$_2$OH)—(CH$_2$)$_n$—NH$_2$, where R$^{PR}$ is —H, a counter ion or a protecting group and chiral carbon atoms are in the D-, -L or -DL configuration), 4 is an S-linked amino acid, an S-linked amino acid ester or a salt (e.g., —S—C(O)—CH$_2$—NHR$^{PR}$, —S—C(O)—CH$_2$—NH$_2$, —S—C(O)—CH$_2$—CH$_2$—NHR$^{PR}$, —S—C(O)—(CH$_2$)$_n$—NH$_2$, —S—C(O)—(CH$_2$)$_n$—NHR$^{PR}$, —S—C(O)—CH(CH$_2$OH)—(CH$_2$)$_n$—NH$_2$, —S—C(O)—(CH$_2$)$_n$—NH—C1-C6 optionally substituted alkyl, where R$^{PR}$ is —H, a counter ion or a protecting group and chiral carbon atoms are in the D-, -L or -DL configuration), 5 is a sulfate ester (e.g., —O—S(O)(OR$^{PR}$)—O-optionally substituted alkyl), 6 is —O—S(O)—O-optionally substituted alkyl, 7 is —F, —Cl —Br or —I, 8 is a polymer or polymer mixture such as one, two or more of PEG-100, PEG-200, PEG-300 or PEG-400, 9 is an N-linked heterocycle (e.g., N-morpholino, N-pyrrolidinyl or N-piperidinyl) and 10 is a C-linked heterocycle, e.g., 2-pyrimidinyl or 2-piperidinyl, where for any of these moieties, n is 1, 2, 3, 4, 5, 6, 7, 8, 9, 10, 11, 12 and R$^{PR}$ is a protecting group or optionally substituted alkyl such as —CH$_3$, —CF$_3$ or —C$_2$H$_5$. When R$^1$ is a polymer, exemplary compounds have structures such as steroid 3-position-O—C(O)—(OCH$_2$—CH$_2$)$_m$—OH, steroid 3-position-O—C(O)—(OCH$_2$—CH$_2$)$_m$—OR$^{PR}$, steroid 3-position-O—C(O)—(OCH$_2$—CH$_2$)$_m$—CH$_3$, steroid 3-position-S—C(O)—(OCH$_2$—CH$_2$)$_m$—OH, steroid 3-position-S—C(O)—(OCH$_2$—CH$_2$)$_m$—OR$^{PR}$, steroid 3-position-S—C(O)—(OCH$_2$—CH$_2$)$_m$—CH$_3$, where the polymer is in the α- or β-configuration when no double bond is present at the 3-position and m is one, two or more of about 1, 2, 3, 4, 5, 6, 7, 8, 9, 10, 11, 12, 13, 14, 15, 16, 18, 20, 22, 25, 30, 35, 40, 45, 50, 55, 60 or more or where the average value of m is one of these integers.

(3) Compounds in any of the foregoing groups 1 through 56-55-54-53-52-51-50-47 where there is no double bond at the 2-3 or 3-4 position and R$^1$ moieties 1 through 10 in Table A are replaced with the following moieties: 1 is =O, 2 is =S, 3 is =NOH, 4 is =NOCH$_3$, 5 is =NOC$_2$H$_5$, 6 is =N-optionally substituted alkyl, 7 is =NO-optionally substituted alkyl, 8 is =NH, 9 is =CH$_2$ and 10 is =C-optionally substituted alkyl. Exemplary group 57(3)-6 (i.e., group 57 paragraph 3 compounds from group 6, which described 1,5-dienes) compounds include compound 1.2.4.1, which is 3-oxo-7β-hydroxy-16α-fluoro-17β-aminoandrost-1,5-diene, 1.1.4.1, which is 3-oxo-16α-fluoro-17β-aminoandrost-1,5-diene, 1.1.5.9, which is 3-oxo-17β-hydroxyandrost-1,5-diene, 1.1.7.1, which is 3-oxo-16α-acetoxy-17β-aminoandrost-1,5-diene and compound 1.1.1.10, which is 3β-hydroxy-16α-bromo-17β-acetoxyandrost-1,5-diene and 16α-hydroxy, 16α-methyl, 16α-amino, 16α-aminomethyl, 16α-acetate and 16α-halo analogs of any of these compounds. Exemplary group 57-7 compounds include compound 1.2.4.1, which is 3-oxo-7-hydroxy-16α-fluoro-17β-aminoandrost-1,6-diene, 1.1.4.1, which is 3-oxo-16α-fluoro-17β-aminoandrost-1,6-diene, 1.1.5.9, which is 3-oxo-17β-dihydroxyandrost-1,6-diene, 1.1.7.1, which is 3-oxo-16α-acetoxy-17β-aminoandrost-1,6-diene and compound 1.1.1.10, which is 3β-hydroxy-16α-bromo-17β-acetoxyandrost-1,6-diene and 16α-hydroxy, 16α-methyl, 16α-amino, 16α-aminomethyl, 16α-acetate and 16α-halo analogs of any of these compounds. Exemplary group 57-8 compounds include compound 1.2.4.1, which is 3-oxo-7-hydroxy-16α-fluoro-17β-amino-5β-androst-1,6-diene, 1.1.4.1, which is 3-oxo-16α-fluoro-17β-amino-5β-androst-1,6-diene, 1.1.5.9, which is 3-oxo-17β-dihydroxy-5β-androst-1,6-diene, 1.1.7.1, which is 3-oxo-16α-acetoxy-17β-amino-5β-androst-1,6-diene and compound 1.1.1.10, which is 3β-hydroxy-16α-bromo-17β-acetoxy-5β-androst-1,6-diene and 16α-hydroxy, 16α-methyl, 16α-amino, 16α-aminomethyl, 16α-acetate and 16α-halo analogs of any of these compounds. Other group 57 compounds include any of these compounds where R$^1$ is in the α-configuration, and/or R$^3$ is in the β-configuration and/or R$^4$ is in the α-configuration and/or R$^5$ is a moiety other than methyl, e.g., —CH$_2$OH, —CHO, —C$_2$H$_5$, —C$_3$H$_7$ or another R$^5$ described herein and/or R$^6$ is a moiety other than methyl, e.g., —H, —F, —Cl, —OH, —SH, —NH$_2$, —NHR$^{PR}$, an ester or ether, —CH$_2$OH, —C—C≡CH, —C$_2$H$_5$, —C$_3$H$_7$ or another R$^6$ described herein and/or R$^{10G}$ is a moiety other than —H, e.g., —F, —Cl, —Br, —CH$_3$, —OH, —SH, —NHR$^{PR}$ or another R$^{10G}$ moiety described herein and/or R$^8$ is a moiety other than methylene, e.g., —O—, —S—, —NH—, =N—, —N(CH$_3$)—, —N(C$_2$H$_5$)—, —CH(α-optionally substituted C1-C6 alkyl)-, —CH(β-optionally substituted C1-C6 alkyl)-, —CH(α-OH)—, —CH(β-OH)—, —C(O)—, —CH(α-SH)—, —CH(β-SH)—, —CH(α-F)—, —CH(β-F)—, —CH(α-I)—, —CH(β-I)— or another R$^8$ moiety described herein or R$^8$ is absent, leaving a 5-membered ring and/or R$^9$ is a moiety other than methylene, e.g., —O—, —S—, —NH—, —N(CH$_3$)—, —N(C$_2$H$_5$)—, —CH(α-optionally substituted C1-C6 alkyl)-, —CH(β-optionally substituted C1-C6-CH(α-OH)—, —CH(β-OH)—, —C(O)—, —CH(α-SH)—, —CH(β-SH)—, —CH(α-F)—, —CH(β-F)—, —CH(α-I)—, —CH(β-I)— or another R$^9$ moiety described herein or R$^9$ is absent, leaving a 5-membered ring. Other exemplary compounds include analogs of any of these compounds where (i) R$^7$ is another R$^7$ moiety described herein such as —O—, —NH—, =N—, —NCH$_3$—, —NC$_2$H$_5$—, —CH=CH—, —CR$^{10}$=CR$^{10}$—, —CH$_2$—CH(α-R$^{10}$)—, —CH$_2$—CH(β-R$^{10}$)—, —O—, —CH$_2$—C(β-R$^{10}$)(α-R$^{10}$)—, —C(β-R$^{10}$)(α-R$^{10}$)—, where R$^{10}$ independently or together are —OH, =O, —NH$_2$, —NHR$^{PR}$, —SH, halogen, —C(O)—OR$^{PR}$, an ester, an ether, C1-C8 optionally substituted alkyl, a heterocycle, a monosaccharide, a polymer or another R$^{10}$ moiety described herein or (ii) R$^{10H}$ is a moiety other than —H such as —OH, —OR$^{PR}$, —SH, —SR$^{PR}$, —NH$_2$, —NHR$^{PR}$, —NHCH$_3$, —N(CH$_3$)$_2$, —CH$_3$ or C1-C6 optionally substituted alkyl. Other groups and analogous compounds include those in group 57-9, 57-10, 57-11, 57-12, 57-13, 57-14, 57-15, 57-16, 57-17, 57-18, 57-19, 57-20, 57-21, 57-22, 57-23, 57-24, 57-30, 57-31, 57-32, 57-33, 57-40, 57-41, 57-42, 57-43, 57-44, 57-45, 57-46, 57-47, 57-48, 57-49 and analogs or epimers where R$^1$ is =O, =S or =NOH, and/or R$^2$ is in the α-configuration, and/or R$^3$ is in the β-configuration and/or R$^4$ is in the α-configuration and/or R$^5$ is a moiety other than methyl such as —H, ethyl, ethynyl, 1-propynyl or C2-C6 optionally substituted alkyl and/or R$^6$ is a moiety other than methyl such as —H, —F, —Cl, —Br, —OH, —SH, —NH$_2$, —NHR$^{PR}$, ethyl, ethynyl, 1-propynyl or C2-C6 optionally substituted alkyl and/or R$^{10G}$ is a moiety other than —H such as —F or —Cl, and/or R$^8$ is a moiety other than methylene or R$^8$ is absent, leaving a 5-membered ring and/or R$^9$ is a moiety other than methylene or R$^9$ is absent, leaving a 5-membered ring. In any of these compounds, R$^{PR}$ in dependently or together are —H or a protecting group.

(4) Compounds in any of the foregoing groups 1 through 56-55-54-53-52-51-50-47 where R$^1$ moieties 1 through 10 in Table A are replaced with the following moieties: 1 is a phosphate, phosphate ester or a salt, e.g., —O—P(O)(OH)—OH, —O—P(O)(OH)—O$^-$Na$^+$, —O—P(O)(OH)—O-optionally substituted alkyl, —O—P(O)(OR$^{PR}$)—O-optionally substituted alkyl, 2 is a thiophosphate or thiophosphate ester, 3 is a sulfamate, 4 is a phosphonate, 5 is a thiophosphonate, 6 is a sulfonate, 7 is a polymer, 8 is an optionally substituted oligosaccharide, 9 is a thionoester and 10 is an amide. Exemplary $R^1$ moieties include (i) —O—P(O)(O—(C(O))$_m$—(CH$_2$)$_n$—CH$_3$)—OH, —O—P(O)(O—(C(O))$_m$—(CH$_2$)$_n$—CH$_3$)—O—(CH$_2$)$_n$—CH$_3$ where m independently are 0 or 1 and n independently are 1, 2, 3, 4, 5, 6, 7, 8, 9, 10 or 11, (ii) —O—P(O)(SH)—OH, —O—P(O)(SH)—O$^-$Na$^+$, —O—P(O)(OH)—S-optionally substituted alkyl, —O—P(O)(S—(C(O))$_m$—(CH$_2$)$_n$—CH$_3$)—OH, —O—P(O)(S—(C(O))$_m$—(CH$_2$)$_n$—CH$_3$)—O—(CH$_2$)$_n$—CH$_3$ where m independently are 0 or 1 and n independently are 1, 2, 3, 4, 5, 6, 7, 8, 9, 10 or 11, (iii)-(OCH$_2$HC$_2$)$_n$—OH, —(OCH$_2$HC$_2$)$_n$—CH$_3$, —(OCH$_2$HC$_2$)$_n$—OR$^{PR}$, —(OCH$_2$HC$_2$)$_n$—SH, —(OCH$_2$HC$_2$)$_n$—SR$^{PR}$, —(OCH$_2$HC$_2$)$_n$—NH$_2$ or —(OCH$_2$HC$_2$)$_n$—NHR$^{PR}$ where n is an integer such as an integer from about 4, 8, 12 or 20 to about 30, 40, 50 or 100, (vi) —O—S(O)(O)—NH—(C(O))$_m$—(CH$_2$)$_n$—X—(CH$_2$)$_n$—CH$_3$, —O—S(O)(O)—NH—(C(O))$_m$—(CH$_2$)$_n$—CH$_3$, —O—S(O)(O)—NH—(CH$_2$)$_n$—X—CH$_3$, —O—S(O)(O)—NH—(CH$_2$)$_n$—(C(O))$_m$—X—(C(O))$_m$—(CH$_2$)$_m$—CH$_3$, —O—S(O)(O)—NH$_2$, —O—S(O)(O)—NH—C1-C8 optionally substituted alkyl, —O—S(O)(O)—N—(C1-C8 optionally substituted alkyl)$_2$, —NH—S(O)(O)—O—(CH$_2$)$_n$—X—CH$_3$, —NH—S(O)(O)—O—(C(O))$_m$—(CH$_2$)$_n$—X—CH$_3$, —NH—S(O)(O)—O—(CH$_2$)$_n$—(C(O))$_m$—X—CH$_3$, —NH—S(O)(O)—O—(CH$_2$)$_n$—X—(C(O))$_m$—CH$_3$ or —NH—S(O)(O)—O—(CH$_2$)$_m$-optionally substituted heterocycle, where X is —O—, —S—, —NH—, —N(C1-C8 optionally substituted alkyl)-, m independently are 0 or 1, n independently are 1, 2, 3, 4, 5, 6, 7, 8, 9, 10 or 11 and optionally substituted alkyl are each independently selected, (vii) —O—S(O)(O)—(C(O))$_m$—(CH$_2$)$_n$—X—(CH$_2$)$_n$—CH$_3$, —O—S(O)(O)—(C(O))$_m$—(CH$_2$)$_n$—CH$_3$, —O—S(O)(O)—(CH$_2$)$_n$—X—CH$_3$, —O—S(O)(O)—(CH$_2$)$_n$—(C(O))$_m$—X—(C(O))$_m$—(CH$_2$)$_m$—CH$_3$, —O—S(O)(O)—CH$_3$, —O—S(O)(O)—C1-C8 optionally substituted alkyl, —S(O)(O)—O—(CH$_2$)$_n$—X—CH$_3$, —S(O)(O)—O—(C(O))$_m$—(CH$_2$)$_n$—X—CH$_3$, —S(O)(O)—O—(CH$_2$)$_n$—(C(O))$_m$—X—CH$_3$, —S(O)(O)—O—(CH$_2$)$_n$—X—(C(O))$_m$—CH$_3$ or —S(O)(O)—O—(CH$_2$)$_m$-optionally substituted heterocycle, where X is —O—, —S—, —NH—, —N(C1-C8 optionally substituted alkyl)-, m independently are 0 or 1, n independently are 1, 2, 3, 4, 5, 6, 7, 8, 9, 10 or 11 and optionally substituted alkyl are each independently selected, (viii) —O—P(O)(OR$^{PR}$)—(C(O))$_m$—(CH$_2$)$_n$—X—(CH$_2$)$_n$—CH$_3$, —O—P(O)(OR$^{PR}$)—(C(O))$_m$—(CH$_2$)$_n$—CH$_3$, —O—P(O)(OR$^{PR}$)—(CH$_2$)$_n$—X—CH$_3$, —O—P(O)(OR$^{PR}$)—(CH$_2$)$_n$—(C(O))$_m$—X—(C(O))$_m$—(CH$_2$)$_m$—CH$_3$, —O—P(O)(OR$^{PR}$)—CH$_3$, —O—P(O)(OR$^{PR}$)—C1-C8 optionally substituted alkyl, —P(O)(OR$^{PR}$)—O—(CH$_2$)$_n$—X—CH$_3$, —P(O)(OR$^{PR}$)—O—(C(O))$_m$—(CH$_2$)$_n$—X—CH$_3$, —P(O)(OR$^{PR}$)—O—(CH$_2$)$_n$—(C(O))$_m$—X—CH$_3$, —P(O)(OR$^{PR}$)—O—C1-C8 optionally substituted alkyl or —P(O)(OR$^{PR}$)—O—(CH$_2$)$_m$-optionally substituted heterocycle, where X is —O—, —S—, —NH—, —N(C1-C8 optionally substituted alkyl)-, m independently are 0 or 1, n independently are 1, 2, 3, 4, 5, 6, 7, 8, 9, 10 or 11, R$^{PR}$ independently are —H or a protecting group and optionally substituted alkyl are each independently selected, (ix) —O—P(S)(OR$^{PR}$)—(C(O))$_m$—(CH$_2$)$_n$—X—(CH$_2$)$_n$—CH$_3$, —O—P(S)(OR$^{PR}$)—(C(O))$_m$—(CH$_2$)$_n$—CH$_3$, —O—P(S)(OR$^{PR}$)—(CH$_2$)$_n$—X—CH$_3$, —O—P(S)(OR$^{PR}$)—(CH$_2$)$_n$—(C(O))$_m$—X—(C(O))$_m$—(CH$_2$)$_m$—CH$_3$, —O—P(S)(OR$^{PR}$)—CH$_3$, —O—P(S)(OR$^{PR}$)—C1-C8 optionally substituted alkyl, —P(S)(OR$^{PR}$)—O—(CH$_2$)$_n$—X—CH$_3$, —P(S)(OR$^{PR}$)—O—(C(O))$_m$—(CH$_2$)$_n$—X—CH$_3$, —P(S)(OR$^{PR}$)—O—(CH$_2$)$_n$—(C(O))$_m$—X—CH$_3$, —P(S)(OR$^{PR}$)—O—C1-C8 optionally substituted alkyl or —P(S)(OR$^{PR}$)—O—(CH$_2$)$_m$-optionally substituted heterocycle, where X is —O—, —S—, —NH—, —N(C1-C8 optionally substituted alkyl)-, m independently are 0 or 1, n independently are 1, 2, 3, 4, 5, 6, 7, 8, 9, 10 or 11, R$^{PR}$ independently are —H or a protecting group and optionally substituted alkyl are each independently selected and (x) —C(O)—NH—(C(O))$_m$—(CH$_2$)$_n$—X—(CH$_2$)$_n$—CH$_3$, —C(O)—NH—(C(O))$_m$—(CH$_2$)$_n$—CH$_3$, —C(O)—NH—(CH$_2$)$_n$—X—CH$_3$, —C(O)—NH—(CH$_2$)$_n$—(C(O))$_m$—X—(C(O))$_m$—(CH$_2$)$_m$—CH$_3$, —C(O)—NH—CH$_3$, —C(O)—NH—C1-C8 optionally substituted alkyl, —C(O)—NH—CH$_2$—CH$_2$—CH$_3$, —C(O)—NH—CH$_2$OR$^{PR}$, —C(O)—NH—CH$_2$—CH$_2$—CH$_2$OR$^{PR}$, —C(O)—NH—CH$_2$—CH$_2$—CH$_2$—CH$_3$, —C(O)—NH—CH$_2$—CH$_2$—CH$_2$—CH$_2$C(O)OR$^{PR}$, —C(O)—NH—CH$_2$—CH$_2$C(O)OR$^{PR}$, —NH—C(O)—(CH$_2$)$_n$—X—CH$_3$, —NH—C(O)—(C(O))$_m$—(CH$_2$)$_n$—X—CH$_3$, —NH—C(O)—(CH$_2$)$_n$—(C(O))$_m$—X—CH$_3$, or —NH—C(O)—(CH$_2$)$_m$-optionally substituted heterocycle, where X is —O—, —S—, —NH—, —N(C1-C8 optionally substituted alkyl)-, m independently are 0 or 1, n independently are 1, 2, 3, 4, 5, 6, 7, 8, 9, 10 or 11, R$^{PR}$ independently are —H or a protecting group and optionally substituted alkyl are each independently selected.

(5) Compounds in any of the foregoing groups 1 through 56-55-54-53-52-51-50-47 and in paragraphs (1), (2), (3) and (4) in this group 57 where $R^4$ moieties 1 through 10 in Table A are replaced with the following moieties: 1 is —O-optionally substituted alkyl, 2 is an ester (e.g., —O—C(O)—CH$_3$, —O—C(O)—CH$_2$CH$_3$, —O—C(O)—(CH$_2$)$_n$—CH$_3$, —O—C(O)—CF$_3$, —O—C(O)—(CH$_2$)$_n$—CF$_3$, —O—C(O)—(CH$_2$)$_n$—C(O)OR$^{PR}$, —O—C(O)—CH$_2$—C(O)OR$^{PR}$, —O—C(O)—(CH$_2$)$_2$—C(O)OR$^{PR}$, —O—C(O)—(CH$_2$)$_3$—C(O)OR$^{PR}$, —O—C(O)—(CH$_2$)$_4$—C(O)OR$^{PR}$, —O—C(O)—(CH$_2$)$_n$—NH$_2$, —O—C(O)—(CH$_2$)$_n$—N(R$^{PR}$)$_2$, —O—C(O)—(CH$_2$)$_n$—CH$_2$ZR$^{PR}$, —O—C(O)—CH(ZR$^{PR}$)—(CH$_2$)$_n$—CH$_3$ or another ester described herein, where n is 0, 1, 2, 3, 4, 5, 6, 7 or 8, Z is —O—, —NH— or —S— and R$^{PR}$ independently or together are —H, a protecting group or a counter ion, e.g., methoxymethyl, Na$^+$, K$^+$, —CH$_3$ or —C$_2$H$_5$), 3 is a thioester (e.g., —S—C(O)—(CH$_2$)$_n$—CH$_3$, —S—C(O)—(CH$_2$)$_n$—NH$_2$, —S—C(O)—(CH$_2$)$_n$—NHR$^{PR}$, —S—C(O)—(CH$_2$)$_n$—CH$_2$ZR$^{PR}$, —S—C(O)—CH(ZR$^{PR}$)—(CH$_2$)$_n$—CH$_3$ or another thioester described herein, where n is 0, 1, 2, 3, 4, 5, 6, 7 or 8, Z is oxygen or sulfur and R$^{PR}$ is —H or a protecting group, e.g., —CH$_3$ or —C$_2$H$_5$), 4 is a carbonate (e.g., —O—C(O)—O-Optionally substituted alkyl), 5 is optionally substituted alkylamine (e.g., —NH-Optionally substituted alkyl), 6 is optionally substituted dialkylamine (e.g., —N(Optionally substituted alkyl)$_2$, where each optionally substituted alkyl is independently chosen), 7 is an N linked carbamate (e.g., —NH—C(O)—O-Optionally substituted alkyl or —NH—C(O)—OH), 8 is an O linked carbamate (e.g., —O—C(O)—NH$_2$ or —O—C(O)—NH-Optionally substituted alkyl), 9 is —O-optionally substituted monosaccharide and 10 is —H. Exemplary optionally substituted alkyl moieties include any such moiety described herein for any variable group and moieties such as —CF$_3$, —CF$_2$CF$_3$, —CH$_2$CF$_3$, —CF$_2$CF$_2$CF$_3$, —CH$_2$CH$_2$CF$_3$, —CF$_2$CF$_2$CF$_2$CF$_3$, —C(O)—CH$_3$, —C(O)—C$_2$H$_5$, —C(O)—C$_3$H$_7$, —C(O)—C$_4$H$_9$, —C(O)—C$_6$H$_{13}$, —CH(OH)—CH$_3$, —CH(OH)—C$_2$H$_5$, —CH(OH)—C$_3$H$_7$, —CH(OH)—C$_4$H$_9$, —CH(OH)—C$_6$H$_{13}$, —C(O)—C$_2$H$_4$OR$^{PR}$, —C(O)—C$_3$H$_6$OR$^{PR}$, —C(O)—C$_4$H$_8$OR$^{PR}$, —C(O)—C$_6$H$_{13}$OR$^{PR}$, —C(O)—C$_2$H$_4$SR$^{PR}$, —C(O)—C$_3$H$_6$SR$^{PR}$, —C(O)—C$_4$H$_8$SR$^{PR}$, —C(O)—C$_6$H$_{13}$SR$^{PR}$, —C(O)—C$_2$H$_4$NHR$^{PR}$, —C(O)—

$C_3H_6NHR^{PR}$, —C(O)—$C_4H_8NHR^{PR}$, —C(O)—$C_6H_{13}NHR^{PR}$, —C(O)$OR^{PR}$, —$CH_2$C(O)$OR^{PR}$, —$CH_2CH_2$C(O)$OR^{PR}$, —C(O)—O—$CH_2$C(O)$OR^{PR}$, —C(O)—O—$CH_2CH_2$C(O)$OR^{PR}$, —C(O)—O—$CH_2CH_2CH_2$C(O)$OR^{PR}$, where $R^{PR}$ is —H, a protecting group or a counter ion such as $Cl^-$, $Na^+$ or $K^+$.

(6) Compounds in any of the foregoing groups 1 through 56-55-54-53-52-51-50-47 and in paragraphs (1), (2), (3) and (4) in this group 57 where $R^4$ moieties 1 through 10 in Table A are replaced with the following moieties: 1 is —O-optionally substituted disaccharide, 2 is an N-linked amino acid, an N-linked amino acid ester or a salt (e.g., —NH—$CH_2$—C(O)OH, —NH—$CH_2$—C(O)$OR^{PR}$, —NH—$CH_2$—C(O)$OCH_3$, —NH—$CHCH_3$—C(O)$OR^{PR}$ or —NH—$CH_2$—$CH_2$—C(O)$OR^{PR}$, where $R^{PR}$ is —H, a counter ion or a protecting group and chiral carbon atoms are in the D-, -L or -DL configuration), 3 is an O-linked amino acid, an O-linked amino acid ester or a salt (e.g., —O—C(O)—$CH_2$—$NHR^{PR}$, —O—$CH_2$—$NH_2$, or —O—C(O)—$CH_2$—$CH_2$—$NHR^{PR}$, where $R^{PR}$ is —H, a counter ion or a protecting group and chiral carbon atoms are in the D-, -L or -DL configuration), 4 is an S-linked amino acid, an S-linked amino acid ester or a salt (e.g., —S—C(O)—$CH_2$—$NHR^{PR}$, —S—$CH_2$—$NH_2$, or —S—C(O)—$CH_2$—$CH_2$—$NHR^{PR}$, where $R^{PR}$ is —H, a counter ion or a protecting group and chiral carbon atoms are in the D-, -L or -DL configuration), 5 is a sulfate ester (e.g., —O—S(O)($OR^{PR}$)—O-Optionally substituted alkyl), 6 is —O—S(O)—O-Optionally substituted alkyl, 7 is a halogen such as —Br or —I, 8 is a halogen such as —F or —Cl, 9 is an N-linked heterocycle (e.g., N-morpholino) and 10 is a C-linked heterocycle (e.g., 2-pyrimidinyl).

(7) Compounds in any of the foregoing groups 1 through 56-55-54-53-52-51-50-47 and in paragraphs (1), (2), (3) and (4) in this group where there is no double bond at the 16-17 position and $R^4$ moieties 1 through 10 in Table A are replaced with the following moieties: 1 is =O, 2 is =S, 3 is =NOH, 4 is =$NOCH_3$, 5 is =$NOC_2H_5$, 6 is =N— optionally substituted alkyl, 7 is =NO-optionally substituted alkyl, 8 is =NH, 9 is =$CH_2$ and 10 is =C-optionally substituted alkyl. Exemplary compounds and compound genera include 3β-amino-17-oxoandrost-5(10)-ene, 3α-amino-17-oxoandrost-5(10)-ene, 3,17-dioxoandrost-5(10)-ene, 3β-hydroxy-3α-methyl-17-oxoandrost-5(10)-ene, 3α-hydroxy-3β-ethynyl-17-oxoandrost-5(10)-ene, 3β-mercapto-17-oxoandrost-5(10)-ene, 3α-mercapto-17-oxoandrost-5(10)-ene, 3β-amino-17-oxoandrost-5,7-diene, 3α-amino-17-oxoandrost-5,7-diene, 3β-hydroxy-3α-methyl-17-oxoandrost-5,7-diene, 3α-hydroxy-3β-ethynyl-17-oxoandrost-5,7-diene, 3-amino-17-oxoandrost-1,3-diene, 3-hydroxy-17-oxoandrost-1,3-diene, 3-hydroxy-17-oxoandrost-1,3-diene, 3-amino-17-oxo-5β-androst-1,3-diene, 3-amino-17-oxo-5β-androst-1,3-diene, 3-hydroxy-17-oxo-5β-androst-1,3-diene, 3-hydroxy-17-oxo-5β-androst-1,3-diene, 3-amino-17-oxoandrost-2,5(10)-diene, 3-amino-17-oxoandrost-2,5(10)-diene, 3-hydroxy-17-oxoandrost-2,5(10)-diene, 3-hydroxy-17-oxoandrost-2,5(10)-diene, 3-amino-17-oxo-5β-androst-2,5(10)-diene, 3-amino-17-oxo-5β-androst-2,5(10)-diene, 3-hydroxy-17-oxo-5β-androst-2,5(10)-diene, 3-hydroxy-17-oxo-5β-androst-2,5(10)-diene, 3-amino-17-oxoandrost-2,5-diene, 3-amino-17-oxoandrost-2,5-diene, 3-hydroxy-17-oxoandrost-2,5-diene, 3-hydroxy-17-oxoandrost-2,5-diene, 3-amino-17-oxo-5β-androst-2,5-diene, 3-amino-17-oxo-5β-androst-2,5-diene, 3-hydroxy-17-oxo-5β-androst-2,5-diene, 3-hydroxy-17-oxo-5β-androst-2,5-diene, 3-amino-17-oxoandrost-1,3,5-triene, 3-hydroxy-17-oxoandrost-1,3,5-triene, 3-amino-17-oxoandrost-1,3,6-triene, 3-hydroxy-17-oxoandrost-1,3,6-triene, 3-amino-17-oxo-5β-androst-1,3,6-triene, 3-hydroxy-17-oxo-5β-androst-1,3,6-triene, 3-amino-17-oxoandrost-1,3,5(10)-triene, 3-hydroxy-17-oxoandrost-1,3,5(10)-triene, 3-amino-17-oxoandrost-1,3,5(10),8(14)-tetraene, 3-hydroxy-17-oxoandrost-1,3,5(10),8(14)-tetraene, 3-amino-17-oxoandrost-1,3,5(10),8(9)-tetraene, 3-hydroxy-17-oxoandrost-1,3,5(10),8(9)-tetraene, 3-amino-17-oxoandrost-1,3,5(10),6-tetraene, 3-hydroxy-17-oxoandrost-1,3,5(10),6-tetraene, 3-amino-17-oxoandrost-1,3,5(10),7-tetraene, 3-hydroxy-17-oxoandrost-1,3,5(10),7-tetraene, 3-amino-17-oxoandrost-1,3,5(10),15-tetraene, 3-hydroxy-17-oxoandrost-1,3,5(10),15-tetraene and an analog of any of these compounds wherein (i) the 3-position ($R^1$) is substituted with one or two independently selected $R^1$ moieties as described herein such as —SH, =O, =S, ester, ether, carbonate, thioester, thioether, polymer, O-linked carbamate, N-linked amide, N-linked carbamate, —NH—C1-C10 optionally substituted alkyl or —N(C1-C10 optionally substituted alkyl)$_2$ such as methyl, ethyl, propyl or butyl, or one or two other independently selected $R^1$ moieties described herein, instead of —OH, —SH or —$NH_2$, where each optionally substituted alkyl group is the same or different, and/or (ii) the 17-position ($R^4$) is a double bonded moiety as described herein such as =S, =$CH_2$, =$CHCH_3$, =$CHC_2H_5$, =C(OH)—$C_2H_5$, =C(SH)—$C_2H_5$, =C(OH)—$CH_3$, =C(SH)—$CH_3$, =$CHCH_2OH$, =$CHC_2H_4OH$, =CH—C1-C10 optionally substituted alkyl, =NOH, =NO—$CH_3$, =NO—C1-C10 optionally substituted alkyl, =N—$CH_3$, =N—C1-C10 optionally substituted alkyl, ethylene ketal (—O—$CH_2$—$CH_2$—O—) or another double bonded moiety or group described herein, is present at the 17-position instead of =O, and/or (iii) the 16-position ($R^3$) is substituted with one or two independently selected moieties described herein such as —F, —Cl, —Br, —I, —OH, —$NHCH_3$, —N($CH_3$)$_2$, —$NHC_2H_5$, —N($C_2H_5$)$_2$, —$NHC_3H_7$, —N($C_3H_7$)$_2$, —$NHC_3H_5$, —N($C_3H_5$)$_2$, —$NHC_4H_9$, —N($C_4H_9$)$_2$, =O, =S, =$CH_2$, —C1-C10 optionally substituted alkyl such as methyl, ethynyl or 1-propynyl, -heterocycle, —($CH_2$)-heterocycle, a polymer, =$CHCH_3$, =$CHC_2H_5$, =C(OH)—$C_2H_5$, =C(SH)—$C_2H_5$, =C(OH)—$CH_3$, =C(SH)—$CH_3$, =$CHCH_2OH$, =$CHC_2H_4OH$, =CH—C1-C10 optionally substituted alkyl, =NOH, =NO—$CH_3$, =NO—C1-C10 optionally substituted alkyl, =N—$CH_3$, =N—C1-C10 optionally substituted alkyl, =N—$CH_2CH_3$, =N—$CH_2CH_2OR^{PR}$, =N—$CH_2CH_2SR^{PR}$, =N—$CH_2CH_2NHR^{PR}$, ethylene ketal and/or one or two other independently selected $R^3$ moieties described herein, where the substituent(s) is in the α-configuration or the β-configuration when no double bond is present at the 16-position and $R^{PR}$ is —H or a protecting group, and/or (iv) the 2-position ($R^9$) is substituted with one or two independently selected substituents described herein such as —F, —Cl, —Br, —I, —OH, —$OR^{PR}$, —SH, —$SR^{PR}$, —$NH_2$, —$NHR^{PR}$, —$NHCH_3$, —N($CH_3$)$_2$, —$NHC_2H_5$, —N($C_2H_5$)$_2$, —$NHC_3H_7$, —N($C_3H_7$)$_2$, —$NHC_3H_5$, —N($C_3H_5$)$_2$, —$NHC_4H_9$, —N($C_4H_9$)$_2$, =O, =S, =$CH_2$, =$CHCH_3$, =$CHC_2H_5$, =C(OH)—$C_2H_5$, =C(SH)—$C_2H_5$, =C(OH)—$CH_3$, =C(SH)—$CH_3$, =$CHCH_2OH$, =$CHC_2H_4OH$, =CH—C1-C10 optionally substituted alkyl, =NOH, =NO—$CH_3$, =NO—C1-C10 optionally substituted alkyl, =N—$CH_3$, =N—C1-C10 optionally substituted alkyl, =N—$CH_2CH_3$, =N—$CH_2CH_2OR^{PR}$, =N—$CH_2CH_2SR^{PR}$, =N—$CH_2CH_2NHR^{PR}$, =N—C1-C10 optionally substituted alkyl, ethylene ketal, C1-C10 optionally substituted alkyl such as methyl, ethynyl or 1-propynyl, C1-C10 alkoxy such as methoxy or ethoxy, -heterocycle, —($CH_2$)-heterocycle, or a polymer where, when no double bond is present at the 2-position, the substituent(s) is in the α-configuration or the β-configuration, and/or (v) $R^{10G}$ at the 9-position, when present, is —F, —Cl, —Br, —I, —OH, C1-C10 optionally substituted alkyl such as methyl, ethyl, ethynyl or 1-propynyl or cyclopropyl with the 11-position or another moiety described herein, and/or (vi) the 7-position ($R^2$) is substituted with one or two independently selected substituents described herein such as —OH, =O, =S, =CH$_2$, —NH$_2$, —NHCH$_3$, —N(CH$_3$)$_2$, —NHC$_2$H$_5$, —N(C$_2$H$_5$)$_2$, —NHC$_3$H$_7$, —N(C$_3$H$_7$)$_2$, —NHC$_3$H$_5$, —N(C$_3$H$_5$)$_2$, —NHC$_4$H$_9$, —N(C$_4$H$_9$)$_2$, =NOH, =NO—CH$_3$, =NO—C1-C10 optionally substituted alkyl, =N—CH$_3$, =N—C1-C10 optionally substituted alkyl, =N—CH$_2$CH$_3$, =N—CH$_2$CH$_2$OR$^{PR}$, =N—CH$_2$CH$_2$SR$^{PR}$, =N—CH$_2$CH$_2$NHR$^{PR}$, =N—C1-C10 optionally substituted alkyl, ethylene ketal, —NH—C1-C10 optionally substituted alkyl such as hydroxymethyl, hydroxyethyl, hydroxypropyl or another optionally substituted alkyl described herein, —N(C1-C10 optionally substituted alkyl)$_2$, C1-C10 optionally substituted alkyl such as methyl, ethynyl, 1-propynyl or another optionally substituted alkyl described herein, -heterocycle, —(CH$_2$)-heterocycle, a polymer or one or two other substituents described elsewhere herein, where, when no double bond is present at the 7-position, the substituent(s) is in the α-configuration or the β-configuration, and/or (vii) the 6-position ($R^{10C}$) is substituted with a substituent such as —F, —Cl, —Br, —I, —OH, —NH$_2$, —NH—C1-C10 optionally substituted alkyl, —N(C1-C10 optionally substituted alkyl)$_2$ where each optionally substituted alkyl is one or two independently selected $R^1$, $R^4$ or $R^{10C}$ C1-C10 optionally substituted alkyl moieties described herein, =O, =S, =CH$_2$, C1-C10 optionally substituted alkyl such as methyl, ethynyl, 1-propynyl or another optionally substituted alkyl described herein, -heterocycle, —(CH$_2$)-heterocycle, or a polymer where, when no double bond is present at the 6-position, the substituent is in the α-configuration or the β-configuration, and/or (viii) the 11-position ($R^8$) is —O—, —S—, —NH—, —N(CH$_3$)—, —N(C$_2$H$_5$)—, —N(C$_3$H$_7$)—, =N— or is substituted with one or two independently selected substituents described herein such as —F, —Cl, —Br, —I, —OH, =O, —SH, =S, =CH$_2$, C1-C10 optionally substituted alkyl such as methyl, ethynyl or 1-propynyl, -heterocycle, —(CH$_2$)-heterocycle, a polymer or another $R^8$ moiety described herein, where, when no double bond is present at the 11-position, the substituents are in the α-configuration or the β-configuration, e.g., $R^8$ is —CH(α-C1-C10 optionally substituted alkyl)-, —CH(β-C1-C10 optionally substituted alkyl)-, —CH(β-F)—, —CH(α-F)—, —CF$_2$—-CH(β-OH)—, —CH(α-OH)—, —C(O)—, —CH(β-SH)—, —CH(α-SH)—, —CH(β-NH$_2$)—, —CH(α-NH$_2$)—, —CH(β-NHCH$_3$)—, —CH(α-NHCH$_3$)—, —CH(β-N(CH$_3$)$_2$)—, —CH(α-N(CH$_3$)$_2$)—, —CH(β-NHC$_2$H$_5$)—, —CH(α-NHC$_2$H$_5$)—, —CH(α-heterocycle)-, —CH(β-heterocycle)-, —CH(α-polymer)-, —CH(β-polymer)-, —CH(α-ether)-, —CH(β-ether)-, —CH(α-thioether)-, —CH(β-thioether)-. Analogs of any of these compounds include compounds where substitutions described at two or three of (i), (ii), (iii), (iv), (v), (vi), (vii) and (viii) are present, e.g., substitutions as described at (i) and (ii), (i) and (iii), (i) and (iv), (i) and (vi), (i) and (vii), (i) and (viii), (i), (ii) and (iii), (i), (ii) and (vi), (i), (ii) and (v), (i), (ii) and (vi), (i), (ii) and (vii), (i), (ii) and (viii), (i), (ii) and (iii), (i), (ii) and (iv), (i), (ii) and (v), (i), (ii) and (vi), (i), (ii) and (vii), (i), (ii) and (viii), (iii) and (iv), (iii) and (v), (iii) and (vi), (iii) and (vii), (iii) and (viii), (iii), (iv), (i), (iii) and (v), (i), (iii) and (vi), (i), (iii) and (vii), (i), (iii) and (viii), (iv) and (v), (iv) and (vi), (iv) and (vii), (iv) and (viii), (i), (iv) and (v), (i), (iv) and (vi), (i), (iv) and (vii), (i), (iv) and (viii), (v) and (vi), (v) and (vii), (v) and (viii), (i), (v) and (vi), (i), (v) and (vii), (i), (v) and (viii), (vi) and (vii), (vi) and (viii), (i), (vi) and (vii), (i), (vi) and (viii), (ii), (iii) and (iv), (ii), (iii) and (v), (ii), (iii) and (vi), (ii), (iii) and (vii) or at (ii), (iii) and (viii).

(8) Compounds in any of the foregoing groups 1 through 56-55-54-53-52-51-50-47 and in paragraphs (1), (2), (3) and (4) in this group 57 where $R^4$ moieties 1 through 10 in Table A are replaced with the following moieties: 1 is a phosphate, phosphate ester or a salt, e.g., —O—P(O)(OH)—OH, —O—P(O)(OH)—O$^-$Na$^+$, —O—P(O)(OH)—O-optionally substituted alkyl, —O—P(O)(OR$^{PR}$)—O-optionally substituted alkyl, 2 is a thiophosphate or thiophosphate ester, 3 is a sulfamate, 4 is a phosphonate, 5 is a thiophosphonate, 6 is a sulfonate, 7 is a polymer, 8 is an optionally substituted oligosaccharide, 9 is a thionoester and 10 is an amide. Exemplary $R^4$ moieties include (i) —O—P(O)(O—(C(O))$_m$—(CH$_2$)$_n$—CH$_3$)—OH, —O—P(O)(O—(C(O))$_m$—(CH$_2$)$_n$—CH$_3$)—O—(CH$_2$)$_n$—CH$_3$ where m independently are 0 or 1 and n independently are 1, 2, 3, 4, 5, 6, 7, 8, 9, 10 or 11, (ii) —O—P(O)(SH)—OH, —O—P(O)(SH)—O$^-$Na$^+$, —O—P(O)(OH)—S-optionally substituted alkyl, —O—P(O)(S—(C(O))$_m$—(CH$_2$)$_n$—CH$_3$)—OH, —O—P(O)(S—(C(O))$_m$—(CH$_2$)$_n$—CH$_3$)—O—(CH$_2$)$_n$—CH$_3$ where m independently are 0 or 1 and n independently are 1, 2, 3, 4, 5, 6, 7, 8, 9, 10 or 11, (iii)-(OCH$_2$HC$_2$)$_n$—OH, —(OCH$_2$HC$_2$)$_n$—CH$_3$, —(OCH$_2$HC$_2$)$_n$—OR$^{PR}$, —(OCH$_2$HC$_2$)$_n$—SH, —(OCH$_2$HC$_2$)$_n$—SR$^{PR}$, —(OCH$_2$HC$_2$)$_n$—NH$_2$ or —(OCH$_2$HC$_2$)$_n$—NHR$^{PR}$ where n is an integer such as an integer from about 4, 8, 12 or 20 to about 30, 40, 50 or 100, (vi) —O—S(O)(O)—NH—(C(O))$_m$—(CH$_2$)$_n$—X—(CH$_2$)$_n$—CH$_3$, —O—S(O)(O)—NH—(C(O))$_m$—(CH$_2$)$_n$—CH$_3$, —O—S(O)(O)—NH—(CH$_2$)$_n$—X—CH$_3$, —O—S(O)(O)—NH—(CH$_2$)$_n$—(C(O))$_m$—X—(C(O))$_m$—(CH$_2$)$_m$—CH$_3$, —O—S(O)(O)—NH$_2$, —O—S(O)(O)—NH—C1-C8 optionally substituted alkyl, —O—S(O)(O)—N—(C1-C8 optionally substituted alkyl)$_2$, —NH—S(O)(O)—O—(CH$_2$)$_n$—X—CH$_3$, —NH—S(O)(O)—O—(C(O))$_m$—(CH$_2$)—X—CH$_3$, —NH—S(O)(O)—O—(CH$_2$)$_n$—(C(O))$_m$—X—CH$_3$, —NH—S(O)(O)—O—(CH$_2$)$_n$—X—(C(O))$_m$—CH$_3$ or —NH—S(O)(O)—O—(CH$_2$)$_m$-optionally substituted heterocycle, where X is —O—, —S—, —NH—, —N(C1-C8 optionally substituted alkyl)-, m independently are 0 or 1, n independently are 1, 2, 3, 4, 5, 6, 7, 8, 9, 10 or 11 and optionally substituted alkyl are each independently selected, (vii) —O—S(O)(O)—(C(O))$_m$—(CH$_2$)$_n$—X—(CH$_2$)$_n$—CH$_3$, —O—S(O)(O)—(C(O))$_m$—(CH$_2$)$_n$—CH$_3$, —O—S(O)(O)—(CH$_2$)$_n$—X—CH$_3$, —O—S(O)(O)—(CH$_2$)$_n$—(C(O))$_m$—X—(C(O))$_m$—(CH$_2$)$_m$—CH$_3$, —O—S(O)(O)—CH$_3$, —O—S(O)(O)—C1-C8 optionally substituted alkyl, —S(O)(O)—O—(CH$_2$)$_n$—X—CH$_3$, —S(O)(O)—O—(C(O))$_m$—(CH$_2$)$_n$—X—CH$_3$, —S(O)(O)—O—(CH$_2$)$_n$—(C(O))$_m$—X—CH$_3$, —S(O)(O)—O—(CH$_2$)$_n$—X—(C(O))$_m$—CH$_3$ or —S(O)(O)—O—(CH$_2$)$_m$-optionally substituted heterocycle, where X is —O—, —S—, —NH—, —N(C1-C8 optionally substituted alkyl)-, m independently are 0 or 1, n independently are 1, 2, 3, 4, 5, 6, 7, 8, 9, 10 or 11 and optionally substituted alkyl are each independently selected, (viii) —O—P(O)(OR$^{PR}$)—(C(O))$_m$—(CH$_2$)$_n$—X—(CH$_2$)$_n$—CH$_3$, —O—P(O)(OR$^{PR}$)—(C(O))$_m$—(CH$_2$)$_n$—CH$_3$, —O—P(O)(OR$^{PR}$)—(CH$_2$)$_n$—X—CH$_3$, —O—P(O)(OR$^{PR}$)—(CH$_2$)$_n$—(C(O))$_m$—X—(C(O))$_m$—(CH$_2$)$_m$—CH$_3$, —O—P(O)(OR$^{PR}$)—CH$_3$, —O—P(O)(OR$^{PR}$)—C1-C8 optionally substituted alkyl, —P(O)(OR$^{PR}$)—O—(CH$_2$)$_n$—X—CH$_3$, —P(O)(OR$^{PR}$)—O—(C(O))$_m$—(CH$_2$)$_n$—X—CH$_3$, —P(O)(OR$^{PR}$)—O—(CH$_2$)$_n$—(C(O))$_m$—X—CH$_3$, —P(O)(OR$^{PR}$)—O—C1-C8 optionally substituted alkyl or —P(O)(OR$^{PR}$)—O—(CH$_2$)$_m$-optionally substituted heterocycle, where X is —O—, —S—, —NH—, —N(C1-C8 optionally substituted alkyl)-, m independently are 0 or 1, n independently are 1, 2, 3, 4, 5, 6, 7, 8, 9, 10 or 11, R$^{PR}$ independently are —H or a protecting group and optionally substituted alkyl are each independently selected, (ix) —O—P(S)(OR$^{PR}$)—(C(O))$_m$—(CH$_2$)$_n$—X—(CH$_2$)$_n$—CH$_3$, —O—P(S)(OR$^{PR}$)—(C(O))$_m$—(CH$_2$)$_n$—CH$_3$, —O—P(S)(OR$^{PR}$)—(CH$_2$)$_n$—X—CH$_3$, —O—P(S)(OR$^{PR}$)—(CH$_2$)$_n$—(C(O))$_m$—X—(C(O))$_m$—(CH$_2$)$_m$—CH$_3$, —O—P(S)(OR$^{PR}$)—CH$_3$, —O—P(S)(OR$^{PR}$)—C1-C8 optionally substituted alkyl, —P(S)(OR$^{PR}$)—O—(CH$_2$)$_n$—X—CH$_3$, —P(S)(OR$^{PR}$)—O—(C(O))$_m$—(CH$_2$)$_n$—X—CH$_3$, —P(S)(OR$^{PR}$)—O—(CH$_2$)$_n$—(C(O))$_m$—X—CH$_3$, —P(S)(OR$^{PR}$)—O—C1-C8 optionally substituted alkyl or —P(S)(OR$^{PR}$)—O—(CH$_2$)$_m$-optionally substituted heterocycle, where X is —O—, —S—, —NH—, —N(C1-C8 optionally substituted alkyl)-, m independently are 0 or 1, n independently are 1, 2, 3, 4, 5, 6, 7, 8, 9, 10 or 11, R$^{PR}$ independently are —H or a protecting group and optionally substituted alkyl are each independently selected and (x) —C(O)—NH—(C(O))$_m$—(CH$_2$)$_n$—X—(CH$_2$)$_n$—CH$_3$, —C(O)—NH—(C(O))$_m$—(CH$_2$)$_n$—CH$_3$, —C(O)—NH—(CH$_2$)$_n$—X—CH$_3$, —C(O)—NH—(CH$_2$)$_n$—(C(O))$_m$—X—(C(O))$_m$—(CH$_2$)$_m$—CH$_3$, —C(O)—NH—CH$_3$, —C(O)—NH—C1-C8 optionally substituted alkyl, —C(O)—NH—CH$_2$—CH$_2$—CH$_3$, —C(O)—NH—CH$_2$OR$^{PR}$, —C(O)—NH—CH$_2$—CH$_2$—CH$_2$OR$^{PR}$, —C(O)—NH—CH$_2$—CH$_2$—CH$_2$—CH$_3$, —C(O)—NH—CH$_2$—CH$_2$—CH$_2$—CH$_2$C(O)OR$^{PR}$, —C(O)—NH—CH$_2$—CH$_2$C(O)OR$^{PR}$, —NH—C(O)—(CH$_2$)$_n$—X—CH$_3$, —NH—C(O)—(C(O))$_m$—(CH$_2$)$_n$—X—CH$_3$, —NH—C(O)(CH$_2$)$_n$—(C(O))$_m$—X—CH$_3$, or —NH—C(O)—(CH$_2$)$_m$-optionally substituted heterocycle, where X is —O—, —S—, —NH—, —N(C1-C8 optionally substituted alkyl)-, m independently are 0 or 1, n independently are 1, 2, 3, 4, 5, 6, 7, 8, 9, 10 or 11, R$^{PR}$ independently are —H or a protecting group and optionally substituted alkyl are each independently selected.

(9) Compounds in any of the foregoing groups 1 through 56-55-54-53-52-51-50-47 and in paragraphs (1), (2), (3), (4), (5), (6), (7) and (8) in this group 57 where R$^3$ moieties 1 through 10 in Table A are replaced with the following moieties: 1 is —O-optionally substituted alkyl, 2 is an ester (e.g., —O—C(O)—(CH$_2$)$_n$—CH$_3$, —O—C(O)—(CH$_2$)$_n$—NH$_2$, —O—C(O)—(CH$_2$)$_n$—NHR$^{PR}$, —O—C(O)—(CH$_2$)$_n$—CH$_2$ZR$^{PR}$, —O—C(O)—CH(ZR$^{PR}$)—(CH$_2$)$_n$—CH$_3$ or another ester described herein, where n is 0, 1, 2, 3, 4, 5, 6, 7 or 8, Z is —NH—, —O— or —S— and R$^{PR}$ independently or together are —H, a protecting group or a counter ion, e.g., methoxymethyl, —CH$_3$ or —C$_2$H$_5$), 3 is a thioester (e.g., —S—C(O)—(CH$_2$)$_n$—CH$_3$, —S—C(O)—(CH$_2$)$_n$—NH$_2$, —S—C(O)—(CH$_2$)$_n$—N(R$^{PR}$)$_2$, —S—C(O)—(CH$_2$)$_n$—CH$_2$ZR$^{PR}$, —S—C(O)—CH(ZR$^{PR}$)—(CH$_2$)$_n$—CH$_3$ or another thioester described herein, where n is 0, 1, 2, 3, 4, 5, 6, 7 or 8, Z is —NH—, —O— or —S— and R$^{PR}$ is —H or a protecting group, e.g., —CH$_3$ or —C$_2$H$_5$), 4 is a carbonate (e.g., —O—C(O)—O-Optionally substituted alkyl), 5 is optionally substituted alkylamine (e.g., —NH—Optionally substituted alkyl), 6 is optionally substituted dialkylamine (e.g., —N(Optionally substituted alkyl)$_2$, where each optionally substituted alkyl is independently chosen), 7 is an N linked carbamate (e.g., —NH—C(O)—O-Optionally substituted alkyl or —NH—C(O)—OH), 8 is an O linked carbamate (e.g., —O—C(O)—NH$_2$ or —O—C(O)—NH-Optionally substituted alkyl), 9 is —O-optionally substituted monosaccharide and 10 is —H.

(10) Compounds in any of the foregoing groups 1 through 56-55-54-53-52-51-50-47 and in paragraphs (1), (2), (3), (4), (5), (6), (7) and (8) in this group 57 R$^3$ moieties 1 through 10 in Table A are replaced with the following moieties: 1 is —O-optionally substituted disaccharide, 2 is an N-linked amino acid, an N-linked amino acid ester or a salt (e.g., —NH—CH$_2$—C(O)OH, —NH—CH$_2$—C(O)OR$^{PR}$, —NH—CH$_2$—C(O)OCH$_3$, —NH—CHCH$_3$—C(O)OR$^{PR}$ or —NH—CH$_2$—CH$_2$—C(O)OR$^{PR}$, where R$^{PR}$ is —H, a counter ion or a protecting group and chiral carbon atoms are in the D-, -L or -DL configuration), 3 is an O-linked amino acid, an O-linked amino acid ester or a salt (e.g., —O—C(O)—CH$_2$—NHR$^{PR}$, —O—CH$_2$—NH$_2$, or —O—C(O)—CH$_2$—CH$_2$—NHR$^{PR}$, where R$^{PR}$ is —H, a counter ion or a protecting group and chiral carbon atoms are in the D-, -L or -DL configuration), 4 is an S-linked amino acid, an S-linked amino acid ester or a salt (e.g., —S—C(O)—CH$_2$—NHR$^{PR}$, —S—CH$_2$—NH$_2$, or —S—C(O)—CH$_2$—CH$_2$—NHR$^{PR}$, where R$^{PR}$ is —H, a counter ion or a protecting group and chiral carbon atoms are in the D-, -L or -DL configuration), 5 is a sulfate ester (e.g., —O—S(O)(OR$^{PR}$)—O-Optionally substituted alkyl), 6 is —O—S(O)—O-Optionally substituted alkyl, 7 is a halogen such as —Br or —I, 8 is a halogen such as —F or —Cl, 9 is an N-linked heterocycle (e.g., N-morpholino) and 10 is a C-linked heterocycle (e.g., 2-pyrimidinyl).

(11) Compounds in any of the foregoing groups 1 through 56-55-54-53-52-51-50-47 and in paragraphs (1), (2), (3), (4), (5), (6), (7) and (8) in this group 57 where there is no double bond at the 15-16 or the 16-17 position and R$^3$ moieties 1 through 10 in Table A are replaced with the following moieties: 1 is =O, 2 is =S, 3 is =NOH, 4 is =NOCH$_3$, 5 is =NOC$_2$H$_5$, 6 is =N—C1-C10 optionally substituted alkyl, 7 is =NO—C1-C10 optionally substituted alkyl, 8 is =NH, 9 is =CH$_2$ and 10 is =C-Optionally substituted alkyl. Exemplary compounds and compound genera include 3β-amino-16-oxo-17β-hydroxyandrost-5(10)-ene, 3β-amino-16-oxo-17β-hydroxyandrost-5(10)-ene, 3,16-dioxo-17β-aminoandrost-5(10)-ene, 3β-hydroxy-3α-methyl-16-oxo-17β-aminoandrost-5(10)-ene, 3β-hydroxy-3α-methyl-16-oxo-17α-aminoandrost-5(10)-ene, 3α-hydroxy-3β-ethynyl-16-oxo-17β-aminoandrost-5(10)-ene, 3β-mercapto-16-oxo-17β-hydroxyandrost-5(10)-ene, 3αmercapto-16-oxo-17β-hydroxyandrost-5(10)-ene, 3β-amino-16-oxo-17β-hydroxyandrost-5,7-diene, 3α-amino-16-oxo-17β-hydroxyandrost-5,7-diene, 3β-amino-16-oxo-17α-hydroxyandrost-5,7-diene, 3β-hydroxy-3α-methyl-16-oxo-17β-aminoandrost-5,7-diene, 3α-hydroxy-3β-ethynyl-16-oxo-17β-aminoandrost-5,7-diene, 3β-hydroxy-16-oxo-17β-aminoandrost-5,7-diene, 3α-hydroxy-16-oxo-17β-aminoandrost-5,7-diene, 3β-hydroxy-16-oxo-17α-aminoandrost-5,7-diene, 3-amino-16-oxo-17β-hydroxyandrost-1,3-diene, 3-hydroxy-16-oxo-17β-methoxyandrost-1,3-diene, 3-hydroxy-16-oxo-17α-methoxyandrost-1,3-diene, 3-amino-16-oxo-17β-hydroxy-5β-androst-1,3-diene, 3-amino-16-oxo-17β-methoxy-5β-androst-1,3-diene, 3-hydroxy-16-oxo-17α-methoxy-5β-androst-1,3-diene, 3-hydroxy-16-oxo-17β-methoxy-5β-androst-1,3-diene, 3-amino-16-oxo-17β-methoxy-androst-2,5(10)-diene, 3-amino-16-oxo-17α-methoxyandrost-2,5(10)-diene, 3-hydroxy-16-oxo-17β-methoxyandrost-2,5(10)-diene, 3-hydroxy-16-oxo-17α-methoxyandrost-2,5(10)-diene, 3-amino-16-oxo-17β-methoxy-5β-androst-2,5(10)-diene, 3-amino-16-oxo-17α-methoxy-5β-androst-2,5(10)-diene, 3-hydroxy-16-oxo-17β-propionoxy-5β-androst-2,5(10)-diene, 3-hydroxy-16-oxo-17α-propionoxy-5β-androst-2,5(10)-diene, 3-amino-16-oxo-17β-methoxyandrost-2,5- diene, 3-amino-16-oxo-17α-methoxyandrost-2,5-diene, 3-hydroxy-16-oxo-17β-aminoandrost-2,5-diene, 3-hydroxy-16-oxo-17α-aminoandrost-2,5-diene, 3-amino-16-oxo-17β-methoxy-5β-androst-2,5-diene, 3-amino-16-oxo-17β-hydroxy-5β-androst-2,5-diene, 3-amino-16-oxo-17α-methoxy-5β-androst-2,5-diene, 3-amino-16-oxo-17β-mercapto-5β-androst-2,5-diene, 3-amino-16-oxo-17α-mercapto-5β-androst-2,5-diene, 3-hydroxy-16-oxo-17β-propionoxy-5β-androst-2,5-diene, 3-hydroxy-16-oxo-17α-propionoxy-5β-androst-2,5-diene, 3-amino-16-oxo-17β-methoxyandrost-1,3,5-triene, 3-hydroxy-16-oxo-17α-methoxyandrost-1,3,5-triene, 3-amino-16-oxo-17β-methoxyandrost-1,3,9(11)-triene, 3-amino-16-oxo-17α-methoxyandrost-1,3,9(11)-triene, 3-hydroxy-16-oxo-17β-methoxyandrost-1,3,9(11)-triene, 3-hydroxy-16-oxo-17α-methoxyandrost-1,3,9(11)-triene, 3-amino-16-oxo-17β-methoxy-5β-androst-1,3,9(11)-triene, 3-amino-16-oxo-17α-methoxy-5β-androst-1,3,9(11)-triene, 3-hydroxy-16-oxo-17β-methoxy-5β-androst-1,3,9(11)-triene, 3-hydroxy-16-oxo-17α-methoxy-5β-androst-1,3,9(11)-triene, 3-amino-16-oxo-17β-methoxyandrost-1,3,5(10)-triene, 3-amino-16-oxo-17α-methoxyandrost-1,3,5(10)-triene, 3-amino-16-oxo-17β-hydroxyandrost-1,3,5(10)-triene, 3-amino-16-oxo-17α-hydroxyandrost-1,3,5(10)-triene, 3-hydroxy-16-oxo-17β-methoxyandrost-1,3,5(10)-triene, 3-hydroxy-16-oxo-17α-methoxyandrost-1,3,5(10)-triene, 3-methylamino-16-oxo-17β-hydroxyandrost-1,3,5(10)-triene, 3-methylamino-16-oxo-17α-hydroxyandrost-1,3,5(10)-triene, 3-amino-16-oxo-17β-methoxyandrost-1,3,5(10),8(14)-tetraene, 3-amino-16-oxo-17α-methoxyandrost-1,3,5(10),8(14)-tetraene, 3-hydroxy-16-oxo-17β-methoxyandrost-1,3,5(10),8(14)-tetraene, 3-hydroxy-16-oxo-17α-methoxyandrost-1,3,5(10),8(14)-tetraene, 3-amino-16-oxo-17β-methoxyandrost-1,3,5(10),8(9)-tetraene, 3-amino-16-oxo-17α-methoxyandrost-1,3,5(10),8(9)-tetraene, 3-hydroxy-16-oxo-17β-methoxyandrost-1,3,5(10),8(9)-tetraene, 3-hydroxy-16-oxo-17α-methoxyandrost-1,3,5(10),8(9)-tetraene, 3-amino-16-oxo-17β-hydroxyandrost-1,3,5(10),6-tetraene, 3,17β-dihydroxy-16-oxoandrost-1,3,5(10),6-tetraene, 3-amino-16-oxo-17β-methoxyandrost-1,3,5(10),7-tetraene, and an analog of any of these compounds wherein (i) the 16-position ($R^3$) is substituted with =O, =S, =CH$_2$, =CHCH$_3$, =CHCH$_2$OH, =CH—C1-C8 optionally substituted alkyl, =NOH, =NO—CH$_3$, =NO—C1-C8 optionally substituted alkyl, =N—CH$_3$, =N—C1-C8 optionally substituted alkyl or another double bonded moiety described herein, and/or (ii) =S, =CH$_2$, =CHCH$_3$, =CHCH$_2$OH, =CH—C1-C8 optionally substituted alkyl, =NOH, =NO—CH$_3$ or another double bonded moiety described herein is present at the 17-position ($R^4$) or where two independently selected $R^4$ moieties are present at the 17-position, and/or (iii) the 3-position ($R^1$) is substituted with one or two independently selected substituents such as —F, —Cl, —Br, —I, —OH, =O, —SH, =S, =CH$_2$, —C1-C10 optionally substituted alkyl such as methyl, ethynyl or 1-propynyl, -heterocycle, —(CH$_2$)-heterocycle, a polymer, or one or two other independently selected $R^1$ moieties described herein, where the substituent(s) is in the α-configuration or the β-configuration, and/or (iv) the 2-position ($R^9$) is substituted with one or two independently selected substituents such as —F, —Cl, —Br, —I, —OH, =O, =S, =CH$_2$, C1-C10 optionally substituted alkyl such as methyl, ethynyl or 1-propynyl, C1-C10 alkoxy such as methoxy or ethoxy, -heterocycle, —(CH$_2$)— heterocycle, or a polymer where, when no double bond is present at the 2-position, the substituent(s) is in the α-configuration or the β-configuration, and/or (v) $R^{10G}$ at the 9-position, when present, is —F, —Cl, —Br, —I, —OH, C1-C10 optionally substituted alkyl such as methyl, ethyl, ethynyl or 1-propynyl or cyclopropyl with the 11-position or another $R^{10}$ or $R^{10G}$ moiety described herein, and/or (vi) the 7-position ($R^2$) is substituted with one or two independently selected substituents such as —OH, =O, =S, =CH$_2$, —NH$_2$, =N—C1-C10 optionally substituted alkyl, =CH—C1-C10 optionally substituted alkyl, —NH—C1-C10 optionally substituted alkyl such as methyl, hydroxymethyl, ethyl, hydroxyethyl, propyl or another optionally substituted alkyl described herein, —N(C1-C10 optionally substituted alkyl)$_2$, —C1-C10 optionally substituted alkyl such as methyl, ethynyl, 1-propynyl or another optionally substituted alkyl described herein, -heterocycle, —(CH$_2$)-heterocycle, a polymer or one or two other substituents described elsewhere herein, where, when no double bond is present at the 7-position, the substituent(s) is in the α-configuration or the β-configuration, and/or (vii) the 6-position ($R^{10C}$) is substituted with a substituent described herein such as sulfate, phosphate, an ester, an ether, a thioester, a thioether, a monosaccharide, an oligosaccharide, ethylene ketal (—O—CH$_2$CH$_2$—O—), a polymer, a carbonate, a carbamate, —F, —Cl, —Br, —I, —OH, —OR$^{PR}$, —SH, —SR$^{PR}$, —NH$_2$, —NHR$^{PR}$, —C(O)—OR$^{PR}$, —NHCH$_2$—C(O)—OR$^{PR}$, —NHCH$_2$CH$_2$—C(O)—OR$^{PR}$, —NHC(O)—CH$_3$, —NHC(O)—C$_2$H$_5$, —NHC(O)—OCH$_3$, —NHC(O)—OC$_2$H$_5$, —NHC(O)—OC$_3$H$_7$, —OC(O)—NHR$^{PR}$, —OC(O)—NHCH$_3$, —OC(O)—NHC$_2$H$_5$, —OC(O)—NHC$_3$H$_7$, =O, =S, =CH$_2$, =CH—C1-C10 optionally substituted alkyl, —C1-C10 optionally substituted alkyl, =N—C1-C10 optionally substituted alkyl, =N—O—C1-C10 optionally substituted alkyl, —NH—C1-C10 optionally substituted alkyl, —N(C1-C10 optionally substituted alkyl)$_2$, C1-C10 optionally substituted alkyl, -heterocycle, —(CH$_2$)-heterocycle, where each optionally substituted alkyl is one or two independently selected optionally substituted alkyl moieties described herein such as methyl, ethynyl, 1-propynyl or another optionally substituted alkyl described herein, where, when no double bond is present at the 6-position, the substituent is in the α-configuration or the β-configuration, and/or (viii) the 11-position ($R^8$) is substituted with a substituent described herein such as sulfate, phosphate, an ester, an ether, a thioester, a thioether, a monosaccharide, —O—, —S—, —NH—, —N(CH$_3$)—, —N(C$_2$H$_5$)—, —N(C$_3$H$_7$)—, =N— or is substituted with one or two independently selected $R^{10}$ substituents such as —F, —Cl, —Br, —I, —OH, =O, —SH, =S, =CH$_2$, C1-C10 optionally substituted alkyl such as methyl, ethynyl or 1-propynyl, -heterocycle, —(CH$_2$)-heterocycle, a polymer or another moiety described herein, where, when no double bond is present at the 11-position, the substituents are in the α-configuration or the β-configuration, e.g., $R^8$ is —CH(α-C1-C10 optionally substituted alkyl)-, —CH(β-C1-C10 optionally substituted alkyl)-, —CH(β-F)—, —CH(α-F)—, —CF$_2$— —CH(β-OH)—, —CH(α-OH)—, —CH(α-SH)—, —CH(β-NH$_2$)—, —CH(α-NH$_2$)—, —CH(β-NHCH$_3$)—, —CH(α-NHCH$_3$)—, —CH(β-N(CH$_3$)$_2$)—, —CH(α-N(CH$_3$)$_2$)—, —CH(β-NHC$_2$H$_5$)—, —CH(α-NHC$_2$H$_5$)—, —CH(α-heterocycle)-, —CH(β-heterocycle)-, —CH(α-polymer)-, —CH(β-polymer)-, —CH(α-ether)-, —CH(β-ether)-, —CH(α-thioether)-, —CH(β-thioether)-. Analogs of any of these compounds include compounds where substitutions described at two or three of (i), (ii), (iii), (iv), (v), (vi), (vii) and (viii) are present, e.g., substitutions as described at (i) and (ii), (i) and (iii), (i) and (iv), (i) and (vi), (i) and (vii), (i) and (viii), (i), (ii) and (iii), (i), (ii) and (vi), (i), (ii) and (v), (i), (ii) and (vi), (i), (ii) and (vii), (i), (ii) and (viii), (ii) and (iii), (ii) and (iv), (ii) and (v), (ii) and (vi), (ii) and (vii), (ii) and (viii), (i), (ii) and (iii), (i), (ii) and (iv), (i), (ii) and (v), (i), (ii) and (vi), (i), (ii) and (vii), (i), (ii) and (viii), (iii) and (iv), (iii) and (v), (iii) and (vi), (iii) and (vii), (iii) and (viii), (i), (iii) and (iv), (i), (iii) and (v), (i), (iii) and (vi), (i), (iii) and (vii), (i), (iii) and (viii), (iv) and (v), (i), (iv) and (vi), (i), (iv) and (vii), (iv) and (viii), (i), (iv) and (v), (i), (iv) and (vi), (i), (iv) and (vii), (i), (iv) and (viii), (v) and (vi), (v) and (vii), (v) and (viii), (i), (v) and (vi), (i), (v) and (vii), (i), (v) and (viii), (vi) and (vii), (vi) and (viii), (i), (vi) and (vii), (i), (vi) and (viii), (ii), (iii) and (iv), (ii), (iii) and (v), (ii), (iii) and (vi), (ii), (iii) and (vii) or at (ii), (iii) and (viii) are present.

(12) Compounds in any of the foregoing groups 1 through 56-55-54-53-52-51-50-47 and in paragraphs (1), (2), (3), (4), (5), (6), (7), (8), (9), (10) and (11) in this group 57 where $R^2$ moieties 1 through 10 in Table A are replaced with the following moieties: 1 is —O-optionally substituted alkyl, 2 is an ester (e.g., —O—C(O)—$(CH_2)_n$—$CH_3$, —O—C(O)—$(CH_2)_n$—$NH_2$, —O—C(O)—$(CH_2)_n$—$NHR^{PR}$, —O—C(O)—$(CH_2)_n$—$CH_2ZR^{PR}$, —O—C(O)—CH($ZR^{PR}$)—$(CH_2)_n$—$CH_3$ or another ester described herein, where n is 0, 1, 2, 3, 4, 5, 6, 7 or 8, Z is —NH—, —O— or —S— and $R^{PR}$ is —H or a protecting group, e.g., methoxymethyl, —$CH_3$ or —$C_2H_5$), 3 is a thioester (e.g., —S—C(O)—$(CH_2)_n$—$CH_3$, —S—C(O)—$(CH_2)_n$—$NH_2$, —S—C(O)—$(CH_2)_n$—N$(R^{PR})_2$, —S—C(O)—$(CH_2)_n$—$CH_2ZR^{PR}$, —S—C(O)—CH($ZR^{PR}$)—$(CH_2)_n$—$CH_3$ or another thioester described herein, where n is 0, 1, 2, 3, 4, 5, 6, 7 or 8, Z is —NH—, —O— or —S— and $R^{PR}$ independently or together are —H, a protecting group or a counter ion, e.g., —$CH_3$ or —$C_2H_5$), 4 is a carbonate (e.g., —O—C(O)—O-Optionally substituted alkyl), 5 is optionally substituted alkylamine (e.g., —NH-Optionally substituted alkyl), 6 is optionally substituted dialkylamine (e.g., —N(Optionally substituted alkyl)$_2$, where each optionally substituted alkyl is independently chosen), 7 is an N linked carbamate (e.g., —NH—C(O)—O-Optionally substituted alkyl or —NH—C(O)—OH), 8 is an O linked carbamate (e.g., —O—C(O)—$NH_2$ or —O—C(O)—NH-Optionally substituted alkyl), 9 is —O-optionally substituted monosaccharide and 10 is —H.

(13) Compounds in any of the foregoing groups 1 through 56-55-54-53-52-51-50-47 and in paragraphs (1), (2), (3), (4), (5), (6), (7), (8), (9), (10) and (11) in this group 57 where $R^2$ moieties 1 through 10 in Table A are replaced with the following moieties: 1 is —O-optionally substituted disaccharide, 2 is an N-linked amino acid, an N-linked amino acid ester or a salt (e.g., —NH—$CH_2$—C(O)OH, —NH—$CH_2$—C(O)OR$^{PR}$, —NH—$CH_2$—C(O)OCH$_3$, —NH—CHCH$_3$—C(O)OR$^{PR}$ or —NH—$CH_2$—$CH_2$—C(O)OR$^{PR}$, where $R^{PR}$ is —H, a counter ion or a protecting group and chiral carbon atoms are in the D-, -L or -DL configuration), 3 is an O-linked amino acid, an O-linked amino acid ester or a salt (e.g., —O—C(O)—$CH_2$—NHR$^{PR}$, —O—$CH_2$—$NH_2$, or —O—C(O)—$CH_2$—$CH_2$—NHR$^{PR}$, where $R^{PR}$ is —H, a counter ion or a protecting group and chiral carbon atoms are in the D-, -L or -DL configuration), 4 is an S-linked amino acid, an S-linked amino acid ester or a salt (e.g., —S—C(O)—$CH_2$—NHR$^{PR}$, —S—$CH_2$—$NH_2$, or —S—C(O)—$CH_2$—$CH_2$—NHR$^{PR}$, where $R^{PR}$ is —H, a counter ion or a protecting group and chiral carbon atoms are in the D-, -L or -DL configuration), 5 is a sulfate ester (e.g., —O—S(O)(OR$^{PR}$)—O-Optionally substituted alkyl), 6 is —O—S(O)—O-Optionally substituted alkyl, 7 is a halogen such as —Br or —I, 8 is a halogen such as —F or —Cl, 9 is an N-linked heterocycle (e.g., N-morpholino) and 10 is a C-linked heterocycle (e.g., 2-pyrimidinyl).

(14) Compounds in any of the foregoing groups and in (1), (2), (3), (4), (5), (6), (7), (8) and (9) in this group where there is no double bond at the 6-7 or the 7-8 position and $R^2$ moieties 1 through 10 in Table A are replaced with the following moieties: 1 is =O, 2 is =S, 3 is =NOH, 4 is =NOCH$_3$, 5 is =NOC$_2$H$_5$, 6 is =N—C1-C10 optionally substituted alkyl, 7 is =NO—C1-C10 optionally substituted alkyl, 8 is =NH, 9 is =CH$_2$ and 10 is =CH-optionally substituted alkyl.

(15) Compounds in any of the foregoing groups and in (1), (2), (3), (4), (5), (6), (7), (8), (9), (10), (11), (12), (13) and (14) in this group where (i) no double bond is present at the 10-position and $R^6$ is a moiety other than —CH$_3$. Exemplary $R^6$ moieties are —H, —F, —Cl, —Br, —I, —OH, —OR$^{PR}$, —SH, —SR$^{PR}$, —NH$_2$, —NHR$^{PR}$, —CHO, —CH$_2$OH, optionally substituted alkyl, ether, thioether, —NH-optionally substituted alkyl, ethynyl, 1-propynyl, vinyl, allyl, —O—C(O)—O-optionally substituted alkyl, —O—C(O)-optionally substituted alkyl, —O—C(O)—S-optionally substituted alkyl, —O-optionally substituted monosaccharide and a polymer.

As is apparent from the description of F1Cs, when no double bond is present at the carbon atoms at the 1-, 4- or 6-positions, $R^{10A}$, $R^{10B}$, $R^{10C}$ and $R^{10D}$ respectively can be in the α,α,α,α, α,α,α,β, α,α,β,α, α,β,α,α, β,α,α,α, α,α,β,β, α,β,α,β, β,α,α,β, α,β,β,α, β,α,β,α, β,β,α,α, α,β,β,β, β,α,β,β, β,β,α,β, β,β,β,α or β,β,β,β configurations. As used here, reference to, e.g., $R^{10A}$, $R^{10B}$, $R^{10C}$ and $R^{10D}$ respectively being in the α,β,α,β configurations means that $R^{10A}$ is in the α-configuration, $R^{10B}$ is in the β-configuration, $R^{10C}$ is in the α-configuration and $R^{10D}$ is in the β-configuration. Similarly, when $R^{10A}$, $R^{10B}$, $R^{10C}$ and $R^{10D}$ respectively are in the α,α, β,α configurations, $R^{10A}$ is in the α-configuration, $R^{10B}$ is in the α-configuration, $R^{10C}$ is in the β-configuration and $R^{10D}$ is in the α-configuration.

Thus, when a double bond is present at one or more of the 1-, 4- or 6-positions, the corresponding $R^{10S}$, $R^{10B}$ or $R^{10C}$ moiety will not be in a specified configuration. Thus, this group contains compounds having structures where (1) a double bond is present at the 1-position, $R^{10B}$, $R^{10C}$ and $R^{10D}$ respectively are in the α,α,α, α,α,β, α,β,α, β,α,α, α,β,β, β,α,β, β,β,α or β,β,β configurations and $R^{10A}$ is present at the 1-position with no specified configuration, (2) a double bond is present at the 4-position, $R^{10A}$, $R^{10C}$ and $R^{10D}$ respectively are in the α,α,α, α,α,β, α,β,α, β,α,α, α,β,β, β,α,β, β,β,α or β,β,β configurations and $R^{10B}$ is present at the 4-position with no specified configuration, (3) a double bond is present at the 6-position $R^{10A}$, $R^{10B}$ and $R^{10D}$ respectively are in the α,α,α, α,α,β, α,β,α, β,α,α, α,β,β, β,α,β, β,β,α or β,β,β configurations, and $R^{10C}$ is present at the 6-position with no specified configuration, (4) a double bond is present at the 1-position and at the 4-position, $R^{10C}$ and $R^{10D}$ respectively are in the α,α, α,β, β,α, or β,β configurations and $R^{10A}$ and $R^{10B}$ are present at the 1- and 4-positions with no specified configuration, (5) a double bond is present at the 1-position and at the 6-position, $R^{10B}$ and $R^{10D}$ respectively are in the α,α, α,β, β,α, or β,β configurations and $R^{10A}$ and $R^{10C}$ are present at the 1- and 6-positions with no specified configuration, (6) a double bond is present at the 4-position and at the 6-position, $R^{10A}$ and $R^{10D}$ respectively are in the α,α, α,β, β,α, or β,β configurations and $R^{10B}$ and $R^{10C}$ are present at the 4- and 6-positions with no specified configuration, (7) a double bond is present at the 1-, 4- and 6-position, $R^{10D}$ is in the α-configuration or the β-configuration, while $R^{10A}$, $R^{10B}$ and $R^{10C}$ are present at the 1-, 4- and 6-positions with no specified configuration and (8) one, two or more additional double bonds are optionally also present at the 8-, 9-, 11-, 14-, 15- or 16-positions for any compound or genus of compounds described in (1), (2), (3), (4), (5), (6) or (7).

As is apparent from the F1Cs described in groups 1 through 57, compound groups 14 through 57 contain a number of defined subgroups, e.g., group 14-3 is a subgroup as described for group 14 compounds where $R^1$, $R^2$, $R^3$ and $R^4$ can be in the configurations described in group 14, e.g., α,β, α,β, α,α,α,β, β,β,β,β, β,β,β,α or β,β,α,α respectively. Similarly, group 49 includes subgroups such as 49-18-17-14-3, 49-18-17-14-4, 49-18-17-14-5, 49-18-17-14-5A, 49-18-17-14-6, 49-18-17-14-7 and 49-18-17-14-9, which are subgroups where $R^9$ is substituted, e.g., $R^9$ is —O— or a moiety described in group 18, and such subgroups, although not specifically named or described, are expressly included in group 49. The F1C therefore include all possible subgroups in each group, regardless of whether each subgroup is specifically named or described in a given group or not. For example, groups such as 22, 23, 26, 26B, 26C, 26D and 26E, all include subgroups analogous to those described in group 26A and additional subgroups that are not expressly described, e.g., subgroups such as 26-18-1, 26-18-2, 26-18-3, 26-18-4, 26-18-5, 26-18-5A, 26-18-6, 26-18-14-1, 26-18-14-2, 26-18-14-3, 26-18-14-4, 26-18-14-5, 26-18-14-5A and 26-18-14-6 are not described expressly in group 26 above, but are included in group 26. Similarly, groups 29, 30, 33, 33B, 33C, 33D and 33E, all include subgroups analogous to those described in group 33A, while groups 36, 37, 40B, 40C, 40D, 40E and 41 all include subgroups analogous to those described in group 40A and groups 47B, 47C, 47D, 47E and 48 all include subgroups analogous to those described in group 47A. Thus, subgroups such as 33-18-3 and 33-18-14-3, which are not described expressly in group 33 above, are included in group 33.

The F1Cs include compounds in groups 1 through 57 where ROOF and/or $R^{10H}$ is a moiety other than hydrogen, e.g., a halogen, an ether, a thioether, a polymer or optionally substituted alkyl such as —F, —Cl, —Br, —I, —CH$_3$, —OCH$_3$, —SCH$_3$, —OH, —OR$^{PR}$, —SH, —SR$^{PR}$, —NH$_2$ or —NHR$^{PR}$ where R$^{PR}$ independently are —H or a protecting group. Thus, for any of the compounds or genera of compounds in groups 1 through 57, $R^{10F}$ can be —F, —Cl, —CH$_3$ or —OH in the α- or β-configuration. Similarly, in groups 1 through 57, $R^{10H}$ can be —F, —NH$_2$, —OH, —SH, —CH$_3$, —C$_2$H$_5$ or —CH$_2$OH in the α- or β-configuration or an epoxide or cyclopropyl ring with $R^7$ where the ring bonds are in the α- or β-configuration.

The F1Cs include analogs of compounds in groups 1 through 57 where $R^{11}$ is a moiety such as —O—, =N—, —NH—, —NCH$_3$—, —NC$_2$H$_5$—, —S—, —S(O)(O)— or another moiety disclosed herein within the scope of the $R^{11}$ definition. As is apparent from the F1C structures, when $R^{11}$ is a moiety such as —O— or —S—, a double bond at the 3-4 or 4-5 position will not be present. Exemplary F1Cs where $R^{11}$ is one of these moieties includes 3β,17β-dihydroxy-3α-C1-8 optionally substituted alkyl-4-aza-androst-1,5-diene, 3β,17β-dihydroxy-4-aza-androst-1,5-diene, 3α,17β-dihydroxy-3β-C1-8 optionally substituted alkyl-4-aza-androst-1,5-diene, 3α,17β-dihydroxy-4-aza-androst-1,5-diene, 3β-hydroxy-3α-C1-8 optionally substituted alkyl-4-aza-17-thioxoandrost-1,5-diene, 3β-hydroxy-4-aza-17-thioxoandrost-1,5-diene, 3α-hydroxy-3β-C1-8 optionally substituted alkyl-4-aza-17-thioxoandrost-1,5-diene, 3α-hydroxy-4-aza-17-thioxoandrost-1,5-diene, 3β,17β-dihydroxy-3α-C1-8 optionally substituted alkyl-2,4-dioxa-androst-1,5-diene, 3β,17β-dihydroxy-2,4-dioxa-androst-1,5-diene, 3α,17β-dihydroxy-3β-C1-8 optionally substituted alkyl-2,4-dioxa-androst-1,5-diene, 3α,17β-dihydroxy-2,4-dioxa-androst-1,5-diene, 3β,17β-dihydroxy-3α-C1-8 optionally substituted alkyl-4-thia-androst-1,5-diene, 3β,17β-dihydroxy-4-thia-androst-1,5-diene, 3α,17β-dihydroxy-3β-C1-8 optionally substituted alkyl-4-thia-androst-1,5-diene, 3α,17β-dihydroxy-4-thia-androst-1,5-diene, 3β,17β-dihydroxy-3α-C1-8 optionally substituted alkyl-4-oxa-androst-1,5-diene, 3β,17β-dihydroxy-4-oxa-androst-1,5-diene, 3α,17β-dihydroxy-3β-C1-8 optionally substituted alkyl-4-oxa-androst-1,5-diene, 3α,17β-dihydroxy-4-oxa-androst-1,5-diene, 3β,17β-dihydroxy-3α-C1-8 optionally substituted alkyl-4-aza-androstane, 3β,17β-dihydroxy-4-aza-androstane, 3α,17β-dihydroxy-3β-C1-8 optionally substituted alkyl-4-aza-androstane, 3α,17β-dihydroxy-4-aza-androstane, 3β,17β-dihydroxy-3α-C1-8 optionally substituted alkyl-4-aza-5β-androstane, 3β,17β-dihydroxy-4-aza-5β-androstane, 3α,17β-dihydroxy-3β-C1-8 optionally substituted alkyl-4-aza-5β-androstane, 3α,17β-dihydroxy-4-aza-5β-androstane and analogs of any of these compounds where independently selected —OH, —NH$_2$, —NHCH$_3$, —SH, —F, —Cl, —Br, —I, C1-8 optionally substituted alkyl or another oxygen-, nitrogen- or sulfur-linked moiety is present at 1, 2 or 3 of the 2-position, the 6-position, the 7-position, the 12-position and/or the 16-position, any of which are in the α- or β-configuration when no double bond is present at the substituted position, or analogs wherein one or more of these positions is substituted with a double bonded moiety such as =O, =S, =NOH, =N—C1-8 optionally substituted alkyl, or =CH—C1-8 optionally substituted alkyl, or a 19-nor, D ring homo, 1-ene, 2-ene, 3-ene, 4-ene, 5-ene (i.e., 5(6)-ene), 5(10)-ene, 9(11)-ene, 11-ene, 12-ene, 15-ene, 16-ene 1,4-diene, 1,15-diene, 1,16-diene, 3,5-diene, 5,7-diene or aromatic A ring analog of any of these compounds or analogs. Other exemplary analogs include compounds and genera of compounds of any of these compounds where the moiety at the 3- and/or 17-position is replaced with independently selected moieties as described herein such as =O, =S, =NOH, —SH, —NH$_2$, —NHCH$_3$, —NHC$_2$H$_5$, —N(CH$_3$)$_2$, —N(C$_2$H$_5$)$_2$, —NH(C1-8 optionally substituted alkyl), —N(C1-8 optionally substituted alkyl)$_2$, —C(O)—CH$_3$, —O—C(O)—CH$_3$, —O—C(O)—CF$_3$, —C(S)—CH$_3$, —S—C(O)—CH$_3$, —C(O)—CH$_2$Cl, —C(O)—CH$_2$OH, ester such as a C2-8 ester, thioester such as a C2-8 thioester, ether such as a C1-8 ether, thioether such as C1-8 thioether, a carbamate such as a C1-8 carbamate, a carbonate such as a C1-8 carbonate, an optionally substituted monosaccharide or a polymer.

Metabolites.

The invention includes the therapeutic or other uses disclosed herein for metabolites of F1C, which include biologically active metabolites. Metabolites can arise from in vivo or in vitro metabolism. Metabolites of F1C include compounds that are new. Metabolites of a given F1C can include conjugates consisting of sulfate, sulfate ester, phosphate, phosphate ester, glucuronide or fatty acid adducts, usually at a hydroxyl group. Other F1C metabolites include derivatives that contain an additional double bond due to reductase or other enzyme activity and/or additional hydroxyl or ketone moieties at one or more ring positions, e.g., at one, two or more of the 2-, 4-, 7-, 11-, 14-, 15- or 16-positions, any of which can also be further metabolized or conjugated. Metabolites may result for example from the oxidation, reduction, hydrolysis, amidation, esterification, glycosidation and the like of the administered F1C, due to enzymatic or chemical processes. Metabolites may be generated in vivo in a subject or they may arise ex vivo from cells or tissues, e.g., from a mammal such as a human, rodent or a primate. Accordingly, the invention includes new F1Cs produced by a process comprising contacting an F1C with a subject or a subject's cells or tissue for a period of time sufficient to yield detectable amounts of a metabolic product thereof. Such products typically are identified by preparing a radiolabeled or mass labeled F1C that comprises, e.g., 1, 2, 3 or more $^{13}$C, $^{14}$C, $^{3}$H, $^{2}$H, $^{131}$I, $^{32}$P, $^{35}$S or $^{99}$Tc atoms bonded to the compound, and administering it as a trace labeled compound along with the unlabeled compound. The labeled and unlabeled compounds are administered by any suitable route (by, e.g., a buccal, sublingual, parenteral, topical oral route) in a detectable dose (e.g. greater than about 0.1 µg/kg, or at least about 10 µg/kg or at least about 0.5 mg/kg of the labeled compound) to a subject, e.g., an animal or mammal such as rat, mouse, guinea pig, primate, or to a human. After administration sufficient time is allowed for metabolism to occur (typically about 30 seconds to 30 hours) and conversion products are isolated from one or more of the urine, blood, plasma, feces or other suitable biological sources. The amount of labeled formula 1 compound that is administered to a subject will vary with the specific activity of the labeled compound. Exemplary metabolic conversions of formula 1 compounds include modification of hydrogen atoms or other moieties that are bonded to, e.g., one or more of the 1, 2, 3, 4, 6, 7, 11, 15, 16 or 17 positions. Exemplary conversions at these one or more of positions include hydroxylation of ring atoms, e.g., ring carbon atoms, conjugation of hydroxyl groups that are bonded to one or more of those positions with moieties such as sulfate, phosphate or a monosaccharide or disaccharide such as glucuronic acid and hydrolysis of moieties such as esters or alkoxy groups.

Analytical Characterization and Reference Standards.

Individual F1Cs described or disclosed herein are suitable for use as standards for determining chemical or physical properties using one, two or more analytical methods, e.g., for use in HPLC, reverse phase HPLC, MS (mass spectrometry), quadrupole MS, GC-MS, LC-MS, NMR (nuclear magnetic resonance spectrometry), $^{2}$H-NMR, $^{3}$H-NMR, $^{13}$C-NMR, $^{14}$C-NMR, infrared spectrometry (IR), Fourier transform-IR, optical rotary dispersion, loss on drying for water and solvent measurement, Karl Fisher titration for water determination, differential scanning calorimetry, melting point, density, refractive index, solubility characteristics in organic solvents, aqueous systems or aqueous-organic solvent mixtures, the partition coefficient in immiscible solvent systems, e.g., octanol:water partition coefficient, heat stability or epimerization rate or characteristics of a given enantiomer. These analytical or chemical properties of each F1C are collectively referred to as analytical characteristics. For general methods, see, e.g., H. L. J. Makin et al., eds. *Steroid Analysis* 1995, Chapman & Hall, ISBN 0751401285. Thus, to aid in the determination of, e.g., the structure of a metabolite of a F1C or a structurally related compound, the parent compound or another structurally related F1C could be used as a standard. Metabolism of F1Cs will often include one or more of oxidation, reduction, hydroxylation or conjugation, e.g., oxidation or reduction to a —OH or =O moiety, or conjugation with a moiety such as sulfate, phosphate, amino acid, dipeptide or a monosaccharide such as glucuronic acid at, e.g., the 2, 3, 6, 7, 11, 15, 16, 17 or other positions on the steroid nucleus. In these embodiments, the appropriate use of a F1C of known structure as a standard can aid in or verify the identification of metabolites that are projected to have closely related structures. Information regarding the identification can be useful or sometimes is necessary for, e.g., obtaining regulatory approval to market a therapeutic agent such as a F1C or understanding the potential biological role that a F1C or its metabolite can play in one of the applications disclosed herein or in a cited reference. To facilitate such uses, the F1C may be labeled as appropriate, e.g., using a F1C with, e.g., one or more $^{2}$H, $^{3}$H, $^{13}$C, $^{14}$C, $^{15}$N, $^{18}$O, $^{18}$F, $^{35}$S, $^{32}$P or $^{123}$I, at 1, 2 or more of the 1, 2, 3, 4, 5, 6, 7, 8, 9, 10, 11, 12, 13, 14, 15, 16, 17, 18, 19, 20, 21, 22 or other positions in any formula 1 steroid. Radiolabel or heavy isotope atoms may be directly bonded to, or for carbon atoms, replace a steroid nucleus atom, or they may be bonded through one, two or more intervening atoms, e.g., steroid-O—$^{32}$P(O)(OH)(OH). Suitably labeled compounds include any of the F1Cs disclosed herein. Such labeled compounds may comprise, e.g., a $^{13}$C at the 18 or 19 positions and 1, 2, 3 or 4 $^{3}$H may be bonded to the $^{13}$C atom(s) or to a ring carbon(s). Other formula 1 compounds may comprise one or two $^{2}$H or $^{3}$H atoms bonded to one or more of the 1, 2, 4, 5, 6, 11 or 12 positions and optionally a $^{13}$C at the 18 or 19 position(s). F1Cs and their metabolites are isolated or characterized using radiolabeled or mass labeled atoms. F1Cs are also optionally isolated by the use of antibodies capable of binding to epitopes in F1Cs or in metabolites.

In general, analysis of F1C metabolites is accomplished in the same way as conventional drug metabolism studies, which are known to those skilled in the art. The conversion products, especially when they are not otherwise found in vivo, are useful in diagnostic assays for therapeutic dosing of the formula 1 compounds even if they possess only limited therapeutic activity of their own.

Embodiments include a method (the "characterization method") to characterize or at least partially characterize a formula 1 compound that is at least partially uncharacterized for one or more given chemical or analytical properties, e.g., a known or potential metabolite of a parent formula 1 compound, comprising (a) providing a formula 1 compound having one, two or more known characteristics, e.g., a known or at least partially known or characterized chemical structure, XRD spectrum or melting point (a "CF1C"), and a formula 1 compound that is unknown or at least partially uncharacterized, i.e., is uncharacterized for at least one of the same analytical characteristics (a "UCF1C"), (b) obtaining one, two or more analytical characteristics of the UCF1C, and (c) comparing the 1, 2 or more analytical characteristics of the CF1C with the analytical characteristics of the UCF1C. The steps in this method may be conducted in any suitable order, e.g., analytical or chemical data for the CF1C will usually be obtained before or at about the same time as one obtains the analytical or chemical data for the UCF1C. Usually the CF1C will be more completely characterized than the UCF1C, particularly with regard to its chemical structure or its relative degree of purity or with regard to the analytical or chemical data that is being sought. This method allows further characterization of the UCF1C, e.g., by confirming the UCF1C's chemical structure or by determining the UCF1C's stability under various storage or temperature conditions or in various formulations or by determining other analytical or chemical properties of interest. In this method, the CF1C itself may not be completely characterized, however, for the one, two or more analytical characteristics of interest, the CF1C will usually have a known or confirmed property or properties, while the UCF1C is unknown or at least unconfirmed for the same property or properties.

In some embodiments the characterization method is conducted by comparing dissimilar analytical characteristics. For example, the CF1C may be well characterized by GC-MS or by NMR, while an insufficient amount of the UCF1C is available for analysis with the same technique. In these cases, one can then, e.g., compare the GC-MS of the $CF_1C$ with the NMR of the UCF1C to obtain the same or essentially the same information for the UCF1C. Other examples of where this can be done are where DSC data is available for the CF1C, and only melting point data is available for the UCF1C. In this case, the CF1C DSC data is compared to the UCF1C's melting point data. Also, in conducting the characterization method, one can optionally derivatize or chemically modify the CF1C and/or the UCF1C to facilitate analysis of the compound(s). For example, in conducting MS, GC-MS or NMR analysis, one or more free hydroxyl or ketone moieties on the CF1C and/or the F2C can be silylated using, e.g., trimethylsilyl chloride, t-butyl-dimethylsilyl chloride or other suitable silylating agents. Similarly, the UCF1C may be treated or incubated with a cell line or tissue or with a glucuronidase, sulfatase or steroid sulfatase, phosphatase, esterase, lipase, oxidoreductase, or another enzyme and then characterized. This treatment may in some cases convert the UCF1C into the CF1C, but this conversion would usually be confirmed by one, two or more suitable analytical methods. Such treatments will usually generate additional data about the structure, properties origin of the UCF1C.

Embodiments include modifications of the characterization method that use a CF1C and a second formula 1 compound that is believed or known to have a related structure or empirical formula. In these modifications, the CF1C is used as described and a second formula 1 compound or a UCF1C that is believed or known to be, e.g., an epimer or a salt, of the CF1C is compared to the CF1C. Invention embodiments include other modifications of the characterization method such as (1) comparing analytical or chemical data from a single CF1C with 2, 3, 4 or more UCF1C, (2) comparing analytical or chemical data from 2, 3, 4 or more CF1C with a single UCF1C and (3) comparing analytical or chemical data from 2, 3, 4 or more CF1C with 2, 3, 4 or more UCF1C. In these modifications, the CF1C or UCF1C are used essentially as described for the characterization method, except that data is obtained for the added formula 1 compounds.

Typically, when the 1, 2 or more analytical characteristics of a CF1C or a UCF1C are obtained, which may be for use in the characterization method or for other purposes, each compound is analyzed under the same or essentially the same analytical conditions using the same or essentially the same analytical technique or instrument. Variations in an analytical technique may be used where the properties of a CF1C or a UCF1C require slightly different handling or specimen preparation. An example of a variation in analytical conditions is the comparison of a property of a CF1C, e.g., its stability to heat, humidity or prolonged storage at a given temperature, with the same property of the $CF_1C$ in a composition containing an excipient(s) or in a formulation (where the CF1C in a composition is then considered the UCF1C for the characterization method). This allows the determination of the stability of the $CF_1C$ as a pure compound compared to its stability in any desired composition.

When characterizing a CF1C by MS, particularly by GC-MS, one will usually conduct an initial characterization of a formula 1 compound or a CF1C in the characterization method using a known GC-MS method (e.g., H. L. J. Makin et al., *Mass Spectra and GC Data of Steroids: Androgens and Estrogens* 1999 John Wiley & Sons, pages XIII-XIV) or a suitable variation of this method. For F1Cs that contain free hydroxyls or oxo groups, the hydroxyl groups can be derivatized to an ester such as acetate, hydroxyl and oxo or groups can be derivatized to trimethylsilyl ether, i.e., —O—Si(CH$_3$)$_3$, and oxo groups can be derivatized to a an oxime such as =N—O—CH$_3$ before GC-MS analysis. Other functional groups can also be suitably derivatized. For embodiments of the characterization method that use a GC-MS analysis method, the CF1C or the UCF1C is analyzed by the GC-MS method or a suitable variation to obtain or to confirm chemical structure information about the CF1C or the UCF1C. Suitable variations include, e.g., a change in the carrier gas from helium to hydrogen to increase the sensitivity of detection or a decrease in the ionization from 70 eV to 50 eV can give a better parent mass ion.

In cases where a F1C is an analog of a naturally occurring steroid or conjugate, e.g., a steroid having a sulfate group at, e.g., the 3-, 16- and/or 17-position, some of the F1Cs can modulate the activity of one or more enzymes, e.g., sulfatases such as steroid sulfatase that can otherwise metabolize the F1C. Thus, F1Cs containing, e.g., a sulfamate, phosphonate, thiophosphonate and/or sulfonate group can modulate, typically inhibit, sulfatase or phosphatase enzymes. Similarly, thiophosphates or ethers can be used to modulate or inhibit esterase activity. Such F1Cs can be used to treat diseases or conditions where modulation of these enzymes can provide therapeutic benefit, e.g., in inflammation, trauma, infections, neurological disorders or immune suppression conditions. Alternatively, such F1Cs can be used to characterize one or more of their biological characteristics in one or more animal models, cell assays in vitro or in cell free assay systems. Typically such characterization will be accompanied by comparison of the F1C's activity with one or more suitable reference or control compounds or treatments.

As is apparent from the present disclosure, the F1C may be prepared synthetically and typical embodiments will utilize a purified or at least partially purified F1C. Purified F1C can be free, essentially free or partially free, of other F1C or other compounds such as excipients. Thus, any given purified F1C can be present as a solid that contains, e.g., less than about 15% w/w or less than about 10% w/w or less than about 8% w/w or less than about 5% w/w or less than about 3% w/w or less than about 2% w/w or less than about 1% w/w of one, two or more other F1Cs, excipients, synthetic by-products, decomposition products or synthesis or purification reactants or reagents. Similarly, the F1C can be present in a solution or suspension that contains at least about 90% w/w or at least about 95% w/w or at least about 97% w/w of the F1C and one or more excipients and less than about 10% or 8% or 5% or 3% w/w or 1% w/w of one, two or more other F1Cs, excipients, synthetic by-products, decomposition products or synthesis or purification reactants or reagents.

Various groups that F1Cs contain as described herein, e.g., hydroxyl groups or ketones bonded to the steroid nucleus, or substituted alkyl groups, substituted heterocycles, amino acids and peptides, which can contain one or more reactive moieties such as hydroxyl, oxo (=O), thioxo (=S), carboxyl, amino or thiol or mercapto (—SH) moieties. Intermediates used to make F1Cs may be protected as is apparent in the art, e.g., using suitable $R^{PR}$ moieties. Protecting groups can be used to prepare F1Cs or F1C prodrugs. Noncyclic and cyclic protecting groups and corresponding cleavage reactions are described in "Protective Groups in Organic Chemistry", Theodora W. Greene (John Wiley & Sons, Inc., New York, 1991, ISBN 0-471-62301-6) (hereafter "Greene") and will not be detailed here. In the context of the present invention, these protecting groups are groups that can be removed from a F1C without irreversibly changing the covalent bond structure or oxidation/reduction state of the remainder of the molecule. For example, the protecting group, —$R^{PR}$, that is bonded to an —$OR^{PR}$, —$SR^{PR}$, —$NHR^{PR}$ or =$NR^{PR}$ group can generally be removed to form, e.g., —OH, =O, —SH, =S, —NH$_2$ or =NH, without affecting other covalent bonds in the molecule. Protecting groups for carbonyl or ketone moieties include ethylene ketals, e.g., —O—CH$_2$—CH$_2$—O—. At times, when desired, more than one protecting group can be removed at a time, or they can be removed sequentially.

In F1Cs containing more than one protecting group, the protecting groups are the same or different.

Protecting groups are removed by known procedures, although it will be understood that the protected intermediates fall within the scope of this invention. The removal of the protecting group may be arduous or straightforward, depending upon the economics and nature of the conversions involved. In general, one will use a protecting group with exocyclic amines or with carboxyl groups during synthesis of a F1C. For most therapeutic applications amine groups should be deprotected. Protecting groups commonly are employed to protect against covalent modification of a sensitive group in reactions such as alkylation or acylation. Ordinarily, protecting groups are removed by, e.g. hydrolysis, elimination or aminolysis. Thus, simple functional considerations will suffice to guide the selection of a reversible or an irreversible protecting group at a given locus on the F1Cs. Suitable protecting groups and criteria for their selection are described in T. W. Greene and P. G. M. Wuts, Eds. "Protective Groups in Organic Synthesis" 2nd edition, Wiley Press, at pgs. 10-142, 143-174, 175-223, 224-276, 277-308, 309-405 and 406-454.

Characterization of a protecting group is made in the conventional manner, e.g., as described by Kocienski, Philip J.; "*Protecting Groups*" (Georg Thieme Verlag Stuttgart, New York, 1994) (hereafter "Kocienski"), Section 1.1, page 2, and Greene Chapter 1, pages 1-9. In particular, a group is a protecting group if when, based on mole ratio, 90% of that protecting group has been removed by a deprotection reaction, no more than 50%, typically 25%, more typically 10%, of the deprotected product molecules have undergone changes to their covalent bond structure or oxidation/reduction state other than those occasioned by the removal of the protecting group. When multiple protecting groups of the same type are present in the molecule, the mole ratios are determined when all of the groups of that type are removed. When multiple protecting groups of different types are present in the molecule, each type of protecting group is treated (and the mole ratios are determined) independently or together with others depending on whether the deprotection reaction conditions pertinent to one type are also pertinent to the other types present. In one embodiment, a group is a protecting group if when, based on mole ratio determined by conventional techniques, 90% of that protecting group has been removed by a conventional deprotection reaction, no more than 50%, typically 25%, more typically 10%, of the deprotected product molecules have undergone irreversible changes to their covalent bond structure or oxidation/reduction state other than those occasioned by the removal of the protecting group. Irreversible changes require chemical reactions (beyond those resulting from aqueous hydrolysis, acid/base neutralization or conventional separation, isolation or purification) to restore the covalent bond structure or oxidation/reduction state of the deprotected F1C.

Protecting groups are also described in detail together with general concepts and specific strategies for their use in Kocienski, Philip J.; "Protecting Groups" (Georg Thieme Verlag Stuttgart, New York, 1994), which is incorporated by reference in its entirety herein. In particular Chapter 1, Protecting Groups: An Overview, pages 1-20, Chapter 2, Hydroxyl Protecting Groups, pages 21-94, Chapter 3, Diol Protecting Groups, pages 95-117, Chapter 4, Carboxyl Protecting Groups, pages 118-154, Chapter 5, Carbonyl Protecting Groups, pages 155-184, Chapter 6, Amino Protecting Groups, pages 185-243, Chapter 7, Epilog, pages 244-252, and Index, pages 253-260, are incorporated with specificity in the context of their contents. More particularly, Sections 2.3 Silyl Ethers, 2.4 Alkyl Ethers, 2.5 Alkoxyalkyl Ethers (Acetals), 2.6 Reviews (hydroxy and thiol protecting groups), 3.2 Acetals, 3.3 Silylene Derivatives, 3.4 1,1,3,3-Tetraisopropyldisiloxanylidene Derivatives, 3.5 Reviews (diol protecting groups), 4.2 Esters, 4.3 2,6,7-Trioxabicyclo[2.2.2]octanes [OBO] and Other Ortho Esters, 4.4 Oxazolines, 4.5 Reviews (carboxyl protecting groups), 5.2 O,O-Acetals, 5.3 S,S-Acetals, 5.4 O,S-Acetals, 5.5 Reviews (carbonyl protecting groups), 6.2 N-Acyl Derivatives, 6.3 N-Sulfonyl Derivatives, 6.4 N-Sulfenyl Derivatives, 6.5 N-Alkyl Derivatives, 6.6 N-Silyl Derivatives, 6.7 Imine Derivatives, and 6.8 Reviews (amino protecting groups), are each incorporated with specificity where protection/deprotection of the requisite functionalities is discussed. Further still, the tables "Index to the Principal Protecting Groups" appearing on the inside front cover and facing page, "Abbreviations" at page xiv, and "reagents and Solvents" at page xv are each incorporated in their entirety herein at this location.

Typical hydroxy protecting groups are described in Greene at pages 14-118 and include Ethers (Methyl); Substituted Methyl Ethers (Methoxymethyl, Methylthiomethyl, t-Butylthiomethyl, (Phenyldimethylsilyl)methoxymethyl, Benzyloxymethyl, p-Methoxybenzyloxymethyl, (4-Methoxyphenoxy)methyl, Guaiacolmethyl, t-Butoxymethyl, 4-Pentenyloxymethyl, Siloxymethyl, 2-Methoxyethoxymethyl, 2,2,2-Trichloroethoxymethyl, Bis(2-chloroethoxy) methyl, 2-(Trimethylsilyl)ethoxymethyl, Tetrahydropyranyl, 3-Bromotetrahydropyranyl, Tetrahydropthiopyranyl, 1-Methoxycyclohexyl, 4-methoxytetrahydropyranyl, 1,4-Dioxan-2-yl, Tetrahydrofuranyl, Tetrahydrothiofuranyl); Substituted Ethyl Ethers (1-Ethoxyethyl, 1-(2-Chloroethoxy) ethyl, 1-Methyl-1-methoxyethyl, 1-Methyl-1-benzyloxyethyl, 1-Methyl-1-benzyloxy-2-fluoroethyl, 2,2,2-Trichloroethyl, 2-Trimethylsilylethyl, 2-(Phenylselenyl) ethyl, t-Butyl, Allyl, p-Chlorophenyl, p-Methoxyphenyl, 2,4-Dinitrophenyl, Benzyl); Substituted Benzyl Ethers (p-Methoxybenzyl, 3,4-Dimethoxybenzyl, o-Nitrobenzyl, p-Nitrobenzyl, p-Halobenzyl, 2,6-Dichlorobenzyl, p-Cyanobenzyl, p-Phenylbenzyl, 2- and 4-Picolyl, 3-Methyl-2-picolyl N-Oxido, Diphenylmethyl, p, p'-Dinitrobenzhydryl, 5-Dibenzosuberyl, Triphenylmethyl, 1,3-Benzodithiolan-2-yl, Benzisothiazolyl, S,S-Dioxido); Silyl Ethers (Trimethylsilyl, Triethylsilyl, Triisopropylsilyl, Dimethylisopropylsilyl, Diethylisopropylsily, Dimethylthexylsilyl, t-Butyldimethylsilyl, t-Butyldiphenylsilyl, Tribenzylsilyl, Tri-p-xylylsilyl, Triphenylsilyl, Diphenylmethylsilyl, t-Butylmethoxyphenylsilyl); Esters (Formate, Benzoylformate, Acetate, Choroacetate, Dichloroacetate, Trichloroacetate, Trifluoroacetate, Methoxyacetate; Carbonates (Methyl, 9-Fluorenylmethyl, Ethyl, 2,2,2-Trichloroethyl, 2-(Trimethylsilyl)ethyl, 2-(Phenylsulfonyl)ethyl, 2-(Triphenylphosphonio)ethyl, Isobutyl, Vinyl, Allyl, p-Nitrophenyl, Benzyl, p-Methoxybenzyl, 3,4-Dimethoxybenzyl, o-Nitrobenzyl, p-Nitrobenzyl); Groups With Assisted Cleavage (2-Iodobenzoate, 4-Azidobutyrate, 4-Nitro-4-methylpentanoate, o-(Dibromomethyl)benzoate, 2-Formylbenzenesulfonate, 2-(Methylthiomethoxy)ethyl Carbonate, 4-(Methylthiomethoxy)butyrate, 2-(Methylthiomethoxymethyl)benzoate); Other Esters (2,6-Dichloro-4-methylphenoxyacetate, 2,6-Dichloro-4-(1,1,3,3-tetramethylbutyl)phenoxyacetate, Isobutyrate, Monosuccinoate, (E)-2-Methyl-2-butenoate (Tigloate), o-(Methoxycarbonyl) benzoate, p-poly-Benzoate, α-Naphthoate, Nitrate, Alkyl N,N,N',N'-Tetramethylphosphorodiamidate, N-Phenylcarbamate, Borate, Dimethylphosphinothioyl, 2,4-Dinitro-phenylsulfenate); and Sulfonates (Sulfate, Methanesulfonate (Mesylate), Benzylsulfonate, Tosylate (Tos)). More typically hydroxy protecting groups include substituted methyl ethers, substituted benzyl ethers, silyl ethers, and esters including sulfonic acid esters, still more typically, esters, trialkylsilyl ethers and tosylates, such as acetates, trimethylsilyl and methoxymethyl.

Typical 1,2- and 1,3-diol protecting groups are described in Greene at pages 118-142 and include Cyclic Acetals and Ketals (Methylene, Ethylidene, 1-t-Butylethylidene, 1-Phenylethylidene, (4-Methoxyphenyl)ethylidene, 2,2,2-Trichloroethylidene, Acetonide (Isopropylidene), Cyclopentylidene, Cyclohexylidene, Cycloheptylidene, Benzylidene, p-Methoxybenzylidene, 2,4-Dimethoxybenzylidene, 3,4-Dimethoxybenzylidene, 2-Nitrobenzylidene); Cyclic Ortho Esters (Methoxymethylene, Ethoxymethylene, Dimethoxymethylene, 1-Methoxyethylidene, 1-Ethoxyethylidine, 1,2-Dimethoxyethylidene, alpha-Methoxybenzylidene, 1-(N,N-Dimethylamino)ethylidene Derivative, alpha-(N,N-Dimethylamino)benzylidene Derivative, 2-Oxacyclopentylidene); and Silyl Derivatives (Di-t-butylsilylene Group, 1,3-(1,1,3,3-Tetraiso-propyldisiloxanylidene) Derivative, Tetra-t-butoxydisiloxane-1,3-diylidene Derivative, Cyclic Carbonates, Cyclic Boronates, Ethyl Boronate, Phenyl Boronate). More typically, 1,2- and 1,3-diol protecting groups include epoxides and acetonides.

Typical amino protecting groups are described in Greene at pages 315-385 and include Carbamates (Methyl and Ethyl, 9-Fluorenylmethyl, 9(2-Sulfo)fluoroenylmethyl, 9-(2,7-Dibromo)fluorenylmethyl, 2,7-Di-t-buthyl-[9-(10,10-dioxo-10,10,10,10-tetrahydrothioxanthyl)]-methyl, 4-Methoxyphenacyl); Substituted Ethyl (2,2,2-Trichoroethyl, 2-Trimethylsilylethyl, 2-Phenylethyl, 1-(1-Adamantyl)-1-methylethyl, 1,1-Dimethyl-2-haloethyl, 1,1-Dimethyl-2,2-dibromoethyl, 1,1-Dimethyl-2,2,2-trichloroethyl, 1-Methyl-1-(4-biphenylypethyl, 1-(3,5-Di-t-butylphenyl)-1-methylethyl, 2-(2'- and 4'-Pyridyl)ethyl, 2-(N,N-Dicyclohexylcarboxamido)ethyl, t-Butyl, 1-Adamantyl, Vinyl, Allyl, 1-Isopropylallyl, Cinnamyl, 4-Nitrocinnamyl, 8-Quinolyl, N-Hydroxypiperidinyl, Alkyldithio, Benzyl, p-Methoxybenzyl, p-Nitrobenzyl, p-Bromobenzyl, p-Chorobenzyl, 2,4-Dichlorobenzyl, 4-Methylsulfinylbenzyl, 9-Anthrylmethyl, Diphenylmethyl); Groups With Assisted Cleavage (2-Methylthioethyl, 2-Methylsulfonylethyl, 2-(p-Toluenesulfonyl)ethyl, [2-(1,3-Dithianyl)]methyl, 4-Methylthiophenyl, 2,4-Dimethylthiophenyl, 2-Phosphonioethyl, 2-Triphenylphosphonioisopropyl, 1,1-Dimethyl-2-cyanoethyl, m-Choro-p-acyloxybenzyl, p-(Dihydroxyboryl)benzyl, 5-Benzisoxazolylmethyl, 2-(Trifluoromethyl)-6-chromonylmethyl); Groups Capable of Photolytic Cleavage (m-Nitrophenyl, 3,5-Dimethoxybenzyl, o-Nitrobenzyl, 3,4-Dimethoxy-6-nitrobenzyl, Phenyl(o-nitrophenyl)methyl); Urea-Type Derivatives (Phenothiazinyl-(10)-carbonyl Derivative, N'-p-Toluenesulfonylaminocarbonyl, N'-Phenylaminothiocarbonyl); Other Carbamates (t-Amyl, S-Benzyl Thiocarbamate, p-Cyanobenzyl, Cyclobutyl, Cyclohexyl, Cyclopentyl, Cyclopropylmethyl, p-Decyloxybenzyl, Diisopropylmethyl, 2,2-Dimethoxycarbonylvinyl, o-(N,N-Dimethyl-carboxamido)benzyl, 1,1-Dimethyl-3-(N,N-dimethylcarboxamido)propyl, 1,1-Dimethylpropynyl, Di(2-pyridyl)methyl, 2-Furanylmethyl, 2-Iodoethyl, Isobutyl, Isonicotinyl. More typically, amino protecting groups include carbamates and amides, still more typically, N-acetyl groups.

Groups capable of biological cleavage typically include prodrugs. Some exemplary groups are described in "Design of Prodrugs", Hans Bundgaard (Elsevier, N.Y., 1985, ISBN 0-444-80675-X) (Bundgaard) and will not be detailed here. In particular, Bundgaard, at pages 1-92, describes prodrugs and their biological cleavage reactions for a number of functional group types. Prodrugs for carboxyl and hydroxyl groups are detailed in Bundgaard at pages 3 to 10, for amides, imides and other NH-acidic compounds at pages 10 to 27, amines at pages 27 to 43, and cyclic prodrugs at pages 62 to 70. These moieties are optionally bonded to the steroid at one, two or more of the variable groups that are bonded to the rings in the F1Cs, e.g., one or more $R^1$-$R^8$, $R^{10}$, $R^{15}$, $R^{17}$ and $R^{18}$.

In some embodiments one or more F1Cs or groups of F1Cs may be excluded from one or more of the uses disclosed herein. For example, if the subject has or is susceptible to developing a memory impairing neurological disorder or memory impairment condition, excluded compounds can include 5-androstene-3β-ol-7,17-dione or 5-androstene-3β, 7-diol-17-one or a derivative of these compounds that can has a group at the 7-position that can convert to —OH or ═O by hydrolysis. In other cases, the F1Cs can exclude one or more of 4-pregnene-11β,17α,21-triol-3,20-dione, 17α,21-dihydroxypregn-4-ene-3,11,20-trione, 11β,21-dihydroxy-3,20-dioxopregn-4-en-18-al, 11β,17α,21-trihydroxypregna-1,4-diene-3,20-dione, 17α,21-dihydroxypregna-1,4-diene-3,11, 20-trione, 3β-hydroxypregn-5-ene-20-one, 3β-hydroxyandrost-5-ene-17-one, pregn-4-ene-3,20-dione, 21-hydroxypregn-4-ene-3,20-dione, 9-fluoro-11β,16α,21-trihydroxy-16-methylpregna-1,4-diene-3,20-dione, 9-fluoro-11β,16α,17,21-tetrahydroxypregna-1,4-diene-3, 20-dione, 9-fluoro-11β,17α,21-trihydroxy-16-methylpregna-1,4-diene-3,20-dione, dehydroepiandrosterone-3-sulfate, 1,4-pregnadiene-17α,21-diol-3,11,20-trione, androsterone, androsterone acetate, androsterone propionate, androsterone benzoate, androst-5-ene-3β,17β-diol, androst-5-ene-3β,17β-diol-3-acetate, androst-5-ene-3β,17β-diol-17-acetate, androst-5-ene-3β,17β-diol-3,17-diacetate, androst-5-ene-3β,17β-diol-17-benzoate, androst-5-ene-3β,17β-diol-3-acetate-17-benzoate, androst-4-ene-3,17-dione, androst-5-ene-3β,7β,17β-triol, androst-5-ene-3β,7α,17β-triol, dehydroepiandrosterone, 4-dihydrotestosterone, 5α-dihydrotestosterone, dromostanolone, dromostanolone propionate, ethylestrenol, nandrolone phenpropionate, nandrolone decanoate, nandrolone furylpropionate, nandrolone cyclohexanepropionate, nandrolone benzoate, nandrolone cyclohexanecarboxylate, oxandrolone, stanozolol, testosterone, methyl testosterone, testolactone, oxymetholone, fluoxymesterone, acetoxypregnenolone, allylestrenol, anagestone acetate, chlormadinone acetate, cyproterone, cyproterone acetate, desogestrel, dihydrogesterone, dimethisterone, ethisterone (17α-ethynyltestosterone), ethynodiol diacetate, fluorogestone acetate, gestadene, hydroxyprogesterone, hydroxyprogesterone acetate, hydroxyprogesterone caproate, 3-ketodesogestrel, hydroxymethylprogesterone, hydroxymethylprogesterone acetate, levonorgestrel, lynestrenol, medrogestone, medroxyprogesterone acetate, megestrol, megestrol acetate, melengestrol acetate, norethindrone, norethindrone acetate, norethisterone, norethisterone acetate, norethynodrel, norgestimate, norgestrel, norgestrienone, normethisterone, and progesterone, progesterone, cyproterone acetate, norethindrone, norethindrone acetate, levonorgestrel, an ester of any of the foregoing compounds (e.g., acetate, enanthate, propionate, isopropionate, cyclopropionate, isobutyrate, butyrate, valerate, caproate, isocaproate, hexanoate, heptanoate, octanoate, nonanoate, decanoate, undecanoate, phenylacetate or benzoate esters, e.g., hydroxyl esters), a naturally occurring glucorcorticoid, a glucocorticoid or other steroid described in any reference cited herein, a species disclosed herein or a derivative of any of these that can convert to these molecules by hydrolysis or metabolism, e.g., a metabolizable or hydrolyzable ester or ether such as a cyclic ketal, an acetate, a diacetete, a proprionate, a diproprionate, or an O-alkyl, an acyl, e.g., —C(O)—C1-C6 alkyl or another moiety that is bonded at, e.g., a variable group such as for $R^1$-$R^6$.

Dosages of F1C and Dosing Protocols or Methods.

In treating any of the conditions or symptoms disclosed herein, one can continuously or intermittently administer the F1C(s) to a subject having or susceptible to developing the condition or symptom. In treating a condition such as an infection, a hyperproliferation condition, an inflammation condition or another condition disclosed herein with a F1C using an intermittent dosing can avoid or ameliorate some of the undesired aspects normally associated with discontinuous dosing. Such undesired aspects include development of resistance of a pathogen such as a pathogen disclosed herein, e.g., a virus or bacterium such as HIV or *Staphylococcus aureus* or a parasite such as a *Plasmodium* parasite, to the therapeutic agent, failure of the patient or subject to adhere to a daily dosing regimen or reduction of the dosages of other therapeutic agents and/or their associated unwanted side effects or toxicities, e.g., reduction or a toxic effect of a chemotherapy or radiation exposure. In any of the continuous or intermittent dosing protocols described herein, other appropriate treatments can be applied as the subject's clinical situation dictates. Suitable other appropriate treatments or therapeutic agents are described elsewhere herein and in the cited references.

In any of continuous daily dosing protocol, e.g., as described herein, or in any step(s) in the intermittent dosing protocols described herein, or in treating any of the diseases, conditions or symptoms described herein, the F1C(s) can be administered by one or more suitable routes, e.g., oral, buccal, sublingual, intramuscular (i.m.), subcutaneous (s.c.), intravenous (i.v.), intradermal, another parenteral route or by an aerosol. The effective daily dose in such methods will typically comprise about 0.05 mg/kg/day to about 200 mg/kg/day, about 0.1 to about 100 mg/kg/day, about 0.4 to about 80 mg/kg/day, about 1-45 mg/kg/day or about 1-6 mg/kg/day, including about 0.2 mg/kg/day, 0.5 mg/kg/day, about 1 mg/kg/day, about 2 mg/kg/day, about 4 mg/kg/day, about 6 mg/kg/day, about 10 mg/kg/day, about 20 mg/kg/day, about 40 mg/kg/day or about 100 mg/kg/day. Higher dosages, e.g., about 250 mg/kg/day, about 300 mg/kg/day or about 350 mg/kg/day can also be utilized, e.g., in veterinary applications. One can administer the F1C(s) orally using about 4 to about 60 mg/kg/day, usually about 6-30 mg/kg/day. In some embodiments, the intermittent dosing methods exclude dosing protocols that are commonly used to deliver contraceptive steroids to, e.g., human females, such as daily dosing for 21 days, followed by no dosing for 7 days. For humans, dosing is generally about 0.05 mg/kg/day to about 30 mg/kg/day, typically about 0.5-10 mg/kg/day. Low dosages for humans such as about 0.005 mg/kg/day to about 0.2 mg/kg/day or about 0.25-10 mg/day, can be used with, e.g., local, topical, transmucosal or intravenous administration and higher dosages such as about 0.1 mg/kg/day to about 20 mg/kg/day or about 5-200 mg/day, can be used, e.g., for oral, subcutaneous or other systemic or local administration route. For non-human subjects, e.g., mammals such as rodents or primates, the effective daily dosage may comprise about 0.05 mg/kg/day to about 350 mg/kg/day.

F1C formulation dosages or daily doses or unit doses or subdoses for subjects such as humans and mammals include, e.g., dosages of about 1 mg, about 5 mg or about 10 mg to about 100 mg, about 200 mg or about 1000 mg, e.g., unit doses of about 1, 5, 10, 15, 20, 25, 50, 75, 80, 100, 120, 125, 150, 175, 200, 225, 250, 275, 300, 325, 350, 400 or 450 mg of the F1C. An effective amount of a F1C, e.g., for human therapeutic use, may be a single dose or two or more subdoses of a F1C administered in one day, or it may be administered as multiple doses over a period of time, e.g., over 1, 2, 3, 4 or about 7 days to about 1 year. For any radiation exposure situation where delayed radiation effects may arise, e.g., a radiation exposure as disclosed herein, daily administration may comprise administering about 0.01 mg/kg to about 500 mg/kg of the F1C to a subject per day. Exemplary dosages are about 0.1-100 mg/kg/day and about 0.2-30 mg/kg/day. Exemplary unit doses comprise about 1, 5, 10, 15, 20, 25, 30, 40, 50, 75, 100, 200, 300 or 500 mg of a F1C in a suitable formulation. Exemplary unit dosages for humans or other subjects disclosed herein comprise a formulation or unit dose that comprises about 1-1000 mg of a F1C or about 5-400 mg or about 10-300 mg. Larger unit or daily dosages, e.g., about 5-400 mg, will generally be used with larger subjects such as humans, while smaller subjects such as rodents or dogs will generally utilize lower unit or daily dosages, e.g., about 0.3-25 mg.

An effective dosage or an effective amount of a F1C(s) is one that is sufficient to result in, e.g., a detectable change in a symptom or an immune parameter such as one described herein. Such changes may be transient or prolonged, e.g., lasting for hours, days or weeks. An effective dosage (or daily dosage) may be administered to a subject over a period of time, e.g., at least about 1-14 days before a symptom change or an immune parameter detectably changes. Effective amounts of a F1C can be delivered using the dosages and dosing protocols described herein. For effective dosing, the level of the F1C in circulation or in tissues will generally be about 1 nM to about 2 µM, typically about 10 nM to about 50 nM, about 10 nM to about 300 nM, about 20 nM to about 300 nM, about 20 nM to about 200 nM or about 100 nM to about 300 nM, which may be maintained for periods of about 15 minutes to about 16 hours or about 30 minutes to about 6 hours on days when a F1C is administered to a subject. To attain or maintain these, or other, blood, serum or tissue levels for longer periods of time, the F1C will typically be administered in a controlled release formulation or a depot formulation once per day or administered on two or more occasions per day using rapid, controlled or depot release formulations. Such dosing allows at least transient attainment or maintenance of higher F1C levels in the subject, e.g., levels of about 1.5 µM or about 2.1 µM to about 2.5 µM, about 3.5 µM or more.

By controlling the dosing or formulation, systemic delivery of a F1C can be attained by a relatively rapid increase in the level of the F1C, e.g., where peak blood or serum levels are reached within about 15 minutes to about 60 minutes after dosing. Using slow release or depot formulations, the peak F1C levels can be attained at later times for a given course of dosing, e.g., at about 2 hours to about 2 weeks after the last dose is administered. Depot formulations include parenteral preparations, e.g., solutions, suspensions or gels that contain a F1C. In some embodiments, these formulations are administered by, e.g., subcutaneous or intramuscular injection, and significant amounts of the F1C remains at or near the injection site for some period of time, e.g., for about 2 hours to about 5 days or about 7 days or more. Such depots can be attained using a single dose of the F1C or multiple doses that are administered, e.g., daily over a period of 2, 3, 4, 5, 7 or more days. In these embodiments, the F1C is released from the depot over time, which can then lead to a sustained level of the compound, e.g., sustained levels for 1, 2 or 3 days to about 4, 5, 7, 14, 21 or more days at, e.g., about 10 nM, about 20 nM, about 40 nM, about 60 nM or higher levels.

In some embodiments, F1C are used to treat, ameliorate, prevent, delay the onset of or slow the progression of a condition or disease described herein by continuous daily or intermittent dosing of the F1C for 1 day to 1, 2, 3 years or more. Thus, F1C can be used to treat, ameliorate, prevent, delay the onset of or slow the progression of a condition or disease described herein by continuous dosing the F1C every other day or dosing every third, fourth, fifth, sixth, seventh or $14^{th}$ day over a time period of 3 days to 1, 2, 3 years or more, e.g., dosing for about 2, 3, 4, 5, 6 or 7 days or about 1, 2, 3, 4, 6, 8, 10, 12, 16, 20, 24 or more weeks. Daily doses in any of these dosing regimens or protocols may be subdivided into 2 or 3 subdoses.

Intermittent dosing protocols include administration of a F1C, e.g., orally, topically or parenterally as follows: (1) daily dosing or dosing every other day or dosing every third day or dosing every fourth day or dosing every fifth day or dosing every seventh day for about 2, 3, 4, 5, 6, 7, 8, 9, 10, 11, 12, 13, 14, 15, 16, 17, 18, 19, 20, 21 or 28 days to about 190 days or more, e.g., 1 or 2 years, (2) no dosing of the F1C for 1 to about 190 consecutive days (e.g., about 2, 3, 4, 5, 6, 7, 8, 9, 10, 11 or 12 days to about 20 days), (3) daily dosing for about 3 to about 190 days (e.g., about 3 to about 20 days), and (4) optionally repeating step (2) or a variation of step (2) and (5) optionally repeating the steps (1), (2), (3) and (4) 1, 2, 3, 4, 5, 6, 10, 15, 20, 30 or more times. In some embodiments, the dosing of steps (1) and (3) are the same, while in others, step (1) dosing is for a longer time than step (3). Less frequently, step (1) dosing will be for a shorter time. In some embodiments, steps (1)-(4) or (1)-(5) of the dosing protocol described above where step (4) is included, is repeated at least one time, e.g., at least 2, 3, 4, 5 or 6 times. For conditions that tend to remain chronic, e.g., HIV infection or other chronic conditions described herein, any of these intermittent dosing protocols can be maintained over a relatively long time period, e.g., for at least about 4 months or 6 months to about 5 or more years.

In some embodiments, the number of days of dosing in steps (1) and (3) is the same in each round of treatment, i.e., each time period in step (1) and (3) is the same in the initial and subsequent rounds of the method. In other embodiments they differ. Thus, in some embodiments, step (1) may comprise dosing of about 1 mg/day to about 1500 mg/day of a F1C for 1, 2, 3, 4, 5, 6, 7, 8, 9 or 10 or more consecutive days. Then, step (2) may comprise not administering any F1C for at least about 2, 3, 4, 5, 6, 7, 14, 21, 28, 42, 56, 84, 98, 112 or more consecutive days. Step (3) could comprise dosing of a F1C for 1, 2, 3, 4, 5, 6, 7, 8, 9, 10 or more consecutive days. When step (4) is included it is typically about 1 day to about 3 months, usually 3 days to about 6 weeks. On days when the F1C is administered to the subject, it may be delivered in a single dose or in two, three or more subdoses at, e.g., about 12 hour or about 8 hour time intervals.

Exemplary embodiments comprise (1) administering a F1C(s) once every (as a single dose or as 2 or 3 daily subdoses) 2 days, every 3 days or every 4 days or once per week for about 3, 5, 7, 9, 11, 13, 14, 15, 21, 28 or more days, followed by (2) no dosing for about 2, 3, 4, 5, 6, 10, 14, 15, 21, 20, 25, 28, 30, 35, 40, 42, 45, 49, 56, 60, 70, 77, 84, 98, 112 or more days and then (3) administering the F1C(s) at least once more on one day, e.g., administering the F1C(s) as described in step (1), (4) not dosing for 2, 3, 4, 5, 7 or more days, e.g., as described in step (2) for 1, 2, 3, 4, 5, 6, 7 or 8 weeks, and (5) optionally repeating steps (1), (2), (3) and (4) 1, 2, 3, 4, 5 or 6 times or more. Any of the dosing protocols described herein may be coincident or essentially coincident with the appearance or expected appearance of a clinical condition, e.g., dosing with a F1C may commence at about 1, 2 or 3 hours after to about 1, 2, 3, 4 or 5 days after exposure of a subject to radiation or a chemotherapy such as a cancer chemotherapy, to prevent or treat, e.g., reduce the length and/or severity of an acute or chronic side-effect such as neutropenia, such as grade 3 or grade 4 neutropenia, thrombocytopenia, lung fibrosis or inflammation that can be associated with the radiation exposure or the chemotherapy.

Other embodiments comprise (1) administering a F1C(s) once every day (as a single dose or as 2 or 3 daily subdoses) for 3-15 or about 8-12 days, followed by (2) no dosing for 1, 2, 3, 4, 5, 6, 10, 15, 20, 25, 30, 35, 40, 45, 50, 56, 70, 84, 98, 112 or more days and then (3) administering the F1C(s) at least once more on one day, e.g., administering the F1C(s) once per day for about 3-15 or about 8-12 consecutive days essentially as described in step (1) and (4) optionally repeating steps (1), (2) and (3) 1, 2, 3, 4, 5 or 6 times or more. In a subset of these embodiments (1) comprises administering a F1C(s) once every day for about 5, 6, 7, 8, 9 or 10 days, followed by (2) no dosing for about 10-40 days, (3) administering the F1C(s) at least once more on one day, e.g., administering the F1C(s) once per day for about 10 days (4) repeating step (2) or a variation, e.g., no dosing for about 5-45 days, and (5) optionally repeating steps (1), (2), (3) and (4) or a variation thereof those steps 1, 2, 3, 4, 5 or 6 times or more, (5) administering by s.c. or i.m. injection of about 5-45 mg/kg/dose, about 6-43 mg/kg/dose or about 7-43 mg/kg/dose of a group 3 compound such as compound 1.1.5.9 in group 3 described below, once each 1, 2, 3, 4, 5, 6, 7, 8 or 10 days over a period of about 15-28 days, optionally beginning at about 1-72 hours after, about 1-48 hours after, about 1-24 hours after or about 24-72 hours after exposure of the subject to radiation or a cytotoxic chemotherapy, (6) administering orally or by s.c. or i.m. injection about 0.5-10 mg/kg/dose, e.g., about 1.5-3 mg/kg/dose of a group 3 compound such as compound 1.1.5.1 described below, once each 1, 2, 3, 4, 5, 6, 7 or 8 days over a period of about 15-30 days, e.g., over a period of 12, 14, 15, 16, 17, 19, 20, 21, 22, 23, 24, 25, 26 or 32 days, optionally beginning at about 1-72 hours after, about 1-48 hours after, about 1-24 hours after or about 24-72 hours after exposure of the subject to radiation or a cytotoxic chemotherapy.

Any of the dosing protocols described herein may be repeated or maintained to coincide or essentially coincide as described above or elsewhere herein with cycles of a chemotherapy or radiation exposure, or with the appearance of symptoms of a clinical condition or disease, e.g., fever, fatigue, motor function impairment, cognitive impairment, pain or another symptom of a condition described herein. Thus periods of 1 week or 2 weeks or 4 weeks to several months, e.g., 2, 3, 4, 5, 6, 7, 8 or more months to about 24 months or about 36 months or more may separate cycles of continuous or intermittent dosing with a F1C. Any given dosing protocol may be selected to provide selected levels of the F1C in serum, blood or tissue for selected time periods. Thus, a dosing protocol may be selected to attain a blood, serum or tissue level of a F1C that is about 0.1 nM to about 4000 nM, e.g., about 1-1000 nm, about 10-800 nm, about 30-650 nM or about 3 nM to about 500 nM (e.g., about 1-800 ng/mL, 10-250 ng/mL or 1-50 ng/mL in blood, serum or tissue), for at least about 1-24 hours per day, e.g., for about 1-2 hours, about 2-8 hours or about 2-12 hours per day, during an entire dosing period or most of a dosing period, e.g., beginning at about 1, 2, 3 or 4 days into a continuous (daily) or intermittent dosing protocol, and/or on days when dosing occurs and/or for several days after to about 1, 2, 3, 4, 5, 6, 7 or 8 weeks after a dosing protocol has ended. For some F1Cs, administration of the F1C can give rise to a blood, serum or tissue levels of the F1C of about 1-25 nM and higher levels, e.g., about 100-500 nM of one or more metabolites.

In cases where a depot or deposit of the F1C is formed in a subject in vivo, e.g., by parenteral delivery of the compound to skin or muscle, levels of the F1C can be maintained for relatively long periods of time, e.g., for at least about 1, 2, 4, 8, 12 or more weeks. In these methods, blood or serum levels of the F1C or one, two or more metabolites of the F1C can be maintained at levels of about 2 or 5 nM to about 30, 60, 100 nM or more can be achieved and maintained continuously or essentially continuously, e.g., maintained for at least about 13 or 14 hours per day. The F1Cs that are suitable for forming depots in vivo will generally be relatively hydrophobic or lipophilic, e.g., F1Cs with a log P of at least about −0.8, 0.0 or 0.3 to about 2, 3 or 4.5. Such F1Cs will usually have a low solubility in aqueous systems such as water, serum or blood, e.g., a solubility of about 0.1 nM to about 0.4 µM or about 0.1 or 1 ng/mL to about 50 or 100 ng/mL. In general, F1Cs having a log P of about 0.0 or 0.4 to about 0.8, 2 or more will form depots when administered by subcutaneous, peritoneal or intramuscular delivery. The log P parameter is a measure of a compound's lipophilicity based on the log of the partition coefficient of a compound between an aqueous phase or water and an nonaqueous organic solvent. The nonaqueous phase usually is an organic solvent such as a C6-C10 alcohol, typically n-octanol or n-heptane, that is not miscible with water or buffered water, e.g., where buffer sets the aqueous pH at about 2 or 3 to about 9 or 10, typically at about 6-8 or about 7. When n-octanol is used as the nonaqueous solvent, the partition coefficient is expressed as log $P_{oct}$. The log $P_{oct}$ is commonly used to express a compound's lipophilicity in biological systems. Methods such as HPLC retention times to measure log P for various compounds or portions of compounds have been described. See, e.g., U.S. Pat. No. 4,716,225, C. Hansch et al., *J. Pharm Sci.* 61: 1-19 1972, G. D. Veith et al., *Water Research* 13: 43-47 1979, A. K. Ghose et al., *J. Comp. Chem.* 9: 80-90 1988, R. F. Rekker et al., *Calculation of Drug Lipophilicity*, VCH, Weinheim, 1992, A. Hulshoff et al., *J. Chromatogr.* 120:65-80 1976, J. Ostergaard et al., *Electrophoresis* 24:1038-1046 2003 and W. M. Meylan et al., *J. Pharm. Sci.* 84: 83-92 1995. Computation of the log P or log $P_{oct}$ values of individual portions or moieties of a compound can permit identification of localized hydrophobic and hydrophilic regions of the molecule.

One aspect of the continuous and intermittent dosing protocols is monitoring the subject's response to a particular dosing regimen or schedule, e.g., to any intermittent administration method disclosed herein. For example, while dosing a subject who has a viral infection (e.g., HCV, HIV, SIV, SHIV), one can measure the subject's or pathogen's response, e.g., amelioration of one or more symptoms or a change in infectious particles or viral DNA or RNA in the serum or a change in an immune parameter of interest. Once a response is observed dosing can be continued for one, two or three additional days, followed by discontinuing the dosing for at least one day (at least 24 hours), usually for at least about 2, 3, 4, 5, 6, 7, 14, 21, 28, 42, 56, 70, 84, 98, 112 or more days. Once the subject's response shows signs of remission (e.g., a symptom begins to intensify, viral serum DNA or RNA begins to increase or an immune parameter, e.g., as described herein, begins to deteriorate), dosing can be resumed for another course. An aspect of the subject's response to F1C(s) is that the subject may show a measurable response within a short time, usually about 5-10 days, which allows straightforward tracking of the subject's response, e.g., by monitoring viral titer in peripheral white blood cells ("PBMC"), by measuring viral nucleic acid levels in the blood or by measuring a white blood cell population(s) or expression of a cytokine or interleukin by e.g., white blood cells or a subset(s) thereof. One may monitor one or more immune cell subsets, e.g., NK, LAK, dendritic cells or cells that mediate ADCC immune responses, during and after intermittent dosing to monitor the subject's response and to determine when further administration of the F1C is indicated. These cell subsets are monitored as described herein, e.g., by flow cytometry.

For any of the treatments or methods described herein, prolonged beneficial effects or a sustained immune response by a subject may result from a single administration or short course, e.g., about 1-5 days or about 8 days to about 4 months, of continuous or intermittent administration of a F1C. A single administration means that a F1C is administered to the subject in one, two, three or more doses within a 24 hour period and no further administration of any F1C to the subject occurs for at least about 4-90 days, e.g., about for at least about 30 days to about 2 months, or for about 1.5, 2, 3, 4, 5, 6 or more months. Prolonged beneficial effects or immune responses may also persist after a short course of treatment has been completed (e.g., daily dosing for 2, 3, 4, 5 or 6 days) and the subject is no longer receiving any F1C, or, in some cases, any other therapeutic treatment to treat the primary cause of the subject's pathological condition. Such beneficial effects can persist for more than about 5-30 days, e.g., for at least about 21, 28, 42, 56, 70, 84, 98, 112 or more days. Thus, administration of a F1C provides a method to help protect a subject against progression of an infection or against adverse consequences of unwanted immune reactions, e.g., inflammation or immunosuppression or as disclosed herein, without any dosing of the compound for at least 1, 2 or 3 months after an initial dosing protocol.

Other intermittent dosing embodiments comprise administering to a subject having or susceptible to a condition as described herein an effective amount of a F1C using an initial induction or high dosing regimen. The high dosing regimen may comprise, e.g., 1, 2, 3, 4, 5, 6, 7 or more daily doses of about 4 to about 40 mg/kg that are administered daily, every other day, every $3^{rd}$ day, every $4^{th}$ day or every $5^{th}$ day. Then, the subject is not dosed with a F1C for a period, e.g., about 5, 7, 14, 21, 28, 42, 56, 70, 84, 98, 112 or more consecutive days. Then a lower daily dosing regimen is administered to the subject, e.g., about 0.2 mg/kg to about 4 or about 6 mg/kg, essentially as described for the high dosing regimen. Alternatively, this low dosing regimen may comprise 1, 2, 3, 6 or more rounds of a low to moderate initial level, e.g., about 2 to about 10 mg/kg/day, optionally followed by subsequent rounds of daily dosing that decrease the initial low to moderate level by about 10%, 20%, 30%, 40% or more in each subsequent round of treatment, which is continued until administration is discontinued. These embodiments can be used with any of the dosing protocols described herein.

Dosages of the F1C, continuous or intermittent dose protocols, routes of administration and the use of combination therapies with other standard therapeutic agents or treatments could be applied essentially as described above for any of the diseases or conditions that are disclosed herein. Thus, the F1Cs may be administered prophylactically or therapeutically in chronic or acute conditions. In acute conditions, the F1Cs may also be administered at the time of occurrence or relatively soon after an acute event such as the onset of surgery, a migraine or the occurrence of trauma, e.g., a central nervous system injury, a radiation exposure or treatment, a cerebral stroke or myocardial infarction. For acute events, a F1C may thus be administered concurrently, e.g., within about 15 minutes or about 30 minutes or about 45 minutes of the onset or occurrence of the acute event, or at a later time, e.g., at about 1, 2, 3, 4, 5, 6, 7, 8, 9, 10, 11, 12, 13, 14, 15, 16, 18, 20, 22, 24, 26, 28, 30, 36, 42, 48, 54, 60, 72, 84, 96, 108 or 120 hours after the onset or occurrence of the acute event or at any range of times defined by any two of these later times. The F1Cs may thus be administered beginning at about 4-120 hours, about 6-120 hours, about 8-48 hours, 8-24 hours, 8-12 hours, 10-12 hours, 10-14 hours, 10-16 hours, about 10-24 hours, 12-14 hours, about 12-16 hours, about 12-20 hours, about 13-16 hours, about 13-20 hours, about 14-16 hours, about 14-20 hours, about 24-48 hours, about 48-72 hours or about 72-96 hours after an acute event starts, occurs or is believed to have begun, e.g., after a surgical procedure has been completed, after a subject or human has suffered an infarction or a nervous system injury or after a radiation treatment or exposure has ended or after a cytotoxic chemotherapy or a myelosuppressive cancer chemotherapy has been administered to the subject.

Alternatively, the F1Cs may be administered before, e.g., beginning within about 15 minutes, about 30 minutes or about 45 minutes before the onset or occurrence of a planned or anticipated acute event, or at an earlier time, e.g., at about 1, 2, 3, 4, 5, 6, 7, 8, 9, 10, 11, 12, 13, 14, 15, 16, 18, 20, 22, 24, 26, 28, 30, 36, 42, 48, 54, 60, 72, 84, 96, 108 or 120 hours before the onset or occurrence of the acute event. The F1Cs may thus be administered at about 6-120 hours, about 8-48 hours, about 10-24 hours, about 10-16, or about 12-16 hours before the planned or anticipated acute event, e.g., before a planned surgery or a radiation treatment starts or occurs. Such treatments can be continued during or after the planned or anticipated event. Typically such events will be biological insults that can potentially lead to death, especially if untreated, or significant injury, which may be difficult to fully recover from, e.g., a serious cerebral infarction or exposure to a potentially lethal radiation dose.

Formulations and Compositions for Preparing Formulations.

Invention embodiments include formulations described here and elsewhere in this disclosure. While it is possible for the F1C(s) to be administered to a subject or incubated with a subject's cells in vitro as the compound alone, it is usual to use F1C in a formulation or at least in a composition that contains 1, 2, 3, 4, 5, 6 or more excipients. The formulations, which are useful for veterinary or human pharmaceutical use, comprise at least one F1C, together with 1, 2, 3, 4, 5, 6 or more excipients and optionally one or more additional therapeutic ingredients. The formulations can contain one or more classes of excipients such as solubilizers, surfactants, co-solvents, complexation agents, lubricants, binding agents or binders, bulking agents, preservatives, buffers, disintegrants, colorants, sweeteners, souring agents, glidants, flavorants, flavor enhancers, oils such as hydrogenated oils, polymers such as starches, effervescent couples, amino acids, monosaccharides, disaccharides, oligosaccharides, dyes or colorants.

Exemplary effervescent couples include sodium bicarbonate and citric acid. Exemplary monosaccharides, disaccharides and oligosaccharides include sorbitol, glucose, dextrose, fructose, maltose, xylitol, sucrose, lactose, glucose, galactose, mannitol, dextrates and maltodextrins. Glidants include silicone dioxide. Lubricants include magnesium stearate. Flavorants include strawberry aroma, raspberry aroma, cherry flavor, magnasweet 135, key lime flavor, grape flavor, trusil art 5-11815, fruit extracts and prosweet. Flavor enhancers and sweeteners include aspartame, sodium saccharine, sorbitol, glucose and sucrose. Souring agents include citric acid.

The invention includes compositions comprising one or more pharmaceutically acceptable excipients or carriers. The compositions are used to prepare formulations suitable for human or animal use. Formulations may be designed or intended for oral, rectal, nasal, topical or transmucosal (including buccal, sublingual, ocular, vaginal and rectal) and parenteral (including subcutaneous, intramuscular, intravenous, intradermal, intrathecal, intraocular and epidural) administration. In general, aqueous and non-aqueous liquid or cream formulations are delivered by a parenteral, oral or topical route. In other embodiments, the F1C(s) may be present as an aqueous or a non-aqueous liquid formulation or a solid formulation suitable for administration by any route, e.g., oral, topical, buccal, sublingual, parenteral, aerosol, a depot such as a subcutaneous depot or an intraperitoneal or intramuscular depot or a rectal or vaginal suppository. The preferred route may vary with, for example, the subject's pathological condition or weight or the subject's response to therapy with a F1C or other therapy that is used or that is appropriate to the circumstances. The F1C formulations can also be administered by two or more routes, e.g., subcutaneous injection and buccal or sublingual, where these delivery methods are essentially simultaneous or they may be essentially sequential with little or no temporal overlap in the times at which the compound is administered to the subject.

The formulations include those suitable for the foregoing administration routes. The formulations may conveniently be presented in unit dosage form and may be prepared by any of the methods known in the art of pharmacy. Techniques, dosage forms and excipients such as binders, diluents, disintegrants, viscosity enhancers, stabilizing agents, water absorbing agents, suspending agents and lubricants, are found in, e.g., A. R. Gennaro et al., eds., *Remington: The Science and Practice of Pharmacy*, Lippincott Williams & Wilkins., Baltimore, Md. 2000, $20^{th}$ edition; Nema et al., *PDA J. Pharm. Sci. Tech.* 1997 51:166-171; *Pharmaceutical Coating Technology*, 1995, G. Cole, et al., editors, Taylor & Francis, ISBN 0 136628915; *Pharmaceutical Dosage Forms*, 1992 $2^{nd}$ revised edition, volumes 1 and 2, H. A. Lieberman, et al., editors, Marcel Dekker, ISBN 0824793870; *Pharmaceutical Preformulation*, 1998, pages 1-306, J. T. Carstensen, Technomic Publishing Co. ISBN 1566766907; *Encyclopedia of Pharmaceutical Technology*, volumes 1, 2 and 3, $2^{nd}$ edition, 2002, J. Swarbrick and J. C Boylan, editors, Marcel Dekker, Inc., New York, N.Y.; and A. H. Kibbe, ed. *Handbook of Pharmaceutical Excipients*, $3^{rd}$ ed., 2000, American Pharmaceutical Association, Washington, D.C.

Methods to make invention formulations include the step of bringing into association or contacting a F1C(s) with one or more excipient, such as one described herein or in the cited references. In general the formulations are prepared by uniformly and intimately bringing into association the F1C(s) with liquid excipients or finely divided solid excipients or both, and then, if appropriate, shaping the product.

Formulations suitable for oral administration are prepared as discrete units or unit doses such as capsules, soft gelatin capsules (softgels), cachets, tablets or caplets each containing a predetermined amount of the F1C(s). F1C formulations can also be present as a powder or granules or as a solution or a suspension, colloid or gel in an aqueous liquid or base or in a non-aqueous liquid or base; or as an oil-in-water liquid emulsion or a water-in-oil liquid emulsion. The F1C formulations may also be a bolus, electuary or paste. Suspension formulations will typically contain about 0.5% w/w or about 1% w/w to about 5%, 10%, 15% or 20% w/w of the F1C, which can be for parenteral use or for other routes of administration, e.g., oral softgels.

A tablet is made by compression or molding, optionally with one or more accessory ingredients. Compressed tablets may be prepared by compressing in a suitable machine the F1C(s) in a free-flowing form such as a powder or granules, optionally mixed with a binder, lubricant, inert diluent, preservative, surface active or dispersing agent. Molded tablets may be made by molding in a suitable machine a mixture of the powdered or granulated F1C and one or more excipients, which are optionally moistened, with an inert liquid diluent or excipient. The tablets may optionally be coated or scored and optionally are formulated so as to provide slow or controlled release of the F1C(s) therefrom. An exemplary tablet or caplet formulation suitable for buccal or sublingual delivery of a F1C to a subject's tissues comprises about 25 or 50 mg of a F1C comprising per 25 mg of the F1C about 6.2 mg povidone, about 0.62 mg magnesium stearate, about 45 mg mannitol and about 48 mg of compressible sucrose.

For formulations adapted for administration to the eye or other external tissues e.g., the mouth, oral mucosa or skin, the formulations can be applied as a topical ointment or cream or sterile eye drops containing the F1C(s) in an amount of, for example, about 0.075 to about 20% w/w (including F1C(s) in a range between about 0.1% and 20% in increments of 0.1% w/w such as about 0.6% w/w, about 0.7% w/w, about 1% w/w, about 1.5% w/w, about 2% w/w, about 2.5 w/w, about 3% w/w, about 5% w/w, about 7% w/w, about 10% w/w etc.), including about 0.2 to 15% w/w and about 0.5 to 10% w/w. When formulated in an ointment, the F1C(s) may be employed with either a paraffinic or a water-miscible ointment base. Alternatively, they may be formulated in a cream with an oil-in-water cream base. Ocular administration formulations are usually sterile and include a F1C(s) dissolved or suspended in a suitable excipient(s), including an aqueous solvent for a F1C(s) that comprise at least about 0.5, one, two or more charges at pH values near neutrality, e.g., about pH 6-8. The F1C(s) is typically present in such formulations in a concentration of about 0.5-20% w/w, about 1-10% w/w or about 2-5% w/w.

If desired, the aqueous phase of a cream base may include, for example, at least 30% w/w of a polyhydric alcohol, i.e. an alcohol having two or more hydroxyl groups such as propylene glycol, butane 1,3-diol, butane 1,4-diol, mannitol, sorbitol, glycerol and a polyethylene glycol (including, e.g., PEG 300 and PEG 400) and mixtures thereof. The topical formulations may include a compound that enhances absorption or penetration of the F1C(s) through the skin or other affected areas. Examples of such dermal penetration enhancers include dimethyl sulphoxide and related analogs.

The oily phase of the emulsion formulations may be constituted from known excipients in a known manner. While the phase may comprise an emulsifier or emulgent, it typically comprises a mixture of at least one emulsifier with a fat or an oil or with both a fat and an oil. A hydrophilic emulsifier may be included together with a lipophilic emulsifier, which acts as a stabilizer. Some embodiments include both an oil and a fat. Together, the emulsifier(s) with or without stabilizer(s) make up the so-called emulsifying wax, and the wax together with the oil and fat make up the so-called emulsifying ointment base, which forms the oily dispersed phase of the cream formulations.

Emulgents and emulsion stabilizers suitable for use in the formulations include Tween60™, Span80™, cetostearyl alcohol, benzyl alcohol, myristyl alcohol, glyceryl monostearate and sodium lauryl sulfate. Other excipients include emulsifying wax, propyl gallate, citric acid, lactic acid, polysorbate 80, sodium chloride, isopropyl palmitate, glycerin and white petrolatum.

The choice of suitable oils or fats for the formulation is based on achieving the desired cosmetic properties. Creams are generally a non-greasy, non-staining and washable products with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used. These may be used alone or in combination depending on the properties required. Alternatively, high melting point lipids such as white soft paraffin and/or liquid paraffin or other mineral oils are used.

Formulations suitable for topical administration to oral mucosa include lozenges or tablets comprising the F1C(s) in a flavored basis or a monosaccharide or disaccharide such as sucrose, lactose or glucose and acacia or tragacanth; pastilles comprising the F1C(s) in an inert basis such as gelatin and glycerin, or sucrose and acacia; and mouthwashes comprising the F1C(s) in a suitable liquid excipient(s). In some embodiments, the lozenges or tablets optionally comprise the property of rapid dissolution or disintegration, e.g., disintegration within about 15 seconds to about 2 minutes, while in others, the lozenges or tablets comprise the property of slower dissolution or disintegration, e.g., disintegration within about 2 minutes to about 10 minutes or more.

Formulations for rectal administration may be presented as a suppository with a suitable base comprising for example cocoa butter or a salicylate.

Formulations suitable for vaginal administration may be presented as pessaries, tampons, creams, gels, pastes, foams or spray formulations containing in addition to the F1C(s) such excipients as are known in the art to be appropriate.

Formulations suitable for parenteral administration include aqueous and non-aqueous sterile injection solutions which may contain anti-oxidants, buffers, bacteriostats, salts (e.g., NaCl, potassium or sodium carbonate or bicarbonate or potassium or sodium phosphates) and solutes which render the formulation isotonic with the blood of the intended subject; and aqueous and non-aqueous sterile suspensions which may include suspending agents or thickening agents. In general, the F1C that is present in liquid compositions or formulations is completely dissolved in aqueous or non-aqueous excipients. However, in some embodiments, e.g., transient compositions or some formulations, the F1C is partially dissolved while the remaining portion is present as a solid, which can be a suspension or a colloid.

Formulations suitable for parenteral delivery of F1Cs to subjects such as humans or animals typically comprise 1, 2, 3, 4, 5, 6 or more excipients. Exemplary embodiments include (1) any two, three or four of propylene glycol, PEG200, PEG300, ethanol, benzyl alcohol and benzyl benzoate and (2) any two, three or four of propylene glycol, PEG100, PEG200, PEG300, PEG400, benzyl alcohol and benzyl benzoate. Typically such formulations will contain both propylene glycol and one or more PEGs, e.g., PEG100, PEG200, PEG300 or PEG400, which enhance the solubility of the F1C by a cosolvent effect.

Formulations, or compositions disclosed herein for use to make formulations suitable for administration by the routes disclosed herein optionally comprise an average particle size in the range of about 0.01 to about 500 microns, about 0.1 to about 100 microns or about 0.5 to about 75 microns. Average particle sizes include a range between 0.01 and 500 microns in 0.05 micron or in 0.1 micron or other increments, e.g., an average particle size of about 0.05, 0.1, 0.2, 0.3, 0.4, 0.5, 0.7, 1, 1.5, 2.0, 2.5, 3.0, 3.5, 4.0, 4.5, 5.0, 5.5, 6, 7, 8, 9, 10, 15, 20, 25, 30, 35, 40, 50, 60, 75, 85, 100, 120, 150, etc. microns). The F1C itself that is used to make a formulation can have one, two or more of these average particle sizes. When F1Cs or compositions that comprise a F1C are used as intermediates to make a formulation, they may comprise one, two, three or more of these average particle sizes, or size ranges. In preparing any of the compositions or formulations that are disclosed herein and that comprise a F1C (and optionally one or more excipients), one may optionally mill, sieve or otherwise granulate the compound or composition to obtain a desired particle size, e.g., as described above.

Milling or micronization by any other method may occur before or after the F1C is contacted with one or more excipients. For example, one may mill a F1C to obtain an average particle size (or diameter) of about 0.05-50 μM or about 0.5-10 μM (e.g., about 0.02, 0.04, 0.05, 0.07, 0.1, 0.5, 1, 1.5, 2, 2.5, 5, 10, 15, 20, 30, 40, 50, 60, 80, 100 or 120 μM average particle size or diameter) before contacting the milled F1C with a liquid or solid excipient. In some cases the F1C is milled or sieved to obtain an average particle size of about 5 μm or about 10 μm before it is contacted with a solid or liquid excipient(s) to obtain a solution or suspension or a powder suitable for making a tablet, capsule or other dosage form as described herein or in the cited references. Micronized compound may be prepared using any suitable process for obtaining small particles, e.g., controlled precipitation from a solution, micronizing or milling, a number of which are known in the art. The micronized particles may include a percentage of particles that are less than or equal to about 0.1-20 μm in diameter. Ranges of average particle sizes include F1Cs of about 0.04-0.6 μm, about 0.04-1.0 μm, about 0.05-0.6 μm, about 0.05-1.0 μm, about 0.1-0.4 μm, about 0.5-1 μm, about 1-20 μm or about 2-50 μm.

As used herein, reference to an average particle size or an average particle diameter means that the material, e.g., a F1C(s), an excipient(s) or a composition that comprises both, is ground, milled, sieved or otherwise treated so as to comprise the specified average size. It is to be understood that some particles may be larger or smaller, but the composition or the F1C(s) will comprise a significant proportion of the material with the specified size or within an acceptable range of the specified size, e.g., at least about 70% or about 80% of the particles within about 30% to about 50% of the average size or diameter. Micronization methods include milling by ball mills, pin mills, jet mills (e.g., fluid energy jet mills) and grinding, sieving and precipitation of a compound(s) from a solution, see, e.g., U.S. Pat. Nos. 4,919,341, 5,202,129, 5,271,944, 5,424,077 and 5,455,049. Average particle size is determined by known methods, e.g., transmission electron microscopy, scanning electron microscopy, light microscopy, X-ray diffractometry, light scattering methods or Coulter counter analysis.

Thus, the F1Cs may comprise a powder that consists of one, two or more of these average particle sizes and the powder may be contacted with a solid excipient(s), suitably mixed and optionally compressed or formed into a desired shape. Alternatively, such a F1C(s) is contacted with a liquid excipient(s) to prepare a liquid formulation or a liquid composition that is incorporated into a solid formulation. Suitable micronized formulations thus include aqueous or oily solutions or suspensions of the F1C(s).

Formulations suitable for aerosol administration typically will comprise a fine powder, e.g., having an average particle size of about 0.1 to about 20 microns or any one, two or more of the average particle sizes within this range that are described above. The powder is typically delivered by rapid inhalation through the nasal passage or by inhalation through the mouth so as to reach the bronchioles or alveolar sacs of the lungs.

Formulations suitable for aerosol, dry powder or tablet administration may be prepared according to conventional methods and may be delivered with other therapeutic agents such as compounds heretofore used in the treatment or prophylaxis of viral or other infections as described herein. Such formulations may be administered, e.g., orally, parenterally (e.g., intravenous, intramuscular, subcutaneous, intradermal, intrathecal), topically, sublingually or by a buccal or sublingual route.

Micronized F1C is useful, e.g., to facilitate mixing, dissolution or uniform suspension of the F1C in one or more liquid or solid excipients, e.g., a PEG such as PEG 300 or PEG 400, propylene glycol, benzyl benzoate, a complexing agent, such as a cyclodextrin (e.g., an α-, β- or γ-cyclodextrin such as hydroxypropyl-β-cyclodextrin). Micronized F1C is also useful to facilitate uniformly distributing drug substance when the micronized compound is contacted with one or more solid excipients (e.g., a filler, a binder, a disintegrant, complexing agent (e.g., a cyclodextrin such as hydroxypropyl-β-cyclodextrin), a preservative, a buffer or a lubricant).

In related embodiments, suitable compositions or formulations comprise a F1C that is present in two or more physical forms. For example, a liquid composition or formulation may comprise a F1C that is present in solution and as undissolved particles, which may be milled as described herein. Alternatively, a solid composition or formulation may comprise a F1C that is present as an amorphous form and as a crystal or in an encapsulated granule. Such encapsulated granules may comprise a slow release type formulation and the F1C that is present may be in one or more physical forms, e.g., liquids or solids as described herein, but usually as a solid in tablets or other solid formulations.

The formulations are presented in unit-dose or multi-dose containers, for example sealed ampules and vials, and may be stored in a freeze-dried (lyophilized) condition requiring only the addition of the sterile liquid excipient, for example water for injection, immediately prior to use. In general, solid, liquid or other formulations or compositions that comprise a F1C, e.g., unit dosages for solid or liquid formulations, are stored in a sealed container, which may optionally be opaque or nearly opaque (e.g., amber or blue glass or brown plastic) to reduce the amount of light that reaches the formulation or composition. Such containers are also optionally sealed, e.g., hermetically sealed, to prevent or limit exchange of air, water or other gases between the containers contents and air. Extemporaneous injection solutions and suspensions are prepared from sterile powders, granules and tablets as described above. Unit dosage formulations are those containing a daily dose or unit daily sub-dose, as recited herein, or an appropriate fraction thereof, of the F1C(s).

It should be understood that in addition to the ingredients particularly mentioned above the formulations of this invention may include other agents or excipients conventional in the art having regard to the type of formulation in question, for example those suitable for oral administration may include flavoring agents. Excipients include liquids, such as benzyl benzoate, cottonseed oil, N,N-dimethylacetamide, a $C_{2-12}$ alcohol (e.g., ethanol), glycerol, peanut oil, vitamin E, poppy seed oil, safflower oil, sesame oil, soybean oil and vegetable oil. Excipients may optionally exclude one or more excipient, e.g., chloroform, dioxane, vegetable oil, DMSO, other excipients or any combination of these. Other excipients are components typically used in the pharmaceutical formulation arts, e.g., one, two or more of fillers, binders, disintegrants, dispersants, preservatives, glidants and lubricants, e.g., povidone, crospovidone, corn starch, carboxymethyl cellulose, hydroxypropyl methylcellulose, microcrystalline cellulose, gum arabic, polysorbate 80, butylparaben, propylparaben, methylparaben, BHA, EDTA, sodium lauryl sulfate, sodium chloride, potassium chloride, titanium dioxide, magnesium stearate, castor oil, olive oil, vegetable oil, buffering agents such as sodium hydroxide, monobasic sodium phosphate, dibasic sodium phosphate, potassium hydroxide, monobasic potassium phosphate, dibasic potassium phosphate, tribasic potassium phosphate, potassium carbonate, potassium bicarbonate, ammonium hydroxide, ammonium chloride, saccharides such as mannitol, glucose, fructose, sucrose or lactose any of which may be compressible or any of which may be spray dried, milled, micronized or otherwise treated to obtained desired characteristics.

Formulations made from or comprising a F1C are optionally stored under conditions that limit the amount of light or water that reaches the formulation, e.g., in a sealed container that holds a formulation or unit dosage form and optionally contains silica gel or activated carbon. Water permeation characteristics of containers have been described, e.g., Containers—Permeation, Chapter, USP 23, 1995, U.S. Pharmacopeial Convention, Inc., Rockville, Md., p. 1787.

The invention further provides veterinary compositions comprising at least one F1C together with a veterinary excipient(s) therefor. Veterinary excipients are materials useful for the purpose of administering the composition and may be solid, liquid or gaseous materials that are otherwise inert or acceptable in the veterinary art and are compatible with the F1C(s). These veterinary compositions may be administered orally, parenterally or by any other desired route.

Invention formulations include controlled release or slow release formulations containing a F1C(s) in which the release of the F1C(s) is controlled or regulated to allow less frequency dosing or to improve the pharmacokinetic or toxicity profile of a given F1C(s). Polymers and other materials that are suitable to prepare controlled release formulations that comprise a F1C have been described, e.g., U.S. Pat. Nos. 4,652,443, 4,800,085, 4,808,416, 5,013,727, 5,188,840.

Formulations may comprise a liposome or lipid complex that comprises or contains a F1C(s). Such formulations are prepared according to known methods, e.g., U.S. Pat. Nos. 4,427,649, 5,043,165, 5,714,163, 5,744,158, 5,783,211, 5,795,589, 5,795,987, 5,798,348, 5,811,118, 5,820,848, 5,834,016 and 5,882,678. The liposomes optionally contain an additional therapeutic agent(s), e.g., amphotericin B, cisplatin, adriamycin, a protease inhibitor, a nucleoside or a nucleotide analog, such as one of those mentioned herein. Formulations that comprise liposomes can be delivered to a subject by any standard route, e.g., oral, aerosol or parenteral (e.g., s.c., i.v. or i.m.).

Invention embodiments include the product made by a process of combining, mixing or otherwise contacting a F1C and one, two or more excipients. Such products are produced by routine methods of contacting the ingredients. Such products optionally contain a diluent, a disintegrant, a lubricant, a binder, or other excipients described herein.

Other embodiments include compositions that transiently occur when a method step or operation is performed. For example, when a F1C, containing less than about 3% w/w water is contacted with an excipient, e.g., a PEG, an alcohol, propylene glycol benzyl alcohol or benzyl benzoate, the composition before addition of one ingredient with another is a non-homogenous mixture. As the ingredients are contacted, the mixture's homogeneity increases and the proportion of ingredients relative to each other approaches a desired value. Thus, invention compositions, which contain less than about 3% w/w or less than about 2% w/w or less than about 1% w/w or less than about 0.5% w/w water can comprise about 0.0001-99% w/w of a F1C and 1, 2, 3 or more excipients. These transient compositions are intermediates that necessarily arise when one makes an invention composition or formulation and they are included in invention embodiments.

When a F1C and an excipient(s) is contacted or mixed, the final composition may comprise a homogenous mixture or it may comprise a mixture that is not homogenous for one or more of the compounds that are present in the composition. Compositions and formulations that are either homogenous or non-homogenous are included in the scope of the invention. Non-homogenous compositions can be used, e.g., to make controlled release formulations.

Invention embodiments include compositions and formulations that comprise less than about 3% water, a F1C and a compound that is not generally considered suitable for human use but is useful to make an invention formulation for veterinary use. Veterinary formulations are compositions useful for the purpose of administering invention compositions to primates, cats, dogs, horses, cows, rabbits and other subjects and may contain excipients acceptable in the veterinary art and are compatible with F1Cs. These veterinary compositions may not always be suitable for human use because they contain an excipient that is not suitable for human use, e.g., an alcohol other than ethanol such as methanol, propanol or butanol. Typically such excipients will be present at relatively low levels, e.g., about 1-30%, usually about 1-5%.

Invention embodiments include non-aqueous compositions and formulations, e.g., unit dosage forms and sterile solutions or suspensions, that comprise about 1-25% w/w of a F1C, about 20-60% w/w propylene glycol, about 15-55% w/w of more or more PEGs, e.g., PEG100 or PEG200, about 0-5% w/w benzyl benzoate, about 0-5% w/w benzyl alcohol and optionally one or more additional excipients. These non-aqueous formulations will usually contain less than about 3%, 2%, 1%, 0.8%, 0.5%, 0.4%, 0.3%, 0.2% or 0.1% w/w of water. In formulations that contain non-aqueous excipients, the F1C will usually be relatively hydrophobic and will usually not contain any easily charged or ionizable moieties such as free carboxyl groups.

F1Cs may be administered to subjects by transmucosal dosing, e.g., by buccal or sublingual administration. The buccal area generally refers to the subject's mouth and pharynx, and the buccal mucosa includes the mucosa of the mouth and pharynx. The sublingual area refers generally to the mucosa below and adjacent to the tongue. Formulations suitable for buccal or sublingual administration typically comprise about 1-100 mg of F1C per unit dose, often about 2-60 mg. Transmucosal dosages may comprise a slow release or a rapid release formulation or tablet that contains about 1, 5, 10, 15, 20, 25, 30, 35, 40, 50 or 60 mg of a F1C. Slow release formulations will generally degrade or release the F1C from the dosage over a period of about 2 minutes to about 60 minutes or more. Rapid release formulations will generally release the F1C over a period of about 4 seconds to about 2 minutes, typically over about 0.1 to about 1 minute. Solid and liquid buccal or sublingual formulations optionally include one, two, three or more excipients such as fillers, binders, lubricants, antioxidants, preservatives, flavoring agents or disintegrants, e.g., lactose, sucrose, mannitol, Tween-80, magnesium stearate, butylated hydroxyanisole, butylated hydroxytoluene, cyclodextrins (e.g., α-cyclodextrins, β-cyclodextrins, γ-cyclodextrins, hydroxypropyl-β-cyclodextrin, β-cyclodextrin ether comprising one or more hydroxybutyl sulfonate moieties, cyclodextrins as described in U.S. Pat.

No. 6,610,671 or U.S. Pat. No. 6,566,347), carbomers, hydrolyzed polyvinylalcohol, polyethylene oxide, polyacrylates, hydroxypropylmethylcellulose, hydroxypropylcellulose, and combinations thereof. Such formulations may be a unit solid such as a tablet or powder or a liquid. Buccal tablets may comprise a concave surface for contacting the buccal mucosa and adhering to it. A buccal or sublingual dosage may comprise a compressed tablet of a substantially uniform mixture of a bioerodible polymeric carrier, which on sustained contact with the oral mucosa, substantially or completely erodes within a predetermined period in the range of about 10 minutes to about 24 hours. In some embodiments, the F1C is administered by a method for administering the compound to the subject, e.g., to a mammal or a human, comprising affixing a unit dosage or tablet to the subject's buccal mucosa in a region at or near the upper gum between the first bicuspid on the left and the first bicuspid on the right (or an alternative location for the dosage unit is the inner lip area opposing the this upper gum area) and optionally allowing the tablet to remain in place until erosion thereof is complete or nearly complete. Exemplary excipients may comprise a combination of polyethylene oxide and a carbomer, e.g., wherein the polyethylene oxide and the carbomer are in an approximately 1:5 to 5:1 ratio by weight.

Tablets or unit dosages for buccal or sublingual delivery may be about 5 mm in diameter and 2 mm in height, so that the unit dosage occupies about 40 mm$^3$. Such dosages will typically weigh less than about 100 mg (e.g., about 5 to 60 mg), with a contact surface area of about 10-30 mm$^2$, e.g., about 15-20 mm$^2$. Such dosages will generally be about 4-10 mm in diameter and about 1-3 mm in height. When a polymer excipient is used, it optionally comprises a polymer having sufficient tack to ensure that the dosage unit adheres to the buccal mucosa for a sufficient time period, e.g., the time period during which drug is to be delivered to the buccal mucosa. The polymeric excipient is gradually "bioerodible," and it hydrolyzes, dissolves, erodes or disintegrates (collectively "erodes") at a predetermined rate upon contact with water or saliva. The polymeric carrier is generally sticky when moist, but not when dry, for convenience in handling. The average molecular weight of the polymer may be about 400 to 1,000,000, or about 1,000 to 100,000. Higher the molecular weight polymers generally erode more slowly.

For these buccal and sublingual dosages, a pharmaceutically acceptable polymer(s) can be used. Such polymers will provide a suitable degree of adhesion and the desired drug release profile, and are generally compatible with the drug to be administered and any other components that may be present in the buccal dosage unit. The polymeric carriers optionally comprise hydrophilic (water-soluble and water-swellable) polymers that adhere to the wet surface of the buccal mucosa. Examples of polymeric carriers that are useful herein include acrylic acid polymers, e.g., those known as "carbomers" (Carbopol™, which may be obtained from B.F. Goodrich, is one such polymer). Other suitable polymers include hydrolyzed polyvinylalcohol; polyethylene oxides (e.g., Sentry Polyox™ water soluble resins, available from Union Carbide); polyacrylates (e.g., Gantrez™, which may be obtained from GAF); vinyl polymers and copolymers; polyvinylpyrrolidone; dextran; guar gum; pectins; starches; and cellulosic polymers such as hydroxypropyl methylcellulose, (e.g., Methocel™, which may be obtained from the Dow Chemical Company), hydroxypropyl cellulose (e.g., Klucel™, which may be obtained from Dow), hydroxypropyl cellulose ethers (see, e.g., U.S. Pat. No. 4,704,285 to Alderman), hydroxyethyl cellulose, carboxymethyl cellulose, sodium carboxymethyl cellulose, methylcellulose, ethyl cellulose, cellulose acetate phthalate, cellulose acetate butyrate, and the like. The carrier may also comprise two or more suitable polymers in combination, for example, a carbomer combined in an approximately 1:5 to 5:1 ratio, by weight, with a polyethylene oxide.

Buccal dosages may contain only the F1C and the polymer(s). However, it may be desirable in some cases to include one or more additional excipients. For example, a lubricant may be included to facilitate the process of manufacturing the dosage units; lubricants may also optimize erosion rate and drug flux. If a lubricant is present, it may optionally represent about 0.01 wt. % to about 2 wt. %, or about 0.01 wt. % to 0.5 wt. %, of the dosage unit. Suitable lubricants include, but are not limited to, magnesium stearate, calcium stearate, stearic acid, sodium stearylfumarate, talc, hydrogenated vegetable oils and polyethylene glycol. However, modulating the particle size of the components in the dosage unit and/or the density of the unit can provide a similar effect, e.g., improved manufacturability, and optimization of erosion rate and drug flux without addition of a lubricant.

Other excipients are also optionally incorporated into buccal unit dosages. Such additional optional excipients include, one or more disintegrants, diluents, binders, enhancers, or the like. Examples of disintegrants that may be used include, but are not limited to, cross-linked polyvinylpyrrolidones, such as crospovidone (e.g., Polyplasdone™ XL, which may be obtained from GAF), cross-linked carboxylic methylcelluloses, such as croscarmelose (e.g., Ac-di-sol™, which may be obtained from FMC), alginic acid, and sodium carboxymethyl starches (e.g., Explotab™, which may be obtained from Edward Medell Co., Inc.), methylcellulose, agar bentonite and alginic acid. Suitable diluents are those which are generally useful in pharmaceutical formulations prepared using compression techniques, e.g., dicalcium phosphate dihydrate (e.g., Di-Tab™, which may be obtained from Stauffer), sugars that have been processed by cocrystallization with dextrin (e.g., co-crystallized sucrose and dextrin such as Di-Pak™, which may be obtained from Amstar), lactone, calcium phosphate, cellulose, kaolin, mannitol, sodium chloride, dry starch, powdered sugar and the like. Binders, if used, are those that enhance adhesion. Examples of such binders include, but are not limited to, starch, gelatin and sugars such as sucrose, dextrose, molasses, and lactose. Permeation enhancers may also be present in the novel dosage units in order to increase the rate at which the active agent passes through the buccal mucosa. Examples of permeation enhancers include, but are not limited to, polyethylene glycol monolaurate ("PEGML"), glycerol monolaurate, lecithin, the 1-substituted azacycloheptan-2-ones, particularly 1-n-dodecylcyclaza-cycloheptan-2-one (available under the trademark Azone™ from Nelson Research & Development Co., Irvine, Calif.), lower alkanols (e.g., ethanol), SEPA™ (available from Macrochem Co., Lexington, Mass.), cholic acid, taurocholic acid, bile salt type enhancers, and surfactants such as Tergitol™, Nonoxynol-9™ and TWEEN-80™.

Flavorings are optionally included in buccal or sublingual formulations. Any suitable flavoring may be used, e.g., one or more of mannitol, sucrose, glucose, lactose, lemon, lemon lime, orange, menthol or artificial sweeteners such as aspartame, saccharin sodium, dipotassium glycyrrhizinate, stevia and thaumatin. Some sweeteners such as sucrose may also aid in dissolution or erosion of solid formulations. Coloring agents may also be added, e.g., any of the water soluble FD&C dyes or mixtures thereof, e.g., one or more of FD&C Yellow No. 5, FD&C RED No. 2, FD&C Blue No. 2, etc., food lakes or red iron oxide. In addition such formulations dosages may be formulated with one or more preservatives or bacteriostatic agents, e.g., methyl hydroxybenzoate, propyl hydroxybenzoate, chlorocresol, benzalkonium chloride, or the like.

Other embodiments include solid buccal or sublingual formulations comprising (i) a F1C and (ii) erythritol, (iii) crystalline cellulose and (iv) a disintegrant, e.g., crospovidone. These formulations are capable of buccal disintegration or dissolution and may further comprise mannitol. These formulations may dissolve completely in solely saliva within about 1-10 minutes of administration to a subject. The erythritol is optionally contained in a proportion of about 5-90 parts by weight, based on 100 parts by weight of the solid buccal formulation. The crystalline cellulose is optionally contained in a proportion of about 3-50 parts by weight, based on 100 parts by weight of the formulation. The disintegrant is optionally contained in a proportion of 1-10 parts by weight. In any of the solid buccal or sublingual formulations the ingredients are generally uniformly mixed, although non-uniform mixtures may be used. An exemplary formulation comprises a solid capable of buccal disintegration or dissolution, which comprises (i) about 0.3-50 parts by weight of a F1C, (ii) about 50-80 parts by weight of erythritol, (iii) about 5-20 parts by weight of crystalline cellulose and (iv) about 3-7 parts by weight of a disintegrant, which optionally is one or more of crospovidone, croscarmellose, croscarmellose sodium, carmellose calcium, carboxymethylstarch sodium, low substituted hydroxypropyl cellulose or corn starch. Examples of the crystalline cellulose include products of various grade such as CEOLUS KG801, avicel PH101, avicel PH102, avicel PH301, avicel PH302, avicel RC-591 (crystalline cellulose carmellose sodium) and so on. One crystalline cellulose may be used or two or more species may be used in combination. The disintegrant, e.g., crospovidone, may be used singly or in combination with other disintegrants. Crospovidone includes any cross-linked 1-ethenyl-2-pyrrolidinone homopolymer, and may comprise a polymer of molecular weight of 1,000,000 or more. Examples of commercially available crospovidone include Cross-linked povidone, Kollidon CL, Polyplasdone XL, Polyplasdone XL-10, INF-10 (manufactured by ISP, Inc.), polyvinylpolypyrrolidone, PVPP and 1-vinyl-2-pyrrolidinone homopolymer. The disintegrants are optionally incorporated in a proportion of about 1-15 parts by weight, or about 1-10 parts by weight, or about 3-7 parts by weight, based on 100 parts by weight of the solid formulation.

Some embodiments include a solid buccal or sublingual formulation containing a F1C where unit doses of the formulation substantially or completely disintegrates or erodes within about 20-120 seconds in water at 37° C. or on insertion of the unit dose into the buccal area or upon placement under the tongue. Such formulations may comprise a swellable hydrophilic excipient, a water-soluble or a water-dispersible excipient, e.g., one or more of partially hydrolyzed gelatin, hydrolyzed dextran, dextrin, mannitol, alginates, polyvinyl alcohol, polyvinyl pyrrolidine, water soluble cellulose derivatives, methylcellulose, ethyl cellulose, carboxymethyl cellulose, hydroxymethylcellulose, hydroxypropyl methylcellulose, microcrystalline cellulose, alginates, gelatin, guar gum, gum tragacanth, gum acacia, polyacrylic acid, polymethacrylic acid, polysilicic acid, polylactic acid, polymaleic acid, polyvinyl alcohol, polyethylene glycol, polyvinyl pyrrolidone, nonionic blocked polymers, carbomers, polycarbophils, a water soluble starch, dicalcium phosphate, calcium carbonate, silica or polyethyleneglycol, e.g., PEG1000, PEG2000 or a polyethylene oxide ("PEO"), PEO1000, PEO100000 or PEO5000000.

Other embodiments include the product obtained by storing invention compositions or formulations, e.g., unit dosage forms or compositions used to make formulations, at about 4-40° C. for at least about 30 days, e.g., storage at ambient temperature for about 1-24 months. Invention formulations will typically be stored in hermetically or induction sealed containers for these time periods. Compositions and formulations that comprise a F1C will typically be held in closed or sealed containers, particularly when the composition is a formulation for pharmaceutical or veterinary use.

Typical containers for storage of compositions and formulations that comprise a F1C will limit the amount of water that reaches the materials contained therein. Typically, formulations are packaged in hermetically or induction sealed containers. The containers are usually induction sealed. Water permeation characteristics of containers have been described, e.g., Containers—Permeation, chapter, USP 23 <671>, United States Pharmacopeial Convention, Inc., 12601 Twinbrook Parkway, Rockville, Md. 20852, pp.: 1787 et seq. (1995).

The F1Cs are useful in reestablishing normal immune function in various immune dysregulation or immune suppression conditions, including in subjects having a genetic defect such as cystic fibrosis or sickle cell disease. For example, they are useful to treat, slow progression of or to ameliorate one or more symptoms associated with one or more of an autoimmune condition(s), a inflammation condition(s), neurological or neurodegenerative disease(s).

Clinical indications that have an association with or have a symptom(s) that is consistent or associated with an excessive or unwanted Th2 immune response include, e.g., fatigue, pain, fever or an increased incidence of infection, schizophrenia, acute myelitis, tumor progression, progressive systemic sclerosis, Omenn's syndrome, atopic disease, atopy, allergen hypersensitivity, atopic asthma, atopic dermatitis, burns, trauma (e.g., bone fracture, hemorrhage, surgery), immune responses to xenotransplantation, chronic periodontitis, SLE (systemic lupus erythematosus), discoid lupus erythematosus, osteoporosis, myasthenia gravis, Graves disease, mite-associated ulcerative dermatitis, rheumatoid arthritis and osteoarthritis. Excessive Th2 immune responses are also associated with an unwanted symptom or pathology, e.g., fatigue, pain, fever or an increased incidence of infection, that is associated with aging, allergy and inflammation conditions such as allergic bronchopulmonary aspergillosis in cystic fibrosis patients, allergic respiratory disease, allergic rhinitis, atopic dermatitis, subepithelial fibrosis in airway hyperresponsiveness, chronic sinusitis, perennial allergic rhinitis, fibrosing alveolitis (lung fibrosis). This common underlying immune component is at least part of the pathology or symptoms of all of these conditions. This allows a F1C to be effectively used to prevent or treat the condition or to treat or ameliorate one or more symptoms that are associated with these conditions. Thus, in some embodiments, an unwanted or excessive Th2 response is present and amelioration of one or more symptoms associated with this condition is accomplished by administering an effective amount of a F1C according to the methods described herein, e.g., F1C is administered using a formulation and a route of administration essentially as described herein on an intermittent or a daily basis.

Typically, unwanted Th2 immune responses are associated with, or caused by, increased expression of one or more cytokines or interleukins such as one, two, three or more of cortisol, IL-4, IL-5, IL-6, IL-10 and IL-13. Administration of a F1C will generally reduce the expression of one or more of the Th2-associated cytokines or interleukins. At the same time, the compounds generally enhance the expression of one or more cytokines or interleukins associated with Th1 immune responses. Because of their capacity to modulate or to balance Th1 and Th2 immune responses, the compounds are useful for a variety of clinical conditions, e.g., infection, immunosuppression or cancer, where an enhanced Th1 immune response is desired. Effects of the F1Cs in treating, preventing or slowing the progression of the clinical conditions described herein can include one or more of (1) enhancing the Th1 character of a subject's immune response or immune status, (2) increasing the intensity of a Th1 or a Th2 immune response or both and (3) decreasing inflammation or a symptom thereof.

Exemplary conditions where an immune imbalance or an excessive Th1 immune response is involved include autoimmune diseases such as multiple sclerosis, Crohn's disease (regional enteritis), ulcerative colitis, inflammatory bowel disease, rheumatoid arthritis, reactive arthritis, acute allograft rejection, sarcoidosis, type 1 diabetes mellitus, *Helicobacter pylori* associated peptic ulcer, graft versus host disease and Hashimotos' thyroiditis. Because these conditions are associated with a similar type immune dysfunction, a F1C can be effectively used to prevent or treat these conditions or to treat or ameliorate one or more symptoms associated therewith. Thus, in some embodiments, an unwanted or excessive Th1 response is present and amelioration of one or more symptoms associated with this condition is accomplished by administering an effective amount of a F1C according to the methods described herein, e.g., F1C is administered using a formulation and a route of administration essentially as described herein on an intermittent or a daily basis. In other embodiments, a deficient Th1 response is enhanced, which is optionally observed as a detectable increase in one or more of IFNγ, IL-2, IL-12 or IL-18 in Th1 cells or in accessory cells such as a dendritic cell or macrophage. In all of the conditions where an insufficient or excess Th1, Th2, Tc1 or Tc2 response is present, amelioration of one or more symptoms associated with the condition is accomplished by administering an effective amount of a F1C according to the methods described herein.

Thus, in some embodiments, the migration of one or more stem cell types or immune cell subsets such as $CD11C^+$ cells from tissue such as skin or lung through the blood to immune tissue such as lymph nodes or GALT is seen as a transient increase in the level of circulating $CD11C^+$ cells in response to exposure of the subject's tissues to a suitable amount of a F1C. Thus, the level of $CD11C^+$ cells in the blood will generally detectably increase, e.g., a statistically significant increase, plateau and then decrease as migration of the cells to immune tissue subsides. In these embodiments, the proportion of the cells of the stem cell type or the affected immune cell subset is typically relatively low in most physiological immune states, e.g., normal or abnormal immune conditions, compared to the total cell population.

Treatment of a subject with a F1C can result in a change of at least about 20-80% or about 25-50% above or below (e.g., at least 30% or at least 40% above or below) the control or basal level of affected immune cell subsets. For example, increases of more than about 30% in the total numbers of activated $CD8^+$ T cells, e.g., $CD8^+$, $CD69^+$, $CD25^+$ T cells, $CD8^+$, $CD69^+$, $CD25^-$ T cells or $CD8^+$, $CD69^-$, $CD25^+$ T cells, can occur by 7 days after a single dose of a F1C to a subject. Such increases may be greater than 50%, 60% or 100% in the total numbers of activated $CD8^+$ T cells or subsets of activated $CD8^+$ T cells in individual subjects. Typically such increases are about in the total numbers of activated $CD8^+$ T cells or subsets of activated $CD8^+$ T cells averages about 30-40%, with individual subjects experiencing increases over 100% in the numbers of activated $CD8^+$ T cells per unit blood volume compared to the basal level.

Administration of the F1Cs can affect other immune cell subsets. For example, the concentration of circulating $CD4^+$, $CD69^+$, $CD25^-$ (Th1 helper cells) and $CD8^+$, $CD16^+$, $CD38^+$ LAK cells or CD8-, $CD16^+$, $CD38^+$ LAK cells typically increases during or after the course of dosing a subject with a F1C. Also, $CD8^-$, $CD16^+$, $CD38^+$ and $CD8^+$, $CD16^+$, $CD38^+$ (ADCC effector cells) and low side scatter $Lin^-$, $DR^+$, $CD123^+$ (dendritic precursors) or low side scatter $Lin^-$, $DR^+$, $CD11c^+$ (dendritic cells or precursors) may show modest to significant increases.

In subjects that are immunosuppressed, e.g., from certain infections (e.g., viral (HIV, HCV), bacterial infection or parasite infection) or from chemotherapy (e.g., an antiviral therapy, a cancer chemotherapy or a radiation therapy), administration of the F1Cs to the subject results in a favorable shift in the balance of Th1 or Th2 responses the subject can mount in the face of immunosuppression. When Th1 responses are suboptimal or insufficient, treatment with a F1C results in enhancement of Th1 responses or a reduction in Th2 responses. Conversely, when Th2 responses are suboptimal or insufficient, treatment with a F1C results in enhancement of Th2 responses, which may occur with a concomitant modulation (increase or decrease) in Th1 responses. The F1Cs can thus be used to shift the nature of a subject's immune response to result in a more balanced immune response from immunosuppression. Alternatively, the compounds can selectively suppress inappropriate or unwanted immune responses. Enhanced Th1 responses appears to be at least partly due to one or more of (i) a reduction in biological restraints, e.g., high levels of IL-4 or IL-10, on Th1 functions by preexisting primed Th1 effector cells, (ii) enhanced differentiation of Th0 cells to Th1 cells or enhanced responses mediated by Th1 cells, (iii) enhanced function of accessory cell function, e.g., antigen presentation by dendritic cells, dendritic precursor or progenitor cells or by macrophages or their precursors or progenitors, (iv) enhanced proliferation and differentiation of Th1 precursor or progenitor cells, (v) enhanced IL-12 expression in dendritic cells or their precursors, which results in enhanced differentiation of Th1 cells from Th0 precursors, (vi) enhanced expression or activity of factors associated with Th1 functions, e.g., IL-2, gamma interferon (γIFN or IFNγ), IL-18 or lymphotoxin.

An aspect of the invention methods is an alteration in the expression of IL-4 or IL-10 that occurs after administration of a F1C to a subject. A consistent observation is that extracellular IL-4 or IL-10 levels rapidly decrease to levels that are undetectable by ELISA. Intracellular IL-10 levels are reduced to levels that are near or below the limits of detection by flow cytometry. The administration of a F1C to a subject thus provides a means to inhibit either or both of these interleukins. Such inhibition may be associated with enhancement of Th1 immune responses relative to Th2 or Th0 responses, e.g., in subjects where Th1 responses are suppressed (e.g., from viral, bacterial or parasite infection (HIV, HCV, etc) or chemotherapy) or are otherwise suboptimal. In many subjects, levels of either IL-4 or IL-10, usually IL-10, before dosing with a F1C is low or undetectable. In these subjects, dosing with the F1C results in a rapid drop in the interleukin that is detectable, usually IL-4.

Clinical conditions are described in more detail below where the F1Cs are useful for treating, preventing, slowing the progression of, or ameliorating one or more symptoms associated with the described conditions. In any these conditions, any F1C disclosed herein can be used according to one or more of the dosing methods that are disclosed herein. For these conditions, dosages for the F1Cs, formulations and routes of administration are as described herein. Additional information regarding these and other clinical conditions or symptoms that can be treated, prevented or ameliorated with the F1Cs are found at e.g., *The Merck Manual*, 17$^{th}$ edition, M. H. Beers and R. Berkow editors, 1999, Merck Research Laboratories, Whitehouse Station, N.J., ISBN 0911910-10-7, or in other references cited herein.

Responses to treatment of a subject having a condition disclosed herein with a F1C is optionally monitored by observing changes in one or more immune or other appropriate clinical parameters, e.g., as described herein or in D. S. Jacobs et al., editors, *Laboratory Test Handbook*, 4$^{th}$ edition, pages 11-686, Lexi-Comp Inc., Hudson, Ohio, ISBN 0-916589-36-6, or in any of the references cited herein, or by monitoring the progression or severity of the underlying condition according to known methods, e.g., J. B. Peter, editor, *Use and Interpretation of Laboratory Tests in Infectious Disease*, 5$^{th}$ Edition, pages 1-309, 1998, Specialty Laboratories, Santa Monica, Calif., ISBN 1-889342-13-0.

Infection Treatments.

In some embodiments, the F1C(s) is administered to a subject who has a pathogen infection, such as a viral, bacterial, fungal, yeast, intracellular parasite or extracellular parasite infection. The F1Cs can be considered for use in a broad scope of infections (see, e.g., J. B. Peter, editor, *Use and Interpretation of Laboratory Tests in Infectious Disease*, 5$^{th}$ edition, Specialty Laboratories, Santa Monica, Calif. 90404, 1998, pages 1-271), since the compounds generally enhance Th1 immune responses and/or reduce Th2 immune responses and/or reduce inflammation or its symptoms. Difficulty in treating many infections, e.g., progressive toxoplasmic encephalitis, malaria, tuberculosis, Leishmaniasis and schistosomiasis, often appear to be associated with one or more of an unwanted Th2 immune responses, a suboptimal Th1 response or the development of resistance of the infectious agent to antimicrobial agents. For example, in disseminated or diffuse tuberculosis, a reduced Th2 response would be desirable to allow a patient to slow progression of the disease or to clear infected cells more efficiently. In treating chloroquine resistant or sensitive malaria, the F1Cs have essentially the same activity.

Exemplary viral infections that the F1Cs can be used to treat, prevent or ameliorate include infections by one or more DNA or RNA viruses, or a symptom(s) associated with such infection(s), such as a genogroup, Glade, serotype, serotype subtypes, isolate, strain, subtype or so forth of influenza viruses (e.g., a human influenza A virus, a human influenza B virus, an avian (e.g., chicken, duck, goose) influenza virus, a swine influenza virus or a recombinant avian-swine influenza virus), respiratory syncytial viruses, Rotaviruses, Hantaviruses, animal or human Papillomaviruses (e.g., HPV-1, HPV-2, HPV-6, HPV-7, HPV-10, HPV-11, HPV-13, HPV-16, HPV-18, HPV-32, HPV-33, HPV-35, HPV-39, HPV-42, HPV-43, HPV-44, HPV-45, HPV-61, HPV-72 or HPV-83), Poxviruses, Poliovirus, rabies viruses, human and animal Retroviruses (e.g., HIV-1, HIV-2, LAV, human T-cell leukemia virus I ("HTLV I"), HTLV II, HTLV III, SIV, SHIV, FIV or FeLV), Togaviruses and Flaviviruses (e.g., West Nile Virus, Yellow Fever Virus, Dengue viruses), Herpesviruses (e.g., CMV, EBV, Varicella Zoster Virus (human Herpesvirus 3), Herpes simplex virus 1 ("HSV-1"), Herpes simplex virus 2 ("HSV-2"), human Herpesvirus 6 ("HHV-6"), human Herpesvirus 7, human Herpesvirus 8 ("HHV-8")), measles viruses, mumps viruses, rubella virus, Hepadnaviruses or hepatitis viruses, Adenoviruses, Retroviruses, Togaviruses, Alphaviruses, Arboviruses, Coronaviruses (e.g., human severe acute respiratory syndrome virus, Urbani SARS-associated coronavirus, human respiratory coronaviruses such as HCV-229E or HCV-OC43, including serogroups, genotypes, strains or variants of any of these viruses), Flaviviruses, Filoviruses, Rhinoviruses, Picornaviruses, Papovaviruses, Bunyaviruses, Picornaviruses, Poxviruses, Parvoviruses (e.g., human B19 parvovirus) and/or Pestiviruses.

Specific viruses, including their genogroups, clades, isolates, serotypes, serotype subtypes, strains and so forth, that may establish a virus infection susceptible to the treatment methods disclosed herein include one or more of human hepatitis C virus ("HCV"), human hepatitis B virus ("HBV"), human hepatitis A virus ("HAV"), human hepatitis delta virus, human hepatitis E virus, duck hepatitis virus, woodchuck hepatitis virus, one or more of human herpesviruses 1, 2, 3, 4, 5, 6A, 6B, 7 or 8, human SARS virus, one or more of human papilloma viruses 1-60, e.g., HPV 6, HPV 11, HPV 16, HPV 18, HPV 31, HPV 45, animal papilloma viruses, poliovirus 1, poliovirus 2, poliovirus 3, one or more of Dengue virus types 1, 2, 3 or 4, one or more of foot-and-mouth disease virus 1-7, including serotypes O, A, C, SAT 1, SAT 2, SAT 3 and ASIA 1, one or more of coxsackievirus A1-A22, A24, and B1-B6, one or more of human echovirus 1-9, 11-27 and 29-34, one or more of human enterovirus 68-71, one or more of adenovirus 1-49, one or more of Parainfluenza viruses 1, 2, 3 or 4, Human respiratory coronaviruses 229E and OC43, one or more of Human rotaviruses, BK virus, Bunyamwera virus, California Encephalitis Virus, Central European Encephalitis Virus, encephalomyocarditis virus, Colorado tick fever virus, Cowpox virus, Eastern equine encephalitis virus, Venezuelan equine encephalitis virus, Argentine hemorrhagic fever virus, Bolivian hemorrhagic fever virus, Lacrosse virus, Hantaan virus, JC virus, Lassa virus, Lymphocytic choriomeningitis virus, Kyasanur forest virus, Marburg virus, Measles virus, Mokola virus, Monkeypox virus, Molluscum contagiosum virus, Mumps virus, Murray Valley encephalitis virus, Norwalk virus, O'nyong-nyong virus, Omsk hemmorhagic virus, Orf virus, Rabies virus, RA-1 virus, Western equine encephalitis virus, Japanese encephalitis virus, Yellow Fever Virus, West Nile virus, Variola (smallpox) virus, cowpox virus, Vaccinia virus, Ebola virus, Respiratory syncytial virus, human cytomegalovirus, Rhinoviruses 1-113, Rift Valley fever virus, Ros river virus, Rubella virus, Russian spring-summer encephalitis virus, Sandfly fever viruses, St. Louis encephalitis virus, SV40 virus, vaccinia virus, Varicella-zoster virus, Vesicular stomatitis viruses and Bovine Viral Diarrhea Virus. These and other exemplary viruses have been described. See, for example B. N. Fields, et al., editors, *Fundamental Virology*, 3$^{rd}$ edition, 1996, Lippencott-Raven Publishers, see chapter 2 at pages 23-57, including table 4 at pages 26-27, table 5 at pages 28-29, chapter 17 at pages 523-539, chapters 26-27 at pages 763-916, chapter 32 at pages 1043-1108 and chapter 35 at pages 1199-1233, T. G. Ksiazek et al., New Engl. J. Med., electronic publication on Apr. 10, 2003 at www.nejm.org.

In related embodiments, the F1Cs are used to treat, prevent or ameliorate Arbovirus infections, Arenavirus infections, Hantavirus infections and hemorrhagic fever virus infections, or a symptom(s) or complication(s) thereof, in subjects such as humans. In these infections the F1Cs can treat, prevent or ameliorate one or more symptoms including fever, headache, drowsiness, vomiting, stiff neck, mental confusion, muscle trembling, convulsions, and coma. Hemorrhagic fevers in humans are associated with infection by Hantaviruses and Filoviruses such as Ebola and Marburg viruses, which can cause infections that include Korean, Bolivian and Argentinean hemorrhagic fevers, Congo fever and Lassa fever.

Hantavirus infection is a viral disease that rodents can transmit to humans and the infection is associated with serious lung or kidney infection. Symptoms of Hantavirus infection of the lungs include one or more of fever, muscle pain, myalgia, headache, abdominal pain, conjunctival bleeding, diarrhea, or coughing. Hantavirus kidney infection may be mild or severe and is associated with fever, headache, backache, abdominal pain, small bruise-like patches on the whites of the eyes, abdominal rash, impaired kidney function, nausea, loss of appetite, fatigue and intracranial bleeding.

The F1Cs can also be used to treat, prevent or ameliorate infections caused by members of the Poxviridae family, e.g., members of the Orthopoxvirus genus in subjects such as mammals or humans. The compounds can be used to treat, ameliorate or prevent one or more symptoms associated with Orthopoxvirus infections. For example, the variola or smallpox virus causes a serious infection with symptoms that include fever, chills, backache, headache, skin lesions and death. In treating Orthopoxvirus infections such as a variola infection, the F1Cs can result in enhanced efficacy of host factors such as cytokines or interferons such as IFN-α or IFN-γ. The subject may also be optionally treated with another agent such as IFN-γ, a nucleoside analog or a nucleotide analog such as one described herein or in the cited references. Treatment of a subject such as a human who is anticipated to potentially come in contact with a virus, e.g., an Orthopoxvirus such as the variola virus or the vaccinia virus is accomplished by administering a F1C to the subject by, e.g., daily or intermittent dosing, beginning at about 1-14 days before an anticipated potential exposure.

Parasites that can be treated using a F1C(s) include malaria parasites, sleeping sickness parasites and parasites associated with gastrointestinal infections. Exemplary parasite, fungi, yeast and bacterial infections that can be treated, prevented or ameliorated in subjects such as mammals or humans, include ones caused by or associated with species, groups, genotypes, serotypes, strains, genomovars or isolates of gastrointestinal helminths, microsporidia, isospora, cryptococci, cryptosporidia (*Cryptosporidium parvum*), *Trypanosoma* sp. (e.g., *T. brucei, T. gambiense, T. cruzi, T. evansi*), *Leishmania* sp. (e.g., *L. donovani, L. major, L. braziliensis*), *Plasmodium* sp. (e.g., *P. falciparum, P. knowlesi, P. vivax, P. berghei, P. yoelli*), *Ehrlichia* sp. (e.g., *E. canis, E. chaffeensis, E. phagocytophila, E. equi, E. sennetsu*), *Entamoeba* sp., *Babesia microti*, *Bacillus anthracis, Borrelia* sp. (e.g., *B. burgdorferi*), *Brucella* sp. (e.g., *B. militensis, B. abortus*), *Bartonella* sp. (*B. henselae*), *Bordetella* sp. (e.g., *B. bronchiseptica, B. pertussis*), *Burkholderia* sp., (e.g., *B. pseudomallei, B. cepacia*), *Campylobacter* sp., *Clostridium* sp. (e.g., *C. perfringens, C. difficile, C. tetani, C. septicum*), *Chlamidya* sp. (e.g., *C. pneumoniae*), *Francisella* sp. (e.g., *F. tularensis*), *Enterococcus* sp. (e.g., *E. faecalis, E. faecium*), *Enterobacter* sp., *Bacteroides* sp. (e.g., *B. fragilis, B. thetaiomicron*), *Prevotella* sp., *Fusobacterium* sp., *Porphyromonas* sp., *Erysipelothrix rhusiopathiae, Escherichia* sp. (*E. coli*), *Gardnerella vaginalis, Haemophilus* sp. (e.g., *H. somnus, H. influenzae, H. parainfluenzae*), *Klebsiella* sp. (*K. pneumoniae*), *Leptospira* sp., *Legionella pneumonia, Listeria* (e.g., *L. monocytogenes, L. ivanovii*), *Morganella* sp. (e.g., *M. morganii*), *Mycobacterium* sp. (e.g., *M. avium, M. bovis, M. leprae, M. tuberculosis, M. pneumoniae. M. penetrans*), *Mycoplasma* sp. (e.g., *M. fermentans, M. penetrans, M. pneumoniae*), *Neisseria* (e.g., *N. gonorrhoeae, N. meningitidis*), *Nocardia asteroides, Proteus* sp. (e.g., *P. mirabilis, P. vulgaris, P. myxofaciens*), *Providencia* sp. (e.g., *P. rettgeri, P. stuartii*), *Pseudomonas* sp. (*P. aeruginosa*), *Salmonella* sp. (e.g., *S. typhimurium, S. tyhpi, S. paratyhpi, S. dublin, S. enteritidis, S. schottmuelleri, S. hirschfeldii*), *Serratia* sp., *Shigella* sp. (e.g., *S. flexneri, S. sonnei, S. dysenteriae*), *Streptococcus* sp. (e.g., *S. pneumoniae, S. pyogenes, S. faecalis, S. faecium, S. agalactiae, S. mutans, S. sanguis*), *Staphylococcus* sp. (e.g., *S. aureus*), *Rickettsia* sp. (e.g., *R. rickettsii, R. prowazekii, R. tsutsugamushi*), *Treponema* sp. (e.g., *T. pallidum, T. carateum*), *Vibrio* sp. (e.g., *V. cholerae, V. parahaemolyticus, V. mimicus*), *Yersinia* sp. (e.g., *Y. enterocolitica, Y. pestis*), *Pneumocystis* sp. (e.g., *P. carinii*), *Aspergillus* sp. (e.g., *A. fumigatus, A. terreus, A. flavus*), *Candida* sp. (e.g., *C. albicans, C. krusei, C. tropicalis*), *Chlamidya* sp. (e.g., *C. trachomatis*), *Schistosoma* sp. (e.g., *S. mansoni, S. japonicum, S. haematobium*), *Strongyloides stercoralis, Wucheria bancrofti, Brugia* sp. (e.g., *B. malayi, B. timori*), *Trichomonas* sp., (e.g., *T. vaginalis*) and *Taenia* sp., (e.g., *T. pedis, T. solium*).

Human *Aspergillus* infections that can be treated include invasive aspergilliosis, allergic bronchopulmonary aspergillosis, aspergilloma and chronic necrotizing aspergillosis. Bacterial infections that can be treated, prevented or ameliorated thus include infections by intracellular or extracellular gram positive bacteria, gram-negative bacteria, acid fast bacteria, *Mycoplasma* or rickettsial infections (e.g., a rickettsial spotted fever infection or a rickettsial typhus or scrib typhus infection). Other pathogens that are amenable to F1C treatments are as described. See, e.g., J. B. Peter, editor, *Use and Interpretation of Laboratory Tests in Infectious Disease*, 5$^{th}$ Edition, pages 1-309, 1998, Specialty Laboratories, Santa Monica, Calif., ISBN 1-889342-13-0.

Symptoms and conditions associated with infections that the F1C can treat include one or more of sepsis, septicemia, fever, e.g., moderate to high fever, inflammation, pain, e.g., chest pain, muscle pain, joint pain, back pain or headache, chills, itching, rash, skin lesions, erythema, e.g., peripheral erythema, lymphadenopathy, e.g., local, regional or systemic lymphadenopathy, nausea, vomiting, cyanosis, shock, coma, necrosis, hemorrhage, encephalitis, meningoencephalitis, cramping, mild to severe diarrhea, cough, weakness, splenomegaly, anorexia and weight loss. Other symptoms that can be treated are known. See, e.g., *The Merck Manual*, 17$^{th}$ edition, M. H. Beers and R. Berkow editors, 1999, Merck Research Laboratories, Whitehouse Station, N.J., ISBN 0911910-10-7, J. B. Peter, editor, *Use and Interpretation of Laboratory Tests in Infectious Disease*, 5$^{th}$ Edition, pages 1-309, 1998, Specialty Laboratories, Santa Monica, Calif., ISBN 1-889342-13-0.

Cardiovascular Applications.

Any of the F1Cs disclosed herein, may be used to treat, prevent or slow the progression of one or more of congenital heart defects, cardiovascular diseases, disorders, abnormalities and/or conditions, or to ameliorate one or more symptoms thereof in a subject. These include peripheral artery disease, arterio-arterial fistula, arteriovenous fistula, cerebral arteriovenous malformations, aortic coarctation, cor triatum, coronary vessel anomalies, patent ductus arteriosus, Ebstein's anomaly, hypoplastic left heart syndrome, levocardia, transposition of great vessels, double outlet right ventricle, tricuspid atresia, persistent truncus arteriosus, and heart septal defects, such as aortopulmonary septal defect, endocardial cushion defects, Lutembacher's Syndrome, ventricular heart septal defects, cardiac tamponade, endocarditis (including bacterial), heart aneurysm, cardiac arrest, congestive heart failure, congestive cardiomyopathy, paroxysmal dyspnea, cardiac edema, post-infarction heart rupture, ventricular septal rupture, heart valve diseases, myocardial diseases, pericardial effusion, pericarditis (including constrictive and tuberculous), pneumopericardium, postpericardiotomy syndrome, pulmonary heart disease, rheumatic heart disease, ventricular dysfunction, hyperemia, cardiovascular pregnancy complications, cardiovascular syphilis, cardiovascular tuberculosis, arrhythmias such as sinus arrhythmia, atrial fibrillation, atrial flutter, bradycardia, extrasystole, Adams-Stokes Syndrome, bundle-branch block, sinoatrial block, long QT syndrome, parasystole, sick sinus syndrome, ventricular fibrillations, tachycardias such as paroxysmal tachycardia, supraventricular tachycardia, accelerated idioventricular rhythm, atrioventricular nodal reentry tachycardia, ectopic atrial tachycardia, ectopic junctional tachycardia, sinoatrial nodal reentry tachycardia, sinus tachycardia, Torsades de Pointes, and ventricular tachycardia and heart valve diseases such as aortic valve insufficiency, aortic valve stenosis, hear murmurs, aortic valve prolapse, mitral valve prolapse, tricuspid valve prolapse, mitral valve insufficiency, mitral valve stenosis, pulmonary atresia, pulmonary valve insufficiency, pulmonary valve stenosis, tricuspid atresia, tricuspid valve insufficiency, and tricuspid valve stenosis.

The F1Cs can be used to treat, prevent or ameliorate one or more symptoms of myocardial diseases or pathological myocardial or vascular conditions such as alcoholic cardiomyopathy, congestive cardiomyopathy, hypertrophic cardiomyopathy, aortic subvalvular stenosis, pulmonary subvalvular stenosis, restrictive cardiomyopathy, Chagas cardiomyopathy, endocardial fibroelastosis, myocardial fibrosis, endomyocardial fibrosis, Kearns Syndrome, myocardial reperfusion injury, myocarditis, cardiovascular or vascular diseases such as dissecting aneurysms, false aneurysms, infected aneurysms, ruptured aneurysms, aortic aneurysms, cerebral aneurysms, coronary aneurysms, heart aneurysms, and iliac aneurysms, angiodysplasia, angiomatosis, bacillary angiomatosis, Sturge-Weber Syndrome, angioneurotic edema, aortic diseases, Takayasu's Arteritis, aortitis, Leriche's Syndrome, arterial occlusive diseases, arteritis, enarteritis, polyarteritis nodosa, cerebrovascular diseases, disorders, and/or conditions, diabetic angiopathies, diabetic retinopathy, thrombosis, erythromelalgia, hemorrhoids, hepatic veno-occlusive disease, hypertension, hypotension, idiopathic pulmonary fibrosis, peripheral vascular diseases, phlebitis, pulmonary veno-occlusive disease, Raynaud's disease, CREST syndrome, retinal vein occlusion, Scimitar syndrome, superior vena cava syndrome, telangiectasia, atacia telangiectasia, hereditary hemorrhagic telangiectasia, varicocele, varicose veins, varicose ulcer, vasculitis, venous insufficiency and arterial occlusive diseases such as arteriosclerosis, intermittent claudication, carotid stenosis, fibromuscular dysplasias, mesenteric vascular occlusion, Moyamoya disease retinal artery occlusion, thromboangiitis obliterans or atherosclerosis, any of which may be at an early stage or at a more advanced or late stage.

The F1Cs can also be used to treat, prevent or ameliorate one or more symptoms of cerebrovascular diseases, thrombosis, and/or conditions such as carotid artery diseases, cerebral amyloid angiopathy, cerebral aneurysm, cerebral anoxia, cerebral arteriosclerosis, cerebral arteriovenous malformation, cerebral artery diseases, cerebral embolism and thrombosis, carotid artery thrombosis, sinus thrombosis, Wallenberg's syndrome, cerebral hemorrhage, epidural hematoma, subdural hematoma, subarachnoid hemorrhage, cerebral infarction, cerebral ischemia (including transient), subclavian steal syndrome, periventricular leukomalacia, vascular headache, cluster headache, migraine, vertebrobasilar insufficiency, air embolisms, embolisms such as cholesterol embolisms, fat embolisms, pulmonary embolisms or amniotic fluid embolism, thromboembolisms, thrombosis such as coronary thrombosis, hepatic vein thrombosis, retinal vein occlusion, carotid artery thrombosis, sinus thrombosis, Wallenberg's syndrome, and thrombophlebitis.

The F1Cs can also be used to treat, prevent or ameliorate one or more symptoms of vascular ischemia or myocardial ischemias, vasculitis and coronary diseases, including angina pectoris, coronary aneurysm, coronary arteriosclerosis, coronary thrombosis, coronary vasospasm, myocardial infarction and myocardial stunning, cerebral ischemia, ischemic colitis, compartment syndromes, anterior compartment syndrome, myocardial ischemia, reperfusion injuries, peripheral limb ischemia, aortitis, arteritis, Behcet's Syndrome, mucocutaneous lymph node syndrome, thromboangiitis obliterans, hypersensitivity vasculitis, Schoenlein-Henoch purpura, allergic cutaneous vasculitis, Wegener's granulomatosis or metabolic syndrome, which may be accompanied by one, two or more of obesity, insulin resistance, dyslipidemia, hypertension or other related symptoms or conditions.

Exemplary symptoms that the use of the F1Cs can ameliorate include one or more of pain such as arm, jaw or chest pain, edema or swelling, high blood pressure, shortness of breath or dyspnea, e.g., on exertion or while prone, fatigue or malaise and low cardiac injection fraction. In treating a cardiovascular condition in a subject or in improving one or more symptoms thereof, the F1Cs may accomplish one or more of increasing cardiac ejection volume or fraction, decreasing levels of IL-6, decreasing levels of C reactive protein, fibrinogen, cardiac creatinine kinase, increasing fatty acid metabolism or utilization by cardiac tissue, increasing carnityl palmitoyl fatty acid transferase or other cardiac metabolic enzymes, activating potassium dependent calcium channels, vasodilating or enhancing oxygen delivery to ischemic tissues or decreasing levels of scarring or plaque formation that occurs, e.g., after vascular damage. Symptoms associated with a cardiovascular condition such as ischemia that can be ameliorated also include acidosis, expression of one or more immediate early genes in, e.g., glial cells, vascular smooth muscle cells or endothelial cells, neuronal membrane depolarization and increased neuronal extracellular calcium and glutamate concentration. Other biological effects associated with treatment using a F1C may also be monitored, e.g., and increase or decrease of a cell surface antigen, a cytokine or an interleukin as disclosed herein.

Useful biological effects of the F1Cs in cardiovascular indications such as myocardial ischemias also include preventing or reducing heart or vascular cell death and subsequent fibrosis. These effects are associated with a decreased oxidative capacity of heart cells or myocytes, which is associated with a decreased capacity of the cells to metabolize fatty acids efficiently. The compounds enhance fatty acid metabolism and ameliorate the deleterious effects of a limited oxidative capacity.

The F1Cs also can limit inflammation or cell injury that is associated with ischemia or oxygen reperfusion after ischemia. Ischemia, which is a detrimental decrease in oxygenated blood delivery to affected cells or tissues, may arise from a cardiovascular condition or event such as an infarction, or from thermal injury or burns. Ischemia may also arise from accidental or surgical trauma. Reperfusion after cells have become hypoxic for a sufficient period of time can lead to tissue or cell injury that varies from slight to lethal. The compounds can reduce cell or tissue injury or death associated with ischemia and reperfusion, by, e.g., reducing inflammation or the level of a molecule associated with inflammation. Thus, levels of a proinflammatory cytokine or molecule such as leukotriene B4, platelet activating factor or levels of extracellular P-selectin may result from administration of a F1C to a subject who may experience reperfusion injury.

Thus, the compounds can reduce injury or death of, e.g., neuron, cardiac, vascular endothelium, myocardial, pulmonary, hepatic or renal cells or tissues. Without wishing to be bound by any theory, the compounds may act in part by reducing one or more of neutrophil activation, platelet activation, platelet aggregation, endothelial cell activation and neutrophil adherence or adhesion to endothelial cells in these conditions.

The F1Cs are useful to treat autoimmune or abnormal metabolic conditions or disorders, or their symptoms, in subjects such as mammals or humans, that relate to impaired insulin synthesis or use or that relate to abnormal or pathological lipid or cholesterol metabolism or levels. Such conditions and symptoms include polycystic ovarian syndrome, Type 1 diabetes (including Immune-Mediated Diabetes Mellitus and Idiopathic Diabetes Mellitus), Type 2 diabetes (including forms with (1) predominant or profound insulin resistance, (2) predominant insulin deficiency and some insulin resistance, (3) forms intermediate between these), obesity, hyperglycemia and dyslipidemia, unwanted hyperlipidemia conditions such as hypertriglyceridemia and hypercholesterolemias such as hyper-LDL cholesterolemia, (4) unwanted hypolipidemias, e.g., hypo-HDL cholesterolemia or low HDL cholesterol levels and (5) angina pectoris. In diabetes, the compounds are useful to (1) enhance $\beta$-cell function in the islets of Langerhans (e.g., increase insulin secretion), (2) reduce the rate of islet cell damage, (3) increase insulin receptor levels or activity to increase cell sensitivity to insulin and/or (4) modulate glucocorticoid receptor activity to decrease insulin resistance in cells that are insulin resistant. The compounds are thus useful to treat, prevent, ameliorate or slow the progression of a metabolic or cardiovascular condition such as diabetes or hyperglycemia, or a related symptom or condition such as a dyslipidemia in a subject such as a human or a mammal.

The F1Cs can be used to complement or replace deficiencies in one or more steroid or other hormones in subjects that have deficiencies in such hormones. In some cases, the F1Cs have a degree of androgen or estrogen activity and can be used to replace an androgen and/or estrogen deficiency, e.g., in hormone replacement therapies in post menopausal subjects or in unwanted catabolic or wasting conditions such as osteoporosis or conditions such as lupus or asthma that are sometimes treated using glucocorticoids.

Beneficial effects that can the F1Cs can exert on such related symptoms or conditions include improved glucose tolerance, improved glucose utilization, decreased severity or slowed progression of vascular disease (e.g., microvascular or macrovascular disease, including nephropathy, neuropathy, retinopathy, hypertension, cerebrovascular disease and coronary heart disease) or a decreased severity or slowed progression of atherosclerosis, an arteriosclerosis condition (e.g., coronary arteriosclerosis, hyperplastic arteriosclerosis, peripheral arteriosclerosis or hypertensive arteriosclerosis), decreased severity or slowed progression of diabetic osteoarthropathy, skin lesions, rhabdomyolysis, ketosis, detectably decreased generation of islet cell autoantibodies, decreased levels or activity of inflammatory macrophages (foam cells) in atherosclerotic plaques, or detectably decreased expression or levels of one or more of human (or mammalian) angiopoietin-like 3 gene product, apolipoprotein C-1, inducible or constitutive nitric oxide synthase, e.g., in endothelial cells, macrophages or the like, pyruvate dehydrogenase kinase 4, carboxyl ester lipase, cholesteryl ester transfer protein, endothelial lipase, vascular wall lipoprotein lipase, anti-lipoprotein lipase autoantibodies, triglyceride-rich lipoproteins, LDL cholesterol, C-reactive protein, high sensitivity C-reactive protein, fibrinogen, plasma homocysteine, VCAM-1, IL-1 (e.g., IL-1$\beta$), IL-6, a TNF (e.g., TNF$\alpha$), AP-1, NF-$\kappa$B, and IFN-$\gamma$. In these any of these diseases or conditions, the F1Cs can also modulate, e.g., detectably increase, the activity or level of one, two or more of human (or mammalian) LOX-1, apolipoprotein A-1, apolipoprotein A-2, LPDL lipase, hormone sensitive lipase, paraoxonase, brain natriuretic peptide, a brain natriuretic peptide receptor, e.g., Npr1 or Npr3, hepatic lipase, LDL receptor, HDL apolipoprotein E, HDL apoliporpotein J, HDL cholesterol, VLDL receptor, ATP-binding casette transporter 1, leukemia inhibitory factor, CD36, LXR$\beta$, LXR$\beta$, CAR$\beta$, RXR, PPAR$\alpha$, PPAR$\beta$, PPAR$\gamma$ or a lipoprotein lipase, e.g., macrophage lipoprotein lipase. As used herein, obesity includes a human with a body mass index of at least about 25, 26, 27, 28, 29, 30, 31, 32, 33, 34, 35, 36 or greater. Obese mammals or humans that are treated with a F1C may have one or more of the conditions described here and can be treated using the dosages or the continuous or intermittent dosing protocols described herein, e.g., daily doses of about 5 mg or about 10 mg to about 100 mg or about 200 mg by, e.g., an oral or a parenteral route.

The F1Cs are useful in treating insulin resistance and associated symptoms and conditions. Insulin resistance is typically observed as a diminished ability of insulin to exert its biological action across a broad range of concentrations. This leads to less than the expected biologic effect for a given level of insulin. Insulin resistant subjects or human have a diminished ability to properly metabolize glucose or fatty acids and respond poorly, if at all, to insulin therapy. Manifestations of insulin resistance include insufficient insulin activation of glucose uptake, oxidation and storage in muscle and inadequate insulin repression of lipolysis in adipose tissue and of glucose production and secretion in liver. Insulin resistance can cause or contribute to polycystic ovarian syndrome, impaired glucose tolerance, gestational diabetes, hypertension, obesity, atherosclerosis and a variety of other disorders. Insulin resistant individuals can progress to a diabetic state. The compounds can also be used in the treatment or amelioration of one or more condition associated with insulin resistance or glucose intolerance including an increase in plasma triglycerides and a decrease in high-density lipoprotein cholesterol, high blood pressure, hyperuricemia, smaller denser low-density lipoprotein particles, and higher circulating levels of plasminogen activator inhibitor-1. Such diseases and symptoms have been described, see, e.g., G. M. Reaven, *J. Basic Clin. Phys. Pharm.* 1998, 9: 387-406, G. M. Reaven, *Physiol. Rev.* 1995, 75: 47$\beta$-486 and J. Flier, *J. Ann. Rev. Med.* 1983, 34:145-60.

The compounds can thus be used in diabetes, obesity, hyperlipidemia or hypercholesterolemia conditions to reduce body fat mass, increase muscle mass or to lower one or more of serum or blood low density lipoprotein, triglyceride, cholesterol, apolipoprotein B, free fatty acid or very low density lipoprotein compared to a subject that would otherwise be considered normal for one or more of these characteristics. These beneficial effects are typically obtained with little or no effect on serum or blood high density lipoprotein levels. The F1Cs are useful to reduce or slow the rate of myocardial tissue or myocyte damage, e.g., fibrosis, or to enhance cardiac fatty acid metabolism in conditions, such as inflammation, where fatty acid metabolism is depressed or decreased. Elevated cholesterol levels are often associated with a number of other disease states, including coronary artery disease, angina pectoris, carotid artery disease, strokes, cerebral arteriosclerosis, and xanthoma, which the F1Cs can ameliorate or slow the progression or severity of. Abnormal lipid and cholesterol conditions that can be treated include exogenous hypertriglyceridemia, familial hypercholesterolemia, polygenic hypercholesterolemia, biliary cirrhosis, familial combined hyperlipidemia, dysbetalipoproteinemia, endogenous hypertriglyceridemia, mixed hypertriglyceridemia and hyperlipidemia or hypertriglycidemia secondary to alcohol consumption, diabetic lipemia, nephrosis or drug treatments, e.g., corticosteroid, estrogen, colestipol, cholestyramine or retinoid treatments. Dosages, routes of administration and dosing protocols for the F1Cs are essentially as described herein. Where the condition is chronic, the F1Cs will generally be administered to a subject such as a human for a relatively long time period, e.g., for about 3 months to about 10 years or more. Dosages, routes of administration and dosing protocols for the F1Cs are essentially as described herein. Dosing of the compound can be daily or intermittent using a dosing protocol using dosages as described herein, e.g., about 0.01 to about 20 mg/kg of a F1C administered to a subject once or twice per day daily or intermittently. The use of the F1Cs can be combined with one, two or more other suitable treatments, e.g., treatment for cessation of smoking, diet control, e.g., caloric restriction, reduced fat intake or reduced carbohydrate intake, or treatment with fibrates, non-steroidal anti-inflammatory drugs, angiotensin-converting enzyme inhibitors or HMG-CoA reductase inhibitors such as aspirin, clofibrate, fenofibrate, ciprofibrate, gemfibrozil, Simvastatin™, Pravastatin™, Mevastatin™ or Lovastatin™.

The use of any F1C or species in any genus of F1Cs disclosed herein to treat, prevent or ameliorate any of these cardiovascular or metabolic disorders or symptoms will generally use one or more of the routes of administration, dosages and dosing protocols as disclosed herein. Thus, in exemplary embodiments, about 0.5 to about 100 mg/kg or about 1 to about 25 mg/kg, of the F1C will be administered per day by an oral, buccal, sublingual or parenteral route. Such administration can be, e.g., daily for about 5 to about 60 days in acute conditions or it can be intermittent for about 3 months to about 2 years or more for chronic conditions. Alternatively, intermittent dosing can be used essentially as described herein for acute cardiovascular conditions. In some embodiments, for conditions such as ischemia or trauma, administration of the F1C is provided before or as soon after the ischemic or traumatic event as possible, e.g., within about 6 hours of an ischemic or traumatic event or about 12-24 hours before an anticipated ischemic or traumatic event. In other embodiments, administration of the F1C can be delayed for, e.g., about 6, 7, 8, 9, 10, 11, 12, 13, 14, 15, 16, 18, 19, 20, 21, 24, 28, 32, 36, 40, 48 or more hours after an ischemic or traumatic event has occurred and a course of daily or intermittent dosing is initiated of one of these times, or in a range between any of these times after the event. Thus, administration of the F1C can begin at about 10-14 hours, at about 11-13 hours or at about 8-16 hours after the ischemic or traumatic event.

In another aspect of the invention, the F1Cs can be used to prevent, treat or to reduce the severity of vascular or microvascular occlusions in human sickle cell diseases (SCD). SCD is heterogenous and includes subgroups with high transcranial velocities, which is a group with an increased risk of infarctive stroke or cerebral thrombosis. SCD types also include sickle cell-$\beta^+$ thalassemia, sickle cell-$\beta^O$ thalassemia, sickle cell-$\delta\beta^O$ thalassemia and sickle cell-HPFH (hereditary of persistent fetal hemoglobin). Another subgroup of SCD patients is characterized by the presence of a *Plasmodium* parasite infection. SCD is usually accompanied by acute vaso-occlusive episodes such as microvascular occlusions, ischemia and infarctions that arise from adhesion of sickle cells and other blood cell types, e.g., platelets or leukocytes, to vascular endothelial cells. Reduced sickle cell adhesion in response to treatment with a F1C and related responses is facilitated at least in part by decreased production or activity of one or more biological response mediators such as one, two, three or more of thrombospondin, von Willebrand factor, epinephrine, C reactive protein, cAMP, basal cell adhesion molecule/Lutheran (BCAM/Lu), P-selectin, L-selectin, E-selectin, VCAM-1, ICAM-1, fibronectin, annexin V, placenta growth factor, superoxide, CD11α, CD11b, CD11c, CD15, CD18, CD31, CD36, TNFα, NF-κB, IL-1β or IL-6 by endothelial cells or one or more immune cell types as described herein. In treating sickle cell disease, the F1Cs will also increase the activity or levels of one, two or more desired response mediators including fetal hemoglobin, erythropoietin, heme oxygenase, nitric oxide, PPARα, PPARγ or GM-CSF. The F1Cs will thus ameliorate one or more symptoms of sickle cell disease such as anemia, stroke, pain, e.g., chest or abdominal pain, skin ulcers, dyspnea, organ damage, retinopathy or the level of infected red cells in *Plasmodium*-infected subjects. Treatment of acute SCD episodes or of chronic SCD with F1Cs can be combined with other suitable therapies, e.g., inhaled nitric oxide, hydroxyurea treatment, anti-adhesion molecule antibody treatment or analgesic use such as morphine, oxycodone, or codeine. The F1Cs can also be used to reduce cellular damage from reactive oxygen species associated with hydroxyurea treatment, since the F1Cs will enhance cellular antioxidant capacity.

As is apparent from the foregoing, the use of the F1C is optionally combined with one or more additional therapies for cardiovascular or related disorders, e.g., insulin therapy, vascular surgery, cardiac surgery, angioplasty, or treatment with andrenergic blockers, coronary vasodilators, calcium channel blockers, nitrates, angiotensin converting enzyme inhibitors, anti-hypertensives, anti-inflammatory agents, diuretics, anti-arrhythmia agents, thrombolytic agents, enzyme inhibitors such as hydroxymethylglutaryl CoA reductase inhibitors or xanthine oxidase inhibitors. Exemplary hydroxymethylglutaryl CoA reductase inhibitors include statins such as mevastatin, lovastatin, pravastatin, simvastatin or compounds described in U.S. Pat. No. 4,346,227, 4,448,979, 4,739,073, 5,169,857, 5,006, 530 or 5401746. Other therapies that can be applied include diet control, dietary calorie restriction or diet modification for subjects who are or who are susceptible to developing a cardiovascular or related condition such as pulmonary hypertension, diabetes, a dyslipidemia or obesity, e.g., humans having a body mass index of 27, 28, 29, 30, 31, 32, 33, 34, 35, 36 or greater. Diet modifications include limiting or restricting salt, alcohol, caffeine, cigarette, drugs, e.g., opiate, hallucinogen, sedative, narcotic or amphetamine, sugar, refined sugar and/or fat or cholesterol intake, use or abuse. Additional therapies include treatment with one or more of digoxin, nitroglycerin, doxazosin mesylate, nifedipine, enalapril maleate, indomethicin, tissue plasminogin activator, urokinase, acetylsalicylic acid or the like. Any of such additional therapies would be used essentially according to standard protocols and such therapies would precede, be concurrent with or follow treatment with a F1C. In some embodiments, such additional therapies will be administered at the same time that a F1C is being used or within about 1 day to about 16 weeks before or after at least one round of treatment with the F1C is completed. Other exemplary therapeutic agents and their use have been described in detail, see, e.g., *Physicians Desk Reference* 54th edition, 2000, pages 303-3251, ISBN 1-56363-330-2, Medical Economics Co., Inc., Montvale, N.J.; *Harrison's Principles of Internal Medicine*, 15th edition, 2001, E. Braunwald, et al., editors, McGraw-Hill, New York, N.Y., ISBN 0-07-007272-8, especially chapters 231, 241-248 and 258-265 at pages 1309-1318, 1377-1442 and 1491-1526. One or more of these exemplary agents or treatments can be used in combination with a F1C to treat any of the appropriate cardiovascular and related disorders described herein and in the references cited herein.

Respiratory and Pulmonary Conditions.

F1Cs can be used to treat, ameliorate, prevent or slow the progression of a number of pulmonary conditions or their symptoms such as 1, 2, 3 or more of cystic fibrosis, bronchiectasis, cor pulmonale, pneumonia, lung abscess, acute bronchitis, chronic bronchitis, a chronic obstructive pulmonary disease (COPD) condition, bronchopulmonary dysplasia, emphysema, pneumonitis, e.g., hypersensitivity pneumonitis or pneumonitis associated with radiation exposure, alveolar lung diseases and interstitial lung diseases, e.g., associated with asbestos, fumes or gas exposure, aspiration pneumonia, pulmonary hemorrhage syndromes, amyloidosis, connective tissue diseases, systemic sclerosis, ankylosing spondylitis, allergic granulomatosis, granulomatous vasculitides, asthma, e.g., mild intermittent asthma, mild persistent asthma, moderate persistent asthma, severe persistent asthma, acute asthma, chronic asthma, atopic asthma, allergic asthma or idiosyncratic asthma, cystic fibrosis and associated conditions, e.g., allergic bronchopulmonary aspergillosis, chronic sinusitis, pancreatic insufficiency, lung or vascular inflammation, bacterial or viral infection, e.g., *Haemophilus influenzae, S. aureus, Pseudomonas aeruginosa* or RSV infection or an acute or chronic adult or pediatric respiratory distress syndrome (RDS) such as grade I, II, III or IV RDS or an RDS associated with, e.g., sepsis, pneumonia, reperfusion, atelectasis or chest trauma. Chronic obstructive pulmonary diseases include conditions where airflow obstruction is located at upper airways, intermediate-sized airways, bronchioles or parenchyma, which can be manifested as, or associated with, tracheal stenosis, tracheal right ventricular hypertrophy, pulmonary hypertension, polychondritis, bronchiectasis, bronchiolitis, e.g., idiopathic bronchiolitis, ciliary dyskinesia, asthma, emphysema, connective tissue disease, bronchiolitis of chronic bronchitis or lung transplantation. The F1C can be used to treat or ameliorate acute or chronic asthma or their symptoms or complications, including airway smooth muscle spasm or hyperresponsiveness, airway mucosa edema, increased mucus secretion, excessive T cell activation, airway epithelium injury or desquamation, atelectasis, cor pulmonale, pneumothorax, subcutaneous emphysema, dyspnea, coughing, wheezing, shortness of breath, tachypnea, fatigue, decreased forced expiratory volume in the 1$^{st}$ second (FEV$_1$), arterial hypoxemia, respiratory acidosis, inflammation including unwanted elevated levels of mediators such as IL-4, IL-5, IgE, histamine, substance P, neurokinin A, calcitonin gene-related peptide or arachidonic acid metabolites such as thromboxane or leukotrienes (LTD$_4$ or LTC$_4$), and cellular airway wall cellular infiltration, e.g., by eosinophils, lymphocytes, macrophages or granulocytes. Any of these and other pulmonary conditions or symptoms that can be treated with F1C are described elsewhere, e.g., *The Merck Manual*, 17th edition, M. H. Beers and R. Berkow editors, 1999, Merck Research Laboratories, Whitehouse Station, N.J., ISBN 0911910-10-7, or in other references cited herein. In some of these conditions where inflammation plays a role in the pathology of the condition, the F1Cs can ameliorate or slow the progression of the condition by reducing damage from inflammation. In other cases, the F1Cs act to limit pathogen replication or pathogen-associated lung tissue damage. Other standard treatments can be combined with the use of the F1Cs to treat these conditions or symptoms, e.g., asthma, RDS or COPD, including the use of anticholinergic agents, β2-adrenoreceptor agonists such as formoterol or salmeterol, corticosteroids, antibiotics or antihypertension agents.

For these conditions, the severity of the disease or the type or severity of associated symptoms can vary. For example, in humans having pediatric, e.g., infants or children of about 1 month or about 4 months of age to about 16 or 17 years of age, or adult cystic fibrosis ("CF"), the disease may be associated with the presence of one or more symptoms, syndromes, genetic mutations or the like. Symptoms or syndromes that can be observed in human CF patients include 1, 2, 3, 4 or more of *Staphylococcus* (e.g., *S. aureus*), *Haemophilus influenzae, Pseudomonas* or *Burkholderia* respiratory tract or lung infection or propensity to develop detectable infection or colonization, coughing, wheezing, cyanosis, bronchiolitis, bronchospasm, pneumothorax, hemoptysis, pancreatic exocrine insufficiency, bronchiectatic lung disease, atelectasis-consolidation, pulmonary edema, increased lung vascular hydrostatic pressure, increased lung vascular permeability, sinusitis, respiratory insufficiency, bronchial wall or interlobular septa thickening, reduction of forced expiratory volume in 1 second, dyspnea, impaired male fertility, elevated sweat chloride (e.g., >60 mmol/L), mucous plugging, tree-in-bud sign, mosaic perfusion pattern, glucose intolerance or abnormal elevation of one or more of IL-4, IL-8, RANTES, neutrophil elastase, eosinophils, macrophages, neutrophils, eosinophil cationic protein or cysteinyl leukotrienes. Any of these symptoms or syndromes can be acute, intermittent or chronic and/or mild, moderate or severe. Relevant mutations include, e.g., a homozygous or heterozygous, dominant or recessive deletion, insertion and/or point mutation in (1) the cationic trypsinogen gene or (2) the cystic fibrosis transmembrane conductance regulator (CFTR) gene, such as one, two or more of, a CFTR F508del deletion mutation or CFTR lacking phe508, 3272-26A>G/F508del, 3659delC, 394delTT, S1455X or Δ26, I1234V, 2183AA>G, 2043delG, 548A>T, I148T, R334W, S1196X, 4041C>G, 1161delC, 1756G>T or 3120+1G>A mutation.

The use of a F1C to treat, ameliorate or slow the progression of conditions such as CF can be optionally combined with other suitable treatments. For CF, this includes, e.g., one, two or more of oral or aerosol corticosteroid treatment, ibuprofen treatment, DNAse or IL-10 treatment, diet control, e.g., vitamin E supplementation, vaccination against pathogens, e.g., *Haemophilus influenzae*, or chest physical therapy, e.g., chest drainage or percussion.

Humans or other subjects who have one or more of these conditions can be treated with other suitable therapeutics. Pulmonary conditions that can be treated with the F1Cs and other therapeutic methods and agents that can be used in conjunction with the F1Cs have been described in detail, see, e.g., *Harrison's Principles of Internal Medicine*, 15th edition, 2001, E. Braunwald, et al., editors, McGraw-Hill, New York, N.Y., ISBN 0-07-007272-8, especially chapters 252-265 at pages 1456-1526; *Physicians Desk Reference* 54th edition, 2000, pages 303-3251, ISBN 1-56363-330-2, Medical Economics Co., Inc., Montvale, N.J. One or more of these exemplary agents or treatments can be used in combination with a F1C to treat any of the appropriate cardiovascular and related disorders described herein and in the references cited herein. Treatment of any of these respiratory and pulmonary conditions using a F1C is accomplished using the treatment regimens described herein. For chronic conditions, intermittent dosing of the F1C can be used to reduce the frequency of treatment. Intermittent dosing protocols are as described herein.

Applications in Autoimmunity, Allergy, Inflammation and Related Conditions.

As mentioned above, the F1Cs may be used to treat, prevent or slow the progression of one or more autoimmune allergic or inflammatory diseases, disorders, or conditions, or to ameliorate one or more symptoms thereof in a subject. These diseases and conditions include Addison's Disease, autoimmune hemolytic anemia, autoimmune sensorineural hearing loss, antiphospholipid syndrome, acute or chronic rheumatoid arthritis and other synovial disorders, an osteoarthritis including post-traumatic osteoarthritis and hypertrophic pulmonary osteoarthropathy, psoriatic arthritis, polyarthritis, epichondylitis, type I diabetes, type II diabetes, rheumatic carditis, bursitis, ankylosing spondylitis, multiple sclerosis, a dermatitis such as contact dermatitis, atopic dermatitis, exfoliative dermatitis or seborrheic dermatitis, mycosis fungoides, allergic encephalomyelitis, autoimmune glomerulonephritis, Goodpasture's Syndrome, Graves' Disease, Hashimoto's Thyroiditis, multiple sclerosis, myasthenia gravis, neuritis, bullous pemphigoid, pemphigus, polyendocrinopathies, purpura, Reiter's Disease, autoimmune thyroiditis, systemic lupus erythematosus, systemic lupus erythematosus, lupus erythematosus-related arthritis, discoid lupus erythematosus, subacute cutaneous lupus erythematosus, scleroderma, fibromyalgia, chronic fatigue syndrome, autoimmune pulmonary inflammation, Guillain-Barre Syndrome, type 1 or insulin dependent diabetes mellitus, autoimmune inflammatory eye disease, hepatitis C virus associated autoimmunity, postinfectious autoimmunity associated with, e.g., virus or bacterial infection such as a parvovirus such as human parvovirus B19 or with rubella virus, autoimmune skin and muscle conditions such as pemphigus vulgaris, pemphigus foliaceus, systemic dermatomyositis or polymyositis or another inflammatory myopathy, myocarditis, asthma such as allergic asthma, allergic encephalomyelitis, allergic rhinitis, a vasculitis condition such as polyarteritis nodosa, giant cell arteritis or systemic necrotizing vasculitis, chronic and an acute or chronic inflammation condition such as chronic prostatitis, granulomatous prostatitis and malacoplakia, ischemia-reperfusion injury, endotoxin exposure, complement-mediated hyperacute rejection, nephritis, cytokine or chemokine induced lung injury, cachexia, sarcoidosis, inflammatory bowel disease, regional enteritis, ulcerative colitis, Crohn's disease, inflammatory bowel disease or inflammation associated with an infection, e.g., septic shock, sepsis, or systemic inflammatory response syndrome. Any of these diseases or conditions or their symptoms may be acute, chronic, mild, moderate, severe, stable or progressing before, during or after the time administration of the F1C to a subject such as a human, is initiated. In general, a detectable improvement is observed in the subject within a period of about 3 days to about 12 months after initiation of a dosing protocol, e.g., the severity of the disease or condition will detectably decrease, the rate of progression will detectably slow or the severity of a symptom(s) will detectably decrease.

As used herein, acute inflammation conditions are characterized as an inflammation that typically has a fairly rapid onset, quickly becomes moderate or severe and usually lasts for only a few days or for a few weeks. Chronic inflammation conditions as used herein are characterized as an inflammation that may begin with a relatively rapid onset or in a slow, or even unnoticed manner, tends to persist for at least several weeks, e.g., about 3-6 weeks, months, or years and may have a vague or indefinite termination. Chronic inflammation may result when the injuring agent (or products resulting from its presence) persists in the lesion, and the subject's tissues respond in a manner (or to a degree) that is not sufficient to overcome completely the continuing effects of the injuring agent. Other exemplary conditions are described in, e.g., *Textbook of Autoimmune Diseases*, R. G. Lahita, editor, Lippincott Williams & Wilkins, Philadelphia, Pa., 2000, ISBN 0-7817-1505-9, pages 175-851 and *Rheumatology*, $2^{nd}$ edition, J. H. Klippel et al., editors, 1998, ISBN 0-7234-2405-5, volume 1, sections 1-5 and volume 2, sections 6-8, Mosby International, London, UK.

The F1Cs are suitable for enhancing immune responses in aging in subjects such as humans or primates. In humans at about 50 to 60 years of age and later, one or more aspects of immune responses will typically decrease by a detectable amount compared to typical immune responses at younger ages, e.g., at about 18-50 years of age. The F1Cs can be used on an intermittent basis or continuously in aged subjects. Intermittent administration of a F1C can occur as described herein, e.g., daily dosing or dosing every other day or every third day for about 1, 2, 3, 4, 5, 6, 7, 8 or 9 days, followed by about 2, 3, 4, 5, 6, 7, 8, 9 or 10 weeks of no dosing, optionally followed by about 1, 2, 3, 4, 5, 6, 7 or 8 days of daily dosing or dosing every other day or every third day and then followed by about 2, 3, 4, 5, 6, 7, 8, 9 or 10 weeks of no dosing. Such dosing cycles can be repeated indefinitely or as needed. Such treatments can be used prophylactically or therapeutically. In prophylaxis the F1C are administered, e.g., before or during influenza outbreaks, or in aged patients in hospitals or in aged patients in long term living or care facilities such as retirement communities or nursing homes. In therapeutic applications, the F1C are used to treat trauma, e.g., bone fractures or active infections. The F1C treatments in these embodiments will result in enhanced immune responses, including increased innate and specific responses to, e.g., infectious agents. These treatments will typically also have other beneficial effects including enhancing bone marrow production of blood cells or blood components such as neutrophils or improving levels of dysregulated immune response mediators, e.g., decreasing elevated cortisol, IL-6, IL-10, COX-2 or C reactive protein levels or increasing low IL-2 or IL-12 levels.

Where a natural or synthetic antiinflammatory glucocorticoid is used to treat one more of the conditions disclosed herein or wherein endogenous levels of glucocorticoid such as cortisol are elevated to an unwanted level in a subject, the use of a F1C will ameliorate unwanted side-effects of such glucocorticoid use or excess. Typically the F1C will be administered during, before and/or after glucocorticoid levels are elevated or during, before and/or after a therapeutic glucocorticoid is administered to the subject, e.g., within about 1, 2, 3, 4, 5, 6 or 7 days or within about 2, 3, 4, 5, 6, 7, 8, 9, 10, 11, 12, 14, 16, 20 or 24 weeks before or after glucocorticoid use or elevated glucocorticoid levels exist. Typically, the use of the F1C to counteract unwanted side-effects of therapeutic glucocorticoid use In these embodiments, will reduce or ameliorate the onset, severity or progression of one or more unwanted side-effects of glucocorticoid therapy such as a detectable immune suppression, an increased occurrence or incidence of infection, an undesirable alteration of mood (e.g., increased anxiety, depression or schizophrenia) or a detectable loss or alteration of memory.

Tissue and Organ Regeneration and Maintenance and Wound Healing.

The F1Cs can be used to facilitate cell differentiation, dedifferentiation, proliferation or repair where regeneration or maintenance of tissues or organs is indicated. The regeneration of tissues could be used to repair, replace, protect or limit the effects of tissue damaged by congenital defects, trauma (wounds, burns, incisions, or ulcers), age, disease (e.g. osteoporosis, osteoarthritis, periodontal disease, liver failure), surgery, including cosmetic plastic surgery, fibrosis, reperfusion injury, toxin exposure or systemic cytokine damage. Ulcers or skin lesions can arise from ionizing radiation exposure, cytotoxic chemotherapy or pressure, e.g., a pressure or decubitis ulcer or vascular insufficiency, e.g., associated with diabetes or vascular occlusion. Tissues for which regeneration may be enhanced include organs (e.g., pancreas, liver, lung, intestine, kidney, skin, endothelium, oral mucosa, gut or intestinal mucosa), muscle (e.g., smooth, skeletal or cardiac), vasculature (including vascular and lymphatics), central or peripheral nervous tissue, hematopoietic tissue, and skeletal tissue (e.g., bone, cartilage, tendon, and ligament). Decreased scarring or fibrosis can result from the treatments.

The F1C can be used to modulate the rate of stem cell self-renewal, stem cell differentiation to more differentiated progeny or dedifferentiation of stem cells to less differentiated progenitor cell types in vivo or in vitro. Stem cell self-renewal or symmetric stem cell division is stem cell division that results in two progeny cells that are essentially the same with regard to their relative degree of differentiation. Such cells retain essentially the same potential to give rise to fully differentiated cell types that the parent cell had. Asymmetric stem cell division results in one or both progeny cells that are less primitive than the parent cell. The differences between the parent and the more differentiated progeny cell(s) may be apparent or not. Thus, when a $CD34^+$ stem cell derived from blood or bone marrow, several rounds of asymmetric division may be needed before expression of the $CD34^+$ surface antigen is no longer readily detected. Similarly, one or more asymmetric cell divisions may be needed for the expression of a marker associated with a more differentiated or fully differentiated cell type becomes readily detectable. Cell divisions where some degree of stem cell dedifferentiation occurs, 'super symmetric divisions', may also not be readily apparent unless several rounds of such division occurs. Stem cells that can undergo such super symmetric division are typically relatively primitive, e.g., stem cells before or during expression of the CD34 antigen, but not more differentiated forms, although in adults animals they will often not have the full potential that true embryonic stem cells may have.

Uses of F1c to modulate stem cell activity include administration of a F1C to a subject, typically a mammal, that has been injured or that has a cytopenia condition or an immune suppression or immune dysfunction condition. Injury can arise from normal aging or immune dysfunction, e.g., arthritis or osteoporosis. In other uses, cells are obtained from such subjects, or from normal autologous individuals who serve as donors, and the cells are expanded in vitro and then transferred to the subject. Transfer of cells to the subject is optionally accompanied by administration of a F1C to increase the efficiency of cell engraftment or to increase stem cell self-renewal and/or asymmetric stem cell division. Growth of stem cells in vitro in the presence of a F1C can be used to prolong the number of cell divisions that the cells can undergo without significant loss of their potential to differentiate.

When stem cells or cell populations that contain stem cells are cultured with cells in vitro, the F1C will typically be present at a concentration of about 10 pM or about 50 pM to about 100 nM, usually about 100 pM or about 1 nM to about 50 nM, although higher concentrations, e.g., about 100 nM to about 250 nM, can be used, e.g., where the F1C is sufficiently water soluble or can be formulated in excipients that are compatible with the tissue culture system. F1C concentrations in growth media that can be used include about 100 pM, about 0.1 nM, about 1 nM, about 5 nM, about 10 mM, about 20 nM, about 30 nM, about 40 nM, about 50 nM, about 60 nM, about 70 nM, about 80 nM, about 90 nM, about 100 nM, about 120 nM, about 150 nM or about 200 nM. The F1C can be maintained in the medium as long as stem cells are grown in vitro, or the F1C can be present to establish a culture over about 1, 2, 3, 4, 5, 6, 7, 10, 14 or 21 days and then withdrawn. Such tissue culture systems will normally contain growth media and growth factors, substrates and differentiation modulators that are often used to expand or maintain stem cells in vitro. Growth factors, substrates and differentiation modulators that can be used include one or more of thrombopoietin, erythropoietin, IL-2, IL-3, IL-6, G-CSF, GM-CSF, stem cell factor, FLT-3 ligand, a fibroblast growth factor such as FGF-4 or basic fibroblast growth factor, TGFα, TGF-β1, insulin, oncostatin-M, collagen, laminin, vascular endothelial growth factor and 5-azacytidine.

Stem cell types that can be used in vitro or affected in vivo include stem cells that express one or more of CD34+, c-kit, Sca-1, c-mpl, Thy-1, CD38, endoglin, CXCR4, CD41, CD4, IL-6R, IL-3, CD45, Mac-1, AC133, TGFβ, PECAM, VLA-4, endoglin, CSF-1, LIF, VE-cadherin, steel factor, SSEA-4 and alkaline phosphatase. These markers and methods to obtain and use stem cells have been described, see, e.g., P. J. Quesenberry et al., *Stem Cell Reviews*, 1:29-36, 2005, S. Sell, *Stem Cell Reviews*, 1:1-7, 2005, J. S. Van Arnam et al., *Stem Cell Reviews*, 1:21-27, 2005, J. R. Bickenbach et al., *Stem Cell Reviews*, 1:71-77, 2005, C. Dorrell et al., *Stem Cell Reviews*, 1:61-64, 2005, B. N. Jahagirdar et al., *Stem Cell Reviews*, 1:53-59, 2005, D. S. Vieyra et al., *Stem Cell Reviews*, 1:65-69, 2005, A. M. Schor et al., *Clin. Orthop. Relat. Res.*, 313:81-91 1995, M. J. Doherty et al., *Crit. Rev. Eukaryot. Gene Expr.*, 9(1):1-17 1999 and U.S. Pat. Nos. 6,852,533, 6,586,243, 6,528,245, 6,528,245, 6,146,888, 6,174,526, 6,228,640, 6,054,121, 6,004,743, 5,922,847, 6,200,806, 5,843,780, 5,861,315, 5,846,796, 5,840,580, 5,827,742, 5,807,686, 5,804,446, 5,665,557, 5,541,103, 6,897,061, 6,833,269, 6,830,927, 6,680,198, 6,498,018, 6,497,872, 6,060,270, 5,834,312, 5,650,317, 6,872,389, 6,852,330, 6,001,647, 5,981,211, 5,905,041, 6,773,713, 6,767,737, 6,752,831, 6,936,281, 6,866,991, 6,534,084, 6,149,902, 5,733,541, 6,936,281, 6,835,377, 6,737,053, 6,752,834, 6,645,763, 6,576,015, 6,150,164 and 6,699,471 and U.S. patent application publication Nos. 20020173464 and 20050153889. As is apparent from the foregoing, the F1C can be used with the methods described in these references to facilitate recovery or maintenance of the stem cells. The F1C can be used to modulate the expression of one or more of these markers to allow characterization of the effect of the F1C on different stem cell types.

Stem cell types that the F1C can modulate have been described in these references and elsewhere include embryonic stem cells, embryonic stem cell progenitors, hemeangioblast stem cells, angiohematopoietic stem cells, multipotent adult progenitor cells, tissue-derived pluripotent stem cell, optionally muscle-derived stem cells, a fat-derived stem cells or a bone-derived stem cells, mesenchymal stem cells, neural stem cells, multipotent adult progenitor cells (MAPCs), vascular pericytes, blood or marrow derived CFU-GEMM, blood or marrow derived $CD34^+$ stem cells or hematopoietic stem cells, CFU-blast, satellite cells (skeletal myoblast progenitors), angioblasts (endothelial cell progenitors), mesenchymal stem cells, embryonic stem cells. Some of these stem cells, e.g., neural stem cells, CD34+ cells or multipotent adult progenitor cells can differentiate into one or more of osteoblasts, chrondroblasts or chondrocytes, fibroblasts, adipocytes, skeletal myoblasts, smooth muscle cells, cardiac myocytes, endothelial cells, hepatocytes, neurons, glial cells, astrocytes or oligodendrocytes.

Stem cells derived from bone marrow or cord blood can differentiate and give rise to pancreas β cells, hepatocytes, osteoblasts, cardiomyocytes, neural cells, endothelial cells, bone, cartilage or ligament, intestinal epithelia, heart tissue and skin or integument. F1Cs can be used to facilitate or enhance this type of differentiation in vivo. In cases where a subject has a condition that leads to loss or impairment of a tissue or cell type, e.g., a neurodegeneration condition such as Parkinson's disease or Alzheimer's disease, administration the F1C can be used to slow or stop disease progression by increasing symmetric or asymmetric replication of stem cells in vivo that can participate in treating or at least partially reversing the condition. In cases of aging where normal tissue or organ maintenance or repair is decreased, the F1C can be administered to at least partially reverse the subject's impaired capacity to maintain or repair the affected tissue or organ. In the case of an acute trauma such as a myocardial infarction or a trauma that causes bleeding, administration of a F1C after the trauma can be used to increase stem cell numbers, e.g., $CD34^+$ or mesenchymal stem cells, in the affected individual by increasing symmetric or asymmetric divisions in vivo. Such cells could then be recovered and further expanded in vitro or purified in vitro without expansion in tissue culture and implanted at the site of the infarction or bleeding, which would facilitate healing of the injured tissue. These effects of the F1Cs on stem cells in vivo can be used to treat or ameliorate other conditions described herein. For treating human patients, the patients will typically be diagnosed with one or more clinical condition and/or will be treated and/or periodically monitored for the effect of an F1C treatment regimen on disease symptoms or on stem cell number or activity or on the efficiency with which stem cells engraft when transplanted into a subject, e.g., in an autologous transplant or in an allograft procedure such as a bone marrow transplant.

The F1C with a capacity to modulate or enhance stem cell self-renewal, differentiation or dedifferentiation will usually comprise structures where (1) an independently selected heteroatom, e.g., —OH, ester, carbonate, carbamate, polymer, =O, —SH, =S, thioether, or =NOH, is bonded at the 3- and 17-positions, the 3-, 16- and 17-positions, the 3-, 7- and 17-positions, 3-, 6- and 17-positions, the 3-, 7-, 16- and 17-positions, the 3-, 6-, and 17-positions, the 3-, 6-, 16- and 17-positions, the 2-, 3- and 17-positions, 2-, 6- and 17-positions, 2-, 7- and 17-positions, the 2-, 16- and 17-positions, the 2-, 3-, 7- and 17-positions or the 2-, 3-, 16- and 17-positions, (2) $R^8$ is a moiety such as —O—, —S—, —NH—, —NCH$_3$—, —CHR$^{10}$— or —C(R$^{10}$)$_2$—, where $R^{10}$ are independently carbon-bonded moieties, e.g., optionally substituted alkyl and (3) optionally where —H or a carbon bonded moiety, e.g., C1-6 optionally substituted alkyl such as —CH$_3$ or —CCH, is at the one or two of the 2-, 3-, 6-, 7-, 16-, or 17-positions, e.g., at the 17-position and/or at the 3-position, when a heteroatom that is bonded to those positions by a single bond. For these compounds, other variable groups, e.g., $R^{10E}$ or $R^{10F}$, will typically comprise —H, or one or two relatively small independently selected moieties such as halogen, —OH, —SH, ester, carbonate, carbamate or thioester containing 2-6 carbon atoms, ether or thioether containing 1-6 carbon atoms or optionally substituted alkyl containing 1-6 carbon atoms, e.g., —CH$_3$, —CF$_3$, —C$_2$H$_5$ or —C$_2$H$_4$OH. The $R^5$ variable group, when present, in these compounds usually is C1-4 optionally substituted alkyl and $R^6$ variable group, when present, usually is —H, halogen, —OH or C1-4 optionally substituted alkyl. Such substituents can also be used in other methods described herein. Such structures will usually have little or no easily discernable glucocorticoid activity, although they can have mild to moderate systemic or endocrine antiinflammatory activity and activity to decrease oxidative stress or oxidative stress-related tissue or organ damage with some mild or moderate local, autocrine or paracrine, pro-inflammatory activity, which is typically transient.

The F1Cs are thus useful to an increased rate or quality of healing may accompany these effects. The F1C can enhance healing or tissue repair in a subject having a bone fracture(s), e.g., a simple or compound skull, spine, hip, arm or leg bone fracture. Similarly, nerve or brain tissue treatment using a F1C allows treating, slowing the progression of, ameliorating or preventing diseases such as central and peripheral nervous system diseases, neuropathies, or mechanical and traumatic diseases, disorders, and/or conditions (e.g., spinal cord disorders, head trauma, cerebrovascular disease, and stoke). The compounds are useful to treat diseases associated with peripheral nerve injuries, peripheral neuropathy (e.g., resulting from chemotherapy, radiation exposure or therapy or other medical therapies), localized neuropathies, and central nervous system diseases such as Alzheimer's disease, Parkinson's disease, Huntington's disease and amyotrophic lateral sclerosis. The subjects undergoing treatment in these conditions may be elderly, e.g., a human at least about 55, 60, 65 or 70 years of age. Where the condition is acute, e.g., a bone fracture or a burn, the treatment may comprise administration of a F1C to the subject on a daily or intermittent basis for about 3 days to about 12 months, e.g., administration for about 2-12 weeks beginning after the subject sustains an injury.

An aspect of the F1Cs is their capacity to facilitate wound or trauma healing or to slow or at least partially reverse tissue organ impairment or damage associated with surgery, aging, chemotherapy or radiation exposure by increasing the proliferation or self-renewal of stem cells and pluripotent derivatives of stem cells and/or by increasing the rate of differentiation of stem cells or their pluripotent derivatives to more mature cell types. Thus, the F1Cs can increase the numbers, rate of differentiation, growth or activity of stem cells in, e.g., skin, central or nervous system tissue, blood vessels, heart tissue, lung, liver, pancreas, kidney, thymus, spleen, oral mucosa, intestine, bone marrow, or connective tissue some of which is discussed elsewhere herein. Stem cell types that can be affected include cells that give rise to neurons, glial cells, astrocytes, hepatocytes, thymus cells, spleen cells, lung tissue, skin tissue, fibroblasts, myocytes such as smooth muscle and striated muscle, including cardiac muscle cells, chondrocytes, osteoblasts and other stem cell types in other organs or tissue. Increased numbers of mature cell types typically is observed beginning at about 2-28 days after treatment with a F1C is started, usually after about 2-21 days. Thus, the F1Cs can enhance the numbers, activities or differentiation of, e.g., crypt cells in intestinal mucosa, skin cells, e.g., stem cells, in the oral mucosa or cardiac precursor cells after damage to those cells or tissues. Such damage can arise, e.g., from trauma, infection, ionizing radiation exposure, toxin exposure and/or cytotoxic chemotherapy. The F1Cs can thus be used to facilitate or enhance healing, reepithelialization or reendothelialization of skin, intestine, mucosal or endothelial cells after the occurrence of a wound, infarction, burn or other event that damages or impairs the barrier function or hemostasis capacity of such tissues. The barrier function or hemostasis capacity of such tissues includes their capacity to act as a physical barrier against infection or to maintain normal blood flow or composition. Optimal modulation of stem cell survival, self-renewal and differentiation in these embodiments is usually obtained by dosing the F1C at a time period near the time that the subject is exposed to an agent, event or treatment that can cause significant tissue damage. Typically this time period is about 1, 2, 3, 4 or 5 days before, on the same day as or within 1, 2, 3, 4 or 5 days after the damaging event or exposure occurs. For chronic toxin exposure, e.g., alcohol, chronic continuous or intermittent administration of the F1C can be used. Dosages of the F1Cs, routes of administration and dosing protocols for these embodiments are as described herein.

As noted above, the F1Cs are useful to enhance healing in a subject who has experienced or who is expected to experience one or more traumas or acute injuries such as a wound, burn, bone fracture, nervous system tissue trauma, gastrointestinal damage or intestinal cell damage or other traumatic events. In some embodiments, such subjects have experienced a trauma and who are immune suppressed or are anticipated to become immune suppressed. The immune suppression may arise from, e.g., a myelosuppressive cancer therapy, a glucocorticoid therapy or from radiation exposure. Thus, in some cases a subject such as a human or a primate who has experienced a trauma, e.g., a bone fracture, a chemical or thermal burn, a cut or a laceration, is also exposed to, e.g., an ionizing radiation as described herein such as γ-radiation, β-radiation, X-radiation or neutron radiation in an immune suppressive amount or dose, e.g., about 0.3 Gy ("gray") to about 30 Gy, typically about 0.5 Gy to about 12 Gy or about 0.7 Gy to about 8 Gy. The subject's radiation exposure can be localized or whole body and can occur rapidly, e.g., over a period of up to about 20 minutes, or more slowly, e.g., over a period of about 5-25 minutes to about 5-72 hours or more. A Gy of radiation is 1 joule per kg of absorbed ionizing radiation. The trauma event and the radiation exposure event may occur at about the same time, e.g., on the same day, or within a time period of about 1, 2, 3, 4, 5 or 6 days to about 1, 2, 3 or 4 weeks, when detectable clinical effects of both events are present. Treatment with the F1C will use the dosing protocols, dosages and routes of F1C administration as described herein, e.g., dosing daily or every other day for about 1-12 days using dosages of about 0.1 mg/kg to about 30 mg/kg, depending on the route of administration and the subject's condition. Dosing of the F1C will usually commence within a few days of the radiation exposure event, e.g., within 0, 1, 2, 3 or 4 days. Similarly, such healing or repair of traumas in subjects who are or are expected to become immune suppressed, e.g., from an immunosuppressive chemotherapy, cancer, stress, infection or from aging, can be treated in the same manner.

The F1Cs are also useful in the prophylaxis or treatment of nosocomial infections, such as those associated with elderly or special population patients that are hospitalized for trauma or other treatments. Such treatments include treatment of cancer, stroke or bone fracture patients with a F1C to prevent or to reduce the severity of nosocomial or other infections. Typical bone fractures include hip, arm or leg fractures. F1Cs in these treatments include those described herein such as 3β,17β-dihydroxyandrostane, 3α,17β-dihydroxyandrostane, 3-oxo-17β-hydroxyandrostane, 3-oxo-17α-hydroxyandrostane, 3β,17β-dihydroxyandrost-5-ene, 3α,17β-dihydroxyandrost-5-ene, 3β,17β-dihydroxyandrost-5(10)-ene, 3β-hydroxy-17β-mercaptoandrost-5-ene, 3α-hydroxy-17β-mercaptoandrost-5-ene, 3β-hydroxy-17β-mercaptoandrost-5(10)-ene and analogs of these compounds that contain (1) an oxygen-, nitrogen- or sulfur-linked moiety as described herein in the α- or β-configuration such as —OH, =O, —SH, =S, —NH$_2$, —NHCH$_3$, —N(CH$_3$)$_2$, =NOH, ether, ester at one, two or more of, e.g., the 2-, 6-, 7-, 12- or 16-position, (2) —F, —Cl, —Br or —I at the 9-position in the α- or β-configuration and/or (3) one or more double bonds at the 1-, 2-, 7- 11-, 14- or 15-positions. In these embodiments, the F1C can be given as a depot injection at the time of hospital admission and periodically thereafter, e.g., every second or third day, to the hospital or as daily doses as needed. In other embodiments, the F1C is administered to hospitalized patients who are given antibiotics or antimicrobials prophylactically or to treat an existing infection.

Neurological Conditions.

Nervous system diseases, disorders, conditions, or their symptoms (collectively 'neurological conditions') that can be ameliorated, treated or prevented with any of the F1Cs disclosed herein include, but are not limited to, nervous system trauma or injury, and neurological conditions that result in an unwanted pathology or symptom, e.g., demyelination, pain, impairment of cognitive function, discernable memory loss, depression, anxiety, a disconnection of axons, a diminution of neuron, astrocyte or glia function or degeneration or death of nervous system cells or tissues such as one or more of those described herein.

Neurological conditions, including nervous system lesions that may be treated, prevented, or ameliorated in a subject include but are not limited to, the following lesions of either the central (including spinal cord, brain) or peripheral nervous systems. Exemplary neurological conditions include (1) ischemic lesions, in which a lack of oxygen in a portion of the nervous system results in neuronal injury or death, including cerebral infarction, ischemia or stroke, or spinal cord infarction or ischemia, (2) traumatic lesions, including lesions caused by physical injury or associated with surgery, for example, lesions which sever a portion of the nervous system, or compression injuries, (3) malignant lesions, in which a portion of the nervous system is destroyed or injured by malignant tissue which is either a nervous system associated malignancy or a malignancy derived from non-nervous system tissue, (4) infectious lesions, in which a portion of the nervous system is destroyed or injured as a result of infection, for example, by an abscess or associated with infection by human immunodeficiency virus, herpes zoster, or herpes simplex virus or with Lyme disease, tuberculosis or syphilis, (5) degenerative lesions or conditions, in which a portion of the nervous system is destroyed or injured as a result of a degenerative process including but not limited to degeneration associated with Parkinson's disease, Alzheimer's disease, Huntington's chorea, AIDS associated dementia, epileptic dementia, presenile dementia, senile dementia, vascular dementia, post stroke dementia, post traumatic dementia or amyotrophic lateral sclerosis (ALS), (6) lesions associated with nutritional diseases, disorders, and/or conditions, in which a portion of the nervous system is destroyed or injured by a nutritional disorder or disorder of metabolism including but not limited to, vitamin B12 deficiency, folic acid deficiency, Wernicke disease, tobacco-alcohol amblyopia, Marchiafava-Bignami disease (primary degeneration of the corpus callosum), and alcoholic cerebellar degeneration, (7) neurological lesions associated with systemic diseases including, but not limited to, diabetes (diabetic neuropathy, Bell's palsy), systemic lupus erythematosus, carcinoma, or sarcoidosis, (8) lesions caused by toxic substances including alcohol, lead, or neurotoxins, (9) demyelinated lesions in which a portion of the nervous system is destroyed or injured by a demyelinating disease including, but not limited to, multiple sclerosis, human immunodeficiency virus-associated myelopathy, progressive multifocal leukoencephalopathy, and central pontine myelinolysis or a myelopathy, e.g., diabetic myelopathy or a transverse myelopathy, (10) neurological conditions such as insomnia (e.g., transient or chronic), epilepsy, schizophrenia, psychosis, delusion, a unipolar mood disorder, a bipolar mood disorder, psychomotor dysfunction, depression, anxiety, addiction to or abuse of a drug substance such as tobacco, nicotine, caffeine, alcohol, a barbiturate, a tranquilizer, a narcotic such as hydromorphone HCl, propoxyphene napsylate, meperidine HCl, valium, codeine, cocaine, morphine, heroin or methadone, (11) cognitive dysfunction conditions or diseases such as one or more of impaired long-term or short-term memory, impaired concentration, impaired attention or impaired learning, where the cognitive dysfunction condition or disease is optionally associated with chemotherapy, radiation therapy or exposure, aging, trauma, e.g., CNS trauma, or neurodegeneration and (12) genetic disorders with a neurological pathology or component such as Down's syndrome or Tay Sach's disease.

The F1Cs are useful to ameliorate, treat or prevent the onset, severity or length of other neurological diseases or conditions such as headache or a migraine condition or symptom such as classic migraine, cluster headache, abdominal migraine, common migraine, hemiplegic migraine, ocular migraine, fulminating migraine, complicated migraine or a symptom of any of these such as head pain, vertigo, nausea, vomiting or potophobia.

In some embodiments, the F1C is used to protect neural cells from the damaging effects of cerebral hypoxia, cerebral ischemia or neural cell injury associated with cerebral infarction, heart attack, stroke or elevated levels of glucocorticoids such as cortisol. The compounds that are also useful for treating or preventing a nervous system disorder may be selected, e.g., by assaying their biological activity in promoting the survival or differentiation of neurons. For example, and not by way of limitation, the F1Cs can be used to elicit any of the following useful effects: (1) increased survival time of neurons in culture, (2) increased sprouting of neurons in culture or in vivo, (3) increased production of a neuron-associated molecule in culture or in vivo, e.g., dopamine or choline acetyltransferase or acetylcholinesterase with respect to motor neurons or (4) decreased symptoms of neuron dysfunction in vivo. Such effects may be measured by any method known in the art. Increased survival of neurons may be measured using known methods, such as, for example, the method set forth in Arakawa et al. (*J. Neurosci.* 10:3507-3515 1990); increased sprouting of neurons may be detected by methods known in the art, such as the methods set forth in Pestronk et al. (*Exp. Neurol.* 70:65-82 1980) or Brown et al. (*Ann. Rev. Neurosci.* 4:17-42 1981). Increased production of neuron-associated molecules may be measured by, e.g., bioassay, enzymatic assay, antibody binding or Northern blot assay, using techniques known in the art and depending on the molecule to be measured. Motor neuron dysfunction may be measured by assessing the physical manifestation of motor neuron disorder, e.g., weakness, motor neuron conduction velocity, or functional disability. Motor neuron conditions may arise from infarction, cancer, infection, exposure to toxin, trauma, surgical damage or a degenerative disease that affects motor neurons as well as other components of the nervous system.

Other neurological conditions that can be treated using F1Cs include conditions that selectively affect neurons or adjacent tissues such as amyotrophic lateral sclerosis, progressive spinal muscular atrophy, progressive bulbar palsy, primary lateral sclerosis, infantile and juvenile muscular atrophy, poliomyelitis and the post polio syndrome, hereditary motorsensory neuropathy, spinal cord compression and a myelitis such as necrotizing myelitis, transverse myelitis, ascending myelitis, bulbar myelitis, concussion myelitis, demyelinated myelitis, postinfectious myelitis, systemic myelitis or transverse myelitis.

In some neurological conditions such as mood changes, depression, anxiety, memory loss or motor function impairment, the F1Cs can modulate one or more biological activities of a transcription factor or a nuclear hormone receptor such as ERα in tissue such as the hypothalamus or amygdala or ERβ in tissue such as the hippocampus, thalamus or entorhinal cortex.

In neurological conditions or other conditions where loss or damage to nervous system cells or tissue is typically present, e.g., multiple sclerosis, cerebral infarction, cerebral trauma, elevated glucocorticoid levels or Alzheimer's disease, use of the F1Cs can lead to detectable repair of damaged cells or replacement of at least some killed cells. Elevated glucocorticoids can result from endogenous production of natural glucocorticoids, e.g., cortisol or hydrocortisone, or from administration of synthetic glucocorticoids, e.g., dexamethasone, triamcinolone, betamethasone or other synthetic agents disclosed herein or in the cited references. Repair or replacement can occur for cell types that are present in nervous system tissues, e.g., neurons, Schwann cells, glial cells, astrocytes, oligodendrocytes, macroglia cells, endothelial cells, or stem or progenitor cells of any of these cell types. The cells may reside in discrete regions of nervous organs, e.g., hippocampus, cerebrum or cerebellum, or they may reside in multiple regions. Any of the neurological conditions that can be treated with the F1Cs may be acute, subacute or chronic and they may be subclinical (having few or no overt symptoms), mild, moderate or severe.

In treating neurological conditions, the F1Cs will generally enhance function, self renewal and/or differentiation of stem or progenitor cells and/or they will reduce the severity of cell damage or impairment compared to similar subjects that are not treated with the F1Cs. In cases where myelin damage or nerve death occurs, the F1Cs can reduce the rate at which damage or death occurs or they can detectably reverse damage or enhance replacement of killed cells, particularly where the extent of such damage or killing is mild or moderate. Without wishing to be bound to any theory, the F1Cs may exert these properties (1) by directly acting as a hormone, growth factor or modulator of a biomolecule disclosed herein such as an enzyme, a glucocorticoid receptor, PPARα, a neural stem cell helix-loop-helix transcription factor such as HES1 or an estrogen receptor to enhance replication, synaptogenesis or other repair or maintenance functions, (2) by enhancing recruitment and/or differentiation of cells involved in cell or tissue repair, e.g., enhanced recruitment and differentiation of oligodendrocyte cells to a demyelinated lesion in multiple sclerosis and/or (3) indirectly by modulating the level or activity of autocrine, paracrine or endocrine factors such as one or more inflammatory cytokines or markers as disclosed herein that can modulate disease progression, e.g., cortisol, IL-1α, IL-1β, TNF-α, IL-6, a thromboxane, a prostaglandin or a neuregulin.

In treating chronic or progressive disorders such as multiple sclerosis or Alzheimer's disease, the F1Cs will typically slow the rate of progression of the disease. The F1Cs act at least in part by decreasing the activity or levels of chemokines and/or pro-inflammatory cytokines, e.g., one, two or more of MCP-1, MIP-1, ICAM, V-CAM, E-selectin, RANTES, IL-1α, IL-1β, IL-6, IL-8 and TNF-α. This reduction can be accompanied by a reduced rate of deposition of amyloid-β (Aβ) protein, which results in slowed disease progression and in reduced severity and/or frequency of one or more symptoms such as short term memory loss, impaired concentration, impaired judgement, episodes of disorientation or confusion and periods of mood or behavior changes such as irritability, anxiety or aggression. Treatment of chronic or progressive disorders such as Alzheimer's disease with a F1C is optionally accompanied by other suitable treatments, e.g., treatment with one or more non-steroidal anti-inflammatory drugs or other palliative measures.

Factors such as increased levels of cortisol or thromboxane, that are associated with increased cell or tissue damage or with inhibition of cell growth or differentiation are generally decreased or reregulated to express in a normal manner by the appropriate cells such as neurons, astrocytes, glial cells or their stem or precursor cells. Factors that facilitate normal differentiation or repair, e.g., basic fibroblast growth factor 2 or neuregulin, are generally increased or reregulated to express in a normal manner by the appropriate cells such as neurons, astrocytes, glial cells or their stem or precursor cells.

Because of these properties, the F1Cs can be used in various protocols or methods to enhance differentiation or proliferation of these cell types in vivo or in vitro. Typically, the concentration of the F1Cs will exert one or more of these beneficial effects at extracellular concentrations of about $1 \times 10^{-12}$ M to about $5 \times 10^{-6}$ M, e.g., about $1 \times 10^{-11}$ M to about $5 \times 10^{-7}$ M or about $1 \times 10^{-10}$ M to about $1 \times 10^{-7}$ M. Such concentrations can suitably be established transiently, e.g., for about 10 minutes to about 6 hours or about 12 hours once or twice per day on one, two or more days. Alternatively, such concentrations may be maintained more or less constantly, e.g., within these ranges for at least about 12 hours per day for one, two or more days, particularly for in vitro use to enhance cell or tissue growth, differentiation or viability in tissue culture. Methods to administer the F1Cs for in vivo use are essentially as described herein.

For any of these neurological conditions or their associated symptoms, the presence of the condition or its pathological manifestation, e.g., cell or tissue damage, or symptom may be determined by suitable objective or subjective means, e.g., assays to detect tissue damage, levels of diagnostic markers or an etiological agent, performance of histopathological examination of cells or tissues, patient questionnaires or behavior performance tests, measurement of a diagnostic marker(s), e.g., an enzyme, hormone, cytokine or drug substance in blood or tissue, electroencephalography, imaging methods such as X-ray, MRI scan or CAT scan, observation and diagnosis of clinical features or symptoms or biopsy of affected tissue or cells, e.g., aspiration biopsy, needle biopsy, incision biopsy or punch biopsy of tissue or cells. Neurological conditions, diseases and symptoms, which the F1Cs can be used to treat or ameliorate and methods to diagnose and characterize such conditions or diseases have been described. See, e.g., Ph. Demaerel, A. L. Baert et al., eds. *Recent Advances in Diagnostic Neuroradiology (Medical Radiology: Diagnostic Imaging)* 2001 Springer Verlag, ISBN: 3504657231, W. G. Bradley et al., Neurology in *Clinical Practice: Principles of Diagnosis and Management* 1995, see, e.g., vol. 1 Ch. 1-55 and vol. 2. Ch. 1-66, Butterworth-Heinemann Medical, ISBN 0750694777, H. J. M. Barnett et al., eds. *Stroke: Pathophysiology, Diagnosis and Management* $3^{rd}$ edition, 1998, see, e.g., pages 10-1450, Churchill Livingstone, ISBN 0443075514, P. J. Vinken et al., eds. *Neurodystrophies and Neurolipidoses* $2^{nd}$ ed. 1996, see, e.g., pages 8-780, Elsevier Science, ISBN 0444812857, P. L. Peterson and J. W. Phillis eds. *Novel Therapies for CNS Injuries: Rationales and Results* 1995, see, e.g., pages 8-380, CRC Press, ISBN 0849376521, D. Schiffer, *Brain Tumors: Pathology and Its Biological Correlates* $2^{nd}$ ed. 1997, see, e.g., pages 5-450, Springer Verlag, ISBN 3540616225 and E. Niedermeyer and F. Lopes Da Silva, eds. *Electroencephalography: Basic Principles, Clinical Applications and Related Fields* $4^{th}$ ed. 1999 see, e.g., pages 13-1238, Lippincott, Williams & Wilkins, ISBN 0683302841.

The use of the F1Cs in these conditions is optionally combined with one or more of the therapeutic treatments that are described in these references. The F1C may be administered before, during or after another treatment is employed to prevent, treat or ameliorate a given neurological condition or symptom thereof. Any of these neurological conditions or symptoms may be mild or at an early stage, moderate or severe or advanced.

Dosages of the F1C, routes of administration and the use of combination therapies with other standard therapeutic agents or treatments could be applied essentially as described above for cardiovascular conditions or as disclosed elsewhere herein. Thus, the F1Cs may be administered prophylactically or therapeutically in chronic conditions or they may be administered at the time of or relatively soon before or after an acute event such as an epileptic seizure, onset of a migraine or occurrence of trauma, before, during or after surgery, accidental head or central nervous system injury or a cerebral stroke or infarction. For acute events, the formula 1 compounds may thus be administered concurrently, e.g., within about 15 minutes or about 30 minutes of the onset or occurrence of the acute event, or at a later time, e.g., at about 1, 2, 3, 4, 5, 6, 7, 8, 9, 10, 11, 12, 13, 14, 15, 16, 18, 20, 22, 24, 26, 28, 30, 36, 42, 48, 54, 60, 72, 84, 96, 108 or 120 hours after the onset or occurrence of the acute event. The F1Cs may thus be administered at about 6-120 hours, or about 8-48 hours, about 10-24 hours or about 12-16 hours after an acute event starts or occurs. In other embodiments, the F1C can be administered before an expected acute event such as a planned surgery. In these cases, the F1Cs may be administered before, e.g., within about 15 minutes or about 30 minutes of the onset or occurrence of the acute event, or at an earlier time, e.g., at about 1, 2, 3, 4, 5, 6, 7, 8, 9, 10, 11, 12, 13, 14, 15, 16, 18, 20, 22, 24, 26, 28, 30, 36, 42, 48, 54, 60, 72, 84, 96, 108 or 120 hours before the onset or occurrence of the acute event.

Skin Treatments.

The affect of the F1Cs on immune function permits their use to improve the function of organs organ systems that rely on the optimal functioning of one or more immune responses. Thus, the F1Cs can be administered to a subject to prevent, treat, ameliorate, slow the progression of or enhance the healing of certain skin conditions such as skin inflammation, lesions, atrophy or rash. Conditions that can give rise to skin pathology or an unwanted skin condition include autoimmune diseases, inflammation, allergy, age, exposure to sunlight, cancer, infection or the like.

As used here, skin includes external skin and internal skin or surfaces such as oral, intestinal and rectal mucosa. These conditions include lesions, rashes or inflammation associated with, e.g., burns, infections and the thinning or general degradation of the dermis often characterized by a decrease in collagen or elastin as well as decreased number, size and doubling potential of fibroblast cells. Such skin conditions include keratoses such as actinic keratosis, psoriasis, eczema, warts such as papillomavirus-induced warts, ulcers or lesions such as herpesvirus-induced ulcers or lesions or diabetes associated ulcers or lesions, discoid lupus erythematosus, erythema nodosum, erythema multiform, cutaneous T cell lymphoma, atopic dermatitis, inflammatory vasculitis, relapsing polychondritis, exfoliative dermatitis, sarcoidosis, burns, melanoma, rash or irritation from poison oak, poison ivy or poison Sumac, blemished or hyperpigmented skin, hyperkeratotic skin, dry skin, dandruff, acne, inflammatory dermatoses, scarring such as from a chemical or thermal burn and age-related skin changes. In these embodiments, treatment with the F1Cs is optionally combined with other appropriate treatments or therapies essentially as described herein, e.g., one or more of a corticosteroid such as hydrocortisone or cortisol, prednisone, or prednisolone, an α-hydroxybenzoic acid or an α-hydroxycarboxylic acid(s) is coadministered with a F1C to treat, prevent or ameliorate a skin condition such as atrophy or a lesion. α-Hydroxybenzoic acids and α-hydroxycarboxylic acids suitable for use in these embodiments are described in, e.g., U.S. Pat. Nos. 5,262,407, 5,254,343, 4,246,261, 4,234,599 and 3,984,566. The F1C can be used to minimize cutaneous atrophy caused by corticosteroids, a common side effect of their application to the skin.

In embodiments that address skin conditions, dosages, routes of administration and dosing protocols for the F1Cs are essentially as described herein. In some embodiments, the F1C is administered to the subject in the form of a topical cream, ointment, spray, foam, gel or the like. These topical formulations will optionally comprise about 0.1% w/w to about 20% w/w, or about 0.2% w/w to about 10% w/w of a F1C in a composition that comprises one or more excipients that are suitable for such topical formulations, including, e.g., one or more agents that enhance penetration or delivery of the F1C into the skin. In topical cosmetic preparations or formulations, the F1C will typically be present as about 0.01%, about 0.05% or about 0.1% to about 0.5%, about 1% or about 3% of the total weight of the composition. Such topical formulations can be administered, e.g., once, twice or three times per day using about 0.1 g to about 8 g or about 0.2 g to about 5 g of the topical formulation on each occasion. Administration may be daily for about 1 to about 28 days, or it may be intermittent and used as needed. The amount of a topical formulation that can be administered may be higher, e.g., about 15 g or about 20 g, if the size of the area to be treated is relatively large, e.g., at least about 30 cm$^2$ to about 100 cm$^2$ or more. Alternatively, systemic administration of the F1C such as oral, parenteral, sublingual or buccal delivery may be used, particularly when the area of the skin to be treated is relatively large. In some cases, both topical and systemic administration of a F1C can be used. Excipients that topical or other formulations may contain include those described herein, or agents that enhance permeation or solubilization of the F1C, e.g., DMSO or an alkylalkanol, such as a 2-alkylalkanol or a 3-alkyloctanol that comprises about 8-36 carbon atoms (e.g., 8, 9, 10, 11, 12, 13, 14, 15, 16, 17, 18, 19 or 20 carbon atoms) such as 2-ethyloctanol, 2-propyloctanol, 2-octyldodecanol, 2-butyloctanol, 2-hexyldecanol, 2-pentylnonanol, 3-ethyloctanol, 3-propyloctanol, 3-octyldodecanol, 3-butyloctanol, 3-hexyldecanol, 3-pentylnonanol, isostearyl alcohol, isocetyl alcohol, or mixtures thereof. Such alkylalkanol moieties include those having the structure HO—CH$_2$—(CH$_2$)$_{0-4}$—CH(C1-10 alkyl)-(CH$_2$)$_{0-6}$—CH$_3$, any of which are optionally substituted at the alkanol or the alkyl moiety with one, two, three or more independently selected substituents as described herein, e.g., with one, two, three or more independently selected —O—, —F, —OH, —CN or —CH═CH— moieties. Such formulations can be used in therapeutic applications described herein or in cosmetic applications.

Enhancement of Hematopoiesis.

The invention includes methods to modulate hematopoiesis by administering a F1C to a subject, which can be used to treat or prevent various blood cell deficiencies such as thrombocytopenia ("TP") or neutropenia ("NP"). Hematopoiesis or hemopoiesis is the formation and development of the various types of blood cells and their progenitor cells. Mature cells are found in circulation or tissues such as the lymph nodes, spleen or the thymus. Many of the stem cells that give rise to mature forms reside in the bone marrow, although some may circulate in the blood for some time. Clinical blood cell deficiencies such as thrombocytopenia, neutropenia or erythropenia can arise from causes such as impaired hematopoiesis or abnormal loss or destruction of mature or immature blood cells.

Without being bound to any theory, the treatment methods at least in part result in enhanced hematopoiesis, enhanced movement of blood cells into the circulation and/or in reduced loss of blood cells such as platelets or neutrophils. The F1Cs can enhance self-renewal or numbers of hematopoietic stem cells, precursor cells, mature blood cells and/or they can enhance or accelerate differentiation of stem or any progenitor cell that can give rise to a mature blood cell. The stem or progenitor cells include early lineage cells showing little or no characteristics of fully differentiated blood cells and/or they can be partially differentiated. Increased platelet or neutrophil production, enhanced survival or reduced loss is typically observed as increased circulating blood cell counts. Increases in blood cells appear to arise from enhanced proliferation of precursor cells and/or from enhanced or accelerated differentiation of precursor cells. Increased cell numbers, e.g., platelets or neutrophils, can also arise from reduced loss or death of such cells, increased demargination of cells such as neutrophils from the vasculature into circulating blood or other tissues and/or shorter transit time of mature or precursor cells from the bone marrow into blood.

Thus, invention embodiments comprise a method to treat or prevent a blood cell deficiency such as TP or NP in a subject in need thereof, comprising administering to the subject, or delivering to the subject's tissues, an effective amount of a F1C. Related embodiments include a method to increase self-renewal of hematopoietic stem cells or hematopoietic progenitor cells or to increase the commitment of such cells to transition to a more differentiated blood precursor cell or mature blood cell. In other embodiments, the invention provides a method for stimulating the proliferation or differentiation of neutrophil precursors or to increase demargination of neutrophils or to reduce transit time from bone marrow to blood in a subject having or susceptible to developing NP comprising administering an effective amount of a F1C to the subject in need thereof. The F1C treatment will stimulate the activity of, e.g., neutrophils, or enhance their production from progenitor cells, enhance their survival and/or limit their loss. Hematopoietic stem cells, e.g., GEMM cells, are pluripotent and can give rise to more than one type of mature blood cell, while hematopoietic progenitor cells are usually not pluripotent, but are bipotent or monopotent. Hematopoietic progenitor cells reside primarily in bone marrow, but can also be found in blood, spleen or lymph tissue or fluids.

Normal ranges of various white blood cells or blood components in adult (about 18-49 years of age) human blood are as follows. Total adult white blood cell counts average about 7500/mm$^3$, with an approximate normal range of about 4.5-11.0×10$^3$/mm$^3$. The normal basophil level is about 35/mm$^3$, with a normal range of about 10/mm$^3$ to about 100/mm$^3$. The normal adult neutrophil level is about 4400/mm$^3$, with a normal range of about 2000-7700/mm$^3$. The normal eosinophil level is about 275/mm$^3$, with a normal range of about 150-300/mm$^3$. The normal monocyte level is about 540/mm$^3$, with a normal range of about 300-600/mm$^3$. The normal adult platelet level is about 2.5×10$^5$/mm$^3$, with a normal range of about 2.1×10$^5$-2.9×10$^5$/mm$^3$. The normal human adult red cell mass corresponds to about 4.6×10$^{12}$ red cells/L in females and about 5.2×10$^{12}$ red cells/L in males.

A human patient in need of treatment will typically have, or be subject to developing, a cell count below these values. For example, the subject may have a cell count that is about 2% to about 90% below the lower or upper values of these ranges, e.g., about 5%, about 10%, about 20%, about 30%, about 50% or about 70% below any of these values. As used herein, neutropenia means generally a circulating neutrophil count of less than about 2000/mm$^3$, typically less than about 1500/mm$^3$ or usually less than about 1300/mm$^3$. Under the common terminology criteria for adverse events, version 3.0, published at http://ctep.cancer.gov, grade 1 neutropenia in humans is the lower limit of normal to 1500 neutrophils/mm$^3$, less than 1500 to 1000 neutrophils/mm$^3$ is grade 2 neutropenia, about 1000-500 neutrophils/mm$^3$ is grade 3 neutropenia and less than about 500 neutrophils/mm$^3$ is considered to be grade 4 neutropenia. Febrile NP is NP accompanied by a fever, e.g., about 39.5° C. to about 43° C. or more, that is at least transient, e.g., lasting about 2 or more hours.

Thrombocytopenia generally means a circulating platelet count of less than the normal circulating range, e.g., less than about 1.6×10$^5$/mm$^3$, less than about 1.5×10$^5$/mm$^3$, less than about 1.3×10$^5$/mm$^3$ or less than about 1.0×10$^5$/mm$^3$. Under the common terminology criteria for adverse events, version 3.0, grade 1 thrombocytopenia is the lower normal limit to 75,000 platelets/mm$^3$, grade 2 thrombocytopenia is <75,000-50,000 platelets/mm$^3$, grade 3 thrombocytopenia is <50,000-25,000 platelets/mm$^3$ and grade 4 is <25,000 platelets/mm$^3$. Anemia generally means a red cell mass corresponding to less than about 4.0×10$^{12}$ red cells/L in adult females and less than about 4.5×10$^{12}$ red cells/L in adult males (a hemoglobin level of less than about 12.0 g/dL in adult females and less than about 13.5 g/dL in adult males).

In some cases, the diagnosis of a deficiency may cover a cell count that falls outside these ranges, due, e.g., to individual variations in a subject's age, sex, race, animal strain or normal blood cell status for the individual. Such variations are identified by known means such as by identification of a change from the subject's normal status or by multiple cell measurements over time that reveal a deficiency. See, e.g., *Hematology—Basic Principles and Practice*, 2$^{nd}$ edition, R. Hoffman, E. J. Benz Jr. et al., editors, Churchill Livingstone, New York, 1995. Subjects with an identified or identifiable deficiency outside these standard ranges are included in the definition of a blood cell deficiency or a subject in need of treatment, as used herein.

In exemplary embodiments, use of the F1Cs for treating subjects including primates or humans who are subject to developing a NP condition will typically result in a decreased in the severity and/or duration of NP. Typically, the F1C treatment will comprise treating the subject daily, every other day or every third day for about 1, 2, 3, 4, 5, 6, 7, 8, 9, 10, 11 or 12 days with about 0.1 mg/kg to about 5 mg/kg, usually about 0.5 mg/kg to about 4 mg/kg. For these dosages, the F1C is typically administered by parenteral, e.g., intravenous, subcutaneous or intramuscular, or transmucosal delivery. Oral administration will generally use dosages that are about 3-25 mg/kg higher, e.g., about 4-30 mg/kg of the F1C. Human unit dosages will typically comprise about 1-1500 mg, usually about 10-150 mg, which can be subdivided, e.g., into two or three subdoses. Treatment of subjects who may develop a NP condition from a chronic or slow onset condition will generally begin when reduced neutrophil counts are observed, e.g., when the subject has grade 1 or 2 NP. In situations where NP can arise over a short time period, e.g., from an inducing event such as a chemotherapy, an acute infection or radiation exposure, treatment with the F1C will generally begin at about the time of the inducing event. Thus, for subjects who will be subjected a chemotherapy or radiation therapy, dosing with the F1C can begin about 1, 2, 3 or 4 days before, during (essentially simultaneous with or on the same day as) or about 1, 2, 3 or 4 after the inducing event. Typically dosing the F1C begins in a period from 2 days before to 2 days after the subject is exposed to the NP inducing event.

Treatment with a F1C will reduce the severity of NP, e.g., by preventing the development of grade 3 or 4 NP or febrile NP in subjects who would otherwise be expected to develop or susceptible to developing grade 3 or 4 NP. The F1C will also typically reduce the duration of, e.g., grade 3 or 4 NP, in subjects who would otherwise be expected to develop or susceptible to developing such NP. The reduction in the duration of NP, grade 3 or 4 NP, can range from 100% to a detectable level, e.g., a reduction of at least about 10%. Typically, the reduction of the period during which a subject has grade 3 or 4 NP or febrile NP is about 25% to about 85%, e.g., about 30%, 40%, 50%, 60%, 70%, 80% or more.

Individual responses can vary depending on factors such as the subject's initial neutrophil status, when dosing with the F1C is initiated, dosage of the F1C and the route of administration of the F1C. NP in subjects susceptible to developing NP can arise from conditions or treatments as described herein, e.g., autoimmune conditions, cancer, cancer chemotherapy, an infection, antimicrobial chemotherapy, bone marrow transplantation, an immunosuppressive therapy, bone marrow damage or exposure to or treatment with an ionizing radiation such as one or more of γ-radiation, X-rays, fast neutrons, β-radiation or α-radiation.

TP, abnormally low platelet counts, can arise from impaired platelet production, sequestration of platelets in the spleen or abnormal loss of circulating platelets. Impaired production can result from causes such as chemotherapy, radiation exposure, e.g., a radiation therapy, or an from autoimmune condition. Abnormal loss of circulating platelets is often associated with autoreactive antibodies that bind to platelets and reduce their life span. These underlying causes give rise to the various clinical forms of TP, such as autoimmune neonatal TP, immune thrombocytopenic purpura, radiation induced TP, chemotherapy induced TP and amegakaryocytic TP.

Other conditions that are amenable to prophylaxis or treatment by the invention methods include the acquired blood cell deficiencies. Exemplary deficiencies or groups of deficiencies that can be treated are neonatal alloimmune TP, immune TP, immune thrombocytopenic purpura, thrombotic thrombocytopenic purpura, post-transfusion purpura, radiation associated TP, chemotherapy associated TP (e.g., an anti-cancer, antiviral, antibacterial, antifungal or antiparasite therapy, NSAID treatments such as with indomethicin, ibuprofen, naproxen, phenylbutazone, piroxicam or zompirac, or β-lactam antibiotic treatments such as with ampicillin, carbenicillin, penicillin G, ticarcillin, or cephalosporin treatments such as with cefazolin, cefoxitin or cephalothin, anti-coagulant treatments such as heparin, hirudin, lepirudin or aspirin, treatment with plasma expanders or psychotropic drugs), amegakaryocitic TP, radiation associated TP, TP associated with solid organ allograft or xenograft rejection or immune suppression therapy in solid organ or other tissue transplants (e.g., liver, lung, kidney, heart, bone marrow, hematopoietic stem cell or endothelial cell transplant, implant or transfusion), cardiopulmonary bypass surgery, cardiovascular disease or therapy associated TP (e.g., congenital cyanotic heart disease, valvular heart disease, pulmonary embolism, pulmonary hypertension disorders or diltiazem, nifedipine, nitroglycerin or nitroprusside therapy), TP associated with chronic or acute renal failure or treatment for these conditions (e.g., dialysis), TP associated with infection such as a virus or bacterial infection. NP conditions that can be treated include postinfectious NP, autoimmune NP, chronic idiopathic NP, basophilic leukopenia, eosinophilic leukopenia, monocytic leukopenia, neutrophilic leukopenia, cyclic NP, periodic NP, chemotherapy associated NP, radiation associated NP, NP associated with solid organ allograft or xenograft rejection or immune suppression therapy in solid organ or other tissue transplants (e.g., liver, lung, kidney, heart, bone marrow, hematopoietic stem cell or endothelial cell transplant, implant or transfusion), chemotherapy associated leukopenia, radiation associated leukopenia, leukopenia associated with solid organ allograft or xenograft rejection or immune suppression therapy in solid organ or other tissue transplants (e.g., liver, lung, kidney, heart, bone marrow, hematopoietic stem cell or endothelial cell transplant, implant or transfusion), immune hemolytic anemias, anemia associated with chronic or acute renal failure or treatment for these conditions (e.g., dialysis), anemia associated with chemotherapy (e.g., isoniazid, prednisone) or anemia associated with radiation exposure.

The F1Cs are thus useful to facilitate or speed up immune system recovery in autologous bone marrow transplant or stem cell transplant situations. In many cases it would be medically sound to continue the treatment associated with causing or exacerbating the blood cell deficiency. Thus, in some embodiments a F1C treatment is conducted with subjects who are undergoing another therapy at the same time or near the same time, e.g., within about 1, 2, 3, 4 or several days to within about 1-6 months. Such subjects typically will have an identified blood cell deficiency such as a NP or a TP, e.g., as disclosed herein. However, the F1Cs can be generally suitable for preventing the onset or reducing the severity of such deficiencies, and they can thus be used prophylactically in these indications, e.g., by administering a F1C beginning at about 1-60 days before administering another therapy that could lead to a cytopenia condition such as TP or NP.

In conditions such as NP, the F1Cs will typically function at least in part by modulating, e.g., increasing, the level or activity of biomolecules such as IL-1β, G-CSF, GM-CSF or one or more of their receptors, that can enhance generation or survival of a desired cell type such as neutrophils. In this regard, the F1Cs can act as inducers of endogenous growth or differentiation factors that facilitate increased production or survival of neutrophils or other blood cell types. This aspect of the F1Cs allows one to eliminate or reduce the use of such molecules in treating conditions such as NP.

Use of a F1C in treating cytopenia conditions is thus optionally combined with the use of an effective amount of one or more growth factors or cytokines as a means to further enhance the effect of the F1Cs for their intended uses or to modulate, e.g., enhance, their effects or efficacy. Suitable growth factors and cytokines are as described herein or in the cited references. For example, when one administers the F1C to enhance generation of platelets in humans or other subjects, or their precursor cells such as CFU-blast cells, multipotent thymic precursor cells (CD34$^+$, CD38$^+$, CD7$^+$, CD44$^+$, CD33$^+$, CD2$^-$, CD5$^-$, CD1a$^-$), Pro-DC2 cells, immature DC2 cells, immature NK cells, CFU-GEMM, BFU-Mk, CFU-Mk, CFU-G, CFU-GM, immature megakaryocytes or mature postmitotic megakaryocytes, one can also administer one or more of G-CSF, GM-CSF, SCF, Steel factor ("SF"), leukemia inhibitory factor ("LIF"), interleukin-1α, ("IL-1α"), IL-3, IL-6, IL-11, TPO, EPO, their isoforms, their derivatives (e.g., linked to a PEG or fusions such as PIXY321) or their isoforms, orthologs or homologs for other species. Similarly, administration of the F1C to enhance the generation or function of myelomonocytic cells such as neutrophils, basophils or monocytes in humans or other subjects, can also be combined with administration of one or more of G-CSF, GM-CSF, M-CSF, LIF, TPO, SF, interleukin-1 ("IL-1"), IL-2, IL-3, IL-4, interleukin-5 ("IL-5"), IL-6, IL-11, interleukin-12 ("IL-12"), interleukin-13 ("IL-13"), FLT3 ligand, their isoforms, orthologs, homologs or derivatives (e.g., linked to a PEG or fusions such as PIXY321) or their isoforms, orthologs or homologs for other species. To enhance generation of red cells or their precursor cells such as CFU-GEMM, BFU-E or CFU-E in humans being treated with a F1C, one can co-administer one or more of G-CSF, GM-CSF, IL-1, IL-3, IL-6, TPO, EPO, transforming growth factor-β1, their isoforms, their derivatives (e.g., linked to a PEG or fusions such as PIXY321) or their isoforms, orthologs or homologs for other species. See, e.g., *Hematology—Basic Principles and Practice*, 3$^{rd}$ edition, R. Hoffman, E. J. Benz Jr. et al., editors, Churchill Livingstone, New York, 2000 (see, e.g., Chapters 14-17 at pages 154-260). The co-administration of such factors in these methods is intended to enhance the efficacy of the F1C treatment, which is optionally measured by taking suitable blood or tissue, e.g., bone marrow, samples at one or more times before and after the compounds have been administered. Such co-administration will generally be compatible with a subject's condition and other therapeutic treatments. Co-administration of such factors can precede, be simultaneous with, or follow the times of administration of the F1C(s) to the subject. Dosages of such growth factors would generally be similar to those previously described, e.g., typically an initial course of treatment comprises administering about 1.0 to about 20 μg/kg/d for about 1-10 days, or as described in, e.g., *Hematology—Basic Principles and Practice*, 3$^{rd}$ edition, R. Hoffman, E. J. Benz Jr. et al., editors, Churchill Livingstone, New York, 2000 (see, e.g., Chapter 51 at pages 939-979 and the references cited therein).

In cases where a subject's blood cell deficiency is caused by, or associated with another therapy, the invention contemplates that the other therapy will continue, if this is reasonable under the circumstances. The timing of other therapies can precede, be simultaneous with, or follow the times of administration of the F1C(s) to the subject. For example, chemotherapy for some malignancies is accompanied by myelosuppression or a deficiency in one or more blood cell types, e.g., TP or NP. Continued treatment would be called for in some cases, and then the invention methods would be employed to deliver to the subject an effective amount of a F1C. Thus, alkylating agents, antimicrotubule agents, antimetabolites, vinca alkaloids, topoisomerase I or II inhibitors, or platinum compounds such as one or more of mechlorethamine, vincristine, vinblastine, bleomycin, doxorubicin, epirubicin, tamoxifen, cyclophosphamide, etoposide, methotrexate, ifosfamide, melphalan, chlorambucil, busulfan, carmustine, lomustine, streptozocin, dacarbazine, vinorelbine, paclitaxel (taxol), docetaxel, cytosine arabinoside, hydroxyurea, fludarabine, 2'-chlorodeoxyadenosine, 2'-deoxycoformycin, 6-thioguanine, 6-mercaptopurine, 5-azacytidine, gemcitabine, arabinofuranosylguanine, daunorubicin, mitoxantrone, amsacrine, topotecan, irinotecan, cisplatin, carboplatin, pilcamycin, procarbazine, aspariginase, aminoglutethimide, actinomycin D, azathioprine and gallium nitrate may be administered in conjunction with administration of any F1C(s) that is disclosed herein. Treatments with other therapeutic agents such as heparin or nucleoside analogs such as 3-thiacytosine, azidothymidine or dideoxycytosine, or other antimicrobials such as cephalosporin, quinine, quinidine, gold salts (e.g., aurothioglucose), a fluoroquinolone (e.g., ciprofloxacin), clarithromycin, fluconazole, fusidic acid, gentamycin, nalidixic acid, penicillins, pentamidine, rifampicin, sulfa antibiotics, suramin or vancomycin may result in a blood cell deficiency(s) and they can thus be combined with administration of a F1C to treat the deficiency, or to ameliorate a symptom thereof. Similarly, anti-inflammatory drugs (e.g., salicylates, entanercept (a dimeric fusion comprising a portion of the human TNF receptor linked to the Fc portion of human IgG1 containing the $C_H2$ and $C_H3$ domain and hinge regions of IgG1) or a COX-2 inhibitor such as celexicob (4-5[-(4-methylphenyl)-3-(trifluoromethyl)-1H-pyrazole-1-yl]benzenesulfonamide) or rofecoxib (4-[4-methylsulfonyl) phenyl]-3-phenyl-2(5H)-furanone) or an IL-1 receptor antagonist such as anakinra), cardiac drugs (e.g., digitoxin), β-blockers or antihypertensive drugs (e.g., oxprenolol or captopril), diuretics (e.g., spironolactone), benzodiazepines, (e.g., diazepam) or antidepressants (e.g., amitriptyline, doxepin). Any of these methods also optionally include co-administration of one or more of the growth factors described above, e.g., IL-3, G-CSF, GM-CSF or TPO.

Other therapies for treating a blood cytopenia such as TP or NP also include administering one or more of glucocorticoid steroids (e.g., prednisone, prednisolone), human IgG antibodies, anti-Rh(D)+ antibodies for Rh(D)+ patients, an androgen such as danazol, vinca alkaloids (e.g., vincristine, vinblastine), thrombopoietin and immunosuppressants (e.g., azathioprine, cyclophosphamide, FK506 or cyclosporin). Splenectomy may also be indicated, for example when first line treatments fail. The goal of treatment for TP in humans is typically to increase platelet counts to at least about 20,000/$mm^3$ or more typically to at least about 50,000/$mm^3$ and to maintain these levels.

Although the treatment options to increase platelet levels are generally known, they usually have a number of drawbacks. For example, infusion of IgG antibodies is not always effective and the treatment is relatively expensive. Other treatments, such as prednisone are also not always effective and they typically are discontinued or tapered off after several weeks due to toxicity or unwanted side effects. Splenectomy, which is relatively expensive and invasive, is also not always effective. The sources of thrombocytopenia and treatment options have been described. See, e.g., *Hematology—Basic Principles and Practice*, 3$^{rd}$ edition, R. Hoffman, E. J. Benz Jr. et al., editors, Churchill Livingstone, New York, 2000 (see, e.g., Chapters 126-129 and 131 at pages 2096-2154 and 2172-2186), PCT publication WO 200035466.

Neutropenia ("NP"), is considered to exist clinically when neutrophils drop to below a level considered normal. NP can arise from impaired production of neutrophil precursors or mature neutrophils, movement of neutrophils from the circulation to tissue, abnormal circulating neutrophil loss or a combination of these causes. Impaired neutrophil production can be acquired from, e.g., treatment with a cytotoxic or cytostatic drug, chemotherapy, radiation therapy or an autoimmune response as described herein. The abnormal loss of circulating neutrophils in autoimmunity is typically associated with autoreactive antibodies that bind to the cells and reduce their life span. These underlying causes give rise to the various clinical forms of NP, such as postinfectious NP, drug-induced NP, autoimmune NP, or chronic idiopathic NP. The sources of NP and treatment options have been described. See, e.g., *Hematology—Basic Principles and Practice*, 3$^{rd}$ edition, R. Hoffman, E. J. Benz Jr. et al., editors, Churchill Livingstone, New York, 2000 (see, e.g., Chapters 19, 41, 51, 79, 134 and 137 at pages 297-331, 720-762, 939-979, 1443-1500, 2220-2248 and 2257-2263).

In some embodiments, the F1Cs that are used to enhance hematopoiesis or to treat associated conditions such as a TP or a NP disease or condition as disclosed herein, are characterized by having a lack of appreciable androgenicity. In these embodiments, the F1Cs are characterized by having about 15% or less, about 10% or less, about 5% or less, about 2% or less, about 1% or less or about 0.5% or less of the androgenicity of a reference androgen such as testosterone, testosterone proprionate, dihydrotestosterone or dihydrotestosterone proprionate as measured in a suitable assay using suitable positive and/or negative controls. F1Cs having, e.g., a substitution at the 6- or 7-position or having no double bond at the 4-5 or 5-6 positions, will generally have relatively low levels of androgen activity. Suitable assays for androgenicity of various compounds have been described, e.g., J. R. Brooks, et al., *Prostate* 1991, 18:215-227, M. Gerrity et al., *Int. J. Androl.* 1981 4:494-504, S. S. Rao et al., *Indian J. Exp. Biol.* 1969 7:20-22, O. Sunami et al., *J. Toxicol. Sci.* 2000 25:403-415, G. H. Deckers et al., *J. Steroid Biochem. Mol. Biol.* 2000 74:83-92. The androgenicity of the F1Cs are optionally determined as described or essentially as described in one or more of these assays or any other assay. Thus, one such embodiment comprises a method to enhance hematopoiesis or to treat TP or NP comprising administering to a subject in need thereof an effective amount of a F1C, or delivering to the subject's tissues an effective amount of a F1C, wherein the F1C has about 30% or less, about 20% or less, about 10% or less or about 5% or less of the androgenicity of an androgen such as testosterone, testosterone proprionate, dihydrotestosterone or dihydrotestosterone proprionate as measured in a suitable assay, e.g., as described in the citations above. In conducting such methods, the subjects, e.g., rodents, humans or primates, are optionally monitored for e.g., amelioration, prevention or a reduced severity of a disease, condition or symptom. Such monitoring can optionally include measuring one or more of cytokines (e.g., TNFα, IL-1β), WBCs, platelets, granulocytes, neutrophils, RBCs, NK cells, macrophages or other immune cell types, e.g., as described herein or in the cited references, in circulation at suitable times, e.g., at baseline before treatment is started and at various times during or after treatment with a F1C, e.g., at about 2-45 days after treatment with a F1C has ended.

In conducting any of these methods, one can monitor the subject's clinical condition at any relevant time before, during or after administration of the F1Cs, which treatments are optionally combined with any of the other agents or treatments described above. The subject's blood can be drawn on one, two or more occasions in advance of treatment to, e.g., obtain a baseline or initial level of white or red blood cells, to verify a presumptive diagnosis of a blood cell deficiency or to determine a blood parameter such as circulating myelomonocyte counts, circulating neutrophil counts or circulating platelet counts. Then, during the course of treatment or thereafter the subject's blood can be drawn on one, two or more occasions to follow the subject's response, e.g., once treatment with a F1C has ended.

Invention embodiments include methods that comprise administering to a subject in need thereof an effective amount of a F1C and an effective amount of at least one form of interferon, such as γ-Interferon or a growth factor or interleukin such as G-CSF or IL-6. Interferons can enhance the biological activity of the white cells that arise from increased hematopoiesis. This can be particularly useful when the subject's circulating blood cell deficiency is associated with, e.g., an infection or a chemotherapy that suppresses hematopoiesis. Administration of a growth factor or an interleukin such as IL-6 can facilitate hematopoiesis by stimulating quiescent stem cells or other progenitors that give rise to deficient cell types. Related embodiments replace growth factor or interferon administration partially or completely by increasing endogenous production in the subject using conventional methods, e.g., administering double stranded RNA to stimulate γ-IFN.

In these embodiments, the subject may have thrombocytopenia or neutropenia or the subject's circulating platelets, red cells, mature myelomonocytic cells, or their precursor cells, in circulation or in tissue may be detectably increased. In some cases the subject has renal failure. These methods may further comprise the steps of obtaining blood from the subject before administration of the F1C and measuring the subject's white or red cell counts and optionally, on one, two, three or more occasions, measuring the subject's circulating white cell or red cell counts after administration of the F1C, e.g., within about 12 weeks after an initial administration of a F1C or during or within about 12 weeks after a course of treatment as described herein.

Delayed Radiation Effects.

Invention embodiments include a method to prevent, treat or ameliorate a symptom or condition associated with one or more delayed adverse effect, symptom or condition from ionizing radiation exposure in a subject in need thereof comprising administering to the subject, or delivering to the subject's tissues, an effective amount of a F1C. In these embodiments, administration of the F1C commences at least 2 weeks after the subject has been exposed to a dose or subdose of radiation that could give rise to a delayed radiation effect. Dosing with the F1C can thus begin at 14 days to about 2 years or more after ionizing radiation exposure. Typically dosing will begin at about 2 weeks, 3 weeks, or 1, 2, 3 or 4 months after exposure of the subject to sufficient ionizing radiation to potentially cause delayed effects. Radiation exposure may arise from a radiation therapy where exposure is intentional, or it may arise from an accidental exposure.

Radiation therapy ("RT") can generate a number of late delayed-onset conditions or symptoms. Delayed radiation effects are conditions or symptoms that generally arise or become detectable to the subject or to a health care provider at least about 1 month after exposure to radiation. Thus the conditions or symptoms may be detectable at about 2 months, about 3 months, about 4 months, about 5 months, about 1 year, about 20 years or more after radiation exposure. For example, transient nervous system symptoms may develop early after RT, but progressive, permanent, often disabling nervous system damage may appear months or years later. The total radiation dose, size of the fractions, duration of RT, and volume of tissue irradiated influence the probability of the injury and its severity. Individual patient and tissue susceptibility to delayed injuries is variable, which factors into the selection of safe and effective radiation doses for RT. Total radiation doses that a subject may receive may comprise single doses or 2, 3, 4, or more doses within a range of about 1 to about 400 Gy, e.g., about 1, 1.4, 1.6, 1.8, 2, 2.5, 3, 5, 10, 20, 40, 50, 80, 100, 130, 150, 180, 200, 250, 300, 400 Gy. Typical doses are about 1-12 Gy or about 1-8 Gy. Such doses in a given course of treatment may be the same or different and can occur over a period of time, e.g., over 1 day to about 1 or 2 years.

In some embodiments, the total radiation dose occurs on a single exposure that occurs in a relatively short time period, e.g., about 1-20 minutes to about 12 hours. In other embodiments, the total dose is delivered to the subject in multiple doses or over a longer time, e.g., over about 2 days to about 12 months or more in multiple doses in, e.g., 2, 3, 4, 6, 8, 10 or more individual doses. Ameliorating a side effect may comprise detectably slowing the progression of a symptom or condition or detectably reducing the ultimate expected severity of a symptom or condition. The affected condition or symptom may be detectably reduced as determined by the subject or the health care provider. Thus, after administration of a F1C, the target symptom or condition may be moderately reduced, slightly reduced, essentially nonexistent or subclinical, e.g., present at a low level that is not deemed significant by the subject or the health care provider. Amelioration of one or more conditions or symptoms that can be suitably quantified may be observed as a decrease of about 5% or more, e.g., at least about 10%, at least about 20%, at least about 30%, at least about 40%, at least about 50%, at least about 70%, at least about 80% or at least about 90% in the relative expected or potential severity or extent of the condition or symptom.

For example, in lung pneumonitis, administration of a F1C can lead to detectably increased oxygen saturation in the subject's blood by about 5% or by about 10% or more, e.g., oxygen saturation can rise from about 83% to about 88%, which would typically be detectable by the subject and the health care provider. Such decreased severity of a condition or symptom may be objectively measured in some instances, e.g., by determining the number or activity of circulating platelets or neutrophils or by evaluation of fever, severity or frequency of diarrhea or blood oxygen saturation levels. For other symptoms or conditions, prevention may be subjectively observed by a significant or detectable improvement in a relevant score, e.g., decreased fever or pain or a decreased need for treatment of fever, pain or inflammation.

Symptoms or conditions of radiation exposure that can be treated also include encephalopathy, myelopathy, nausea, diarrhea, acute inflammation, chronic inflammation, edema, pain, fever, headache, depression, malaise, weakness, hair loss, skin atrophy, skin ulceration, skin lesion, keratosis, telangiectasia, infection, e.g., bacterial, viral, fungal or yeast infection, hypoplasia, atrophy, marrow hypoplasia, hemorrhage, fibrosis, e.g., lung fibrosis, pneumonitis, bone marrow hypoplasia, hemorrhage or cytopenia, e.g., anemia, leukopenia or thrombocytopenia, edema, fibrosis or hemorrhage or the need for edema, fibrosis or hemorrhage treatment. Such symptoms or conditions may arise from one or more radiation-damaged tissues or cells, including lymphoid cells, bowel or intestinal epithelium or tissue, bone marrow, testicles, ovaries, brain tissue, spinal cord tissue or skin epithelium.

Exemplary symptoms or conditions associated with late effects of radiation exposure include (1) acute or chronic radiation-induced enteritis or diarrhea, e.g., in patients receiving pelvic radiotherapy, (2) pseudomembranous inflammation, (3) perivascular fibrosis, (4) endothelial cell damage or death, e.g., associated with vascular radiation therapy, (5) cardiac tissue inflammation or damage or pericardial disease, e.g., in pediatric or adult patients receiving radiation therapy for a leukemia, thoracic neoplasm or other malignancy, (6) pulmonary tissue inflammation or damage, (7) hematopoietic or marrow cell inflammation or damage, e.g., in wide field radiation therapy, (8) endocrine or thyroid dysfunction, e.g., in thalamic or hypothalamic tumors in pediatric or other patients, (9) decreased growth or decreased bone development or density, e.g., in pediatric patients receiving radiation therapy for a childhood leukemia or other malignancy, (10) central nervous system inflammation or damage, e.g., in pediatric or adult patients receiving radiation therapy for a leukemia (e.g., CNS acute lymphocytic leukemia) or other malignancy, (11) connective tissue damage after radiation therapy, (12) incidence or severity of a secondary leukemia such as acute myelogenous leukemia or myelodysplasia and (13) gastric ulceration, bleeding, small bowel obstruction or fistula formation in, e.g., patients receiving radiation therapy to the gastrointestinal tract. These symptoms or conditions are treated or ameliorated using the F1Cs essentially as disclosed herein.

In treating such symptoms or conditions, slowing the progression of a symptom, condition or side effect will detectably reduce the rate at which the condition, symptom or side effect worsens or intensifies. In some embodiments, pronounced slowing of the rate of progression is, e.g., the time needed to progress to an expected or a measurable point, which may be increased by a period of about 1, 2, 3, 4, 5, 10, 20, 30 or more days to a period of about 1, 2, 3, 4, 6, 8, 10, 12, 18, 24, 36, 48, 72 or more months.

Radiation-associated brain damage can give rise to acute encephalopathy with symptoms such as headache, nausea, vomiting, somnolence, depression, disorientation, and worsening neurologic signs. The encephalopathy may arise from the first, second or a subsequent radiation fraction, e.g., when high intracranial pressure has not been treated with, e.g., corticosteroids. Late-delayed radiation damage to the brain or nervous system can arise at about 2, 3, 4, 5, 6, 7, 8, 9, or 10 months to 1, 2, 3 or more years after leukemia prophylaxis in children or after brain tumor prophylaxis or treatment in adults. Symptoms often include pain or headache and progressive dementia without focal signs and adults typically also develop an unsteady gait. Cerebral atrophy appears on CT scans in some cases. Late-delayed damage can arise at about 1 week, about 2 weeks about 2 months or about 1-2 years after irradiation of extracranial tumors or high-dose irradiation of intracranial tumors, e.g., brachytherapy or radiosurgery, although the symptoms are generally more focal. The invention method would be used during the time period when such symptoms would be expected to arise, e.g., commencing at about 1-5 days or about 7-60 days after radiation exposure and ending at about 0.5, 1, 2, 3, 4, 5 or more years later. Exemplary brachytherapies and unsealed source therapies include prostate $^{125}$I seed implants in prostate conditions such as prostate cancer, $^{90}$Yt conjugated to monoclonal antibodies or in endovascular brachial radiotherapy.

Early-delayed radiation spinal cord myelopathy follows radiation therapy to the spinal cord, neck, upper thorax or lumbar region or and it is often characterized by Lhermitte's sign, i.e., an electric shock-like sensation radiating down the back and into the legs on neck flexion. Late-delayed radiation myelopathy can arise months or years after therapy for extraspinal tumors, e.g., Hodgkin's disease. Other symptoms can include progressive weakness and sensory loss, such as a Brown-Séquard type, i.e., a proprioceptive sensory loss and weakness on one side of the body and loss of temperature and pain sensation on the other side. Progression times vary, but many human patients suffering from late-delayed radiation spinal cord myelopathy become paraplegic. Late-delayed radiation neuropathy may produce brachial neuropathy, e.g., after treatment for breast or lung cancer. Radiation can also give rise to gliomas, meningiomas, or peripheral nerve sheath tumors at about 1, 2, 3, 4, 5 or more years after therapy. The F1Cs will generally be administered at about the time period when these symptoms would be expected to arise, e.g., commencing at about 1-5 days, or about 7-60 days or about 6 or 12 months after radiation exposure and ending at about 3, 4, 6 months later or about 1, 2, 3, 4, 5, 6 or more years later. In some embodiments, the F1C is administered to the subject on the same day that a planned or accidental radiation exposure occurs and dosing is continued for about 1, 2, 3, 4, 8, 12 or more weeks to about 2, 3, 4, 5, 6 or more years, or for a time as disclosed elsewhere herein.

Administration of the F1C will typically commence at about 1 day to about 6 months after a subject has received a total radiation exposure, e.g., any dose or dose range disclosed herein. Typically, the F1C is used in the invention method commencing at about 2-120 days after radiation exposure or at about the time that radiation delayed effects become apparent to the subject or the subject's health care provider, e.g., within about 1-30 days after a condition or symptom is detected. Administration of the F1C may continue for a period of about 5 days to about 60 days for conditions or symptoms that tend to resolve over a relatively short time period. In other embodiments, the F1C is administered for a period of 2, 3, 4, 5, 6, 8, 10, 12, 15, 18, 24, 36, 48, 60 or more months for conditions or symptoms that tend to be chronic (e.g., neurological damage or inflammation), arise over a long time period (e.g., secondary cancers or neurological damage) or to progress over a relatively long time, e.g., about 1-5 years or more (e.g., cancers or neurological damage).

In any of the radiation exposure embodiments or dosing protocols disclosed herein, the F1C can be administered to the subject daily or on an intermittent basis, e.g., on about 1-5 days/week or about 2-10 days/month. In daily dosing embodiments, the F1C is administered to the subject daily for about 3 days to about 5 years or longer. Exemplary daily dosing embodiments include daily administration of a F1C for about 14, 30, 60, 90, 120, 180, 360 or more days. Daily doses may be administered in a single dose or as divided subdoses that are given, e.g., twice, three times, four times or more per day. In intermittent dosing embodiments, the F1C can be administered to the subject on 1, 2, 3, 4 or 5 days within a one week period, followed by a period of about 1, 2, 3, 4, 5, 6, 7, 8, 9, 10, 12, 16, 20, 24, 28 or 32 weeks without administration of the F1C, followed by administration of the F1C to the subject on 1, 2, 3, 4 or 5 days within a one week period. In other intermittent dosing embodiments, the F1C is administered to the subject every other day, every two days, every three days, every 4 days or every seven days.

Drug Product.

As used herein, a "drug product" typically comprises (a) a drug in a dosage form such as a solid or liquid formulation suitable for, e.g., oral, parenteral, topical or aerosol administration. Packaging for the drug and/or a package insert or label will have information about the drug's efficacy, mechanism of action, the intended patient population, dosage, dose regimen, route of administration, effect of the drug or treatment on one or more surrogate markers for efficacy, toxicity or morbidity. When the biological insult is radiation exposure, the package insert or label can contain information about the radiation dose or dose range for which the drug product can be used or is approved. The drug product can optionally contain information about the effect of the drug on stem cell proliferation, migration or engraftment. In these embodiments, the drug, typically a F1C, can be used to enhance healing or repair of a wound or impaired tissue, or the drug can be used to treat a cytopenia condition such as neutropenia, thrombocytopenia or anemia. Information about the capacity of the drug to affect stem cell numbers or activity would provide information about, e.g., the drug's efficacy or mechanism of action.

A drug product as used herein means a product that has been reviewed and approved for marketing or sale by a regulatory agency or entity with authority to review or approve applications for sale or medical use. Uses of drug products include its marketing or sales and offers to sell or buy it for consideration. These activities will typically adhere to terms of the regulatory approval that may affect or govern marketing, sales, purchases or product handling. The drug in a drug product can be a new drug, a generic drug, a biological, a medical device or a protocol for the use of any of these. The drug product usually results from marketing approval by the U.S. Food and Drug Administration of a new drug application, an abbreviated new drug application, a biological license application or an application to market a medical device. Uses for the drug product include its sale to public or private buyers such as the U.S. Department of Defense, the U.S. Department of Energy, U.S. Department of Health and Human Services or a private drug buyer or distributor entity. Other uses include use of the drug to treat indicated or approved medical conditions and physician approved uses or off label uses.

Pre-approval drug products are other invention embodiments, which can be used, e.g., for preparing to make commercial scale product in anticipation of regulatory marketing approval and other drug development and review activities.

Information that the drug product can contain includes a description of when dosing is to start. Exposure to a biological insult such as a potentially lethal amount of radiation can lead to death due to killing of cells such as stem cells or their progeny in bone marrow or blood. At least some cell death after a radiation exposure is due to induction of apoptosis in damaged cells and in adjacent cells. N. Daniak, *Experimental Hematology* 30(6):513-528 2002, C. Mothersill and C. Seymour, *Radiation Research* 155(6):759-767 2001. A significant portion of radiation-induced irreversible cell damage occurs within about 24 hours to about 48 hours after the exposure. Thus, drugs that act at least in part by reducing radiation-induced cell death will tend to be more effective when they are administered shortly after a radiation exposure. Starting treatment with a drug after about 24-48 hours after an acute biological insult can limit the drug's efficacy.

The intended patient population identified by the drug product can also specify excluded populations, if any, that may apply such as pediatric patients or elderly patients. Information about dosage will typically specify daily doses of the drug, while the dose regimen will describe how often and how long the drug is to be administered or taken. The route of administration will identify one or more routes that are suitable for use of the drug, although a given formulation will typically be approved for only one route of administration. Dosages, dose regimens and routes of administration that the package or label may identify are described elsewhere herein.

In one embodiment, the drug product is for treatment, prevention or amelioration of acute radiation syndrome or of the side-effects of a radiation exposure and it comprises or includes a formulation that contains androst-5-ene-3β,17β-diol or another F1C formulated with an excipient(s) for oral or parenteral administration, e.g., intramuscular, subcutaneous or subdermal injection, with a package insert or label describing administration of a daily dose as described herein, e.g., a daily dose of 25 mg, 50 mg, 100 mg, 150 mg, 175 mg, 200 mg, 225 mg, 250 mg, 300 mg, 350 mg, 400 mg, 450 mg or 500 mg, which can be administered for 1, 2, 3, 4, 5, 6, 7, 8, 9 or 10 consecutive days beginning after an actual or potential exposure to a biological insult such as radiation. Information that the package insert or label can contain includes information about biological responses to the drug or the treatment regimen. The information can include a description of one or more of (a) one or more side-effects or toxicities associated with use of the drug in humans or mammals such as non-human primates, (b) its effect on acute radiation syndrome or a component(s) thereof such as its capacity to affect neutrophils, platelets, neutropenia, thrombocytopenia, precursors of neutrophils or platelets, e.g., CD34+ stem cells or their progeny, infections, bleeding or fever in humans or mammals such as non-human primates, (c) the range of radiation doses that the drug may be used or effective to treat in humans or mammals such as non-human primates, (d) protocols for the use of additional therapeutic agents such as G-CSF or GM-CSF with the drug, (f) the time or time period when administration of the drug should begin for best or known therapeutic benefit or (e) the capacity of the drug to increase survival of mammals such as non-human primates that have been exposed to one or more lethal or potentially lethal radiation doses, e.g., about an $LD_{30}$, about an $LD_{40}$, about an $LD_{50}$, about an $LD_{60}$, or about an $LD_{70}$, where the mammals are usually not treated with other ameliorative treatments known to affect survival after a potentially lethal radiation exposure other than agents for treating pain if needed.

The use of additional therapeutic agents such as G-CSF or GM-CSF will usually be in accord with, or similar to, known dosages and dosing regimens. For use of the recombinant methionyl human granulocyte colony stimulating factor known as Filgrastim (r-metHuG-CSF), daily doses of 300 μg/day or 480 μg/day of material having a specific activity of $1.0\pm0.6\times10^8$ U/mg (cell mitogenesis units) can be used with the androst-5-ene-3β,17β-diol or the F1C. Dosing of Filgrastim can begin on the same day that dosing with the androst-5-ene-3β,17β-diol or the F1C begins and daily dosing will continue for about 10 to 14 days. Subcutaneous parenteral dosing with 6 mg of pegfilgrastim, which is Filgrastim covalently bonded to a 20 kD monomethoxypolyethylene glycol molecule at the N-terminal Filgrastim methionyl residue, can begin on the same day that dosing with the androst-5-ene-3β,17β-diol or the F1C begins and weekly dosing will continue for 1 or 2 weeks thereafter. Treatment with human recombinant GM-CSF known as sargramostim can begin on the same day that dosing with the androst-5-ene-3β,17β-diol or the F1C begins and daily dosing of 250 μg/m²/day administered subcutaneously or intravenously may continue for several days thereafter, e.g., for about 5-20 days, or until absolute neutrophil counts are at least 1,500 cells/mm³ for 3 consecutive days or when absolute neutrophil counts are above 20,000 cells/mm³. Daily doses of Filgrastim, pegfilgrastim or sargramostim that are administered to humans can be modified, e.g., reduced by about 50%, reduced by about 80% or reduced by about 90%, when the effects of androst-5-ene-3β,17β-diol or the F1C add to therapeutic efficacy of Filgrastim, pegfilgrastim or sargramostim.

Such ameliorative treatments are as described herein, e.g., the use of antibiotics to treat or prevent infection or transfusion of blood or platelets to treat a hematopoietic cytopenia such as neutropenia or thrombocytopenia. The use of ameliorative treatments in addition to the use of the drug in the drug product can make accurate assessment of the drug's efficacy difficult or impossible to accurately assess. This arises because ameliorative treatments can increase survival and their relative contribution to clinical benefit can be difficult or impossible to accurately separate from therapeutic activity of the drug itself. When the drug in the drug product can be used without other ameliorative treatments, its use on a mass scale can be possible without a need to hospitalize patients. In a situation where a nuclear weapon is detonated in a city, there can be tens of thousands of patients with actual or potential acute radiation exposure. In this situation, local hospitals would be unable to admit and provide ameliorative treatments such as blood or platelet transfusions for more than a few hundreds of actually or potentially exposed persons. The drug product can be used to treat actually or potentially exposed persons. Distinguishing persons who have been exposed to a potentially lethal radiation dose from persons who have not been exposed is time consuming and requires blood analysis.

In conducting a protocol to determine the survival rates of exposed treated subjects and exposed placebo subjects that have been exposed to radiation, the radiation exposure will typically be exposure to one or two doses of γ-radiation or X-rays from, e.g., a $^{60}$Co source. This permits assessment of the drug's capacity to treat an acute radiation exposure. The total exposure will usually occur over a relatively short time such as about 10 minutes to about 45 minutes on a single day. Spacing of radiation doses by more than about 1 day can affect the relative lethality of radiation exposure. When a total radiation dose is administered as two or more subdoses that are spaced apart by one day or more, the relative lethality or damage can be reduced or even eliminated. However, two or three subdoses, e.g., one anteroposterior irradiation and one posteroanterior irradiation, that are administered sequentially over a relatively short time, e.g., less than about 1 or 2 hours, can provide a more uniform whole body radiation exposure than a single exposure.

In conducting studies to obtain a drug product for treating acute radiation exposure or acute radiation syndrome, control of the radiation dose is typically accomplished using standard dosimetry calibration techniques (P. R. Almond et al, *Medical Physics* 26(9):1847-1870 1999). The relative LD value of a given radiation dose can vary with the dose rate. Low dose rates, e.g., 1 cGy/minute, are usually somewhat less lethal or damaging than high dose rates, e.g., 1000 cGy/minute. The rate of exposure of the mammals to radiation will usually be about 20 cGy/minute to about 300 cGy/minute, usually about 40 cGy/minute to about 60 cGy/minute. The radiation that is used will have sufficient energy to penetrate the body of the mammal and a radiation source such as $^{60}$Co can be used to irradiate most mammals, including non-human primates and canines.

Specific Embodiments.

Aspects of the invention and related subject matter include the following specific embodiments. In the following embodiments and elsewhere herein, when reference is made to a variable group such as $R^1$, $R^4$, $R^6$ or $R^{10}$ in the α-configuration or the β-configuration, a double bond will usually not be present at the carbon or at the position to which the variable group is bonded. Thus, $R^1$ in the α-configuration or the β-configuration usually means that no double bond is present at the 3-position or the position to which $R^1$ is bonded, or if a double bond is present, the variable group is bonded to the ring without a defined configuration.

1. A method to treat, prevent, ameliorate, delay the onset of or slow the progression of one or more of a condition or symptom described herein such as an unwanted inflammation, allergy, immune suppression condition (e.g., an innate immune suppression condition, an adaptive immune suppression condition or an adaptive immune suppression condition), immunosenescence, autoimmune disorder, infection, cancer or precancer, hereditary condition, blood cell deficiency (such as grade III or IV neutropenia, anemia or thrombocytopenia), a neurological disorder, a cardiovascular disorder, trauma, hemorrhage, bone fracture, unwanted or excess bone loss, androgen deficiency, estrogen deficiency, a congenital or hereditary disorder or a symptom of any of these conditions in a subject who has the condition or who is subject to developing the condition, comprising administering to a subject, or delivering to the subject's tissues, an effective amount of a formula 1 compound

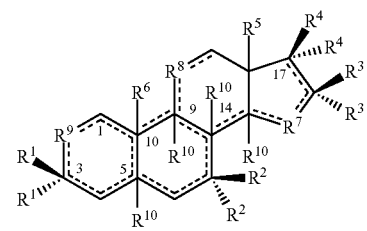

or a metabolic precursor, a metabolite, salt or tautomer thereof, wherein the dotted lines are optional double bonds; each $R^1$, $R^2$, $R^3$, $R^4$, $R^5$, $R^6$ and $R^{10}$ independently or together are —H, —OH, —OR$^{PR}$, —SR$^{PR}$, —SH, —N(R$^{PR}$)$_2$, —NH$_2$, —O—Si—(R$^{13}$)$_3$, —CHO, —CHS, —CN, —SCN, —NO$_2$, —COOH, —OSO$_3$H, —OPO$_3$H$_2$, =O, =S, =N—OH, =N—OCH$_3$, =CH$_2$, =CH—CH$_3$, =CH-optionally substituted alkyl, =N—O-optionally substituted alkyl, =N-optionally substituted alkyl, an ester, a thioester, a thionoester, a phosphoester, a phosphothioester, a phosphonate, a phosphonate ester, a thiophosphonate, a thiophosphonate ester, a phosphiniester, a sulfite ester, a sulfate ester, a sulfamate, a sulfonate, a sulfonamide, an amide, an amino acid, a peptide, an ether, a thioether, an acyl group, a thioacyl group, a carbonate, a carbamate, a halogen, optionally substituted alkyl, optionally substituted alkenyl, optionally substituted alkynyl, an optionally substituted aryl moiety, an optionally substituted heteroaryl moiety, an optionally substituted heterocycle, an optionally substituted monosaccharide, an optionally substituted oligosaccharide, a polymer, a spiro ring, an epoxide, an acetal, a thioacetal, a ketal or a thioketal; $R^7$ is —O—, —S—, —NR$^{PR}$—, —C(R$^{10}$)$_2$—, —C(R$^{10}$)$_2$—C(R$^{10}$)$_2$—, —C(R$^{10}$)$_2$—C(R$^{10}$)$_2$—C(R$^{10}$)$_2$—, —C(R$^{10}$)$_2$—O—C(R$^{10}$)$_2$—, —C(R$^{10}$)$_2$—S—C(R$^{10}$)$_2$—, —C(R$^{10}$)$_2$—NR$^{PR}$—C(R$^{10}$)$_2$—, —O—C(R$^{10}$)$_2$—, —S—C(R$^{10}$)$_2$— or —NR$^{PR}$—C(R$^{10}$)$_2$—; $R^8$ and $R^9$ independently are —C(R$^{10}$)$_2$—, —C(R$^{10}$)$_2$—C(R$^{10}$)$_2$—, —O—, —O—C(R$^{10}$)$_2$—, —S—, —S—C(R$^{10}$)$_2$—, —NR$^{PR}$— or —NR$^{PR}$—C(R$^{10}$)$_2$—, or one or both of $R^8$ or $R^9$ independently are absent, leaving a 5-membered ring; $R^{13}$ independently is $C_{1-6}$ alkyl; R$^{PR}$ independently are —H or a protecting group; and optionally wherein one, two or three of the 1-, 4-, 6- and/or 12-positions are optionally substituted with (i) an independently selected $R^{10}$ moiety when a double bond is present at the corresponding 1-, 4-, 6- or 12-position, or (ii) one or two independently selected $R^{10}$ moieties when no double bond is present at the corresponding 1-, 4-, 6- and/or 12-position.

2. The method of embodiment 1 wherein one each of $R^1$, $R^2$, $R^3$ and $R^4$ are —H, no double bond is present at the 3-, 7-, 16-, or 17-position, the second $R^1$, $R^2$, $R^3$ and $R^4$ are bonded by a single bond and respectively are in the α,α,α,α, α,α,α,β, α,α,β,α, α,β,α,α, β,α,α,α, α,α,β,β, α,β,α,β, β,α,α,β, β,α,β, α, β,β,α,α, α,β,β,α, α,β,β,β, β,α,β,β, β,β,α,β, β,β,β,α or β,β,β,β configurations and the second $R^1$, $R^2$, $R^3$ and $R^4$ are optionally independently selected from —H, —F, —Cl, —Br, —I, —OH, —SH, —NH$_2$, —COOH, —CH$_3$, —C$_2$H$_5$, —C(CH$_3$)$_3$, —OCH$_3$, —OC$_2$H$_5$, —CF$_3$, —CH$_2$OH, —C(O)CH$_3$, —C(O)CH$_2$OH, —C(O)CH$_2$F, —C(O)CH$_2$Cl, —C(O)CH$_2$Br, —C(O)CH$_2$I, —C(O)CF$_3$, —C$_2$F$_5$, =O, =CH$_2$, =CHCH$_3$, amino acid, carbamate, carbonate, optionally substituted C1-C20 alkyl, optionally substituted C1-C20 ether, optionally substituted C1-C20 ester, optionally substituted C1-C20 thioether, optionally substituted C1-C20 thioester, optionally substituted monosaccharide, optionally substituted disaccharide, optionally substituted oligosaccharide and polymer.

3. The method of embodiment 1 or 2 wherein the F1C is (1) a compound or genus of compounds described in a compound group described herein, or (2) an androstane, a 5β-androstane, 1-ene, 2-ene, 3-ene, 5(6)-ene (or a "5-ene"), 5(10)-ene, 6-ene, 7-ene, 8(9)-ene, 8(14)-ene, 9(10)-ene, 9(11)-ene, 11-ene, 12-ene, 13(17)-ene, 14-ene, 15-ene, 16-ene, 1,3-diene, 1,5-diene, 1,5(10)-diene, 1,6-diene, 1,7-diene, 1,8(9)-diene, 1,8(14)-diene, 1,9(11)-diene, 1,11-diene, 1,12-diene, 1,13(17)-diene, 1,15-diene, 1,16-diene, 2,4-diene, 2,5-diene, 2,5(10)-diene, 2,6-diene, 2,7-diene, 2,8(9)-diene, 2,8(14)-diene, 2,11-diene, 2,12-diene, 2,13(17)-diene, 2,14-diene, 2,15-diene, 2,16-diene, 3,5-diene, 3,6-diene, 3,7-diene, 3,8(9)-diene, 3,8(14)-diene, 3,9(10)-diene, 3,9(11)-diene, 3,11-diene, 3,12-diene, 3,13(17)-diene, 3,14-diene, 3,15-diene, 3,16-diene, 4,6-diene, 4,7-diene, 4,8(9)-diene, 4,8(14)-diene, 4,9(10)-diene, 4,9(11)-diene, 4,11-diene, 4,12-diene, 4,13(17)-diene, 4,14-diene, 4,15-diene, 4,16-diene, 5(6),15-diene (or a "5,15-diene"), 5,7-diene, 5,8(9)-diene, 5,8(14)-diene, 5,9(11)-diene, 5,11-diene, 5,12-diene, 5,13(17)-diene, 5,14-diene, 5,15-diene, 5,16-diene, 5(10),7-diene, 5(10),8(9)-diene, 5(10),8(14)-diene, 5,9(11)-diene, 5(10),11-diene, 5(10),12-diene, 5(10),13(17)-diene, 5(10),14-diene, 5(10),15-diene, 5(10),16-diene, 6,9(11)-diene, 6,9(14)-diene, 6,10-diene, 6,11-diene, 6,13(17)-diene, 6,14-diene, 6,15-diene, 6,16-diene, 7,9(10)-diene, 7,9(11)-diene, 7,12-diene, 7,13(17)-diene, 7,14-diene, 7,15-diene, 7,16-diene, 8(9),11-diene, 8(9),12-diene, 8(9),13(17)-diene, 8(9),14-diene, 8(9),15-diene, 8(9),16-diene, 8(14),9-diene, 8(14),11-diene, 8(14),12-diene, 8(14),13(17)-diene, 8(14),15-diene, 8(14),16-diene, 9(10),11-diene, 9(10),12-diene, 9(10),13(17)-diene, 9(10),14-diene, 9(10),15-diene, 9(10),16-diene, 9(11),β-diene, 9(11),13(17)-diene, 9(11),14-diene, 9(11),15-diene, 9(11),16-diene, 11,13(17)-diene, 11,14-diene, 11,15-diene, 11,16-diene, 12,14-diene, 12,15-diene, 12,16-diene, 13(17),14-diene, 13(17),15-diene, 14,16-diene, 1,3,5-triene, 1,3,5(10)-triene, 1,3,6-triene, 1,3,7-triene, 1,3,8-triene, 1,3,8(14)-triene, 1,3,9-triene, 1,3,9(11)-triene, 1,3,12-triene, 1,3,13(17)-triene, 1,3,14-triene, 1,3,15-triene, 1,3,16-triene, 1,4,6-triene, 1,4,7-triene, 1,4,8-triene, 1,4,8(14)-triene, 1,4,9-triene, 1,4,9(11)-triene, 1,4,12-triene, 1,4,13(17)-triene, 1,4,14-triene, 1,4,15-triene, 1,4,16-triene, 1,5,7-triene, 1,5,8-triene, 1,5,8(14)-triene, 1,5,9-triene, 1,5,9(11)-triene, 1,5,12-triene, 1,5,13(17)-triene, 1,5,14-triene, 1,5,15-triene, 1,5,16-triene, 1,5(10),6-triene, 1,5(10),7-triene, 1,5(10),8-triene, 1,5(10),8(14)-triene, 1,5(10),9(11)-triene, 1,5(10),12-triene, 1,5(10),13(17)-triene, 1,5(10),14-triene, 1,5(10),15-triene, 1,5(10),16-triene, 1,6,8-triene, 1,6,8(14)-triene, 1,6,9-triene, 1,6,9(11)-triene, 1,6,12-triene, 1,6,13(17)-triene, 1,6,14-triene, 1,6,15-triene, 1,6,16-triene, 1,7,9-triene, 1,7,9(11)-triene, 1,7,12-triene, 1,7,13(17)-triene, 1,7,14-triene, 1,7,15-triene, 1,7,16-triene, 2,4,6-triene, 2,5,6-triene, 2,5(10),6-triene, 2,4,7-triene, 2,5,7-triene, 2,5(10),7-triene, 2,4,8-triene, 2,5,8-triene, 2,5(10),8-triene, 2,4,8(14)-triene, 2,5,8(14)-triene, 2,5(10),8(14)-triene, 2,4,9(11)-triene, 2,5,9(11)-triene, 2,5(10),9(11)-triene, 2,4,11-triene, 2,5,11-triene, 2,5(10),11-triene, 2,4,12-triene, 2,5,12-triene, 2,5(10),12-triene, 2,4,14-triene, 2,5,14-triene, 2,5(10),14-triene, 2,4,15-triene, 2,5,15-triene, 2,5(10),15-triene, 2,4,16-triene, 2,5,16-triene, 2,5(10),16-triene, 2,6,8-triene, 2,6,8(14)-triene, 2,6,9-triene, 2,6,9(11)-triene, 2,6,12-triene, 2,6,13(17)-triene, 2,6,14-triene, 2,6,15-triene, 2,6,16-triene, 2,7,9-triene, 2,7,9(11)-triene, 2,7,12-triene, 2,7,13(17)-triene, 2,7,14-triene, 2,7,15-triene, 2,7,16-triene, 3,5,9-triene, 3,5,11-triene, 3,5,12-triene, 3,5,13-triene, 3,5,14-triene, 3,5,15-triene, 3,5,16-triene, 3,6,8-triene, 3,6,8(14)-triene, 3,6,9-triene, 3,6,9(11)-triene, 3,6,11-triene, 3,6,12-triene, 3,6,13(17)-triene, 3,6,14-triene, 3,6,15-triene, 3,6,16-triene, 3,7,9-triene, 3,7,11-triene, 3,7,12-triene, 3,7,13(17)-triene, 3,7,14-triene, 3,7,15-triene, 3,7,16-triene, 3,8,11-triene, 3,8,12-triene, 3,8,13(17)-triene, 3,8,14-triene, 3,8,15-triene, 3,8,16-triene, 3,8(14),11-triene, 3,8(14),12-triene, 3,8(14),13(17)-triene, 3,8(14),15-triene, 3,8(14),16-triene, 3,9,11-triene, 3,9,12-triene, 3,9,13(17)-triene, 3,9,14-triene, 3,9,15-triene, 3,9,16-triene, 3,9(11),12-triene, 3,9(11),13(17)-triene, 3,9(11),14-triene, 3,9(11),15-triene, 3,9(11),16-triene, 3,11,13(17)-triene, 3,11,14-triene, 3,11,15-triene, 3,11,16-triene, 3,12,14-triene, 3,12,15-triene, 3,12,16-triene, 3,13(17),14-triene, 3,13(17),15-triene, 3,14,16-triene, 4,6,8-triene, 4,6,8(14)-triene, 4,6,9-triene, 4,6,9(11)-triene, 4,6,11-triene, 4,6,12-triene, 4,6,13(17)-triene, 4,6,14-triene, 4,6,15-triene, 4,6,16-triene, 4,7,9-triene, 4,7,11-triene, 4,7,12-triene, 4,7,13(17)-triene, 4,7,14-triene, 4,7,15-triene, 4,7,16-triene, 4,8,9-triene, 4,8,9(11)-triene, 4,8,11-triene, 4,8,12-triene, 4,8,13(17)-triene, 4,8,14-triene, 4,8,15-triene, 4,8,16-triene, 4,8(14),9-triene, 4,8(14),9(11)-triene, 4,8(14),11-triene, 4,8(14),12-triene, 4,8(14),13(17)-triene, 4,8(14),15-triene, 4,8(14),16-triene, 4,9,11-triene, 4,9,12-triene, 4,9,13(17)-triene, 4,9,14-triene, 4,9,15-triene, 4,9,16-triene, 4,9(11),12-triene, 4,9(11),13(17)-triene, 4,9(11),14-triene, 4,9(11),15-triene, 4,9(11),16-triene, 4,11,13(17)-triene, 4,11,14-triene, 4,11,15-triene, 4,11,16-triene, 4,12,14-triene, 4,12,15-triene, 4,12,16-triene, 4,13(17),14-triene, 4,13(17),15-triene, 4,14,16-triene, 5,7,9-triene, 5,7,9(11)-triene, 5,7,12-triene, 5,7,13(17)-triene, 5,7,14-triene, 5,7,15-triene, 5,7,16-triene, 5,8,11-triene, 5,8,12-triene, 5,8,13(17)-triene, 5,8,14-triene, 5,8,15-triene, 5,8,16-triene, 5,8(14),9-triene, 5,8(14),9(11)-triene, 5,8(14),12-triene, 5,8(14),13(17)-triene, 5,8(14),15-triene, 5,8(14),16-triene, 5,9,11-triene, 5,9,12-triene, 5,9,13(17)-triene, 5,9,14-triene, 5,9,15-triene, 5,9,16-triene, 5,9(11),12-triene, 5,9(11),13(17)-triene, 5,9(11),14-triene, 5,9(11),15-triene, 5,9(11),16-triene, 5,11,13(17)-triene, 5,11,14-triene, 5,11,15-triene, 5,11,16-triene, 5,12,14-triene, 5,12,15-triene, 5,12,16-triene, 5,13(17),14-triene, 5,13(17),15-triene, 5,14,16-triene, 6,8,11-triene, 6,8,12-triene, 6,8,13(17)-triene, 6,8,14-triene, 6,8,15-triene, 6,8,16-triene, 6,8(14),9-triene, 6,8(14),9(11)-triene, 6,8(14),11-triene, 6,8(14),12-triene, 6,8(14),13(17)-triene, 6,8(14),15-triene, 6,8(14),16-triene, 6,9,11-triene, 6,9,12-triene, 6,9,13(17)-triene, 6,9,14-triene, 6,9,15-triene, 6,9,16-triene, 6,9(11),12-triene, 6,9(11),13(17)-triene, 6,9(11),14-triene, 6,9(11),15-triene, 6,9(11),16-triene, 6,11,13(17)-triene, 6,11,14-triene, 6,11,15-triene, 6,11,16-triene, 6,12,14-triene, 6,12,15-triene, 6,12,16-triene, 6,13(17),14-triene, 6,13(17),15-triene, 6,14,16-triene, 7,9,11-triene, 7,9,12-triene, 7,9,13(17)-triene, 7,9,14-triene, 7,9,15-triene, 7,9,16-triene, 7,9(11),12-triene, 7,9(11),13(17)-triene, 7,9(11),14-triene, 7,9(11),15-triene, 7,9(11),16-triene, 7,12,14-triene, 7,12,15-triene, 7,12,16-triene, 7,13(17),14-triene, 7,13(17),15-triene, 7,14,16-triene, 8,11,13(17)-triene, 8,11,14-triene, 8,11,15-triene, 8,11,16-triene, 8,12,14-triene, 8,12,15-triene, 8,12,16-triene, 8,13(17),14-triene, 8,13(17),15-triene, 8,14,16-triene, 8(14),9,11-triene, 8(14),9,12-triene, 8(14),9,13(17)-triene, 8(14),9,15-triene, 8(14),9,16-triene, 8(14),9(11),12-triene, 8(14),9(11),13(17)-triene, 8(14),9(11),15-triene, 8(14),9(11),16-triene, 9,11,13(17)-triene, 9,11,14-triene, 9,11,15-triene, 9,11,16-triene, 9(11),13(17),14-triene, 9(11),13(17),15-triene, 11,13(17),14-triene, 11,13(17),15-triene, 12,14,16-triene, 1,3,5(10),6-tetraene, 1,3,5(10),7-tetraene, 1,3,5(10),8(9)-tetraene, 1,3,5(10),8(14)-tetraene, 1,3,5(10),9(11)-tetraene, 1,3,5(10),11-tetraene, 1,3,5(10),12-tetraene, 1,3,5(10),13(17)-tetraene, 1,3,5(10),14-tetraene, 1,3,5(10),15-tetraene, 1,3,5(10),16- tetraene, 1,3,5,7-tetraene, 1,3,5,8-tetraene, 1,3,5,8(14)-tetraene, 1,3,5,9-tetraene, 1,3,5,9(11)-tetraene, 1,3,5,12-tetraene, 1,3,5,13(17)-tetraene, 1,3,5,14-tetraene, 1,3,5,15-tetraene, 1,3,5,16-tetraene, 1,3,6,8-tetraene, 1,3,6,8(14)-tetraene, 1,3,6,9-tetraene, 1,3,6,9(11)-tetraene, 1,3,6,12-tetraene, 1,3,6,13(17)-tetraene, 1,3,6,14-tetraene, 1,3,6,15-tetraene, 1,3,6,16-tetraene, 1,3,7,9-tetraene, 1,3,7,9(11)-tetraene, 1,3,7,11-tetraene, 1,3,7,12-tetraene, 1,3,7,13(17)-tetraene, 1,3,7,14-tetraene, 1,3,7,15-tetraene, 1,3,7,16-tetraene, 1,3,8,9-tetraene, 1,3,8,9(11)-tetraene, 1,3,8,12-tetraene, 1,3,8,13(17)-tetraene, 1,3,8,14-tetraene, 1,3,8,15-tetraene, 1,3,8,16-tetraene, 1,3,8(14)-9-tetraene, 1,3,8(14)9(11)-tetraene, 1,3,8(14)12-tetraene, 1,3,8(14)13(17)-tetraene, 1,3,8(14)15-tetraene, 1,3,8(14)16-tetraene, 1,3,9,11-tetraene, 1,3,9,12-tetraene, 1,3,9,13(17)-tetraene, 1,3,9,14-tetraene, 1,3,9,15-tetraene, 1,3,9,16-tetraene, 1,3,9(11),12-tetraene, 1,3,9(11),113(17)-tetraene, 1,3,9(11),14-tetraene, 1,3,9(11),15-tetraene, 1,3,9(11),16-tetraene, 1,3,12,14-tetraene, 1,3,12,15-tetraene, 1,3,12,16-tetraene, 1,3,13(17),14-tetraene, 1,3,13(17),15-tetraene, 1,3,13(17),16-tetraene, 1,3,14,16-tetraene, 1,4,6,8-tetraene, 1,4,6,8(14)-tetraene, 1,4,6,9-tetraene, 1,4,6,9(11)-tetraene, 1,4,6,11-tetraene, 1,4,6,12-tetraene, 1,4,6,13(17)-tetraene, 1,4,6,14-tetraene, 1,4,6,15-tetraene, 1,4,6,16-tetraene, 1,5,7,9-tetraene, 1,5,7,9(11)-tetraene, 1,5,7,11-tetraene, 1,5,7,12-tetraene, 1,5,7,13(17)-tetraene, 1,5,7,14-tetraene, 1,5,7,15-tetraene, 1,5,7,16-tetraene, 1,5,8,11-tetraene, 1,5,8,12-tetraene, 1,5,8,13(17)-tetraene, 1,5,8,14-tetraene, 1,5,8,15-tetraene, 1,5,8,16-tetraene, 1,5,8(14),9-tetraene, 1,5,8(14),9(11)-tetraene, 1,5,8(14),11-tetraene, 1,5,8(14),12-tetraene, 1,5,8(14),13(17)-tetraene, 1,5,8(14),15-tetraene, 1,5,8(14),16-tetraene, 1,5,9,11-tetraene, 1,5,9,12-tetraene, 1,5,9,13(17)-tetraene, 1,5,9,14-tetraene, 1,5,9,15-tetraene, 1,5,9,16-tetraene, 1,5,9(11),12-tetraene, 1,5,9(11),13(17)-tetraene, 1,5,9(11),14-tetraene, 1,5,9(11),15-tetraene, 1,5,9(11),16-tetraene, 1,5,11,13(17)-tetraene, 1,5,11,14-tetraene, 1,5,11,15-tetraene, 1,5,11,16-tetraene, 1,5,12,14-tetraene, 1,5,12,15-tetraene, 1,5,12,16-tetraene, 1,5,13(17),14-tetraene, 1,5,13(17),15-tetraene, 1,5,14,16-tetraene, 1,4,7,15-tetraene, 1,5,7,15-tetraene, 1,3,7,16-tetraene, 1,4,6,8-tetraene, 1,4,6,9-tetraene, 1,4,6,9(11)-tetraene, 1,4,6,11-tetraene, 1,4,6,12-tetraene, 1,4,6,13(17)-tetraene, 1,4,6,14-tetraene, 1,4,6,15-tetraene, 1,4,6,16-tetraene, 1,4,7,9-tetraene, 1,4,7,9(11)-tetraene, 1,4,7,11-tetraene, 1,4,7,12-tetraene, 1,4,7,13(17)-tetraene, 1,4,7,14-tetraene, 1,4,7,15-tetraene, 1,4,7,16-tetraene, 1,6,8,11-tetraene, 1,6,8,12-tetraene, 1,6,8,13(17)-tetraene, 1,6,8,14-tetraene, 1,6,8,15-tetraene, 1,6,8,16-tetraene, 1,6,8(14),9-tetraene, 1,6,8(14),9(11)-tetraene, 1,6,8(14),11-tetraene, 1,6,8(14),12-tetraene, 1,6,8(14),13(17)-tetraene, 1,6,8(14),15-tetraene, 1,6,8(14),16-tetraene, 1,6,9,11-tetraene, 1,6,9,12-tetraene, 1,6,9,13(17)-tetraene, 1,6,9,14-tetraene, 1,6,9,15-tetraene, 1,6,9,16-tetraene, 1,6,9(11),12-tetraene, 1,6,9(11),13(17)-tetraene, 1,6,9(11),14-tetraene, 1,6,9(11),15-tetraene, 1,6,9(11),16-tetraene, 1,6,11,13(17)-tetraene, 1,6,11,14-tetraene, 1,6,11,15-tetraene, 1,6,12,14-tetrane, 1,6,12,15-tetrane, 1,6,12,16-tetrane, 1,6,13(17),14-tetraene, 1,6,13(17),15-tetraene, 1,6,14,16-tetraene, 1,7,9,11-tetraene, 1,7,9,12-tetraene, 1,7,9,13(17)-tetraene, 1,7,9,14-tetraene, 1,7,9,15-tetraene, 1,7,9,16-tetraene, 1,8,11,13(17)-tetraene, 1,8,11,14-tetraene, 1,8,11,15-tetraene, 1,8,11,16-tetraene, 1,8(14),9,11-tetraene, 1,8(14),9,12-tetraene, 1,8(14),9,13(17)-tetraene, 1,8(14),9,15-tetraene, 1,8(14),9,16-tetraene, 1,9,11,13(17)-tetraene, 1,9,11,14-tetraene, 1,9,11,15-tetraene, 1,9,11,16-tetraene, 1,9(11),12,14-tetraene, 1,9(11),12,15-tetraene, 1,9(11),12,16-tetraene, 1,11,13(17),14-tetraene, 1,11,13(17),15-tetraene, 1,11,13(17),16-tetraene, 1,12,14,16-tetraene, 1,8,11,13(17)-tetraene, 1,8,11,14-tetraene, 1,8,11,15-tetraene, 1,9,11,13(17)-tetraene, 1,9,11,14-tetraene, 1,9,11,15-tetraene, 1,9,11,16-tetraene, 1,9(11),12,14-tetraene, 1,9(11),12,15-tetraene, 1,9(11),12,16-tetraene, 1,11,13(17),14-tetraene, 1,11,13(17),15-tetraene, 1,11,13(17),16-tetraene, 1,12,14,16-tetraene, 2,4,6,8-tetraene, 2,4,6,8(14)-tetraene, 2,4,6,9-tetraene, 2,4,6,9(11)-tetraene, 2,4,6,11-tetraene, 2,4,6,12-tetraene, 2,4,6,13(17)-tetraene, 2,4,6,14-tetraene, 2,4,6,15-tetraene, 2,4,6,16-tetraene, 2,5,7,9-tetraene, 2,5,7,9(11)-tetraene, 2,5,7,11-tetraene, 2,5,7,12-tetraene, 2,5,7,13(17)-tetraene, 2,5,7,14-tetraene, 2,5,7,15-tetraene, 2,5,7,16-tetraene, 2,5,8,11-tetraene, 2,5,8,12-tetraene, 2,5,8,13(17)-tetraene, 2,5,8,14-tetraene, 2,5,8,15-tetraene, 2,5,8,16-tetraene, 2,5,8(14),9-tetraene, 2,5,8(14),9(11)-tetraene, 2,5,8(14),11-tetraene, 2,5,8(14),12-tetraene, 2,5,8(14),13(17)-tetraene, 2,5,8(14),15-tetraene, 2,5,8(14),16-tetraene, 2,5,9,11-tetraene, 2,5,9,12-tetraene, 2,5,9,13(17)-tetraene, 2,5,9,14-tetraene, 2,5,9,15-tetraene, 2,5,9,16-tetraene, 2,5,9(11),12-tetraene, 2,5,9(11),13(17)-tetraene, 2,5,9(11),14-tetraene, 2,5,9(11),15-tetraene, 2,5,9(11),16-tetraene, 2,5,11,13(17)-tetraene, 2,5,11,14-tetraene, 2,5,11,15-tetraene, 2,5,11,16-tetraene, 2,5,12,14-tetraene, 2,5,12,15-tetraene, 2,5,12,16-tetraene, 2,5,13(17),14-tetraene, 2,5,13(17),15-tetraene, 2,5,14,16-tetraene, 2,4,7,15-tetraene, 2,5,7,15-tetraene, 2,4,6,8-tetraene, 2,4,6,9-tetraene, 2,4,6,9(11)-tetraene, 2,4,6,11-tetraene, 2,4,6,12-tetraene, 2,4,6,13(17)-tetraene, 2,4,6,14-tetraene, 2,4,6,15-tetraene, 2,4,6,16-tetraene, 2,4,7,9-tetraene, 2,4,7,9(11)-tetraene, 2,4,7,11-tetraene, 2,4,7,12-tetraene, 2,4,7,13(17)-tetraene, 2,4,7,14-tetraene, 2,4,7,15-tetraene, 2,4,7,16-tetraene, 2,6,8,11-tetraene, 2,6,8,12-tetraene, 2,6,8,13(17)-tetraene, 2,6,8,14-tetraene, 2,6,8,15-tetraene, 2,6,8,16-tetraene, 2,6,8(14),9-tetraene, 2,6,8(14),9(11)-tetraene, 2,6,8(14),11-tetraene, 2,6,8(14),12-tetraene, 2,6,8(14),13(17)-tetraene, 2,6,8(14),15-tetraene, 2,6,8(14),16-tetraene, 2,6,9,11-tetraene, 2,6,9,12-tetraene, 2,6,9,13(17)-tetraene, 2,6,9,14-tetraene, 2,6,9,15-tetraene, 2,6,9,16-tetraene, 2,6,9(11),12-tetraene, 2,6,9(11),13(17)-tetraene, 2,6,9(11),14-tetraene, 2,6,9(11),15-tetraene, 2,6,9(11),16-tetraene, 2,6,11,13(17)-tetraene, 2,6,11,14-tetraene, 2,6,11,15-tetraene, 2,6,12,14-tetrane, 2,6,12,15-tetrane, 2,6,12,16-tetrane, 2,6,13(17),14-tetraene, 2,6,13(17),15-tetraene, 2,6,14,16-tetraene, 2,7,9,11-tetraene, 2,7,9,12-tetraene, 2,7,9,13(17)-tetraene, 2,7,9,14-tetraene, 2,7,9,15-tetraene, 2,7,9,16-tetraene, 2,8,11,13(17)-tetraene, 2,8,11,14-tetraene, 2,8,11,15-tetraene, 2,8,11,16-tetraene, 2,8(14),9,11-tetraene, 2,8(14),9,12-tetraene, 2,8(14),9,13(17)-tetraene, 2,8(14),9,15-tetraene, 2,8(14),9,16-tetraene, 2,9,11,13(17)-tetraene, 2,9,11,14-tetraene, 2,9,11,15-tetraene, 2,9,11,16-tetraene, 2,9(11),12,14-tetraene, 2,9(11),12,15-tetraene, 2,9(11),12,16-tetraene, 2,11,13(17),14-tetraene, 2,11,13(17),15-tetraene, 2,11,13(17),16-tetraene, 2,12,14,16-tetraene, 2,8,11,13(17)-tetraene, 2,8,11,14-tetraene, 2,8,11,15-tetraene, 2,9,11,13(17)-tetraene, 2,9,11,14-tetraene, 2,9,11,15-tetraene, 2,9,11,16-tetraene, 2,9(11),12,14-tetraene, 2,9(11),12,15-tetraene, 2,9(11),12,16-tetraene, 2,11,13(17),14-tetraene, 2,11,13(17),15-tetraene, 2,11,13(17),16-tetraene, 2,12,14,16-tetraene, 3,5,7,9-tetraene, 3,5,7,9(11)-tetraene, 3,5,7,11-tetraene, 3,5,7,12-tetraene, 3,5,7,13(17)-tetraene, 3,5,7,14-tetraene, 3,5,7,15-tetraene, 3,5,7,16-tetraene, 3,5,8,11-tetraene, 3,5,8,12-tetraene, 3,5,8,13(17)-tetraene, 3,5,8,14-tetraene, 3,5,8,15-tetraene, 3,5,8,16-tetraene, 3,5,8(14),9-tetraene, 3,5,8(14),9(11)-tetraene, 3,5,8(14),11-tetraene, 3,5,8(14),12-tetraene, 3,5,8(14),13(17)-tetraene, 3,5,8(14),15-tetraene, 3,5,8(14),16-tetraene, 3,5,9,11-tetraene, 3,5,9,12-tetraene, 3,5,9,13(17)-tetraene, 3,5,9,14-tetraene, 3,5,9,15-tetraene, 3,5,9,16-tetraene, 3,5,9(11),12-tetraene, 3,5,9(11),13(17)-tetraene, 3,5,9(11),14-tetraene, 3,5,9(11),15-tetraene, 3,5,9(11),16- tetraene, 3,5,11,13(17)-tetraene, 3,5,11,14-tetraene, 3,5,11,15-tetraene, 3,5,11,16-tetraene, 3,5,12,14-tetraene, 3,5,12,15-tetraene, 3,5,12,16-tetraene, 3,5,13(17),14-tetraene, 3,5,13(17),15-tetraene, 3,5,14,16-tetraene, 3,4,7,15-tetraene, 3,5,7,15-tetraene, 3,5,7,16-tetraene, 3,4,6,8-tetraene, 3,4,6,9-tetraene, 3,4,6,9(11)-tetraene, 3,4,6,11-tetraene, 3,4,6,12-tetraene, 3,4,6,13(17)-tetraene, 3,4,6,14-tetraene, 3,4,6,15-tetraene, 3,4,6,16-tetraene, 3,4,7,9-tetraene, 3,4,7,9(11)-tetraene, 3,4,7,11-tetraene, 3,4,7,12-tetraene, 3,4,7,13(17)-tetraene, 3,4,7,14-tetraene, 3,4,7,15-tetraene, 3,4,7,16-tetraene, 3,6,8,11-tetraene, 3,6,8,12-tetraene, 3,6,8,13(17)-tetraene, 3,6,8,14-tetraene, 3,6,8,15-tetraene, 3,6,8,16-tetraene, 3,6,8(14),9-tetraene, 3,6,8(14),9(11)-tetraene, 3,6,8(14),11-tetraene, 3,6,8(14),12-tetraene, 3,6,8(14),13(17)-tetraene, 3,6,8(14),15-tetraene, 3,6,8(14),16-tetraene, 3,6,9,11-tetraene, 3,6,9,12-tetraene, 3,6,9,13(17)-tetraene, 3,6,9,14-tetraene, 3,6,9,15-tetraene, 3,6,9,16-tetraene, 3,6,9(11),12-tetraene, 3,6,9(11),13(17)-tetraene, 3,6,9(11),14-tetraene, 3,6,9(11),15-tetraene, 3,6,9(11),16-tetraene, 3,6,11,13(17)-tetraene, 3,6,11,14-tetraene, 3,6,11,15-tetraene, 3,6,12,14-tetrane, 3,6,12,15-tetrane, 3,6,12,16-tetrane, 3,6,13(17),14-tetraene, 3,6,13(17),15-tetraene, 3,6,14,16-tetraene, 3,7,9,11-tetraene, 3,7,9,12-tetraene, 3,7,9,13(17)-tetraene, 3,7,9,14-tetraene, 3,7,9,15-tetraene, 3,7,9,16-tetraene, 3,8,11,13(17)-tetraene, 3,8,11,14-tetraene, 3,8,11,15-tetraene, 3,8,11,16-tetraene, 3,8(14),9,11-tetraene, 3,8(14),9,12-tetraene, 3,8(14),9,13(17)-tetraene, 3,8(14),9,15-tetraene, 3,8(14),9,16-tetraene, 3,9,11,13(17)-tetraene, 3,9,11,14-tetraene, 3,9,11,15-tetraene, 3,9,11,16-tetraene, 3,9(11),12,14-tetraene, 3,9(11),12,15-tetraene, 3,9(11),12,16-tetraene, 3,11,13(17),14-tetraene, 3,11,13(17),15-tetraene, 3,11,13(17),16-tetraene, 3,12,14,16-tetraene, 3,8,11,13(17)-tetraene, 3,8,11,14-tetraene, 3,8,11,15-tetraene, 3,9,11,13(17)-tetraene, 3,9,11,14-tetraene, 3,9,11,15-tetraene, 3,9,11,16-tetraene, 3,9(11),12,14-tetraene, 3,9(11),12,15-tetraene, 3,9(11),12,16-tetraene, 3,11,13(17),14-tetraene, 3,11,13(17),15-tetraene, 3,11,13(17),16-tetraene, 3,12,14,16-tetraene, 3,5(10),7,9(11)-tetraene, 3,5(10),7,11-tetraene, 3,5(10),7,12-tetraene, 3,5(10),7,13(17)-tetraene, 3,5(10),7,14-tetraene, 3,5(10),7,15-tetraene, 3,5(10),7,16-tetraene, 3,5(10),8,11-tetraene, 3,5(10),8,12-tetraene, 3,5(10),8,13(17)-tetraene, 3,5(10),8,14-tetraene, 3,5(10),8,15-tetraene, 3,5(10),8,16-tetraene, 3,5(10),8(14),9-tetraene, 3,5(10),8(14),9(11)-tetraene, 3,5(10),8(14),11-tetraene, 3,5(10),8(14),12-tetraene, 3,5(10),8(14),13(17)-tetraene, 3,5(10),8(14),15-tetraene, 3,5(10),8(14),16-tetraene, 3,5(10),9,11-tetraene, 3,5(10),9,12-tetraene, 3,5(10),9,13(17)-tetraene, 3,5(10),9,14-tetraene, 3,5(10),9,15-tetraene, 3,5(10),9,16-tetraene, 3,5(10),9(11),12-tetraene, 3,5(10),9(11),13(17)-tetraene, 3,5(10),9(11),14-tetraene, 3,5(10),9(11),15-tetraene, 3,5(10),9(11),16-tetraene, 3,5(10),11,13(17)-tetraene, 3,5(10),11,14-tetraene, 3,5(10),11,15-tetraene, 3,5(10),11,16-tetraene, 3,5(10),12,14-tetraene, 3,5(10),12,15-tetraene, 3,5(10),12,16-tetraene, 3,5(10),13(17),14-tetraene, 3,5(10),13(17),15-tetraene, 3,5(10),14,16-tetraene, 4,6,8,11-tetraene, 4,6,8,12-tetraene, 4,6,8,13(17)-tetraene, 4,6,8,14-tetraene, 4,6,8,15-tetraene, 4,6,8,16-tetraene, 4,6,8(14),9-tetraene, 4,6,8(14),9(11)-tetraene, 4,6,8(14),11-tetraene, 4,6,8(14),12-tetraene, 4,6,8(14),13(17)-tetraene, 4,6,8(14),15-tetraene, 4,6,8(14),16-tetraene, 4,6,9,11-tetraene, 4,6,9,12-tetraene, 4,6,9,13(17)-tetraene, 4,6,9,14-tetraene, 4,6,9,15-tetraene, 4,6,9,16-tetraene, 4,6,9(11),12-tetraene, 4,6,9(11),13(17)-tetraene, 4,6,9(11),14-tetraene, 4,6,9(11),15-tetraene, 4,6,9(11),16-tetraene, 4,6,11,13(17)-tetraene, 4,6,11,14-tetraene, 4,6,11,15-tetraene, 4,6,12,14-tetrane, 4,6,12,15-tetraene, 4,6,12,16-tetraene, 4,6,13(17),14-tetraene, 4,6,13(17),15-tetraene, 4,6,14,16-tetraene, 4,7,9,11-tetraene, 4,7,9,12-tetraene, 4,7,9,13(17)-tetraene, 4,7,9,14-tetraene, 4,7,9,15-tetraene, 4,7,9,16-tetraene, 4,8,11,13(17)-tetraene, 4,8,11,14-tetraene, 4,8,11,15-tetraene, 4,8,11,16-tetraene, 4,8(14),9,11-tetraene, 4,8(14),9,12-tetraene, 4,8(14),9,13(17)-tetraene, 4,8(14),9,15-tetraene, 4,8(14),9,16-tetraene, 4,9,11,13(17)-tetraene, 4,9,11,14-tetraene, 4,9,11,15-tetraene, 4,9,11,16-tetraene, 4,9(11),12,14-tetraene, 4,9(11),12,15-tetraene, 4,9(11),12,16-tetraene, 4,11,13(17),14-tetraene, 4,11,13(17),15-tetraene, 4,11,13(17),16-tetraene, 4,12,14,16-tetraene, 4,8,11,13(17)-tetraene, 4,8,11,14-tetraene, 4,8,11,15-tetraene, 4,9,11,13(17)-tetraene, 4,9,11,14-tetraene, 4,9,11,15-tetraene, 4,9,11,16-tetraene, 4,9(11),12,14-tetraene, 4,9(11),12,15-tetraene, 4,9(11),12,16-tetraene, 4,11,13(17),14-tetraene, 4,11,13(17),15-tetraene, 4,11,13(17),16-tetraene, 4,12,14,16-tetraene, 5,7,9,11-tetraene, 5,7,9,12-tetraene, 5,7,9,13(17)-tetraene, 5,7,9,14-tetraene, 5,7,9,15-tetraene, 5,7,9,16-tetraene, 5,8,11,13(17)-tetraene, 5,8,11,14-tetraene, 5,8,11,15-tetraene, 5,8,11,16-tetraene, 5,8(14),9,11-tetraene, 5,8(14),9,12-tetraene, 5,8(14),9,13(17)-tetraene, 5,8(14),9,15-tetraene, 5,8(14),9,16-tetraene, 5,9,11,13(17)-tetraene, 5,9,11,14-tetraene, 5,9,11,15-tetraene, 5,9,11,16-tetraene, 5,9(11),12,14-tetraene, 5,9(11),12,15-tetraene, 5,9(11),12,16-tetraene, 5,11,13(17),14-tetraene, 5,11,13(17),15-tetraene, 5,11,13(17),16-tetraene, 5,12,14,16-tetraene, 5,8,11,13(17)-tetraene, 5,8,11,14-tetraene, 5,8,11,15-tetraene, 5,9,11,13(17)-tetraene, 5,9,11,14-tetraene, 5,9,11,15-tetraene, 5,9,11,16-tetraene, 5,9(11),12,14-tetraene, 5,9(11),12,15-tetraene, 5,9(11),12,16-tetraene, 5,11,13(17),14-tetraene, 5,11,13(17),15-tetraene, 5,11,13(17),16-tetraene, 5,12,14,16-tetraene, 5(10),8,11,13(17)-tetraene, 5(10),8,11,14-tetraene, 5(10),8,11,15-tetraene, 5(10),8,11,16-tetraene, 5(10),8(14),9,11-tetraene, 5(10),8(14),9,12-tetraene, 5(10),8(14),9,13(17)-tetraene, 5(10),8(14),9,15-tetraene, 5(10),8(14),9,16-tetraene, 5(10),9,11,13(17)-tetraene, 5(10),9,11,14-tetraene, 5(10),9,11,15-tetraene, 5(10),9,11,16-tetraene, 5(10),9(11),12,14-tetraene, 5(10),9(11),12,15-tetraene, 5(10),9(11),12,16-tetraene, 5(10),11,13(17),14-tetraene, 5(10),11,13(17),15-tetraene, 5(10),11,13(17),16-tetraene, 5(10),12,14,16-tetraene, 5(10),8,11,13(17)-tetraene, 5(10),8,11,14-tetraene, 5(10),8,11,15-tetraene, 5(10),9,11,13(17)-tetraene, 5(10),9,11,14-tetraene, 5(10),9,11,15-tetraene, 5(10),9,11,16-tetraene, 5(10),9(11),12,14-tetraene, 5(10),9(11),12,15-tetraene, 5(10),9(11),12,16-tetraene, 5(10),11,13(17),14-tetraene, 5(10),11,13(17),15-tetraene, 5(10),11,13(17),16-tetraene, 5(10),12,14,16-tetraene, 6,8,11,13(17)-tetraene, 6,8,11,14-tetraene, 6,8,11,15-tetraene, 6,8,11,16-tetraene, 6,9,11,13(17)-tetraene, 6,9,11,14-tetraene, 6,9,11,15-tetraene, 6,9,11,16-tetraene, 6,9(11),12,14-tetraene, 6,9(11),12,15-tetraene, 6,9(11),12,16-tetraene, 6,11,13(17),14-tetraene, 6,11,13(17),15-tetraene, 6,12,14,16-tetraene, 7,9,11,13(17)-tetraene, 7,9,11,14-tetraene, 7,9,11,15-tetraene, 7,9,11,16-tetraene, 7,9(11),12,14-tetraene, 7,9(11),12,15-tetraene, 7,9(11),12,16-tetraene, 8,11,13(17),14-tetraene, 8,11,13(17),15-tetraene, 8(14),9,11,13(17)-tetraene, 8(14),9,11,15-tetraene, 8(14),9,11,16-tetraene, 9,11,13(17),14-tetraene, 9,11,13(17),15-tetraene, 9(11),12,14,16-tetraene, 11,13(17),14,16-tetraene, 1,3,5(10),6,8-pentaene, 1,3,5(10),6,9(11)-pentaene, 1,3,5(10),6,11-pentaene, 1,3,5(10),6,12-pentaene, 1,3,5(10),6,13(17)-pentaene, 1,3,5(10),6,14-pentaene, 1,3,5(10),6,15-pentaene, 1,3,5(10),6,16-pentaene, 1,3,5(10),7,9(11)-pentaene, 1,3,5(10),7,11-pentaene, 1,3,5(10),7,12-pentaene, 1,3,5(10),7,13(17)-pentaene, 1,3,5(10),7,14-pentaene, 1,3,5(10),7,15-pentaene, 1,3,5(10),7,16-pentaene, 1,3,5(10),8,11-pentaene, 1,3,5(10),8,12-pentaene, 1,3,5(10),8,13(17)-pentaene, 1,3,5(10),8,14-pentaene, 1,3,5(10),8,15-pentaene, 1,3,5(10),8,16-pentaene, 1,3,5(10),8(14),9(11)-pentaene, 1,3,5(10),8(14),11-pentaene, 1,3,5(10),8(14),12-pentaene, 1,3,5(10),8(14),13(17)-pentaene, 1,3,5(10),8(14),15-pentaene, 1,3,5(10),8(14),16-pentaene, 1,3,5(10),9(11),12-pentaene, 1,3,5(10),9(11),13(17)-pentaene, 1,3,5(10),9(11),14-pentaene, 1,3,5(10),9(11),15-pentaene, 1,3,5(10),9(11),16-pentaene, 1,3,5(10),11,13(17)-pentaene, 1,3,5(10),11,14-pentaene, 1,3,5(10),11,15-pentaene, 1,3,5(10),11,16-pentaene, 1,3,5(10),12,14-pentaene, 1,3,5(10),12,15-pentaene, 1,3,5(10),12,16-pentaene, 1,3,5(10),13(17),14-pentaene, 1,3,5(10),13(17),15-pentaene or a 1,3,5(10),14,16-pentaene androstene or, when no double bond is present at the 5-position or a 5α-androstene or a 5β-androstene.

4. The method of embodiment 1, 2 or 3 wherein (1) $R^5$ and $R^6$ respectively are in the α,α, α,β, β,α or β,β configuration and $R^5$ and $R^6$ are optionally both —CH$_3$ or are optionally selected from —H, —F, —OH, —CH$_3$, —C$_2$H$_5$, —C≡CH, —C≡CCH$_3$, and —CH$_2$OH or (2) $R^5$ and $R^6$ are both in the β-configuration and $R^5$ and $R^6$ are optionally both —H, —F, —CH$_3$—C≡CH or —CH$_2$OH.

5. The method of embodiment 1, 2, 3 or 4 wherein $R^{10}$ at the 5, 8, 9 and 14-positions (if present) respectively are (1) —H, —H, —H, —H; (2) —H, —H, halogen (—F, —Cl, —Br or —I), —H; (3) —H, —H, —H, —OH; (4) —H, —H, halogen (—F, —Cl, —Br or —I), —OH; (5)-optionally substituted alkyl (e.g., —CH$_3$, —CH$_2$OH, —CH$_2$O-ester, —C$_2$H$_5$), —H, —H, —H; (6)-optionally substituted alkyl (e.g., —CH$_3$, —CH$_2$OH, —CH$_2$O-ester, —C$_2$H$_5$), —H, halogen (—F, —Cl, —Br or —I), —H; (7)-optionally substituted alkyl (e.g., —CH$_3$, —CH$_2$OH, —CH$_2$O-ester, —C$_2$H$_5$), —H, —H, —OH; (8)-acyl (e.g., —C(O)—(CH$_2$)$_{0-2}$—CH$_3$), —H, —H, —H; (9) -ester (e.g., acetoxy or propionoxy), —H, —H, —H; (10)-ether (e.g., —O—(CH$_2$)$_{0-2}$—CH$_3$), —H, —H, —H; (11)-ester (e.g., acetoxy, propionoxy, —O—C(O)—(CH$_2$)$_{1-6}$—H), —H, halogen (e.g., —F, —Cl, —Br), —H; (12)-ester (e.g., acetoxy or propionoxy), —H, —H, —OH; (13) —H, —H, —H, -acyl (e.g., —C(O)—(CH$_2$)$_{0-2}$—CH$_3$); (14) —H, —H, —H, -ester (e.g., acetoxy or propionoxy); or (15) —H, —H, —H, -ether (e.g., —O—(CH$_2$)$_{0-2}$—CH$_3$, —OCH$_3$, —OC$_2$H$_5$, —OCH$_2$OH, —OCH$_2$F, —OCH$_2$Br, —OCH$_2$COOH, —OCH$_2$NH$_2$, —OCH$_2$CH$_2$OH, —OCH$_2$CH$_2$F, —OCH$_2$CH$_2$Br, —OCH$_2$CH$_2$COOH or —OCH$_2$CH$_2$NH$_2$).

6. The method of embodiment 1, 2, 3, 4 or 5 wherein $R^7$ is —CH$_2$—, —CHOH—, —CH(α$R^{10}$)—, —CH(β$R^{10}$)—, —C($R^{10}$)$_2$—, —CH(ester)-, —CH(alkoxy)- or —CH(halogen)- where $R^{10}$ are independently selected, the hydroxyl, ester or alkoxy group or the halogen atom is present in the α-configuration or the β-configuration and the alkoxy group is optionally selected from —OCH$_3$, —OC$_2$H$_5$ and —OC$_3$H$_7$ and the halogen atom is —F, —Cl, —Br or —I.

7. The method of embodiment 1, 2, 3, 4, 5 or 6 wherein $R^8$ is —CH$_2$—, —CF$_2$—, —CH(α-OH)—, —CH(β-OH)—, —CH(α-$R^{10}$)—, —CH(β-$R^{10}$)—, —CH(β-ester), —CH(α-ester)-, —CH(β-alkoxy)-, —CH(α-alkoxy)-, —CH(β-halogen)- or —CH(α-halogen) where the alkoxy group is optionally selected from —OCH$_3$, —OC$_2$H$_5$ and —OC$_3$H$_7$ and the halogen atom is —F, —Cl, —Br or —I.

8. The method of embodiment 1, 2, 3, 4, 5, 6 or 7 wherein the subject has, or is subject or susceptible to developing, neutropenia or thrombocytopenia, optionally wherein the subject is a human or another primate and optionally wherein the neutropenia is postinfectious neutropenia, autoimmune neutropenia, chronic idiopathic neutropenia or a neutropenia resulting from or potentially resulting result from a cancer chemotherapy, chemotherapy for an autoimmune disease, an antiviral therapy, radiation exposure, tissue or solid organ allograft or xenograft rejection or immune suppression therapy in tissue or solid organ transplantation or aging or immune senescence.

9. The method of embodiment 1, 2, 3, 4, 5, 6, 7 or 8 wherein (1) the formula 1 compound is a compound in groups 1 through 57, or (2) one $R^4$ in the α-configuration is —H or a C-linked moiety such as optionally substituted alkyl moiety and the other $R^4$, or both $R^4$ together, is in the β-configuration and is an N-linked moiety such as —NH$_2$, —NHR$^{PR}$, —N(R$^{PR}$)$_2$, —NO$_2$, —N$_3$, =NOH, =NO-optionally substituted alkyl, =N-optionally substituted alkyl, an N-linked amino acid, a substituted amine, a sulfamate having the structure —NH—S(O)(O)—S—O-optionally substituted alkyl, a carbamate having the structure —NH—C(O)—O-optionally substituted alkyl, a sulfurous diamide having the structure —NH—S(O)—NH-optionally substituted alkyl, —NH—S(O)—NH$_2$ or —NH—S(O)—NHR$^{PR}$, a sulfamide having the structure —NH—S(O)(O)—NH$_2$, —NH—S(O)(O)—NHR$^{PR}$, —NH—S(O)(O)—NH-optionally substituted alkyl or —NH—S(O)(O)—N(optionally substituted alkyl)$_2$, a sulfinamide having the structure —NH—S(O)-optionally substituted alkyl or an amide having the structure —NH—C(O)-optionally substituted alkyl or a salt of any of these moieties, where each optionally substituted alkyl is independently selected and optionally is a C1-12 moiety or a C1-8 moiety, or (3) one $R^4$ in the β-configuration is —H or a C-linked moiety such as optionally substituted alkyl and the other $R^4$, or both $R^4$ together, is in the α-configuration and is an N-linked moiety such as —NH$_2$, —NHR$^{PR}$, —N(R$^{PR}$)$_2$, —NO$_2$, —N$_3$, =NOH, =NO-optionally substituted alkyl, =N-optionally substituted alkyl, an N-linked amino acid, a substituted amine, a sulfamate having the structure —NH—S(O)(O)—S—O-optionally substituted alkyl, a carbamate having the structure —NH—C(O)—O-optionally substituted alkyl, a sulfurous diamide having the structure —NH—S(O)—NH-optionally substituted alkyl, —NH—S(O)—NH$_2$ or —NH—S(O)—NHR$^{PR}$, a sulfamide having the structure —NH—S(O)(O)—NH$_2$, —NH—S(O)(O)—NHR$^{PR}$, —NH—S(O)(O)—NH-optionally substituted alkyl or —NH—S(O)(O)—N(optionally substituted alkyl)$_2$, a sulfinamide having the structure —NH—S(O)-optionally substituted alkyl or an amide having the structure —NH—C(O)-optionally substituted alkyl or a salt of any of these moieties, where each optionally substituted alkyl is independently selected and optionally is a C1-16 moiety, a C1-12 moiety or a C1-8 moiety, or (4) $R^4$ in the β-configuration is —H or a C-linked moiety such as optionally substituted alkyl and the other $R^4$, or both $R^4$ together, is in the α-configuration and is an O-linked moiety or a S-linked moiety such as —OH, —SH, =O, =S, —O—S(O)(O), —OR$^{PR}$, —SR$^{PR}$, —SCN, —O-optionally substituted alkyl, —S-optionally substituted alkyl, —O—C(O)-optionally substituted alkyl, —S—C(O)-optionally substituted alkyl, —O—C(S)-optionally substituted alkyl, a sulfonate such as —S(O)(O)—O-optionally substituted alkyl or —O—S(O)(O)-optionally substituted alkyl, a sulfate ester such as —O—S(O)(O)—O-optionally substituted alkyl, a sulfite ester such as —O—S(O)—O-optionally substituted alkyl, a sulfamate having the structure —O—S(O)(O)—NH$_2$, —O—S(O)(O)—NH-optionally substituted alkyl or —O—S(O)(O)—N-(optionally substituted alkyl)$_2$, an O-linked polymer, an S-linked polymer, an optionally substituted monosaccharide, an optionally substituted disaccharide, an optionally substituted oligosaccharide, a phosphate or thiophosphate such as —O—P(O)(OH)—OH, —O—P(O)(OH)—O—(CH$_2$)$_n$—CH$_3$, —O—P(O)[O(CH$_2$)$_n$—CH$_3$]-O—(CH$_2$)$_n$—CH$_3$, —O—P(O)(SH)—OH, —O—P(O)(SH)—O—(CH$_2$)$_n$—CH$_3$, —O—P(O)(OH)—

S—$(CH_2)_n$—$CH_3$ or a salt of any of these moieties, or (5) $R^4$ in the α-configuration is —H or a C-linked moiety such as optionally substituted alkyl and the other $R^4$, or both $R^4$ together, is in the β-configuration and is an O-linked moiety or a S-linked moiety such as —OH, —SH, =O, =S, —O—S(O)(O), —$OR^{PR}$, —$SR^{PR}$, —SCN, —O-optionally substituted alkyl, —S-optionally substituted alkyl, —O—C(O)-optionally substituted alkyl, —S—C(O)-optionally substituted alkyl, —O—C(S)-optionally substituted alkyl, a sulfonate such as —S(O)(O)—O-optionally substituted alkyl or —O—S(O)(O)-optionally substituted alkyl, a sulfate ester such as —O—S(O)(O)—O-optionally substituted alkyl, a sulfite ester such as —O—S(O)—O-optionally substituted alkyl, a sulfamate having the structure —O—S(O)(O)—$NH_2$, —O—S(O)(O)—NH-optionally substituted alkyl or —O—S(O)(O)—N-(optionally substituted alkyl)$_2$, an O-linked polymer, an S-linked polymer, an optionally substituted monosaccharide, an optionally substituted disaccharide, an optionally substituted oligosaccharide, a phosphate or thiophosphate such as —O—P(O)(OH)—OH, —O—P(O)(OH)—O—$(CH_2)_n$—$CH_3$, —O—P(O)[O$(CH_2)_n CH_3$]-O—$(CH_2)_n$—$CH_3$, —O—P(O)(SH)—OH, —O—P(O)(SH)—O—$(CH_2)_n$—$CH_3$, —O—P(O)(OH)—S—$(CH_2)_n$—$CH_3$ or a salt of any of these moieties, where for any of the moieties in (2), (3), (4) or (5) each optionally substituted alkyl is independently selected and optionally is a C1-16 moiety, a C1-12 moiety or a C1-8 moiety.

N-Linked $R^4$ moieties can optionally be selected from —$NHCH_3$, —$N(CH_3)_2$, —$NHC_2H_5$, —$N(C_2H_5)_2$, —$NHC_3H_7$, —$N(C_3H_7)_2$, —$NHC_4H_9$, —$N(C_4H_9)_2$, —NH—C1-8 optionally substituted alkyl, —N(C1-8 optionally substituted alkyl)$_2$, —NH—C(O)—H, —NH—C(O)—$CH_3$, —NH—C(O)—$OCH_3$, —NH—C(O)—$OC_2H_5$, —NH—C(O)—$OC_3H_7$, —NH—C(O)—O—C1-8 optionally substituted alkyl, —NH—C(O)—C1-8 optionally substituted alkyl, —NH—$(CH_2)_3$—$CH_3$, —NH—$(CH_2)_4$—$CH_3$, —NH—$(CH_2)_5$—$CH_3$, —NH—$(CH_2)_6$—$CH_3$, —NH—$(CH_2)_7$—$CH_3$, —NH—$CH_2$—$C_6H_5$, —NH—$CH_2$—$C_6H_4OH$, —NH—$CH_2$—$C_6H_4F$, —NH—$CH_2$—$C_6H_4Cl$, —NH—$CH_2$—$C_6H_4OCH_3$, —NH—$CH_2$—$C_6H_4CH_3$, —NH—$CH_2$—$C_6H_4$—O—C(O)—$(CH_2)_n$—$CH_3$, —NH—$CH_2$—$C_6H_4$—C(O)—O—$(CH_2)_n$—$CH_3$, —NH—$CH_2$—COOH, —NH—$(CH_2)_2$—COOH, —NH—$(CH_2)_3$—COOH, —NH—$(CH_2)_4$—COOH, —NH—$(CH_2)_5$—COOH, —NH—$CH_2$—C(O)—$OCH_3$, —NH—$CH_2$—C(O)—$OC_2H_5$, —NH—$CH_2$—C(O)—$OC_3H_7$, —NH—$(CH_2)_2$—C(O)—OH, —NH—$(CH_2)_2$—C(O)—$OCH_3$, —NH—$(CH_2)_2$—C(O)—$OC_2H_5$, —NH—$(CH_2)_2$—C(O)—$OC_3H_7$, —NH—$(CH_2)_3$—C(O)—$OCH_3$, —NH—$(CH_2)_3$—C(O)—$OC_2H_5$, —NH—$(CH_2)_3$—C(O)—$OC_3H_7$, —NH—$(CH_2)_4$—C(O)—$OCH_3$, —NH—$(CH_2)_4$—C(O)—$OC_2H_5$, —NH—$(CH_2)_4$—C(O)—$OC_3H_7$, —NH—$(CH_2)_n$—C(O)—$NH_2$, —NH—$(CH_2)_n$—C(O)—NH—$(CH_2)_n$—$CH_3$, —N[$(CH_2)_n$—C(O)—NH—$(CH_2)_n$—$CH_3$]$_2$, —NH—$(CH_2)_n$—OH, —NH—$(CH_2)_n$—F, —NH—$(CH_2)_n$—Cl, —NH—$(CH_2)_n$—CHO, —NH—$(CH_2)_n$—SH, —NH—$(CH_2)_n$—O—$CH_3$, —NH—$(CH_2)_n$—S—$CH_3$ or —NH—$(CH_2)_n$—$CH_2$—NH—$CH_3$, where each n independently is 0, 1, 2, 3 or 4.

C-Linked $R^4$ moieties can optionally be selected from —C(O)—$(CH_2)_n$—$CH_3$, —C(O)$(CH_2)_n$—$CH_2OH$, —C(O)$(CH_2)_n$—$CH_2C(O)OH$, —$CH_3$, —$C_2H_5$, —$C_3H_7$, —$C_4H_9$, —C=$CH_2$, —C≡CH, —C=CF, —C=CCl, —C=CBr, —C=Cl, —C=COH, —C=$CH_2$, —C=C—$(CH_2)_n$—$CH_3$, —$(CH_2)_m$—O—$CH_3$, —$(CH_2)_m$—S—$CH_3$, —$(CH_2)_m$—NH—$CH_3$, —$(CH_2)_m$—O—$CH_2OH$, —$(CH_2)_m$—S—$CH_2OH$, —$(CH_2)_m$—NH—$CH_2OH$, —$(CH_2)_m$—O—$CH_2SH$, —$(CH_2)_m$—S—$CH_2SH$, —$(CH_2)_m$—NH—$CH_2SH$, —$(CH_2)_m$—O—$CH_2NH_2$, —$(CH_2)_m$—S—$CH_2NH_2$ and —$(CH_2)_m$—NH—$CH_2NH_2$, where each n independently is 0, 1, 2, 3 or 4 and m is 1, 2, 3 or 4.

13. A method to treat or to reduce the severity of a chronic obstructive pulmonary disease, a respiratory distress syndrome, asthma, a chronic allergy or an atopic disease, or one or more symptoms of the chronic obstructive pulmonary disease, respiratory distress syndrome, asthma, chronic allergy or atopic disease in a subject, comprising administering an effective amount of a F1C, e.g., a F!C described herein such as at embodiment 1, 2, 3, 4, 5, 6, 7, 8, 9 or 10, optionally wherein one $R^1$ is, or both $R^1$ together are, —OH, —$OR^{PR}$, —$SR^{PR}$, —O—Si—$(R^{13})_3$, —COOH, —$OSO_3H$, —$OPO_3H$, =O, =S, an ester, a thioester, a thionoester, a phosphoester, a phosphothioester, a phosphonoester, a phosphiniester, a sulfite ester, a sulfate ester, an amide, an amino acid, a peptide, an ether, a thioether, a carbonate or a carbamate, and the other $R^1$ is independently chosen; and optionally wherein one $R^4$ is, or both $R^4$ together are, —OH, —$OR^{PR}$, —$SR^{PR}$, —$N(R^{PR})_2$, —O—Si—$(R^{13})_3$, —CHO, —CHS, —CN, —SCN, —$NO_2$, —$NH_2$, —COOH, —$OSO_3H$, —$OPO_3H$, =O, =S, =N—OH, =N—O-optionally substituted alkyl, an ester, a thioester, a thionoester, a phosphoester, a phosphothioester, a phosphonoester, a phosphiniester, a sulfite ester, a sulfate ester, an amide, an amino acid, a peptide, an ether, a thioether, an acyl group, a thioacyl group, a carbonate or a carbamate, and the other $R^4$ is independently chosen.

14. The method of embodiment 13 wherein (1) the level or activity of IgE in the subject is at least transiently detectably reduced and/or (2) the subject is a human who has a sickle cell disease and/or the treatment reduces (a) the severity of pain during vascular or microvascular occlusions, (b) the severity of vascular or microvascular occlusions or (c) the frequency of vascular or microvascular occlusions, and optionally wherein the formula 1 compound is administered by an intermittent administration or dosing protocol.

15. The method of embodiment 13 or 14 wherein one $R^1$ is, or both $R^1$ together are, —H, —OH, —$OR^{PR}$, —$SR^{PR}$, —O—Si—$(R^{13})_3$, —COOH, —$OSO_3H$, —$OPO_3H$, =O, =S, an ester, a thioester, a thionoester, a phosphoester, a phosphothioester, a phosphonoester, a phosphiniester, a sulfite ester, a sulfate ester, an amide, an amino acid, a peptide, an ether, a thioether, a carbonate or a carbamate, and the other $R^1$ is independently chosen; and one $R^4$ is, or both $R^4$ together are, —OH, —$OR^{PR}$, —$SR^{PR}$, —$N(R^{PR})_2$, —O—Si—$(R^{13})_3$, —CHO, —CHS, —CN, —SCN, —$NO_2$, —$NH_2$, —COOH, —$OSO_3H$, —$OPO_3H$, =O, =S, =N—OH, =N—O-optionally substituted alkyl, an ester, a thioester, a thionoester, a phosphoester, a phosphothioester, a phosphonoester, a phosphiniester, a sulfite ester, a sulfate ester, an amide, an amino acid, a peptide, an ether, a thioether, an acyl group, a thioacyl group, a carbonate or a carbamate, and the other $R^4$ is independently chosen.

18. A method to treat a cardiovascular condition, an autoimmune condition, a trauma, an unwanted inflammation condition or an unwanted immune response to an allograft or rejection of an allogeneic tissue, organ or cell population comprising administering to a subject having or who may be expected to develop the cardiovascular condition, autoimmune condition, unwanted inflammation condition or the unwanted immune response to an allograft or acute or chronic rejection of an allogeneic tissue, organ or cell population an effective amount of a F1C disclosed herein, e.g., an F1C in embodiment 1, 2, 3, 4, 5, 6, 7, 8, 9 or 10 or the F1C is a compound or genus of compounds in group 1 through group 57.

19. The method of embodiment 18 wherein (1) the cardiovascular condition is arteriosclerosis, atherosclerosis, hypercholesterolemia, hypertriglyceridemia or a hypertension condition such as pulmonary hypertension, (2) the autoimmune condition or unwanted inflammation is a lupus condition such as systemic lupus erythematosus, rheumatoid arthritis, osteoarthritis or Crohn's disease, inflammatory bowel disease, a scleroderma condition or a vasiculitis such as a giant cell arteritis, polyarteritis nodosa or Kawasaki's disease, and/or (3) the trauma is a bone fracture, a chemical or thermal burn, a hemorrhage, an infarction such as a cerebral infarction or tissue or organ impairment or damage associated with a wound, chemotherapy, toxin or radiation exposure.

20. The method of embodiment 19 wherein the trauma is a skin, central nervous system tissue, blood vessel, heart tissue, lung, liver, pancreas, kidney, thymus, spleen, oral mucosa, intestine, bone marrow, or connective tissue wound, laceration, lesion or trauma.

21. A pharmaceutical formulation comprising one or more excipients and a F1C disclosed herein, e.g., an F1C in embodiment 1, 2, 3, 4, 5, 6, 7, 8, 9 or 10 or the F1C is a compound or genus of compounds in group 1 through group 57.

22. A F1C disclosed herein, e.g., an F1C in embodiment 1, 2, 3, 4, 5, 6, 7, 8, 9 or 10 or a compound or genus of compounds in group 1 through group 57.

23. Use of a F1C for the preparation of a medicament or for the preparation of a medicament for the treatment of a disease, condition or symptom described herein. The medicament can be for the prophylaxis or treatment of a disease, condition or symptom disclosed herein in a subject having or susceptible to developing the disease, condition or symptom.

36. A method to (1) enhance the healing of a trauma or an acute injury in a subject who has experienced or who is expected to experience a trauma or an acute injury or (2) reduce tissue damage or one or more symptoms of a trauma or an acute injury in a subject comprising administering to the subject an effective amount of a F1C, e.g., a F1C or genus of F1Cs disclosed herein, optionally wherein the administration of the F1C is initiated on 1, 2, 3 or more days beginning at about 30 minutes, about 1 hour, about 2 hours, about 3 hours, about 4 hours, about 6 hours, about 8 hours, about 10 hours, about 11 hours, about 12 hours, about 13 hours, about 14 hours or about 16 hours or more after the trauma or acute injury.

37. The method of embodiment 36 wherein the subject will experience or has experienced an immune suppressive event within about 2-3 weeks or about 3-4 weeks of the occurrence of the trauma or acute injury, wherein the immune suppressive event is exposure of the subject to an immune suppressive amount of ionizing radiation.

38. The method of embodiment 37 wherein the ionizing radiation exposure is about 0.3 Gy to about 30 Gy of the ionizing radiation, or about 0.5 Gy to about 12 Gy of the ionizing radiation.

39. The method of embodiment 36, 37 or 38 wherein the subject has experienced an immune suppressive event within 3 weeks of the occurrence of the trauma or acute injury, wherein the immune suppressive event is selected from an immune suppressive amount of an immunosuppressive chemotherapy, optionally wherein the immunosuppressive chemotherapy is an immunosuppressive cancer chemotherapy, an immunosuppressive antimicrobial therapy or an immunosuppressive glucocorticoid therapy, e.g., treatment of the subject with an immunosuppressive amount of dexamethasone, prednisone, hydrocortisone or cortisol, cyclophosphamide, 5-fluorouracil or a platinum compound optionally selected from cisplatin, carboplatin and another chemotherapeutic agent described herein.

51. A kit comprising a formulation that comprises a unit dosage or a multiple dosage comprising a F1C, e.g., any compound described herein or within any structure disclosed herein, and one or more excipients wherein the formulation is dispensed in a suitable container, e.g., a closed or sealed container, wherein the kit optionally further comprises a label that provides information about one or more of (1) the F1C's chemical structure, (2) any recommended dosing regimen, (3) any adverse effects of administering the F1C to a subject that are required to be disclosed and (4) the amount of the F1C that is present in each unit dose or in the entire container.

62. A method to determine a status profile for a subject species comprising, (1) exposing a sufficient number of subjects to a biological insult of at least about an $LD_{10/60}$ to obtain exposed treated subjects; (2) measuring on two or more occasions in or from the exposed subjects one, two or more biological parameters selected from temperature, circadian rhythm, red blood cell counts, hematocrit, reticulocytes, platelets, megakaryocytes and neutrophils; (3) measuring the survival rate of the exposed subjects; (4) obtaining one or more status profiles that corresponds to a defined probability of surviving the biological insult ($P_{survival}$) of at least 0.95 or of not surviving the biological insult ($P_{lethality}$) of at least 0.05; and (5) optionally using the status profile to identify or initiate a profile-based therapy for one or more of the exposed subjects. In this embodiment, the biological insult can be about an $LD_{30/60}$ to about an $LD_{70/60}$, e.g., a radiation dose of about an $LD_{50/60}$ and the temperature can be core body temperature, which is optionally measured (i) using an implanted monitor, and/or (ii) continuously and/or (iii) at intervals of about 1 minute, about 5 minutes or about 10 minutes to about 30 minutes, about 1 hour or about 2 hours. When the biological insult is a radiation exposure, it is optionally selected from γ-radiation, X-rays, β-radiation, fast neutrons and slow neutrons. The status profile can be based on (i) a temperature increase of at least about 1.2° C. above baseline for a period of at least about 1 hour and a decrease of at least about 80% in red blood cell counts, hematocrit and/or reticulocytes; (ii) a temperature increase of at least about 1.0° C. above baseline for a period of at least about 30 minutes and a decrease of at least about 80% in red blood cell counts, hematocrit and/or reticulocytes at one or more time points; (iii) a temperature increase of at least about 1.5° C. above baseline for a period of at least about 15 minutes and a decrease of at least about 80% in red blood cell counts, hematocrit and/or reticulocytes at one or more time points; (iv) a temperature increase of at least about 3° C. above baseline for a period of at least about 3 hours and a decrease of at least about 15% in red blood cell counts, hematocrit and/or reticulocytes at one or more time points; and/or (v) another parameter or clinical condition or situation described herein. One or more status profiles can be obtained by unpaired t-test analysis, paired t-test analysis or other suitable analytic methods. In some embodiments, the $P_{survival}$ or $P_{lethality}$ status profile will predict survival or death with (i) at least about a 90% degree of confidence or P 0.90 or (i) at least about a 95% degree of confidence or P 0.95. Also, the $P_{survival}$ or $P_{lethality}$ status profile can be for radiation exposure, optionally wherein the radiation dose is about an $LD_{10}$, about an $LD_{20}$, about an $LD_{30}$, about an $LD_{40}$, about an $LD_{50}$, about an $LD_{60}$, about an $LD_{70}$, about an $LD_{80}$, about an $LD_{90}$ or about an $LD_{100}$, where survival is measured at 30 days or at 60 days, or wherein the radiation dose is about 2 Gy to about 10 Gy, or wherein the radiation dose is about 6 Gy, optionally where the radiation is $^{60}$Co, $^{127}$Cs radiation, radioactive iodine, and/or optionally where the dose rate is about 50 cGy/minute, about 60 cGy/minute or about 70 cGy/minute.

64. A method to characterize a biological activity of a formula 1 compound described herein in a subject comprising; (1) exposing a sufficient number of subjects to a biological insult of at least about an $LD_{50/30}$ or at least about an $LD_{50/60}$ to obtain exposed subjects and treating the exposed subjects with the formula 1 compound to obtain exposed treated subjects; (2) measuring the survival rate of the exposed treated subjects; (3) comparing the survival rate of the exposed treated subjects with the survival rate of subjects of the same or a closely related species that had been exposed to the same or similar or comparable biological insult, where such untreated subjects had not been treated with the F1C ("control subjects"); (4) optionally measuring the temperature of the exposed treated subjects on one or more occasions, beginning before, during or after exposure of the exposed treated subjects to the biological insult; and (5) optionally comparing the effect of the F1C on the survival rate of the exposed treated subjects with the survival rate of subjects of the same or a closely related species that had been exposed to the same or a similar or a comparable biological insult ("comparison controls"), where such comparison controls were treated with sufficient 3β,17β-dihydroxyandrost-5-ene or 3β-hydroxy-17β-aminoandrost-5-ene to detectably modulate the survival rate of the subjects that had been exposed to the same or similar or comparable biological insult.

65. The method of embodiment 64 wherein the biological insult is exposure of the subject species to a treatment or condition that is or causes an effect of (a) about an $LD_{30/60}$ to about an $LD_{80/60}$, (b) about an $LD_{30/30}$ to about an $LD_{80/30}$, (c) about an $LD_{50/60}$ or (d) about an $LD_{50/30}$.

66. The method of embodiment 64 or 65 wherein the temperature is core body temperature, which is optionally measured (i) using an implanted monitor or another means or technique for measuring core body temperature, and/or (ii) continuously and/or (iii) at intervals of about 1 minute, about 5 minutes or about 10 minutes to about 20 minutes, about 30 minutes, about 1 hour or about 2 hours.

128. A formulation comprising one or more excipients and a compound having the structure

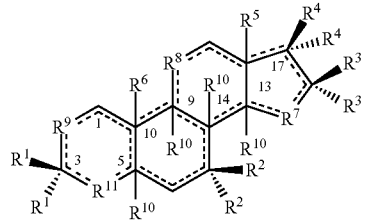

wherein the dotted lines are optional double bonds; each $R^1$, $R^2$, $R^3$, $R^4$, $R^5$, $R^6$ and $R^{10}$ independently or together are —H, —OH, —OR$^{PR}$, —SR$^{PR}$, —SH, —N(R$^{PR}$)$_2$, —NHR$^{PR}$, —NH$_2$, —O—Si—(R$^{13}$)$_3$, —CHO, —CHS, —CN, —SCN, —NO$_2$, —N$_3$, —COOH, —COOR$^{PR}$, —OSO$_3$H, —OSO$_2$H, —OPO$_3$H$_2$, =O, =S, =N—OH, =N—OCH$_3$, =CH$_2$, =CH—CH$_3$, =CH-optionally substituted alkyl, =N-optionally substituted alkyl, =N—O-optionally substituted alkyl, —NH—S(O)(O)-optionally substituted alkyl, —S—S-optionally substituted alkyl, ester, thioester, thionoester, phosphoester, phosphothioester, phosphonate, phosphonate ester, thiophosphonate, thiophosphonate ester, phosphiniester, sulfite ester, sulfate ester, sulfamate, sulfonate, sulfonamide, amide, amino acid, peptide, ether, thioether, acyl, thioacyl, carbonate, carbamate, halogen, optionally substituted alkyl, optionally substituted alkenyl, optionally substituted alkynyl, optionally substituted aryl, optionally substituted heteroaryl, optionally substituted heterocycle, optionally substituted monosaccharide, optionally substituted oligosaccharide, polymer, spiro ring, epoxide, acetal, thioacetal, ketal or a thioketal, =N—O-optionally substituted alkyl, =N-optionally substituted alkyl, —NH-optionally substituted alkyl, —N(optionally substituted alkyl)$_2$ where each optionally substituted alkyl is independently selected, or, one or more of two adjacent $R^1$, $R^2$, $R^3$, $R^4$, $R^5$, $R^6$ and $R^{10}$ comprise an independently selected epoxide or optionally substituted, saturated or unsaturated cyclopropyl, cyclobutyl, cyclopentyl or cyclohexyl ring any of which rings optionally contain one or two independently selected —O—, —S—, —S(O)(O)—, —NH— —N(optionally substituted alkyl)- or =N— heteroatoms; $R^7$ is —O—, —S—, —NR$^{PR}$—, —C(R$^{10}$)$_2$—, —C(R$^{10}$)$_2$—C(R$^{10}$)$_2$—, —C(R$^{10}$)$_2$—C(R$^{10}$)$_2$—C(R$^{10}$)$_2$—, —C(R$^{10}$)$_2$—O—C(R$^{10}$)$_2$—, —C(R$^{10}$)$_2$—S—C(R$^{10}$)$_2$—, —C(R$^{10}$)$_2$—NR$^{PR}$—C(R$^{10}$)$_2$—, —O—C(R$^{10}$)$_2$—, —S—C(R$^{10}$)$_2$— or —NR$^{PR}$—C(R$^{10}$)$_2$—, where each $R^{10}$ is independently selected; $R^8$ and $R^9$ independently are —C(R$^{10}$)$_2$—, —C(R$^{10}$)$_2$—C(R$^{10}$)$_2$—, —O—, —O—C(R$^{10}$)$_2$—, —S—, —S—C(R$^{10}$)$_2$—, —NR$^{PR}$— or —NR$^{PR}$—C(R$^{10}$)$_2$—, or one or both of $R^8$ or $R^9$ independently are absent, leaving a 5-membered ring, where each $R^{10}$ is independently selected; $R^{11}$ is —O—, —S—, —S(O)(O)—, —NR$^{PR}$—, —CH$_2$—, —CHR$^{10}$—, —C(R$^{10}$)$_2$—, —C(R$^{10}$)$_2$—O—C(R$^{10}$)$_2$—, —C(R$^{10}$)$_2$—S—C(R$^{10}$)$_2$—, —C(R$^{10}$)$_2$—S(O)(O)—C(R$^{10}$)$_2$—, —C(R$^{10}$)$_2$—NR$^{PR}$—C(R$^{10}$)$_2$—, —O—C(R$^{10}$)$_2$—, —S—C(R$^{10}$)$_2$—, —S(O)(O)—C(R$^{10}$)$_2$— or —NR$^{PR}$—C(R$^{10}$)$_2$—, where each $R^{10}$ is independently selected; $R^{13}$ independently is $C_{1-6}$ alkyl; and $R^{PR}$ independently are —H or a protecting group, wherein one or two independently selected $R^{10}$ moieties are present at the 1-, b- and 12-positions and wherein compound is a 1,5,9(11)-triene, 1,5,11-triene, 1,5,14-triene, 1,5,15-triene, 1,3,14-triene, 1,3,8(9)-triene, 1,3,8(14)-triene, 1,3,9(11)-triene, 1,3,11-triene or a 1,3,14-triene.

Variations and modifications of these embodiments, the claims and the remaining portions of this disclosure will be apparent to the skilled artisan after a reading thereof. Such variations and modifications are within the scope and spirit of this invention. All citations herein are incorporated herein by reference in their entirety. All citations herein are incorporated herein by reference at this paragraph and/or in a new paragraph(s) that follows this paragraph.

EXAMPLES

The following examples further illustrate the invention and they are not intended to limit it in any way. Variations of these examples that are included in the invention may include, e.g., any of the F1Cs described herein or parts or all of any of the methods, formulations, treatment protocols and/or assays described herein.

Example 1

Treatment of cytopenia. Primates treated to induce neutropenia or thrombocytopenia are used to characterize their response to treatment with a F1C. Mitigation of cytopenia, e.g., neutropenia or thrombocytopenia, by the F1C is observed. In an exemplary protocol, Cynomolgus monkeys of about 3.5-8 years of age and weighing about 2.5 to 8 kg are dosed at 35 mg/kg with carboplatin (sterile 10 mg/mL solution in 0.9% sodium chloride) by intravenous infusion over 30 minutes. Beginning at 1 or 2 days after the carboplatin infusion, each animal is dosed once daily or once every other day with the F1C for 1, 2, 3, 4, 5, 6, 7, 8, 9 or 10 days, e.g., once per day for 5 consecutive days beginning 2 days after carboplatin infusion. The F1C is in a suitable sterile solution or suspension formulation in suitable excipients, e.g., a suspension containing 0.1% w/v carboxymethyl-cellulose, 0.9% w/v sodium chloride and 0.05% v/v phenol. The suspension contains micronized F1C. Control animals receive the formulation without any F1C. The animals are dosed with the F1C subcutaneously in the interscapular region of the back or intramuscularly in the thigh at a dosage of about 1-45 mg/kg, e.g., 1.25, 2.5, 7.65 or 42.5 mg/kg of the F1C. Blood samples of about 1-1.5 mL are withdrawn at various times, e.g., on days −5 (pre-carboplatin), −2 (pre-carboplatin), 1 (4 hr post-dosing), 3, 7, 10, 12, 14, 16, 18, 20, 22, 24, 26, 28, 32 and 36 days, for analysis such as neutrophil, platelet, reticulocyte, erythrocyte counts. The degree of reduced time and/or severity of cytopenia such as anemia, thrombocytopenia or neutropenia are then observed in F1C treated and control animals.

Example 2

Cystic fibrosis treatment. Treatment with a F1C is conducted on human cystic fibrosis ("CF") patients, e.g., 18 years of age or older, who may have two or more of the following characteristics: (1) sweat chloride ≥60 mEq/L, e.g., by quantitative pilocarpine iontophoresis test, (2) homozygosity for the F508 genetic mutation, or heterozygosity for 2 well-characterized mutations, e.g., as described herein, associated with CF, (3) $FEV_1 \geq 40\%$ predicted at screening, (4) $SaO_2 \geq 90\%$ at screening, (5) ability to perform pulmonary function tests and (6) clinical stability, with no evidence of acute upper or lower respiratory tract infection or current pulmonary exacerbation. The treatment regimen consists of 1, 2, 3, 4 or 5 consecutive days of once daily dosing of a F1C or placebo equivalent followed by a 40-day observation period. Daily dosages are about 10-150 mg/day, e.g., about 25 mg/day, 50 mg/day, 75 mg/day or 100 mg/day. The F1C is administered as described herein such as by a parenteral route, e.g., intramuscular or subcutaneous delivery, or by transmucosal delivery, e.g., buccal or sublingual. A follow-up visit will occur 6 weeks after the last treatment course to collect final samples for safety and activity. Patients receive, e.g., 3 treatment courses over a 14-week period, 6 treatment courses over a 28-week period or more courses of treatment over a longer period. The patients are optionally monitored for the status of their condition or in improvement of one or more CF symptoms after dosing, e.g., reduction in the numbers of neutrophils in bronchiolar or alveolar lavage samples, e.g., about a 30%, 40%, 50% or greater reduction, or levels of one or more CF-related inflammation markers, e.g., reduced levels or activity of IL-6, IL-8, IKK-β kinase or neutrophil elastase, or in the reduced occurrence, severity or progression of infections such as a *Burkholderia* (*Pseudomonas*) *cepacia* infection.

Example 3

Human and primate virus treatment protocol. Humans infected with a virus, e.g., HCV, RSV, HBV or a retrovirus such as HIV1 or HIV2 or primates infected with a virus such as HCV, HIV1, HIV2, SIV or $SHIV_{229}$ are treated with a F1C formulation. Daily dosages of about 0.05 to about 25 mg/kg are administered daily or on an intermittent basis. The F1C is administered, e.g., orally, by subcutaneous injection, by intramuscular injection or by transmucosal delivery. A typical intermittent dosing protocol for human patients comprises daily dosing of about 0.1-5 mg/kg of the F1C for 1, 2, 3, 4, 5 or 6 days, followed by no dosing for about 1, 2, 3, 4, 5, 6, 7 or 8 weeks, daily dosing again for 1, 2, 3, 4, 5 or 6 days, no dosing for about 1, 2, 3, 4, 5, 6, 7 or 8 weeks and optionally repeating this dosing schedule as desired, e.g., for 3, 4, 5, 10, 15 or more rounds of dosing. A related dosing protocol involves dosing on every $2^{nd}$ or $3^{rd}$ day to deliver 2, 3, 4, 5 or 6 doses of the F1C, no dosing for about 2, 3, 4, 5, 6, 7 or 8 weeks and optionally repeating this dosing schedule as desired, e.g., for 3, 4, 5, 10, 15 or more rounds of dosing. Typical daily F1C doses in human treatment protocols is about 5 mg to about 1000 mg, usually about 10-150 mg. Daily doses can vary depending on the route of F1C administration and on the patient's weight and clinical condition, with oral administration usually requiring higher daily doses than parenteral or transmucosal administration.

In treating a viral infection such as a human HIV1 or HIV2 infection, one can optionally monitor one or more aspects the patient's response, e.g., periodic assay for viral load or for the level or activity of a given immune cell type or a biomolecule described herein such as $CD4^+$ T cells, $CD123^+$ dendritic cells, IL-6, IL-10 or TNFα. Changes in cell types, viral load or biomolecules can be transient, e.g., detectably changed over a period of about 2-48 hours, or sustained, e.g., detectably changed for about 3-6 days or about 1-8 weeks. Other aspects of the patient's response may also be monitored such as the incidence, severity or rate of progression of symptoms or associated conditions such as coinfection, fatigue, weight loss or side effects of other suitable therapies. In retrovirus-infected patients that are treated with the F1C, the rate or progression of a clinically significant coinfection by *Mycobacteria* or *Pneumocystis* is generally reduced, including for patients with a CD4+ T cell count of less than about 100 cells/mm$^3$ or less than about 75 cells/mm$^3$.

Example 4

Stimulation of phagocytosis. The capacity of F1Cs to influence phagocytosis of *Plasmodium* parasite-infected RBC is examined using adherent human monocytes. The parasitemia level is about 8-10% and human monocytes are obtained from buffy coats from blood as follows. Peripheral blood mononuclear cells are separated from freshly collected platelet-poor buffy coats discarded from blood samples of healthy adult donors of both sexes. Separated cells are washed once with luke-warm PBS supplemented with 10 mM glucose (PBS-G) and resuspended at $5 \times 10^6$ cells/mL in ice-cold RPMI 1640 medium supplemented with 23 mM $NaHCO_3$ and 25 mM Hepes, pH 7.4 (RMBH). Dynabeads M450 Pan B and Pan T (Dynal) are added to cells in a 4:1 ratio for 20 min at 4° C. B-lymphocytes and T-lymphocytes are removed as specified by the manufacturer. The remaining monocytes are washed 2 times in RMBH, resuspended in AIM V cell culture medium (Gibco) at $1 \times 10^6$ cell/mL. The monocyte layer is collected, washed with PBS-G at 37° C. and resuspended in AIM V medium at $1 \times 10^6$ cells/mL. Purified cells are >90% monocytes as assessed by CD14 expression.

Phagocytosis of opsonized parasitized RBC (PE) is determined as follows. Phagocytosis of fresh-serum opsonized PE is initiated by mixing 10 PE/monocyte. Suspensions are briefly centrifuged (150×g for 5 sec at room temperature) to improve contact between PE and monocytes. To avoid attachment of monocytes after centrifugation and during the whole incubation period, cells are kept in suspension at $5 \times 10^6$ cells/5 mL AIM V medium in 6 cm diameter Teflon bottom dishes (Heraeus) in a humidified incubator (95% air, 5% $CO_2$) at 37° C. On average, at least 90% of the monocytes phagocytose PE, as assessed by microscopic inspection. Control cells are kept under similar conditions without phagocytosis. Quantitative assessment of phagocytosis is performed by a previously described bioluminescence method (E. Schwarzer, et al., *Br. J. Haematol.* 1994 88: 740-745).

Erythrocyte treatments and parasite cultures are as follows. Fresh blood (Rh+) is used to isolate erythrocytes (RBC). Washed RBC are infected with schizont/trophozoite parasite stages (Palo Alto strain, mycoplasma-free). Stage specific parasites are isolated by the Percoll-mannitol method. Briefly, normal schizont-stage parasitized RBC (SPE) separated on Percoll-mannitol gradient (parasitemia>95% SPE) are mixed with RBC suspended in growth medium (RPMI 1640 medium containing 25 mmol/L Hepes, 20 mmol/L glucose, 2 mmol/L glutamine, 24 mmol/L $NaHCO_3$, 32 mg/L gentamicin and 10% AB or A human serum, pH 7.30) to start synchronous cultures at selected hematocrit values. The inoculum parasitemia is adjusted to 20% normal SPE for isolation of ring parasitized RBC (RPE) and to 5% normal SPE for isolation of trophozoite-stage parasitized RBC (TPE). At 14-18 hours after inoculum parasites are at ring-stage in the first cycle; at 34-33 hours, parasites are at trophozoite-stage in the first cycle; and at 40-44 hours after inoculum parasites are at schizont-stage in the first cycle. RPE, TPE and SPE are separated on Percoll-mannitol gradients. The parasitemia is usually 8-10% RPE, and >95% TPE. Nonparasitized and parasitized RBC are counted electronically. To assess total parasitemia and relative contribution of RPE, TPE and SPE, slides are prepared from cultures at indicated times, stained with Diff-Quik™ parasite stain and about 400-1000 cells are examined microscopically.

The effect of a formula 1 compound such as F1C in parasitized RBC is examined using various concentrations of the compound, e.g., F1C, e.g., 0.001 µM, 0.01 µM, 0.05 µM, 0.1 µM, 0.5 µM, 1 µM, 10 µM, 25 µM and 50 µM. Trophozoite-parasitized RBC, schizont-parasitized RBC or ring-parasitized RBC are examined as described.

Example 5

Cyclodextrin formulation. A cyclodextrin formulation containing a F1C is prepared by mixing a sulfobutyl β-cyclodextrin and the F1C in one or more liquids such as ethanol, DMSO, N-methylpyrrolidine, pyridine or water. The sulfobutyl β-cyclodextrin contains one or more butyl sulfonate or $-O-(CH_2)_4-SO_3^-Na^+$ moieties, typically about 5, 6 or 7 per cyclodextrin molecule. F1Cs that contain a positive charge are especially helpful in forming complexes with the multiple negative charges of sulfobutyl cyclodextrin. For parenteral formulations, the maximum concentrations could be achieved at about the maximum cyclodextrin concentration that is still syringable, about 50% w:v. The F1C can be added to a solution of sulfobutyl β-cyclodextrin at a molar ratio of about 1:1, e.g., 0.5:1 to about 2:1, and stirred with or without heat for up to about 1 week to form the complex. The solution is optionally filtered or sterilized before filling in vials or injection delivery by any route. The vials can be sterilized by radiation or by sterile filtration. An exemplary preparation is made using 500 grams of sulfobutyl β-cyclodextrin (about 230 mmoles) combined with about 230 mmoles of the F1C. Solutions containing about 20-80 mg/mL of the F1C are typically obtained. For pharmaceutical formulations, the complex is prepared under GMP compliance conditions. The dried complex is prepared by lyophilization and can be reconstituted, e.g., using sterile 0.9% NaCl. The cyclodextrin complex can also be dried for preparation of formulations for oral or transmucosal administration or reconstituted with water for parenteral delivery, e.g., by subcutaneous or intramuscular injection.

Example 6

Inhibition of inflammation. The capacity of formula 1 compounds to limit or inhibit inflammation or symptoms of inflammation is shown using animal models for inflammatory bowel disease. In an exemplary protocol, groups of 3 male Wistar rats (180±20 grams) fasted for 24 hours before 2,4-dinitrobenzene sulfonic acid (DNBS) or saline challenge are used. Distal colitis is induced by intra-colonic instillation of 0.5 mL of an ethanolic solution of DNBS (30 mg in 0.5 mL of a 30% ethanol in saline solution) after which 2 mL of air is injected through the cannula to ensure that the solution remained in the colon. The volume used is 0.1 mL per injection of 2 and 20 mg/mL of a F1C in a liquid formulation, which is administered by subcutaneous injection once a day for 6 days. The formulation contained 100 mg/mL of the F1C in a non-aqueous suspension, e.g., 2% benzyl alcohol w/v, 0.1% Brij 96 w/v and equal volumes of PEG 300 and propylene glycol. Concentrations of 2 mg/mL and 20 mg/mL are obtained by diluting the 20 mg/mL formulation with vehicle that lacked the F1C.

The first F1C dose is given 30 minutes after DNBS challenge. Sulfasalazine (30 mg/mL in 2% Tween 80 in distilled water) is administered orally (PO) once a day (10 mL/kg/day) for 7 days, the first two doses beginning 24 hours and 2 hours before DNBS challenge. The presence of diarrhea is recorded daily by examining the anal area. Animals are fasted for 24 hours prior to being sacrificed. Animals are sacrificed on day 7 or day 8 and their colons are removed and weighed. Before removal of the colon, signs of adhesion between the colon and other organs are recorded. Also, the presence of ulcerations is noted after weighing of each colon. The "net" change of colon-to-body weight (BW) ratio is normalized relative to saline-challenged baseline group. A 30% decrease in "net" colon-to-body weight ratio is considered significant.

Example 7

Modulation of delayed type hypersensitivity. The capacity of F1Cs to modulate delayed type hypersensitivity (DTH) is determined in mice. Groups of five female BALB/cByJ mice (20-25 grams) are anesthetized and 100 μL of a 3% solution of oxazolone is applied on day 0 to the shaved abdomen and dried. Seven days later, on day 7, the mice are challenged by applying 5 μL of oxazolone topically to each side of the right ear. The F1C (at about 20-100 mg/mL) in vehicle is administered by subcutaneous injection (2 mg/day) one time on day 6, 24 hours before the oxazolone challenge. The vehicle as a non-aqueous suspension of the F1C in, e.g., 2% benzyl alcohol w/v, 0.1% Brij 96 w/v and equal volumes of PEG 300 and propylene glycol.

Dexamethasone in saline (0.2 mg/mL) is administered daily for 9 days (day −1 to 7), first dose 24 hours before sensitization, last dose at challenge by subcutaneous injection (0.01 mg/dose, 50 μL/injection). On Day 8, 24 hours following the oxazolone challenge, both the right and left ear thicknesses are measured using a micrometer caliper and the differences are determined. The differential ear thickness is measured as an indicator of the DTH response to topical oxazolone challenge. The DTH response is expressed as the difference in the thickness (mm) between the right and the left ears for each animal.

The differential ear thickness in animals receiving vehicle alone is 0.225 mm and treatment with dexamethasone (high dose) or cyclophosphamide reduced the DTH response (0.144 mm and 0.092 mm, respectively).

Example 8

Reversal of immunosenescence. Healthy aged (20-month) or immunologically-mature (3-month) BALB/c mice are vaccinated with hepatitis B surface antigen (HbsAg) (2 µg; Recombivax-HB; Merck) and Alum (2.75 µg). The aged mice are vaccinated with the antigen and also received a single subcutaneous injection of either 0.3 mg or 3.0 mg of selected F1Cs or the vehicle (placebo control).

Blood samples are collected 14, 21 and 34 days after treatment and the sera are analyzed by ELISA to determine the concentration of HbsAg-specific IgG (total IgG). In addition, samples obtained on day 21 are analyzed to determine the concentration of HbsAg-specific IgG1 and IgG2a subclasses. The results can be summarized as average values obtained with blood samples collected 21 days after vaccination of groups of 8 mice. Subcutaneous injection is performed after shaving the hair from the thighs of each mouse. The injected volume is 50 µL containing 3.0 mg or 0.3 mg of compound or placebo, and for vaccine preparation. The vehicle control consists of carboxymethyl-cellulose (0.5%) in saline (0.9%). Antibody titers are determined by ELISA.

Treatment of aged, vaccinated animals with the F1Cs, can result in higher anti-HbsAg IgG titers than aged animals receiving the vaccination only. Such results would show that the F1Cs can enhance immune response to antigen challenge in immune senescent animals.

The serum samples are also analyzed for the titers of HbsAg-specific, IgG1 or IgG2a immunoglobulin subclasses. A bias to IgG1 is seen in aged mice and this is considered symptomatic of immune senescence or a suboptimal immune response associated with immune senescence. The IgG1/IgG2a ratio is an indicator of immune status. Th2 cells predominantly assist in the generation of humoral immunity, while Th1 cells enhance, e.g., cellular immunity. Humoral immunity (Th2) becomes predominant with age, while the decreasing cellular (Th1) immunity leads to increased susceptibility to, e.g., infectious diseases.

To examine the secondary antibody response, 42 days after the initial exposure to HbsAg, serum samples are taken from the mice and these are tested for anti-HbsAg IgG. At this time-point, vaccine-specific IgG titers are either low or undetectable. Three days later (45 days after first vaccination), the mice are injected again with HbsAg in alum, but this time, none of the mice receive any F1C (secondary vaccination). Serum samples collected 7 days and 14 days after the second exposure to HbsAg vaccine are assayed for anti-HbsAg antibody. In the young mice, a marked increase in specific antibody is seen in response to the second vaccination. In aged mice that had receive no F1C with the first HbsAg injection, levels of anti-HbsAg are measured. The data is analyzed for increases in anti-HbsAg titers following secondary vaccination in aged animals that had been treated with a F1C in conjunction with the first HbsAg exposure.

Example 9

Suppression of TNF-α induced adhesion molecule expression. The recruitment of lymphocytes to areas of inflammation and angiogenesis involves specific receptor-ligand interactions between cell surface adhesion molecules (CAMs) on lymphocytes and the vascular endothelium. The adhesion process, in both normal and pathological settings, follows a multi-step cascade that involves intercellular adhesion molecule-1 (ICAM-1), vascular cell adhesion molecule-1 (VCAM-1), and endothelial leukocyte adhesion molecule-1 (E-selectin) expression on endothelial cells (EC). The expression of these molecules and others on the vascular endothelium determines the efficiency with which leukocytes may adhere to the local vasculature and extravasate into the local tissue during the development of an inflammatory response. The local concentration of cytokines and growth factor participate in the modulation of the expression of these CAMs.

Tumor necrosis factor alpha (TNF-α), is a proinflammatory cytokine and stimulates all three CAMs on endothelial cells. It may be involved in a wide variety of inflammatory responses, often resulting in a pathological outcome. The capacity of a formula 1 compound to mediate a suppression of TNF-α induced CAM expression can be examined. A modified ELISA assay which uses Ecs as a solid phase absorbent is employed to measure the amount of CAM expression on TNF-a treated Ecs when co-stimulated with a member of the FGF family of proteins. To perform the experiment, human umbilical vein endothelial cell (HUVEC) cultures are obtained from pooled cord harvests and maintained in growth medium (EGM-2, Clonetics, San Diego, Calif.) supplemented with 10% FCS and 1% penicillin/streptomycin in a 37° C. humidified incubator containing 5% $CO_2$. HUVECs are seeded in 96-well plates at concentrations of about $1 \times 10^4$ cells/well in EGM medium at 37° C. for 18-24 hrs or until confluent. The monolayers are subsequently washed 3 times with a serum-free solution of RPMI-1640 optionally supplemented with 100 U/mL penicillin and 100 mg/mL streptomycin, and treated with a given cytokine and/or growth 5 factor(s) for 24 h at 37° C. Following incubation, the cells are then evaluated for CAM expression.

HUVECs are grown in a standard 96 well plate to confluence. Growth medium is removed from the cells and replaced with 90 µL of 199 Medium (10% FBS). Samples for testing and positive or negative controls are added to the plate in triplicate (in 10 µL volumes). Plates are incubated at 37° C. for either 5 h (selectin and integrin expression) or 24 h (integrin expression). Plates are aspirated to remove medium and 100 pL of 0.1% paraformaldehyde-PBS (with $Ca^{++}$ and $Mg^{++}$) is added to each well. Plates are held at 4° C. for 30 min. Fixative is then removed from the wells and wells are washed 1× with PBS(+Ca,Mg)+0.5% BSA and drained. Do not allow the wells to dry. 10 pL of diluted primary antibody is added to the test and control wells. Anti-ICAM-1-Biotin, Anti-VCAM1-Biotin and Anti-E-selectin-Biotin are used at a concentration of 10 pg/ml (1:10 dilution of 0.1 mg/ml stock antibody). Cells are incubated at 37° C. for 30 min. in a humidified environment. Wells are washed ×3 with PBS (with Ca, Mg) and 0.5% BSA. Then add 20 pL of diluted ExtrAvidin-Alkaline Phosphotase (1:5,000 dilution) to each well and incubate at 37° C. for 30 min. Wells are washed ×3 with PBS (with Ca, Mg) and 0.5% BSA. 1 tablet of p-Nitrophenol Phosphate pNPP is dissolved in 5 mL of glycine buffer (pH 10.4). 100 pl of pNPP substrate in glycine buffer is added to each test well. Standard wells in triplicate are prepared from the working dilution of the ExtrAvidin-Alkaline Phosphotase in glycine buffer: 5 pL of each dilution is added to triplicate wells and the resulting AP content in each well is 5.50 ng, 1.74 ng, 0.55 ng, 0.18 ng. 100 pl of pNNP reagent is then be added to each of the standard wells. The plate is incubated at 37° C. for 4 h. A volume of 50 pL of 3M NaOH is added to all wells.

The results are quantified on a plate reader at 405 nm. The background subtraction option is used on blank wells filled with glycine buffer only. The template is set up to indicate the concentration of AP-conjugate in each standard well. Results are indicated as amount of bound APconjugate in each sample.

Example 10

Effects on the CNS. The effects of the formula 1 compounds on memory, learning, motor function or the status of a neurological condition or neurodegeneration condition are assayed using standard methods. For example, aged, two year old mice are tested in the Morris water maze procedure by training the mice to locate a pedestal in less than 15 seconds in three consecutive trials. Immediately upon completion of training one group of mice is treated with a formula 1 compound (5-30 mg/kg) and a second group is treated with a placebo. The treatment comprises one, two or three intraperitoneal, subcutaneous, intramuscular or intravenous injections of the formula 1 compound and the vehicle placebo. The injections are given once per day. Two weeks after treatment, the time to rescue is timed in the Morris water maze procedure and the control result is compared to the placebo control. The use of Morris water maze and other procedures to measure the effect of various conditions or compounds on learning, memory or neurological conditions have been described, see e.g., R. Gerlai *Trends Neurosci.* 1996, 19:177-181, J. L. W. Lau et al., *Proc. Nat'l. Acad. Sci.* 2001, 98:4716-4721, U.S. Pat. Nos. 6,348,489, 6,251,942 and 6,277,886.

Scopolamine induced amnesia is examined essentially as follows. Groups of 13 to 16 C57BL76 mice (about 35 gm) are trained in the Morris water maze procedure to locate a pedestal in less than 15 seconds in three consecutive trials. Immediately upon completion of training the mice in each of three groups are treated with scopolamine (1 mg/kg), scopolamine plus a formula 1 compound at one or more dosages (e.g., about 5-50 mg/kg), and scopolamine plus a placebo. The treatment comprises one, two or three intraperitoneal, subcutaneous, intramuscular or intravenous injections of the formula 1 compound and the vehicle placebo. The injections are given once per day. Six days after treatment the average time (sec) to rescue is timed using the Morris water maze procedure and the results from each group are compared. Results for a F1C are optionally compared to the results that are obtained in these protocols using another control compound, e.g., (S)-(−)-N-propargyl-1-aminoindan or nefiracetam, or another F1C.

For subjects having a neurological trauma, e.g., an experimental a brain or spine injury, administration of a F1C can begin at various times relative to the trauma. Administration can begin about 1, 2 or 3 days before the trauma or at times thereafter, e.g., commencing at about 1, 1.5, 2, 2.5, 3, 3.5, 4, 4.5, 5, 5.5, 6, 7, 8, 9, 10, 12, 14, 16, 18, 20, 24, 28, 36, 48 or more hours after the trauma. Administration of the F1C can be daily dosing or intermittent dosing.

Example 11

Ischemia treatment. The capacity of F1Cs to limit injury associated with ischemia and reperfusion is determined in an animal model essentially as follows. Male Sprague-Dawley rats weighing 130-170 g are randomly assigned to no pretreatment, vehicle pre-treatment or formula 1 compound pretreatment using one or more dosages, e.g., about 1-10 mg/kg. Animals are treated with vehicle or F1C the day before and the day of surgery. Anesthesia is induced with intraperitoneal pentobarbital (60-70 mg/kg). The rats are placed on a heating pad, and body temperature is maintained at about 36° C. Detection of the cremaster muscle on its neurovascular pedicle is performed essentially according to conventional techniques, e.g., Anderson, G. L. et al., *Microvascular Res.* 1988 36:56-63, Siemionow, M. et al., *Microcirc. Endoth. Lymphatics* 1991 7:183-197, Siemionow, M. et al., *J. Hand Surgery* 1993 18A:963-971.

Briefly, a skin incision is made from the anterior iliac spine to the tip of the scrotum. The testis with cremaster muscle intact is then dissected away from the scrotum. An opening of 1 cm is made on the ventral surface of the cremaster, and the testis and spermatic cord are removed. Under a microscope, the neurovascular pedicle, consisting of the pubic-epigastric arteries, vein, and genitofemoral nerve, is then completely isolated by dissecting to the origin of the vessels from the external iliac artery and vein. The front wall of the cremaster muscle sac is opened and the island cremaster muscle flap is prepared for intravital videomicroscopy. The rat is secured on a tissue bath, and the cremaster muscle flap is spread over the coverglass in the opening at the bottom of the bath and fixed with 5-0 silk sutures. It is then transilluminated from below, using a fiber optic tungsten lamp. The muscle is kept moist and covered with impermeable plastic film. The tissue bath, designed specifically for temperature control, is filled with 0.9% saline and the temperature maintained at between 35-36° C. The microscope is equipped with a color video camera. The video image of the microcirculation is displayed on a 19" monitor, where the final magnification is 1800×. Measurement of microvascular activity is recorded after isolation of the muscle to establish the pre-ischemia baseline. After proper positioning of clamps to completely shut down blood flow to the muscle flap, the duration of the ischemic period is six hours. Following removal of clamps to induce reperfusion injury, activity in the microvasculature is measured at e.g., 30, 60 and 90 minutes post-reperfusion. In all experimental subjects, ischemia is followed by reflow and then by an initial period of flow of blood through the microcirculation. This burst of circulatory activity is followed by marked reperfusion injury that induces loss of flow.

One or more of the following parameters are used to evaluate the state of the cremaster muscle microvasculatory system prior to ischemia and after reperfusion. The density of perfused capillaries in each of three flap regions is measured by counting the number of flowing capillaries in proximity to the preselected post-capillary venule. Nine visual fields of capillaries are counted at each postcapillary venule site, for a total of 27 fields per cremaster muscle flap.

A leukocyte count in postcapillary venules is taken using video scans of three pre-selected post-capillary venules in proximal, middle and distal flap regions. For each venule, the number of leukocytes rolling through the lumen, the number adhering to the endothelium and the number migrating across the endothelium over a two-minute period are recorded. Results are optionally obtained for rollers, strikers and diapedesis.

Red blood cell velocities in first order and second order arterioles are measured. Red blood cell velocities are recorded in the main arterioles of the cremaster flap using an optical Doppler velocimeter. Results are obtained for velocity of venous and arterial blood.

In an exemplary protocol, six rats are untreated and six rats are pre-treated with vehicle. Under conditions of six hours of ischemia and 90 minutes of reperfusion, the absolute number of rolling, sticking and transmigrated leukocytes is determined within 60 minutes of reperfusion and at 90 minutes. Rats are pre-treated with a formula 1 compound by subcutaneous injection the day before and the day of surgery to measure any protective effect of the therapy. One or more of the three parameters are determined and are compared to normal values. The endothelial-adherent properties compared to baseline values are optionally determined, using numbers of rolling, sticking and transmigrating leukocytes. Red cell velocities in second order arterioles are compared to normal rates of flow at, e.g., 90 minutes post-reperfusion.

Example 12

Pulmonary vasoconstriction. The capacity of F1Cs to limit hypoxia induced pulmonary vasoconstriction is demonstrated using an animal model essentially as follows. Isolated perfused ferret lungs are an established animal model to study secondary pulmonary hypertension. In brief, male ferrets are anesthetized with intraperitoneal pentobarbital sodium and the chest is opened. Stainless steel cannulae are secured in the left atrium and pulmonary artery, and the pulmonary artery and the aorta are ligated. The lungs are perfused with a mixture of autologous blood and Krebs-Henseleit buffer in a circulating manner at a constant rate of about 85 mL/min. The perfusion circuit includes a perfusate reservoir, a roller perfusion pump, filter, and a heat exchanger. The perfusion system is made of, e.g., tygon tubing, which is used for connections and for passage through the perfusion pump. The temperature of the perfusate is kept about 37-38° C. and the pH is maintained at 7.35 to 7.40 by adding sodium bicarbonate to the reservoir as needed. The venous reservoir is placed below the lowermost portion of the lung.

The lungs are ventilated with a hypoxic gas mixture of 5% $CO_2$, 4% $O_2$, and 91% $N_2$ by a tracheotomy with a Harvard animal respirator for 30 minutes. The animals are ventilated with a tidal volume of 30 mL, at a rate of 18 breaths/min. and with 2 cm of $H_2O$ positive end-expiatory pressure. For measurements, pulmonary arterial, left atrial and tracheal pressures are monitored using Gould Statha P231D pressure transducers or an equivalent connected to the inflow circulation and recorded on, e.g., a Grass polygraph. After 30 minutes of ventilation with hypoxic gas mixture, a formula 1 compound in a dose between about 5-25 mg/kg body weight is added to the reservoir, and perfusate is allowed to perfuse the ferret lungs for 1.5 hours. Pulmonary artery pressure is measured until the end of the experiment, i.e., a total of two hours. Pressure that remains at or near basal level indicates the vasodilatory effect of the F1C in pulmonary circulation that is otherwise constricted in response to hypoxia. The effects of the F1Cs can be compared to the effects and duration of nitric oxide, a therapeutic agent that is optionally used in this model as a control.

Example 13

Hematopoiesis modulation. Modulation of hematopoiesis is observed in mammals with injury from, e.g., radiation exposure or from an immunosuppressive chemotherapy to characterize the biological activity of the F1Cs. In an example, animals are used to demonstrate the effect of F1Cs on hematopoiesis after immune system injury due to radiation. Hematopoiesis in the murine or non-human primate immune system after radiation is optionally used because of the similar responses of murine and human hematopoiesis to drugs and toxic insults (see, e.g., J. H. Hendry and B. I. Lord, editors, *Radiation toxicology: Bone marrow and leukaemia* 1995 Taylor & Francis Inc., London).

In an exemplary protocol, B6D2F1/J female mice (Jackson Laboratory, Bar Harbor, Me.), 18-24 weeks of age, 22-30 g body weight, are obtained and held in quarantine for two weeks. Up to 10 mice are housed in sanitized 46×24×15 cm polycarbonate boxes with filter covers (MicroIsolator; Lab Products, Inc, Maywood, N.J.) on autoclaved hardwood chip bedding. Mice are given feed and acidified (pH 2.5) water freely. The animal holding room is maintained with conditioned fresh air at approximately 21° C. and 50° (±10%) relative humidity and with a 12-h light/dark full spectrum lighting cycle.

Mice are placed in ventilated Plexiglas containers and exposed bilaterally to gamma-radiation from a $^{60}Co$ source. Exposure time is adjusted so that each animal received a midline tissue-absorbed dose of 1-12 Gy at a nominal dose rate of 0.4 Gy/min at ambient temperature. Using a standardized technique, the midline dose rate is measured by placing a 0.5 cc tissue-equivalent ionization chamber at the center of a 2.5-cm diameter cylindrical acrylic mouse phantom. The tissue-air ratio, defined as the ratio of the dose rate measured in the phantom to the dose rate in free air, for this array is about 0.96. Variation within the exposure field is less than about 4%. Dosimetric measurements are made in accordance with the American Association of Physicists in Medicine protocol for the determination of absorbed dose from high-energy photon and electron beams (*Med. Phys.* 1983 10:741-771). Sham-irradiated mice are treated in the same way as the irradiated animals, except that the animals are not irradiated.

Various formula 1 compounds are formulated with a suitable vehicle (e.g., PEG-400) or sterile 0.9% NaCl (saline) optionally containing other excipients such as a cyclodextrin. The compounds are injected subcutaneously in a volume of about 0.1 mL or they are delivered orally or they are administered by another route. Doses typically range from about 1 mg/kg to about 350 mg/kg, e.g., about 1, 10, 20, 40, 80, 160 or 320 mg/kg.

Blood (0.6-1.0 mL) is obtained from halothane-anesthetized mice by cardiac puncture using a heparinized syringe attached to a 21-gauge needle. Blood is collected in EDTA-containing sample tubes. Mice are euthanized by cervical dislocation after blood collection. White blood cell (WBC), red blood cell (RBC) and platelet (PLT) counts are performed using, e.g., a Hematology System 9000 (Biochem Immunosystems). Wright-stained blood smears from the same samples are made for differential counts of neutrophils and lymphocytes by light microscopy.

Hemopoietic progenitor cells committed to granulocyte-macrophage differentiation (GM-CFC) are assayed by a single-layer modification of a double-layer semisolid agar technique essentially as described (Patchen et al. *Adv. Space Res.* 1992 12:223-248). For example, femoral marrow is extracted and cell suspensions are prepared by flushing with 3 mL of McCoy's 5A medium containing 10% heat-inactivated fetal bovine serum (HIFBS; Hyclone, Logan, Utah). Each cell suspension represented a pool of marrow from four femurs, i.e., both femurs from each of two mice. The total number of nucleated cells in each suspension is determined with, e.g., a Coulter counter. The agar-medium mixture consisted of equal volumes of 0.66% agar and double-strength supplemented CMRL 1066 medium (Gibco, Grand Island, N.Y.). The medium is supplemented with final concentrations of 10% HIFBS, 5% tryptic soy broth, 5% heat-inactivated horse serum, antibiotics, and L-serine. One milliliter of the agar-medium mixture is added to each 35-mm plastic Petri dish (two dishes per suspension) and mixed with 50 µL of 0.1 ng/µl recombinant mouse GM-CSF (Genzyme, Cambridge, Mass.). Cell suspensions are then mixed into the agar-medium mixture to a final concentration of $0.5 \times 10^5$ cells/mL for unirradiated animals, and $1.0 \times 10^5$ or $1.5 \times 10^5$ cells/mL for irradiated animals to ensure sufficient colonies per plate for quantitation. Control experiments are done to confirm linearity of colonies at cell concentrations of 0.5-1.5×10$^5$ cells/mL. Colonies (>50 cells) are counted after seven days incubation in a 37° C. humidified environment containing 5% $CO_2$. The average of the counts for the two dishes is taken as the value for each pool. About six animals are used per group in each of two experiments.

For histological examination of myeloid hyperplasia in bone marrow after administration of the formula 1 compound, mice are euthanized with halothane, tissues are immersed in formalin, bones are decalcified and routine H&E-stained 6-μm paraffin sections are prepared.

For induced-infection studies, a clinical isolate of *K. pneumoniae*, capsule type 5 (strain AFRRI 7), that is kept frozen at 70° C. in skim milk, is grown overnight at 35° C. on Trypticase Soy Agar (Becton-Dickinson, Sparks, Md.). Five typical colonies are inoculated into 8 mL of brain heart infusion broth (Becton-Dickinson) and incubated overnight at 35° C. Two milliliters of this overnight suspension is inoculated into 95 mL of prewarmed brain heart infusion broth. The culture is incubated at 35° C. with shaking for approximately 2.5 h. The optical density of bacterial growth is monitored with a spectrophotometer at a wavelength of 550 nm. Late log-phase cells are ished and suspended in cold saline to yield 10$^9$ viable bacteria per mL. Appropriate dilutions for inoculations are made in cold saline.

To induce a bacterial infection, all mice are injected sc with *K. pneumoniae* four days after sham-irradiation or irradiation when circulating leukocytes are depressed. Mice are inoculated sc rather than iv or ip, to establish infection leading to sepsis, but not rapid septic shock. After sc inoculations of *K. pneumoniae* in the mice, the infection remains largely localized to the injection site. *K. pneumoniae* are not detectable in blood of inoculated mice until a few hours before death.

Different doses of the bacteria are inoculated for each of three radiation dose levels (0, 1 or 3 Gy) to approximate the $LD_{95/30}$ (radiation dose that is lethal for 30-95% of animals), because the effects of radiation on hematopoiesis and susceptibility to infection are dependent on the dose of radiation. The $LD_{95/30}$ for bacteria at each radiation dose is calculated from probit analysis. The actual doses are estimated by dilution plating of inocula onto Trypticase Soy Agar and incubating overnight at 35° C. Since different bacterial doses are expected to be needed for different radiation doses, the $LD_{95/30}$ is estimated for each group and different mortality rates are observed in the vehicle-injected control groups. Bacterial doses for induced-infection experiments are prepared and calculated in the same manner.

Animals are checked frequently, e.g., once or twice daily, six or seven days per week, to monitor survival and to euthanize mice that are in a moribund state. To verify that mortality in the induced-infection experiments is associated with *K. pneumoniae* injection, heart blood from recently deceased animals (or moribund animals euthanized by cervical dislocation) is cultured overnight at 35° C. on Columbia sheep blood agar plates (Becton-Dickinson, Sparks, Md.). Colonies are identified as *K. pneumoniae* by a suitable means, e.g., Biolog analysis.

For histological analysis of bone marrow, coded slides are scored blind using a five-level semiquantitative scale and the results analyzed with a randomization t-test to obtain exact P-values. Thirty-day survival values are compared using the generalized Savage (Mantel-Cox) procedure (BMDP Statistical Software, Inc, Los Angeles, Calif.). To calculate dose reduction factors (DRFs), probit analysis is performed on mortality data.

To characterize the potency of formula 1 compounds to ameliorate radiation-induced defects in hematopoiesis, mice are exposed to bilateral whole-body gamma-radiation and receive a dose of 3 Gy (or are sham-irradiated). One hour after irradiation or sham-irradiation, mice are injected with 320 mg/kg 3β,17β-dihydroxyandrost-5-ene ("AED") or PEG-400 vehicle. Between-group differences in blood cell elements, e.g., neutrophils, GM-CFC and platelets are generally determined. Irradiation results in a decrease in neutrophils at about four days after radiation compared to sham-irradiated animals.

Example 14

Antiglucocorticoid effects of formula 1 compounds. A series of tests is run in triplicate using BALB/c mouse spleen cells to demonstrate the effect of the F1Cs and hydrocortisone ("Hycort") on cellular proliferation in the absence of a mitogen. Cultures of spleen cells are prepared and F1Cs are added at, e.g., 0.1, 0.5, 1 and 5 μM. Suitable controls are used. Twenty four hours after setup, about 50 μCi [$^3$H]-thymidine is added to each cell. Four to six hours later, the cells are harvested and counted on a scintillation counter.

Spleen cells are obtained from normal BALB/c mice and prepared as a single cell suspension at a concentration of about 1×10$^7$ cells/ml in RPMI 1640 supplemented with 2 mM L-glutamine, 5×10$^{-5}$ M 2-mercaptoethanol, 20 μg/ml gentamycin-sulfate, and 1% Nutridona-NS (Boehringer-Mannheim). Individual aliquots of cells are then pulsed for 30 minutes at 37° C. with selected concentrations of formula 1 compounds. After pulsing, the cells are washed several times in balanced salt solution, resuspended in fresh medium, and then dispensed into 24-well culture plates with a stimulatory concentration of anti-CD3 (e.g., Leo et al. Proc. Natl. Acad. Sci. U.S.A., 84:1374 (1987)). After a 24-hour incubation period, culture supernatants are harvested for assessment of proliferation or cytokine production, e.g., IL-2, IL-3 or IL-4 using, e.g., the method of Mossman (J. Immunol. Meth. 65:55 (1983)). 100% control titers of IL-3, IL-2 or IL-4 from normal stimulated splenocytes are obtained, exemplary values may be about 640 units/mL or IL-2 and 160 units/mL for IL-4.

Effects of formula 1 compounds and Hydrocortisone on Proliferation in the Presence of a Mitogen. A series of spleen cell cultures is run using a formula 1 compound and/or hydrocortisone with cell cultures to which concanavalin A is added. Preliminary tests on cultures to which concanavalin A is added at concentrations of 10.0, 5.0, 2.5 and 1.0 ng/mL. All tests on the effects of invention compounds on cultures stimulated with concanavalin A are performed with concanavalin A at, e.g., about 2.5 ng/mL. A mitogen such as ConA generally increases cell proliferation and the glucocorticoid steroid ("GCS") can decrease proliferation. Detectable partial or complete reversal of the inhibitor effects of hydrocortisone indicate an anti-glucorticoid effect by the formula 1 compounds.

Effect of formula 1 compounds on IL-3 production. Exemplary formula 1 compounds are characterized for their effect on the level of the cytokine IL-3 expression by spleen cells in tissue culture and for their capacity to reverse the effects of a GCS in IL-3 expression. The spleen cell cultures are prepared in accordance with the general method above. After 30 hours the level of IL-3 in the supernatants of the cultures was measured using the IL-3 ELISA kit manufactured by EndoGen Inc., Boston, Mass. A GCS such as hydrocortisone will generally suppress the production of IL-3 and the invention compounds are examined for their capacity to modify this effect. The IL-3 expressed by cells in culture may be recovered from the media containing IL-3 by known methods such as single or sequential reverse-phase HPLC steps on a preparative HPLC column. (See Urdal, et al., J. Chromatog. 296:171 (1984) and U.S. Pat. No. 5,128,450).

Example 15

Treatment of neurodegenerative conditions. Experimental allergic encephalomyelitis (EAE), is demyelinating disease of the central nervous system with many pathological and clinical similarities with multiple sclerosis (MS). EAE is thus a recognized animal model for human autoimmune conditions such as MS. F1Cs are tested for their capacity to delay the onset of EAE or to reduce its symptoms. Female SJL mice (5 animals per group) are immunized with 150 to 200 µg of PLP-139-151 peptide/CFA to induce EAE. Starting 7 days before injection of the peptide, the animals are given daily injections (s.c.) of the compounds (3.0 mg) in 0.1 mL vehicle, or vehicle alone for 33 days. The vehicle consisted of a suspension of the formula 1 compound in saline and carboxymethylcellulose. Delayed onset, reduced peak clinical score (from 5.2±0.6 to 2.8±1.8) and cumulative disease index (>60%) of EAE, and prevention of or significant attenuation of relapses are measured. Reduced numbers of PLP-139-151 specific T cell responses and reduced numbers of TNF-α producing cells in the CNS indicate reduced disease progression or severity. Reduced production of autoimmune Th-1 associated cytokines, is consistent with restoration of a more normal Th-1/Th-2 immune balance and/or with reduction of inflammation in this model.

The efficacy of the formula 1 compounds to treat other autoimmune conditions can be determined by incorporating their use with suitable animal models or assay methods, e.g., collagen-induced arthritis as a model for human autoimmune polyarthritis (e.g., L. K. Myers et al., *Clin. Immunol.* 2002, 102:185-191, A. Matejuk et al., *Endocrinology* 2002, 143: 313-319, S. Thornton et al., *J. Immunol.* 165:1557-1563). The effect of the compounds on markers of inflammation such as TNFα, MIP-1β, IL-13, IL-15, IL-17 or IL-18, e.g., reduced expression or activity, is optionally observed in any autoimmune or inflammatory condition.

Example 16

Modulation of transcription. The effect of a F1C on transcript levels in cells in vitro is studied using a microarray to allow simultaneous monitoring of the expression of many genes to allow detailed analysis of the molecular pathways involved in biological responses to the compound.

In general, microarray technology works by covalently linking short DNA sequences that are complementary to the transcripts of many different genes on a single slide or array chip. mRNAs from test and control samples are generated and labeled with one or more colored fluorescent dyes or probes. The probes are hybridized with the array, which is then scanned by laser. The color and intensity of the fluorescent signal at each spot denotes relative expression level of each gene. The capacity of F1Cs to modulate gene expression is characterized in a similar manner.

An array is used in the protocol as described below. The array contains about 12,000 known genes. The experiment can use U937 human promonocytic leukemia cells that differentiate to monocyte/macrophage cells in the presence of phorbol-12-myristate-β-acetate ("PMA"). The U937 cells are PMA treated and then exposed to a F1C for 1 hr, 2 hrs, or 4 hrs, followed by bacterial lipopolysaccharide ("LPS") stimulation for 1 hr, 2 hrs or 4 hrs. The level of transcripts of the genes on the array is measured at selected time points using RNA prepared from F1C-treated and control (no F1C) cells. U937 cells are plated at $1 \times 10^5$ cells/mL in the presence of 3 ng/mL PMA (Sigma, Catalog #P-8139) for 48 hrs. Cells are then treated with either 10 µM F1C or a vehicle such as DMSO for 1 hr, 2 hr, and 4 hrs. At each time point, cells are harvested and total RNA is extracted using Qiagen Rneasy kit according to manufacturer's specification. Total RNA samples are analyzed by Mergen Ltd. (San Leandro, Calif. www.mergen.com) to perform microarray assay.

For the microarray assay, Dnase-treated total RNA (20 micrograms) is reverse-transcribed using an oligo[(dT)$_{24}$ T7 promoter]$_{65}$ primer (consisting of the nucleotide binding sequence for the T7 RNA polymerase followed by 24 thymidine nucleotides). This is followed by second strand synthesis. The reaction mixture is then treated with Rnase I to digest the remaining RNA. The double-stranded cDNA is phenol-chloroform extracted and used as template for in vitro transcription (T7 MEGAscript, Ambion, Inc.) to generate biotin-labeled cRNA probes. These probes are hybridized overnight at 30° C. with continuous agitation to Mergen's ExpressChip HO5 DNA Microarray System (catalog number HO5-001) containing 12,000 genes. The arrays are then washed, and hybridized probes are detected using Mergen's cyanine-3 fluorescent dye-conjugated protein. Chips are imaged using an Affymetrix 417-418 form Affymetrix/Genetic MicroSystems (www.affymetrix.com) and spot intensity is quantitated using ImaGene from BioDiscovery Inc. (www.biodiscovery.com).

Exemplary genes shown below are optionally analyzed.

| UniGene ID | UniGene symbol | HO5 gene description |
|---|---|---|
| Hs.460 | ATF3 | Activating transcription factor 3 |
| Hs.78546 | ATP2B1 | ATPase, Ca++ transporting, plasma membrane 1 |
| Hs.2128 | DUSP5 | Dual specificity phosphatase 5 |
| Hs.155119 | EHD1 | EH-domain containing 1 |
| Hs.75765 | GRO2 | GRO2 oncogene |
| Hs.89690 | GRO3 | GRO3 oncogene |
| Hs.274402 | HSPA1B | Heat shock 70 kD protein 1B |
| Hs.177781 | MGC5618 | Hypothetical protein MGC5618 |
| Hs.75063 | HIVEP2 | immunodeficiency virus type I enhancer-binding protein 2 |
| Hs.727 | INHBA | Inhibin, beta A (activin A, activin AB alpha polypeptide) |
| Hs.81134 | IL1RN | Interleukin 1 receptor antagonist |
| Hs.126256 | IL1B | Interleukin 1, beta |
| Hs.12503 | IL15RA | Interleukin 15 receptor, alpha |
| Hs.98309 | IL23A | Interleukin 23, alpha subunit p19 |
| Hs.50640 | SSI-1 | JAK binding protein |
| Hs.24684 | KIAA1376 | KIAA1376 protein |

-continued

| UniGene ID | UniGene symbol | HO5 gene description |
|---|---|---|
| Hs.164719 | KIAA1726 | KIAA1726 protein |
| Hs.151988 | MAP3K5 | Mitogen-activated protein kinase kinase kinase 5 |
| Hs.301183 | MAIL | Molecule possessing ankyrin repeats induced by lipopolysaccharide (MAIL), homolog of mouse |
| Hs.75607 | MACS | Myristoylated alanine-rich protein kinase C substrate (MARCKS, 80K-L) |
| Hs.109281 | NAF1 | Nef-associated factor 1 |
| Hs.81328 | NFKBIA | Nuclear factor of kappa light polypeptide gene enhancer in B-cells inhibitor, alpha |
| Hs.77729 | OLR1 | Oxidised low density lipoprotein receptor 1 |
| Hs.2050 | PTX3 | Pentaxin-related gene, rapidly induced by IL-1 beta |
| Hs.80205 | PIM2 | Pim-2 oncogene |
| Hs.239138 | PBEF | Pre-B-cell colony-enhancing factor |
| Hs.3407 | PKIG | Protein kinase (cAMP-dependent, catalytic) inhibitor gamma |
| Hs.103755 | RIPK2 | Receptor-interacting serine-threonine kinase 2 |
| Hs.183601 | RGS16 | Regulator of G-protein signalling 16 |
| Hs.115521 | REV3L | REV3 (yeast homolog)-like, catalytic subunit of DNA polymerase zeta |
| Hs.27018 | LOC51285 | Ris |
| Hs.82085 | SERPINE1 | Serine (or cysteine) proteinase inhibitor, clade E (nexin, plasminogen activator inhibitor type 1), member 1 |
| Hs.1087 | STK2 | Serine/threonine kinase 2 |
| s.167503 | STAT5A | Signal transducer and activator of transcription 5A |
| Hs.72918 | SCYA1 | Small inducible cytokine A1 (I-309, homologous to mouse Tca-3) |
| Hs.75703 | SCYA4 | Small inducible cytokine A4 (homologous to mouse Mip-1b) |
| Hs.75498 | SCYA20 | Small inducible cytokine subfamily A (Cys-Cys), member 20 |
| Hs.271387 | SCYA8 | Small inducible cytokine subfamily A (Cys- Cys), member 8 (monocyte chemotactic protein 2) |
| Hs.318885 | SOD2 | Superoxide dismutase 2, mitochondrial |
| Hs.112259 | TRG@ | T cell receptor gamma locus |
| Hs.2134 | TRAF1 | TNF receptor-associated factor 1 |
| Hs.17839 | GG2-1 | TNF-induced protein |
| Hs.101382 | TNFAIP2 | Tumor necrosis factor, alpha-induced protein 2 |
| Hs.211600 | TNFAIP3 | Tumor necrosis factor, alpha-induced protein 3 |
| Hs.29352 | TNFAIP6 | Tumor necrosis factor, alpha-induced protein 6 |

For any of the uses for F1Cs described herein, the results or biological effects that are obtained using individual F1Cs are optionally compared to the results or biological effects that are obtained using a reference compound such as 3β,17β-dihydroxyandrost-5-ene, 3β,17β-dihydroxyandrost-1,5-diene, 3β,7β,17β-trihydroxyandrost-5-ene, 16α-bromoepiandrosterone, 16α-hydroxyepiandrosterone, 16β-hydroxyepiandrosterone, dehydroepiandrosterone, 3β-amino-17β-hydroxyandrost-5-ene, 3β-amino-1 7β-hydroxy-17α-methylandrost-5-ene or 3β-hydroxy-17β-aminoandrost-5-ene. A reference F1C can serve as a positive control or negative control for modulation of gene transcription or activity. Other known modulators of a gene whose biological activity is associated with a symptom or clinical condition of interest can also be used as a reference control with or without a reference F1C control. Such comparisons provide guidance for using the formula 1 compounds in the different methods or clinical conditions. Such comparison information allows, e.g., tailoring of dosages, dosing schedules, routes of administration or drug interactions with other therapeutic treatments in any selected application for the F1Cs.

Example 17

The effect of F1Cs on transcript or gene product levels in cells in vitro is studied in vitro using a cell type of interest, e.g., the murine macrophage cell line designated RAW264.7 ("RAW" cells). For the RAW cells, the cells are maintained in a suitable medium, e.g., RPMI 1640 supplemented with 10% FBS, standard Penn/Strep antibiotic solution and 2 mM glutamine. The F1C is dissolved in a suitable solvent, e.g., DMSO or pyrrolidone, to generate a 10 mM stock solution. For DMSO solutions, appropriate dilutions are made to give a F1C final concentration in culture media of about 1 nM to about 10 μM, with a final DMSO content of no more than 0.1% v/v. The cells are induced with LPS at 100 ng/ml (stock solution in water, diluted in serum-free culture media).

In a typical protocol, on day 0 the cells are plated at a density to reach a sub-confluent state of greater than about 75% confluency on the following day. For 6-well plates, about 500,000 to 700,000 cells/well are plated. On the following day, day 1, the cells are treated with the F1C or vehicle, e.g., DMSO, with or without LPS, for selected times, e.g., 0.5, 1, 2, 4, 6, 8, 10, 12, 16, 24, 36, 48 hours. After incubation, cells are harvested with a cell scraper and total RNA is extracted to generate samples for PCR analysis. 1 mL of culture media is optionally saved at −20° C. for future ELISA analysis to determine gene transcript levels. On day 2, cells are harvested after, e.g., 24 hr of F1C in DMSO treatment. LPS induction is started in cells pre-treated with F1C in, e.g., DMSO. Exemplary treatment conditions and time points for cell harvesting are as follows:

| No treatment | 0 hr | | | | 24 hr |
|---|---|---|---|---|---|
| DMSO + LPS | | 1 hr | 4 hr | 8 hr | 24 hr |
| F1C 10 µM + LPS | | 1 hr | 4 hr | 8 hr | 24 hr |
| F1C 1 µM + LPS | | 1 hr | 4 hr | 8 hr | 24 hr |
| F1C 10 nM + LPS | | 1 hr | 4 hr | 8 hr | 24 hr |
| DMSO | 24 hr + LPS | 1 hr | 4 hr | 8 hr | 24 hr |
| F1C 10 µM | 24 hr + LPS | 1 hr | 4 hr | 8 hr | 24 hr |
| F1C 1 µM | 24 hr + LPS | 1 hr | 4 hr | 8 hr | 24 hr |
| F1C 10 nM | 24 hr + LPS | 1 hr | 4 hr | 8 hr | 24 hr |

Exemplary genes of interest that can be analyzed by this or a similar protocol include 1, 2, 3, 4, 5, 6 or more of iNOS (inducible nitric oxide synthase), eNOS (constitutive nitric oxide synthase), COX-2 (cycloxygenase-2, PGE2 synthase), IκBβ, TNFα, IL-1β, IL-1Ra (interleukin 1 receptor antagonist), NFκB1 (p105), NFκB2 (p49/p100), IL-6, MCP-1 (monocyte chemoattractant protein-1 or CCL2), MIP-2 (macrophage inflammatory protein-2), MMP9 (matrix metalloproteinase 9), gelatinase B, HO-1 (heme oxygenase 1), HIF1α (hypoxia inducible factor 1, alpha subunit), GCLC (gamma glutamylcycleine synthetase catalytic (heavy) subunit or γGCS-hs), GCLM (gamma glutamylcycleine synthetase modifier (light) subunit or γGCS-ls), xCT (cystine/glutamate exchange transporter), NQO1 (NAD(P)H: quinone oxidoreductase 1), TXNRD1 (thioredoxin reduatase 1), EBBP (estrogen responsive B-box protein), CYP1A1 (cytochrome P450), CD36 (SR-B), SR-A (scavenger receptor A or Msr1), ABCA1 (ATP-binding cassette transporter A1), ABCG1 (ATP-binding cassette transporter G1), LDLR (low-density lipoprotein receptor), NR1H3 (nuclear receptor 1H3 or LXRα), NR1C3 (nuclear receptor 1C3 or PPARγ), SCD-1 (stearoyl-CoA desaturase 1) and NR4A1 (nuclear receptor 4A1 or Nur77).

Example 18

Treatment of allograft rejection. The F1Cs are used as described herein to treat, prevent or ameliorate unwanted immune responses in allograft transplantation. F1Cs in any of groups 1 through 57 can be used in continuous or intermittent dosing protocols to ameliorate or to slow the progression of rejection reactions in the host, such as hyperacute rejection, acute rejection or chronic rejection in allograft recipients in e.g., lung, heart, liver, kidney or bone marrow transplant recipients. Reduction of symptoms in kidney transplant recipients such as kidney enlargement or tenderness or increased serum creatinine levels, or decreased urine output are optionally monitored, e.g., for improvement or stabilization of the symptom. The compounds are also used to reduce graft versus host disease in a similar manner.

Example 19

Exposure of rodents to ionizing radiation exposure. The effect of selected F1Cs on survival of lethally-irradiated female B6D2F1 mice were compared to control animals treated with vehicle alone. The animals were exposed to 10 Gy of total body irradiation at 2.5 Gy/min using a $^{137}$Cs source. Groups of 12 animals were used in a total of 5 groups. For Groups 1, 2, 3, and 5, test article was administered as a 100 µL volume, by subcutaneous injection, for three consecutive days, with the first dose administered 2 to 4 hours following exposure to radiation. For Group 4, test article was administered as a 50 µL volume, by intramuscular injection for three consecutive days. The formulation was a suspension containing 0.1% w/v carboxymethyl-cellulose, 0.9% w/v sodium chloride and 0.05% v/v phenol. The formulations were agitated to uniformly resuspend the F1C before syringing, and injected into animals within a few minutes of drawing into the syringe to prevent settling in the syringe.

The groups of animals were treated as follows. Group 1 received vehicle only by daily subcutaneous injection for 3 consecutive days. Group 2 received 0.6 mg in 100 µL of a suspension of 3β,17β-dihydroxyandrost-5-ene by daily subcutaneous injection for 3 consecutive days. Group 3 received 3.0 mg in 100 µL of a suspension of 3β,17β-dihydroxyandrost-5-ene by daily subcutaneous injection for 3 consecutive days. Group 4 received 0.6 mg in 50 µL of a suspension of 3β,17β-dihydroxyandrost-5-ene by daily intramuscular injection for 3 consecutive days. Group 5 received 0.6 mg in 100 µL of a suspension of 3β-hydroxy-17β-aminoandrost-5-ene by daily subcutaneous injection for 3 consecutive days.

Survival of the animals was monitored for 21 days after irradiation and the following results were obtained. The number of surviving animals is shown for day 6, 7, 12 and 21. The results show that the F1Cs increased the rate of survival of subjects that were exposed to an otherwise lethal dose of ionizing radiation.

| | Day | | | |
|---|---|---|---|---|
| Group | 6 | 7 | 12 | 21 |
| 1 vehicle control | 12 | 11 | 4 | 1 |
| 2 0.6 mg s.c. | 12 | 11 | 10 | 7 |
| 3 3.0 mg s.c. | 12 | 12 | 9 | 7 |
| 4 0.6 mg i.m. | 12 | 12 | 11 | 9 |
| 5 0.6 mg s.c. | 12 | 12 | 12 | 11 |

Example 20

Characterization of F1C biological activity. A F1C is selected and used in a protocol described herein, e.g., as described in example 1 or example 19, to characterize its biological activity. In an exemplary protocol, doses of 0.1 mg, 0.3 mg, 0.6 mg, 1 mg, 2 mg, 3 mg, 4 mg or 5 mg are used on, e.g., one, two, three or four consecutive days, essentially as described in example 19 to characterize the effect of the F1C on survival of animals after lethal radiation. One or more controls, e.g., vehicle control animals and one, two or more reference compounds such as filgrastim, pegfilgrastim, or characterized F1Cs such as 3β,17β-dihydroxyandrost-5-ene, 3β,7β,17β-trihydroxyandrost-5-ene or 3β-hydroxy-17β-aminoandrost-5-ene are optionally used in separate groups of animals to allow evaluation of the relative potency of the F1C. Exemplary F1Cs that can be characterized in this manner are as described herein, e.g., any compound in a compound group, numbered embodiment or claim. Exemplary test protocols include any of the examples described herein. Thus, to characterize effect of F1Cs on transcript or gene product levels in cells in vitro a protocol essentially as described in examples 16 or 17 is performed and the results are optionally compared to a reference compound such as a known modulator of transcription, e.g., a non-steroidal antiinflammatory drug such as aspirin, or to another reference compound such as 3β,17β-dihydroxyandrost-5-ene, 16α-bromoepiandrosterone or 16α-hydroxyepiandrosterone.

Example 21

Measurement of biological parameters in non-human primates after biological insult. A study was conducted to characterize a biological insult of 600cGy of whole body irradiation to male Rhesus (*Macaca mulatta*) primates weighing 2.5 to 4.5 kg at an age range of about 1.75 to 3.5 years. Core body temperature was monitored by telemetry in the monkeys for a period of 40 consecutive days. Two groups of 10 animals each were used in the study. Core body temperature transmitters were surgically implanted in the abdomen prior to initiation of the radiation protocol. Core body temperature was continuously recorded from day −7 to day 41 for correlation with survival, hematology results, and other clinical parameters.

Temperature Transmitters.

Before initiation of the temperature transmitter implantation protocol, all animals were subject to a detailed physical examination and body weight measurement under the direction of a clinical veterinarian. Blood was collected from all animals, which were not food and water deprived, and assessed for basic blood chemistry and hematology. The results of the evaluation was reviewed by the clinical veterinarian to ensure satisfactory health status.

Implantation of the temperature transmitters was accomplished using animals that were fasted overnight prior to surgery and then anesthetized by an intra-muscular (IM) injection of acepromazine (10 mg/mL, 0.14 mg/kg) and ketamine (100 mg/mL, 13.6 mg/kg) and intubated. Where needed, lidocain spray (10% w/w) was administered onto the glottis prior to intubation. An ophthalmic ointment was applied to both eyes to prevent drying of the cornea. Animals were placed on a heating pad and administered isoflurane by inhalation, with an oxygen flow of approximately 200 mg/kg/min. A ventilator was used to maintain the respiratory rate between 8 and 20 breaths/min with a ventilation pressure of 18-25 cm $H_2O$. Monitoring during anesthesia included heart rate and oxygen saturation of the blood using a pulse oximeter. Prophylactic antibiotics (cefazolin 25 mg/kg) were administered by intramuscular injection at least 1-hour prior to surgery, and every 6 to 8 hours post injection for at least 24-hours post surgery. Analgesia (buprenorphine 0.05 mg/kg) was administered by intramuscular injection every 6 to 12 hours for at least 24-hours post surgery. Intravenous fluid therapy were given throughout the anesthesia using sterile Lactate Ringer's solution at a rate of 10 mL/kg/hr.

The surgical site was shaved and aseptically prepared using chlorhexidine gluconate 4% and isopropyl alcohol 70%. A longitudinal incision was performed lateral but close to the linea alba. The internal abdominal oblique muscle was separated from the aponeurosis of the transversus abdominis by blunt dissection. A sterile core body temperature transmitter (Data Science International, TA10TAD70) was inserted between the internal abdominal oblique muscle and the aponeurosis of the transversus abdominis. Hemostasis was maintained using appropriate suture material. Sterile saline was used to allow ease of placement of the transmitters. The incision was closed with absorbable suture material using simple continuous sutures. The skin was closed with discontinuous buried sutures using absorbable suture material. Additional post-operative cares (analgesia and antibiotics) was provided to the animals when needed. Rectal body temperature was monitored in the post-operative period. Once the body temperature was within an acceptable range and the animal was alert, each animal was returned to their cages. A postoperative period of at least 2 weeks was allowed prior to initiation of radiation.

Acclimation and Whole-Body Irradiation.

Before transportation to the radiation facility, the animals were acclimated to the radiotherapy chair and to transportation. During the acclimation period, animals were assigned to their respective dose groups by block randomization based on the absolute neutrophil count. Any animal with unacceptable pretreatment data was replaced by an animal kept under identical environmental conditions. Animals with pretreatment data considered acceptable but marginally different from normal values were assigned to the sham group to allow longer post-operative recovery.

Animals were fasted overnight prior to whole-body irradiation and fed upon return to the holding facility. Animals were transferred to the irradiation facility in a transport vehicle with controlled environment. During transportation, each animal was individually housed in a stainless steel squeeze back cage. The animal's clinical signs were monitored immediately before and after transportation. Group 1 animals, sham irradiated, were subject to the same irradiation procedure as Group 2 animals, however, these animals did receive radiation. The 10 control animals, Group 1, were sham irradiated by placing each animal in the restraint for 10 minutes. The 10 treated animals, Group 2, received a midline $^{60}$Co γ-radiation dose of 6 Gy at a dose rate of about 60 cGy/minute (day 1). The animals receiving this 6 Gy radiation insult were restrained during the radiation exposure by placing each animal in a chair allowing appropriate restraining in a symmetric position. An insulated cover was placed on the radiotherapy chair during transportation between the transport vehicle and the treatment site. Music was provided inside the treatment room to reduce stress to the animals. Animal positioning was confirmed with linear markers installed in the treatment room. To produce a homogenous dose distribution, treatment was divided in two parts. First, the animal received half of the dose by anteroposterior (AP) irradiation. The second half of the dose was delivered by posteroanterior (PA) irradiation. Group 1 animals were placed in an identical restraining chair in the sham treatment site for approximately the same period of time without exposure to radiation. Once the treatment was completed, animals were returned to the transport vehicle and were transported to their housing facility. The radiation dose was calibrated using an acrylic phantom placed in the same experimental set up that was used for animal irradiation.

Animal Maintenance.

Animals were housed individually in stainless steel squeeze back cages equipped with an automatic watering system except during transportation where water bottles were provided. The cages were labeled with a color-coded cage card indicating study number, group, animal number, species, sex and dose level. The animal room environment was controlled (temperature 21±3° C., humidity 30-70%, 10-15 air changes per hour, 12 hours light, 12 hours dark). Temperature and humidity were monitored continuously except during animal transportation and inside the radiation facility where only temperature was recorded. A standard certified commercial primate chow (Teklad Certified Global 25% Primate Diet #2055C) was made available to each monkey daily. Food was withdrawn overnight prior to radiation and necropsy. Maximum allowable concentrations of contaminants in the diet (e.g., heavy metals, aflatoxin, organophosphates, chlorinated hydrocarbons and PCBs) were controlled and routinely analyzed by the manufacturers. If an animal stopped eating during the study, the diet was supplemented at the discretion of the study director. Tap water was purified by reverse osmosis and provided to the animals ad libitum throughout the study. Periodic analyses of the tap water and reverse osmosis water were performed. It was considered that there were no known contaminants in the diet or water. During the pre-treatment period cage side observations of clinical signs were generally performed once daily.

Observations.

Mortality checks were performed twice a day during all phases of the study. Moribund animals were euthanized for humane reasons based on the clinical judgments. Sacrificed animals were subject to a clinical examination. When the core body temperature was 33° C. (91.4° F.) or lower or when an animal experienced a weight loss of more than 20% over a 4 day period, the animal was euthanized. Animals were also euthanized when they displayed complete anorexia for 3 days with deteriorating conditions based on the clinical examination or when they displayed an absence of response to stimuli.

Results obtained from the study were used to correlate the changes in biological parameters such as core body temperature and hematology with clinical signs following whole body irradiation. These results were used to obtain a status profile or surrogate endpoint such as incidence or duration of fever. During the pre-treatment period cage side observations of clinical signs were performed once daily. During the treatment period, clinical signs were recorded at cage-side twice daily for all animals or as often as deemed necessary. A detailed clinical examination was performed on all animals, once prior to irradiation on day 1, weekly thereafter, including on day 41 prior to necropsy.

The core body temperature and activity was recorded at 1 minute intervals for all animals from day −7 to day 41 using the implanted transmitter. Each animal cage was equipped with a telemetry receiver. The values of calibration of the transmitter implanted in each animal were entered in a telemetry computer system to ensure accurate temperature monitoring. Core body temperature was not recorded when animals were handled or during transport, but core temperature was generally monitored continuously at other times. Body weights were recorded for all animals once prior to randomization, prior to treatment on day 1 and weekly thereafter, including on day 40 (non-fasted) and on day 41 before necropsy. Hematology measurements were performed on all animals three times during the pre-treatment period and during the treatment period on days 2, daily from day 5 to day 27 and once on days 30, 33, 36 and 40. Blood samples of 0.5 mL were collected from the femoral vein or artery or from any appropriate vessel by venipuncture for hematological analysis. Food and water was available to the animals before blood collections.

Hematology parameters that were examined at most time points included red blood cell count, hematocrit, hemoglobin, white blood cell count, absolute differential WBC count, relative differential WBC count, relative reticulocyte count, mean corpuscular hemoglobin, platelet count, platelet volume, immature granulocyte count and red cell distribution width. EDTA was used as an anticoagulant and blood smears were prepared for each time point, stained with Modified Wright's stain and evaluated.

On day 41, the irradiated group 2 animals were sedated using ketamine and acepromazine and then euthanized by an overdose of barbiturate (e.g. sodium pentobarbital), which was administered intravenously, followed by exsanguination. For euthanized animals, gross pathology consisted of an external examination, identification of clinically recorded lesions and a detailed internal examination. To avoid autolytic changes, the necropsy examination was conducted as soon as possible on all animals that died while on study or that were euthanized during the study or at termination of the study at day 41. The animals were stored at 2-8° C. before examination. For all animals that were euthanized, the following organs were dissected, trimmed free of fat and weighed: Brain, testes, heart, prostate, kidneys, seminal vesicles, large intestine, small intestine, liver, spleen, lungs with trachea and thymus. The large intestine and small intestine were examined by making a longitudinal incision to open the lumen and removal of contents. The intestinal mucosa was washed with saline and excess saline was removed and the organs weighed. Paired organs were weighed together. Absolute and relative (to body weight) organ weights were calculated. On completion of the gross pathology examination, abnormal tissues brain (right part), femur and marrow, heart (both ventricles and atria, septum with papillary muscle), sternum and marrow, thymus were retained. Neutral buffered 10% formalin was usually used for fixation and preservation. Three femoral bone marrow smears were prepared from each euthanized animal (right femur), stained with Modified Wright's stain and evaluated.

Tissue samples from liver, lungs (right and left separately), kidneys, brain (left) and spleen were collected at necropsy from all euthanized animals for bacteriological culture. Tissue samples were stored refrigerated 2-8° C. pending analysis. A selected area at the surface of the tissue sample was burned to eliminate possible surface contaminant. A sterile culture swab was inserted in the tissue sample through the burned surface for isolation and identification of aerobic and anaerobic bacteria. Histopathological examination was performed on the tissues from euthanized animals. Tissues were prepared for histological examination by embedding in paraffin wax, sectioning and staining with hematoxylin and eosinphloxin.

Example 22

Results and calculation of status profiles for non-human primates using biological parameter measurements. Numerical data obtained from the protocol described in example 21 was subjected to calculation of group means, standard deviations and other statistical analyses.

Statistically significant status profiles were obtained based on five biological parameters, i.e., anemia (based on hematocrit), thrombocytopenia (platelets), neutropenia (neutrophils), elevated temperature and circadian rhythm disruption. Each parameter alone gave statistically significant $P_{lethality}$ and $P_{survival}$ status profiles. When hematocrit nadirs for individual animals fell below 20% of normal, 4 of 4 animals died, while 5 of 6 animals survived when individual hematocrits remained above 20%. Calculation by an unpaired t-test analysis gave $P_{lethality}$ and $P_{survival}$ status profiles of 0.02 for a mean hematocrit nadir of 16.4% and 25.6% respectively.

When platelets for individual animals fell to less than 7,000 per µL, 5 of 6 animals died, while 4 of 4 animals survived when the platelet count nadir remained above about 7,000 per µL Calculation by an unpaired t-test analysis of $P_{lethality}$ and $P_{survival}$ status profiles of 0.01 for a mean platelet nadir of 4,800 platelets per µL blood and 12,800 platelets per µL blood, respectively.

When the neutrophil nadir for individual animals fell to less than 50 per µL, 5 of 6 animals died, while 4 of 4 animals survived when the neutrophil count nadir remained above 50 per µL Calculation by an unpaired t-test analysis of $P_{lethality}$ and $P_{survival}$ were 0.02 for a mean neutrophil nadir of 28 neutrophils per μL blood and 58 neutrophils per μL blood respectively.

For fever, $P_{lethality}$ was less than 0.05 when the animals experienced fever or $P_{survival}$ was greater than 0.95 when the animals did not have an elevated temperature or a fever. For this biological response, fever or elevated temperature was defined as a temperature of at least about 39.0° C. for at least about 15 minutes within 12 hours after the animals were irradiated on day 1. The baseline temperature for the animals was considered to be 37.3° C., although temperatures for the 10 control (non-irradiated) animals in example 1 varied with the animal's circadian rhythm between about 36.8° C. and 37.9° C. The control animal's circadian core body temperature rhythm was quite regular, while irradiated animals that survived the radiation was relatively regular and was indistinguishable from non-irradiated controls by about 5-8 days after irradiation. However, circadian core body temperature rhythm from irradiated animals that did not survive the radiation was destroyed and did not recover at any time after its disruption. $P_{lethality}$ was less than 0.05 when circadian rhythm was disrupted, and $P_{survival}$ was greater than about 0.95 when circadian rhythm was not disrupted. The loss of circadian rhythm was detectable within 24 to 48 hours after the animals were exposed to the 6 Gy dose of γ-radiation.

The $P_{lethality}$ and $P_{survival}$ status profiles for platelets, hematocrit and neutrophils given above was obtained using an unpaired T-test analysis based on the animals described in example 1. Five of the irradiated animals in example 1 survived the 6 Gy radiation exposure and the hematocrit, platelet and neutrophil nadir from irradiated surviving animals (variable 1) was compared to the hematocrit, platelet and neutrophil nadir from the 5 irradiated non-survivors (variable 2).

| Hematocrit t-Test: Two-Sample Assuming Unequal Variances | | |
|---|---|---|
| | variable 1 | variable 2 |
| Mean | 25.6 | 16.4 |
| Variance | 17.3 | 30.8 |
| Observations | 5 | 5 |
| Hypothesized Mean Difference | 0 | |
| df | 7 | |
| t Stat | 2.9662 | |
| P(T <= t) one-tail | 0.0105 | |
| t Critical one-tail | 1.8946 | |
| P(T <= t) two-tail | 0.0209 | |
| t Critical two-tail | 2.3646 | |

| Platelet t-Test: Two-Sample Assuming Unequal Variances | | |
|---|---|---|
| | variable 1 | variable 2 |
| Mean | 12.8 | 4.8 |
| Variance | 21.7 | 1.7 |
| Observations | 5 | 5 |
| Hypothesized Mean Difference | 0 | |
| df | 5 | |
| t Stat | 3.698001 | |
| P(T <= t) one-tail | 0.007014 | |
| t Critical one-tail | 2.015049 | |
| P(T <= t) two-tail | 0.014028 | |
| t Critical two-tail | 2.570578 | |

| Neutrophil t-Test: Two-Sample Assuming Unequal Variances | | |
|---|---|---|
| | variable 1 | variable 2 |
| Mean | 0.058 | 0.028 |
| Variance | 0.00037 | 7E-05 |
| Observations | 5 | 5 |
| Hypothesized Mean Difference | 0 | |
| df | 5 | |
| t Stat | 3.19801 | |
| P(T <= t) one-tail | 0.01202 | |
| t Critical one-tail | 2.01505 | |
| P(T <= t) two-tail | 0.02405 | |
| t Critical two-tail | 2.57058 | |

For the 5 surviving animals, the hematocrit nadirs were 28, 31, 24, 25 and 20, while hematocrit nadirs for the non-surviving animals were 14, 16, 12, 14 and 26. For the 5 surviving animals, the platelet nadirs were $10 \times 10^3$ per μL, $18 \times 10^3$ per μL, $12 \times 10^3$ per μL, $17 \times 10^3$ per μL and $7 \times 10^3$ per μL, while platelet nadirs for the non-surviving animals were $5 \times 10^3$ per μL, $4 \times 10^3$ per μL, $4 \times 10^3$ per μL, $4 \times 10^3$ per μL and $7 \times 10^3$ per μL. For the 5 surviving animals, the neutrophil nadirs were 80 per mm$^3$, 70 per mm$^3$, 50 per mm$^3$, 60 per mm$^3$ and 30 per mm$^3$, while neutrophil nadirs for the non-surviving animals were 20 per mm$^3$, 30 per mm$^3$, 20 per mm$^3$, 40 per mm$^3$ and 30 per mm$^3$. The raw data for hematocrit, platelets and neutrophils from day −6 through day 26 are shown below and this data were used for the unpaired t-test $P_{lethality}$ and $P_{survival}$ calculations above.

| Hematocrits (% or L/L) for irradiated animals at day −6 to day 10 | | | | | | | | |
|---|---|---|---|---|---|---|---|---|
| | day | | | | | | | |
| animal | −6 | 2 | 5 | 6 | 7 | 8 | 9 | 10 |
| 1 | 0.38 | 0.40 | 0.39 | 0.40 | 0.39 | 0.38 | 0.35 | 0.36 |
| 2 | 0.38 | 0.40 | 0.40 | 0.43 | 0.41 | 0.38 | 0.37 | 0.38 |
| 3 | 0.37 | 0.38 | 0.39 | 0.38 | 0.35 | 0.36 | 0.33 | 0.34 |
| 4 | 0.34 | 0.36 | 0.34 | 0.34 | 0.34 | 0.34 | 0.30 | 0.29 |
| 5 | 0.38 | 0.37 | 0.36 | 0.35 | 0.39 | 0.35 | 0.29 | 0.29 |
| 6 | 0.38 | 0.39 | 0.40 | 0.38 | 0.37 | 0.37 | 0.35 | 0.34 |
| 7 | 0.39 | 0.39 | 0.38 | 0.39 | 0.40 | 0.38 | 0.39 | 0.35 |
| 8 | 0.40 | 0.39 | 0.39 | 0.37 | 0.37 | 0.37 | 0.34 | 0.33 |
| 9 | 0.38 | 0.36 | 0.37 | 0.36 | 0.36 | 0.37 | 0.33 | 0.32 |
| 10 | 0.40 | 0.43 | 0.42 | 0.39 | 0.37 | 0.38 | 0.36 | 0.33 |
| mean | 0.38 | 0.39 | 0.38 | 0.38 | 0.38 | 0.37 | 0.34 | 0.33 |

| Hematocrits (% or L/L) for irradiated animals at day 11 to day 18 | | | | | | | | |
|---|---|---|---|---|---|---|---|---|
| | day | | | | | | | |
| animal | 11 | 12 | 13 | 14 | 15 | 16 | 17 | 18 |
| 1 | 0.35 | 0.35 | 0.36 | 0.36 | 0.34 | 0.36 | 0.32 | 0.33 |
| 2 | 0.36 | 0.37 | 0.36 | 0.38 | 0.35 | 0.32 | 0.32 | 0.31 |
| 3 | 0.31 | 0.26 | 0.28 | 0.28 | 0.21 | 0.19 | 0.16 | 0.14 |
| 4 | 0.33 | 0.27 | 0.25 | 0.21 | 0.16 | * | | |
| 5 | 0.29 | 0.26 | 0.25 | 0.25 | 0.20 | 0.20 | 0.17 | 0.15 |
| 6 | 0.35 | 0.34 | 0.32 | 0.33 | 0.31 | 0.28 | 0.29 | 0.27 |
| 7 | 0.34 | 0.35 | 0.33 | 0.32 | 0.29 | 0.28 | 0.28 | 0.27 |
| 8 | 0.32 | 0.33 | 0.31 | 0.27 | 0.26 | 0.24 | 0.24 | 0.20 |
| 9 | 0.33 | 0.30 | 0.30 | 0.27 | 0.21 | 0.18 | 0.16 | 0.14 |
| 10 | 0.34 | 0.35 | 0.31 | 0.30 | 0.29 | 0.27 | 0.26 | 0.26 |
| mean | 0.33 | 0.32 | 0.31 | 0.30 | 0.26 | 0.26 | 0.24 | 0.23 |

* animal euthanized

| Hematocrits (% or L/L) for irradiated animals at day 19 to day 26 | | | | | | | | |
|---|---|---|---|---|---|---|---|---|
| | day | | | | | | | |
| animal | 19 | 20 | 21 | 22 | 23 | 24 | 25 | 26 |
| 1 | 0.31 | 0.30 | 0.29 | 0.28 | 0.33 | 0.30 | 0.31 | 0.32 |
| 2 | 0.32 | 0.32 | 0.32 | 0.31 | 0.34 | 0.33 | 0.34 | 0.34 |
| 3 | * | | | | | | | |
| 4 | * | | | | | | | |
| 5 | ** | ** | 0.14 | 0.14 | 0.12 | ** | 0.12 | * |
| 6 | ** | 0.26 | 0.25 | 0.25 | 0.24 | 0.25 | 0.26 | 0.28 |
| 7 | 0.28 | 0.26 | 0.25 | 0.25 | 0.25 | 0.26 | 0.27 | 0.29 |
| 8 | 0.20 | 0.20 | 0.20 | 0.20 | 0.22 | 0.23 | 0.24 | 0.26 |
| 9 | * | | | | | | | |
| 10 | 0.29 | * | | | | | | |
| mean | 0.28 | 0.27 | 0.24 | 0.23 | 0.25 | 0.27 | 0.26 | 0.30 |

* animal euthanized
** measurement not obtained

| Platelets ($\times 10^{-3}/\mu L$) for irradiated animals at day 11 to day 18 | | | | | | | | |
|---|---|---|---|---|---|---|---|---|
| | day | | | | | | | |
| animal | 11 | 12 | 13 | 14 | 15 | 16 | 17 | 18 |
| 1 | 57 | 42 | 25 | 23 | 22 | 10 | 23 | 45 |
| 2 | 61 | 32 | 25 | 18 | 28 | 55 | 107 | 177 |
| 3 | 30 | 13 | 10 | 6 | 5 | 8 | 7 | 7 |
| 4 | 20 | 6 | 5 | 4 | 5 | * | | |
| 5 | 17 | 11 | 7 | 4 | 6 | 10 | 12 | 16 |
| 6 | 33 | 17 | 19 | 18 | 12 | 12 | 12 | 16 |
| 7 | 88 | 30 | 27 | 20 | 17 | 17 | 27 | 44 |
| 8 | 39 | 12 | 13 | 8 | 7 | 15 | 24 | 48 |
| 9 | 23 | 7 | 8 | 8 | 4 | 7 | 6 | 9 |
| 10 | 24 | 16 | 12 | 11 | 7 | 12 | 20 | 19 |
| mean | 39 | 19 | 15 | 12 | 11 | 16 | 26 | 42 |

* animal euthanized

| Platelets ($\times 10^{-3}/\mu L$) for irradiated animals at day 19 to day 26 | | | | | | | | |
|---|---|---|---|---|---|---|---|---|
| | day | | | | | | | |
| animal | 19 | 20 | 21 | 22 | 23 | 24 | 25 | 26 |
| 1 | 64 | 91 | 118 | 139 | 134 | 156 | 200 | 222 |
| 2 | 261 | 300 | 349 | 343 | 358 | 330 | 327 | 303 |
| 3 | * | | | | | | | |
| 4 | | | | | | | | |
| 5 | ** | ** | 44 | 53 | 74 | * | | |
| 6 | ** | 44 | 104 | 142 | 217 | 259 | 305 | 318 |
| 7 | 89 | 144 | 278 | 353 | 448 | 523 | 519 | 514 |
| 8 | 90 | 92 | 158 | 194 | 246 | 285 | 341 | 406 |
| 9 | * | | | | | | | |
| 10 | 12 | * | | | | | | |
| mean | 103 | 134 | 175.17 | 217.00 | 246.17 | 310.60 | 313.00 | 352.60 |

* animal euthanized
** measurement not obtained

| Platelets ($\times 10^{-3}/\mu L$) for irradiated animals at day −6 to day 10 | | | | | | | | |
|---|---|---|---|---|---|---|---|---|
| | day | | | | | | | |
| animal | −6 | 2 | 5 | 6 | 7 | 8 | 9 | 10 |
| 1 | 608 | 525 | 580 | 538 | 433 | 324 | 232 | 111 |
| 2 | 547 | 397 | 406 | 401 | 324 | 255 | 174 | 113 |
| 3 | 363 | 313 | 356 | 315 | 221 | 169 | 101 | 45 |
| 4 | 295 | 266 | 267 | 253 | 180 | 141 | 71 | 28 |
| 5 | 472 | 325 | 336 | 316 | 273 | 203 | 117 | 22 |
| 6 | 400 | 410 | 443 | 386 | 290 | 193 | 103 | 26 |
| 7 | 485 | 438 | 385 | 489 | 409 | 353 | 275 | 175 |
| 8 | 472 | 380 | 401 | 342 | 305 | 235 | 145 | 59 |
| 9 | 510 | 363 | 307 | 370 | 261 | 109 | 46 | 20 |
| 10 | 419 | 381 | 478 | 409 | 327 | 185 | 79 | 36 |
| mean | 457 | 380 | 396 | 382 | 302 | 217 | 134 | 64 |

| Neutrophils ($\times 10^{-3}/mm^3$) for irradiated animals at day −6 to day 10 | | | | | | | | |
|---|---|---|---|---|---|---|---|---|
| | day | | | | | | | |
| animal | −6 | 2 | 5 | 6 | 7 | 8 | 9 | 10 |
| 1 | 4.30 | 2.59 | 1.07 | 0.58 | 0.34 | 0.39 | 0.40 | 0.39 |
| 2 | 5.10 | 6.08 | 2.10 | 1.41 | 0.28 | 0.27 | 0.34 | 0.36 |
| 3 | 8.17 | 5.09 | 2.05 | 1.02 | 0.76 | 0.68 | 0.60 | 0.48 |
| 4 | 9.46 | 6.98 | 0.68 | 0.30 | 0.25 | 0.32 | 0.30 | 0.22 |
| 5 | 3.01 | 4.45 | 2.53 | 0.76 | 0.29 | 0.28 | 0.35 | 0.13 |
| 6 | 2.07 | 4.55 | 2.39 | 0.80 | 0.33 | 0.30 | 0.38 | 0.27 |
| 7 | 5.94 | 6.01 | 1.19 | 0.79 | 0.34 | 0.35 | 0.54 | 0.36 |
| 8 | 2.59 | 2.50 | 1.13 | 0.28 | 0.15 | 0.26 | 0.28 | 0.14 |
| 9 | 3.62 | 6.36 | 0.46 | 0.25 | 0.31 | 0.43 | 0.57 | 0.21 |
| 10 | 3.22 | 5.34 | 1.30 | 0.46 | 0.37 | 0.34 | 0.31 | 0.13 |
| mean | 4.75 | 5.00 | 1.49 | 0.67 | 0.34 | 0.36 | 0.41 | 0.27 |

Neutrophils (×10$^{-3}$/mm$^3$) for irradiated animals at day 11 to day 18

| animal | 11 | 12 | 13 | 14 | 15 | 16 | 17 | 18 |
|---|---|---|---|---|---|---|---|---|
| 1 | 0.17 | 0.10 | 0.08 | 0.14 | 0.17 | 0.09 | 0.10 | 0.08 |
| 2 | 0.30 | 0.15 | 0.10 | 0.10 | 0.07 | 0.07 | 0.19 | 0.46 |
| 3 | 0.13 | 0.09 | 0.12 | 0.09 | 0.04 | 0.05 | 0.07 | 0.02 |
| 4 | 0.16 | 0.11 | 0.04 | 0.06 | 0.03 | * | | |
| 5 | 0.07 | 0.09 | 0.06 | 0.07 | 0.02 | 0.04 | 0.10 | 0.24 |
| 6 | 0.13 | 0.10 | 0.13 | 0.09 | 0.06 | 0.06 | 0.05 | 0.05 |
| 7 | 0.24 | 0.19 | 0.10 | 0.06 | 0.12 | 0.20 | 0.12 | 0.15 |
| 8 | 0.11 | 0.06 | 0.05 | 0.05 | 0.03 | 0.05 | 0.18 | 0.69 |
| 9 | 0.13 | 0.16 | 0.11 | 0.06 | 0.08 | 0.05 | 0.06 | 0.04 |
| 10 | 0.09 | 0.09 | 0.05 | 0.07 | 0.03 | 0.04 | 0.07 | 0.05 |
| mean | 0.15 | 0.11 | 0.08 | 0.08 | 0.07 | 0.07 | 0.10 | 0.20 |

* animal euthanized

Neutrophils (×10$^{-3}$/mm$^3$) for irradiated animals at day 19 to day 26

| animal | 19 | 20 | 21 | 22 | 23 | 24 | 25 | 26 |
|---|---|---|---|---|---|---|---|---|
| 1 | 0.30 | 1.37 | 1.21 | 1.72 | 2.00 | 2.51 | 3.62 | 4.28 |
| 2 | 0.70 | 1.23 | 2.38 | 3.63 | 5.67 | 6.47 | 6.63 | 5.53 |
| 3 | * | | | | | | | |
| 4 | | | | | | | | |
| 5 | ** | ** | 2.57 | 4.51 | 4.60 | * | | |
| 6 | ** | 0.18 | 0.30 | 1.57 | 1.32 | 2.12 | 5.52 | 6.14 |
| 7 | 0.14 | 0.08 | 0.27 | 0.83 | 1.66 | 3.38 | 5.54 | 11.53 |
| 8 | 1.80 | 0.84 | 1.86 | 4.07 | 2.82 | 3.6 | 3.59 | 6.77 |
| 9 | * | | | | | | | |
| 10 | 0.04 | * | | | | | | |
| mean | 0.60 | 0.74 | 1.43 | 2.92 | 3.01 | 3.62 | 5.16 | 6.85 |

* animal euthanized
** measurement not obtained

Example 23

Soluble steroid polymer conjugates and complexes. A number of covalent polymer conjugates and complexes containing F1Cs were prepared. The reactions described below were conducted at room temperature, unless specified otherwise.

Disuccinyl-PEG 2000. PEG 2000 was treated with succinic anhydride, triethylamine (TEA), and dimethylaminopyridine (DMAP) in dimethylformamide (DMF) to yield disuccinyl-PEG2000. The product was isolated by precipitation with ether, redissolved in chloroform, and precipitated again.

Di-(N-hydroxysuccinimidyl-succinyl) PEG 2000. Disucciniyl-PEG 2000 dissolved in DMF was treated with TEA and di-N-hydroxysuccinimidylcarbonate (DSC) to yield Di-(N-hydroxysuccinimidyl-succinyl) PEG 2000. The product was isolated by precipitation with ether, dissolved in chloroform, and reprecipitated with ether.

Di-(N-17β-amino-3β-hydroxyandrost-5-ene-succinyl) PEG 2000. 3β-Hydroxy-17β-aminoandrost-5-ene was coupled to di-(N-hydroxysuccinimidyl-succinyl)PEG 2000 in DMF with TEA. The product was isolated by precipitation with ether, dissolved in chloroform, and reprecipitated with ether. The product was dissolved in water for activity testing.

PEG 8000 was treated with succinic anhydride, TEA, and DMAP in DMF to yield disuccinyl-PEG 8000. The product was isolated by precipitation with ether, redissolved in chloroform, and precipitated again.

Di-(N-hydroxysuccinimidyl-succinyl) PEG 8000. Disucciniyl-PEG 8000 dissolved in DMF was treated with TEA and di-N-hydroxysuccinimidylcarbonate (DSC) to yield Di-(N-hydroxysuccinidyl-succinyl) PEG 8000. The product was isolated by precipitation with ether, dissolved in chloroform, and reprecipitated with ether.

Di-(N-17β-amino-3β-hydroxyandrost-5-ene-succinyl) PEG 8000. 17β-Amino-3β-hydroxyandrost-5-ene was coupled to Di-(N-hydroxysuccinimidyl-succinyl)PEG 8000 in DMF with TEA. The product was isolated by precipitation with ether, dissolved in chloroform, and reprecipitated with ether. The product was dissolved in water for activity testing.

N-Hydroxysuccinimidyl-3β,17β-dihydroxyandrost-5-ene. The 3β,17β-dihydroxyandrost-5-ene-17β-hemisuccinate (1) was reacted with TEA and DSC in DMSO, and the product was isolated by addition of water.

Amino-PEG-750 of (1). The N-hydroxysuccinimidyl of 1 was reacted with 2-aminoethyl-methyl PEG 750 in DMSO and TEA. The product was isolated by precipitation with ether, dissolved in chloroform, and reprecipitated with ether. N-Hydroxysuccinimidyl-3β,17β-dihydroxyandrost-5-ene was reacted with 2-aminoethyl-methyl PEG 5000 in DMSO and TEA to generate the amino PEG 5000 derivative. The product was isolated by precipitation with ether, dissolved in chloroform, and reprecipitated with ether. N-Hydroxysuccinimidyl-3β,17β-dihydroxyandrost-5-ene was reacted with 2-aminoethyl-methyl PEG 10000 in DMSO and TEA to generate the amino PEG 10000 derivative. The product was isolated by precipitation with ether, dissolved in chloroform, and reprecipitated with ether.

DSC (1.5 equivalents) was reacted with PEG 8000 (1 equivalent) in DMF with TEA. The product, N-hydroxysuccinimidyl-PEG 8000, was isolated by precipitation with ether, dissolved in chloroform, and reprecipitated with ether. DSC (3 equivalents) was reacted with PEG 8000 (1 equivalent) in DMF with TEA. The product, di-(N-hydroxysuccinimidyl)-PEG 8000, was isolated by precipitation with ether, dissolved in chloroform, and reprecipitated with ether.

N-hydroxysuccinimidyl-PEG 8000 was reacted with 1 equivalent of 3β-hydroxy-17β-aminoandrost-5-ene in DMF with TEA. The product, 3β-hydroxy-17β-N-carbamoylandrost-5-ene was isolated by precipitation with ether, dissolved in chloroform, and reprecipitated with ether.

N-hydroxysuccinimidyl-PEG 8000 was reacted with 2 equivalents of 3β-hydroxy-17β-aminoandrost-5-ene in DMF with TEA. The product, 3β-hydroxy-17β-di(N-carbamoyl)-PEG 8000-androst-5-ene was isolated by precipitation with ether, dissolved in chloroform, and reprecipitated with ether.

Di-Lysyl-PEG 2000 was prepared by reacting 2 equivalents of lysine with di-(N-hydroxysuccinimidyl)-PEG 2000 in DMF. The product was isolated by precipitation with ether, dissolved in chloroform, and reprecipitated with ether.

3β-Hydroxy-17β-N-hydroxysuccinimidylandrost-5-ene was reacted with 0.5 equivalents of di-lysyl-PEG 2000 in DMF with TEA. The product, di-lysyl-PEG 2000 esterified with two 3β-hydroxy-17β-hydroxysuccinimidylandrost-5-ene moieties, was isolated by precipitation with ether, dissolved in chloroform, and reprecipitated with ether.

Di-(PEG 2000-Lysyl)-PEG-2000 was prepared by reacting 2 equivalents of Di-NHS PEG 2000 with Di-Lysyl-PEG 2000 in DMF with TEA. The product was isolated by precipitation with ether, dissolved in chloroform, and reprecipitated with ether.

Di-(Lysyl-PEG 2000-Lysyl)-PEG 2000 was prepared by reacting Di-(PEG 2000-Lysyl)-PEG-2000 with DSC and TEA, followed by reaction with 2 equivalents of lysine. The product was isolated by precipitation with ether, dissolved in chloroform, and reprecipitated with ether.

Poly NHS Di-(Lysyl-PEG 2000-Lysyl)-PEG 2000 was prepared by reacting the carboxy groups on lysine with DSC and TEA in DMF. The product was isolated by precipitation with ether, dissolved in chloroform, and reprecipitated with ether.

Poly HE3204-Di-(Lysyl-PEG 2000-Lysyl)-PEG 2000 was prepared as follows. 3β-Hydroxy-17β-aminoandrost-5-ene was reacted with poly NHS di-(lysyl-PEG 2000-lysyl)-PEG 2000 in DMF with TEA. The product was isolated by precipitation with ether, dissolved in chloroform, and reprecipitated with ether.

Polyethylenediamine-di-(lysyl-PEG 2000-lysyl)-PEG 2000 was prepared by reacting di-(lysyl-PEG 2000-lysyl)-PEG 2000 with excess ethylenediamine in DMF with TEA. The product was isolated by precipitation with ether, dissolved in chloroform, and reprecipitated with ether.

Poly-17β-succinic acid ester of 3β,17β-dihydroxyandrost-5-ene-ethylenediamine-di-(lysyl-PEG 2000-lysyl)-PEG 2000 was prepared as follows. The N-hydroxysuccinimide derivative of 3β-hydroxyandrost-5-ene-17β-hemisuccinate was reacted with poly ethylenediamine-di-(dysyl-PEG 2000-lysyl)-PEG 2000 in DMF with TEA. The product was isolated by precipitation with ether, dissolved in chloroform, and reprecipitated with ether.

The aldehyde of dextran 40,000 was prepared by oxidizing dextran 40,000 with sodium metaperiodate at a ratio of 1 equivalent of periodate for every 10 sugar residues in water. The product was extensively dialyzed against water and freeze dried.

Poly-(3β-hydroxy-17β-aminoandrost-5-ene imine)-Dextran 40,000 was prepared as follows. The aldehyde of dextran 40,000 was reacted with 3β-hydroxy-17β-aminoandrost-5-ene in DMSO at 37° C. to form the imine linkage. The product was precipitated with ethanol and dried. The hydrazide of dextran 40,000 was prepared by reacting the aldehyde of dextran 40,000 with hydrazine and sodium cyanoborohydride in water to yield stable hydrazides. The product was dialyzed and freeze dried.

Poly-(3β,17β-di-N-succinimidinyl-NHS-hydroxyandrost-5-ene)-dextran 40,000 was prepared by reaction of (3β-hydroxy-17β-aminoandrost-5-ene imine)-Dextran 40,000 with hydrazide dextran in DMSO and TEA. The product was extracted with water, dialyzed and freeze dried.

PEG 8000-poly-benzoyl-L-lysine was prepared by reacting poly-L-Lysine with N-hydroxysuccinimide-PEG 8000 and then with benzoyl-bromide in potassium t-butyl oxide in DMF. This material forms self-associating mycelles in water having a hydrophobic poly-benzoyl-lysine interior and a hydrophilic PEG exterior.

Polymer for dextran-PEG self-associating micelles was prepared as follows. The aldehyde of dextran was reacted with amino-methyl PEG, followed by reduction of the imines with sodium cyanoborohydride. For this polymer, the dextran forms the exterior hydrophilic phase and the PEG forms the hydrophobic interior of micelles made with this material.

Polymer for PEG-benzoyl dextran self-associating micelles was prepared as follows. After formation of the dextran-PEG 8000 conjugate, the hydroxyl groups were treated with benzoyl bromide to yield benzoyl dextran linked to PEG. The benzoyl dextran forms a hydrophobic micelle interior, and the PEG forms the hydrophilic exterior surface.

Dextran-Epoxide was prepared by treating dextran with epichlorhydrin. Dextran-p-nitro-phenyl conjugate was prepared by treating dextran p-nitrophenyl chloroformate. Dextran-N-hydroxysuccinimide was prepared by reacting dextran and DSC in DMSO with TEA.

The lysine ester of 3β-hydroxy-17β-N-hydroxysuccinimide-androst-5-ene was prepared by reacting lysine and TEA with 3β-hydroxy-17β-N-hydroxysuccinimide-androst-5-ene in DMF. The lysine ester was reacted either with dextran epoxide or with dextran-p-nitrophenyl to prepare the corresponding conjugate.

3β-Hydroxy-17β-N-hydroxysuccinimide-androst-5-ene was reacted with bovine serum albumin in water/THF (1:1), and the resulting conjugate was isolated by dialysis.

3β-Hydroxy-7-carboxymethyl oxime-17-oxoandrost-5-ene was reduced with borohydride in methanol/DMSO. Water was added, the solution was dried, resuspended in methanol, acidified, and the product, 3β,17β-dihydroxy-7-carboxymethyl oxime-androst-5-ene, was crystallized from methanol.

3β,17β-Dihydroxy-7-carboxymethyl oxime-androst-5-ene was reacted with DSC and TEA in DMSO, and the product, 3β-hydroxy-7-carboxymethyl oxime-17-N-hydroxysuccinimide-androst-5-ene, was isolated by adding water.

3β-Hydroxy-7-carboxymethyl oxime-17-N-hydroxysuccinimide-androst-5-ene, was reacted with bovine serum albumin in THF/water (1:1) and the conjugated product was isolated by dialysis in water.

Example 24

Preparation of micelle complexes. The compound 3β,17β-dihydroxyandrost-5-ene is loaded into micelles by drying the compound on the inner surface of a round flask followed by addition of aqueous micelles in water. The compound is incorporated into the interior by sonication, stirring and/or heating.

Example 25

Measurement of biological parameters in non-human primates after biological insult. A study was conducted to characterize a biological insult of 600cGy of whole body irradiation to male Rhesus (*Macaca mulatta*) primates weighing 2.5 to 4.5 kg at an age range of about 1.75 to 3.5 years. Core body temperature was monitored by telemetry in the monkeys for a period of 40 consecutive days. Two groups of 10 animals each were used in the study. Core body temperature transmitters were surgically implanted in the abdomen prior to initiation of the radiation protocol. Core body temperature was continuously recorded from day −7 to day 41 for correlation with survival, hematology results, and other clinical parameters.

Temperature Transmitters.

Before initiation of the temperature transmitter implantation protocol, all animals were subject to a detailed physical examination and body weight measurement under the direction of a clinical veterinarian. Blood was collected from all animals, which were not food and water deprived, and assessed for basic blood chemistry and hematology. The results of the evaluation was reviewed by the clinical veterinarian to ensure satisfactory health status. Implantation of the temperature transmitters was accomplished using animals that were fasted overnight prior to surgery and then anesthetized by an intra-muscular (IM) injection of acepromazine (10 mg/mL, 0.14 mg/kg) and ketamine (100 mg/mL, 13.6 mg/kg) and intubated. Where needed, lidocain spray (10% w/w) was administered onto the glottis prior to intubation. An ophthalmic ointment was applied to both eyes to prevent drying of the cornea. Animals were placed on a heating pad and administered isoflurane by inhalation, with an oxygen flow of approximately 200 mg/kg/min. A ventilator was used to maintain the respiratory rate between 8 and 20 breaths/min with a ventilation pressure of 18-25 cm $H_2O$. Monitoring during anesthesia included heart rate and oxygen saturation of the blood using a pulse oximeter. Prophylactic antibiotics (cefazolin 25 mg/kg) were administered by intramuscular injection at least 1-hour prior to surgery, and every 6 to 8 hours post injection for at least 24-hours post surgery. Analgesia (buprenorphine 0.05 mg/kg) was administered by intramuscular injection every 6 to 12 hours for at least 24-hours post surgery. Intravenous fluid therapy were given throughout the anesthesia using sterile Lactate Ringer's solution at a rate of 10 mL/kg/hr.

The surgical site was shaved and aseptically prepared using chlorhexidine gluconate 4% and isopropyl alcohol 70%. A longitudinal incision was performed lateral but close to the linea alba. The internal abdominal oblique muscle was separated from the aponeurosis of the transversus abdominis by blunt dissection. A sterile core body temperature transmitter (Data Science International, TA10TAD70) was inserted between the internal abdominal oblique muscle and the aponeurosis of the transversus abdominis. Hemostasis was maintained using appropriate suture material. Sterile saline was used to allow ease of placement of the transmitters. The incision was closed with absorbable suture material using simple continuous sutures. The skin was closed with discontinuous buried sutures using absorbable suture material. Additional post-operative cares (analgesia and antibiotics) was provided to the animals when needed. Rectal body temperature was monitored in the post-operative period. Once the body temperature was within an acceptable range and the animal was alert, each animal was returned to their cages. A postoperative period of at least 2 weeks was allowed prior to initiation of radiation.

Acclimation and Whole-Body Irradiation.

Before transportation to the radiation facility, the animals were acclimated to the radiotherapy chair and to transportation. During the acclimation period, animals were assigned to their respective dose groups by block randomization based on the absolute neutrophil count. Any animal with unacceptable pretreatment data was replaced by an animal kept under identical environmental conditions. Animals with pretreatment data considered acceptable but marginally different from normal values were assigned to the sham group to allow longer post-operative recovery.

Animals were fasted overnight prior to whole-body irradiation and fed upon return to the holding facility. Animals were transferred to the irradiation facility in a transport vehicle with controlled environment. During transportation, each animal was individually housed in a stainless steel squeeze back cage. The animal's clinical signs were monitored immediately before and after transportation. Group 1 animals, sham irradiated, were subject to the same irradiation procedure as Group 2 animals, however, these animals did receive radiation. The 10 control animals, Group 1, were sham irradiated by placing each animal in the restraint for 10 minutes. The 10 treated animals, Group 2, received a midline $^{60}Co$ γ-radiation dose of 6 Gy at a dose rate of about 60 cGy/minute (day 1). The animals receiving this 6 Gy radiation insult were restrained during the radiation exposure by placing each animal in a chair allowing appropriate restraining in a symmetric position. An insulated cover was placed on the radiotherapy chair during transportation between the transport vehicle and the treatment site. Music was provided inside the treatment room to reduce stress to the animals. Animal positioning was confirmed with linear markers installed in the treatment room. To produce a homogenous dose distribution, treatment was divided in two parts. First, the animal received half of the dose by anteroposterior (AP) irradiation. The second half of the dose was delivered by posteroanterior (PA) irradiation. Group 1 animals were placed in an identical restraining chair in the sham treatment site for approximately the same period of time without exposure to radiation. Once the treatment was completed, animals were returned to the transport vehicle and were transported to their housing facility. The radiation dose was calibrated using an acrylic phantom placed in the same experimental set up that was used for animal irradiation.

Animal Maintenance.

Animals were housed individually in stainless steel squeeze back cages equipped with an automatic watering system except during transportation where water bottles were provided. The cages were labeled with a color-coded cage card indicating study number, group, animal number, species, sex and dose level. The animal room environment was controlled (temperature 21±3° C., humidity 30-70%, 10-15 air changes per hour, 12 hours light, 12 hours dark). Temperature and humidity were monitored continuously except during animal transportation and inside the radiation facility where only temperature was recorded. A standard certified commercial primate chow (Teklad Certified Global 25% Primate Diet #2055C) was made available to each monkey daily. Food was withdrawn overnight prior to radiation and necropsy. Maximum allowable concentrations of contaminants in the diet (e.g., heavy metals, aflatoxin, organophosphates, chlorinated hydrocarbons and PCBs) were controlled and routinely analyzed by the manufacturers. If an animal stopped eating during the study, the diet was supplemented at the discretion of the study director. Tap water was purified by reverse osmosis and provided to the animals ad libitum throughout the study. Periodic analyses of the tap water and reverse osmosis water were performed. It was considered that there were no known contaminants in the diet or water. During the pre-treatment period cage side observations of clinical signs were generally performed once daily.

Observations.

Mortality checks were performed twice a day during all phases of the study. Moribund animals were euthanized for humane reasons based on the clinical judgments. Sacrificed animals were subject to a clinical examination. When the core body temperature was 33° C. (91.4° F.) or lower or when an animal experienced a weight loss of more than 20% over a 4 day period, the animal was euthanized. Animals were also euthanized when they displayed complete anorexia for 3 days with deteriorating conditions based on the clinical examination or when they displayed an absence of response to stimuli.

Results obtained from the study were used to correlate the changes in biological parameters such as core body temperature and hematology with clinical signs following whole body irradiation. These results were used to obtain a status profile or surrogate endpoint such as incidence or duration of fever, followed by salvage with clinical support (antibiotics and blood transfusion), to assess the probability of survival or death of the treated individuals or similarly situated individuals that may have been subject to similar biological insults. During the pre-treatment period cage side observations of clinical signs were performed once daily. During the treatment period, clinical signs were recorded at cage-side twice daily for all animals or as often as deemed necessary. A detailed clinical examination was performed on all animals, once prior to irradiation on day 1, weekly thereafter, including on day 41 prior to necropsy.

The core body temperature and activity was recorded at 1 minute intervals for all animals from day −7 to day 41 using the implanted transmitter. Each animal cage was equipped with a telemetry receiver. The values of calibration of the transmitter implanted in each animal were entered in a telemetry computer system to ensure accurate temperature monitoring. Core body temperature was not recorded when animals were handled or during transport, but core temperature was generally monitored continuously at other times. Body weights were recorded for all animals once prior to randomization, prior to treatment on day 1 and weekly thereafter, including on day 40 (non-fasted) and on day 41 before necropsy. Hematology measurements were performed on all animals three times during the pre-treatment period and during the treatment period on days 2, daily from day 5 to day 27 and once on days 30, 33, 36 and 40. Blood samples of 0.5 mL were collected from the femoral vein or artery or from any appropriate vessel by venipuncture for hematological analysis. Food and water was available to the animals before blood collections.

Hematology parameters that were examined at most time points included red blood cell count, hematocrit, hemoglobin, white blood cell count, absolute differential WBC count, relative differential WBC count, relative reticulocyte count, mean corpuscular hemoglobin, platelet count, platelet volume, immature granulocyte count and red cell distribution width. EDTA was used as an anticoagulant and blood smears were prepared for each time point, stained with Modified Wright's stain and evaluated.

On day 41, the irradiated group 2 animals were sedated using ketamine and acepromazine and then euthanized by an overdose of barbiturate (e.g. sodium pentobarbital), which was administered intravenously, followed by exsanguination. For euthanized animals, gross pathology consisted of an external examination, identification of clinically recorded lesions and a detailed internal examination. To avoid autolytic changes, the necropsy examination was conducted as soon as possible on all animals that died while on study or that were euthanized during the study or at termination of the study at day 41. The animals were stored at 2-8° C. before examination. For all animals that were euthanized, the following organs were dissected, trimmed free of fat and weighed: Brain, testes, heart, prostate, kidneys, seminal vesicles, large intestine, small intestine, liver, spleen, lungs with trachea and thymus. The large intestine and small intestine were examined by making a longitudinal incision to open the lumen and removal of contents. The intestinal mucosa was washed with saline and excess saline was removed and the organs weighed. Paired organs were weighed together. Absolute and relative (to body weight) organ weights were calculated. On completion of the gross pathology examination, abnormal tissues brain (right part), femur and marrow, heart (both ventricles and atria, septum with papillary muscle), sternum and marrow, thymus were retained. Neutral buffered 10% formalin was usually used for fixation and preservation. Three femoral bone marrow smears were prepared from each euthanized animal (right femur), stained with Modified Wright's stain and evaluated.

Tissue samples from liver, lungs (right and left separately), kidneys, brain (left) and spleen were collected at necropsy from all euthanized animals for bacteriological culture. Tissue samples were stored refrigerated 2-8° C. pending analysis. A selected area at the surface of the tissue sample was burned to eliminate possible surface contaminant. A sterile culture swab was inserted in the tissue sample through the burned surface for isolation and identification of aerobic and anaerobic bacteria. Histopathological examination was performed on the tissues from euthanized animals. Tissues were prepared for histological examination by embedding in paraffin wax, sectioning and staining with hematoxylin and eosinphloxin.

Example 26

Results and calculation of clinical status profiles for non-human primates using biological parameter measurements. Numerical data obtained from the protocol described in example 1 was subjected to calculation of group means, standard deviations and other statistical analyses.

Statistically significant status profiles were obtained based on five biological parameters, i.e., anemia (based on hematocrit), thrombocytopenia (platelets), neutropenia (neutrophils), elevated temperature and circadian rhythm disruption. Each parameter alone gave statistically significant $P_{lethality}$ and $P_{survival}$ status profiles. When hematocrit nadirs for individual animals fell below 20% of normal, 4 of 4 animals died, while 5 of 6 animals survived when individual hematocrits remained above 20%. Calculation by an unpaired t-test analysis gave $P_{lethality}$ and $P_{survival}$ status profiles of 0.02 for a mean hematocrit nadir of 16.4% and 25.6% respectively.

When platelets for individual animals fell to less than 7,000 per μL, 5 of 6 animals died, while 4 of 4 animals survived when the platelet count nadir remained above about 7,000 per μL. Calculation by an unpaired t-test analysis of $P_{lethality}$ and $P_{survival}$ status profiles of 0.01 for a mean platelet nadir of 4,800 platelets per μL blood and 12,800 platelets per μL blood, respectively.

When the neutrophil nadir for individual animals fell to less than 50 per μL, 5 of 6 animals died, while 4 of 4 animals survived when the neutrophil count nadir remained above 50 per μL. Calculation by an unpaired t-test analysis of $P_{lethality}$ and $P_{survival}$ were 0.02 for a mean neutrophil nadir of 28 neutrophils per μL blood and 58 neutrophils per μL blood respectively.

For fever, $P_{lethality}$ was less than 0.05 when the animals experienced fever or $P_{survival}$ was greater than 0.95 when the animals did not have an elevated temperature or a fever. For this biological response, fever or elevated temperature was defined as a temperature of at least about 39.0° C. for at least about 15 minutes within 12 hours after the animals were irradiated on day 1. The baseline temperature for the animals was considered to be 37.3° C., although temperatures for the 10 control (non-irradiated) animals in example 1 varied with the animal's circadian rhythm between about 36.8° C. and 37.9° C. The control animal's circadian core body temperature rhythm was quite regular, while irradiated animals that survived the radiation was relatively regular and was indistinguishable from non-irradiated controls by about 5-8 days after irradiation. However, circadian core body temperature rhythm from irradiated animals that did not survive the radiation was destroyed and did not recover at any time after its disruption. $P_{lethality}$ was less than 0.05 when circadian rhythm was disrupted, and $P_{survival}$ was greater than about 0.95 when circadian rhythm was not disrupted. The loss of circadian rhythm was detectable within 24 to 48 hours after the animals were exposed to the 6 Gy dose of γ-radiation.

The $P_{lethality}$ and $P_{survival}$ status profiles for platelets, hematocrit and neutrophils given above was obtained using an unpaired T-test analysis based on the animals described in example 1. Five of the irradiated animals in example 1 survived the 6 Gy radiation exposure and the hematocrit, platelet and neutrophil nadir from irradiated surviving animals (variable 1) was compared to the hematocrit, platelet and neutrophil nadir from the 5 irradiated non-survivors (variable 2).

| Hematocrit t-Test: Two-Sample Assuming Unequal Variances | | |
|---|---|---|
| | variable 1 | variable 2 |
| Mean | 25.6 | 16.4 |
| Variance | 17.3 | 30.8 |
| Observations | 5 | 5 |
| Hypothesized Mean Difference | 0 | |
| df | 7 | |
| t Stat | 2.9662 | |
| P(T <= t) one-tail | 0.0105 | |
| t Critical one-tail | 1.8946 | |
| P(T <= t) two-tail | 0.0209 | |
| t Critical two-tail | 2.3646 | |

| Platelet t-Test: Two-Sample Assuming Unequal Variances | | |
|---|---|---|
| | variable 1 | variable 2 |
| Mean | 12.8 | 4.8 |
| Variance | 21.7 | 1.7 |
| Observations | 5 | 5 |
| Hypothesized Mean Difference | 0 | |
| df | 5 | |
| t Stat | 3.698001 | |
| P(T <= t) one-tail | 0.007014 | |
| t Critical one-tail | 2.015049 | |
| P(T <= t) two-tail | 0.014028 | |
| t Critical two-tail | 2.570578 | |

| Neutrophil t-Test: Two-Sample Assuming Unequal Variances | | |
|---|---|---|
| | variable 1 | variable 2 |
| Mean | 0.058 | 0.028 |
| Variance | 0.00037 | 7E-05 |
| Observations | 5 | 5 |
| Hypothesized Mean Difference | 0 | |
| df | 5 | |
| t Stat | 3.19801 | |
| P(T <= t) one-tail | 0.01202 | |
| t Critical one-tail | 2.01505 | |
| P(T <= t) two-tail | 0.02405 | |
| t Critical two-tail | 2.57058 | |

For the 5 surviving animals, the hematocrit nadirs were 28, 31, 24, 25 and 20, while hematocrit nadirs for the non-surviving animals were 14, 16, 12, 14 and 26. For the 5 surviving animals, the platelet nadirs were $10\times10^3$ per µL, $18\times10^3$ per µL, $12\times10^3$ per µL, $17\times10^3$ per µL and $7\times10^3$ per µL, while platelet nadirs for the non-surviving animals were $5\times10^3$ per µL, $4\times10^3$ per µL, $4\times10^3$ per µL, $4\times10^3$ per µL and $7\times10^3$ per µL. For the 5 surviving animals, the neutrophil nadirs were 80 per mm$^3$, 70 per mm$^3$, 50 per mm$^3$, 60 per mm$^3$ and 30 per mm$^3$, while neutrophil nadirs for the non-surviving animals were 20 per mm$^3$, 30 per mm$^3$, 20 per mm$^3$, 40 per mm$^3$ and 30 per mm$^3$. The raw data for hematocrit, platelets and neutrophils from day −6 through day 26 are shown below and this data were used for the unpaired t-test $P_{lethality}$ and $P_{survival}$ calculations above.

Hematocrits (% or L/L) for irradiated animals at day −6 to day 10

| animal | −6 | 2 | 5 | 6 | 7 | 8 | 9 | 10 |
|---|---|---|---|---|---|---|---|---|
| 1 | 0.38 | 0.40 | 0.39 | 0.40 | 0.39 | 0.38 | 0.35 | 0.36 |
| 2 | 0.38 | 0.40 | 0.40 | 0.43 | 0.41 | 0.38 | 0.37 | 0.38 |
| 3 | 0.37 | 0.38 | 0.39 | 0.38 | 0.35 | 0.36 | 0.33 | 0.34 |
| 4 | 0.34 | 0.36 | 0.34 | 0.34 | 0.34 | 0.34 | 0.30 | 0.29 |
| 5 | 0.38 | 0.37 | 0.36 | 0.35 | 0.39 | 0.35 | 0.29 | 0.29 |
| 6 | 0.38 | 0.39 | 0.40 | 0.38 | 0.37 | 0.37 | 0.35 | 0.34 |
| 7 | 0.39 | 0.39 | 0.38 | 0.39 | 0.40 | 0.38 | 0.39 | 0.35 |
| 8 | 0.40 | 0.39 | 0.39 | 0.37 | 0.37 | 0.37 | 0.34 | 0.33 |
| 9 | 0.38 | 0.36 | 0.37 | 0.36 | 0.36 | 0.37 | 0.33 | 0.32 |
| 10 | 0.40 | 0.43 | 0.42 | 0.39 | 0.37 | 0.38 | 0.36 | 0.33 |
| mean | 0.38 | 0.39 | 0.38 | 0.38 | 0.38 | 0.37 | 0.34 | 0.33 |

Hematocrits (% or L/L) for irradiated animals at day 11 to day 18

| animal | 11 | 12 | 13 | 14 | 15 | 16 | 17 | 18 |
|---|---|---|---|---|---|---|---|---|
| 1 | 0.35 | 0.35 | 0.36 | 0.36 | 0.34 | 0.36 | 0.32 | 0.33 |
| 2 | 0.36 | 0.37 | 0.36 | 0.38 | 0.35 | 0.32 | 0.32 | 0.31 |
| 3 | 0.31 | 0.26 | 0.28 | 0.28 | 0.21 | 0.19 | 0.16 | 0.14 |
| 4 | 0.33 | 0.27 | 0.25 | 0.21 | 0.16 | * | | |
| 5 | 0.29 | 0.26 | 0.25 | 0.25 | 0.20 | 0.20 | 0.17 | 0.15 |
| 6 | 0.35 | 0.34 | 0.32 | 0.33 | 0.31 | 0.28 | 0.29 | 0.27 |
| 7 | 0.34 | 0.35 | 0.33 | 0.32 | 0.29 | 0.28 | 0.28 | 0.27 |
| 8 | 0.32 | 0.33 | 0.31 | 0.27 | 0.26 | 0.24 | 0.24 | 0.20 |
| 9 | 0.33 | 0.30 | 0.30 | 0.27 | 0.21 | 0.18 | 0.16 | 0.14 |
| 10 | 0.34 | 0.35 | 0.31 | 0.30 | 0.29 | 0.27 | 0.26 | 0.26 |
| mean | 0.33 | 0.32 | 0.31 | 0.30 | 0.26 | 0.26 | 0.24 | 0.23 |

* animal euthanized

Hematocrits (% or L/L) for irradiated animals at day 19 to day 26

| animal | 19 | 20 | 21 | 22 | 23 | 24 | 25 | 26 |
|---|---|---|---|---|---|---|---|---|
| 1 | 0.31 | 0.30 | 0.29 | 0.28 | 0.33 | 0.30 | 0.31 | 0.32 |
| 2 | 0.32 | 0.32 | 0.32 | 0.31 | 0.34 | 0.33 | 0.34 | 0.34 |
| 3 | * | | | | | | | |
| 4 | * | | | | | | | |
| 5 | ** | ** | 0.14 | 0.14 | 0.12 | ** | 0.12 | * |
| 6 | ** | 0.26 | 0.25 | 0.25 | 0.24 | 0.25 | 0.26 | 0.28 |
| 7 | 0.28 | 0.26 | 0.25 | 0.25 | 0.25 | 0.26 | 0.27 | 0.29 |
| 8 | 0.20 | 0.20 | 0.20 | 0.20 | 0.22 | 0.23 | 0.24 | 0.26 |
| 9 | * | | | | | | | |
| 10 | 0.29 | * | | | | | | |
| mean | 0.28 | 0.27 | 0.24 | 0.23 | 0.25 | 0.27 | 0.26 | 0.30 |

* animal euthanized
** measurement not obtained

Platelets ($\times 10^{-3}$/µL) for irradiated animals at day −6 to day 10

| animal | −6 | 2 | 5 | 6 | 7 | 8 | 9 | 10 |
|---|---|---|---|---|---|---|---|---|
| 1 | 608 | 525 | 580 | 538 | 433 | 324 | 232 | 111 |
| 2 | 547 | 397 | 406 | 401 | 324 | 255 | 174 | 113 |
| 3 | 363 | 313 | 356 | 315 | 221 | 169 | 101 | 45 |
| 4 | 295 | 266 | 267 | 253 | 180 | 141 | 71 | 28 |

-continued

Platelets (×10⁻³/μL) for irradiated animals at day −6 to day 10

| animal | −6 | 2 | 5 | 6 | 7 | 8 | 9 | 10 |
|---|---|---|---|---|---|---|---|---|
| 5 | 472 | 325 | 336 | 316 | 273 | 203 | 117 | 22 |
| 6 | 400 | 410 | 443 | 386 | 290 | 193 | 103 | 26 |
| 7 | 485 | 438 | 385 | 489 | 409 | 353 | 275 | 175 |
| 8 | 472 | 380 | 401 | 342 | 305 | 235 | 145 | 59 |
| 9 | 510 | 363 | 307 | 370 | 261 | 109 | 46 | 20 |
| 10 | 419 | 381 | 478 | 409 | 327 | 185 | 79 | 36 |
| mean | 457 | 380 | 396 | 382 | 302 | 217 | 134 | 64 |

Platelets (×10⁻³/μL) for irradiated animals at day 11 to day 18

| animal | 11 | 12 | 13 | 14 | 15 | 16 | 17 | 18 |
|---|---|---|---|---|---|---|---|---|
| 1 | 57 | 42 | 25 | 23 | 22 | 10 | 23 | 45 |
| 2 | 61 | 32 | 25 | 18 | 28 | 55 | 107 | 177 |
| 3 | 30 | 13 | 10 | 6 | 5 | 8 | 7 | 7 |
| 4 | 20 | 6 | 5 | 4 | 5 | * | | |
| 5 | 17 | 11 | 7 | 4 | 6 | 10 | 12 | 16 |
| 6 | 33 | 17 | 19 | 18 | 12 | 12 | 12 | 16 |
| 7 | 88 | 30 | 27 | 20 | 17 | 17 | 27 | 44 |
| 8 | 39 | 12 | 13 | 8 | 7 | 15 | 24 | 48 |
| 9 | 23 | 7 | 8 | 8 | 4 | 7 | 6 | 9 |
| 10 | 24 | 16 | 12 | 11 | 7 | 12 | 20 | 19 |
| mean | 39 | 19 | 15 | 12 | 11 | 16 | 26 | 42 |

* animal euthanized

Platelets (×10⁻³/μL) for irradiated animals at day 19 to day 26

| animal | 19 | 20 | 21 | 22 | 23 | 24 | 25 | 26 |
|---|---|---|---|---|---|---|---|---|
| 1 | 64 | 91 | 118 | 139 | 134 | 156 | 200 | 222 |
| 2 | 261 | 300 | 349 | 343 | 358 | 330 | 327 | 303 |
| 3 | * | | | | | | | |
| 4 | | | | | | | | |
| 5 | ** | ** | 44 | 53 | 74 | * | 186 | |
| 6 | ** | 44 | 104 | 142 | 217 | 259 | 305 | 318 |
| 7 | 89 | 144 | 278 | 353 | 448 | 523 | 519 | 514 |
| 8 | 90 | 92 | 158 | 194 | 246 | 285 | 341 | 406 |
| 9 | * | | | | | | | |
| 10 | 12 | * | | | | | | |
| mean | 103 | 134 | 175.17 | 217.00 | 246.17 | 310.60 | 313.00 | 352.60 |

* animal euthanized
** measurement not obtained

Neutrophils (×10⁻³/mm³) for irradiated animals at day −6 to day 10

| animal | −6 | 2 | 5 | 6 | 7 | 8 | 9 | 10 |
|---|---|---|---|---|---|---|---|---|
| 1 | 4.30 | 2.59 | 1.07 | 0.58 | 0.34 | 0.39 | 0.40 | 0.39 |
| 2 | 5.10 | 6.08 | 2.10 | 1.41 | 0.28 | 0.27 | 0.34 | 0.36 |
| 3 | 8.17 | 5.09 | 2.05 | 1.02 | 0.76 | 0.68 | 0.60 | 0.48 |
| 4 | 9.46 | 6.98 | 0.68 | 0.30 | 0.25 | 0.32 | 0.30 | 0.22 |
| 5 | 3.01 | 4.45 | 2.53 | 0.76 | 0.29 | 0.28 | 0.35 | 0.13 |
| 6 | 2.07 | 4.55 | 2.39 | 0.80 | 0.33 | 0.30 | 0.38 | 0.27 |
| 7 | 5.94 | 6.01 | 1.19 | 0.79 | 0.34 | 0.35 | 0.54 | 0.36 |
| 8 | 2.59 | 2.50 | 1.13 | 0.28 | 0.15 | 0.26 | 0.28 | 0.14 |
| 9 | 3.62 | 6.36 | 0.46 | 0.25 | 0.31 | 0.43 | 0.57 | 0.21 |
| 10 | 3.22 | 5.34 | 1.30 | 0.46 | 0.37 | 0.34 | 0.31 | 0.13 |
| mean | 4.75 | 5.00 | 1.49 | 0.67 | 0.34 | 0.36 | 0.41 | 0.27 |

Neutrophils (×10⁻³/mm³) for irradiated animals at day 11 to day 18

| animal | 11 | 12 | 13 | 14 | 15 | 16 | 17 | 18 |
|---|---|---|---|---|---|---|---|---|
| 1 | 0.17 | 0.10 | 0.08 | 0.14 | 0.17 | 0.09 | 0.10 | 0.08 |
| 2 | 0.30 | 0.15 | 0.10 | 0.10 | 0.07 | 0.07 | 0.19 | 0.46 |
| 3 | 0.13 | 0.09 | 0.12 | 0.09 | 0.04 | 0.05 | 0.07 | 0.02 |
| 4 | 0.16 | 0.11 | 0.04 | 0.06 | 0.03 | * | | |
| 5 | 0.07 | 0.09 | 0.06 | 0.07 | 0.02 | 0.04 | 0.10 | 0.24 |
| 6 | 0.13 | 0.10 | 0.13 | 0.09 | 0.06 | 0.06 | 0.05 | 0.05 |
| 7 | 0.24 | 0.19 | 0.10 | 0.06 | 0.12 | 0.20 | 0.12 | 0.15 |
| 8 | 0.11 | 0.06 | 0.05 | 0.05 | 0.03 | 0.05 | 0.18 | 0.69 |
| 9 | 0.13 | 0.16 | 0.11 | 0.06 | 0.08 | 0.05 | 0.06 | 0.04 |
| 10 | 0.09 | 0.09 | 0.05 | 0.07 | 0.03 | 0.04 | 0.07 | 0.05 |
| mean | 0.15 | 0.11 | 0.08 | 0.08 | 0.07 | 0.07 | 0.10 | 0.20 |

* animal euthanized

Neutrophils (×10⁻³/mm³) for irradiated animals at day 19 to day 26

| animal | 19 | 20 | 21 | 22 | 23 | 24 | 25 | 26 |
|---|---|---|---|---|---|---|---|---|
| 1 | 0.30 | 1.37 | 1.21 | 1.72 | 2.00 | 2.51 | 3.62 | 4.28 |
| 2 | 0.70 | 1.23 | 2.38 | 3.63 | 5.67 | 6.47 | 6.63 | 5.53 |
| 3 | * | | | | | | | |
| 4 | | | | | | | | |
| 5 | ** | ** | 2.57 | 4.51 | 4.60 | * | 6.04 | |
| 6 | ** | 0.18 | 0.30 | 1.57 | 1.32 | 2.12 | 5.52 | 6.14 |
| 7 | 0.14 | 0.08 | 0.27 | 0.83 | 1.66 | 3.38 | 5.54 | 11.53 |
| 8 | 1.80 | 0.84 | 1.86 | 4.07 | 2.82 | 3.6 | 3.59 | 6.77 |

-continued

Neutrophils (×10$^{-3}$/mm$^3$) for irradiated animals at day 19 to day 26

| animal | day | | | | | | | |
|---|---|---|---|---|---|---|---|---|
| | 19 | 20 | 21 | 22 | 23 | 24 | 25 | 26 |
| 9 | * | | | | | | | |
| 10 | 0.04 | * | | | | | | |
| mean | 0.60 | 0.74 | 1.43 | 2.92 | 3.01 | 3.62 | 5.16 | 6.85 |

* animal euthanized
** measurement not obtained

Example 3

Treatment of whole body lethal radiation and characterization of mortality surrogate markers. Two groups of 10 *Macaca mulatta* (Rhesus monkey) were exposed to a 6 Gy dose of γ-radiation from a $^{60}$Co source. This dose is an LD$_{50/30}$ dose for this species. After irradiation, one group of animals was treated with test article, 15 mg/kg of 3β,17β-dihydroxyandrost-5-ene ("AED") in vehicle, and the other 10-animal group was treated with the vehicle alone. The animals in each group were treated once per day for 5 consecutive days beginning on the day the animals were exposed to radiation. The animals consisted of 12 males and 8 females with a body weight range of about 2.5-5.5 kg at the onset of treatment. The age range was 1.75-5.0 years at the onset of treatment. Procedures involving the care and use of animals in this protocol was reviewed and approved by the Institutional Animal Care and Use Committee before conduct. During the study, the care and use of animals were conducted in accordance with the applicable rules and codes.

The animals were housed individually in stainless steel squeeze back cages equipped with an automatic watering system except during transportation where water bottles were provided. The cages were clearly labeled with a color-coded cage card indicating study number, group, animal number, species, sex and dose level. The animal room environment was controlled (temperature 21±3° C., humidity 30-70%, 10-15 air changes per hour, 12 hours light, 12 hours dark). Temperature and humidity was monitored continuously except during animal transportation and inside the radiation facility where only temperature was recorded. During transportation, only temperature was controlled. Air was not filtered during animal transportation and inside the radiation facility. A standard certified commercial primate chow (Teklad Certified Global 25% Primate Diet #2055C) was made available to each monkey daily. Food was withdrawn overnight prior to radiation and necropsy. Maximum allowable concentrations of contaminants in the diet (e.g., heavy metals, aflatoxin, organophosphates, chlorinated hydrocarbons and PCBs) were controlled and routinely analyzed by the manufacturer. When an animal became inappetent during the study, the diet could be supplemented.

Tap water purified by reverse osmosis was provided to the animals ad libitum throughout the study. There were no known contaminants in the diet or water. Before transportation to the radiation facility, animals were acclimated to the radiotherapy chair and to transportation. Positive reinforcement was used to facilitate acclimation. Certified non human primate treats were given after acclimation periods. Twelve male and eight female rhesus monkeys were assigned to the study. Each group comprised of seven male and three female animals. During the acclimation period, animals were assigned to their respective dose groups by randomization based on the absolute neutrophil count. The average of 3 pretreatment absolute neutrophil counts were used for each animal.

The test article (100 mg/mL 3β,17β-dihydroxyandrost-5-ene) and vehicle or control article in aliquots of 10 mL. Test article was an aqueous suspension in vehicle. The vehicle article consists of a solution of sodium chloride (0.9% w/v), carboxymethylcellulose (0.5% w/v), polysorbate 80 (2% v/v), benzalkonium chloride (0.02% v/v) and sodium phosphate (10 mM, pH 6.5). Immediately prior to drawing into a syringe, the test article formulation was briefly vortexed to uniformly distribute sedimented test article. Once drawn into a syringe, the test article was administered within 10 minutes. Just prior to injection, the syringe containing the test article was rotated end-over-end to uniformly disperse the compound.

During the pre-treatment period, body temperature transmitters were surgically implanted to allow core body temperature and physical activity monitoring. The animals were fasted overnight before the implant surgery. The animals were anesthetized by an intra-muscular injection of acepromazine (10 mg/mL, 0.14 mg/kg) and ketamine (100 mg/mL, 13.6 mg/kg) and intubated. Where needed, lidocain spray (10% w/w) was administered onto the glottis prior to intubation. An ophthalmic ointment was applied to both eyes to prevent drying of the cornea. Animals were then placed on a heating pad and administered isoflurane by inhalation, with an oxygen flow of approximately 200 mL/kg/min or as needed. A ventilator was used to maintain the respiratory rate between 8 and 20 breaths/min with a ventilation pressure of 18-25 cm H$_2$O. Monitoring during anesthesia included heart rate and oxygen saturation of the blood using a pulse oximeter.

Prophylactic antibiotics (cefazolin 25 mg/kg) were administered by intramuscular injection at least 1-hour prior to surgery, and every 4 to 8 hours post injection for at least 24-hours post surgery. Analgesia (buprenorphine 0.05 mg/kg) was administered by intramuscular injection every 6 to 12 hours for at least 24-hours post surgery. Intravenous fluid therapy was given throughout the anesthesia using sterile Lactate Ringer's solution at a rate of 10 ml/kg/hr. The surgical site was shaved and was aseptically prepared using chlorhexidine gluconate 4% and isopropyl alcohol 70%. A longitudinal incision was performed lateral but close to the linea alba. The internal abdominal oblique muscle was separated from the aponeurosis of the transversus abdominis by blunt dissection. A sterile core body temperature transmitter (Data Science International, TA10TAD70) was inserted between the internal abdominal oblique muscle and the aponeurosis of the transversus abdominis. The serial number of the transmitter was recorded. Hemostasis was maintained using appropriate suture material. Sterile saline was used to allow ease of placement of the transmitters. The incision was closed with absorbable suture material using simple continuous sutures. The skin was closed with discontinuous buried sutures using absorbable suture material. Additional post-operative care (analgesia and antibiotics) were given to all animals where required. Rectal body temperature was monitored in the post-operative period. Once the body temperature was within an acceptable range and the animal was alert, each animal was returned to its cage. A post-operative period of at least 2 weeks was allowed prior to initiation of treatment. Core body temperature was monitored at 1 minute intervals beginning 6 days before radiation exposure and continued until 40 days after exposure.

Whole Body Radiation.

The animals were exposed to ionizing as follows. Dosimetry measurements using phantoms, the dose rate and duration of irradiation and the actual time of irradiation for each individual animal was recorded. Animals were fasted overnight prior to whole-body irradiation and fed upon return to the housing facility. Animals were transferred to the treatment facility in a transport vehicle with controlled environment. During transportation, each animal was individually housed in a stainless steel squeeze back cage. Temperature in the transport vehicle was automatically recorded every 5 minutes during transportation. Clinical signs were monitored immediately before and after transportation.

Upon arrival to the site of irradiation, each animal was placed in a chair allowing appropriate restraining in a symmetric position. An insulated cover was placed on the radiotherapy chair during transportation between the truck and the treatment room. Each animal was brought in the treatment room. Music was provided inside the treatment room to reduce stress to the animals. Animal positioning was confirmed with linear markers installed in the treatment room.

The animals received a midline treatment dose of 600 cGy. The dose rate of the $^{60}$Co gamma source was about 60 cGy per minute and the actual rate was recorded for each animal. To obtain a homogenous dose distribution, the radiation treatment was divided in two parts. First, the animal received half of the dose by anteroposterior irradiation. The second half of the dose was delivered by posteroanterior irradiation. Once the treatment was completed, animals were returned to the transport vehicle and transported to the housing facility. The radiation dose was calibrated using an acrylic phantom placed in the same experimental set up that was used for animal irradiation.

Administration of 3β,17β-dihydroxyandrost-5-ene and vehicle control. The animals received the vehicle control once daily for five consecutive days by intramuscular injections. The first injection on day 1 was administered at 2-3 hours after irradiation. The dose volume was 0.15 mL/kg for all animals. The dose volume was evenly divided between two distinct sites (approximately 0.075 mL/kg per site). The actual volume delivered was calculated and adjusted based on each animal's body weight. To verify the concentration and homogeneity of the test and control articles in the dosing formulation, duplicate samples (1 mL/sample) from the bottom of each dosing formulation was taken prior to dosing on days 1, 2, 3, 4 and 5 and stored frozen (−70±10° C.) pending analysis.

During the pre-treatment period cage side observations of clinical signs were performed once daily. A detailed clinical examination was performed on all animals once prior to irradiation on day 1, day 9, weekly thereafter and at day 40 and 41. After radiation, the animals and clinical signs were observed twice a day during the protocol or as often as deemed necessary. Moribund animals were euthanized for humane reasons. Euthanasia criteria consisted of (i) a core body temperature of 35.9° C. after a period of febrile neutropenia, (ii) more than a 20% weight loss over a 3 day period, (iii) complete anorexia for 3 days with deteriorating conditions based on clinical examination or (iv) absence of response to stimuli.

Core body temperature and activity was recorded every minute for all animals from Day −10 to sacrifice using the implanted transmitter. Core body temperature and activity was recorded when animals were housed in their designated cage. Each designated cage was equipped with a telemetry receiver. Core body temperature was not recorded when animals were handled or during transport to the radiation facility. Body weights were recorded for all animals on the day following transfer, once before randomization, prior to treatment on day 1, day 9, weekly thereafter, at on the day the protocol ended. Laboratory hematology investigations were performed on all animals three times during the pre-treatment period and during the treatment period on day 2, daily from day 5 to day 27 and once on days 30, 33, 36 and 40.

For hematology analyses, blood samples of 0.5 mL were collected from the femoral vein or artery or from any appropriate vessel by venipuncture. EDTA was used as an anticoagulant. Animals were not deprived of food or water prior to blood collections. Parameters such as red blood cell count, hematocrit, hemoglobin, mean corpuscular volume, red blood cell count, mean corpuscular hemoglobin, white blood cell count, WBC differential (absolute), platelet count, WBC differential (relative), red cell distribution width, reticulocyte count and immature granulocyte count were measured. Blood smears were prepared for each time point, stained with Modified Wright's stain and evaluated.

For pharmacokinetic evaluation, blood samples (approximately 1.0 mL) were collected from all animals at about 22.0 to 23.5 hours following the first compound and control vehicle article administration on day 2. Each blood sample was collected into an EDTA potassium tube and kept on wet ice, for a maximum of 30 minutes, until centrifugation. The samples were centrifuged under refrigeration (2 to 8° C.) for approximately 10 minutes at 1500 g (RCF). The harvested plasma was transferred in one aliquot per sample. Blood samples (approximately 2.0 mL) were collected from all animals prior to sacrifice on days 40 and 41. Each blood sample was collected into an EDTA potassium tube and kept on wet ice, for a maximum of 30 minutes, until centrifugation. The samples were centrifuged under refrigeration (2 to 8° C.) for approximately 10 minutes at 1500 g (RCF). The harvested plasma was transferred in two separate aliquots per sample.

Liver, lung (right and left separately), kidney, brain (left) and spleen tissues were collected at necropsy from all euthanized animals for bacteriological culture. The tissue samples were stored refrigerated (2-10° C.) pending analysis. A selected area at the surface of the tissue sample was burned to eliminate possible surface contaminants. A sterile culture swab was inserted in the tissue sample through the burned surface for isolation and identification of aerobic and anaerobic bacteria.

Numerical data obtained during the conduct of the study was subjected to calculation of group means and standard deviations. Data was analyzed using the Analysis of Variance (ANOVA) and the significance of inter-group differences were analyzed by Dunnett's "t" test or other appropriate tests using the SPSS for Windows, version 12.0, SPSS, Inc.

In the vehicle-treated control animal group, 4 of 10 animals survived, with 3 of the four non-survivors having febrile severe neutropenia, which was defined as a core body temperature of >40.4° C., i.e., ≥40.5° C., and an absolute neutrophil count of less than 500 cells/4. In the 3β,17β-dihydroxyandrost-5-ene treated animal group, 9 of 10 animals survived, with the non-survivor not having febrile severe neutropenia and 2 survivors having the condition at some time during the protocol. Mortality in the untreated control group thus was 40% and 10% in the treated group. When the two control groups from this protocol and from the protocol described in examples 1 and 2 were combined, the total combined mortality of the 20 irradiated untreated animals was 45%. A reduction of mortality was observed (Fisher's exact test mid p=0.073) in the treated group compared to these two control groups. In the control group from this example only (vehicle treated) the animals experienced a median of 5 days of febrile severe neutropenia (95% CI 0.8) while the animals treated with 3β,17β-dihydroxyandrost-5-ene experienced a median of 0 days of febrile severe neutropenia (95% CI 0.2), giving a p=0.037 by the exact log rank test.

In the vehicle treated control animals from this example the animals collectively experienced 51 days of severe thrombocytopenia, less than 20,000 platelets/μL, while the animals treated with 3β,17β-dihydroxyandrost-5-ene collectively experienced 32 days of severe thrombocytopenia. This difference was p=0.009 by the exact test of homogeneity.

To the extent not already indicated, it will be understood by those of ordinary skill in the art that any of the various specific embodiments, compounds or compositions described herein may be modified to incorporate other appropriate features, e.g., as shown in any other of the specific embodiments disclosed herein or in the cited references.

What is claimed is:

1. A compound having the structure

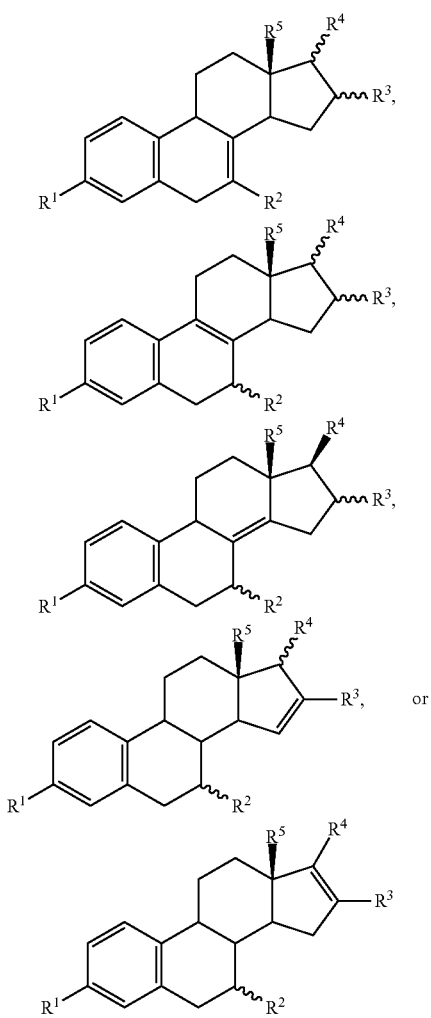

wherein,
$R^1$ is —OH, ester or ether;
$R^2$ is —OH an oxygen linked ester or an oxygen linked ether;
$R^3$ is —OH, ester, ether or halogen;
$R^4$ is —OH, ester, ether or optionally substituted amine; and
$R_5$ is —CH$_3$, —CH$_2$OH, —CHO, —C$_2$H$_5$ or —C$_3$H$_7$.

2. The compound of claim 1 wherein $R^1$, $R^2$ and $R^4$ independently are —OH or —O—C(O)—CH$_3$ and $R^3$ is —OH, —F or —O—C(O)—CH$_3$.

3. The compound of claim 2 wherein $R^1$, $R^2$ and $R^4$ are —OH and $R^3$ is —OH or —F.

4. The compound of claim 2 wherein the compound has the structure

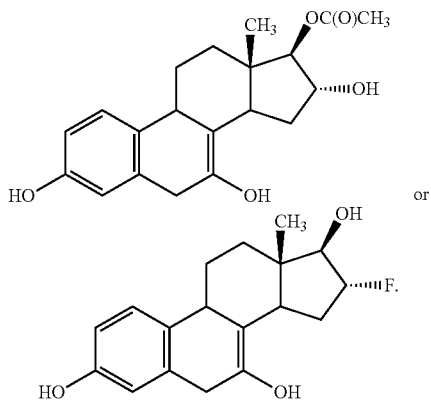

5. The compound of claim 2 wherein the compound has the structure

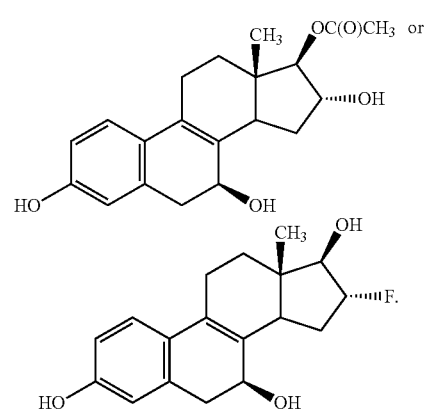

6. The compound of claim 2 wherein the compound has the structure

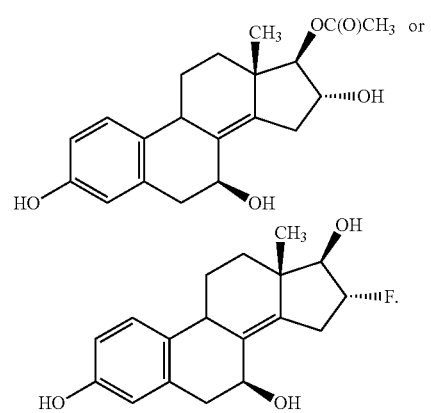

7. The compound of claim 2 wherein the compound has the structure

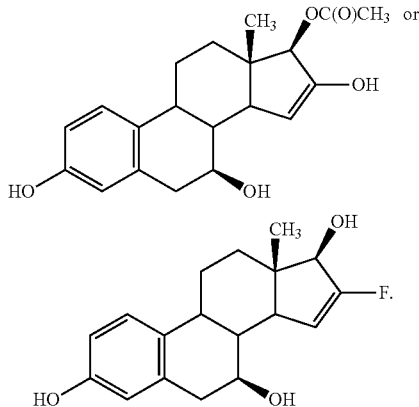

8. The compound of claim 2 wherein the compound has the structure

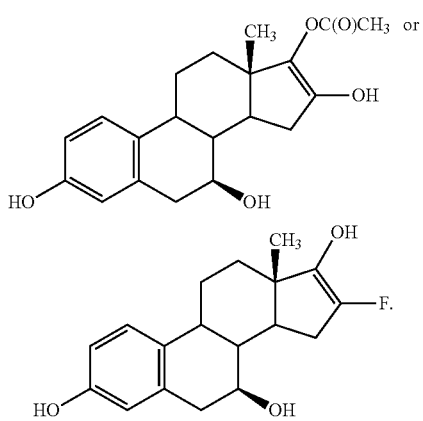

9. The compound of claim 1 wherein R⁴ is —O—C(O)—CH₃, —O—C(O)—CH₂CH₃, —NH—C(O)—CH₃, —NH—C(O)—OCH₃, —NHCH₃, —NH(CH₃)₂, alkylamine, dialkylamine, an N-linked carbamate, an N-linked amino acid or an N-linked heterocycle.

10. The compound of claim 9 wherein R¹ and R² independently are —OH or —O—C(O)—CH₃ and R³ is —OH, —F or —O—C(O)—CH₃.

11. The compound of claim 1 wherein R² is —OH.

12. A compound having the structure

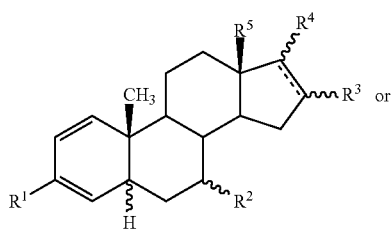

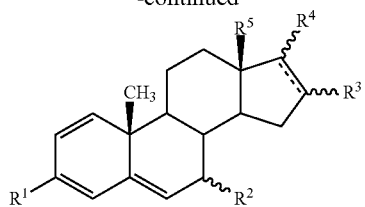

wherein the dotted line is an optional double bond,
R¹ is ester or ether;
R² is —OH, ester or ether;
R³ is —OH, ester, ether or halogen;
R⁴ is optionally substituted amine; and
R₅ is —CH₃, —CH₂OH, —CHO, —C₂H₅ or —C₃H₇.

13. The compound of claim 12 wherein R⁴ is NH—C(O)—CH₃, —NH—C(O)—OCH₃, —NHCH₃, —NH(CH₃)₂, alkylamine, dialkylamine, an N-linked carbamate, an N-linked amino acid or an N-linked heterocycle.

14. The compound of claim 13 wherein R² is —OH or —O—C(O)—CH₃ and R³ is —OH, —F or —O—C(O)—CH₃.

15. A compound having the structure

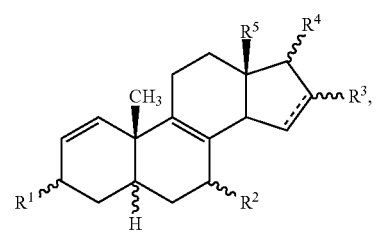

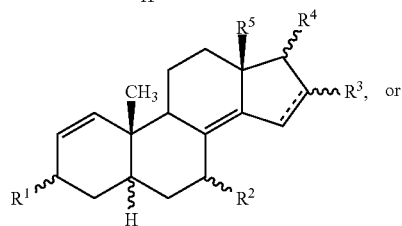

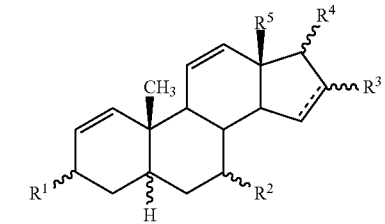

wherein the dotted line is an optional double bond,
R¹ is —OH, ester or ether;
R² is —OH, ester or ether;
R³ is —OH, ester, ether or halogen;
R⁴ is —OH, ester, ether or optionally substituted amine; and
R₅ is —CH₃, —CH₂OH, —CHO, —C₂H₅ or —C₃H₇.

16. The compound of claim 15 wherein R¹, R² and R⁴ independently are —OH or —O—C(O)—CH₃ and R³ is —OH, —F or —O—C(O)—CH₃.

17. The compound of claim 16 wherein the compound has the structure

307

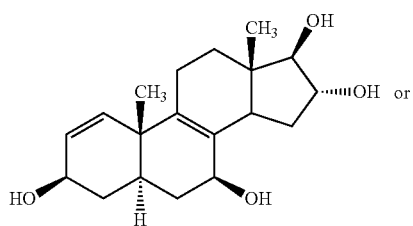

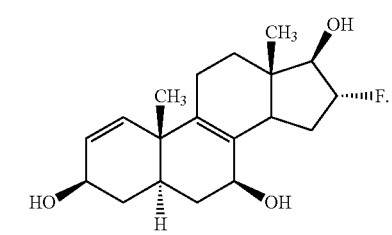

18. The compound of claim 16 wherein the compound has the structure

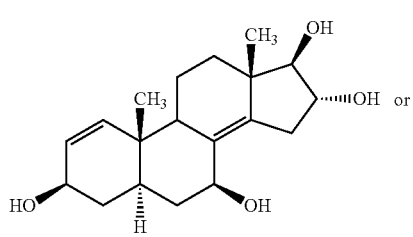

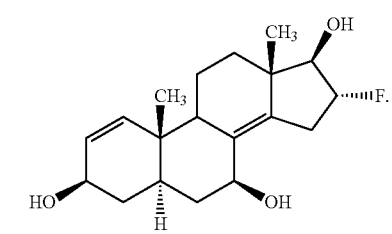

19. The compound of claim 15 wherein R⁴ is —O—C(O)—CH₃, —O—C(O)—CH₂CH₃, —NH—C(O)—CH₃, —NH—C(O)—OCH₃, —NHCH₃, —NH(CH₃)₂, alkylamine, dialkylamine, an N-linked carbamate, an N-linked amino acid or an N-linked heterocycle.

20. The compound of claim 15 wherein R¹ and R² independently are —OH or —O—C(O)—CH₃ and R³ is —OH, —F or —O—C(O)—CH₃.

21. A compound having the structure

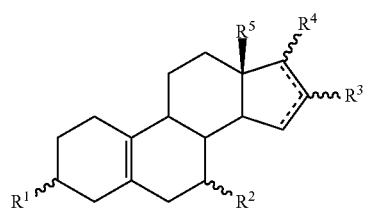

308

-continued

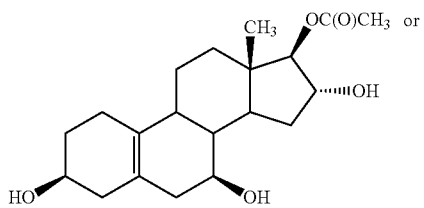

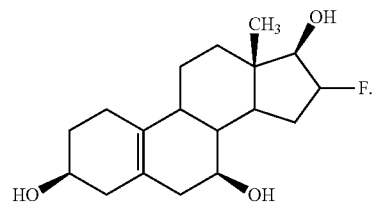

wherein the dotted lines are optional double bonds,

R¹ is —OH, ester or ether;

R² is —OH, ester or ether;

R³ is —OH, ester, ether or halogen;

R⁴ is —OH, ester, ether or optionally substituted amine; and

R₅ is —CH₃, —CH₂OH, —CHO, —C₂H₅ or —C₃H₇.

22. The compound of claim 21 wherein R¹, R² and R⁴ independently are —OH or —O—C(O)—CH₃ and R³ is —OH, —F or —O—C(O)—CH₃.

23. The compound of claim 22 wherein the compound has the structure

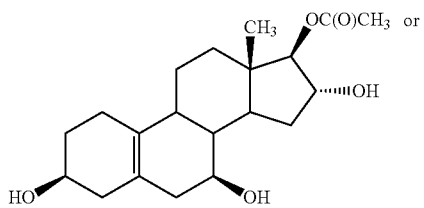

24. The compound of claim 22 wherein the compound has the structure

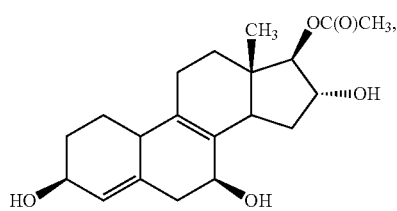

-continued
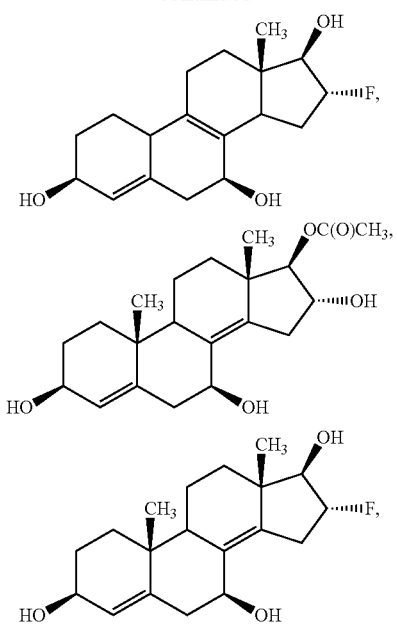
-continued
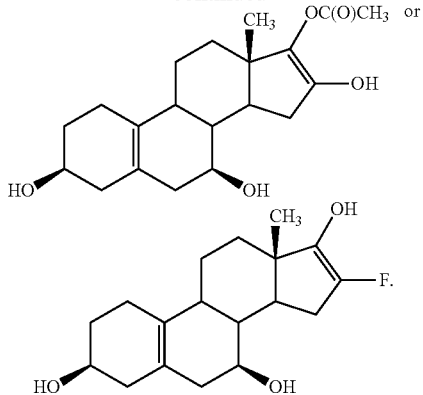
25. The compound of claim 21 wherein $R^4$ is —O—C(O)—CH$_3$, —O—C(O)—CH$_2$CH$_3$, —NH—C(O)—CH$_3$, —NH—C(O)—OCH$_3$, —NHCH$_3$, —NH(CH$_3$)$_2$, alkylamine, dialkylamine, an N-linked carbamate, an N-linked amino acid or an N-linked heterocycle.
26. The compound of claim 25 wherein $R^1$ and $R^2$ independently are —OH or —O—C(O)—CH$_3$ and $R^3$ is —OH, —F or —O—C(O)—CH$_3$.
* * * * *